US012584109B2

(12) United States Patent
Dhadwar et al.

(10) Patent No.: US 12,584,109 B2
(45) Date of Patent: Mar. 24, 2026

(54) ENGINEERING CELL LINES CAPABLE OF PROLIFERATION IN GROWTH FACTOR FREE MEDIA FORMULATIONS

(71) Applicant: Upside Foods, Inc., Berkeley, CA (US)

(72) Inventors: Sukhdeep Singh Dhadwar, El Cerrito, CA (US); Rachel Michele Schumaker, Emeryville, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

(21) Appl. No.: 18/331,092

(22) Filed: Jun. 7, 2023

(65) Prior Publication Data

US 2023/0392120 A1     Dec. 7, 2023

Related U.S. Application Data

(60) Provisional application No. 63/349,865, filed on Jun. 7, 2022.

(51) Int. Cl.
| | |
|---|---|
| *C12N 15/85* | (2006.01) |
| *A23L 13/00* | (2016.01) |
| *C07K 14/49* | (2006.01) |
| *C07K 14/50* | (2006.01) |
| *C07K 14/65* | (2006.01) |
| *C12N 5/077* | (2010.01) |
| *C12N 9/12* | (2006.01) |

(52) U.S. Cl.
CPC ............ *C12N 5/0658* (2013.01); *A23L 13/00* (2016.08); *C07K 14/49* (2013.01); *C07K 14/50* (2013.01); *C07K 14/65* (2013.01); *C12N 9/1241* (2013.01); *C12N 15/85* (2013.01); *C12N 2800/107* (2013.01)

(58) Field of Classification Search
None
See application file for complete search history.

(56) References Cited

U.S. PATENT DOCUMENTS

| | | | |
|---|---|---|---|
| 5,624,840 | A | 4/1997 | Naughton et al. |
| 6,579,549 | B1 | 6/2003 | Thrasher et al. |
| 6,593,275 | B1 | 7/2003 | Unkefer et al. |
| 6,767,719 | B1 | 7/2004 | Morin et al. |
| 6,835,390 | B1 | 12/2004 | Vein |
| 7,001,633 | B2 | 2/2006 | Pasch et al. |
| 7,033,744 | B2 | 4/2006 | Kobayashi et al. |
| 7,147,871 | B2 | 12/2006 | Voytik-Harbin et al. |
| 7,270,829 | B2 | 9/2007 | Van Eelen |
| 7,476,409 | B2 | 1/2009 | Singh et al. |
| 7,476,410 | B2 | 1/2009 | Singh et al. |
| 7,661,355 | B2 | 2/2010 | Kremer |
| 8,105,575 | B2 | 1/2012 | Kim et al. |
| 8,703,216 | B2 | 4/2014 | Forgacs et al. |
| 8,883,502 | B2 | 11/2014 | Zhang et al. |
| 9,102,739 | B2 | 8/2015 | Lazar et al. |
| 9,408,407 | B2 | 8/2016 | Shekdar et al. |

| | | | |
|---|---|---|---|
| 10,674,740 | B2 | 6/2020 | Tjornelund et al. |
| 11,479,792 | B2 | 10/2022 | Genovese et al. |
| 2002/0054942 | A1 | 5/2002 | Olson et al. |
| 2002/0068706 | A1 | 6/2002 | Gyuris et al. |
| 2005/0058751 | A1 | 3/2005 | Brotsky et al. |
| 2005/0260748 | A1 | 11/2005 | Chang et al. |
| 2006/0029922 | A1 | 2/2006 | Wan Eelen et al. |
| 2006/0121006 | A1 | 6/2006 | Chancellor et al. |
| 2007/0248716 | A1 | 10/2007 | Kruse et al. |
| 2009/0068316 | A1 | 3/2009 | Phelps et al. |
| 2010/0047251 | A1* | 2/2010 | Yayon .................... A61P 35/00 |
| | | | 530/391.1 |
| 2010/0173061 | A1 | 7/2010 | Wilkes |
| 2010/0319079 | A1 | 12/2010 | Kruse et al. |
| 2011/0091604 | A1 | 4/2011 | Miller |
| 2011/0191871 | A1 | 8/2011 | Walsh et al. |
| 2011/0225664 | A1 | 9/2011 | Smith |
| 2011/0301249 | A1 | 12/2011 | Challakere |
| 2013/0004466 | A1 | 1/2013 | Tremblay et al. |
| 2013/0029008 | A1 | 1/2013 | Forgacs et al. |
| 2013/0171731 | A1 | 7/2013 | Ivashchenko et al. |
| 2013/0224855 | A1 | 8/2013 | Gupta et al. |
| 2013/0255003 | A1 | 10/2013 | Forgacs et al. |
| 2014/0093618 | A1 | 4/2014 | Forgacs et al. |

(Continued)

FOREIGN PATENT DOCUMENTS

| | | |
|---|---|---|
| CA | 2333966 C | 12/1999 |
| CA | 2780087 A1 | 12/2012 |

(Continued)

OTHER PUBLICATIONS

Knežić, T.; Janjušević, L.; Djisalov, M.; Yodmuang, S.; Gadjanski, I. Using Vertebrate Stem and Progenitor Cells for Cellular Agriculture, State-of-the-Art, Challenges, and Future Perspectives. Biomolecules 2022, 12, 699. (Year: 2022).*

Onuma, Y., Higuchi, K., Aiki, Y., Shu, Y., Asada, M., Asashima, M., Suzuki, M., Imamura, T. and Ito, Y., 2015. A stable chimeric fibroblast growth factor (FGF) can successfully replace basic FGF in human pluripotent stem cell culture. PLoS One, 10(4), p. e0118931. (Year: 2015).*

Ferguson, H.R., Smith, M.P. and Francavilla, C., 2021. Fibroblast growth factor receptors (FGFRs) and noncanonical partners in cancer signaling. Cells, 10(5), p. 1201. (Year: 2021).*

Addgene. "pBABE-hygro-hTERT." Plasmid #1773, Dec. 1998, 6 pages, [Online] [Retrieved Dec. 3, 2020], Retrieved from the Internet <UR: https://www.addgene.org/1773/>.

(Continued)

*Primary Examiner* — Brian Whiteman
*Assistant Examiner* — Khaleda B Hasan
(74) *Attorney, Agent, or Firm* — Ballard Spahr, LLP

(57) ABSTRACT

Provided herein are methods of engineering a cell line for reduced dependence on exogenous growth factor(s). In some embodiments, the method includes introducing into a cell one or more of: a polynucleotide comprising a coding sequence of a growth factor ligand; a polynucleotide comprising a coding sequence of a growth factor receptor; or a polynucleotide comprising a coding sequence of an activated downstream growth factor target, and culturing the cells in a cultivation infrastructure.

22 Claims, 48 Drawing Sheets

Specification includes a Sequence Listing.

(56) References Cited

U.S. PATENT DOCUMENTS

| | | | |
|---|---|---|---|
| 2014/0113029 | A1 | 4/2014 | Timm et al. |
| 2014/0242155 | A1 | 8/2014 | Ramunas et al. |
| 2014/0370537 | A1 | 12/2014 | Sakurai et al. |
| 2015/0025128 | A1 | 1/2015 | Cain et al. |
| 2015/0079238 | A1 | 3/2015 | Marga et al. |
| 2015/0087532 | A1 | 3/2015 | Brown et al. |
| 2015/0133520 | A1 | 5/2015 | Czech et al. |
| 2015/0216216 | A1 | 8/2015 | Marga |
| 2015/0231209 | A1 | 8/2015 | Hsueh et al. |
| 2015/0289541 | A1 | 10/2015 | Brown et al. |
| 2015/0296834 | A1 | 10/2015 | Geistlinger |
| 2015/0296835 | A1 | 10/2015 | Anderson et al. |
| 2015/0305361 | A1 | 10/2015 | Holz-Schietinger et al. |
| 2015/0305390 | A1 | 10/2015 | Vrljic et al. |
| 2016/0227830 | A1 | 8/2016 | Genovese et al. |
| 2016/0251625 | A1 | 9/2016 | Genovese et al. |
| 2017/0035076 | A1 | 2/2017 | Geistlinger et al. |
| 2017/0101629 | A1 | 4/2017 | Minshull et al. |
| 2017/0114382 | A1 | 4/2017 | Follit et al. |
| 2017/0369849 | A1 | 12/2017 | Hanson et al. |
| 2019/0024079 | A1 | 1/2019 | Genovese et al. |
| 2019/0075820 | A1 | 3/2019 | Redl et al. |
| 2019/0174778 | A1 | 6/2019 | Van Dorn |
| 2020/0140810 | A1 | 5/2020 | Ben-Ayre et al. |
| 2020/0165569 | A1 | 5/2020 | Genovese et al. |
| 2020/0190524 | A1 | 6/2020 | Minshull et al. |
| 2020/0377895 | A1* | 12/2020 | Faust .................... C12N 15/85 |
| 2021/0106032 | A1 | 4/2021 | Leung et al. |
| 2021/0145031 | A1 | 5/2021 | Leung et al. |
| 2021/0171912 | A1 | 6/2021 | Genovese et al. |
| 2021/0340570 | A1* | 11/2021 | Genovese ............. C07K 14/76 |

FOREIGN PATENT DOCUMENTS

| | | | |
|---|---|---|---|
| CN | 1942576 | A | 4/2007 |
| CN | 101291596 | A | 10/2008 |
| CN | 101624570 | A | 1/2010 |
| CN | 103747693 | B | 8/2017 |
| EP | 0435617 | A1 | 7/1991 |
| EP | 1037966 | B1 | 5/2003 |
| JP | 2013-081783 | A | 5/2013 |
| WO | WO 1993/009236 | A1 | 5/1993 |
| WO | WO 1999/031222 | A1 | 6/1999 |
| WO | WO 1999/031223 | A1 | 6/1999 |
| WO | WO 2006/041429 | A2 | 4/2006 |
| WO | WO 2007/071339 | A1 | 6/2007 |
| WO | WO 2007/077256 | A1 | 7/2007 |
| WO | WO 2009/116864 | A1 | 9/2009 |
| WO | WO 2010/068897 | A2 | 6/2010 |
| WO | WO 2012/095514 | A1 | 7/2012 |
| WO | WO 2012/170995 | A1 | 12/2012 |
| WO | WO 2012/176023 | A1 | 12/2012 |
| WO | WO 2013/007656 | A1 | 1/2013 |
| WO | WO 2013/016547 | A2 | 1/2013 |
| WO | WO 2013/073246 | A1 | 5/2013 |
| WO | WO 2015/038988 | A1 | 3/2015 |
| WO | WO 2015/066377 | A1 | 5/2015 |
| WO | WO 2015/120174 | A1 | 8/2015 |
| WO | WO 2015/167959 | A1 | 11/2015 |
| WO | WO 2016/052472 | A1 | 4/2016 |
| WO | WO 2016/087560 | A1 | 6/2016 |
| WO | WO 2017/019125 | A1 | 2/2017 |
| WO | WO 2017/120089 | A1 | 7/2017 |
| WO | WO 2017/124100 | A1 | 7/2017 |
| WO | WO 2018/011805 | A2 | 1/2018 |
| WO | WO 2018/208628 | A1 | 11/2018 |
| WO | WO 2019/016795 | A1 | 1/2019 |
| WO | WO-2019014652 | A1 * | 1/2019 ............. C07K 14/65 |
| WO | WO 2020/243324 | A1 | 12/2020 |
| WO | WO-2022104373 | A1 * | 5/2022 ............. A23L 13/00 |

OTHER PUBLICATIONS

Addgene. "pBABE-neo-hTERT." Plasmid #1774, Dec. 1998, 5 pages, [Online] [Retrieved Dec. 4, 2020], Retrieved from the Internet <URL: https://www.addgene.org/1774/>.

Ahmad, R.S., Imran, A., Hussain, M.B., "Nutritional Composition of Meat", 2018, Meat Science and Nutrition, pp. 61-77.

Albini, S., et al., "Epigenetic Reprogramming of Human Embryonic Stem Cells into Skeletal Muscle Cells and Generation of Contractile Myospheres," Cell Reports 3:661-670 (2013).

Amaral, A.B. et al., "Lipid oxidation in meat: mechanisms and protective factors—a review," Food Science and Technology, vol. 38 (Suppl. 1), Dec. 2018, pp. 1-15.

Animal Sake Farm Animals List. downloaded May 24, 2022; on the web at animalsake.com/farm-animals-list. pp. 1-10.

Baquero-Perez et al. A simplified but robust method for the isolation of avian and mammalian satellite cells. BMC Cell Biology, vol. 13:16, Jun. 12, 2012, printed as pp. 1/11-11/11.

Barberi, T., et al., "Derivation of Engraftable Skeletal Myoblasts from Human Embryonic Stem Cells," Nature Medicine 13(5):642-648(2007).

Barnes, et al., Advances in animal cell recombinant protein production: GS-NS0 expression system, Cytotechnology 2000, vol. 32, pp. 109-123.

Barroeta, A.C., "Nutritive value of poultry meat: relationship between vitamin E and PUFA", 2007, World's Poultry Science Journal, pp. 277-284.

Bartholet, J., "Inside the Meat Lab a Handful of Scientists Aim to Satisfy the World's Growing Appetite for Steak Without Wrecking the Planet. The First Step: Grab a Petri Dish," Scientific American, pp. 65-69 (2011).

Bell et al., "Understanding TERT Promoter Mutations: A Common Path to Immortality," Mol Cancer Res 14:315-323 (2016). Published OnlineFirst Mar. 3, 2016, retrieved Jul. 6, 2017 from mcr.aacrjournals.org, 10 pages.

Ben-Arye, T. et al., "Tissue Engineering for Clean Meat Production," Front. Sustain. Food Syst., Jun. 2019, vol. 3, article 46, pp. 1-19.

Benjaminson, M., et al., "In Vitro Edible Muscle Protein Production System (MPPS): Stage 1, FISH," Acta Astronautica 51(12):879-889 (2002).

Bentzinger, C., et al., "Building Muscle: Molecular Regulation of Myogenesism," Cold Spring Harb Perspect Biol 4(2):1-16 (2012).

Bernardes De Jesus et. al., "The telomerase activator TA-65 elongates short telomeres and increases health span of adult /old mice without increasing cancer incidence," Aging Cell 10:604-621 (2011).

Betti et al., "Processing, Products, and Food Safety: Omega-3-enriched broiler meat: Fatty acid distribution between triacylglycerol and phospholipid classes," Poultry Science, vol. 88, 2009, pp. 1740-1754.

Bhagavati and Xu., "Generation of Skeletal Muscle from Transplanted Embryonic Stem Cells in Dystrophic Mice," Biochemical and Biophysical Research Communications 333:644-649 (2005).

Bhat and Bhat, "Animal-Free Meat Biofabrication," American Journal of Food Technology 6(6):441-459, (2011).

Bhat, S.F. et al., "Tissue engineered meat—future meat," Journal of Stored Products and Postharvest Research, vol. 2, 2011, pp. 1-10.

Bhat, Z.F. et al., "Prospectus of cultured meat—Advancing meat alternatives," Journal of Food Science and Technology 48(2), Apr. 2010, pp. 125-140.

Bian, W. et al., "Engineered skeletal muscle tissue networks with controllable architecture," Biomaterials, 30, Dec. 12, 2008, pp. 1401-1412.

Black, Brian L., and Eric N. Olson. "Transcriptional control of muscle development by myocyte enhancer factor-2 (MEF2) proteins" Annual review of cell and developmental biology 14.1 (1998): 167-196.

Blomberg et al. Twenty years of embryonic stem cell research in farm animals. Reproduction in Domestic Animals, vol. 47, Suppl. 4 , pp. 80-85, Aug. 2012. (Year: 2012).

Boonen and Post, "The Muscle Stem Cell Niche: Regulation of Satellite Cells During Regeneration," Tissue Engineering—Part B: Reviews 14(4):419-431 (2008).

Boz, M.A. et al. "The Carcass Traits, Carcass Nutrient Composition, Amino Acid, Fatty Acid, and Cholesterol Contents of Local Turkish Goose Varieties Reared in an Extensive Production System." Poultry Science, vol. 98, No. 7, Jul. 1, 2019, pp. 3067-3080.

(56) References Cited

OTHER PUBLICATIONS

Broedel, S.E. et al., "The Case for Serum-Free Media," Bio Process International, Feb. 2003, pp. 56-58.

Brunner, D. et al. "Serum-Free Cell Culture: The Serum-Free Media Interactive Online Database." Altex, vol. 27, No. 1, Feb. 1, 2010, pp. 53-62.

Canizo et al., "Exogenous human OKSM factors maintain pluripotency gene expression of bovine and porcine iPS-like cells obtained with STEMCCA delivery system," BMC Research Notes vol. 11, Article No. 509 (2018), 8 pages.

Cenciarelli et al. Critical role played by cyclin D3 in the MyoD-mediated arrest of cell cycle during myoblast differentiation. Molecular and Cellular Biology, vol. 19, No. 7, pp. 5203-5217, Jul. 1999.

Chang, et al., "Generation of Transplantable, Functional Satellite-Like Cells from Mouse Embryonic Stem Cells," FASEB J. 23, 1907-1919 (2009).

Chen et al. DNA methyltransferase inhibitor CDA-II inhibits myogenic differentiation. Biochemical and Biophysical Research Communications, vol. 422, pp. 522-526, May 22, 2012. (Year: 2012).

Chen et al. Potentiation of MyoD1 activity by 5-aza-2'-deoxycytidine. Cell Growth & Differentiation, vol. 1, pp. 383-392, Aug. 1990.

Chen, et al., Homeostatic control of Hippo signaling activity revealed by an endogenous activating mutation in YAP, Genes & Development, 29, Jun. 2015, 1285-1297.

Chiu and Blau, "5-5 Azacytidine Permits Gene Activation in a Previously Noninducible Cell Type," Cell, vol. 40, 417-424 (1985).

Choi, Sang-Woon, and Simonetta Friso. "Epigenetics: a new bridge between nutrition and health" Advances in nutrition 1.1 (2010): 8-16.

Chriki, S. et al., "The Myth of Cultured Meat: A Review," Frontiers in Nutrition, Feb. 2020, vol. 7, article 7, pp. 1-9.

Cox et al., "Yap reprograms glutamine metabolism to increase nucleotide biosynthesis and enable liver growth," Nat. Cell. Biol. 18(8), Jan. 18, 2017, pp. 886-896.

Darabi, R., et al, "Perspective Lineage-Specific Reprogramming as a Strategy for Cell Therapy," Cell Cycle 7(12):1732-1737 (2008).

Darabi, R., et al., "Assessment of the Myogenic Stem Cell Compartment Following Transplantation of Pax3/Pax7-Induced Embryonic Stem Cell-Derived Progenitors," Lillehei Heart Institute, Department of Medicine, University of Minnesota, Minneapolis, MN, USA, 27 pages (2011).

Darabi, R., et al., Functional Skeletal Muscle Regeneration From Differentiating Embryonic Stem Cells, Nature and Medicine 14(2):134-143 (2008).

Datar and Betti, "Possibilities for an In Vitro Meat Production System," Innovative Food Science & Emerging Technologies 11(1):13-22(2010).

Dave, D. et al., "Meat Spoilage Mechanisms and Preservation Techniques: A Critical Review," American Journal of Agricultural and Biological Sciences, Apr. 2011, 6(4), pp. 486-510.

Davis, R., et al., "Expression of a Single Transfected cDNA Converts Fibmblasts to Myoblasts," Cell, vol. 51. 987-1000 (1987).

Dekel, I., et al., "Conditional Conversion of ES Cells to Skeletal Muscle by an Exogenous MyoDI Gene," (1992).

Delany, M. E. et al. "Telomeres in the Chicken: Genome Stability and Chromosome Ends." Poultry Science, vol. 82, No. 6, Jun. 1, 2003, pp. 917-926.

Demeure et al., "Liver X receptor a regulates fatty acid synthase expression in chickem," Poultry Science, vol. 88, 2009, pp. 2628-2635.

Desbois-Mouthon, Christele, et al. "Insulin and IGF-1 stimulate the .beta.-catenin pathway through two signalling cascades involving GSK-3.beta. inhibition and Ras activation" Oncogene 20.2 (2001): 252-259.

dictionary.com, "myogenic" definition, Date Unknown, one page, [Online] [Retrieved on Aug. 19, 2022] Retrieved from the Internet <URL: https://www.dictionary.com/browse/myogenic>.

Ding, Vanessa MY, et al. "FGF-2 modulates Wnt signaling in undifferentiated hESC and iPS cells through activated PI3-K/GSK3.beta. signaling" Journal of cellular physiology 225.2 (2010): 417-428.

Dominguez et. al., "Beyond editing: repurposing CRISPR—Cas9 for precision genome regulation and interrogation," Nature Reviews Molecular Cell Biology 17:Jan. 5-15, 2016.

Dong, J. et al. "Elucidation of a Universal Size-Control Mechanism in *Drosophila* and Mammals," Cell, vol. 130, No. 6, pp. 1120-1133, Sep. 21, 2007.

Doyle, E., "Human Safety of Hormone Implants Used to Promote Growth in Cattle," Food Research Institute, Jul. 2000, pp. 1-24.

Edelman, P., et al., "In Vitro-Cultured Meat Production," Tissue Engineering 11(5/6):659-662 (2005).

Enser, "Muscle lipids and meat quality," Proceedings of the British Society of Animal Science, vol. 2001, 2001, pp. 243-246.

European Patent Office, Extended European Search Report and Opinion, EP Patent Application No. 18797874.7, May 21, 2021, 15 pages.

European Patent Office, Extended European Search Report and Opinion, EP Patent Application No. 18832585.6, Apr. 9, 2021, nine pages.

Extended European Search Report dated May 19, 2017, from the European patent Office for Application No. 14858383.4, filed Oct. 30, 2014, 10 pages.

Fan, L. et al., "The use of glutamine synthetase as a selection marker: recent advances in Chinese hamster ovary cell line generation processes," Pharmaceutical Bioprocessing 1(15), 2013, pp. 487-502.

Fao, "The production of fish meal and oil," Fisheries Industries Division, Food and Agriculture Organization of the United Nations, Rome, Italy, Fisheries Technical Papers—T142, 1986, 71 pages.

FDA—CFR—Code of Federal Regulations Title 21, Apr. 1, 2019, 24 pages.

Feng et al., "BAM Chapter 4: Enumeration of *Escherichia coli* and the Coliform Bacteria," retrieved online Feb. 3, 2021, 18 pages, https://www.fda.gov/food/laboratory-methods-food/bam-chapter-4-enumeration-escherichia-coli-and-coliform-bacteria#conventional.

Finnie, "Is Lab Grown Meat the Coup de Gras to the Vegan Argument," Mar. 17, 2016, 3 pages, http://trn.tv/blog/blog/2016/03/17/is-lab-grown-meat-the-coup-de-gras-to-theveaan-argument/.

Flatow, "Biting Into the First In Vitro Burger," NPR, Aug. 9, 2013, 19 pages.

Garrels et al. Ectopic expression of human telomerase KNA component results In increased telomerase activity and elongated telomeres in bovine blastocysts. Biol Reprod. 2012, 87(4):95, 1-7.

Gasteratos K., "90 Reasons to Consider Cellular Agriculture," 2019, 27 pages, http://nrs.harvard.edu/urn-3:HUL.InstRepos:38573490.

GenBank. "Bos Taurus Cyclin-Dependent Kinase 4, mRNA (cDNA Clone MGC: 133903 Image:8041087), Complete CDS." NCBI, GenBank: BC109858.1, Nov. 2005, 2 pages, [Online] [Retrieved Dec. 7, 2020], Retrieved from the Internet <URL:https://www.ncbi.nlm.nih.gov/nuccore/BC109858>.

GenBank. "Gallus Gallus Gallus Telomerase Reverse Transcriptase (TERT) mRNA, Complete CDS." GenBank: NCBI, AY502592.1, 2004, 3 pages, [Online] [Retrieved Dec. 7, 2020], Retrieved from the Internet <URL:https://www.ncbi.nlm.nih.gov/nuccore/AY502592>.

Genovese et al., "Enhanced Development of Skeletal Myotubes form Porcine Induced Pluripotent Stem Cells," Scientific Reports, vol. 7, Feb. 2017, 12 pages.

George et al. "Exploiting Expression of Hippo Effector, Yap, for Expansion of Functional Islet Mass," Molecular Endocrinology. Sep. 2015, vol. 29, Iss. 11, pp. 1594-1607.

Gerhardt C. et al., "How Will Cultured Meat and Meat Alternatives Disrupt the Agricultural and Food Industry?" 2019, A.T. Kearney, Inc.

Ghaly et al., "Fish spoilage mechanisms and preservation techniques: Review," Am. J. Applied Sci., 7: 846-864, 2010, ISSN 1546-9239.

(56) References Cited

OTHER PUBLICATIONS

Gianakopoulos, P., et al., "MyoD Directly Up-regulates Premyogenic Mesoderm Factors during Induction of Skeletal Myogenesis in Stem Cells," The Journal of Biological Chemistry 286(4):2517-2525 (2011).

Good Food Institute, "Deep Dive: Cultivated Meat Cell Lines," Feb. 25, 2021, 13 pages, [Online] [Retrieved on Oct. 25, 2022] Retrieved from the Internet <URL: https://gfi.org/science/the-science-of-cultivated-meat/deep-dive-cultivated-meat-cell-lines/>.

Goudenege, S., et al., "Myoblasts Derived From Normal hESCs and Dystrophic hiPSCs Efficiently Fuse With Existing Muscle Fibers Following Transplantation," Molecular Therapy 20(11):2153-2167 Nov. 2012 (2012).

Hanas et al. Potentiation of myogenesis by 5-azacytidine. Journal of Cell Biology, vol. 91, No. 2, p. 27, Abstract 1051, Nov. 1981.

Harley. Telomerase is not an oncogene. Oncogene 2002, 21(4):494-502.

Hartwig et al., "Physiological quantities of naturally occurring steroid hormones (androgens and progestogens), precursors and metabolites in beef of differing sexual origin," Z Lebensm Unters Forsch 205, 5-10 (1997).

He Rong et al., "Expression and clinical significance of p15 protein, mRNA in nasopharyngeal carcinoma," Chinese Journal of Laboratory Diagnosis, vol. 13, No. 5, Jun. 19, 2009, pp. 618-622, (with English abstract).

Ho, S., "10 Reasons Why Cultivated Meat Is The Future Of Protein: The Case For Lab-Grown," May 13, 2020.

Hollenberg, S., et al., "Use of a conditional MyoD transcription factor in studies of MyoD trans-activation and muscle determination," Proc. Natl. Acad. Sci. USA vol. 90, pp. 8028-8032 1993).

Hopkins and Dacey, "Vegetarian meat: Could Technology Save Animals and Satisfy Meat Eaters?" Journal of Agricultural and Environmental Ethics 21(6):579-596 (2008).

Hu, Yang "Exercise molecule biology," Beijing Sport University press, pp. 152-157 (2013).

Huang et al. "Zfp423 Promotes Adipogenic Differentiation of Bovine Stromal Vascular Cells," PLOS One, Oct. 2012, vol. 7, Issue 10, 10 pages.

Huis, J.H.J., "Microbial and biochemical spoilage of foods: An overview," Int. J. Food Microbiology, 1996, 33: 1-18.

Hupkes et al. Epigenetics: DNA demethylation promotes skeletal myyotube maturation. The FASEB Journal, vol. 25, No. 11, pp. 3861-3872, Nov. 2011. (Year: 2011).

Hupkes, Marlinda, et al. "DNA methylation restricts spontaneous multi-lineage differentiation of mesenchymal progenitor cells, but is stable during growth factor-induced terminal differentiation" Biochimica et Biophysica Acta (BBA)—Molecular Cell Research 1813.5 (2011): 839-849.

Hwang, Y., et al., "Directed In Vitro Myogenesis of Human Embryonic Stem Cells and Their In Vivo Engraftment," PLOS One e72023 8(8):1-10 (2013).

Iacovino, M., et al., "Inducible Cassette Exchange: A Rapid and Efficient System Enabling Conditional Gene Expression in Embryonic Stem and Primary Cells," Stem Cells 2011;29:1580-1587 (2011).

Iemata, M., et al., "Suppression by Glutamate of Proliferative Activity Through Glutathione Depletion Mediated by the Cystine/Glutamate Antiporter in Mesenchymal C3H10T1/2 Stem Cells," Journal of Cellular Physiology 213:721-729 (2007).

International Preliminary Report on Patentability in corresponding PCT Application No. PCT/US2014/063250, dated May 3, 2016, Form PCT/IB/373 only.

International Search Report and Written Opinion in corresponding PCT Application No. PCT/US2014/063250, dated Jan. 21, 2015.

International Search Report and Written Opinion issued by the International Searching Authority for Application No. PCT/US17/13782, dated Apr. 10, 2017, 7 pages.

International Search Report and Written Opinion issued by The International Searching Authority for Application No. PCT/US2018/031276, dated Sep. 10, 2018, 10 pages.

International Search Report and Written Opinion issued by the International Searching Authority for Application No. PCT/US2018/042187, dated Nov. 1, 2018, 15 pages.

International Search Report and Written Opinion mailed on May 20, 2021, in International Application No. PCT/US2021/016681, 13 pages.

Jones, N., "A Taste of Things to Come?" Nature 468:752-753 (2010).

Judson, R.N. et al., "The Hippo Pathway Member Yap Plays a Key Role in Influencing Fate Decisions in Muscle Satellite Cells," Journal of Cell Science, 125, Dec. 2012, pp. 6009-6019.

Kadim, I.T. et al., "Cultured meat from muscle stem cells: A review of challenges and prospects," Journal of Integrative Agriculture 14(2), Feb. 2015, pp. 222-233.

Kanzaki et al. 2002; Telomerase rescues the expression levels of keratinocyte growth factor and insulin-like growth factor-ll in senescent human fibroblasts. Environmental Cell Research. 279: 321-329.

Kim et al., "Assessment of the Microbial Level for Livestock Products in Retail Meat Shops Implementing HACCP System," Korean J Food Sci Anim Resour. Oct. 31, 2016; 36(5): 594-600.

Kim et al., "Monitoring of Microbial Contaminants of Beef, Pork, and Chicken in HACCP Implemented Meat Processing Plants of Korea," Korean J Food Sci Anim Resour. Apr. 2018; 38(2): 282-290.

Kirschner's Korner, "Memphis Meats CEO Discuss the Future of Meat," Nov. 26, 2016, 4 pages, https://kirschnerskorner.com/2016/11/26/uma-valeti-interview/.

Knox et al., "A streamlined implementation of the glutamine synthetase-based protein expression system," BMC Biotechnol. Sep. 24, 2013;13:74, 10 pages.

Kolkmann et al., "Serum-free media for the growth of primary bovine myoblasts," Cytotechnology, Kluwer Academic Publishers, Dordrecht, NL, vol. 72, No. 1, Dec. 28, 2019, pp. 111-120.

Kuang, S. et al., "Asymmetric Self-Renewal and Commitment of Satellite Stem Cells in Muscle," Cell, 129, Jun. 1, 2007, pp. 999-1010.

Kucharczak, J. et al., "R-Cadherin Expression Inhibits Myogenesis and Induces Myoblast Transformation via Rac1 GTPase," Cancer Research, vol. 68, No. 16, Aug. 15, 2008, pp. 6559-6568.

Langelaan, et al., "Meet the New Meat: Tissue Engineered Skeletal Muscle," Trends in Food Science & Technology 21:59-66 (2010).

Lassar, A., et al., "Transfection of a DNA Locus That Mediates the Conversion of IOTV2 Fibroblasts to Myoblasts," Cell 47:649-656 (1986).

Lavial et al. Chicken embryonic stem cells as a non-mammalian embryonic stem cell model. Development, Growth & Differentiation, vol. 52, pp. 101-1114, 2010.

Lee et al. "Establishment of an immortal chicken embryo liver-derived cell line," Feb. 2013 Poultry Science, vol. 92, No. 6, 9 pages.

Lei, et al., TAZ promotes cell proliferation and epithelial-mesenchymal transition and is inhibited by the hippo pathway, Molecular and Cellular Biology, 28(7): Apr. 2008, pp. 2426-2436.

Leung, M., et al., "Nanofiber-Based in Vitro System for High Myogenic Differentiation of Human Embryonic Stem Cells," Biomacromolecules 14:4207-4216 (2013).

Li et al. Short-term serum-free culture reveals that inhibition fo Gsk3beta induces the tumor-like growth fo mouse embryonic stem cells. PLoS One, vol. 6, No. 6, e21355, Jun. 23, 2011, printed as pp. 1/10-10/10.

Li, J., "Cultured Meat: Growing Meat in the Lab," Berkeley Scientific Journal, vol. 26, Issue 1, Fall 2021, pp. 67-70.

Lian et al. Directed cardiomyocyte differentiation from human pluripotent stem cells by modulating Wnt/beta-catenin signaling under fully defined conditions. Nature Protocols, vol. 8, No. 1, pp. 162-175, 2013, published online Dec. 20, 2012.

Liu et al., "Linking Telomere Regulation to Stem Cell Pluripotency," Trends in Genetics 33(1): 16-33 (2017).

Maak et al. Identification and analysis of putative regulatory sequences for the MYF5/MYF6 locus in different vertebrate species. Gene, vol. 379, pp. 141-147, May 2006.

(56)          References Cited

OTHER PUBLICATIONS

Mah, "Lab-Grown Meats Will Change the Food Industry Forever," Synthego, May 15, 2019, 20 pages.
Mahmood, A., Enhanced Differentiation of Human Embryonic Stem Cells to Mesenchymal Progenitors by Inhibition of TGF-beta/Activin/Nodal Signaling Using SB-431542 Journal of Bone and Mineral Research 25(6):1216-1233 (2010).
Mannaerts et al. The Hippo pathway effector YAP controls mouse hepatic stellate cell activation, Journal of Hepatology, 63, Sep. 2015, 679-688.
Maturin et al., "BAM Chapter 3: Aerobic Plate Count," retrieved online Feb. 3, 2021, 11 pages, https://www.fda.gov/food/laboratory-methods-food/bam-chapter-3-aerobic-plate-count#conventional.
McFarlane et al. Myostatin signals through Pax7 to regulate satellite cell self-renewal. Experimental Cell Research, vol. 314, pp. 317-329, 2008, available online Sep. 2007.
McKinnon, T. et al., "Kras activation in p53-deficient myoblasts results in high-grade sarcoma formation with impaired myogenic differentiation," Oncotarget, vol. 6, No. 16, Jun. 10, 2015, p. 14220-14232.
Merriam-Webster, "Game" definition, Date Unknown, one page, [Online] [Retrieved on Aug. 19, 2022] Retrieved from the Internet <URL: https://www.merriam-webster.com/dictionary/game>.
Merriam-Webster, "Livestock" definition, Date Unknown, one page, [Online] [Retrieved on Aug. 19, 2022] Retrieved from the Internet <URL: https://www.merriam-webster.com/dictionary/livestock>.
Merriam-Webster. "Substantial." Merriam-Webster Dictionary, Jun. 1, 2020, 1 page, [Online] [Retrieved May 9, 2022], Retrieved from the Internet Archive <URL:https://web.archive.org/web/20200601153902/https://www.merriam-webster.com/dictionary/substantial>.
Messing, L., "Handling, Using, & Storing Poultry", 2014, Michigan State University, Extension Bulletin E3232.
Metzen, E. et al., "Pericellular P$_{O2}$ and O$_2$ consumption in monolayer cell cultures," Respiration Physiology, 100, 1995, pp. 101-106.
Microbiological Guidelines: Support for Interpretation of Microbiological . . . By Collective, Section 3.3.1.1. Listeria monocvtogenes, 2 pages (2018).
Milicevic et al., "The role of total fats, saturated/unsaturated fatty acids and cholesterol content in chicken meat as cardiovascular risk factors", 2014, Lipids in Health and Disease, 13:42.
Min et al., "Mechanism of Lipid Peroxidation in Meat and Meat Products—A Review," Food Sci. Biotechnol., vol. 14, No. 1, Jan. 2005, pp. 152-163.
Minniti, C.P. et al., "Insulin-like growth factor II overexpression in myoblasts induces phenotypic changes typical of the malignant phenotype," Cell Growth & Differentiation, vol. 6, Mar. 1995, pp. 263-269.
Minzuno, Y., et al., "Generation of Skeletal Muscle Stem/Progenitor Cells from Murine Induced Pluripotent Stem Cells," The FASEB Journal 24:2245-2243 (2010).
Miranda, A.F. et al., "Transformation of human skeletal muscle cells by simian virus 40," PNAS, vol. 80, Nov. 1983, pp. 6581-6585.
Mohamed, A. et al., "The Hippo effector TAZ (WWTR1) transforms myoblasts and TAZ abundance is associated with reduced survival in embryonal rhabdomyosarcoma," Journal of Pathology, 240, Sep. 2016, pp. 3-14.
Molkentin et al. Cooperative activation of muscle gene expression by MEF2 and myogenic bHLH proteins. Cell, vol. 83, pp. 1125-1136, Dec. 1995. (Year: 1995).
Munro, et al. Histone deacetylase inhibitors induce a senescence-like state in human cells by a p16-dependent mechanism that is independent of a mitotic clock. Exp Cell Res. 2004 295(2):525-538.
Nagashima et al., "The Hippo Pathway as Drug Targets in Cancer Therapy and Regenerative Medicine," Current Drug Targets, (2017), vol. 18, pp. 447-454.
Nguyen, H.T. et al., "Viral Small T Oncoproteins Transform Cells by Alleviating Hippo-Pathway-Mediated Inhibition of the YAP Proto-oncogene," Cell Reports, vol. 8, No. 3, Aug. 7, 2014, pp. 707-713.

Noh et al., "Reduction of ammonia and lactate through the coupling of glutamine synthetase selection and downregulation of lactate dehydrogenase-A in CHO cells," Appl Microbial Biotechnol. Feb. 2017; 101(3): 1035-1045.
Nowicka, K. et al. "Variability in Nutritional Value of Traditional Goose Meat Product." Animal Science Papers and Reports, vol. 36, No. 4, 2018, pp. 405-420.
Nowak-Imialek et al. Pluripotent cells in farm animals: state of the art and future perspectives. Reproduction, Fertility and Development, vol. 25, No. 1, pp. 103-108, 2012. (Year: 2012).
Okruszek, A. et al. "Chemical Composition and Amino Acid Profiles of Goose Muscles from native Polish Breeds." Poultry Science, vol. 92, No. 4, Apr. 1, 2013, pp. 1127-1133.
Overholtzer, M. et al., "Transforming properties of YAP, a candidate oncogene on the chromosome 11a22 amplicon," PNAS, vol. 103, No. 33, Aug. 15, 2006, pp. 12405-12410.
Ozasa et al. Efficient conversion of ES cells into myogenic lineage using the gene-inducible system. Biochemical and Biophysical Research Communications, vol. 357, pp. 957-963, Apr. 2007.
Pandurangan, et al. A novel approach for in vitro meat production. Appl Microbiol Biotechnol. Jul. 2015; 99(13):5391-5395. doi: 10.1007/s00253-015-6671-5. Epub May 14, 2015.
Paredes, C. et al., "Modification of glucose and glutamine metabolism in hybrid om a cells through metabolic engineering," Cytotechnology, vol. 30, Jul. 1999, pp. 85-93.
Park et al. Generation of porcine induced pluripotent stem cells and evaluation of their major histocompatibility complex protein expression in vitro. Veterinary Research Communications, vol. 37, No. 4, pp. 293-301, Dec. 2013, published online Aug. 23, 2013. (Year: 2013).
Poon et al., The sterile 20-like kinase Tao-1 controls tissue growth by regulating the Salvador-Warts- Hippo pathway, Developmental Cell, 21, Nov. 15, 2011, pp. 896-906.
Post, M., "Cultured beef: Medical Technology to Produce Food," Journal of the Science of Food and Agriculture 94(6):1039-1041 (2014).
Post, M., "Cultured Meat From Stem Cells: Challenges and Prospects," Meat Sci. 92(3):297-301 (2012).
Powers, D.E. et al., "Accurate Control of Oxygen Level in Cells During Culture on Silicone Rubber Membranes with Application to Stem Cell Differentiation," Biotechnology Progress, 26(3), Dec. 28, 2009, pp. 805-818.
Rao, L., et al., "Highly Efficient Derivation of Skeletal Myotubes from Human Embryonic Stem Cells," Stem Cell Rev and Rep 8:1109-1119 (2012).
Reynolds, M. "The Clean Meat Industry is Racing to Ditch its Reliance on Foetal Blood." Wired UK, Science, Mar. 20, 2010, 9 pages, [Online] [Retrieved Jul. 13, 2022], Retrieved from the Internet <URL:https://www.wired.co.uk/article/scaling-clean-meat-serum-just-finless-foods-mosa-meat>.
Rezanejad et al. Induced pluripotent stem cells: Progress and future perspectives in the stem cell world. Cellular Reprogramming, vol. 14, No. 6, pp. 459-470, Oct. 4, 2012.
Rinkevich, B. Cell cultures from marine invertebrates: New insights for capturing endless stemness. Marine Biotechnology (New York, N.Y.), vol. 13, No. 3, pp. 345-354, Jun. 2011, Epub Jan. 7, 2011. (Year: 2011).
Rohwedel, J., et al., "Muscle Cell Differentiation of Embryonic Stem Cells Reflects Myogenesis In Vivo: Developmentally Regulated Expression of Myogenic Determination Genes and Functional Expression of Ionic Currents.," Dev Biol. 164(1):87-101 (1994). (Abstract).
Rommel, C., "Mediation of IGF-1-Induced Skeletal Myotube Hypertrophy by PI(3)K/Akt/mTOR and PI(3)K/Akt/GSK3 Pathways," Nature Cell Biology 3:1009-1013 (2001).
Ryan, T., "Retinoic Acid Enhances Skeletal Myogenesis in Human Embryonic Stem Cells by Expanding the Premyogenic Progenitor Population," Stem Cell Rev and Rep 8:482-493 (2012).
Safety assurance during food processing, edited by Frans J.M. Smulders, John D. Collins, published 2004, 3 pages.
Sakurai, H., et al., "Bidirectional Induction Toward Paraxial Mesodermal Derivatives from Mouse ES Cells in Chemically Defined Medium," Stem Cell Research 3:157-169 (2009).

(56)                    References Cited

OTHER PUBLICATIONS

Sakurai, H., et al., "Paraxial Mesodermal Progenitors Derived from Mouse Embryonic Stem Cells Contribute to Muscle Regeneration via Differentiation into Muscle Satellite Cells," Stem Cells 26:1865-1873 (2008).

Salani, S., et al., "Generation of Skeletal Muscle Cells from Embryonic and Induced Pluripotent Stem Cells as an In Vitro Model and for Therapy of Muscular Dystrophies," J. Cell. Mol. Med. 16(7):1353-1364 (2012).

Sasaki, T., et al., "Generation of a Multi-Layer Muscle Fiber Sheet from Mouse ES Cells by the Spermine Action at Specific Timing and Concentration," Differentiation 76:1023-1030(2008).

Schnapp, Esther, et al. "Induced early expression of mrf4 but not myog rescues myogenesis in the myod/myf5 double-morphant zebrafish embryo" Journal of Cell Science 122.4 (2009): 481-488.

Schutte, U. et al., "Hippo Signaling Mediates Proliferation, Invasiveness, and Metastatic Potential of Clear Cell Renal Cell Carcinoma," Translational Oncology, vol. 7, Iss. 2, Apr. 2014, pp. 309-321.

Shahidi, F., "Assessment of lipid oxidation and off-flavour development in meat and meat products," In: Flavor of meat and meat products. Chapman and Hall, London, U.K, 1994, pp. 247-266. ISBN: 0-7514-0484-5.

Sharpless, et al. Forging a signature of in vivo senescence. Nature Reviews Cancer Jul. 2015, 15(7):397-408.

Simitzis, P.E. and S.G. Deligeorgis, "Lipid oxidation of meat and use of essential oils as antioxidants in meat products," 2010.

Specht L., "Is the Future of Meat Animal-Free?" Food Technology Magazine, Jan. 1, 2018, 18 pages.

Stadler, G. et al. "Establishment of Clonal Myogenic Cell Lines from Severely Affected Dystrophic Muscles—CDK4 Maintains the Myogenic Population." Skeletal Muscle, vol. 1, Article 12, Mar. 2011, pp. 1-10.

Stephens et al., Bringing cultured meat to market: Technical, socio-political, and regulatory challenges in cellular agriculture, Trends in Food Science & Technology, vol. 78, Aug. 2018, pp. 155-166.

Strakova et al., "Differences in the amino acid composition of muscles from pheasant and broiler chickens", 2006, Arch. Tierz., Dummerstorf, vol. 49, 5, pp. 508-514.

Swientek, "Meat production without animals," Jun. 27, 2017, 4 pages.

Synthetic Meat On Our Tables By 2021. Are We Ready?, Apr. 3, 2020, Flick on Food, 4 pages, https://www.flickonfood.com/en/synthetic-meat-on-our-tables-bv-2021-are-we-ready/.

Tako, E. et al. "Using the Domestic Chicken (Gallus gallus) as an In Vivo Model for Iron Bioavailability." Poultry Science, vol. 89, No. 3, Mar. 1, 2010, pp. 514-521.

Tan et al. Efficient derivation of lateral plate and paraxial mseoderm subtypes from human embryonic stem cells through GSKi-mediated differentiation. Stem Cells and Development, vol. 22, No. 13, pp. 1893-1906, Feb. 2013.

Tanaka, et al., "Efficient and Reproducible Myogenic Differentiation from Human iPS Cells: Prospects for Modeling Miyoshi Myopathy In Vitro," PLOS One e61540 8(4):1-14 (2013).

Taylor et al. Multiple new phenotypes induced in 10T1/2 and 3T3 cells treated with 5-azacytidine. Cell, vol. 17, pp. 771-779, Aug. 1979.

Telugu, B., et al., "Leukemia Inhibitory Factor (LIF)-dependent, Pluripotent Stem Cells Established from Inner Cell Mass of Porcine Embryos," Journal of Biological Chemistry, 2011, 286(33):28948-28953.

Telugu, B., et al., "Lif-Dependent, Pluripotent Stem Cells Established From Inner Cell Mass of Porcine Embryos," The American Society for Biochemistry and Molecular Biology, Inc. Jun. 24, 2011, 13 pages.

Toldra, "The role of muscle enzymes in dry-cured meat products with different drying conditions," Trends in Food Science & technology, Apr. 2006;17(4):164-168.

Tseng et al. The GSK-3 inhibitor BIO promotes proliferation in mammalian cardiomyocytes. Chemistry & Biology, vol. 13, pp. 957-963, Sep. 2006. (Year: 2006).

Tuomisto, et al., "Environmental Impacts of Cultured Meat Production," Environ. Sci. Technol. 45(14):6117-6123 (2011).

USDA, "Food Central Data," 2019, retrieved from <URL: https ://fdc.nal.usda .gov/fdc-app.html#/food-details/171077/nutrients>.

Valeti, U., "The Opposite of a Slaughter House," 5 pages, https://eatforum. org/learn-and- discover/the-opposite-of-a-slaughter-house-dr-uma-valeti/. 2017.

Van Der Schaft, D., et al., "Engineering Skeletal Muscle Tissues From Murine Myoblast Progenitor Cells and Application of Electrical Stimulation," J. Vis. Exp. 73:1-6 (2013)).

Van Der Velden, J., et al., "Inhibition of Glycogen Synthase Kinase-3beta-activity is Sufficient to Stimulate Myogenic Differentiation," Am J Physiol Cell Physiol 290: C453-C462, (2006).

Van Der Weele et al. Cultured meat: every village its own factory?, Trends in Biotechnology, Jun. 2014, vol. 32, No. 6, 3 pages.

Van Der Weele, C., "In Vitro Meat," Encyclopedia of Food and Agricultural Ethics, pp. 1-8 (2014).

Van Der Weele, C., "In Vitro Meat: Promises and Responses: Cooperation Between Science, Social Research and Ethics," Global Food Security: Ethical and Legal Challenges: EurSafe 2010 Bilbao, Spain Sep. 16-18, 2010, pp. 507-512.

Vyas, D., et al., " GSK-3 Negatively Regulates Skeletal Myotube Hypertrophy," Am J Physiol Cell Physiol 283: C545-C551 (2002).

Wagers, AJ. Wnt Not, Waste Not. Cell Stem Cell, vol. 2, pp. 6-7, 2008.

Wang et al., "Immortalization of chicken preadipocytes by retroviral transduction of chicken TERT and TR," (2017), PLoS One 12(5): e0177348. retrieved May 9, 2017 at https://doi.org/10.1371/journal. pone.0177348.

Watson, "Cell-based meat cos: Please stop calling US 'lab-grown' meat . . . and we don't use antibiotics in full-scale production," Oct. 25, 2018, 5 pages https://www.foodnavigator-usa.com/ article/2018/10/25/cell-based-meat-cosplease-stop-calling-us-lab-grown-meat-and-we-don-t-use-antibiotics-infull-scale-production.

Watson, E., "Memphis Meats: 'What's common in Silicon Valley is that you move fast and break things, but that's an awful way to approach making food'", 2018, Food Navigator USA.com, <https://www.foodnavigator-usa.com/Article/2018/05/02/Memphis-Meats-VP-Science-does-not-occur-in-a-cultural-vacuum>.

Watt et al. "Regulation of Tissue Growth by the Mammalian Hippo Signaling Pathway," Frontiers in Physiology. Nov. 24, 2017 (Nov. 24, 2017), vol. B, Article 942, pp. 1-12.

Weintraub et al. Activation of muscle-specific genes in pigment, nerve, fat, liver and fibroblast cell lines by forced expression of MyoD. Proceedings of the National Academy of Sciences, USA, vol. 86, pp. 5434-5438, Jul. 1989.

West et al. Porcine induced pluripotent stem cells produce chimeric offspring. Stem Cells and Development, vol. 19, No. 8, 2010, pp. 1211-1220, 2010. (Year: 2010).

Williams, P.G., "Nutritional composition of red meat", Sep. 2007, University of Wollongong, pp. 1-14.

Wilschut, K., et al., "Alpha 6 Integrin is Important for Myogenic Stem Cell Differentiation," Stem Cell Research 7:112-123 (2011).

Wilschut, K., et al., "Extracellular Matrix Components Direct Porcine Muscle Stem Cell Behavior," Experimental Cell Research 316:341-352 (2010).

Wilschut, K., et al., "Isolation and Characterization of Porcine Adult Muscle-Derived Progenitor Cells," Journal of Cellular Biochemistry 105:1228-1239 (2008).

Wooton et al. "Telomerase Alone Extends the Replicative Life Span of Human Skeletal Muscle Cells Without Compromising Genomic Stability," Human Gene Therapy, vol. 14, No. 15, Oct. 10, 2003, 15 pages.

Wu, G., et al., "Production and Supply of High-Quality Food Protein for Human Consumption: Sustainability, Challenges, and Innovations," Annals of the New York Academy of Sciences 1321(1):1-19 (2014).

Xu et al., "Effects of glutamine and asparagine on recombinant antibody production using CHO-GS cell lines," Biotechnol Prog. Nov.-Dec. 2014;30(6):1457-68.

(56) References Cited

OTHER PUBLICATIONS

Yokoyama et al. The myogenic transcriptional network. Cellular and Molecular Life Sciences, vol. 68, pp. 1843-1849, Feb. 2011.

Youtube, "Uma Valeti from Memphis Meats at EAT Stockholm Food Forum 2017", 2017, <URL: https://www.youtube.com/watch?v=S2m_YtqkGGk.>.

Yu et al., "Chinese Disease Signal Pathway and Targeted Therapy," Anhui Science and Technology Press, p. 372 (2013).

Zaraska, M., "Is Lab-Grown Meat Good for US?" The Atlantic, Aug. 19, 2013, 5 pages.

Zeng, Q. et al., "The Emerging Role of the Hippo Pathway in Cell Contact Inhibition, Organ Size Control, and Cancer Development in Mammals," Cancer Cell, vol. 13, Mar. 2008, pp. 188-192.

Zhao, B. et al., "Cell detachment activates the Hippo pathway via cytoskeleton reorganization to induce anoikis," Genes & Development, vol. 26, Jan. 2012, pp. 54-68.

Zheng, J., K., et al., "Skeletal Myogenesis by Human Embryonic Stem Cells," Cell Research 713-722 (2006).

Zhu, C-H. et al. "Cellular Senescence in Human Myoblasts is Overcome by Human Telomerase Reverse Transcriptase and Cyclin-Dependent Kinase 4: Consequences in Aging Muscle and Therapeutic Strategies for Muscular Dystrophies." Aging Cell, vol. 6, No. 4, Aug. 2007, pp. 515-523.

\* cited by examiner

3. Overexpress both growth factor protein and downstream targets

2. Overexpress active downstream targets

1. Overexpress growth factors in cells

Consensus (SEQ ID NO: 123)
FGF2 Chicken (SEQ ID NO: 1)
FGF2 Bovine (SEQ ID NO: 83)
FGF2 Human (SEQ ID NO: 124)

Consensus (SEQ ID NO: 125)
IGF1 Chicken (SEQ ID NO: 17)
IGF1 Bovine (SEQ ID NO: 126)
IGF1 Pig (SEQ ID NO: 127)
IGF1 Human (SEQ ID NO: 128)

PDGF Ligand:

Consensus (SEQ ID NO: 129)
PGDFb Chicken (SEQ ID NO: 18)
PDGFb Bovine (SEQ ID NO: 130)
PDGFb Human (SEQ ID NO: 131)

FIG. 2C

FC550A–empty vector
hEF1a promoter driving Gene of Interest

FC551A–empty vector
mPGK promoter driving Gene of Interest

FIG. 4

Viable cell densities after 4 passages in Suspension in Serum Free Media 0ng/mL FGF2

FIG. 11

SEQUENCE LISTING

```
Sequence total quantity: 131
SEQ ID NO: 1              moltype = AA  length = 158
FEATURE                  Location/Qualifiers
source                   1..158
                         mol_type = protein
                         organism = synthetic construct
SEQUENCE: 1
MAAGAAGSIT TLPALPDDGG GGAFPPGHFK DPKRLYCKNG GFFLRINPDG RVDGVREKSD  60
PHIKLQLQAE ERGVVSIKGV SANRFLAMKE DGRLLALKCA TEECFFFERL ESNNYNTYRS  120
RKYSDWYVAL KRTGQYKPGP KTGPGQKAIL FLPMSAKS               158

SEQ ID NO: 2              moltype = AA  length = 158
FEATURE                  Location/Qualifiers
source                   1..158
                         mol_type = protein
                         organism = synthetic construct
SEQUENCE: 2
MAAGAAGSIT TLPALPDDGG GGAFPPGHFK DPKRLYCKNG GFFLLINPDG RVDGTREKSD  60
PFIKLQLQAE ERGVVSIKGV SANRFLAMKE DGRLYALKYA TEECFFFERL EENNYNTYRS  120
RKYSDWYVAL KRTGQYKPGP KTGPGQKAIL FLPMSAKS               158

SEQ ID NO: 3              moltype = AA  length = 175
FEATURE                  Location/Qualifiers
```

```
source                          1..175
                                mol_type = protein
                                organism = synthetic construct
SEQUENCE: 3
MRAWIFFLLC LAGRALAMAA GAAGSITTLP ALPDDGGGGA FPPGHFKDPK RLYCKNGGFF  60
LRINPDGRVD GVREKSDPHI KLQLQAEERG VVSIKGVSAN RFLAMKEDGR LLALKCATEE  120
CFFFERLESN NYNTYRSRKY SDWYVALKRT GQYKPGPKTG PGQKAILFLP MSAKS       175

SEQ ID NO: 4                    moltype = AA   length = 179
FEATURE                         Location/Qualifiers
source                          1..179
                                mol_type = protein
                                organism = synthetic construct
SEQUENCE: 4
MMCKVLIFGC ISVAMLMTTA YMAAGAAGSI TTLPALPDDG GGGAFPPGHF KDPKRLYCKN  60
GGFFLRINPD GRVDGVREKS DPHIKLQLQA EERGVVSIKG VSANRFLAMK EDGRLLALKC  120
ATEECFFFER LESNNYNTYR SRKYSDWYVA LKRTGQYKPG PKTGPGQKAI LFLPMSAKS   179

SEQ ID NO: 5                    moltype = AA   length = 175
FEATURE                         Location/Qualifiers
source                          1..175
                                mol_type = protein
                                organism = synthetic construct
SEQUENCE: 5
MGVKVLFALI CIAVAEAMAA GAAGSITTLP ALPDDGGGGA FPPGHFKDPK RLYCKNGGFF  60
LRINPDGRVD GVREKSDPHI KLQLQAEERG VVSIKGVSAN RFLAMKEDGR LLALKCATEE  120
CFFFERLESN NYNTYRSRKY SDWYVALKRT GQYKPGPKTG PGQKAILFLP MSAKS       175

SEQ ID NO: 6                    moltype = AA   length = 178
FEATURE                         Location/Qualifiers
source                          1..178
                                mol_type = protein
                                organism = synthetic construct
SEQUENCE: 6
MYRMQLLSCI ALSLALVTNS MAAGAAGSIT TLPALPDDGG GGAFPPGHFK DPKRLYCKNG  60
GFFLRINPDG RVDGVREKSD PHIKLQLQAE ERGVVSIKGV SANRFLAMKE DGRLLALKCA  120
TEECFFFERL ESNNYNTYRS RKYSDWYVAL KRTGQYKPGP KTGPGQKAIL FLPMSAKS    178

SEQ ID NO: 7                    moltype = AA   length = 177
FEATURE                         Location/Qualifiers
source                          1..177
                                mol_type = protein
                                organism = synthetic construct
SEQUENCE: 7
MRMQLLLLIA LSLALVTNSM AAGAAGSITT LPALPDDGGG GAFPPGHFKD PKRLYCKNGG  60
FFLRINPDGR VDGVREKSDP HIKLQLQAEE RGVVSIKGVS ANRFLAMKED GRLLALKCAT  120
EECFFFERLE SNNYNTYRSR KYSDWYVALK RTGQYKPGPK TGPGQKAILF LPMSAKS     177

SEQ ID NO: 8                    moltype = AA   length = 178
FEATURE                         Location/Qualifiers
source                          1..178
                                mol_type = protein
                                organism = synthetic construct
SEQUENCE: 8
MRRMQLLLLI ALSLALVTNS MAAGAAGSIT TLPALPDDGG GGAFPPGHFK DPKRLYCKNG  60
GFFLRINPDG RVDGVREKSD PHIKLQLQAE ERGVVSIKGV SANRFLAMKE DGRLLALKCA  120
TEECFFFERL ESNNYNTYRS RKYSDWYVAL KRTGQYKPGP KTGPGQKAIL FLPMSAKS    178

SEQ ID NO: 9                    moltype = AA   length = 179
FEATURE                         Location/Qualifiers
source                          1..179
                                mol_type = protein
                                organism = synthetic construct
SEQUENCE: 9
MMCKVLIFGC ISVAMLMTTA YMAAGAAGSI TTLPALPDDG GGGAFPPGHF KDPKRLYCKN  60
GGFFLLINPD GRVDGTREKS DPFIKLQLQA EERGVVSIKG VSANRFLAMK EDGRLYALKY  120
ATEECFFFER LEENNYNTYR SRKYSDWYVA LKRTGQYKPG PKTGPGQKAI LFLPMSAKS   179

SEQ ID NO: 10                   moltype = AA   length = 178
FEATURE                         Location/Qualifiers
source                          1..178
                                mol_type = protein
                                organism = synthetic construct
SEQUENCE: 10
MYRMQLLSCI ALSLALVTNS MAAGAAGSIT TLPALPDDGG GGAFPPGHFK DPKRLYCKNG  60
GFFLLINPDG RVDGTREKSD PFIKLQLQAE ERGVVSIKGV SANRFLAMKE DGRLYALKYA  120
TEECFFFERL EENNYNTYRS RKYSDWYVAL KRTGQYKPGP KTGPGQKAIL FLPMSAKS    178

SEQ ID NO: 11                   moltype = AA   length = 208
```

-continued

```
FEATURE            Location/Qualifiers
source             1..208
                   mol_type = protein
                   organism = synthetic construct
SEQUENCE: 11
MNFTEGCEAT GRRPGSAGSR RRRAPRPGPV ALLPLLLPLL LPPAAAVPLP MAAGAAGSIT   60
TLPALPDDGG GGAFPPGHFK DPKRLYCKNG GFFLRINPDG RVDGVREKSD PHIKLQLQAE  120
ERGVVSIKGV SANRFLAMKE DGRLLALKCA TEECFFFERL ESNNYNTYRS RKYSDWYVAL  180
KRTGQYKPGP KTGPGQKAIL FLPMSAKS                                    208

SEQ ID NO: 12          moltype = AA  length = 187
FEATURE            Location/Qualifiers
source             1..187
                   mol_type = protein
                   organism = synthetic construct
SEQUENCE: 12
MNSFSTSAFG PVAFSLGLLL VLPAAFPAPM AAGAAGSITT LPALPDDGGG GAFPPGHFKD   60
PKRLYCKNGG FFLRINPDGR VDGVREKSDP HIKLQLQAEE RGVVSIKGVS ANRFLAMKED  120
GRLLALKCAT EECFFFERLE SNNYNTYRSR KYSDWYVALK RTGQYKPGPK TGPGQKAILF  180
LPMSAKS                                                          187

SEQ ID NO: 13          moltype = AA  length = 178
FEATURE            Location/Qualifiers
source             1..178
                   mol_type = protein
                   organism = synthetic construct
SEQUENCE: 13
MYRMQLLSCI ALSLALVTNS MAAGAAGSIT TLPALPDDGG GGAFPPGHFK DPKRLYCKNG   60
GFFLLINPDG RVDGTREKSD PFIKLQLQAE ERGVVSIKGV SANRFLAMKE DGRLYALKYA  120
TEECFFFERL EENNYNTYRS RKYSDWYVAL KRTGQYKPGP KTGPGQKAIL FLPMSAKS    178

SEQ ID NO: 14          moltype = AA  length = 185
FEATURE            Location/Qualifiers
source             1..185
                   mol_type = protein
                   organism = synthetic construct
SEQUENCE: 14
MALTFALLVA LLVLSCKSSC SVGMVSKMAA GAAGSITTLP ALPDDGGGGA FPPGHFKDPK   60
RLYCKNGGFF LRINPDGRVD GVREKSDPHI KLQLQAEERG VVSIKGVSAN RFLAMKEDGR  120
LLALKCATEE CFFFERLESN NYNTYRSRKY SDWYVALKRT GQYKPGPKTG PGQKAILFLP  180
MSAKS                                                            185

SEQ ID NO: 15          moltype = AA  length = 179
FEATURE            Location/Qualifiers
source             1..179
                   mol_type = protein
                   organism = synthetic construct
SEQUENCE: 15
MWWRLWWLLL LLLLLWPMVW AMAAGAAGSI TTLPALPDDG GGGAFPPGHF KDPKRLYCKN   60
GGFFLRINPD GRVDGVREKS DPHIKLQLQA EERGVVSIKG VSANRFLAMK EDGRLLALKC  120
ATEECFFFER LESNNYNTYR SRKYSDWYVA LKRTGQYKPG PKTGPGQKAI LFLPMSAKS   179

SEQ ID NO: 16          moltype = AA  length = 153
FEATURE            Location/Qualifiers
source             1..153
                   mol_type = protein
                   organism = synthetic construct
SEQUENCE: 16
MEKINSLSTQ LVKCCFCDFL KVKMHTVSYI HFFYLGLCLL TLTSSAAAGP ETLCGAELVD   60
ALQFVCGDRG FYFSKPTGYG SSSRRLHHKG IVDECCFQSC DLRRLEMYCA PIKPPKSARS  120
VRAQRHTDMP KAQKEVHLKN TSRGNTGNRN YRM                              153

SEQ ID NO: 17          moltype = AA  length = 71
FEATURE            Location/Qualifiers
source             1..71
                   mol_type = protein
                   organism = synthetic construct
SEQUENCE: 17
MGPETLCGAE LVDALQFVCG DRGFYFSKPT GYGSSSRRLH HKGIVDECCF QSCDLRRLEM   60
YCAPIKPPKS A                                                      71

SEQ ID NO: 18          moltype = AA  length = 251
FEATURE            Location/Qualifiers
source             1..251
                   mol_type = protein
                   organism = synthetic construct
SEQUENCE: 18
MCPQPARLEP GMNFGVVFAV ILSLPLARLE GDPIPEDIYE ILGGSSVRSI SDLQRALRID   60
SVEEDSSSLD LNATQPSQNH VSLSRERRSL DALAAAEPAV LAECKTRTVV FEISRDMVDS  120
```

-continued

```
TNANFVVWPP CVEVQRCSGC CNNRNVQCRP MQIRVRHVQV NKIEFFQRKP IFKKVIVPLE    180
DHVQCRCEVV SRPPPRSNRP ASREQRRFSP SFTTAAISQR KRVRRPPAQK RKHKKYKHVN    240
DKKVLKEILI A                                                        251

SEQ ID NO: 19            moltype = AA   length = 219
FEATURE                  Location/Qualifiers
source                   1..219
                         mol_type = protein
                         organism = synthetic construct
SEQUENCE: 19
MCPQPARLEP GMNFGVVFAV ILSLPLARLE GDPIPEDIYE ILGGSSVRSI SDLQRALRID    60
SVEEDSSSLD LNATQPSQNH VSLSRERRSL DALAAAEPAV LAECKTRTVV FEISRDMVDS    120
TNANFVVWPP CVEVQRCSGC CNNRNVQCRP MQIRVRHVQV NKIEFFQRKP IFKKVIVPLE    180
DHVQCRCEVV SRPPPRSNRP ASREQRRFSP SFTTAAISQ                          219

SEQ ID NO: 20            moltype = AA   length = 45
FEATURE                  Location/Qualifiers
source                   1..45
                         mol_type = protein
                         organism = synthetic construct
SEQUENCE: 20
MADYKDDDDK KGGIIVAILL LIVMLAIEIL LLITLIIAVT SGGSG                    45

SEQ ID NO: 21            moltype = AA   length = 37
FEATURE                  Location/Qualifiers
source                   1..37
                         mol_type = protein
                         organism = synthetic construct
SEQUENCE: 21
MAKGGIIVAI LLLIVMLAIE ILLLITLIIA VTSGGSG                            37

SEQ ID NO: 22            moltype = AA   length = 20
FEATURE                  Location/Qualifiers
source                   1..20
                         mol_type = protein
                         organism = synthetic construct
SEQUENCE: 22
MYRMQLLSCI ALSLALVTNS                                               20

SEQ ID NO: 23            moltype = AA   length = 19
FEATURE                  Location/Qualifiers
source                   1..19
                         mol_type = protein
                         organism = synthetic construct
SEQUENCE: 23
MRMQLLLLIA LSLALVTNS                                                19

SEQ ID NO: 24            moltype = AA   length = 20
FEATURE                  Location/Qualifiers
source                   1..20
                         mol_type = protein
                         organism = synthetic construct
SEQUENCE: 24
MRRMQLLLLI ALSLALVTNS                                               20

SEQ ID NO: 25            moltype = AA   length = 21
FEATURE                  Location/Qualifiers
source                   1..21
                         mol_type = protein
                         organism = synthetic construct
SEQUENCE: 25
MMCKVLIFGC ISVAMLMTTA Y                                             21

SEQ ID NO: 26            moltype = AA   length = 27
FEATURE                  Location/Qualifiers
source                   1..27
                         mol_type = protein
                         organism = synthetic construct
SEQUENCE: 26
MALTFALLVA LLVLSCKSSC SVGMVSK                                       27

SEQ ID NO: 27            moltype = AA   length = 29
FEATURE                  Location/Qualifiers
source                   1..29
                         mol_type = protein
                         organism = synthetic construct
SEQUENCE: 27
MNSFSTSAFG PVAFSLGLLL VLPAAFPAP                                     29
```

```
SEQ ID NO: 28              moltype = AA  length = 50
FEATURE                    Location/Qualifiers
source                     1..50
                           mol_type = protein
                           organism = synthetic construct
SEQUENCE: 28
MNFTEGCEAT GRRPGSAGSR RRRAPRPGPV ALLPLLLPLL LPPAAAVPLP              50

SEQ ID NO: 29              moltype = AA  length = 17
FEATURE                    Location/Qualifiers
source                     1..17
                           mol_type = protein
                           organism = synthetic construct
SEQUENCE: 29
MGVKVLFALI CIAVAEA                                                  17

SEQ ID NO: 30              moltype = AA  length = 21
FEATURE                    Location/Qualifiers
source                     1..21
                           mol_type = protein
                           organism = synthetic construct
SEQUENCE: 30
MWWRLWWLLL LLLLLWPMVW A                                             21

SEQ ID NO: 31              moltype = AA  length = 17
FEATURE                    Location/Qualifiers
source                     1..17
                           mol_type = protein
                           organism = synthetic construct
SEQUENCE: 31
MRAWIFFLLC LAGRALA                                                  17

SEQ ID NO: 32              moltype = AA  length = 819
FEATURE                    Location/Qualifiers
source                     1..819
                           mol_type = protein
                           organism = synthetic construct
SEQUENCE: 32
MFTWRCLILW AVLVTATLSA ARPAPTLPDQ ALPKANIEVE SHSAHPGDLL QLRCRLRDDV   60
QSINWVRDGV QLPENNRTRI TGEEVEVRDA VPEDSGLYAC MTNSPSGSET TYFSVNVSDA   120
LPSAEDDDDE DDSSSEEKEA DNTKPNQAVA PYWTYPEKME KKLHAVPAAK TVKFKCPSGG   180
TPNPTLRWLK NGKEFKPDHR IGGYKVRYAT WSIIMDSVVP SDKGNYTCIV ENKYGSINHT   240
YQLDVVERSP HRPILQAGLP ANKTVALGSN VEFVCKVYSD PQPHIQWLKH IEVNGSKIGP   300
DNLPYVQILK TAGVNTTDKE MEVLHLRNVS FEDAGEYTCL AGNSIGISHH SAWLTVLEAT   360
EQSPAMMTSP LYLEIIIYCT GAFLISCMVV TVIIYKMKST TKKTDFNSQL AVHKLAKSIP   420
LRRQVTVSAD SSSSMNSGVM LVRPSRLSSS GTPMLAGVSE YELPEDPRWE LPRDRLILGK   480
PLGEGCFGQV VLAEAIGLDK DKPNRVTKVA VKMLKSDATE KDLSDLISEM EMMKMIGKHK   540
NIINLLGACT QDGPLYVIVE YASKGNLREY LQARRPPGME YCYNPTRIPE EQLSFKDLVS   600
CAYQVARGME YLASKKCIHR DLAARNVLVT EDNVMKIADF GLARDIHHID YYKKTTNGRL   660
PVKWMAPEAL FDRIYTHQSD VWSFGVLLWE IFTLGGSPYP GVPVEELFKL LKEGHRMDKP   720
SNCTNELYMM MRDCWHAVPS QRPTFKQLVE DLDRIVAMTS NQEYLDLSVP LDQYSPGFPA   780
TRSSTCSSGE DSVFSHDPLP DEPCLPRCPP HSHGALKRH                          819

SEQ ID NO: 33              moltype = AA  length = 819
FEATURE                    Location/Qualifiers
source                     1..819
                           mol_type = protein
                           organism = synthetic construct
SEQUENCE: 33
MFTWRCLILW AVLVTATLSA ARPAPTLPDQ ALPKANIEVE SHSAHPGDLL QLRCRLRDDV   60
QSINWVRDGV QLPENNRTRI TGEEVEVRDA VPEDSGLYAC MTNSPSGSET TYFSVNVSDA   120
LPSAEDDDDE DDSSSEEKEA DNTKPNQAVA PYWTYPEKME KKLHAVPAAK TVKFKCPSGG   180
TPNPTLRWLK NGKEFKPDHR IGGYKVRYAT WSIIMDSVVP SDKGNYTCIV ENKYGSINHT   240
YQLDVVERSP HRPILQAGLP ANKTVALGSN VEFVCKVYSD PQPHIQWLKH IEVNGSKIGP   300
DNLPYVQILK TAGVNTTDKE MEVLHLRNVS FEDAGEYTCL AGNSIGISHH SAWLTVLEAT   360
EQSPAMMTSP LYLEIIIYCT GAFLISCMVV TVIIYKMKST TKKTDFNSQL AVHKLAKSIP   420
LRRQVTVSAD SSSSMNSGVM LVRPSRLSSS GTPMLAGVSE YELPEDPRWE LPRDRLILGK   480
PLGEGCFGQV VLAEAIGLDK DKPNRVTKVA VKMLKSDATE KDLSDLISEM EMMKMIGKHK   540
NIIKLLGACT QDGPLYVIVE YASKGNLREY LQARRPPGME YCYNPTRIPE EQLSFKDLVS   600
CAYQVARGME YLASKKCIHR DLAARNVLVT EDNVMKIADF GLARDIHHID YYKKTTNGRL   660
PVKWMAPEAL FDRIYTHQSD VWSFGVLLWE IFTLGGSPYP GVPVEELFKL LKEGHRMDKP   720
SNCTNELYMM MRDCWHAVPS QRPTFKQLVE DLDRIVAMTS NQEYLDLSVP LDQYSPGFPA   780
TRSSTCSSGE DSVFSHDPLP DEPCLPRCPP HSHGALKRH                          819

SEQ ID NO: 34              moltype = AA  length = 819
FEATURE                    Location/Qualifiers
source                     1..819
                           mol_type = protein
                           organism = synthetic construct
```

```
SEQUENCE: 34
MFTWRCLILW AVLVTATLSA ARPAPTLPDQ ALPKANIEVE SHSAHPGDLL QLRCRLRDDV   60
QSINWVRDGV QLPENNRTRI TGEEVEVRDA VPEDSGLYAC MTNSPSGSET TYFSVNVSDA  120
LPSAEDDDDE DDSSSEEKEA DNTKPNQAVA PYWTYPEKME KKLHAVPAAK TVKFKCPSGG  180
TPNPTLRWLK NGKEFKPDHR IGGYKVRYAT WSIIMDSVVP SDKGNYTCIV ENKYGSINHT  240
YQLDVVERSP HRPILQAGLP ANKTVALGSN VEFVCKVYSD PQPHIQWLKH IEVNGSKIGP  300
DNLPYVQILK TAGVNTTDKE MEVLHLRNVS FEDAGEYTCL AGNSIGISHH SAWLTVLEAT  360
EQSPAMMTSP LYLEIIIYCT GAFLISCMVV TVIIYKMKST TKKTDFNSQL AVHKLAKSIP  420
LRRQVTVSAD SSSSMNSGVM LVRPSRLSSS GTPMLAGVSE YELPEDPRWE LPRDRLILGK  480
PLGEGCFGQV VLAEAIGLDK DKPNRVTKVA VKMLKSDATE KDLSDLISEM EMMKMIGKHK  540
NIINLLGACT QDGPLYVIVE YASKGNLREY LQARRPPGME YCYNPTRIPE EQLSFKDLVS  600
CAYQVARGME YLASKKCIHR DLAARNVLVT EDNVMKIADF GLARDIHHID YYKETTNGRL  660
PVKWMAPEAL FDRIYTHQSD VWSFGVLLWE IFTLGGSPYP GVPVEELFKL LKEGHRMDKP  720
SNCTNELYMM MRDCWHAVPS QRPTFKQLVE DLDRIVAMTS NQEYLDLSVP LDQYSPGFPA  780
TRSSTCSSGE DSVFSHDPLP DEPCLPRCPP HSHGALKRH                          819

SEQ ID NO: 35              moltype = AA   length = 819
FEATURE                    Location/Qualifiers
source                     1..819
                           mol_type = protein
                           organism = synthetic construct
SEQUENCE: 35
MFTWRCLILW AVLVTATLSA ARPAPTLPDQ ALPKANIEVE SHSAHPGDLL QLRCRLRDDV   60
QSINWVRDGV QLPENNRTRI TGEEVEVRDA VPEDSGLYAC MTNSPSGSET TYFSVNVSDA  120
LPSAEDDDDE DDSSSEEKEA DNTKPNQAVA PYWTYPEKME KKLHAVPAAK TVKFKCPSGG  180
TPNPTLRWLK NGKEFKPDHR IGGYKVRYAT WSIIMDSVVP SDKGNYTCIV ENKYGSINHT  240
YQLDVVERSP HRPILQAGLP ANKTVALGSN VEFVCKVYSD PQPHIQWLKH IEVNGSKIGP  300
DNLPYVQILK TAGVNTTDKE MEVLHLRNVS FEDAGEYTCL AGNSIGISHH SAWLTVLEAT  360
EQSPAMMTSP LYLEIIIYCT GAFLISCMVV TVIIYKMKST TKKTDFNSQL AVHKLAKSIP  420
LRRQVTVSAD SSSSMNSGVM LVRPSRLSSS GTPMLAGVSE YELPEDPRWE LPRDRLILGK  480
PLGEGCFGQV VLAEAIGLDK DKPNRVTKVA VKMLKSDATE KDLSDLISEM EMMKMIGKHK  540
NIIKLLGACT QDGPLYVIVE YASKGNLREY LQARRPPGME YCYNPTRIPE EQLSFKDLVS  600
CAYQVARGME YLASKKCIHR DLAARNVLVT EDNVMKIADF GLARDIHHID YYKETTNGRL  660
PVKWMAPEAL FDRIYTHQSD VWSFGVLLWE IFTLGGSPYP GVPVEELFKL LKEGHRMDKP  720
SNCTNELYMM MRDCWHAVPS QRPTFKQLVE DLDRIVAMTS NQEYLDLSVP LDQYAPGFPA  780
TRSSTCSSGE DSVFSHDPLP DEPCLPRCPP HSHGALKRH                          819

SEQ ID NO: 36              moltype = AA   length = 438
FEATURE                    Location/Qualifiers
source                     1..438
                           mol_type = protein
                           organism = synthetic construct
SEQUENCE: 36
MGSSKSKPKD PSQRKMKSTT KKTDFNSQLA VHKLAKSIPL RRQVTVSADS SSSMNSGVML   60
VRPSRLSSSG TPMLAGVSEY ELPEDPRWEL PRDRLILGKP LGEGCFGQVV LAEAIGLDKD  120
KPNRVTKVAV KMLKSDATEK DLSDLISEME MMKMIGKHKN IINLLGACTQ DGPLYVIVEY  180
ASKGNLREYL QARRPPGMEY CYNPTRIPEE QLSFKDLVSC AYQVARGMEY LASKKCIHRD  240
LAARNVLVTE DNVMKIADFG LARDIHHIDY YKETTNGRLP VKWMAPEALF DRIYTHQSDV  300
WSFGVLLWEI FTLGGSPYPG VPVEELFKLL KEGHRMDKPS NCTNELYMMM RDCWHAVPSQ  360
RPTFKQLVED LDRIVAMTSN QEYLDLSVPL DQYSPGFPAT RSSTCSSGED SVFSHDPLPD  420
EPCLPRCPPH SHGALKRH                                                 438

SEQ ID NO: 37              moltype = AA   length = 840
FEATURE                    Location/Qualifiers
source                     1..840
                           mol_type = protein
                           organism = synthetic construct
SEQUENCE: 37
MGLKSTWRYG NGPGTYSKKM VSWDSGCLIC LVVVTMAGLS LARPSFNLVV EDATLEPEEP   60
PTKYQISQPD VHSALPGEPL ELRCQLKDAV MISWTKDGVP LGPDNRTVII GEYLQIKDAS  120
PRDSGLYACT AIRTLDSDTL YFIVNVTDAL SSGDDEDDND GSEDFVNDSN QMRAPYWTHT  180
DKMEKRLHAV PAANTVKFRC PAMGNPTPTM RWLKNGKEFK QEHRIGGYKV RNQHWSLIME  240
SVVPSDKGNY TCIVENQYGS INHTYHLDVV ERSPHRPILQ AGLPANASAV VGGDVEFVCK  300
VYSDAQPHIQ WIKHVERNGS KYGPDGLPYL QVLKAAGVNT TDKEIEVLYI RNVTFEDAGE  360
YTCLAGNSIG ISFHTAWLTV LPAPEKEKEF PTSPDYLEIA IYCIGVFLIA CMVLTVILCR  420
MKNTTKKPDF SSQPAVHKLT KRIPLRRQVS ADSSSSMNSN TPLVRITTRL SSTADAPMLA  480
GVSEYELPED PKWEFPRDKL TLGKPLGEGC FGQVVMAEAV GIDKDRPKEA VTVAVKMLKD  540
DATEKDLSDL VSEMEMMKMI GKHKNIINLL GACTQDGPLY VIVEYASKGN LREYLRARRP  600
PGMEYSFDIN RVPEEQMTFK DLVSCTYQLA RGMEYLASQK CIHRDLAARN VLVTENNVMK  660
IADFGLARDI NNIDYYKKTT NGRLPVKWMA PEALFDRVYT HQSDVWSFGV LMWEIFTLGG  720
SPYPGIPVEE LFKLLKEGHR MDKPANCTNE LYMMMRDCWQ AVPSQRPTFK QLVEDLDRIL  780
TLTTNEEYLD LSGPLEQYSP SYPDTRSSCS SGDDSVFSPD PMPYEPCLPK YQHMNGSVKT  840

SEQ ID NO: 38              moltype = AA   length = 840
FEATURE                    Location/Qualifiers
source                     1..840
                           mol_type = protein
                           organism = synthetic construct
SEQUENCE: 38
```

```
MGLKSTWRYG NGPGTYSKKM VSWDSGCLIC LVVVTMAGLS LARPSFNLVV EDATLEPEEP  60
PTKYQISQPD VHSALPGEPL ELRCQLKDAV MISWTKDGVP LGPDNRTVII GEYLQIKDAS  120
PRDSGLYACT AIRTLDSDTL YFIVNVTDAL SSGDDEDDND GSEDFVNDSN QMRAPYWTHT  180
DKMEKRLHAV PAANTVKFRC PAMGNPTPTM RWLKNGKEFK QEHRIGGYKV RNQHWSLIME  240
SVVPSDKGNY TCIVENQYGS INHTYHLDVV ERSPHRPILQ AGLPANASAV VGGDVEFVCK  300
VYSDAQPHIQ WIKHVERNGS KYGPDGLPYL QVLKAAGVNT TDKEIEVLYI RNVTFEDAGE  360
YTCLAGNSIG ISFHTAWLTV LPAPEKEKEF PTSPDYLEIA IYCIGVFLIA CMVLTVILCR  420
MKNTTKKPDF SSQPAVHKLT KRIPLRRQVS ADSSSSMNSN TPLVRITTRL SSTADAPMLA  480
GVSEYELPED PKWEFPPRDKL TLGKPLGEGC FGQVVMAEAV GIDKDRPKEA VTVAVKMLKD  540
DATEKDLSDL VSEMEMMKMI GKHKNIIKLL GACTQDGPLY VIVEYASKGN LREYLRARRP  600
PGMEYSFDIN RVPEEQMTFK DLVSCTYQLA RGMEYLASQK CIHRDLAARN VLVTENNVMK  660
IADFGLARDI NNIDYYKKTT NGRLPVKWMA PEALFDRVYT HQSDVWSFGV LMWEIFTLGG  720
SPYPGIPVEE LFKLLKEGHR MDKPANCTNE LYMMMRDCWQ AVPSQRPTFK QLVEDLDRIL  780
TLTTNEEYLD LSGPLEQYSP SYPDTRSSCS SGDDSVFSPD PMPYEPCLPK YQHMNGSVKT  840
```

SEQ ID NO: 39                    moltype = AA   length = 840
FEATURE                          Location/Qualifiers
source                           1..840
                                 mol_type = protein
                                 organism = synthetic construct
SEQUENCE: 39

```
MGLKSTWRYG NGPGTYSKKM VSWDSGCLIC LVVVTMAGLS LARPSFNLVV EDATLEPEEP  60
PTKYQISQPD VHSALPGEPL ELRCQLKDAV MISWTKDGVP LGPDNRTVII GEYLQIKDAS  120
PRDSGLYACT AIRTLDSDTL YFIVNVTDAL SSGDDEDDND GSEDFVNDSN QMRAPYWTHT  180
DKMEKRLHAV PAANTVKFRC PAMGNPTPTM RWLKNGKEFK QEHRIGGYKV RNQHWSLIME  240
SVVPSDKGNY TCIVENQYGS INHTYHLDVV ERSPHRPILQ AGLPANASAV VGGDVEFVCK  300
VYSDAQPHIQ WIKHVERNGS KYGPDGLPYL QVLKAAGVNT TDKEIEVLYI RNVTFEDAGE  360
YTCLAGNSIG ISFHTAWLTV LPAPEKEKEF PTSPDYLEIA IYCIGVFLIA CMVLTVILCR  420
MKNTTKKPDF SSQPAVHKLT KRIPLRRQVS ADSSSSMNSN TPLVRITTRL SSTADAPMLA  480
GVSEYELPED PKWEFPPRDKL TLGKPLGEGC FGQVVMAEAV GIDKDRPKEA VTVAVKMLKD  540
DATEKDLSDL VSEMEMMKMI GKHKNIINLL GACTQDGPLY VIVEYASKGN LREYLRARRP  600
PGMEYSFDIN RVPEEQMTFK DLVSCTYQLA RGMEYLASQK CIHRDLAARN VLVTENNVMK  660
IADFGLARDI NNIDYYKETT NGRLPVKWMA PEALFDRVYT HQSDVWSFGV LMWEIFTLGG  720
SPYPGIPVEE LFKLLKEGHR MDKPANCTNE LYMMMRDCWQ AVPSQRPTFK QLVEDLDRIL  780
TLTTNEEYLD LSGPLEQYSP SYPDTRSSCS SGDDSVFSPD PMPYEPCLPK YQHMNGSVKT  840
```

SEQ ID NO: 40                    moltype = AA   length = 840
FEATURE                          Location/Qualifiers
source                           1..840
                                 mol_type = protein
                                 organism = synthetic construct
SEQUENCE: 40

```
MGLKSTWRYG NGPGTYSKKM VSWDSGCLIC LVVVTMAGLS LARPSFNLVV EDATLEPEEP  60
PTKYQISQPD VHSALPGEPL ELRCQLKDAV MISWTKDGVP LGPDNRTVII GEYLQIKDAS  120
PRDSGLYACT AIRTLDSDTL YFIVNVTDAL SSGDDEDDND GSEDFVNDSN QMRAPYWTHT  180
DKMEKRLHAV PAANTVKFRC PAMGNPTPTM RWLKNGKEFK QEHRIGGYKV RNQHWSLIME  240
SVVPSDKGNY TCIVENQYGS INHTYHLDVV ERSPHRPILQ AGLPANASAV VGGDVEFVCK  300
VYSDAQPHIQ WIKHVERNGS KYGPDGLPYL QVLKAAGVNT TDKEIEVLYI RNVTFEDAGE  360
YTCLAGNSIG ISFHTAWLTV LPAPEKEKEF PTSPDYLEIA IYCIGVFLIA CMVLTVILCR  420
MKNTTKKPDF SSQPAVHKLT KRIPLRRQVS ADSSSSMNSN TPLVRITTRL SSTADAPMLA  480
GVSEYELPED PKWEFPPRDKL TLGKPLGEGC FGQVVMAEAV GIDKDRPKEA VTVAVKMLKD  540
DATEKDLSDL VSEMEMMKMI GKHKNIIKLL GACTQDGPLY VIVEYASKGN LREYLRARRP  600
PGMEYSFDIN RVPEEQMTFK DLVSCTYQLA RGMEYLASQK CIHRDLAARN VLVTENNVMK  660
IADFGLARDI NNIDYYKETT NGRLPVKWMA PEALFDRVYT HQSDVWSFGV LMWEIFTLGG  720
SPYPGIPVEE LFKLLKEGHR MDKPANCTNE LYMMMRDCWQ AVPSQRPTFK QLVEDLDRIL  780
TLTTNEEYLD LSGPLEQYAP SYPDTRSSCS SGDDSVFSPD PMPYEPCLPK YQHMNGSVKT  840
```

SEQ ID NO: 41                    moltype = AA   length = 812
FEATURE                          Location/Qualifiers
source                           1..812
                                 mol_type = protein
                                 organism = synthetic construct
SEQUENCE: 41

```
MSEAGGGAAA AASLPRSRAG GMRAAWGSVW CLCLAAAVGA LPAARRRGAE RSGGQAAEYL  60
RSETAFLEEL VFGSGDTIEL SCNTQSSSVS VFWFKDGIGI APSNRTHIGQ KLLKIINVSY  120
DDSGLYSCKP RHSNEVLGNF TVRVTGVPFW TRPDKMEKKL LAVPAANTVR FRCPAGGNPT  180
PTIYWLKNGK EFKGEHRIGG IKLRHQQWSL VMESVVPSDR GNYTCVVENK YGNIRHTYQL  240
DVLERSPHRP ILQAGLPANQ TVVVGSNVEF HCKVYSDAQP HIQWLKHVEV NGSKYGPDGT  300
PYVTVLKSWI SKNAEADANL NLFNVTEQDE GEYLCRANNF VGIAEKPFWL HIRKPKPAEE  360
LMEMDDSGSV YAGILSYGTG LVLFILVLVI VIICRMKMPN KKAMNTTTVQ KVSKFPLKRQ  420
VTVSLESNSS MNSNTPLVRI TRLSSSDGPM LANVSELELP PDPKWELARS RLTLGKPLGE  480
GCFGQVVMAE AIGIDKDKPN KAITVAVKML KDDATDKDLS DLVSEMEMMK MIGKHKNIIN  540
LLGACTQDGP LYVLVEYASK GNLREYLRAR RPPGMDYSFD TCKLPEEQLT FKDLVSCAYQ  600
VARGMEYLAS QKCIHRDLAA RNVLVTEDNV MKIADFGLAR DVHNIDYYKK TTNGRLPVKW  660
MAPEALFDRV YTHQSDVWSF GVLLWEIFTL GGSPYPGIPV EELFKLLKEG HRMDKPANCT  720
HDLYMIMREC WHAVPSQRPT FKQLVEDLDR VLTMTSTDEY LDLSVPFEQY SPAGQDTHST  780
CSSGDDSVFA HDLLPDEPCL PKHVPCNGVI RT                                812
```

SEQ ID NO: 42                    moltype = AA   length = 812

```
FEATURE            Location/Qualifiers
source             1..812
                   mol_type = protein
                   organism = synthetic construct
SEQUENCE: 42
MSEAGGGAAA AASLPRSRAG GMRAAWGSVW CLCLAAAVGA LPAARRRGAE RSGGQAAEYL   60
RSETAFLEEL VFGSGDTIEL SCNTQSSSVS VFWFKDGIGI APSNRTHIGQ KLLKIINVSY  120
DDSGLYSCKP RHSNEVLGNF TVRVTGVPFW TRPDKMEKKL LAVPAANTVR FRCPAGGNPT  180
PTIYWLKNGK EFKGEHRIGG IKLRHQQWSL VMESVVPSDR GNYTCVVENK YGNIRHTYQL  240
DVLERSPHRP ILQAGLPANQ TVVVGSNVEF HCKVYSDAQP HIQWLKHVEV NGSKYGPDGT  300
PYVTVLKSWI SKNAEADANL NLFNVTEQDE GEYLCRANNF VGIAEKPFWL HIRKPKPAEE  360
LMEMDDSGSV YAGILSYGTG LVLFILVLVI VIICRMKMPN KKAMNTTTVQ KVSKFPLKRQ  420
VTVSLESNSS MNSNTPLVRI TRLSSSDGPM LANVSELELP PDPKWELARS RLTLGKPLGE  480
GCFGQVVMAE AIGIDKDKPN KAITVAVKML KDDATDKDLS DLVSEMEMMK MIGKHKNIIK  540
LLGACTQDGP LYVLVEYASK GNLREYLRAR RPPGMDYSFD TCKLPEEQLT FKDLVSCAYQ  600
VARGMEYLAS QKCIHRDLAA RNVLVTEDNV MKIADFGLAR DVHNIDYYKK TTNGRLPVKW  660
MAPEALFDRV YTHQSDVWSF GVLLWEIFTL GGSPYPGIPV EELFKLLKEG HRMDKPANCT  720
HDLYMIMREC WHAVPSQRPT FKQLVEDLDR VLTMTSTDEY LDLSVPFEQY SPAGQDTHST  780
CSSGDDSVFA HDLLPDEPCL PKHVPCNGVI RT                               812

SEQ ID NO: 43         moltype = AA  length = 812
FEATURE            Location/Qualifiers
source             1..812
                   mol_type = protein
                   organism = synthetic construct
SEQUENCE: 43
MSEAGGGAAA AASLPRSRAG GMRAAWGSVW CLCLAAAVGA LPAARRRGAE RSGGQAAEYL   60
RSETAFLEEL VFGSGDTIEL SCNTQSSSVS VFWFKDGIGI APSNRTHIGQ KLLKIINVSY  120
DDSGLYSCKP RHSNEVLGNF TVRVTGVPFW TRPDKMEKKL LAVPAANTVR FRCPAGGNPT  180
PTIYWLKNGK EFKGEHRIGG IKLRHQQWSL VMESVVPSDR GNYTCVVENK YGNIRHTYQL  240
DVLERSPHRP ILQAGLPANQ TVVVGSNVEF HCKVYSDAQP HIQWLKHVEV NGSKYGPDGT  300
PYVTVLKSWI SKNAEADANL NLFNVTEQDE GEYLCRANNF VGIAEKPFWL HIRKPKPAEE  360
LMEMDDSGSV YAGILSYGTG LVLFILVLVI VIICRMKMPN KKAMNTTTVQ KVSKFPLKRQ  420
VTVSLESNSS MNSNTPLVRI TRLSSSDGPM LANVSELELP PDPKWELARS RLTLGKPLGE  480
GCFGQVVMAE AIGIDKDKPN KAITVAVKML KDDATDKDLS DLVSEMEMMK MIGKHKNIIN  540
LLGACTQDGP LYVLVEYASK GNLREYLRAR RPPGMDYSFD TCKLPEEQLT FKDLVSCAYQ  600
VARGMEYLAS QKCIHRDLAA RNVLVTEDNV MKIADFGLAR DVHNIDYYKE TTNGRLPVKW  660
MAPEALFDRV YTHQSDVWSF GVLLWEIFTL GGSPYPGIPV EELFKLLKEG HRMDKPANCT  720
HDLYMIMREC WHAVPSQRPT FKQLVEDLDR VLTMTSTDEY LDLSVPFEQY SPAGQDTHST  780
CSSGDDSVFA HDLLPDEPCL PKHVPCNGVI RT                               812

SEQ ID NO: 44         moltype = AA  length = 812
FEATURE            Location/Qualifiers
source             1..812
                   mol_type = protein
                   organism = synthetic construct
SEQUENCE: 44
MSEAGGGAAA AASLPRSRAG GMRAAWGSVW CLCLAAAVGA LPAARRRGAE RSGGQAAEYL   60
RSETAFLEEL VFGSGDTIEL SCNTQSSSVS VFWFKDGIGI APSNRTHIGQ KLLKIINVSY  120
DDSGLYSCKP RHSNEVLGNF TVRVTGVPFW TRPDKMEKKL LAVPAANTVR FRCPAGGNPT  180
PTIYWLKNGK EFKGEHRIGG IKLRHQQWSL VMESVVPSDR GNYTCVVENK YGNIRHTYQL  240
DVLERSPHRP ILQAGLPANQ TVVVGSNVEF HCKVYSDAQP HIQWLKHVEV NGSKYGPDGT  300
PYVTVLKSWI SKNAEADANL NLFNVTEQDE GEYLCRANNF VGIAEKPFWL HIRKPKPAEE  360
LMEMDDSGSV YAGILSYGTG LVLFILVLVI VIICRMKMPN KKAMNTTTVQ KVSKFPLKRQ  420
VTVSLESNSS MNSNTPLVRI TRLSSSDGPM LANVSELELP PDPKWELARS RLTLGKPLGE  480
GCFGQVVMAE AIGIDKDKPN KAITVAVKML KDDATDKDLS DLVSEMEMMK MIGKHKNIIK  540
LLGACTQDGP LYVLVEYASK GNLREYLRAR RPPGMDYSFD TCKLPEEQLT FKDLVSCAYQ  600
VARGMEYLAS QKCIHRDLAA RNVLVTEDNV MKIADFGLAR DVHNIDYYKE TTNGRLPVKW  660
MAPEALFDRV YTHQSDVWSF GVLLWEIFTL GGSPYPGIPV EELFKLLKEG HRMDKPANCT  720
HDLYMIMREC WHAVPSQRPT FKQLVEDLDR VLTMTSTDEY LDLSVPFEQY SPAGQDTHST  780
CSSGDDSVFA HDLLPDEPCL PKHVPCNGVI RT                               812

SEQ ID NO: 45         moltype = AA  length = 432
FEATURE            Location/Qualifiers
source             1..432
                   mol_type = protein
                   organism = synthetic construct
SEQUENCE: 45
MGSSKSKPKD PSQRRMKMPN KKAMNTTTVQ KVSKFPLKRQ VTVSLESNSS MNSNTPLVRI   60
TRLSSSDGPM LANVSELELP PDPKWELARS RLTLGKPLGE GCFGQVVMAE AIGIDKDKPN  120
KAITVAVKML KDDATDKDLS DLVSEMEMMK MIGKHKNIIN LLGACTQDGP LYVLVEYASK  180
GNLREYLRAR RPPGMDYSFD TCKLPEEQLT FKDLVSCAYQ VARGMEYLAS QKCIHRDLAA  240
RNVLVTEDNV MKIADFGLAR DVHNIDYYKE TTNGRLPVKW MAPEALFDRV YTHQSDVWSF  300
GVLLWEIFTL GGSPYPGIPV EELFKLLKEG HRMDKPANCT HDLYMIMREC WHAVPSQRPT  360
FKQLVEDLDR VLTMTSTDEY LDLSVPFEQY SPAGQDTHST CSSGDDSVFA HDLLPDEPCL  420
PKHVPCNGVI RT                                                     432

SEQ ID NO: 46         moltype = AA  length = 802
FEATURE            Location/Qualifiers
```

```
source                    1..802
                          mol_type = protein
                          organism = synthetic construct
SEQUENCE: 46
MLPLRLVLAG LLVAAGSAAS HRGEMEPELF ESPLLESEEE HLLLDPGNAL KLYCDVNQSG    60
ASVVWYKESR PLLPGPRVRL QQSVLEIAEV AYEDSGLYVC RARGTGEVLR NFTISVVDSL   120
ASGDDDEDSD GDGPHGDRSE EPVYVHRAPY WTHPHRMDKK LYAVPAGNTV KFRCPASGSP   180
SPSIRWFKNG REFRGEHRIG GIRLRHQHWS LVMESVVPSD RGNYTCLVEN RFGSIRYSYL   240
LDVLERSPHR PILQAGLPAN TTALVGSDVE FFCKVYSDAQ PHIQWLKHIE VNGSSYGPDG   300
VPYVQVLKTA DINSSEVEVL YLRNVTMEDA GEYTCLAGNS IGLSYQSAWL TVLPEELVHE   360
AEAPEAKYTD IIIYTSGSLA VAMALIIVVL CRMQTQSSKQ PLEPMAVHKL SKFPLIRQFS   420
LDSSSSGKSS TSLMRVTRLS SSCAPMLAGV VELDLPLDSK WEFPREKLVL GKPLGEGCFG   480
QVVRAEAYGI DRQWPDRAVT VAVKMLKDNA TDKDLADLIS EMEMMKLMDK HKNIINLLGV   540
CTQDGPLYVI VEFAAKGNLR EYLRARRPPM PDYTFDITEL HEEQLCFKDL VSCVYQVARG   600
MEYLESRRCI HRDLAARNVL VTAENVMKIA DFGLARDVHD IDYYKKTSNG RLPVKWMAPE   660
ALFDRVYTHQ SDVWSFGILM WEIFTLGGSP YPGIPVEELF KLLKEGHRMD CPSNCTHELY   720
MLMRECWHAV PSQRPTFKQL VEGLDKILAA ISEEYLDLSM PFEQYSPSCE DTTSTCSSDD   780
SVFTHDPLPL APCLFACPSG RT                                            802

SEQ ID NO: 47             moltype = AA   length = 802
FEATURE                   Location/Qualifiers
source                    1..802
                          mol_type = protein
                          organism = synthetic construct
SEQUENCE: 47
MLPLRLVLAG LLVAAGSAAS HRGEMEPELF ESPLLESEEE HLLLDPGNAL KLYCDVNQSG    60
ASVVWYKESR PLLPGPRVRL QQSVLEIAEV AYEDSGLYVC RARGTGEVLR NFTISVVDSL   120
ASGDDDEDSD GDGPHGDRSE EPVYVHRAPY WTHPHRMDKK LYAVPAGNTV KFRCPASGSP   180
SPSIRWFKNG REFRGEHRIG GIRLRHQHWS LVMESVVPSD RGNYTCLVEN RFGSIRYSYL   240
LDVLERSPHR PILQAGLPAN TTALVGSDVE FFCKVYSDAQ PHIQWLKHIE VNGSSYGPDG   300
VPYVQVLKTA DINSSEVEVL YLRNVTMEDA GEYTCLAGNS IGLSYQSAWL TVLPEELVHE   360
AEAPEAKCTD IIIYTSGSLA VAMALIIVVL CRMQTQSSKQ PLEPMAVHKL SKFPLIRQFS   420
LDSSSSGKSS TSLMRVTRLS SSCAPMLAGV VELDLPLDSK WEFPREKLVL GKPLGEGCFG   480
QVVRAEAYGI DRQWPDRAVT VAVKMLKDNA TDKDLADLIS EMEMMKLMDK HKNIINLLGV   540
CTQDGPLYVI VEFAAKGNLR EYLRARRPPM PDYTFDITEL HEEQLCFKDL VSCVYQVARG   600
MEYLESRRCI HRDLAARNVL VTAENVMKIA DFGLARDVHD IDYYKKTSNG RLPVKWMAPE   660
ALFDRVYTHQ SDVWSFGILM WEIFTLGGSP YPGIPVEELF KLLKEGHRMD CPSNCTHELY   720
MLMRECWHAV PSQRPTFKQL VEGLDKILAA ISEEYLDLSM PFEQYSPSCE DTTSTCSSDD   780
SVFTHDPLPL APCLFACPSG RT                                            802

SEQ ID NO: 48             moltype = AA   length = 802
FEATURE                   Location/Qualifiers
source                    1..802
                          mol_type = protein
                          organism = synthetic construct
SEQUENCE: 48
MLPLRLVLAG LLVAAGSAAS HRGEMEPELF ESPLLESEEE HLLLDPGNAL KLYCDVNQSG    60
ASVVWYKESR PLLPGPRVRL QQSVLEIAEV AYEDSGLYVC RARGTGEVLR NFTISVVDSL   120
ASGDDDEDSD GDGPHGDRSE EPVYVHRAPY WTHPHRMDKK LYAVPAGNTV KFRCPASGSP   180
SPSIRWFKNG REFRGEHRIG GIRLRHQHWS LVMESVVPSD RGNYTCLVEN RFGSIRYSYL   240
LDVLERSPHR PILQAGLPAN TTALVGSDVE FFCKVYSDAQ PHIQWLKHIE VNGSSYGPDG   300
VPYVQVLKTA DINSSEVEVL YLRNVTMEDA GEYTCLAGNS IGLSYQSAWL TVLPEELVHE   360
AEAPEAKYTD IIIYTSGSLA VAMALIIVVL CRMQTQSSKQ PLEPMAVHKL SKFPLIRQFS   420
LDSSSSGKSS TSLMRVTRLS SSCAPMLAGV VELDLPLDSK WEFPREKLVL GKPLGEGCFG   480
QVVRAEAYGI DRQWPDRAVT VAVKMLKDNA TDKDLADLIS EMEMMKLMDK HKNIINLLGV   540
CTQDGPLYVI VEFAAKGNLR EYLRARRPPM PDYTFDITEL HEEQLCFKDL VSCVYQVARG   600
MEYLESRRCI HRDLAARNVL VTAENVMKIA DFGLARDVHD IDYYKETSNG RLPVKWMAPE   660
ALFDRVYTHQ SDVWSFGILM WEIFTLGGSP YPGIPVEELF KLLKEGHRMD CPSNCTHELY   720
MLMRECWHAV PSQRPTFKQL VEGLDKILAA ISEEYLDLSM PFEQYSPSCE DTTSTCSSDD   780
SVFTHDPLPL APCLFACPSG RT                                            802

SEQ ID NO: 49             moltype = AA   length = 802
FEATURE                   Location/Qualifiers
source                    1..802
                          mol_type = protein
                          organism = synthetic construct
SEQUENCE: 49
MLPLRLVLAG LLVAAGSAAS HRGEMEPELF ESPLLESEEE HLLLDPGNAL KLYCDVNQSG    60
ASVVWYKESR PLLPGPRVRL QQSVLEIAEV AYEDSGLYVC RARGTGEVLR NFTISVVDSL   120
ASGDDDEDSD GDGPHGDRSE EPVYVHRAPY WTHPHRMDKK LYAVPAGNTV KFRCPASGSP   180
SPSIRWFKNG REFRGEHRIG GIRLRHQHWS LVMESVVPSD RGNYTCLVEN RFGSIRYSYL   240
LDVLERSPHR PILQAGLPAN TTALVGSDVE FFCKVYSDAQ PHIQWLKHIE VNGSSYGPDG   300
VPYVQVLKTA DINSSEVEVL YLRNVTMEDA GEYTCLAGNS IGLSYQSAWL TVLPEELVHE   360
AEAPEAKCTD IIIYTSGSLA VAMALIIVVL CRMQTQSSKQ PLEPMAVHKL SKFPLIRQFS   420
LDSSSSGKSS TSLMRVTRLS SSCAPMLAGV VELDLPLDSK WEFPREKLVL GKPLGEGCFG   480
QVVRAEAYGI DRQWPDRAVT VAVKMLKDNA TDKDLADLIS EMEMMKLMDK HKNIINLLGV   540
CTQDGPLYVI VEFAAKGNLR EYLRARRPPM PDYTFDITEL HEEQLCFKDL VSCVYQVARG   600
MEYLESRRCI HRDLAARNVL VTAENVMKIA DFGLARDVHD IDYYKETSNG RLPVKWMAPE   660
ALFDRVYTHQ SDVWSFGILM WEIFTLGGSP YPGIPVEELF KLLKEGHRMD CPSNCTHELY   720
```

```
MLMRECWHAV PSQRPTFKQL VEGLDKILAA ISEEYLDLSM PFEQYSPSCE DTTSTCSSDD  780
SVFTHDPLPL APCLFACPSG RT                                          802

SEQ ID NO: 50           moltype = AA  length = 1363
FEATURE                 Location/Qualifiers
source                  1..1363
                        mol_type = protein
                        organism = synthetic construct
SEQUENCE: 50
MKSGAGGGTL AVFCGLLLAF AALCLCPTNG EICGPNVDIR NDIHELKRLE NCTVVEGFLQ  60
ILLISKAEDY RNFRFPKLTV ITDYLLLFRV AGLESLSDLF PNLTVIRGRN LFYNYALVIF  120
EMTNLKEIGL HNLRNITRGA IRIEKNSDLC YLSTVDWSLI LDAVSNNYIV GNKPPKECGD  180
LCPGTMEEKP LCEKTSINNE YNYRCWTTNH CQKMCPSSCG KRACTDQNEC CHPECLGSCT  240
APDNNTACVA CRNYYYEGVC MPTCPPNTYK FEGWRCVTKE FCSKVPATET SDYERFVIHN  300
DECMAECPSG FIRNGSQSMF CSPCEGPCPK ICEDGKTKTI DSVTSAQMLQ GCTILKGNLL  360
INIRRGNNIA SELENFMGLI ETVTGYVKIR HSHALVSLSF LKNLRYILGE EQVDGNYSFY  420
VLDNHNLQQL WDWNHHNLTI KEGKMYFAFN PKLCVSEIYR MEEVSGTKGR QSKGDINPRN  480
NGERASCESH ILRFVSNTTL KNRIKLTWER YRPPDYRDLI SFTVYYKEAP FKNVTEYDGQ  540
DACGSNSWNM VDVDLPPNKE NDPGILLQGL KPWTQYAIYV KAVTLTMMEN HHIHGAKSEI  600
VYIRTNAAVP SIPLDVISAS NSSSQLIVKW NPPSLPNGNL SYYIVRWQQQ PQDSYLYRHN  660
YCSKDKVPIR RYADGTIDTE EATEPTKPEG CGGEKGPCCA CPKTEAEKQA EKEEAEYRKV  720
FENFLHNSIF VPRPDRKRRD VFRIANATLA TRNRNITGAD HFTNASDAEE SEVEYPFFET  780
KVDGKERTVI SHLQPFTLYR IDIHSCNHEA DTLGCSASNF VFARTMPSEG ADNIPGTVAW  840
EAKEENTVYL KWLEPTNPNG LILMYEIKYG QHGEEKRECV SRQEYKKLGG AKLTHLNPGN  900
YSARVQATSL AGNGSWTEPV SFYVQPKSAN YDNFLHLIIV LPIAFLLIIG GLLIMLYVFN  960
KKRNSDRLGN GVLYASVNPE YFSASDVYVP DEWEVPREKI TMCRELGQGS FGMVYEGIAK  1020
GVVKDEPETR VAIKTVNESA SMRERIEFLN EASVMKEFNC HHVVRLLGVV SQGQPTLVIM  1080
ELMTRGDLKS YLRSLRPDTE SNPGQAPPTL KKMIQMAGEI ADGMAYLNAN KFVHRDLAAR  1140
NCMVAEDFTV KIGDFGMTRD IYETDYYRKG GKGLLPVRWM SPESLKDGVF TTHSDVWSFG  1200
VVLWEIATLA EQPYQGMTNE QVLRFVMEGG LLEKPDNCPD MLFELMRMCW QYNPKMRPSF  1260
LEIISSIKDE LDPAFKEVSF FYSEENKPPD TEELDLETEN MESIPLDPSS TLQPTDKHSG  1320
HKAENGPGVV VLRASFEERQ PYAHMNGGRK NERALPLPQS SAC                    1363

SEQ ID NO: 51           moltype = AA  length = 1363
FEATURE                 Location/Qualifiers
source                  1..1363
                        mol_type = protein
                        organism = synthetic construct
SEQUENCE: 51
MKSGAGGGTL AVFCGLLLAF AALCLCPTNG EICGPNVDIR NDIHELKRLE NCTVVEGFLQ  60
ILLISKAEDY RNFRFPKLTV ITDYLLLFRV AGLESLSDLF PNLTVIRGRN LFYNYALVIF  120
EMTNLKEIGL HNLRNITRGA IRIEKNSDLC YLSTVDWSLI LDAVSNNYIV GNKPPKECGD  180
LCPGTMEEKP LCEKTSINNE YNYRCWTTNH CQKMCPSSCG KRACTDQNEC CHPECLGSCT  240
APDNNTACVA CRNYYYEGVC MPTCPPNTYK FEGWRCVTKE FCSKVPATET SDYERFVIHN  300
DECMAECPSG FIRNGSQSMF CSPCEGPCPK ICEDGKTKTI DSVTSAQMLQ GCTILKGNLL  360
INIRRGNNIA SELENFMGLI ETVTGYVKIR HSHALVSLSF LKNLRYILGE EQVDGNYSFY  420
VLDNHNLQQL WDWNHHNLTI KEGKMYFAFN PKLCVSEIYR MEEVSGTKGR QSKGDINPRN  480
NGERASCESH ILRFVSNTTL KNRIKLTWER YRPPDYRDLI SFTVYYKEAP FKNVTEYDGQ  540
DACGSNSWNM VDVDLPPNKE NDPGILLQGL KPWTQYAIYV KAVTLTMMEN HHIHGAKSEI  600
VYIRTNAAVP SIPLDVISAS NSSSQLIVKW NPPSLPNGNL SYYIVRWQQQ PQDSYLYRHN  660
YCSKDKVPIR RYADGTIDTE EATEPTKPEG CGGEKGPCCA CPKTEAEKQA EKEEAEYRKV  720
FENFLHNSIF VPRPDRKRRD VFRIANATLA TRNRNITGAD HFTNASDAEE SEVEYPFFET  780
KVDGKERTVI SHLQPFTLYR IDIHSCNHEA DTLGCSASNF VFARTMPSEG ADNIPGTVAW  840
EAKEENTVYL KWLEPTNPNG LILMYEIKYG QHGEEKRECV SRQEYKKLGG AKLTHLNPGN  900
YSARVQATSL AGNGSWTEPV SFYVQPKSAN YDNFLHLIIV LPIAFLLIIG GLLIMLYVFN  960
KKRNSDRLGN GVLYASVNPE YFSASDVYVP DEWEVPREKI TMCRELGQGS FGMVYEGIAK  1020
GVVKDEPETR VAIKTVNESA SMRERIEFLN EASVMKEFNC HHVVRLLGVV SQGQPTLVIM  1080
ELMTRGDLKS YLRSLRPDTE SNPGQAPPTL KKMIQMAGEI ADGMAYLNAN KFVHRDLAAR  1140
NCMVAEDFTV KIGDFGMTRD IYETDYYRKG GKGLLPVRWM SPESLKDGVF TTHSDVWSFG  1200
VVLWEIATLA EQPYQGMTNE QVLRFVMEGG LLEKPDNCPD MLFELMRMCW QYNPKMRPSF  1260
LEIISSIKDE LDPAFKEVSF FYSEENKPPD TEELDLETEN MESIPLDPSS TLQPTDKHSG  1320
HKAENGPGVV VLRASFEERQ PYAHMNGGRK NEHALPLPQS SAC                    1363

SEQ ID NO: 52           moltype = AA  length = 1087
FEATURE                 Location/Qualifiers
source                  1..1087
                        mol_type = protein
                        organism = synthetic construct
SEQUENCE: 52
MGTPPRTFLI LGCFLTGPLL TLCQLPLPTI VPNRNEMVVQ LNSNFTLKCS GDSEVSWQYP  60
VTEGSHRIDI RHEENNSGLF VTVLEVGNAS AAHTGMYVCY YNHTQVEDGE VEGKDIYIYV  120
PDPDMPFVPS LPEDQFILVE EGDPTVIPCR TSDPSAEVTL VNSLDKPVYA FYDSKQGFVG  180
NFLAGPYTCK TMVKGVEFKS DEFLIYILRA TSQLPVEIEA LKTVYKTGET IVVTCVVFDN  240
EVVNLQWNYP GKVKEKGLIK LDDIKVPSQK LVYTLTIPDA SVKDTGDYEC TARHATKEVK  300
ENKKVVITVH DKGFIHLEPQ FSPLEAVNLH EVKNFVVDVQ AYPAPKMYWL KDNVTLIENL  360
TEIVTSSNRV QETRFQSVLK LIRAKEEDSG YYTLVAENED EIKRYTFSLL IQVPALILDL  420
MDDHQGSAGR QTVRCLAEGT PLPDVEWLVC KDIKKCSNDT SWTLLTNNIS DIHMEAHLDE  480
RNMVESQVTF QKVEETLAVR CVARNDLGAV TRELKLVAPT LRSELTVAAA VLVLLVIVII  540
SLIVLVIIWK QKPRYEIRWR VIESISPDGH EYIYVDPMQL PYDSRWEFPR DGLVLGRILG  600
```

```
SGAFGKVVEG TAYGLSRSQP VMKVAVKMLK PTARSSEKQA LMSELKIMTH LGPHLNIVNL    660
LGACTKSGPI YIITEYCFYG DLVNYLHKNR DNFLSRHPEK PKKDLDIFGM NPADESTRSY    720
VILSFENTGE YMDMKQADTT QYVPMLERKE GSKYSDIQRS VYDRPASYKK KSLSESEVKN    780
LLSDDGSEGL SLLDLLSFTY QVARGMEFLA SKNCVHRDLA ARNVLLAQGK IVKICDFGLA    840
RDIMHDSNYV SKGSTFLPVK WMAPESIFDN LYTTLSDVWS YGILLWEIFS LGGTPYPGMM    900
VDSTFYNKIK SGYRMAKPDH ATNEVYEIMV KCWNSEPEKR PSFYHLSEIV ESLLPGEYKK    960
SYEKIHLDFL KSDHPAVTRM RGDCDNAYIG VTYKNEDKIK DRESGFDEQR LSADSGYIIP   1020
LPDIDPVSED ELGKRNRHSS QTSEESAIET GSSSSTFIKR EDETIEDIDM MDDIGIDSSD   1080
LVEDSFL                                                             1087
```

```
SEQ ID NO: 53              moltype = AA   length = 1087
FEATURE                    Location/Qualifiers
source                     1..1087
                           mol_type = protein
                           organism = synthetic construct
SEQUENCE: 53
MGTPPRTFLI LGCFLTGPLL TLCQLPLPTI VPNRNEMVVQ LNSNFTLKCS GDSEVSWQYP    60
VTEGSHRIDI RHEENNSGLF VTVLEVGNAS AAHTGMYVCY YNHTQVEDGE VEGKDIYIYV   120
PDPDMPFVPS LPEDQFILVE EGDPTVIPCR TSDPSAEVTL VNSLDKPVYA FYDSKQGFVG   180
NFLAGPYTCK TMVKGVEFKS DEFLIYILRA TSQLPVEIEA LKTVYKTGET IVVTCVVFDN   240
EVVNLQWNYP GKVKEKGLIK LDDIKVPSQK LVYTLTIPDA SVKDTGDYEC TARHATKEVK   300
ENKKVVITVH DKGFIHLEPQ FSPLEAVNLH EVKNFVVDVU AYPAPKMYWL KDNVTLIENL   360
TEIVTSSNRV QETRFQSVLK LIRAKEEDSG YYTLVAENED EIKRYTFSLL IQVPALILDL   420
MDDHQGSAGR QTVRCLAEGT PLPDVEWLVC KDIKKCSNDT SWTLLTNNIS DIHMEAHLDE   480
RNMVESQVTF QKVEETLAVR CVARNDLGAV TRELKLVAPT LRSELTVAAA VLVLLVIVII   540
SLIVLVIIWK QKPRYEIRWR VIESISPDGH EYIYVDPMQL PYDSRWEFPR DGLVLGRILG   600
SGAFGKVVEG TAYGLSRSQP VMKVAVKMLK PTARSSEKQA LMSELKIMTH LGPHLNIVNL   660
LGACTKSGPI YIITEYCFYG DLVNYLHKNR DNFLSRHPEK PKKDLDIFGM NPADESTRSY   720
VILSFENTGE YMDMKQADTT QYVPMLERKE GSKYSDIQRS VYDRPASYKK KSLSESEVKN   780
LLSDDGSEGL SLLDLLSFTY QVARGMEFLA SKNCVHRDLA ARNVLLAQGK IVKICDFGLA   840
RVIMHDSNYV SKGSTFLPVK WMAPESIFDN LYTTLSDVWS YGILLWEIFS LGGTPYPGMM   900
VDSTFYNKIK SGYRMAKPDH ATNEVYEIMV KCWNSEPEKR PSFYHLSEIV ESLLPGEYKK   960
SYEKIHLDFL KSDHPAVTRM RGDCDNAYIG VTYKNEDKIK DRESGFDEQR LSADSGYIIP  1020
LPDIDPVSED ELGKRNRHSS QTSEESAIET GSSSSTFIKR EDETIEDIDM MDDIGIDSSD  1080
LVEDSFL                                                            1087
```

```
SEQ ID NO: 54              moltype = AA   length = 1090
FEATURE                    Location/Qualifiers
source                     1..1090
                           mol_type = protein
                           organism = synthetic construct
SEQUENCE: 54
MLCPSLKASL QLLILTGLLE VTSGGSGLHI EPEDAELVLR LHSTFSLVCY GDGTLVWERD    60
GQPLTAVLEH RDGVFISNLT LRNVTGRHTG EYACFYSPDQ APERAERKAL YIYVPDPSLV   120
FLPAITSEEF FIFITGYTEA TIPCRVTNPE LQVTLYEKKV ENPIPATYDP QQGFKGFFED   180
KTYYCQAIVD DQEVDSDTFY VYRIQVSSVN VSISAVQTVV RQGENVTLMC TVSGNELVNF   240
NWDYPRKQAG KAVEPVTDFL PGSTHDIRSI LIIQNAELED SGTYVCNVSE GYHEKTDRKD   300
ITVQVIERGF VRFHTHLAST VYAEVHKSHI IQVDVEAYPQ PNIVWLKNNK TLTMESSSEF   360
TITNRNLSET RYQTSLVLVR VKQEEGGYYT IRASNEDDAQ ELSFHLQINV PAKVVDLKEN   420
SSASSGEQTV TCSAEGMPQP EISWSTCSNI KWCGSQGQPT QLLGNNSAEI GLHTNATYHA   480
ELQVYRVNST LQLHRVDEPL LLRCTVQNFL GSNSQDITLV PNALPFKVVI ISVILALLVL   540
TVISLIILII LWQKKPRYEI RWKVIESVSS DGHEYIYVDP MQLPYDSSWE VPRDKLVLGR   600
TLGSGAFGRV VEATAHGLSH SQSTMKVAVK MLKSTARSSE KQALMSELKI MSHLGPHLNI   660
VNLLGACTKG GPIYIITEYC RYGDLVDYLH RNKHTFLQSY GEKARREAEL YGNTIKEDHV   720
QSHLSLSVES DGGYMDMSKD ESLDYVPMSD MKGEVKYADI ESSNYGTPYE LDSYSPSAPE   780
RTDRVTLINE SPLLSYMDLV GFSFQVANGM EFLASKNCVH RDLAARNVLI CEGKLVKICD   840
FGLARDIMRD SNYISKGSTF LPLKWMAPES IFNNLYTTLS DVWSFGILLW EIFTLGGTPY   900
PELPMNEQFY NAIKRGYRMS KPTHASDEIY DIMQKCWEEK FEIRPSFSQL VVLMGNLLVD   960
CYRKRYQQVD EEFMKSDHPA VVRTRPTIPG LNNARLPPSS PTLYTAVHQN GGENDYIIPL  1020
PDPKPDAICD LPQEASVSRA SSMLNEANTS STISCDSPLG PRQDEEPECD LQLGCQELAP  1080
GHHEVEESFL                                                         1090
```

```
SEQ ID NO: 55              moltype = AA   length = 1090
FEATURE                    Location/Qualifiers
source                     1..1090
                           mol_type = protein
                           organism = synthetic construct
SEQUENCE: 55
MLCPSLKASL QLLILTGLLE VTSGGSGLHI EPEDAELVLR LHSTFSLVCY GDGTLVWERD    60
GQPLTAVLEH RDGVFISNLT LRNVTGRHTG EYACFYSPDQ APERAERKAL YIYVPDPSLV   120
FLPAITSEEF FIFITGYTEA TIPCRVTNPE LQVTLYEKKV ENPIPATYDP QQGFKGFFED   180
KTYYCQAIVD DQEVDSDTFY VYRIQVSSVN VSISAVQTVV RQGENVTLMC TVSGNELVNF   240
NWDYPRKQAG KAVEPVTDFL PGSTHDIRSI LIIQNAELED SGTYVCNVSE GYHEKTDRKD   300
ITVQVIERGF VRFHTHLAST VYAEVHKSHI IQVDVEAYPQ PNIVWLKNNK TLTMESSSEF   360
TITNRNLSET RYQTSLVLVR VKQEEGGYYT IRASNEDDAQ ELSFHLQINV PAKVVDLKEN   420
SSASSGEQTV TCSAEGMPQP EISWSTCSNI KWCGSQGQPT QLLGNNSAEI GLHTNATYHA   480
ELQVYRVNST LQLHRVDEPL LLRCTVQNFL GSNSQDITLV PNALPFKVVI ISVILALLVL   540
TVISLIILII LWQKKPRYEI RWKVIESVSS DGHEYIYVDP MQLPYDSSWE VPRDKLVLGR   600
TLGSGAFGRV VEATAHGLSH SQSTMKVAVK MLKSTARSSE KQALMSELKI MSHLGPHLNI   660
```

```
VNLLGACTKG GPIYIITEYC RYGDLVDYLH RNKHTFLQSY GEKARREAEL YGNTIKEDHV    720
QSHLSLSVES DGGYMDMSKD ESLDYVPMSD MKGEVKYADI ESSNYGTPYE LDSYSPSAPE    780
RTDRVTLINE SPLLSYMDLV GFSFQVANGM EFLASKNCVH RDLAARNVLI CEGKLVKICD    840
FGLARDIMRD SNYISKGSTF LPLKWMAPES IFNNLYTTLS DVWSFGILLW EIFTLGGTPY    900
PELPMNEQFY NAIKRGYRMS KPTHASDEIY DIMQKCWEEK FEIRPSFSQL VVLMGNLLVD    960
CYRKRYQQVD EEFMKSDHPA VVRTRPTIPG LNNARLPPSS PTLYTAVHQN GGENDYIIPL   1020
PDPKPDAICD LPQEASVSRA SSMLNEANTS STISCDSPLG PRQDEEPECD LQLGCQELAP   1080
GHHEVEESFL                                                          1090

SEQ ID NO: 56              moltype = AA   length = 1090
FEATURE                    Location/Qualifiers
source                     1..1090
                           mol_type = protein
                           organism = synthetic construct
SEQUENCE: 56
MLCPSLKASL QLLILTGLLE VTSGGSGLHI EPEDAELVLR LHSTFSLVCY GDGTLVWERD    60
GQPLTAVLEH RDGVFISNLT LRNVTGRHTG EYACFYSPDQ APERAERKAL YIYVPDPSLV   120
FLPAITSEEF FIFITGYTEA TIPCRVTNPE LQVTLYEKKV ENPIPATYDP QQGFKGFFED   180
KTYYCQAIVD DQEVDSDTFY VYRIQVSSVN VSISAVQTVV RQGENVTLMC TVSGNELVNF   240
NWDYPRKQAG KAVEPVTDFL PGSTHDIRSI LIIQNAELED SGTYVCNVSE GYHEKTDRKD   300
ITVQVIERGF VRFHTHLAST VYAEVHKSHI IQVDVEAYPQ PNIVWLKNNK TLTMESSSEF   360
TITNRNLSET RYQTSLVLVR VKQEEGGYYT IRASNEDDAQ ELSFHLQINV PAKVVDLKEN   420
SSASSGEQTV TCSAEGMPQP EISWSTCSNI KWCGSQGQPT QLLGNNSAEI GLHTNATYHA   480
ELQVYRVNST LQLHRVDEPL LLRCTVQNFL GSNSQDITLV PNALPFKVVI ISVILALLVL   540
TVISLIILII LWQKKPRYEI RWKVIESVSS DGHEYIYVDP MQLPYDSSWE VPRDKLVLGR   600
TLGSGAFGRV VEATAHGLSH SQSTMKVAVK MLKSTARSSE KQALMSELKI MSHLGPHLNI   660
VNLLGACTKG GPIYIITEYC RYGDLVDYLH RNKHTFLQSY GEKARREAEL YGNTIKEDHV   720
QSHLSLSVES DGGYMDMSKD ESLDYVPMSD MKGEVKYADI ESSNYGTPYE LDSYSPSAPE   780
RTDRVTLINE SPLLSYMDLV GFSFQVANGM EFLASKNCVH RDLAARNVLI CEGKLVKICD   840
FGLARDIMRN SNYISKGSTF LPLKWMAPES IFNNLYTTLS DVWSFGILLW EIFTLGGTPY   900
PELPMNEQFY NAIKRGYRMS KPTHASDEIY DIMQKCWEEK FEIRPSFSQL VVLMGNLLVD   960
CYRKRYQQVD EEFMKSDHPA VVRTRPTIPG LNNARLPPSS PTLYTAVHQN GGENDYIIPL  1020
PDPKPDAICD LPQEASVSRA SSMLNEANTS STISCDSPLG PRQDEEPECD LQLGCQELAP  1080
GHHEVEESFL                                                         1090

SEQ ID NO: 57              moltype = AA   length = 1108
FEATURE                    Location/Qualifiers
source                     1..1108
                           mol_type = protein
                           organism = synthetic construct
SEQUENCE: 57
MADYKDDDDK KGGIIVAILL LIVMLAIEIL LLITLIIAVT SGGSGLHIEP EDAELVLRLH    60
STFSLVCYGD GTLVWERDGQ PLTAVLEHRD GVFISNLTLR NVTGRHTGEY ACFYSPDQAP   120
ERAERKALYI YVPDPSLVFL PAITSEEFFI FITGYTEATI PCRVTNPELQ VTLYEKKVEN   180
PIPATYDPQQ GFKGFFEDKT YYCQAIVDDQ EVDSDTFYVY RIQVSSVNVS ISAVQTVVRQ   240
GENVTLMCTV SGNELVNFNW DYPRKQAGKA VEPVTDFLPG STHDIRSILI IQNAELEDSG   300
TYVCNVSEGY HEKTDRKDIT VQVIERGFVR FHTHLASTVY AEVHKSHIIQ VDVEAYPQPN   360
IVWLKNNKTL TMESSSEFTI TNRNLSETRY QTSLVLVRVK QEEGGYYTIR ASNEDDAQEL   420
SFHLQINVPA KVVDLKENSS ASSGEQTVTC SAEGMPQPEI SWSTCSNIKW CGSQGQPTQL   480
LGNNSAEIGL HTNATYHAEL QVYRVNSTLQ LHRVDEPLLL RCTVQNFLGS NSQDITLVPN   540
ALPFKVVIIS VILALLVLTV ISLIILIILW QKKPRYEIRW KVIESVSSDG HEYIYVDPMQ   600
LPYDSSWEVP RDKLVLGRTL GSGAFGRVVE ATAHGLSHSQ STMKVAVKML KSTARSSEKQ   660
ALMSELKIMS HLGPHLNIVN LLGACTKGGP IYIITEYCRY GDLVDYLHRN KHTFLQSYGE   720
KARREAELYG NTIKEDHVQS HLSLSVESDG GYMDMSKDES LDYVPMSDMK GEVKYADIES   780
SNYGTPYELD SYSPSAPERT DRVTLINESP LLSYMDLVGF SFQVANGMEF LASKNCVHRD   840
LAARNVLICE GKLVKICDFG LARDIMRDSN YISKGSTFLP LKWMAPESIF NNLYTTLSDV   900
WSFGILLWEI FTLGGTPYPE LPMNEQFYNA IKRGYRMSKP THASDEIYDI MQKCWEEKFE   960
IRPSFSQLVV LMGNLLVDCY RKRYQQVDEE FMKSDHPAVV RTRPTIPGLN NARLPPSSPT  1020
LYTAVHQNGG ENDYIIPLPD PKPDAICDLP QEASVSRASS MLNEANTSST ISCDSPLGPR  1080
QDEEPECDLQ LGCQELAPGH HEVEESFL                                     1108

SEQ ID NO: 58              moltype = AA   length = 1100
FEATURE                    Location/Qualifiers
source                     1..1100
                           mol_type = protein
                           organism = synthetic construct
SEQUENCE: 58
MAKGGIIVAI LLLIVMLAIE ILLLITLIIA VTSGGSGLHI EPEDAELVLR LHSTFSLVCY    60
GDGTLVWERD GQPLTAVLEH RDGVFISNLT LRNVTGRHTG EYACFYSPDQ APERAERKAL   120
YIYVPDPSLV FLPAITSEEF FIFITGYTEA TIPCRVTNPE LQVTLYEKKV ENPIPATYDP   180
QQGFKGFFED KTYYCQAIVD DQEVDSDTFY VYRIQVSSVN VSISAVQTVV RQGENVTLMC   240
TVSGNELVNF NWDYPRKQAG KAVEPVTDFL PGSTHDIRSI LIIQNAELED SGTYVCNVSE   300
GYHEKTDRKD ITVQVIERGF VRFHTHLAST VYAEVHKSHI IQVDVEAYPQ PNIVWLKNNK   360
TLTMESSSEF TITNRNLSET RYQTSLVLVR VKQEEGGYYT IRASNEDDAQ ELSFHLQINV   420
PAKVVDLKEN SSASSGEQTV TCSAEGMPQP EISWSTCSNI KWCGSQGQPT QLLGNNSAEI   480
GLHTNATYHA ELQVYRVNST LQLHRVDEPL LLRCTVQNFL GSNSQDITLV PNALPFKVVI   540
ISVILALLVL TVISLIILII LWQKKPRYEI RWKVIESVSS DGHEYIYVDP MQLPYDSSWE   600
VPRDKLVLGR TLGSGAFGRV VEATAHGLSH SQSTMKVAVK MLKSTARSSE KQALMSELKI   660
MSHLGPHLNI VNLLGACTKG GPIYIITEYC RYGDLVDYLH RNKHTFLQSY GEKARREAEL   720
```

```
YGNTIKEDHV QSHLSLSVES DGGYMDMSKD ESLDYVPMSD MKGEVKYADI ESSNYGTPYE  780
LDSYSPSAPE RTDRVTLINE SPLLSYMDLV GFSFQVANGM EFLASKNCVH RDLAARNVLI  840
CEGKLVKICD FGLARDIMRD SNYISKGSTF LPLKWMAPES IFNNLYTTLS DVWSFGILLW  900
EIFTLGGTPY PELPMNEQFY NAIKRGYRMS KPTHASDEIY DIMQKCWEEK FEIRPSFSQL  960
VVLMGNLLVD CYRKRYQQVD EEFMKSDHPA VVRTRPTIPG LNNARLPPSS PTLYTAVHQN  1020
GGENDYIIPL PDPKPDAICD LPQEASVSRA SSMLNEANTS STISCDSPLG PRQDEEPECD  1080
LQLGCQELAP GHHEVEESFL                                              1100

SEQ ID NO: 59            moltype = AA   length = 237
FEATURE                  Location/Qualifiers
source                   1..237
                         mol_type = protein
                         organism = synthetic construct
SEQUENCE: 59
MWIKNVGLLC VLILVSQMLL ASCERQKERR RGKQGIEHGG KKQAESNPER EKGRKPKGGK  60
ASPKGKFKSK ENADCSWAVT DMSAATVHIE CRNGDSAFWC EFSGDPSACP HYAANQKSYW  120
KQVSRSLKKQ KQICQDPRSI LKPKICRKGP RGAHLKLTRS SLLAAVDPAK GHPAHHAAED  180
AQGPAASETG KQPEHSPPDC VEDVDYIDQR KVAEEYCPES LLSLCNFFIT MVQDKKC     237

SEQ ID NO: 60            moltype = AA   length = 189
FEATURE                  Location/Qualifiers
source                   1..189
                         mol_type = protein
                         organism = synthetic construct
SEQUENCE: 60
MTEYKLVVVG AVGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
PARTVETRQA QDLARSYGIP YIETSAKTRQ GVEDAFYTLV REIRQHKLRK LNPPDESGPG  180
CMNCKCVIS                                                          189

SEQ ID NO: 61            moltype = DNA   length = 477
FEATURE                  Location/Qualifiers
source                   1..477
                         mol_type = other DNA
                         organism = synthetic construct
SEQUENCE: 61
atggcggcag gagcagctgg ttccataacc acattgcccg ccctcccaga cgatgggggc  60
ggaggcgcat ttcctccagg tcatttcaag accccaaaa ggctgtactg taagaatggt  120
ggttttttcc tgaggataaa ccctgacgga cgggtggacg gcgtacgcga gaaatcagat  180
ccacatatca agctgcagtt gcaagccgag gaacgcgggg tagtctctat aaaaggggtt  240
agcgctaaca gattttggc aatgaaggaa gacggtaggc tcctcgcgct taagtgtgcc  300
accgaggagt gcttcttctt cgaacggctc gaatctaaca actacaacac gtaccgctct  360
cgcaaatact ctgactggta cgtcgcactc aaacgcactg ggcagtataa accgggggcca  420
aagacgggtc cggggcagaa agctatcctg ttccttccaa tgtccgccaa gagttag     477

SEQ ID NO: 62            moltype = DNA   length = 477
FEATURE                  Location/Qualifiers
source                   1..477
                         mol_type = other DNA
                         organism = synthetic construct
SEQUENCE: 62
atggcggcag gagcagctgg ttccataacc acattgcccg ccctcccaga cgatgggggc  60
ggaggcgcat ttcctccagg tcatttcaag accccaaaa ggctgtactg taagaatggt  120
ggtttttttcc tgaggataaa ccctgacgga cgggtggacg gcgtacgcga gaaatcagat  180
ccacatatca agctgcagtt gcaagccgag gaacgcgggg tagtctctat aaaaggggtt  240
agcgctaaca gattttggc aatgaaggaa gacggtaggc tcctcgcgct taagtgtgcc  300
accgaggagt gcttcttctt cgaacggctc gaatctaaca actacaacac gtaccgctct  360
cgcaaatact ctgactggta cgtcgcactc aaacgcactg ggcagtataa accgggggcca  420
aagacgggtc cggggcagaa agctatcctg ttccttccaa tgtccgccaa gagttag     477

SEQ ID NO: 63            moltype = DNA   length = 540
FEATURE                  Location/Qualifiers
source                   1..540
                         mol_type = other DNA
                         organism = synthetic construct
SEQUENCE: 63
atgatgtgta aagttcttat cttcggatgc atctccgtag caatgctcat gactacagct  60
tacatggcgg caggagcagc tggttccata accacattgc ccgccctccc agacgatggg  120
ggcggaggcg catttcctcc aggtcatttc aaggaccca aaaggctgta ctgtaagaat  180
ggtggttttt tcctgaggat aaaccctgac ggacgggtgg acggcgtacg cgagaaatca  240
gatccacata tcaagctgca gttgcaagcc gaggaacgcg gggtagtctc tataaaaggg  300
gttagcgcta acagattttt ggcaatgaag gaagacggta ggctcctcgc gcttaagtgt  360
gccaccgagg agtgcttctt cttcgaacgg ctcgaatcta acaactacaa cacgtaccgc  420
tctcgcaaat actctgactg gtacgtcgca ctcaaacgca ctgggcagta taaaccgggg  480
ccaaagacgg gtccgggggca gaaagctatc ctgttccttc caatgtccgc caagagttag  540

SEQ ID NO: 64            moltype = DNA   length = 528
FEATURE                  Location/Qualifiers
source                   1..528
```

```
                              mol_type = other DNA
                              organism = synthetic construct
SEQUENCE: 64
atggggtca aagtgctgtt tgccttgatc tgtattgctg tggccgaggc aatggcggca   60
ggagcagctg gttccataac cacattgccc gccctcccag acgatggggg cggaggcgca  120
tttcctccag gtcatttcaa ggaccccaaa aggctgtact gtaagaatgg tggttttttc  180
ctgaggataa accctgacgg acgggtggac ggcgtacgcg agaaatcaga tccacatatc  240
aagctgcagt tgcaagccga ggaacgcggg gtagtctcta taaaaggggt tagcgctaac  300
agatttttgg caatgaagga agacggtagg ctcctcgcgc ttaagtgtgc caccgaggag  360
tgcttcttct tcgaacggct cgaatctaac aactacaaca cgtaccgctc tcgcaaatac  420
tctgactggt acgtcgcact caaacgcact gggcagtata aaccgggggcc aaagacgggt  480
ccggggcaga aagctatcct gttccttcca atgtccgcca agagttag              528

SEQ ID NO: 65             moltype = DNA   length = 537
FEATURE                   Location/Qualifiers
source                    1..537
                          mol_type = other DNA
                          organism = synthetic construct
SEQUENCE: 65
atgtatcgca tgcaactgct ttcatgcatt gctcttagcc tggcgctggt cacgaactct   60
atggcggcag gagcagctgg ttccataacc acattgcccg ccctcccaga cgatggggggc  120
ggaggcgcat ttcctccagg tcatttcaag gaccccaaaa ggctgtactg taagaatggt  180
ggttttttcc tgaggataaa ccctgacgga cgggtggacg gcgtacgcga gaaatcagat  240
ccacatatca agctgcagtt gcaagccgag gaacgcgggg tagtctctat aaaagggggtt  300
agcgctaaca gattttttggc aatgaaggaa gacggtaggc tcctcgcgct taagtgtgcc  360
accgaggagt gcttcttctt cgaacggctc gaatctaaca actacaacac gtaccgctct  420
cgcaaatact ctgactggta cgtcgcactc aaacgcactg ggcagtataa accgggggcca  480
aagacgggtc cggggcagaa agctatcctt ttccttccaa tgtccgccaa gagttag      537

SEQ ID NO: 66             moltype = DNA   length = 534
FEATURE                   Location/Qualifiers
source                    1..534
                          mol_type = other DNA
                          organism = synthetic construct
SEQUENCE: 66
atgagaatgc aactgctcct gcttatagcg ctcagtttgg ctctcgtgac caactcaatg   60
gcggcaggag cagctggttc cataaccaca ttgcccgccc tcccagacga tggggggcgga  120
ggcgcatttc ctccaggtca tttcaaggac cccaaaaggc tgtactgtaa gaatggtggt  180
tttttcctga ggataaaccc tgacggacgg gtggacggcg tacgcgagaa atcagatcca  240
catatcaagc tgcagttgca agccgaggaa cgcgggggtag tctctataaa aggggttagc  300
gctaacagat ttttggcaat gaaggaagac ggtaggctcc tcgcgcttaa gtgtgccacc  360
gaggagtgct tcttcttcga acggctcgaa tctaacaact acaacacgta ccgctctcgc  420
aaatactctg actggtacgt cgcactcaaa cgcactgggc agtataaacc ggggccaaag  480
acgggtccgg ggcagaaagc tatcctgttc cttccaatgt ccgccaagag ttag        534

SEQ ID NO: 67             moltype = DNA   length = 537
FEATURE                   Location/Qualifiers
source                    1..537
                          mol_type = other DNA
                          organism = synthetic construct
SEQUENCE: 67
atgaggcgga tgcaattgct gctgttgatc gcactctctc tggcacttgt cactaatagt   60
atggcggcag gagcagctgg ttccataacc acattgcccg ccctcccaga cgatggggggc  120
ggaggcgcat ttcctccagg tcatttcaag gaccccaaaa ggctgtactg taagaatggt  180
ggttttttcc tgaggataaa ccctgacgga cgggtggacg gcgtacgcga gaaatcagat  240
ccacatatca agctgcagtt gcaagccgag gaacgcgggg tagtctctat aaaagggggtt  300
agcgctaaca gattttttggc aatgaaggaa gacggtaggc tcctcgcgct taagtgtgcc  360
accgaggagt gcttcttctt cgaacggctc gaatctaaca actacaacac gtaccgctct  420
cgcaaatact ctgactggta cgtcgcactc aaacgcactg ggcagtataa accgggggcca  480
aagacgggtc cggggcagaa agctatcctg ttccttccaa tgtccgccaa gagttag      537

SEQ ID NO: 68             moltype = DNA   length = 627
FEATURE                   Location/Qualifiers
source                    1..627
                          mol_type = other DNA
                          organism = synthetic construct
SEQUENCE: 68
atgaatttta cagaagggtg tgaagcgact ggcaggagac caggatccgc cgggtcaagg   60
agaagaaggg cccccggcc tgggcctgtc gcgcttcttc ccctgttgct tccgctgttg  120
cttccaccgg cagctgcggt tcccttgccc atggcggcag gagcagctgg ttccataacc  180
acattgcccg ccctcccaga cgatggggggc ggaggcgcat ttcctccagg tcatttcaag  240
gaccccaaaa ggctgtactg taagaatggt ggttttttcc tgaggataaa ccctgacgga  300
cgggtggacg gcgtacgcga gaaatcagat ccacatatca agctgcagtt gcaagccgag  360
gaacgcgggg tagtctctat aaaagggggtt agcgctaaca gattttttggc aatgaaggaa  420
gacggtaggc tcctcgcgct taagtgtgcc accgaggagt gcttcttctt cgaacggctc  480
gaatctaaca actacaacac gtaccgctct cgcaaatact ctgactggta cgtcgcactc  540
aaacgcactg ggcagtataa accgggggcca aagacgggtc cggggcagaa agctatcctg  600
ttccttccaa tgtccgccaa gagttag                                     627
```

```
SEQ ID NO: 69          moltype = DNA   length = 558
FEATURE                Location/Qualifiers
source                 1..558
                       mol_type = other DNA
                       organism = synthetic construct
SEQUENCE: 69
atggcgctca cgtttgccct cttggttgcg cttctcgttc tttcctgcaa gagtagctgt   60
tccgtgggaa tggtatccaa gatggcggca ggagcagctg gttccataac cacattgccc  120
gccctcccag acgatggggg cggaggcgca tttcctccag gtcatttcaa ggaccccaaa  180
aggctgtact gtaagaatgg tggttttttc ctgaggataa acctgacgg acgggtggac  240
ggcgtacgcg agaaatcaga tccacatatc aagctgcagt tgcaagccga ggaacgcggg  300
gtagtctcta taaaaggggt tagcgctaac agattttgg caatgaagga agacggtagg  360
ctcctcgcgc ttaagtgtgc caccgaggag tgcttcttct tcgaacggct cgaatctaac  420
aactacaaca cgtaccgctc tcgcaaatac tctgactggt acgtcgcact caaacgcact  480
gggcagtata aaccggggcc aaagacgggt ccggggcaga aagctatcct gttccttcca  540
atgtccgcca agagttag                                                558

SEQ ID NO: 70          moltype = DNA   length = 540
FEATURE                Location/Qualifiers
source                 1..540
                       mol_type = other DNA
                       organism = synthetic construct
SEQUENCE: 70
atgtggtggc gcttgtggtg gttgctgttg ttgttgctgc tgttgtggcc tatggtctgg   60
gcaatggcgg caggagcagc tggttccata accacattgc ccgccctccc agacgatggg  120
ggcggaggcg catttcctcc aggtcatttc aaggacccca aaaggctgta ctgtaagaat  180
ggtggttttt tcctgaggat aaaccctgac ggacgggtgg acggcgtacg cgagaaatca  240
gatccacata tcaagctgca gttgcaagcc gaggaacgcg gggtagtctc tataaaaggg  300
gttagcgcta acagatttt ggcaatgaag gaagacggta ggctcctcgc gcttaagtgt  360
gccaccgagg agtgcttctt cttcgaacgg ctcgaatcta acaactacaa cacgtaccgc  420
tctcgcaaat actctgactg gtacgtcgca ctcaaacgca ctgggcagta taaaccgggg  480
ccaaagacgg gtccggggca gaaagctatc ctgttccttc caatgtccgc caagagttag  540

SEQ ID NO: 71          moltype = DNA   length = 564
FEATURE                Location/Qualifiers
source                 1..564
                       mol_type = other DNA
                       organism = synthetic construct
SEQUENCE: 71
atgaatagct tcagtacgtc tgcgttcgga cctgtggctt ttagcctcgg actgctgctc   60
gtgctgccgg cggcgtttcc ggcacccatg gcggcaggag cagctggttc cataaccaca  120
ttgcccgccc tcccagacga tggggcgga ggcgcatttc ctccaggtca tttcaaggac  180
cccaaaaggc tgtactgtaa gaatggtggt tttttcctga ggataaaccc tgacggacgg  240
gtggacggcg tacgcgagaa atcagatcca catatcaagc tgcagttgca agccgaggaa  300
cgcgggtag tctctataaa aggggttagc gctaacagat ttttggcaat gaaggaagac  360
ggtaggctc tcgcgcttaa gtgtgccacc gaggagtgct tcttcttcga acggctcgaa  420
tctaacaact acaacacgta ccgctctcgc aaatactctg actggtacgt cgcactcaaa  480
cgcactgggc agtataaacc ggggccaaag acgggtccgg ggcagaaagc tatcctgttc  540
cttccaatgt ccgccaagag ttag                                          564

SEQ ID NO: 72          moltype = DNA   length = 477
FEATURE                Location/Qualifiers
source                 1..477
                       mol_type = other DNA
                       organism = synthetic construct
SEQUENCE: 72
atggcggcag gagcagctgg ttccataacc acattgcccg ccctcccaga cgatggggc   60
ggaggcgcat tcctccagg tcatttcaag accccaaaa ggctgtactg taagaatggt  120
ggttttttcc tgaggataaa ccctgacgga cgggtggacg gcgtacgcga gaaatcagat  180
ccacatatca agctgcagtt gatagccgag gaacgcgggg tagtctctat aaaaggggtt  240
agcgctaaca gattttggc aatgaaggaa gacggtaggc tcctcgcgct taagtgtgcc  300
accgaggagt gcttcttctt cgaacggctc gaatctaacg ctacaacac gtaccgctct  360
cgcaaatact ctgactggta cgtcgcactc aaacgcactg gcagtataa accggggcca  420
aagacgggtc cggggcagaa agctatcctg ttccttccaa tgtccgccaa gagttag      477

SEQ ID NO: 73          moltype = DNA   length = 477
FEATURE                Location/Qualifiers
source                 1..477
                       mol_type = other DNA
                       organism = synthetic construct
SEQUENCE: 73
atggcggcag gagcagctgg ttccataacc acattgcccg ccctcccaga cgatggggc   60
ggaggcgcat tcctccagg tcatttcaag accccaaaa ggctgtactg taagaatggt  120
ggttttttcc tgaggataaa ccctgacgga cgggtggacg gcgtacgcga gaaatcagat  180
ccacatatca agctgcagtt gatagccgag gaacgcgggg tagtctctat aaaaggggtt  240
agcgctaaca gattttggc aatgaaggaa gacggtaggc tcctcgcgct taagtctgcc  300
accgaggagt gcttcttctt cgaacggctc gaatctaacg ctacaacac gtaccgctct  360
cgcaaatact ctgactggta cgtcgcactc aaacgcactg gcagtataa accggggcca  420
aagacgggtc cggggcagaa agctatcctg ttccttccaa tgtccgccaa gagttag      477
```

-continued

```
SEQ ID NO: 74            moltype = DNA  length = 531
FEATURE                  Location/Qualifiers
source                   1..531
                         mol_type = other DNA
                         organism = synthetic construct
SEQUENCE: 74
atgagaatgc aactgctcct gcttatagcg ctcagtttgg ctctcgtgac caactcagcg   60
gcaggagcag ctggttccat aaccacattg cccgccctcc cagacgatgg gggcggaggc  120
gcatttcctc caggtcattt caaggacccc aaaaggctgt actgtaagaa tggtggtttt  180
ttcctgagga taaaccctga cggacggggt gacggcgtac gcgagaaatc agatccacat  240
atcaagctgc agttgcaagc cgaggaacgc ggggtagtct ctataaaagg ggttagcgct  300
aacagatttt tggcaatgaa ggaagacggt aggctcctcg cgcttaagtg tgccaccgag  360
gagtgcttct tcttcgaacg gctcgaatct aacaactaca acacgtaccg ctctcgcaaa  420
tactctgact ggtacgtcgc actcaaacgc actgggcagt ataaaccggg gccaaagacg  480
ggtccggggc agaaagctat cctgttcctt ccaatgtccg ccaagagtta g           531

SEQ ID NO: 75            moltype = DNA  length = 477
FEATURE                  Location/Qualifiers
source                   1..477
                         mol_type = other DNA
                         organism = synthetic construct
SEQUENCE: 75
atggcggcag gagcagctgg ttccataacc acattgcccg ccctcccaga cgatgggggc   60
ggaggcgcat ttcctccagg tcatttcaag accccaaaa ggctgtactg taagaatggt  120
ggtttttccc tgaggataaa ccctgacgga cgggtggacg gcgtacgcga gaaatcagat  180
ccacatatca agctgcagtt gcaagccgag gaacgcgggg tagtctctat aaaaggggtt  240
tgcgctaaca gatatttggc aatgaaggaa gacggtaggc tcctcgcgct taagtgtgcc  300
accgaggagt gcttcttctt cgaacggctc gaatctaaca actacaacac gtaccgctct  360
cgcaaatact ctgactggta cgtcgcactc aaacgcactg gcagtataa accgggggcca  420
aagacgggtc cggggcagaa agctatcctg ttccttccaa tgtccgccaa gagttag     477

SEQ ID NO: 76            moltype = DNA  length = 477
FEATURE                  Location/Qualifiers
source                   1..477
                         mol_type = other DNA
                         organism = synthetic construct
SEQUENCE: 76
atggcggcag gagcagctgg ttccataacc acattgcccg ccctcccaga cgatgggggc   60
ggaggcgcat ttcctccagg tcatttcaag accccaaaa ggctgtactg taagaatggt  120
ggtttttcc tgctgataaa ccctgacgga cgggtggacg gcacccgcga gaaatcagat  180
ccattcatca agctgcagtt gcaagccgag gaacgcgggg tagtctctat aaaaggggtt  240
agcgctaaca gattttggc aatgaaggaa gacggtaggc tctacgcgct taagtatgcc  300
accgaggagt gcttcttctt cgaacggctc gaagagaaca actacaacac gtaccgctct  360
cgcaaatact ctgactggta cgtcgcactc aaacgcactg gcagtataa accgggggcca  420
aagacgggtc cggggcagaa agctatcctg ttccttccaa tgtccgccaa gagttag     477

SEQ ID NO: 77            moltype = DNA  length = 540
FEATURE                  Location/Qualifiers
source                   1..540
                         mol_type = other DNA
                         organism = synthetic construct
SEQUENCE: 77
atgatgtgta aagttcttat cttcggatgc atctccgtag caatgctcat gactacagct   60
tacatggcgg caggagcagc tggttccata accacattgc ccgccctccc agacgatggg  120
ggcggaggcg catttcctcc aggtcatttc aaggaccccca aaaggctgta ctgtaagaat  180
ggtggttttt tcctgctgat aaaccctgac ggacggggtgg acggcacccg cgagaaatca  240
gatccattca tcaagctgca gttgcaagcc gaggaacgcg gggtagtctc tataaaaggg  300
gttagcgcta acagattttt ggcaatgaag gaagacggta ggctctacgc gcttaagtat  360
gccaccgagg agtgcttctt cttcgaacgg ctcgaagaga acaactacaa cacgtaccgc  420
tctcgcaaat actctgactg gtacgtcgca ctcaaacgca ctgggcagta taaaccgggg  480
ccaaagacgg gtccggggca gaaagctatc ctgttccttc caatgtccgc caagagttag  540

SEQ ID NO: 78            moltype = DNA  length = 537
FEATURE                  Location/Qualifiers
source                   1..537
                         mol_type = other DNA
                         organism = synthetic construct
SEQUENCE: 78
atgtatcgca tgcaactgct ttcatgcatt gctcttagcc tggcgctggt cacgaactct   60
atggcggcag gagcagctgg ttccataacc acattgcccg ccctcccaga cgatgggggc  120
ggaggcgcat ttcctccagg tcatttcaag accccaaaa ggctgtactg taagaatggt  180
ggtttttcc tgctgataaa ccctgacgga cgggtggacg gcacccgcga gaaatcagat  240
ccattcatca agctgcagtt gcaagccgag gaacgcgggg tagtctctat aaaaggggtt  300
agcgctaaca gattttggc aatgaaggaa gacggtaggc tctacgcgct taagtatgcc  360
accgaggagt gcttcttctt cgaacggctc gaagagaaca actacaacac gtaccgctct  420
cgcaaatact ctgactggta cgtcgcactc aaacgcactg gcagtataa accgggggcca  480
aagacgggtc cggggcagaa agctatcctg ttccttccaa tgtccgccaa gagttag     537
```

-continued

```
SEQ ID NO: 79            moltype = DNA   length = 477
FEATURE                  Location/Qualifiers
source                   1..477
                         mol_type = other DNA
                         organism = synthetic construct
SEQUENCE: 79
atggcggcag gagcagctgg ttccataacc acattgcccg ccctcccaga cgatgggggc   60
ggaggcgcat ttcctccagg tcatttcaag gaccccaaaa ggctgtactg taagaatggt  120
ggttttttcc tgaggataaa ccctgacgga cgggtggacg cgtacgcga  gaaatcagat  180
ccacatatca agctgcagtt gcaagccgag gaacgcgggg tagtctctat aaaaggggtt  240
tgcgctaaca gatatttggc aatgaaggaa gacggtaggc tcctcgcgct taagtgtgcc  300
accgaggagt gcttcttctt cgaacggctc gaatctaaca actacaacac gtaccgctct  360
cgcaaatact ctgactggta cgtcgcactc aaacgcactg gcagtataa  accgggccca  420
aagacgggtc cggggcagaa agctatcctg ttccttccaa tgtccgccaa gagttag     477

SEQ ID NO: 80            moltype = DNA   length = 477
FEATURE                  Location/Qualifiers
source                   1..477
                         mol_type = other DNA
                         organism = synthetic construct
SEQUENCE: 80
atggcggcag gagcagctgg ttccataacc acattgcccg ccctcccaga cgatgggggc   60
ggaggcgcat ttcctccagg tcatttcaag gaccccaaaa ggctgtactg taagaatggt  120
ggttttttcc tgctgataaa ccctgacgga cgggtggacg gcacccgcga gaaatcagat  180
ccattcatca agctgcagtt gcaagccgag gaacgcgggg tagtctctat aaaaggggtt  240
agcgctaaca gattttttggc aatgaaggaa gacggtaggc tctacgcgct taagtgtgcc  300
accgaggagt gcttcttctt cgaacggctc gaagagaaca actacaacac gtaccgctct  360
cgcaaatact ctgactggta cgtcgcactc aaacgcactg gcagtataa  accgggccca  420
aagacgggtc cggggcagaa agctatcctg ttccttccaa tgtccgccaa gagttag     477

SEQ ID NO: 81            moltype = DNA   length = 477
FEATURE                  Location/Qualifiers
source                   1..477
                         mol_type = other DNA
                         organism = synthetic construct
SEQUENCE: 81
atggcggcag gagcagctgg ttccataacc acattgcccg ccctcccaga cgatgggggc   60
ggaggcgcat ttcctccagg tcatttcaag gaccccaaaa ggctgtactg taagaatggt  120
ggttttttcc tgctgataaa ccctgacgga cgggtggacg gcacccgcga caaatcagat  180
ccattcatca agctgcagtt gcaagccgag gaacgcgggg tagtctctat aaaaggggtt  240
agcgctaaca gattttttggc aatgaaggaa gacggtaggc tctacgcgat aaagaatgcc  300
accgaggagt gcttcttctt cgaacggctc gaagagaaca actacaacac gtaccgctct  360
cgcaaatacc ctgactggta cgtcgcactc aaacgcactg gcagtataa  accgggccca  420
aagacgggtc cggggcagaa agctatcctg ttccttccaa tgtccgccaa gagttag     477

SEQ ID NO: 82            moltype = DNA   length = 477
FEATURE                  Location/Qualifiers
source                   1..477
                         mol_type = other DNA
                         organism = synthetic construct
SEQUENCE: 82
atggcggcag gagcagctgg ttccataacc acattgcccg ccctcccaga cgatgggggc   60
ggaggcgcat ttcctccagg tcatttcaag gaccccaaaa ggctgtactg taagaatggt  120
ggttttttcc tgctgataaa ccctgacgga cgggtggacg gcacccgcga caaatcagat  180
ccattcatca agctgcagtt gcaagccgag gaacgcgggg tagtctctat aaaaggggtt  240
agcgctaaca gattttttggc aatgaaggaa gacggtaggc tctacgcgat aaagtgtgcc  300
accgaggagt gcttcttctt cgaacggctc gaagagaaca actacaacac gtaccgctct  360
cgcaaatacc ctgactggta cgtcgcactc aaacgcactg gcagtataa  accgggccca  420
aagacgggtc cggggcagaa agctatcctg ttccttccaa tgtccgccaa gagttag     477

SEQ ID NO: 83            moltype = DNA   length = 468
FEATURE                  Location/Qualifiers
source                   1..468
                         mol_type = other DNA
                         organism = synthetic construct
SEQUENCE: 83
atggccgccg ggagcatcac cacgctgcca gccctgccgg aggacggcgg cagcggcgct   60
ttcccgccgg gccacttcaa ggaccccaag cggctgtact gcaagaacgg gggcttcttc  120
ctgcgcatcc accccgacgg ccgagtggac ggggtccgcg agaagagcga cccacacatc  180
aaactacaac ttcaagcaga agagagaggg gttgtgtcta tcaaaggagt gtgtgcaaac  240
cgttaccttg ctatgaaaga agatggaaga ttactagctt ctaaatgtgt tacagacgag  300
tgtttctttt ttgaacgatt ggagtctaat aactacaata cttaccggtc aaggaaatac  360
tccagttggt atgtggcact gaaacgaact gggcagtata aacttggacc caaaacagga  420
cctgggcaga aagctatact tttcttcca  atgtctgcta agagctga             468

SEQ ID NO: 84            moltype = DNA   length = 468
FEATURE                  Location/Qualifiers
source                   1..468
                         mol_type = other DNA
```

```
                                organism = synthetic construct
SEQUENCE: 84
atggccacag gagaaatcac cactctaccc gccacacctg aagatggagg cagtggcggc    60
ttccctccag gaaactttaa ggatcccaag aggctgtact gtaaaaacgg gggctacttc   120
ttgagaataa actctaatgg aagcgttggac gggatccgag agaagaacga cccccacatc   180
aagcttcaac tccaggcgac ctcagtaggg gaggtagtga tcaaaggggt ctcagccaac   240
cgttatctgg ccatgaatgg agatggaaga ctgtttggaa cgagacggac aacagatgaa   300
tgctacttca tggagaggct ggagagtaac aactacaaca cctaccgctc acggaagtac   360
cctgacatgt atgtggcgct gaaaaggact ggccagtaca agtcaggatc caaaactgga   420
ccgggccaaa aagccattct ctttctcccc atgtcagcca gacgctga             468

SEQ ID NO: 85       moltype = DNA   length = 570
FEATURE             Location/Qualifiers
source              1..570
                    mol_type = other DNA
                    organism = synthetic construct
SEQUENCE: 85
atgaccgagt acaagctggt ggtagtggga gctgtaggtg tcgggaagag cgctttgacg    60
atacagctca ttcagaacca tttttgttgat gagtacgacc ccacaataga ggattcctac   120
agaaagcaag tcgtcatcga tggagagacc tgtttgctgg acatcctgga tacggcgggg   180
caggaggagt acagtgccat gcgagaccag tacatgagaa cggggggaagg attcctgtgc   240
gtctttgcca ttaacaacac caagtccttt gaggacatcc accagtacag ggagcagatc   300
aagagggtga aagactcaga tgatgtcccc atggtgctgg tgggaaataa atgtgatctg   360
ccagcacgga cagtggagac ccggcaagcg caggacctgg cccggagtta cgggatcccc   420
tacatagaaa cgtcggccaa aaccagacag ggcgtcgaag atgccttcta taccttagtg   480
cgggagatcc gtcagcataa actgcgcaag ctgaacccac cagatgagag tggccctggc   540
tgcatgaact gtaaatgcgt gatatcgtga                                    570

SEQ ID NO: 86       moltype = DNA   length = 2460
FEATURE             Location/Qualifiers
source              1..2460
                    mol_type = other DNA
                    organism = synthetic construct
SEQUENCE: 86
atgttcacgt ggagatgtct catcctgtgg gcggtactgg ttaccgcaac gttgagcgca    60
gctaggcccg cccccacgct gcctgaccag gctctcccta aggcgaatat agaagtagaa   120
tcacattctg cacatccagg agacttgttg caattgcggt gccgcttgag agacgatgtc   180
caatcaatca attgggtcag ggacggggtc caacttccgg agaataaccg gacaaggatt   240
actggagagg aggttgaagt cagggacgct gttcccgaag atagcggctt gtacgcttgc   300
atgactaatt ccccgtcagg gtcagaaacc acgtattttt ctgtaaacgt tagcgatgct   360
cttccgagtg ctgaagacga tgatgatgaa gacgatagca gctccgaaga gaaagaggcg   420
gataatacta aaccaaatca agctgttgca ccatattgga cctaccccga aaaaatggag   480
aaaaagttgc atgctgttcc ggcagccaaa accgtaaaat tcaagtgccc ctccggcggt   540
acccctaatc caactctgag atggttgaag aacggtaagg agttcaaacc ggatcaccgg   600
ataggtggat ataaagttcg gtatgcgacc tggtccatta ttatggactc tgtcgtgccc   660
tccgacaaag gtaactacac ttgtatcgtc gagaacaagt acggcagcat caatcatacg   720
taccaactgg acgtggtaga acgcagtcca caccgcccca ccctccagge cggactccct   780
gccaacaaaa cagttgcgct cggctctaat gttgaatttg tgtgcaaagt ttactcagac   840
cctcaacctc atatccaatg gcttaaacat atcgaagtca acggtagtaa gataggtccc   900
gacaacctgc cgtatgtcca gatccttaaa actgcggggg taaataccac tgacaaggaa   960
atggaggtct tgcatcttcg caacgtgagc tttgaagatg caggtgagta tacttgtttg  1020
gcaggtaata gcatcggaat ctcccaccat tccgcctggc tgacagtgct ggaggccacg  1080
gaacaaagtc cggccatgat gaccagtccg ttgtatctgg aaattatcat ttactgtaca  1140
ggggcctttc tcatatcatg catggtcgta accgtgatta tatataaaat gaagagcaca  1200
acgaagaaga ctgattttaa ttcacaactg gcggtacata aactcgcaaa atctatccca  1260
ttgaggcggc aggttacagt tccgccgac agctccagca gcatgaactc aggagtgatg  1320
cttgttcgcc ccagcagact gagttctagt gggactccga tgcttgctgg agtcagtgaa  1380
tacgaattgc cggaggatcc gcggtgggaa cttcctaggg accgccttat attgggcaaa  1440
cccctcggtg agggctgttt cggacaggtc gtgctcgcag aggccatcgg ccttgacaaa  1500
gataagccga atagagtgac caaggtggcg gttaaaatgc tgaaatcaga cgctacggaa  1560
aaggacctct cagacctcat cagtgaaatg gaaatgatga aaatgatagg gaagcacaaa  1620
aacatcatca atttgctcgg agcttgtacc caggacggtc ccctctacgt gatcgtagaa  1680
tacgcttcca aaggtaatct gcgcgaatat ctgcaagctc ggaggccgcc aggtatggaa  1740
tactgttata atccgacacg gattcccgag gaacagctct ctttgaggga taagccga gggcatggag tatctggcgt ccaagaagtg cattcatagg  1800
tgcgcgtatc aagtggcgag gggcatggag tatctggcgt ccaagaagtg cattcatagg  1860
gacttggctg caagaaatgt cttggtaaca gaagacaacg tcatgaagat cgccgacttc  1920
ggccttgcac gggatattca tcacatcgac tattacaaaa agacgacgaa cggccgcctc  1980
ccagttaagt ggatggcccc cgaagccctg ttcgatcgga tttacacgca tcaatccgac  2040
gtgtggtctt tcggtgtcct gctttgggag atatttacac tcggggatc acctcaccc  2100
ggagtaccgg tggaggagtt gttcaaactt cttaaagaag gtcacagaat ggacaaaccc  2160
agtaactgca ctaacgagct gtatatgatg atgcgcgatt gctggcacgc tgttccgtca  2220
caacggccca ctttttaaaca gctcgtggag gatcttgaca gaatcgtcgc gatgactagc  2280
aaccaagagt atttggattt gtcagtcccg cttgaccaat attcccccgg ttttccggct  2340
acccgctctt ctacttgttc cagcggtgag gatagtgtat tttctcatga cccacttcca  2400
gatgagccgt gcttgcctcg gtgtcctccc cactcccatg gagcgctcaa acgccactga  2460

SEQ ID NO: 87       moltype = DNA   length = 2460
FEATURE             Location/Qualifiers
source              1..2460
```

```
                        mol_type = other DNA
                        organism = synthetic construct
SEQUENCE: 87
atgttcacgt ggagatgtct catcctgtgg gcggtactgg ttaccgcaac gttgagcgca   60
gctaggcccg cccccacgct gcctgaccag gctctcccta aggcgaatat agaagtagaa  120
tcacattctg cacatccagg agacttgttg caattgcggt gccgcttgag agacgatgtc  180
caatcaatca attgggtcag ggacggggtc caacttccgg agaataaccg gacaaggatt  240
actggagagg aggttgaagt cagggacgct gttcccgaag atagcggctt gtacgcttgc  300
atgactaatt ccccgtcagg gtcagaaacc acgtattttt ctgtaaacgt tagcgatgct  360
cttccgagtg ctgaagacga tgatgatgaa gacgatagca gctccgaaga gaaagaggcg  420
gataatacta aaccaaatca agctgttgca ccatattgga cctaccccga aaaaatggag  480
aaaaagttgc atgctgttcc ggcagccaaa accgtaaaat tcaagtgccc ctccggcggt  540
acccctaatc caactctgag atggttgaag aacggtaagg agttcaaacc ggatcaccgg  600
ataggtggat ataaagttcg gtatgcgacc tggtccatta ttatggactc tgtcgtgccc  660
tccgacaaag gtaactacac ttgtatcgtc gagaacaagt acggcagcat caatcatacg  720
taccaactgg acgtggtaga acgcagtcca caccgcccca tcctccaggc cggactccct  780
gccaacaaaa cagttgcgct cggctctaat gttgaatttg tgtgcaaagt ttactcagac  840
cctcaacctc atatccaatg gcttaaacat atcgaagtca acggtagtaa gataggtccc  900
gacaacctgc cgtatgtcca gatccttaaa actgcggggg taaataccac tgacaaggaa  960
atggaggtct tgcatcttcg caacgtgagc tttgaagatg caggtgagta tacttgtttg 1020
gcaggtaata gcatcggaat ctcccaccat tccgcctggc tgacagtgct ggaggccacg 1080
gaacaaagtc cggccatgat gaccagtccg ttgtatctgg aaattatcat ttactgtaca 1140
ggggcctttc tcatatcatg catggtcgta accgtgatta tatataaaat gaagagcaca 1200
acgaagaaga ctgattttaa ttcacaactg gcggtacata aactcgcaaa atctatccca 1260
ttgaggcggc aggttacagt ctccgccgac agctccagca gcatgaactc aggagtgatg 1320
cttgttcgcc ccagcagact gagttctagt gggactccga tgcttgctgg agtcagtgaa 1380
tacgaattgc cggaggatcc gcggtgggaa cttcctaggg accgcccttat attgggcaaa 1440
cccctcggtg agggctgttt cggacaggtc gtgctcgcag aggccatcgg ccttgacaaa 1500
gataagccga atagagtgac caaggtggcg gttaaaatgc tgaaatcaga cgctacggaa 1560
aaggacctct cagacctcat cagtgaaatg gaaatgatga aatgataggg gaagcacaaa 1620
aacatcatca gttgctcgg agcttgtacc caggacggtc ccctctacgt gatcgtagaa 1680
tacgcttcca aaggtaatct gcgcgaatat ctgcaagctc ggaggccgcc aggtatggaa 1740
tactgttata atccgacacg gattcccgag gaacagctct cttttaaaga tttggtttca 1800
tgcgcgtatc aagtggcgag gggcatggag tatctgcgt ccaagaagtg cattcatagg 1860
gacttggctg caagaaatgt cttggtaaca gaagacaacg tcatgagaat cgccgacttc 1920
ggccttgcac gggatattca tcacatcgac tattacaaaa agacgacgaa cggccgcctc 1980
ccagttaagt ggatggcccc cgaagccctg ttcgatcgga tttacacgca tcaatccgac 2040
gtgtggtctt tcggtgtcct gctttgggag atatttacac tcgggggatc accctacccc 2100
ggagtaccgg tggaggagtt gttcaaactt cttaaagaag gtcacagaat ggacaaaccc 2160
agtaactgca ctaacgagct gtatatgatg atgcgcgatt gctggcacgc tgttccgtca 2220
caacggccca ctttttaaaca gctcgtggag gatcttgaca gaatcgtcgc gatgactagc 2280
aaccaagagt atttggattt gtcagtcccg cttgaccaat attcccccgg ttttccggct 2340
acccgctctt ctacttgttc cagcggtgag gatagtgtat tttctcatga cccacttcca 2400
gatgagccgt gcttgcctcg gtgtcctccc cactcccatg gagcgctcaa acgccactga 2460

SEQ ID NO: 88          moltype = DNA  length = 2469
FEATURE                Location/Qualifiers
source                 1..2469
                       mol_type = other DNA
                       organism = synthetic construct
SEQUENCE: 88
gccgccacca tgttcacgtg gagatgtctc atcctgtggg cggtactggt taccgcaacg   60
ttgagcgcag ctaggcccgc ccccacgctg cctgaccagg ctctccctaa ggcgaatata  120
gaagtagaat cacattctgc acatccagga gacttgttgc aattgcggtg ccgcttgaga  180
gacgatgtcc aatcaatcaa ttgggtcagg gacggggtcc aacttccgga gaataaccg  240
acaaggatta ctggagagga ggttgaagtc agggacgctg ttcccgaaga tagcggcttg  300
tacgcttgca tgactaattc cccgtcaggg tcagaaacca cgtatttttc tgtaaacgtt  360
agcgatgctc ttccgagtgc tgaagacgat gatgatgaag acgatagcag ctccgaagag  420
aaagaggcgg ataatactaa accaaatcaa gctgttgcac catattggac ctaccccga  480
aaaatggaga aaaagttgca tgctgttccg gcagccaaaa ccgtaaaatt caagtgcccc  540
tccggcggta cccctaatcc aactctgaga tggttgaaga acggtaagga gttcaaaccg  600
gatcaccgga taggtggata taaagttcgg tatgcgacct ggtccattat tatggactct  660
gtcgtgccct ccgacaaagg taactacact tgtatcgtcg agaacaagta cggcagcatc  720
aatcatacgt accaactgga cgtggtagaa cgcagtccac accgcccat cctccaggcc  780
ggactccctg ccaacaaaac agttgcgctc ggctctaatg ttgaatttgt gtgcaaagtt  840
tactcagacc ctcaacctca tatccaatgg cttaaacata tcgaagtcaa cggtagtaag  900
ataggtcccg acaacctgcc gtatgtccag atccttaaa ctgcgggggt aaataccact  960
gacaaggaaa tggaggtctt gcatcttcgc aacgtgagct ttgaagatgc aggtgagtat 1020
acttgtttgg caggtaatag catcggaatc tcccaccatt ccgcctggct gacagtgct 1080
gaggccacgg aacaaagtcc ggccatgatg accagtccgt tgtatctgga aattatcatt 1140
tactgtacag gggcctttct catatcatgc atggtcgtaa ccgtgattat atataaaatg 1200
aagagcacaa cgaagaagac tgattttaat tcacaactgg cggtacataa actcgcaaaa 1260
tctatcccat tgaggcggca ggttacagtc tccgccgaca gctccagcag catgaactca 1320
ggagtgatgc ttgttcgccc cagcagactg agttctagtg ggactccgat gcttgctgga 1380
gtcagtgaat acgaattgcc ggaggatccg cggtgggaac ttcctaggga ccgccttata 1440
ttgggcaaac ccctcggtga gggctgtttc ggacaggtcg tgctcgcaga ggccatcggc 1500
cttgacaaag ataagccgaa tagagtgacc aaggtggcgg ttaaaatgct gaaatcagac 1560
gctacggaaa aggacctctc agacctcatc agtgaaatgg aaatgatgaa aatgataggg 1620
aagcacaaaa acatcatcaa tttgctcgga gcttgtaccc aggacggtcc cctctacgtg 1680
```

```
atcatggaat acgcttccaa aggtaatctg cgcgaatatc tgcaagctcg gaggccgcca   1740
ggtatggaat actgttataa tccgacacgg attcccgagg aacagctctc ttttaaagat   1800
ttggtttcat gcgcgtatca agtggcgagg ggcatggagt atctggcgtc caagaagtgc   1860
attcataggg acttggctgc aagaaatgtc ttggtaacag aagacaacgt catgaagatc   1920
gccgacttcg gccttgcacg ggatattcat cacatcgact attacaaaaa gacgacgaac   1980
ggccgcctcc cagttaagtg gatggccccc gaagccctgt tcgatcggat ttacacgcat   2040
caatccgacg tgtggtcttt cggtgtcctg ctttgggaga tatttacact cgggggatca   2100
ccctaccccg gagtaccggt ggaggagttg ttcaaacttc ttaaagaagg tcacagaatg   2160
gacaaaccca gtaactgcac taacgagct tatatgatga tgcgcgattg ctggcacgct   2220
gttccgtcac aacggcccac ttttaaacag ctcgtggagg atcttgacag aatcgtcgcg   2280
atgactagca accaagagta tttggatttg tcagtcccgc ttgaccaata ttcccccggt   2340
tttccggcta cccgctcttc tacttgttcc agcggtgagg atagtgtatt ttctcatgac   2400
ccacttccag atgagccgtg cttgcctcgg tgtcctcccc actcccatgg agcgctcaaa   2460
cgccactga                                                            2469
```

```
SEQ ID NO: 89          moltype = DNA  length = 2460
FEATURE                Location/Qualifiers
source                 1..2460
                       mol_type = other DNA
                       organism = synthetic construct
SEQUENCE: 89
atgttcacgt ggagatgtct catcctgtgg gcggtactgg ttaccgcaac gttgagcgca   60
gctaggcccg cccccacgct gcctgaccag gctctcccta aggcgaatat agaagtagaa   120
tcacattctg cacatccagg agacttgttg caattgcggt gccgcttgag agacgatgtc   180
caatcaatca attgggtcag ggacggggtc caacttccgg agaataaccg gacaaggatt   240
actggagagg aggttgaagt cagggacgct gttcccgaag atagcggctt gtacgcttgc   300
atgactaatt ccccgtcagg gtcagaaacc acgtattttt ctgtaaacgt tagcgatgct   360
cttccgagtg ctgaagacga tgatgatgaa gacgatagca gctccgaaga gaaagaggcg   420
gataatacta aaccaaatca agctgttgca ccatattgga cctaccccga aaaaatggag   480
aaaaagttgc atgctgttcc ggcagccaaa accgtaaaat tcaagtgccc ctccggcggt   540
accccctaatc caactctgag atggttgaag aacggtaagg agttcaaacc ggatcaccgg   600
ataggtggat ataaagttcg gtatgcgacc tggtccatta ttatggactc tgtcgtgccc   660
tccgacaaag gtaactacac ttgtatcgtc gagaacaagt acggcagcat caatcatacg   720
taccaactgg acgtggtaga acgcagtcca caccgcccca tcctccaggc cggactccct   780
gccaacaaaa cagttgcgct cggctctaat gttgaatttg tgtgcaaagt ttactcagac   840
cctcaacctc atatccaatg gcttaaacat atcgaagtca acggtagtaa gataggtccc   900
gacaacctgc cgtatgtcca gatccttaaa actgcggggg taaataccac tgacaaggaa   960
atggaggtct tgcatcttcg caacgtgagc tttgaagatg caggtgagta tacttgtttg   1020
gcaggtaata gcatcggaat ctcccaccat tccgcctggc tgacagtgct gggaggccacg   1080
gaacaaagtc cggccatgat gaccagtccg ttgtatctgg aaattatcat ttactgtaca   1140
ggggcctttc tcatatcatg catggtcgta accgtgatta tatataaaat gaagagcaca   1200
acgaagaaga ctgattttaa ttcacaactg gcggtacata aactcgcaaa atctatccca   1260
ttgaggcggc aggttacagt ctccgccgac agctccagca gcatgaactc aggagtgatg   1320
cttgttcgcc ccagcagact gagttctagt gggactccga tgcttgctgg agtcagtgaa   1380
tacgaattgc cggaggatcc gcggtgggaa cttcctaggg accgccttat attgggcaaa   1440
cccctcggtg agggctgttt cggacaggtc gtgctcgcag aggccatcgg ccttgacaaa   1500
gataagccga atagagtgac caaggtggcg gttaaaatgc tgaaatcaga cgctacggaa   1560
aaggacctct cagacctcat cagtgaaatg gaaatgatga aaatgatagg gaagcacaaa   1620
aacatcatca atttgctcgg agcttgtacc caggacggtc ccctctacgt gatcgtagaa   1680
tacgcttcca aaggtaatct gcgcgaatat ctgcaagctc ggaggccgcc aggtatggaa   1740
tactgttata atccgacacg gattcccgag gaacagctct cttttaaaga tttggtttca   1800
tgcgcgtatc aagtggcgag gggcatggag tatctggcgt ccaagaagtg cattcatagg   1860
gacttggctg caagaaatgt cttggtaaca gaagacaacg tcatgaagat cgccgacttc   1920
ggccttgcac gggatattca tcacatcgac tattacaaag acgacgaac cggccgcctc   1980
ccagttaagt ggatggcccc cgaagccctg ttcgatcgga tttacacgca tcaatccgac   2040
gtgtggtctt tcggtgtcct gctttgggag atatttacac tcgggggatc accctacccg   2100
ggagtaccgg tggaggagtt gttcaaactt cttaaagaag gtcacagaat ggacaaaccc   2160
agtaactgca ctaacgagct gtatatgatg atgcgcgatt gctggcacgc tgttccgtca   2220
caacggccca cttttaaaca gctcgtggag gatcttgaca gaatcgtcgc gatgactagc   2280
aaccaagagt atttggattt gtcagtcccg cttgaccaat attcccccggt ttttccggct   2340
acccgctctt ctacttgttc cagcggtgag gatagtgtat tttctcatga cccacttcca   2400
gatgagccgt gcttgcctcg gtgtcctccc cactcccatg gagcgctcaa acgccactga   2460
```

```
SEQ ID NO: 90          moltype = DNA  length = 2460
FEATURE                Location/Qualifiers
source                 1..2460
                       mol_type = other DNA
                       organism = synthetic construct
SEQUENCE: 90
atgttcacgt ggagatgtct catcctgtgg gcggtactgg ttaccgcaac gttgagcgca   60
gctaggcccg cccccacgct gcctgaccag gctctcccta aggcgaatat agaagtagaa   120
tcacattctg cacatccagg agacttgttg caattgcggt gccgcttgag agacgatgtc   180
caatcaatca attgggtcag ggacggggtc caacttccgg agaataaccg gacaaggatt   240
actggagagg aggttgaagt cagggacgct gttcccgaag atagcggctt gtacgcttgc   300
atgactaatt ccccgtcagg gtcagaaacc acgtattttt ctgtaaacgt tagcgatgct   360
cttccgagtg ctgaagacga tgatgatgaa gacgatagca gctccgaaga gaaagaggcg   420
gataatacta aaccaaatca agctgttgca ccatattgga cctaccccga aaaaatggag   480
aaaaagttgc atgctgttcc ggcagccaaa accgtaaaat tcaagtgccc ctccggcggt   540
actcctaatc caactctgag atggttgaag aacggtaagg agttcaaacc ggatcaccgg   600
```

-continued

```
ataggtggat ataaagttcg gtatgcgacc tggtccatta ttatggactc tgtcgtgccc   660
tccgacaaag gtaactacac ttgtatcgtc gagaacaagt acggcagcat caatcatacg   720
taccaactgg acgtggtaga acgcagtcca caccgcccca tcctccaggc cggactccct   780
gccaacaaaa cagttgcgct cggctctaat gttgaatttg tgtgcaaagt ttactcgac   840
cctcaacctc atatccaatg gcttaaacat atcgaagtca acggtagtaa gataggtccc   900
gacaacctgc cgtatgtcca gatccttaaa actgcggggg taaataccac tgacaaggaa   960
atggaggtct tgcatcttcg caacgtgagc tttgaagatg caggtgagta tacttgtttg  1020
gcaggtaata gcatcggaat ctcccaccat tccgcctggc tgacagtgct ggaggccacg  1080
gaacaaagtc cggccatgat gaccagtccg ttgtatctgg aaattatcat ttactgtaca  1140
ggggcctttc tcatatcatg catggtcgta accgtgatta tatataaaat gaagagcaca  1200
acgaagaaga ctgattttaa ttcacaactg gcggtacata aactcgcaaa atctatccca  1260
ttgaggcggc aggttacagt ctccgccgac agctccagca gcatgaactc aggagtgatg  1320
cttgttcgcc ccagcagact gagttctagt gggactccga tgcttgctgg agtcagtgaa  1380
tacgaattgc cggaggatcc gcggtgggaa cttcctaggg accgccttat attgggcaaa  1440
ccctcggtg agggctgttt cggacaggtc gtgctcgcag aggccatcgg ccttgacaaa  1500
gataagccga atagagtgac caaggtggcg gttaaaatgc tgaaatcaga cgctacggaa  1560
aaggacctct cagacctcat cagtgaaatg gaaatgatga aaatgatagg gaagcacaaa  1620
aacatcatca agttgctcgg agcttgtacc caggacggtc ccctctacgt gatcgtagaa  1680
tacgcttcca aagtaatctc gcgcgaatat ctgcaagctc ggaggccgcc aggtatggaa  1740
tactgttata atccgacacg gattcccgag gaacagctct cttttaaaga tttggtttca  1800
tgcgcgtatc aagtggcgag gggcatggag tatctggcgt ccaagaagtg cattcatagg  1860
gacttggctg caagaaatgt cttggtaaca gaagacaacg tgcccgacttc  1920
ggccttgcac gggatattca tcacatcgac tattacaaag agacgacgaa cggccgcctc  1980
ccagttaagt ggatggcccc cgaagccctg ttcgatcgga tttacacgca tcaatccgac  2040
gtgtggtctt tcggtgtcct gctttgggag atatttacac tcgggggatc accctacccc  2100
ggagtaccgg tggaggagtt gttcaaactt cttaaagaag gtcacagaat ggacaaaccc  2160
agtaactgca ctaacgagct gtatatgatg atgcgcgatt gctggcacgc tgttccgtca  2220
caacggccca cttttaaaca gctcgtggag gatcttgaca gaatcgtcgc gatgactagc  2280
aaccaagagt atttggattt gtcagtcccg cttgaccaat atgcccccgg tttccggct  2340
acccgctctt ctacttgttc cagcggtgag gatagtgtat tttctcatga cccacttcca  2400
gatgagccgt gcttgcctcg gtgtcctccc cactcccatg gagcgctcaa acgccactga  2460
```

```
SEQ ID NO: 91          moltype = DNA  length = 1317
FEATURE                Location/Qualifiers
source                 1..1317
                       mol_type = other DNA
                       organism = synthetic construct
SEQUENCE: 91
atgggatcat ccaagtcaaa accgaaagac ccgtcacaga gaaaaatgaa gagcacaacg   60
aagaagactg attttaattc acaactggcg gtacataaac tcgcaaaatc tatcccattg  120
aggcggcagg ttacagtctc cgccgacagc tccagcagca tgaactcagg agtgatgctt  180
gttcgcccca gcagactgag ttctagtggg actccgatgc ttgctggagt cagtgaatac  240
gaattgccgg aggatccgcg gtgggaactt cctagggacc gccttatatt gggcaaaccc  300
ctcggtgagg gctgtttcgg acaggtcgtg ctcgcagagg ccatcggcct tgacaaagat  360
aagccgaata gagtgaccaa ggtggcggtt aaaatgctga aatcagacgc tacggaaaag  420
gacctctcag acctcatcag tgaaatggaa atgatgaaaa tgatagggaa gcacaaaaac  480
atcatcaatt gctcggagc ttgtacccag gacggtcccc tctacgtgat cgtagaatac  540
gcttccaaag gtaatctgcg cgaatatctg caagctcgga ggccgccagg tatggaatac  600
tgttataatc cgacacggat tcccgaggaa cagctctctt ttaaagattt ggtttcatgc  660
gcgtatcaag tggcgagggg catggagtat ctggcgtcca gaagtgcat tcatagggac  720
ttggctgcaa gaaatgtctt ggtaacagaa gacaacgtca tgaagatcgc cgacttcggc  780
cttgcacggg atattcatca tcgactat tacaaagaga cgacgaacgg ccgcctccca  840
gttaagtgga tggccccga gccctgttc gatcggattt acacgcatca atccgacgtg  900
tggtctttcg gtgtcctgct ttgggagata tttacactcg ggggatcacc ctaccccgga  960
gtaccggtgg aggagttgtt caaacttctt aaagaaggtc acagaatgga caaacccagt 1020
aactgcacta acgagctgta tatgatgatg cgcgattgct ggcacgctgt tccgtcacaa 1080
cggcccactt ttaaacagct cgtggaggat cttgacagaa tcgtcgcgat gactagcaac 1140
caagagtatt ggatttgtc agtcccgctt gaccaatat cccccggttt tccggctacc 1200
cgctcttcta cttgttccag cggtgaggat agtgtatttt ctcatgaccc acttccagat 1260
gagccgtgct tgcctcggtg tcctccccac tcccatggag cgctcaaacg ccactga     1317
```

```
SEQ ID NO: 92          moltype = DNA  length = 2523
FEATURE                Location/Qualifiers
source                 1..2523
                       mol_type = other DNA
                       organism = synthetic construct
SEQUENCE: 92
atgggcctta agtcaacttg gagatacggc aatggcccgg gtacgtactc caagaaaatg   60
gtatcttggg attccggttg tctcatttgt ctggtagtgg ttaccatggc gggcctgagt  120
ctggcgagac cctctttaa tctggtagtt gaagacgcta ccttggagcc agaagagccg  180
cccactaagt atcagataag tcagcctgat gtgcactccg cgcttccggg agaacctctc  240
gagttgcgct gtcaactcaa ggatgccgtg atgatcagct ggacgaaaga tggagtgcct  300
cttggaccag ataatcgcac tgttatcatt ggtgaatact tgcaaattaa agatgcatca  360
ccacgggatt ctggccttta cgcgtgcaca gctatcagga gctcgacte cgatacactc  420
tattttatag tcaacgttac cgatgcgttg tcaagcgggg atgatgagga cgacaacgac  480
gggtcagaag acttcgttaa cgattccaat cagatgagag ctcccctattg gacccacact  540
gacaaaatgg aaaaaaggct ccacgctgtc ccggctgcga atactgtgaa gtttagatgt  600
cccgcaatgg gcaaccccac gccaacaatg cggtggttga aaaatggtaa agagttcaaa  660
caggagcatc ggataggtgg gtataaagtg agaaatcaac attggagctt gatcatggag  720
```

-continued

```
tctgtagttc cttcagataa aggaaattat acatgcatcg tcgagaatca atacggctct   780
attaaccata catatcacct ggacgtcgta gagaggagtc cccacaggcc tatcctgcaa   840
gcgggactgc cggcaaatgc ttctgcagtc gtgggcggtg acgttgagtt cgtctgtaag   900
gtgtacagcg acgcacaacc acacatccaa tggataaagc atgttgagag aaatggttca   960
aaatatggcc cggacggctt gccctacctt caggtgctca aagctgcggg agtcaacact  1020
actgataagg aaatcgaggt gctctatatt aggaacgtta cctttgaaga cgccggcgaa  1080
tacacctgtc tcgcgggaaa ctctatcggt atctcatttc acaccgcatg gttgactgtg  1140
cttccagctc cggagaaaga gaaggagttt ccgacctccc ctgattacct cgaaatagcg  1200
atctattgca tcggagtttt tctcatcgcg tgcatggttc ttactgtgat actttgtaga  1260
atgaagaaca ccaccaagaa accggatttt tcctcccaac cggccgtcca caagttgacg  1320
aaacggatcc cattgaggcg ccaggtgagt gctgacagct caagttcaat gaacagtaac  1380
acgccgctcg tgaggatcac tactcggctg agctctaccg cggatgcgcc aatgttggca  1440
ggggtcagtg agtacgaact cccggaagat ccgaagtggg agtttccgcg cgacaaactc  1500
actcttggaa aaccgcttgg agagggatgc ttcggacagg tcgtaatggc cgaggcggtt  1560
ggtatagaca aagatagacc caaagaagct gtcacagtag ctgtaaaaat gcttaaggat  1620
gatgccactg aaaaagattt gagcgacctc gtaagcgaga tggaaatgat gaaaatgata  1680
gggaagcaca aaaatataat taacctcctg ggggcctgca cacaggacgg cccgttgtat  1740
gtcatcgtcg aatatgcctc caaagggaac ctcagggagt accttagagc gcgcagaccg  1800
ccggggatgg agtattcatt tgacatcaat cgggtccccg aagaacaaat gactttcaaa  1860
gaccttgtct cctgtaccta tcaactcgcc cgcgggaatgg aatatttggc tagtcaaaaa  1920
tgcattcacc gcgatcttgc tgcacggaac gtactcgtca ctgagaataa cgttatgaaa  1980
atagcggatt tcggcctcgc aagggacata aacaacatcg actactacaa aaaaaccacg  2040
aatggcagac tgccagtcaa gtggatggcg ccagaagccc tttttgatag agtctacacg  2100
caccagtcag acgtgtggtc ctttggagtg ctcatgtggg aaatctttac gctgggtggt  2160
agcccttacc cggggattcc cgtggaagaa cttttcaagc tgttgaaaga gggccatcgg  2220
atggacaaac ccgcaaattg cacaaatgaa ttgtatatga tgatgcgcga ctgttggcaa  2280
gccgtgcctt cacagagacc tacattcaag cagttggtcg aagacctcga ccggatcctg  2340
acgcttacaa cgaacgaaga atacctggac ttgtctggtc ccttggagca atactcacca  2400
agctaccccg atactcggtc atcttgctct agtggcgacg atagtgtctt ttcacctgat  2460
ccaatgcccct acgaaccgtg tctgccaaag taccaacaca tgaacggttc agtaaagacc  2520
tga                                                                2523
```

SEQ ID NO: 93          moltype = DNA  length = 2523
FEATURE                Location/Qualifiers
source                 1..2523
                       mol_type = other DNA
                       organism = synthetic construct SEQUENCE: 93
```
atgggcctta agtcaacttg gagatacggc aatggcccgg gtacgtactc caagaaaatg    60
gtatcttggg attccggttg tctcatttgt ctggtagtgg ttaccatggc gggcctgagt   120
ctggcgagac cctcttttaa tctggtagtt gaagacgcta ccttggagcc agaagagccg   180
cccactaagt atcagataag tcagcctgat gtgcactccg cgcttccggg agaacctctc   240
gagttgcgct gtcaactcaa ggatgccgtg atgatcagct acgacgaaaga tggagtgcct   300
cttggaccag ataatcgcac tgttatcatt ggtgaatact tgcaaattaa agatgcatca   360
ccacgggatt ctggcctttta cgcgtgcaca gctatcagga cgctcgactc cgatacactc   420
tattttatag tcaacgttac cgatgcgttg tcaagcgggg atgatgagga cgacaacgac   480
gggtcagaag acttcgttaa cgattccaat cagatgaggg ctccctattg gacccacact   540
gacaaaatgg aaaaaaggct ccacgctgtc ccggctgcga atactgtgaa gtttagatgt   600
cccgcaatgg gcaaccccac gccaacaatg cggtggttga aaaatggtaa agagttcaaa   660
caggagcatc ggataggtgg gtataaagtg agaaatcaac attggagctt gatcatggag   720
tctgtagttc cttcagataa aggaaattat acatgcatcg tcgagaatca atacggcggt   780
attaaccata catatcacct ggacgtcgta gagaggagtc cccacaggcc tatcctgcaa   840
gcgggactgc cggcaaatgc ttctgcagtc gtgggcggtg acgttgagtt cgtctgtaag   900
gtgtacagcg acgcacaacc acacatccaa tggataaagc atgttgagag aaatggttca   960
aaatatggcc cggacggctt gccctacctt caggtgctca aagctgcggg agtcaacact  1020
actgataagg aaatcgaggt gctctatatt aggaacgtta cctttgaaga cgccggcgaa  1080
tacacctgtc tcgcgggaaa ctctatcggt atctcatttc acaccgcatg gttgactgtg  1140
cttccagctc cggagaaaga gaaggagttt ccgacctccc ctgattacct cgaaatagcg  1200
atctattgca tcggagtttt tctcatcgcg tgcatggttc ttactgtgat actttgtaga  1260
atgaagaaca ccaccaagaa accggatttt tcctcccaac cggccgtcca caagttgacg  1320
aaacggatcc cattgaggcg ccaggtgagt gctgacagct caagttcaat gaacagtaac  1380
acgccgctcg tgaggatcac tactcggctg agctctaccg cggatgcgcc aatgttggca  1440
ggggtcagtg agtacgaact cccggaagat ccgaagtggg agtttccgcg cgacaaactc  1500
actcttggaa aaccgcttgg agagggatgc ttcggacagg tcgtaatggc cgaggcggtt  1560
ggtatagaca aagatagacc caaagaagct gtcacagtag ctgtaaaaat gcttaaggat  1620
gatgccactg aaaaagattt gagcgacctc gtaagcgaga tggaaatgat gaaaatgata  1680
gggaagcaca aaaatataat taagctcctg ggggcctgca cacaggacgg cccgttgtat  1740
gtcatcgtcg aatatgcctc caaagggaac ctcagggagt accttagagc gcgcagaccg  1800
ccggggatgg agtattcatt tgacatcaat cgggtccccg aagaacaaat gactttcaaa  1860
gaccttgtct cctgtaccta tcaactcgcc cgcgggaatgg aatatttggc tagtcaaaaa  1920
tgcattcacc gcgatcttgc tgcacggaac gtactcgtca ctgagaataa cgttatgaaa  1980
atagcggatt tcggcctcgc aagggacata aacaacatcg actactacaa aaaaaccacg  2040
aatggcagac tgccagtcaa gtggatggcg ccagaagccc tttttgatag agtctacacg  2100
caccagtcag acgtgtggtc ctttggagtg ctcatgtggg aaatctttac gctgggtggt  2160
agcccttacc cggggattcc cgtggaagaa cttttcaagc tgttgaaaga gggccatcgg  2220
atggacaaac ccgcaaattg cacaaatgaa ttgtatatga tgatgcgcga ctgttggcaa  2280
gccgtgcctt cacagagacc tacattcaag cagttggtcg aagacctcga ccggatcctg  2340
acgcttacaa cgaacgaaga atacctggac ttgtctggtc ccttggagca atactcacca  2400
agctaccccg atactcggtc atcttgctct agtggcgacg atagtgtctt ttcacctgat  2460
```

```
ccaatgccct acgaaccgtg tctgccaaag taccaacaca tgaacggttc agtaaagacc  2520
tga                                                                2523

SEQ ID NO: 94        moltype = DNA   length = 2523
FEATURE              Location/Qualifiers
source               1..2523
                     mol_type = other DNA
                     organism = synthetic construct
SEQUENCE: 94
atgggcctta agtcaacttg gagatacggc aatggcccgg gtacgtactc caagaaaatg  60
gtatcttggg attccggttg tctcatttgt ctggtagtgg ttaccatggc gggcctgagt  120
ctggcgagac cctcttttaa tctggtagtt gaagacgcta ccttggagcc agaagagccg  180
cccactaagt atcagataag tcagcctgat gtgcactccg cgcttccggg agaacctctc  240
gagttgcgct gtcaactcaa ggatgccgtg atgatcagct ggacgaaaga tggagtgcct  300
cttggaccag ataatcgcac tgttatcatt ggtgaatact tgcaaattaa agatgcatca  360
ccacgggatt ctggccttta cgcgtgcaca gctatcagga cgctcgactc cgatacactc  420
tattttatag tcaacgttac cgatgcgttg tcaagcgggg atgatgagga cgacaacgac  480
gggtcagaag acttcgttaa cgattccaat cagatgagag ctccctattg gacccacact  540
gacaaaatgg aaaaaaggct ccacgctgtc ccggctgcga atactgtgaa gtttagatgt  600
cccgcaatgg gcaaccccac gccaacaatg cggtggttga aaaatggtaa agagttcaaa  660
caggagcatc ggataggtgg gtataaagtg agaaatcaac attggagctt gatcatggag  720
tctgtagttc cttcagataa aggaaattat acatgcatcg tcgagaatca atacggctct  780
attaaccata catatcacct ggacgtcgta gagaggagtc cccacaggcc tatcctgcaa  840
gcgggactgc cggcaaatgc ttctgcagtc gtgggcggtg acgttgagtt cgtctgtaag  900
gtgtacagcg acgcacaacc acacatccaa tggataaagc atgttgagag aaatggttca  960
aaatatggcc cggacggctt gccctacctt caggtgctca aagctgcggg agtcaacact  1020
actgataagg aaatcgaggt gctctatatt aggaacgtta cctttgaaga cgccggccgaa  1080
tacacctgtc tcgcgggaaa ctctatcggt atctcatttc acaccgcatg gttgactgtg  1140
cttccagctc cggagaaaga gaaggagttt ccgacctccc ctgattacct cgaaatagcg  1200
atctattgca tcggagtttt tctcatcgcg tgcatggttc ttactgtgat actttgtaga  1260
atgaagaaca ccaccaagaa accggatttt tcctcccaac cggccgtcca caagttgacg  1320
aaacggatcc cattgaggcg ccaggtgagt gctgacagct caagttcaat gaacagtaac  1380
acgccgctcg tgaggatcac tactcggctg agctctaccg cggatgcgcc aatgttggca  1440
ggggtcagtg agtacgaact cccggaagat ccgaagtggg agtttccgcg cgacaaaactc  1500
actcttgtaa aaccgcttgg agagggatgc ttcggacagg tcgtaatggc cgaggcggtt  1560
ggtatagaca aagatagacc caaagaagct gtcacagtag ctgtaaaaat gcttaaggat  1620
gatgccactg aaaaagattt gagcgacctc gtaagcgaga tggaaatgat gaaaatgata  1680
gggaagcaca aaaatataat taacctcctg ggggcctgca cacaggacgg cccgttgtat  1740
gtcatcgtcg aatatgcctc caaagggaac ctcaggagt accttagacg gcgcagaccg  1800
ccggggatgg agtattcatt tgacatcaat cgggtccccg aagaacaaat gactttcaaa  1860
gaccttgtct cctgtaccta tcaactcgcc cgcggaatgg aatatttggc tagtcaaaaa  1920
tgcattcacc gcgatcttgc tgcacggaac gtactcgtca ctgagaataa cgttatgaaa  1980
atagcggatt tcggcctcgc aagggacata aacaacatcg actactacaa agaaaccacg  2040
aatggcagac tgccagtcaa gtggatggcg ccagaagccc tttttgatag agtctacacg  2100
caccagtcag acgtgtggtc ctttggagtg ctcatgtggg aaatctttac gctgggtggt  2160
agcccttacc cggggattcc cgtggaagaa ctttttcaagc tgttgaaaga gggccatcgg  2220
atggacaaac ccgcaaattg cacaaatgaa ttgtatatga ttgatgcgcga ctgttggcaa  2280
gccgtgcctt cacagagacc tacattcaag cagttggtcg aagacctcga ccggatcctg  2340
acgcttacaa cgaacgaaga atacctggac ttgtctggtc ccttggagca atactccacca  2400
agctacccca atactcggtc atcttgctct agtggcgacg atagtgtctt ttcacctgat  2460
ccaatgccct acgaaccgtg tctgccaaag taccaacaca tgaacggttc agtaaagacc  2520
tga                                                                2523

SEQ ID NO: 95        moltype = DNA   length = 2523
FEATURE              Location/Qualifiers
source               1..2523
                     mol_type = other DNA
                     organism = synthetic construct
SEQUENCE: 95
atgggcctta agtcaacttg gagatacggc aatggcccgg gtacgtactc caagaaaatg  60
gtatcttggg attccggttg tctcatttgt ctggtagtgg ttaccatggc gggcctgagt  120
ctggcgagac cctctttaa tctggtagtt gaagacgcta ccttggagcc agaagagccg  180
cccactaagt atcagataag tcagcctgat gtgcactccg cgcttccggg agaacctctc  240
gagttgcgct gtcaactcaa ggatgccgtg atgatcagct ggacgaaaga tggagtgcct  300
cttggaccag ataatcgcac tgttatcatt ggtgaatact tgcaaattaa agatgcatca  360
ccacgggatt ctggccttta cgcgtgcaca gctatcagga cgctcgactc cgatacactc  420
tattttatag tcaacgttac cgatgcgttg tcaagcgggg atgatgagga cgacaacgac  480
gggtcagaag acttcgttaa cgattccaat cagatgagag ctccctattg gacccacact  540
gacaaaatgg aaaaaaggct ccacgctgtc ccggctgcga atactgtgaa gtttagatgt  600
cccgcaatgg gcaaccccac gccaacaatg cggtggttga aaaatggtaa agagttcaaa  660
caggagcatc ggataggtgg gtataaagtg agaaatcaac attggagctt gatcatggag  720
tctgtagttc cttcagataa aggaaattat acatgcatcg tcgagaatca atacggctct  780
attaaccata catatcacct ggacgtcgta gagaggagtc cccacaggcc tatcctgcaa  840
gcgggactgc cggcaaatgc ttctgcagtc gtgggcggtg acgttgagtt cgtctgtaag  900
gtgtacagcg acgcacaacc acacatccaa tggataaagc atgttgagag aaatggttca  960
aaatatggcc cggacggctt gccctacctt caggtgctca aagctgcggg agtcaacact  1020
actgataagg aaatcgaggt gctctatatt aggaacgtta cctttgaaga cgccggccgaa  1080
tacacctgtc tcgcgggaaa ctctatcggt atctcatttc acaccgcatg gttgactgtg  1140
cttccagctc cggagaaaga gaaggagttt ccgacctccc ctgattacct cgaaatagcg  1200
```

```
atctattgca tcggagtttt tctcatcgcg tgcatggttc ttactgtgat actttgtaga  1260
atgaagaaca ccaccaagaa accggatttt tcctcccaac cggccgtcca caagttgacg  1320
aaacggatcc cattgaggcg ccaggtgagt gctgacagct caagttcaat gaacagtaac  1380
acgccgctcg tgaggatcac tactcggctg agctctaccg cggatgcgcc aatgttggca  1440
ggggtcagtg agtacgaact cccggaagat ccgaagtggg agtttccgcg gacaaactc   1500
actcttggaa aaccgcttgg agagggatgc ttcggacagg tcgtaatggc cgaggcggtt  1560
ggtatagaca aagatagacc caaagaagct gtcacagtag ctgtaaaaat gcttaaggat  1620
gatgccactg aaaaagattt gagcgacctc gtaagcgaga tggaaatgat gaaaatgata  1680
gggaagcaca aaaatataat taagctcctg ggggcctgca cacaggacgg cccgttgtat  1740
gtcatcgtcg aatatgcctc caaagggaac ctcagggagt accttagagc gcgcagaccg  1800
ccggggatgg agtattcatt tgacatcaat cgggtccccg aagaacaaat gactttcaaa  1860
gaccttgtct cctgtaccta tcaactcgcc cgcggaatgg aatatttggc tagtcaaaaa  1920
tgcattcacc gcgatcttgc tgcacggaac gtactcgtca ctgagaataa cgttatgaaa  1980
atagcggatt tcggcctcgc aagggacata aacaacatcg actactacaa agaaaccacg  2040
aatggcagac tgccagtcaa gtggatggcg ccagaagccc tttttgatag agtctacacg  2100
caccagtcag acgtgtggtc ctttggagtg ctcatgtggg aaatctttac gctgggtggt  2160
agcccttacc cggggattcc cgtggaagaa cttttcaagc tgttgaaaga gggccatcgg  2220
atggacaaac ccgcaaattg cacaaatgaa ttgtatatga tgatgcgcga ctgttggcaa  2280
gccgtgcctt cacagagacc tacattcaag cagttggtcg aagacctcga ccggatcctg  2340
acgcttacaa cgaacgaaga atacctggac ttgtctggtc ccttggagca atacgcacca  2400
agctacccg atactcggtc atcttgctct agtggcgacg atagtgtctt ttcacctgat   2460
ccaatgccct acgaaccgtg tctgccaaag taccaacaca tgaacggttc agtaaagacc  2520
tga                                                                 2523
```

SEQ ID NO: 96          moltype = DNA  length = 2439
FEATURE                Location/Qualifiers
source                 1..2439
                       mol_type = other DNA
                       organism = synthetic construct
SEQUENCE: 96

```
atgtcagaag ctggtggcgg cgccgctgcc gcagcctcac tcccgagatc aagggccggt  60
ggcatgcgcg cggcatgggg atccgtgtgg tgtttgtgcc tcgcggcggc tgtcggagct  120
ctgccggctg caaggcgcag gggagcggaa cggagcggtg gccaggcggc ggagtatctc  180
cggagtgaaa ctgcatttct tgaggagctt gtttccggtt caggggatac catcgagctt  240
tcctgtaaca cacaatcttc aagtgtaagc gtattctggt tcaaagatgg tataggcatt  300
gcgcccagta atagaacaca catcgggcag aaacttttga agatcatcaa cgtttcatat  360
gatgattccg gactgtactc atgtaagcca aggcacagta acgaggtgct tgggaacttc  420
acagtcaggg ttacaggcgt accattctgg acgaggcccg ataagatgga aaaaaaactt  480
ttggcagtgc ccgcagccaa tacagtgcgg ttccgctgcc ccgcaggtgg gaatccgacg  540
cccacaattt attggctgaa gaatggcaag gagttcaaag gagaacatag gatcggcgga  600
atcaaactga ggcaccagca atggtctctg tgatggaat cagtagtccc atctgaccgc   660
ggtaactaca cgtgcgtagt agaaaacaag tatgggaata ttcggcatac ctaccagctc  720
gatgtgctcg agagatctcc tcacaggcct atcttgcagg ctggactgcc agctaatcaa  780
acagtagttg tcggatctaa cgtggagttc cactgcaaag tttactcaga cgcccaaccg  840
cacattcaat ggcttaaaca cgtggaggtt aacggtagca agtatggacc tgatgggact  900
ccctatgtga cagtccttaa gagttggatt tctaagaatg ccgaggcgga tgcgaacttg  960
aacctgttta acgtaaccga gcaggacgag ggcgaatatc tttgtcgcgc taacaacttc  1020
gttggaatag cggagaagcc cttctggctg catatacgga agccaaagcc ggcggaggag  1080
ttgatggaga tggatgactc cggttccgta tacgccggaa tccttagcta cggaaccggg  1140
ctggtgctgt ttatcctcgt tttggttatt gttattatat gccgcatgaa gatgccaaac  1200
aaaaaggcaa tgaatactac aactgtgcag aaagtgtcaa aattcccact taaacggcaa  1260
gtcactgtct cactcgaatc taactcttcc atgaactcca acactccgtt ggtgcggatt  1320
accagattgt cctcatccga cggtcccatg ttggcaaatg tcagtgagct ggaattgccg  1380
cccgatccca aatgggaact tgcaagatcc cggcttactc tcggtaagcc cctgggcgaa  1440
ggttgctttg gacaagtcgt catggccgaa gcgattggaa tcgataaaga caaacccaac  1500
aaggctataa cggtcgcagt aaaaatgttg aaagatgacg cgaccgacaa ggacctgtca  1560
gatctggtct cagagatgga aatgatgaag atgattggta aacacaagaa tataatcaac  1620
ttgcttggag catgtacgca agacggccct ctctacgttc tcgtggagta tgcctctaag  1680
ggcaatttga gggagtacct gagagctcgc agacctccgg gcatggatta gtttttcgac  1740
acttgtaagc tgccggagga gcaacttacc ttcaaggatc ttgtaagttg cgcgtaccag  1800
gttgcaaggg ggatggaata cctcgccagt caaaagtgca tacatagaga tttggcagcg  1860
aggaacgtgc tcgtgactga ggacaacgtc atgaaaattg cggactttgg gcttgcacgg  1920
gatgttcata acatcgatta ctacaagaaa actactaacg gacggctccc tgtgaagtgg  1980
atggctccag aagcgctttt tgatagagtt tacacacatc aaagtgacgt atggagtttt  2040
ggagtattgc tctgggagat tttcaccttg ggagggtctc cttacctgg aatacccgtc   2100
gaagagctct ttaagctgct taaagaaggc cacaggatgg acaagccggc gaactgcact  2160
catgatctgt acatgataat gagagagtgc tggcacgccg ttccctccca gcggccgaca  2220
ttcaagcagc tggtggaaga ccttgatagg gtactcacta tgacgtccac cgatgagtat  2280
ctggacttgt ctgttccatt cgaacaatac tctccggccg gtcagatac gcattccact   2340
tgctccagtg gtgatgattc tgtctttgca cacgatcttc tcccagacga accctgtctt  2400
cctaaacacg taccgtgtaa cggtgtcata aggacatag                          2439
```

SEQ ID NO: 97          moltype = DNA  length = 2439
FEATURE                Location/Qualifiers
source                 1..2439
                       mol_type = other DNA
                       organism = synthetic construct
SEQUENCE: 97

```
atgtcagaag ctggtggcgg cgccgctgcc gcagcctcac tcccgagatc aagggccggt  60
```

-continued

```
ggcatgcgcg cggcatgggg atccgtgtgg tgtttgtgcc tcgcggcggc tgtcggagct    120
ctgccggctg caaggcgcag gggagcggaa cggagcggtg gccaggcggc ggagtatctc    180
cggagtgaaa ctgcatttct tgaggagctt gttttcggtt caggggatac catcgagctt    240
tcctgtaaca cacaatcttc aagtgtaagc gtattctggt tcaaagatgg tataggcatt    300
gcgcccagta atagaacaca catcgggcag aaacttttga agatcatcaa cgtttcatat    360
gatgattccg gactgtactc atgtaagcca aggcacagta acgaggtgct tgggaacttc    420
acagtcaggg ttacaggcgt accattctgg acgaggcccg ataagatgga aaaaaaactt    480
ttggcagtgc ccgcagccaa tacagtgcgg ttccgctgcc ccgcaggtgg gaatccgacg    540
cccacaattt attggctgaa gaatggcaag gagttcaaag gagaacatag gatcggcgga    600
atcaaactga ggcaccagca atggtctctg gtgatggaat cagtagtccc atctgaccgc    660
ggtaactaca cgtgcgtagt agaaaacaag tatgggaata ttcggcatac ctaccagctc    720
gatgtgctcg agagatctcc tcacaggcct atcttgcagg ctggactgcc agctaatcaa    780
acagtagttg tcggatctaa cgtggagttc cactgcaaag tttactcaga cgcccaaccg    840
cacattcaat ggcttaaaca cgtggaggtt aacggtagca agtatggacc tgatgggact    900
ccctatgtga cagtccttaa gagttggatt tctaagaatg ccgaggcgga tgcgaacttg    960
aacctgttta acgtaaccga gcaggacgag ggcgaatatc tttgtcgcgc taacaacttc   1020
gttggaatag cggagaagcc cttctggctg catatacgga agccaaagcc ggcggaggag   1080
ttgatggaga tggatgactc cggttccgta tacgccggaa tccttagcta cggaaccggg   1140
ctggtgctgt ttatcctcgt tttggttatt gttattatat gccgcatgaa gatgccaaac   1200
aaaaaggcaa tgaatactac aactgtgcag aaagtgtcaa aattcccact aaacggcaa    1260
gtcactgtct cactcgaatc taactcttcc atgaactcca acactccgtt ggtgcggatt   1320
accagattgt cctcatccga cggtcccatg ttggcaaatg tcagtgagct ggaattgccg   1380
cccgatccca aatgggaact tgcaagatcc cggcttactc tcggtaagcc cctgggcgaa   1440
ggttgctttg gacaagtcgt catggccgaa gcgattggaa tcgataaaga caaacccaac   1500
aaggctataa cggtcgcagt aaaaatgttg aaagatgacg cgaccgacaa ggacctgtca   1560
gatctggtct cagagatgga aatgatgaag atgattggta aacacaagaa tataatcaag   1620
ttgcttggag catgtacgca agacggccct ctctacgttc tcgtggagta tgcctctaag   1680
ggcaatttga gggagtacct gagagctcgc agacctccgg gcatggatta tagtttcgac   1740
acttgtaagc tgccggagga gcaacttacc ttcaaggatc ttgtaagttg cgcgtaccag   1800
gttgcaaggg ggatggaata cctcgccagt caaaagtgca tacatagaga tttggcagcg   1860
aggaacgtgc tcgtgactga ggacaacgtc atgaaaattg cggactttgg gcttgcacgg   1920
gatgttcata acatcgatta ctacaagaaa actactaacg gacggctccc tgtgaagtgg   1980
atggctccag aagcgctttt tgatagagtt tacacacatc aaagtgacgt atggagtttt   2040
ggagtattgc tctgggagat tttcaccttg ggagggtctc cttaccctgg aatacccgct   2100
gaagagctct ttaagctgct taaagaaggc cacaggatgg acaagccggc gaactgcact   2160
catgatctgt acatgataat gagagagtgc tggcacgccg ttccctccca gcggccgaca   2220
ttcaagcagc tggtggaaga ccttgatagg gtactcacta tgacgtccac cgatgagtat   2280
ctggacttgt ctgttccatt cgaacaatac tctccggccg gtcaggatac gcattccact   2340
tgctccagtg gtgatgattc tgtctttgca cacgatcttc tcccagacga accctgtctt   2400
cctaaacacg taccgtgtaa cggtgtcata aggacatag                          2439
```

SEQ ID NO: 98              moltype = DNA  length = 2439
FEATURE                    Location/Qualifiers
source                     1..2439
                           mol_type = other DNA
                           organism = synthetic construct
SEQUENCE: 98
```
atgtcagaag ctggtggcgg cgccgctgcc gcagcctcac tcccgagatc aagggccggt     60
ggcatgcgcg cggcatgggg atccgtgtgg tgtttgtgcc tcgcggcggc tgtcggagct    120
ctgccggctg caaggcgcag gggagcggaa cggagcggtg gccaggcggc ggagtatctc    180
cggagtgaaa ctgcatttct tgaggagctt gttttcggtt caggggatac catcgagctt    240
tcctgtaaca cacaatcttc aagtgtaagc gtattctggt tcaaagatgg tataggcatt    300
gcgcccagta atagaacaca catcgggcag aaacttttga agatcatcaa cgtttcatat    360
gatgattccg gactgtactc atgtaagcca aggcacagta acgaggtgct tgggaacttc    420
acagtcaggg ttacaggcgt accattctgg acgaggcccg ataagatgga aaaaaaactt    480
ttggcagtgc ccgcagccaa tacagtgcgg ttccgctgcc ccgcaggtgg gaatccgacg    540
cccacaattt attggctgaa gaatggcaag gagttcaaag gagaacatag gatcggcgga    600
atcaaactga ggcaccagca atggtctctg gtgatggaat cagtagtccc atctgaccgc    660
ggtaactaca cgtgcgtagt agaaaacaag tatgggaata ttcggcatac ctaccagctc    720
gatgtgctcg agagatctcc tcacaggcct atcttgcagg ctggactgcc agctaatcaa    780
acagtagttg tcggatctaa cgtggagttc cactgcaaag tttactcaga cgcccaaccg    840
cacattcaat ggcttaaaca cgtggaggtt aacggtagca agtatggacc tgatgggact    900
ccctatgtga cagtccttaa gagttggatt tctaagaatg ccgaggcgga tgcgaacttg    960
aacctgttta acgtaaccga gcaggacgag ggcgaatatc tttgtcgcgc taacaacttc   1020
gttggaatag cggagaagcc cttctggctg catatacgga agccaaagcc ggcggaggag   1080
ttgatggaga tggatgactc cggttccgta tacgccggaa tccttagcta cggaaccggg   1140
ctggtgctgt ttatcctcgt tttggttatt gttattatat gccgcatgaa gatgccaaac   1200
aaaaaggcaa tgaatactac aactgtgcag aaagtgtcaa aattcccact aaacggcaa    1260
gtcactgtct cactcgaatc taactcttcc atgaactcca acactccgtt ggtgcggatt   1320
accagattgt cctcatccga cggtcccatg ttggcaaatg tcagtgagct ggaattgccg   1380
cccgatccca aatgggaact tgcaagatcc cggcttactc tcggtaagcc cctgggcgaa   1440
ggttgctttg gacaagtcgt catggccgaa gcgattggaa tcgataaaga caaacccaac   1500
aaggctataa cggtcgcagt aaaaatgttg aaagatgacg cgaccgacaa ggacctgtca   1560
gatctggtct cagagatgga aatgatgaag atgattggta aacacaagaa tataatcaac   1620
ttgcttggag catgtacgca agacggccct ctctacgttc tcgtggagta tgcctctaag   1680
ggcaatttga gggagtacct gagagctcgc agacctccgg gcatggatta tagtttcgac   1740
acttgtaagc tgccggagga gcaacttacc ttcaaggatc ttgtaagttg cgcgtaccag   1800
gttgcaaggg ggatggaata cctcgccagt caaaagtgca tacatagaga tttggcagcg   1860
aggaacgtgc tcgtgactga ggacaacgtc atgaaaattg cggactttgg gcttgcacgg   1920
```

-continued

```
gatgttcata acatcgatta ctacaaggaa actactaacg gacggctccc tgtgaagtgg   1980
atggctccag aagcgctttt tgatagagtt tacacacatc aaagtgacgt atggagtttt   2040
ggagtattgc tctgggagat tttcaccttg ggagggtctc cttaccctgg aatacccgtc   2100
gaagagctct ttaagctgct taaagaaggc cacaggatgg acaagccggc gaactgcact   2160
catgatctgt acatgataat gagagagtgc tggcacgccg ttccctccca gcggccgaca   2220
ttcaagcagc tggtggaaga ccttgatagg gtactcacta tgacgtccac cgatgagtat   2280
ctggacttgt ctgttccatt cgaacaatac tctccggccg gtcaggatac gcattccact   2340
tgctccagtg gtgatgattc tgtctttgca cacgatcttc tcccagacga accctgtctt   2400
cctaaacacg taccgtgtaa cggtgtcata aggacatag                          2439
```

SEQ ID NO: 99          moltype = DNA  length = 2439
FEATURE              Location/Qualifiers
source               1..2439
                    mol_type = other DNA
                    organism = synthetic construct SEQUENCE: 99
```
atgtcagaag ctggtggcgg cgccgctgcc gcagcctcac tcccgagatc aagggccggt   60
ggcatgcgcg cggcatgggg atccgtgtgg tgtttgtgcc tcgcgcgcgt gtcggagct    120
ctgccggctg caaggcgcag gggagcggaa cggagcggtg gccaggcggc ggagtatctc   180
cggagtgaaa ctgcatttct tgaggagctt gttttcggtt caggggatac catcgagctt   240
tcctgtaaca cacaatcttc aagtgtaagc gtattctggt tcaaagatgg tataggcatt   300
gcgccagta atagaacaca catcgggcag aaacttttga agatcatcaa cgtttcatat    360
gatgattccg gactgtactc atgtaagcca aggcacagta acgaggtgct gggaacttc    420
acagtcaggg ttacaggcgt accattctgg acgaggcccg ataagatgga aaaaaaactt    480
ttggcagtgc ccgcagccaa tacagtgcgg ttccgctgcc ccgcaggtgg gaatccgacg   540
cccacaattt attggctgaa gaatggcaag gagttcaaag gagaacatag gatcggcgga   600
atcaaactga ggcaccagca atggtctctg gtgatggaat cagtagtccc atctgaccgc   660
ggtaactaca cgtgcgtagt agaaaacaag tatgggaata ttcggcatac ctaccagctc   720
gatgtgctcg agagatctcc tcacaggcct atcttgcagg ctggactgcc agctaatcaa    780
acagtagttg tcggatctaa cgtggagttc cactgcaaga tttactcaga cgcccaaccg   840
cacattcaat ggcttaaaca cgtggaggtt aacggtagca agtatggacc tgatgggact   900
ccctatgtga cagtccttaa gagttggatt tctaagaatg ccgaggcgga tgcgaacttg   960
aacctgtttta acgtaaccga gcaggacgag ggcgaatatc tttgtcgcgc taacaacttc   1020
gttggaatag cggagaagcc cttctggctg catatacgga agccaaagcc ggcggaggag   1080
ttgatggaga tggatgactc cggttccgta tacgccggaa tccttagcta cggaaccggg   1140
ctggtgctgt ttatcctcgt tttggttatt gttattatat gccgcatgaa gatgccaaac   1200
aaaaaggcaa tgaatactac aactgtgcag aaagtgtcaa aattcccact taaacggcaa   1260
gtcactgtct cactcgaatc taactcttcc atgaactcca acactccgtt ggtgcggatt   1320
accagattgt cctcatccga cggtcccatg ttggcaaatg tcagtgagct ggaattgccg   1380
cccgatccca aatgggaact tgcaagatcc cggcttactc tcggtaagcc cctgggcgaa   1440
ggttgctttg gacaagtcgt catggccgaa gcgattggaa tcgataaaga caaacccaac   1500
aaggctataa cggtcgcagt aaaaatgttg aaagatgacg cgaccgacaa ggacctgtca   1560
gatctggtct cagagatgga aatgatgaag atgattggta aacacaagaa tataatcaag   1620
ttgcttggag catgtacgca agacggccct ctctacgttc tcgtggagta tgcctctaag   1680
ggcaatttga gggagtacct gagagctcgc agacctccgg gcatggatta tagtttcgac   1740
acttgtaagc tgccggagga gcaacttacc ttcaaggatc ttgtaagttg cgcgtaccag   1800
gttgcaaggg ggatggaata cctcgccagt caaaagtgca tacatagaga tttggcagcg   1860
aggaacgtgc tcgtgactga ggacaacgtc atgaaaattg cggactttgg gcttgcacgg   1920
gatgttcata acatcgatta ctacaaggaa actactaacg gacggctccc tgtgaagtgg   1980
atggctccag aagcgctttt tgatagagtt tacacacatc aaagtgacgt atggagtttt   2040
ggagtattgc tctgggagat tttcaccttg ggagggtctc cttaccctgg aatacccgtc   2100
gaagagctct ttaagctgct taaagaaggc cacaggatgg acaagccggc gaactgcact   2160
catgatctgt acatgataat gagagagtgc tggcacgccg ttccctccca gcggccgaca   2220
ttcaagcagc tggtggaaga ccttgatagg gtactcacta tgacgtccac cgatgagtat   2280
ctggacttgt ctgttccatt cgaacaatac tctccggccg gtcaggatac gcattccact   2340
tgctccagtg gtgatgattc tgtctttgca cacgatcttc tcccagacga accctgtctt   2400
cctaaacacg taccgtgtaa cggtgtcata aggacatag                          2439
```

SEQ ID NO: 100        moltype = DNA  length = 1299
FEATURE              Location/Qualifiers
source               1..1299
                    mol_type = other DNA
                    organism = synthetic construct SEQUENCE: 100
```
atgggatcat ccaagtcaaa accgaaagac ccgtcacaga gacgcatgaa gatgccaaac   60
aaaaaggcaa tgaatactac aactgtgcag aaagtgtcaa aattcccact taaacggcaa   120
gtcactgtct cactcgaatc taactcttcc atgaactcca acactccgtt ggtgcggatt   180
accagattgt cctcatccga cggtcccatg ttggcaaatg tcagtgagct ggaattgccg   240
cccgatccca aatgggaact tgcaagatcc cggcttactc tcggtaagcc cctgggcgaa   300
ggttgctttg gacaagtcgt catggccgaa gcgattggaa tcgataaaga caaacccaac   360
aaggctataa cggtcgcagt aaaaatgttg aaagatgacg cgaccgacaa ggacctgtca   420
gatctggtct cagagatgga aatgatgaag atgattggta aacacaagaa tataatcaac   480
ttgcttggag catgtacgca agacggccct ctctacgttc tcgtggagta tgcctctaag   540
ggcaatttga gggagtacct gagagctcgc agacctccgg gcatggatta tagtttcgac   600
acttgtaagc tgccggagga gcaacttacc ttcaaggatc ttgtaagttg cgcgtaccag   660
gttgcaaggg ggatggaata cctcgccagt caaaagtgca tacatagaga tttggcagcg   720
aggaacgtgc tcgtgactga ggacaacgtc atgaaaattg cggactttgg gcttgcacgg   780
gatgttcata acatcgatta ctacaaggaa actactaacg gacggctccc tgtgaagtgg   840
atggctccag aagcgctttt tgatagagtt tacacacatc aaagtgacgt atggagtttt   900
```

```
ggagtattgc tctgggagat tttcaccttg ggagggtctc cttaccctgg aataccegtc      960
gaagagctct ttaagctgct taaagaaggc cacaggatgg acaagccggc gaactgcact     1020
catgatctgt acatgataat gagagagtgc tggcacgccg ttccctccca gcggccgaca     1080
ttcaagcagc tggtggaaga ccttgatagg gtactcacta tgacgtccac cgatgagtat     1140
ctggacttgt ctgttccatt cgaacaatac tctccggccg gtcaggatac gcattccact     1200
tgctccagtg gtgatgattc tgtctttgca cacgatcttc tcccagacga accctgtctt     1260
cctaaacacg taccgtgtaa cggtgtcata aggacatag                            1299

SEQ ID NO: 101              moltype = DNA   length = 2409
FEATURE                    Location/Qualifiers
source                     1..2409
                           mol_type = other DNA
                           organism = synthetic construct
SEQUENCE: 101
atgcttcctc tgcgcctggt tctcgctggc ctcttggtcg cagcgggttc agcggcgagt      60
catagggggag aaatggagcc ggaactcttt gagtctccac tcttggaatc cgaagaagaa     120
cacctccttc tggacccagg aaacgcattg aaactctatt gtgacgtaaa ccagtccgga      180
gctagtgtgg tttggtataa ggagagtaga cctctgctgc cagggccccg cgtcagattg      240
caacaaagcg ttcttgaaat agcggaagta gcttacgagg attccggcct ctacgtctgt      300
agagctcgcg gaaccggtga ggtccttagg aacttcacca tatcagttgt agattcactt      360
gcctcaggcg atgacgatga agacagcgat ggggatggtc cacatggaga ccgctctgaa      420
gaaccagtat acgttcacag agcaccttat tggacccatc cacacaggat ggataaaaaa      480
ctctacgctg ttcctgcggg caataccgtg aaattccgct gtccagcgag tgggtctcca      540
agcccgtcca ttagatggtt taagaatggc agagagtttc gcggggagca cagaataggg      600
ggcattaggc tccggcatca gcattggtca ctcgttatgg agtcagtcgt gccgtctgat      660
aggggggaatt acacctgctt ggtagagaac cggtttggtt caatccgcta tagttatctg      720
ctggatgtcc tcgaacgctc cccacacaga cccatcttgc aagctggact tccagctaac      780
acaacagctc tggtaggttc agatgtggaa tttttctgca aggtatactc tgatgctcaa      840
ccgcacatac agtggttgaa acacattgaa gttaacgggt cctcatatgg gccagacggt      900
gtaccctacg tgcaggtact gaagacggcc gacattaatt catctgaggt tgaggtgctg      960
tatttgcgga acgtcacaat ggaagacgcc ggggagtata cttgtcttgc cggtaatagt     1020
attgggctgt cctatcagtc cgcgtggctc accgtcctgc cagaagagct ggttcatgag     1080
gctgaggcac ctgaggcgaa atacaccgac atcataattt acacttccgg atcattggcc     1140
gtggccaatgg ctcttatcat cgtcgttctg tgtaggatgc aaactcagag tctaaaacaa     1200
ccccttgaac ccatggcagt cacacaaattg agcaaatttc ctcttattag acagtttttcc    1260
cttgactcaa gtagctcagg gaaatctagc acatcactta tgcgggtgac gagactgtct     1320
tccagctgcg cgcccatgtt ggctgggggtg gtggaacttg atctgcctct ggacagcaag    1380
tgggaatttc gagggagaa actggttctt gggaagccgc tcggcgaagg ctgtttttggt      1440
caggtggtca gggcggaagc gtacgggatc gacagacagt ggcctgatcg cgcagttact     1500
gtcgcagtaa aaatgctgaa agacaacgct actgataagg atctggcaga cctgataagt     1560
gaaatggaga tgatgaaact gatggacaaa cacaagaaca tcattaatct cttgggtgta    1620
tgtacacaag atgggcctct gtatgttata gtagagtttg cggccaaagg caaccttcgg     1680
gagtatcttc gcgctagaag accgccaatg cccgactaca cgttcgatat tacagaactc     1740
catgaggaac aactttgttt taaggatctt gttagctgtg tgtatcaagt cgcccggggg    1800
atggagtatc tggaatcaag acggtgtata caccgcgacc tcgctgccag aaacgttctc     1860
gtcacggcgg aaaatgtgat gaagatcgcc gacttcggac ttgccaggga tgtccatgat    1920
atagacatt acaaaaaaac tctaatgggg cggctccctg tcaagtggat ggcgcccgaa      1980
gcactgtttg acagagtata cacgcaccag tctgacgtgt ggtcatttgg catactgatg     2040
tgggaaattt ttacactcgg tggttcacct tatcctggca tccctgttga ggagcttttt     2100
aaattgctca agagggcca cagaatggac tgtcctagta actgcaccca tgagctgtat      2160
atgctcatgc gcgagtgctg gcatgcggtg cctagtcaaa ggccaacctt caaacagctc    2220
gtcgaaggcc tggacaagat tcttgctgca ataagcgagg agtacctcga cttgtctatg     2280
ccattcgagc aatactcacc ttcttgtgaa gacacgacga gtacatgcag cagcgacgac     2340
tctgtattta cacacgaccc tttgcccctt gctccttgcc tgtttgcctg tcctagtggc    2400
cgcacctag                                                            2409

SEQ ID NO: 102              moltype = DNA   length = 2409
FEATURE                    Location/Qualifiers
source                     1..2409
                           mol_type = other DNA
                           organism = synthetic construct
SEQUENCE: 102
atgcttcctc tgcgcctggt tctcgctggc ctcttggtcg cagcgggttc agcggcgagt      60
catagggggag aaatggagcc ggaactcttt gagtctccac tcttggaatc cgaagaagaa     120
cacctccttc tggacccagg aaacgcattg aaactctatt gtgacgtaaa ccagtccgga      180
gctagtgtgg tttggtataa ggagagtaga cctctgctgc cagggccccg cgtcagattg      240
caacaaagcg ttcttgaaat agcggaagta gcttacgagg attccggcct ctacgtctgt      300
agagctcgcg gaaccggtga ggtccttagg aacttcacca tatcagttgt agattcactt      360
gcctcaggcg atgacgatga agacagcgat ggggatggtc cacatggaga ccgctctgaa      420
gaaccagtat acgttcacag agcaccttat tggacccatc cacacaggat ggataaaaaa      480
ctctacgctg ttcctgcggg caataccgtg aaattccgct gtccagcgag tgggtctcca      540
agcccgtcca ttagatggtt taagaatggc agagagtttc gcggggagca cagaataggg      600
ggcattaggc tccggcatca gcattggtca ctcgttatgg agtcagtcgt gccgtctgat      660
aggggggaatt acacctgctt ggtagagaac cggtttggtt caatccgcta tagttatctg      720
ctggatgtcc tcgaacgctc cccacacaga cccatcttgc aagctggact tccagctaac      780
acaacagctc tggtaggttc agatgtggaa tttttctgca aggtatactc tgatgctcaa      840
ccgcacatac agtggttgaa acacattgaa gttaacgggt cctcatatgg gccagacggt      900
gtaccctacg tgcaggtact gaagacggcc gacattaatt catctgaggt tgaggtgctg      960
tatttgcgga acgtcacaat ggaagacgcc ggggagtata cttgtcttgc cggtaatagt     1020
```

```
attgggctgt cctatcagtc cgcgtggctc accgtcctgc cagaagagct ggttcatgag   1080
gctgaggcac ctgaggcgaa atgtaccgac atcataattt acacttccgg atcattggcc   1140
gtggcaatgg ctcttatcat cgtcgttctg tgtaggatgc aaactcagag ctctaaacaa   1200
ccccttgaac ccatggcagt acacaaattg agcaaatttc ctcttattag acagtttttcc  1260
cttgactcaa gtagctcagg gaaatctagc acatcactta tgcgggtgac gagactgtct   1320
tccagctgcg cgcccatgtt ggctggggtg gtggaacttg atctgcctct ggacagcaag   1380
tgggaatttc cgagggagaa actggttctt gggaagccgc tcggcgaagg ctgtttttggt  1440
caggtggtca gggcggaagc gtacgggatc gacagacagt ggcctgatcg cgcagttact   1500
gtcgcagtaa aaatgctgaa agacaacgct actgataagg atctggcaga cctgataagt   1560
gaaatggaga tgatgaaact gatggacaaa cacaagaaca tcattaatct cttgggtgta   1620
tgtacacaag atgggcctct gtatgttata gtagagtttg cggccaaagg caaccttcgg   1680
gagtatcttc gcgctagaag accgccaatg cccgactaca cgttcgatat tacagaactc   1740
catgaggaac aactttgttt taaggatctt gttagctgtg tgtatcaagt cgcccggggg   1800
atggagtatc tggaatcaag acggtgtata caccgcgacc tcgctgccag aaacgttctc   1860
gtcacggcgg aaaatgtgat gaagatcgcc gacttcggac ttgccaggga tgtccatgat   1920
atagactatt acaaaaaaac atctaatggg cggctccctg tcaagtggat ggcgcccgaa   1980
gcactgtttg acagagtata cacgcaccag tctgacgtgt ggtcatttgg catactgatg   2040
tgggaaattt ttacactcgg tggttcacct tatcctggca tccctgttga ggagctttt    2100
aaattgctca aagagggcca cagaatggac tgtcctagta actgcaccca tgagctgtat   2160
atgctcatgc gcgagtgctg gcatgcggtg cctagtcaaa ggccaacctt caaacagctc   2220
gtcgaaggcc tggacaagat tcttgctgca ataagcgagg agtacctcga cttgtctatg   2280
ccattcgagc aatactcacc ttcttgtgaa gacacgacga gtacatgcag cagcgacgac   2340
tctgtattta cacacgaccc tttgcccctt gctccttgcc tgtttgcctg tcctagtggc   2400
cgcacctag                                                          2409
```

SEQ ID NO: 103    moltype = DNA  length = 2409
FEATURE           Location/Qualifiers
source            1..2409
                  mol_type = other DNA
                  organism = synthetic construct
SEQUENCE: 103

```
atgcttcctc tgcgcctggt tctcgctggc ctcttggtcg cagcgggttc agcggcgagt   60
cataggggag aaatggagcc ggaactcttt gagtctccac tcttggaatc cgaagaagaa   120
cacctccttc tggacccagg aaacgcattg aaactctatt gtgacgtaaa ccagtccgga   180
gctagtgtgg tttggtataa ggagagtaga cctctgctgc cagggccccg cgtcagattg   240
caacaaagcg ttcttgaaat agcggaagta gcttacgagg attccggcct ctacgtctgt   300
agagctcgcg gaaccggtga ggtccttagg aacttcacca tatcagttgt agattccactt  360
gcctcaggcg atgacgatga agacagcgat ggggatggtc cacatggaga ccgctctgaa   420
gaaccagtat acgttcacag agcaccttat tggacccatc cacacaggat ggataaaaaa   480
ctctacgctg ttcctgcggg caataccgtg aaattccgct gtccagcgag tgggtctcca   540
agcccgtcca ttagatggtt taagaatggc agagagtttc gcggggagca cagaataggg   600
ggcattaggc tccggcatca gcattggtca ctcgttatgg agtcagtcgt gccgtctgat   660
aggggggaatt acacctgctt ggtagagaac cggtttggtt caatccgcta tagttatctg   720
ctggatgtcc tcgaacgctc cccacacaga cccatcttgc aagctggact tccagctaac   780
acaacagctc tggtaggttc agatgtggaa ttttctgca aggtatactc tgatgctcaa    840
ccgcacatac agtggttgaa acacattgaa gttaacgggg cctcatatgg gccagacggt   900
gtacctacg tgcaggtact gaaagacggcc gacattaatt catctgaggt tgaggtgctg   960
tatttgcgga acgtcacaat ggaagacgcc ggggagtata cttgtcttgc cggtaatagt   1020
attgggctgt cctatcagtc cgcgtggctc accgtcctgc cagaagagct ggttcatgag   1080
gctgaggcac ctgaggcgaa atacaccgac atcataattt acacttccgg atcattggcc   1140
gtggcaatgg ctcttatcat cgtcgttctg tgtaggatgc aaactcagag ctctaaacaa   1200
cccctttgaac ccatggcagt acacaaattg agcaaatttc ctcttattag acagtttttcc 1260
cttgactcaa gtagctcagg gaaatctagc acatcactta tgcgggtgac gagactgtct   1320
tccagctgcg cgcccatgtt ggctggggtg gtggaacttg atctgcctct ggacagcaag   1380
tgggaatttc cgagggagaa actggttctt gggaagccgc tcggcgaagg ctgtttttggt  1440
caggtggtca gggcggaagc gtacgggatc gacagacagt ggcctgatcg cgcagttact   1500
gtcgcagtaa aaatgctgaa agacaacgct actgataagg atctggcaga cctgataagt   1560
gaaatggaga tgatgaaact gatggacaaa cacaagaaca tcattaatct cttgggtgta   1620
tgtacacaag atgggcctct gtatgttata gtagagtttg cggccaaagg caaccttcgg   1680
gagtatcttc gcgctagaag accgccaatg cccgactaca cgttcgatat tacagaactc   1740
catgaggaac aactttgttt taaggatctt gttagctgtg tgtatcaagt cgcccggggg   1800
atggagtatc tggaatcaag acggtgtata caccgcgacc tcgctgccag aaacgttctc   1860
gtcacggcgg aaaatgtgat gaagatcgcc gacttcggac ttgccaggga tgtccatgat   1920
atagactatt acaaagaaac atctaatggg cggctccctg tcaagtggat ggcgcccgaa   1980
gcactgtttg acagagtata cacgcaccag tctgacgtgt ggtcatttgg catactgatg   2040
tgggaaattt ttacactcgg tggttcacct tatcctggca tccctgttga ggagctttt    2100
aaattgctca aagagggcca cagaatggac tgtcctagta actgcaccca tgagctgtat   2160
atgctcatgc gcgagtgctg gcatgcggtg cctagtcaaa ggccaacctt caaacagctc   2220
gtcgaaggcc tggacaagat tcttgctgca ataagcgagg agtacctcga cttgtctatg   2280
ccattcgagc aatactcacc ttcttgtgaa gacacgacga gtacatgcag cagcgacgac   2340
tctgtattta cacacgaccc tttgcccctt gctccttgcc tgtttgcctg tcctagtggc   2400
cgcacctag                                                          2409
```

SEQ ID NO: 104    moltype = DNA  length = 2409
FEATURE           Location/Qualifiers
source            1..2409
                  mol_type = other DNA
                  organism = synthetic construct
SEQUENCE: 104

-continued

```
atgcttcctc tgcgcctggt tctcgctggc ctcttggtcg cagcgggttc agcggcgagt      60
cataggggag aaatggagcc ggaactcttt gagtctccac tcttggaatc cgaagaagaa     120
cacctccttc tggacccagg aaacgcattg aaactctatt gtgacgtaaa ccagtccgga     180
gctagtgtgg tttggtataa ggagagtaga cctctgctgc cagggccccg cgtcagattg     240
caacaaagcg ttcttgaaat agcggaagta gcttacgagg attccggcct ctacgtctgt     300
agagctcgcg gaaccggtga ggtccttagg aacttcacca tatcagttgt agattcactt     360
gcctcaggcg atgacgatga agacagcgat ggggatggtc cacatggaga ccgctctgaa     420
gaaccagtat acgttcacag agcacctat  tggacccatc cacacaggat ggataaaaaa     480
ctctacgctg ttcctgcggg caataccgtg aaattccgct gtccagcgag tgggtctcca     540
agcccgtcca ttagatggtt taagaatggc agagagtttc gcggggagca cagaataggg     600
ggcattaggc tccggcatca gcattggtca ctcgttatgg agtcagtcgt gccgtctgat     660
aggggggaatt acacctgctt ggtagagaac cggtttggtt caatccgcta tagttatctg     720
ctggatgtcc tcgaacgctc cccacacaga cccatcttgc aagctggact tccagctaac     780
acaacagctc tggtaggttc agatgtggaa tttttctgca aggtatactc tgatgctcaa     840
ccgcacatac agtggttgaa acacattgaa gttaacgggt cctcatatgg gccagacggt     900
gtaccctacg tgcaggtact gaagacggcc gacattaatt catctgaggt tgaggtgctg     960
tatttgcgga acgtcacaat ggaagacgcc ggggagtata cttgtcttgc cggtaatagt    1020
attgggctgt cctatcagtc cgcgtggctc accgtcctgc cagaagagct ggttcatgag    1080
gctgaggcac ctgaggcgaa atgtaccgac atcataattt cacttccgg  atcattggcc    1140
gtggcaatgg ctcttatcat cgtcgttctg tgtaggatgc aaactcagag ctctaaacaa    1200
cccccttgaac ccatggcagt acacaaattg agcaaatttc ctcttattag acagtttttcc    1260
cttgactcaa gtagctcagg gaaatctagc acatcactta tgcgggtgac gagactgtct    1320
tccagctgcg cgcccatgtt ggctgggggtg gtggaacttg atctgcctct ggacagcaag    1380
tgggaatttc cgagggagaa actggttctt gggaagccgc tcggcgaagg ctgtttttggt    1440
caggtggtca gggcggaagc gtacgggatc gacagacagt ggcctgatcg cgcagttact    1500
gtcgcagtaa aaatgctgaa agacaacgct actgataagg atctggcaga cctgataagt    1560
gaaatggaga tgatgaaact gatggacaaa cacaagaaca tcattaatct cttgggtgta    1620
tgtacacaag atgggcctct gtatgttata gaagagtttg cggccaaagg caaccttcgg    1680
gagtatcttc gcgctagaag accgccaatg cccgactaca cgttcgatat tacagaactc    1740
catgaggaac aactttgttt taaggatctt gttagctgtg tgtatcaagt cgcccgggga    1800
atggagtatc tggaatcaag acggtgtata caccgcgacc tcgctgccag aaacgttctc    1860
gtcacggcgg aaaatgtgat gaagatcgcc gacttcggac ttgccaggga tgtccatgat    1920
atagactatt acaaaaaaac atctaatggg cggctccctg tcaagtggat ggcgcccgaa    1980
gcactgtttg acagagtata cacgcaccag tctgacgtgt ggtcatttgg catactgtgg    2040
tgggaaattt ttacactcgg tggttcacct tatcctggca tccctgttga ggagcttttt    2100
aaaattgctca aagagggcca cagaatggac tgtcctagta actgcacccca tgagctgtat    2160
atgctcatgc gcgagtgctg gcatgcggtg cctagtcaaa ggccaaccttt caaacagctc    2220
gtcgaaggcc tggacaagat tcttgctgca ataagcgagg agtacctcga cttgtctatg    2280
ccattcgagc aatactcacc ttcttgtgaa gacacgacga gtacatgcag cagcgacgac    2340
tctgtattta cacacgaccc tttgcccctt gctccttgcc tgtttgcctg tcctagtggc    2400
cgcacctag                                                            2409
```

```
SEQ ID NO: 105          moltype = DNA  length = 462
FEATURE                 Location/Qualifiers
source                  1..462
                        mol_type = other DNA
                        organism = synthetic construct
SEQUENCE: 105
atggaaaaaa tcaacagtct ttcaacacaa ttagttaagt gctgcttttg tgatttcttg      60
aaggtgaaga tgcacactgt gtcctacatt catttcttct accttggcct gtgtttgctt     120
accttaacca gttctgctgc tgccggccca gaaacactgt gtggtgctga gctggttgat     180
gctcttcagt tcgtatgtgg agacagaggc ttctacttca gtaagcctac agggtatgga     240
tccagcagta gacgcttaca ccacaaggga atagtggatg agtgctgctt ccagagttgt     300
gacctgagga ggctggagat gtactgtgct ccaataaagc cacctaaatc tgcacgctct     360
gtacgtgctc agcgccacac tgatatgcca aaagcacaaa aggaagtgca tttgaagaat     420
acaagtagag ggaacacagg aaacagaaac tacagaatgt aa                        462
```

```
SEQ ID NO: 106          moltype = DNA  length = 213
FEATURE                 Location/Qualifiers
source                  1..213
                        mol_type = other DNA
                        organism = synthetic construct
SEQUENCE: 106
ggcccagaaa cactgtgtgg tgctgagctg gttgatgctc ttcagttcgt atgtggagac      60
agaggcttct acttcagtaa gcctacaggg tatggatcca gcagtagacg cttacaccac     120
aagggaatag tggatgagtg ctgcttccag agttgtgacc tgaggaggct ggagatgtac     180
tgtgctccaa taaagccacc taaatctgca taa                                  213
```

```
SEQ ID NO: 107          moltype = DNA  length = 4092
FEATURE                 Location/Qualifiers
source                  1..4092
                        mol_type = other DNA
                        organism = synthetic construct
SEQUENCE: 107
atgaaatctg gggctggggg agggaccctc gccgtattct gtgggctttt gttggcgttc      60
gccgcactct gtctcgtcc  gaccaatggt gaaatatgcg gccgaatgt  ggatattaga     120
aacgatattc acgagctcaa gaggctcgaa aattgtactg tagtggaggg gtttctgcaa     180
atactgctta tcagtaaggc ggaagattac cgcaacttcc gctttcctaa gctgactgtg     240
atcacagact atctcctgct gttcagagtt gccggacttg aatccctctc agatctgtttt     300
```

-continued

```
cctaacctca cagtgatcag gggtagaaac ctgttctaca actatgctct cgtaatattt   360
gagatgacga accttaagga gattggactc cacaatcttc gcaacataac cagggggtgct  420
ataaggatcg aaaaaaatag cgacctgtgc tatctttcta cagtagactg gagtctcata   480
ttggacgcag tatccaacaa ctatatagtt ggcaacaagc ctcccaaaga atgcggtgat   540
ctctgtcctg gaactatgga ggaaaaacct ctctgcgaaa agactagtat aaacaacgag   600
tacaactata ggtgttggac taccaaccac tgccagaaga tgtgcccgag cagctgcggc   660
aagcgcgcgt gcaccgatca gaatgaatgc tgccacccg aatgtcttgg tagctgtacg    720
gctcccgaca ataacacagc ctgcgttgcg tgtcgcaatt actattatga gggtgtctgt   780
atgcctacct gtccgcctaa cacatataag ttcgagggg ggcgctgcgt gacaaaagaa    840
ttttgttcca aggtcccagc aacggagacg tctgactatg aaaggtttgt aattcataat   900
gatgaatgta tggcggaatg cccatctgga tttatcagga acggtagtca gagcatgttt   960
tgctccccat gtgaaggccc atgtcccaaa atttgtgaag acgggaagac gaagacaata  1020
gatagcgtca cttctgctca aatgcttcag ggatgtacca tcttgaaagg aaatctcttg  1080
attaacattc gccggggtaa taatatagca agtgagcttg aaaactttat ggggctcata  1140
gaaacggtaa ctgggtatgt caagatccgc catagtcatg cactcgtgtc actttcattc  1200
ttgaagaatc tccgctatat actcggcgaa gagcaagttg acggcaacta ctcattttac  1260
gttctcgata atcataattt gcagcagctt tgggactgga atcaccacaa cttgaccatt  1320
aaagaaggaa agatgtactt cgctttcaat ccgaaacttt gtgtatccga aatttaccgc  1380
atggaagagg tgtctggaac taaaggacgc cagtcaaaag gagatataaa tcccaggaat  1440
aatggagaaa gggcgtcctg tgagagccat atattgagat tcgtgagcaa taccacgctg  1500
aagaaccgga taaaactcac ctgggagaga tacaggcccc cggattaccg ggacctcatc  1560
tctttcacgg tttattacaa ggaggccccc ttcaaaaacg tcacagagta cgatgggcaa  1620
gatgcctgcg gctccaactc ttggaacatg gtcgacgtag acttgccccc taacaaaag   1680
aatgaccctg gtatattgct tcaaggactt aaaccttgga cgcagtacgc catatacgtc  1740
aaagccgtga cccttacaat gatggaaaac caccacatcc acgggctaa atccgagatt   1800
gtttatataa ggacaaatgc agccgtcccc agcatacctc tgacgtaat atctgcctct   1860
aatagcagca gccagctcat tgtgaagtgg aatcctcctt cacttcccaa cgggaatctg  1920
tcttattaca ttgtccgctg gcaacaacaa cctcaggatt cttatttgta tcggcataac  1980
tactgtagta aagacaaggt gccgattcgc cggtacgcgg acggtactat tgacacggaa  2040
gaagcaacag agccaacaaa acccgaagga tgcggccggtg aaaaaggtcc gtgttgtgca  2100
tgccctaaga ccgaagctga gaagcaagct gaaaaggaag aagctgaata ccgcaaggtg  2160
tttgagaact tcctgcataa ctccatcttc gttcctcgcc cggatagaaa gaggcgcgac  2220
gtggttcagga ttgctaacgc cacgctcgct acgaggaatc ggaacattac tggtgcggat  2280
cacttcacca atgcatccga tgcggaagag tccgaagtag agtacccatt ttttgagacg  2340
aaagtcgacg ggaaggagag aacggtaata tctcatttgc agccttttac cctttatga   2400
atagatatcc acagctgcaa tcacgaagca gacaccttg gttgtagtgc ttctaacttc   2460
gtgtttgccc gcacgatgcc ctctgaaggc gctgacaata tacccggaac cgtagcatgg   2520
gaagcgaagg aggagaacac ggtttatctt aaatggttgg aacccaccaa ccctaacgga   2580
cttatcttga tgtacgagat taaatatgga caacacgggg aggaaaagag ggagtgtgtc   2640
agtaggcaag aatacaaaaa acttggtggc gccaaattga cacacttgaa ccctggtaat   2700
tacagcgcgc gcgtgcaggc gactagcttg gcaggtaatg gttcttggac tgaacccgtc  2760
tccttctatg ttcagcccaa atccgcaaat tacgacaact ttctccattt gataaatagtc  2820
cttccaatag ccttcctgtt gataataggt ggcctcctca ttatgttgta gtctttaat   2880
aagaaacgga actctgaccg gctcggaaat ggtgttctgt atgcaagtgt taatccagaa   2940
tatttctctg catcagacgt ttatgtgccg gacgagtggg aagtgccaag ggagaaaatt  3000
acaatgtgca gagaactcgg acagggttct tttggcatgg tttacgaggg catcgcaaaa  3060
ggcgtggtga aggacgaacc cgagacgaga gttgctatca aaacagtcaa tgagtcagct  3120
tctatgcgcg aacggattga gtttttgaat gaggccagtg taatgaagga gtttaactgc  3180
caccacgtcg tacggttgct tggcgtcgtg tctcaaggac agcccaccct cgttattatg  3240
gagttgatga cccgggggga tctcaagtcc tacttgaggt ctcttcgccc tgacactgag  3300
tcaaacccag ggcaggcacc tcctacgctg aaaaaaatga tacaaatggc tggagaaatc  3360
gccgatggga tggcgtatct caacgctaat aagtttgtac accgcgatct ggccgcaaga  3420
aattgtatgg tcgcagagga ttttactgtc aagatcggcg atttcggcat gacacgcgac  3480
atctatgaga ccgactacta taggaagggg gggaagggtt tgctcccagt aaggtggatg  3540
tcaccggaga gcctcaagga tgggtgttc acgactcaca gcgatgtctg gtctttggga  3600
gttgtactct gggaaatagc tacactggca gagcaaccct accaaggaat gacaaatgaa  3660
caagtcctcc gctttgtaat ggaaggggt cttctcgaaa aaccggacaa ctgcccagac  3720
atgcttttcg agctgatgcg catgtgctgg cagtacaatc ccaaaatgcg cccgtctttt  3780
cttgaaataa tctcaagcat caaggatgaa cttgacccgg cctttaaaga agtatcattt  3840
ttctattccg aagaaaataa accgccagat acagaagaac tcgaccttga gacagaaaac  3900
atggaaagta ttcctctcga tccttcctca actttgcagc cgacggataa acattctggc  3960
cacaaggcgg aaaatggccc gggggttgta gtactcaggg catcatttga agaaaggcag  4020
ccatacgcac atatgaatgg gggtcgcaag aacgagcggg ctttgcctct tccccaatct  4080
tctgcatgct ag                                                       4092
```

```
SEQ ID NO: 108        moltype = DNA   length = 4098
FEATURE               Location/Qualifiers
source                1..4098
                      mol_type = other DNA
                      organism = synthetic construct
SEQUENCE: 108
gaattcatga aatctggggc tggggagg accctcgccg tattctgtgg gcttttgttg     60
gcgttcgccc cactctgtct ctgtccgacc aatggtgaaa tatgcggccc gaatgtggat  120
attagaaacg atattcacga gctcaagagg ctcgaaaatt gtactgtagt ggagggtttt  180
ctgcaaatac tgcttatcag taaggcggaa gattaccgca acttccgctt tcctaagctg  240
actgtgatca cagactatct cctgctgttc agagttgccg gacttgaatc cctctcagat  300
ctgtttccta acctcacagt gatcaggggt agaaacctgt tctacaacta tgctctcgta  360
atatttgaga tgacgaacct taaggagatt ggactccaca atcttcgcaa cataaccagg  420
ggtgctataa ggatcgaaaa aaatagcgac ctgtgctatc tttctacagt agactggagt  480
```

-continued

```
ctcatattgg acgcagtatc caacaactat atagttggca acaagcctcc caaagaatgc    540
ggtgatctct gtcctggaac tatggaggaa aaacctctct gcgaaaagac tagtataaac    600
aacgagtaca actataggtg ttggactacc aaccactgcc agaagatgtg cccgagcagc    660
tgcggcaagc gcgcgtgcac cgatcagaat gaatgctgcc accccgaatg tcttggtagc    720
tgtacggctc ccgacaataa cacagcctgc gttgcgtgtc gcaattacta ttatgagggt    780
gtctgtatgc ctacctgtcc gcctaacaca tataagttcg aggggtggcg ctgcgtgaca    840
aaagaatttt gttccaaggt cccagcaacg gagacgtctg actatgaaag gtttgtaatt    900
cataatgatg aatgtatggc ggaatgccca tctggattta tcaggaacgg tagtcagagc    960
atgttttgct ccccatgtga aggcccatgt cccaaaattt gtgaagacgg gaagacgaag   1020
acaatagata gcgtcacttc tgctcaaatg cttcagggat gtaccatctt gaaaggaaat   1080
ctcttgatta acattcgccg gggtaataat atagcaagtg agcttgaaaa ctttatgggg   1140
ctcatagaaa cggtaactgg gtatgtcaag atccgccata gtcatgcact cgtgtcactt   1200
tcattcttga agaatctccg ctatatactc ggcgaagagc aagtgacgg caactactca   1260
ttttacgttc tcgataatca taatttgcag cagctttggg actggaatca ccacaacttg   1320
accattaaag aaggaaagat gtacttcgct ttcaatccga aactttgtgt atccgaaatt   1380
taccgcatgg aagaggtgtc tggaactaaa ggacgccagt caaaaggaga tataaatccc   1440
aggaataatg agaaagggc gtcctgtgag agccatatat tgagattcgt gagcaatacc   1500
acgctgaaga accggataaa actcacctgg gagagataca ggcccccgga ttaccgggac   1560
ctcatctctt tcacggttta ttacaaggag gcccccttca aaaacgtcac agagtacgat   1620
gggcaagatg cctgcggctc caactcttgg aacatggtcg acgtagactt gcccctaac   1680
aaagagaatg accctggtat attgcttcaa ggacttaaac cttggacgca gtacgccata   1740
tacgtcaaag ccgtgaccct tacaatgatg gaaaaccacc acatccacgg ggctaaatcc   1800
gagattgttt atataaggac aaatgcagcc gtccccagca tacctctcga cgtaatatct   1860
gcctctaata gcagcagcca gctcattgtg aagtggaatc ctccttcact tcccaacggg   1920
aatctgtctt attacattgt ccgctggcaa caacaacctc aggattctta tttgtatcgg   1980
cataactact gtagtaaaga caaggtgccg attcgccggt acgcggacgg tactattgac   2040
acggaagaag caacagagcc aacaaaaccc gaaggatgcg gcggtgaaaa aggtccgtgt   2100
tgtgcgtgcc ctaagaccga agctgagaag caagctgaaa aggaagaagc tgaataccgc   2160
aaggtgtttg agaacttcct gcataactcc atcttcgttc ctcgcccgga tagaaagagg   2220
cgcgacgtgt tcaggattgc taacgccacg ctcgctacga ggaatcggaa cattactggt   2280
gcggatcact tcaccaatgc atccgatgcg gaagagtccg aagtagagta cccatttttt   2340
gagacgaaag tcgacgggaa ggagagaacg gtaatatctc atttgcagcc tttaccctt   2400
tatagaatag atatccacag ctgcaatcac gaagcagaca cccttggttg tagtgcttct   2460
aacttcgtgt ttgcccgcac gatgccctct gaaggcgctg acaatatacc cggaaccgta   2520
gcatgggaag cgaaggagga gaacacggtt tatcttaaat ggttggaacc caccaaccct   2580
aacggactta tcttgatgta cgagattaaa tatggacaac acggggagga aaagaggggag   2640
tgtgtcagta ggcaagaata caaaaaaactt ggtggcgcca aattgacaca cttgaaccct   2700
ggtaattaca gcgcgcgcgt gcaggcgact agcttggcag gtaatggttc ttggactgaa   2760
cccgtctcct tctatgttca gcccaaatcc gcaaattacg acaactttct ccatttgata   2820
atagtccttc caatagcctt cctgttgata ataggtggcc tcctcattat gttgtacgtc   2880
tttaataaga aacggaactc tgaccggctc ggaaatggtg ttctgtatgc aagtgttaat   2940
ccagaatatt tctctgcatc agacgtttat gtgccggacg agtgggaagt gccaagggag   3000
aaaattacaa tgtgcagaga actcggacag ggttcttttg gcatggtttta cgagggcatc   3060
gcaaaaggcg tggtgaagga cgaacccgag acgagagttg ctatcaaaac agtcaatgag   3120
tcagcttcta tgcgcgaacg gattgagttt ttgaatgagg ccagtgtaat gaaggagttt   3180
aactgccacc acgtcgtacg gttgcttggc gtcgtgtctc aaggacagcc caccctcgtt   3240
attatggagt tgatgacccg gggggatctc aagtcctact tgaggtctct tcgccctgac   3300
actgagtcaa acccagggca ggcacctcct acgctgaaaa aaatgataca aatggctgga   3360
gaaatcgccg atgggatggc gtatctcaac gctaataagt ttgtacaccg cgatctggcc   3420
gcaagaaatt gtatggtcgc agaggatttt actgtcaaga tcggcgattt cggcatgaca   3480
cgcgacatct atgagaccga ctactatagg aagggggaga agggtttgct cccagtaagg   3540
tggatgtcac cggagagcct caaggatggg gtgttcacga ctcacagcga tgtctggtct   3600
tttggagttg tactctggga aatagctaca ctggcagagc aaccctacca aggaatgaca   3660
aatgaacaag tcctccgctt tgtaatggaa gggggtcttc tcgaaaaacc ggacaactgc   3720
ccagacatgc ttttcgagct gatgcgcatg tgctggcagt acaatcccaa aatgcgcccg   3780
tcttttcttg aaataatctc aagcatcaag gatgaacttg acccggcctt taaagaagta   3840
tcatttttct attccgaaga aaataaaccg ccagatacag aagaactcga ccttgagaca   3900
gaaaacatgg aaagtattcc tctcgatcct tcctcaactt gcagccgac ggataaacat   3960
tctggccaca aggcggaaaa tggcccgggg gttgtagtac tcagggcatc atttgaagaa   4020
aggcagccat acgcacatat gaatgggggt cgcaagaacg agcatgcttt gcctcttccc   4080
caatcttctg catgctag                                                  4098
```

```
SEQ ID NO: 109          moltype = DNA  length = 3264
FEATURE                 Location/Qualifiers
source                  1..3264
                        mol_type = other DNA
                        organism = synthetic construct
SEQUENCE: 109
atgggtactc ccccaaggac gttcctgatc ctgggatgtt ttctcacagg accgctccta     60
acactttgcc agcttcctct gccgactatt gttcccaata gaaatgagat ggttgtacag    120
ctgaattcca atttcacact caaatgctct ggagacagcg aagtgagctg gcagtaccca    180
gtgaccgagg gaagccacag gatagacatc agacacgagg agaacaacag tggcctcttc    240
gtgacagtgc ttgaagtcgg aaatgcctca gccgctcaca cgggcatgta tgtttgctat    300
tataaccaca cgcaagtgga ggatggggaa gtcgaggtga agcaaacatc catctatgtg    360
cctgacccag acatgccttt cgttccttcc ttaccagaag accagttcat cctagtagaa    420
gaaggtgatc ccactgttat cccttgtcgg acaagtgacc caagtgctga agtgacttta    480
gttaacagtt tagacaagcc tgtctatgct ttctatgaca gcaaacaggg cttcgtaggg    540
aacttccttg caggaccata cacatgcaaa acaatggtta aaggcgtgga gttcaagtcc    600
gatgagttcc tcatctatat tttaagagct acttcacagc tgccggttga aattgaagct    660
```

```
ctgaaaactg tctacaaaac aggcgagacc atcgtagtaa cttgtgtggt cttttgacaat   720
gaggtggtta atttacagtg gaattatccc gggaaagtga aagaaaaagg tctgataaaa   780
cttgatgata tcaaagtccc atcacagaag ttggtttaca cgttgaccat acctgacgca   840
tcagtgaaag acacagggga ttatgaatgt actgcccgac atgcaaccaa ggaggttaag   900
gaaaataaga aagtagtcat tacagttcat gacaaagggt tcattcatct agagcctcaa   960
tttagccctt tggaagctgt caatctacat gaagtcaaaa attttgtcgt cgatgtgcag  1020
gcgtaccccg ctccaaaaat gtactggttg aaggataatg tgactctgat tgaaaacctt  1080
actgagattg ttactagttc aaacagagtc caggaaacac ggtttcaaag tgtactaaaa  1140
ttgatccggg ccaaggaaga agacagtggg tactatactt tggttgctga aaatgaagat  1200
gagattaaga gatacacctt ctcgttgcta atacaagttc cagccttgat cttagacctc  1260
atggacgacc accaaggctc tgctggcagg cagacggtga ggtgcttggc tgaaggtacc  1320
ccgcttcctg atgtggaatg gttggtttgc aaggacatta aaaaatgcag caatgacact  1380
tcctggactc ttctgactaa caatatctct gatatacaca tggaagccca cctggatgag  1440
aggaatatgg tggaaagcca ggtgaccttc cagaaggtag aagaaaccct ggctgtgaga  1500
tgtgtagcaa gaaacgacct tggagctgtt actcgggaac tgaaacttgt ggctcccacc  1560
ttgcgatcag aactgacggt ggctgctgct gtcttagtac tgctggtgat tgtgataatt  1620
tcactgattg tcctggtcat catctggaaa cagaagccaa gatatgagat aagatggaga  1680
gtcattgagt ctatcagccc cgatggccat gaatacattt atgtggaccc aatgcagcta  1740
ccttatgact ccagatggga gtttcctcga gatgggttag tgcttggtcg aatccttggt  1800
tctggtgcat ttgggaaagt ggtggaaggg acagcatatg gattgagtcg ttctcaacct  1860
gtgatgaaag tagccgtgaa aatgctgaaa cctacagcta gatccagtga aaaacaggcg  1920
ctcatgtctg aactgaagat aatgacacat cttgggcccc acctgaatat tgtgaacctg  1980
cttggagctt gtacgaaatc aggtcctatt tacataatca ctgaatactg cttttacggt  2040
gatttggtga actatctgca caagaacagg gacaacttcc tcagccgaca tccagagaaa  2100
ccaaagaaag atctggatat ttttgggatg aacccagctg atgaaagcac aagaagctat  2160
gtgattttat catttgaaaa caccggagaa tatatggata tgaaacaagc tgataccact  2220
cagtatgtgc caatgctgga aaggaaggag ggatctaaat actctgatat tcagagatct  2280
gtatatgatc gacctgcttc atataagaag aaatctttgt cagaatcaga agtaaaaaac  2340
cttcttttcag atgacggttc ggagggtcta agcctactgg atttgctaag cttcacctac  2400
caggtcgac gggggaatgga attcttggct tctaaaaatt gcgtacaccg tgacttggca  2460
gctcgtaatg tccttctggc tcaaggcaaa atcgtgaaga tctgcgactt tgggttggct  2520
agagacatca tgcatgattc caactatgtc tccaagggca gcaccttcct cccagtaaaa  2580
tggatggcac ctgaaagcat ttttgacaat ctgtacacaa cattaagtga tgtctggtct  2640
tatggcattc tgctgtggga aatattttct cttggtggca caccatatcc tggcatgatg  2700
gtcgactcca ccttctacaa taagataaag agtggctacc gaatggcaaa acctgatcat  2760
gctaccaatg aagtgtatga gatcatggta aagtgctgga acagtgaacc agagaaaaga  2820
ccttcgtttt accatctgag tgaaattgtg gagagcttgt tgcctggaga gtacaaaaag  2880
agctacgaga agattcacct ggacttcctg aaaagcgatc acccagctgt cactcgaatg  2940
agagggact gtgacaatgc ttacattggt gtcacctaca gaagtgaaga caagataaag  3000
gatagagaga gtggatttga tgagcagagg ctgagtgctg acagtgggta catcatcccc  3060
ctgcctgaca ttgaccctgt ttctgaagat gagcttggca aaaggaacag gcacagttcc  3120
cagacatctg aagagagtgc cattgaaacc ggttccagta gctctacctt tataaagaga  3180
gaggatgaga ccattgagga cattgacatg atggatgaca ttggaattga ctcctcggat  3240
cttgtagagg acagcttcct gtaa                                          3264
```

```
SEQ ID NO: 110          moltype = DNA   length = 3264
FEATURE                 Location/Qualifiers
source                  1..3264
                        mol_type = other DNA
                        organism = synthetic construct
SEQUENCE: 110
atgggtactc ccccaaggac gttcctgatc ctgggatgtt ttctcacagg accgctccta   60
acactttgcc agcttcctct gccgactatt gttcccaata gaaatgagat ggttgtacag  120
ctgaattcca atttcacact caaatgctct ggagacagcg aagtgagctg gcagtaccca  180
gtgaccgagg gaagccacag gatagacatc agacacgagg agaacaacag tggcctcttc  240
gtgacagtgc ttgaagtcgg aaatgcctca gccgctcaca cgggcatgta tgtttgctat  300
tataaccaca cgcaagtgga ggatggggaa gtcgagggga aggacatcta catctatgtg  360
cctgacccag acatgccttt cgttccttcc ttaccagaag accagttcat cctagtagaa  420
gaaggtgatc ccactgttat cccttgtcgg acaagtgacc caagtgctga agtgacttta  480
gttaacagtt tagacaagcc tgtctatgct ttctatgaca gcaaacaggg cttcgtaggg  540
aacttccttg caggaccata cacatgcaaa acaatggtta aaggcgtgga gttcaagtcc  600
gatgagttcc tcatctatat tttaagagct acttcacagc tgccggttga aattgaagct  660
ctgaaaactg tctacaaaac aggcgagacc atcgtagtaa cttgtgtggt cttttgacaat  720
gaggtggtta atttacagtg gaattatccc gggaaagtga aagaaaaagg tctgataaaa  780
cttgatgata tcaaagtccc atcacagaag ttggtttaca cgttgaccat acctgacgca  840
tcagtgaaag acacagggga ttatgaatgt actgcccgac atgcaaccaa ggaggttaag  900
gaaaataaga aagtagtcat tacagttcat gacaaagggt tcattcatct agagcctcaa  960
tttagcccttt tggaagctgt caatctacat gaagtcaaaa attttgtcgt cgatgtgcag  1020
gcgtaccccg ctccaaaaat gtactggttg aaggataatg tgactctgat tgaaaacctt  1080
actgagattg ttactagttc aaacagagtc caggaaacac ggtttcaaag tgtactaaaa  1140
ttgatccggg ccaaggaaga agacagtggg tactatactt tggttgctga aaatgaagat  1200
gagattaaga gatacacctt ctcgttgcta atacaagttc cagccttgat cttagacctc  1260
atggacgacc accaaggctc tgctggcagg cagacggtga ggtgcttggc tgaaggtacc  1320
ccgcttcctg atgtggaatg gttggtttgc aaggacatta aaaaatgcag caatgacact  1380
tcctggactc ttctgactaa caatatctct gatatacaca tggaagccca cctggatgag  1440
aggaatatgg tggaaagcca ggtgaccttc cagaaggtag aagaaaccct ggctgtgaga  1500
tgtgtagcaa gaaacgacct tggagctgtt actcgggaac tgaaacttgt ggctcccacc  1560
ttgcgatcag aactgacggt ggctgctgct gtcttagtac tgctggtgat tgtgataatt  1620
tcactgattg tcctggtcat catctggaaa cagaagccaa gatatgagat aagatggaga  1680
```

-continued

```
gtcattgagt ctatcagccc cgatggccat gaatacattt atgtggaccc aatgcagcta   1740
ccttatgact ccagatggga gtttcctcga gatgggttag tgcttggtcg aatccttggt   1800
tctggtgcat ttggaaaagt ggtggaaggg acagcatatg gattgagtcg ttctcaacct   1860
gtgatgaaag tagccgtgaa aatgctgaaa cctacagcta gatccagtga aaaacaggcg   1920
ctcatgtctg aactgaagat aatgacacat cttgggcccc acctgaatat tgtgaacctg   1980
cttggagctt gtacgaaatc aggtcctatt tacataatca ctgaatactg cttttacggt   2040
gatttggtga actatctgca caagaacagg gacaacttcc tcagccgaca tccagagaaa   2100
ccaaagaaag atctggatat ttttgggatg aacccagctg atgaaagcac aagaagctat   2160
gtgattttat catttgaaaa caccggagaa tatatggata tgaaacaagc tgataccact   2220
cagtatgtgc caatgctgga aaggaaggag ggatctaaat actctgatat tcagagatct   2280
gtatatgatc gacctgcttc atataagaag aaatctttgt cagaatcaga agtaaaaaac   2340
cttctttcag atgacggttc ggagggtcta agcctactgg atttgctaag cttcacctac   2400
caggttgcac ggggaatgga attcttggct tctaaaaatt gcgtacaccg tgacttggca   2460
gctcgtaatg tccttctggc tcaaggcaaa atcgtgaaga tctgcgactt tgggttggct   2520
agagtcatca tgcatgattc caactatgtc tccaagggca gcaccttcct cccagtaaaa   2580
tggatggcac ctgaaagcat tttttgacaat ctgtacacaa cattaagtga tgtctggtct   2640
tatggcattc tgctgtggga aatattttct cttggtggca caccatatcc tggcatgatg   2700
gtcgactcca ccttctacaa taagataaag agtggctacc gaatggcaaa acctgatcat   2760
gctaccaatg aagtgtatga gatcatggta aagtgctgga acagtgaacc agagaaaaga   2820
ccttcgtttt accatctgag tgaaattgtg gagagcttgt tgcctggaga gtacaaaaag   2880
agctacgaga agattcacct ggacttcctg aaaagcgatc acccagctgt cactcgaatg   2940
agaggggact gtgacaatgc ttacattggt gtcacctaca agaataaag caagataaag   3000
gatagagaga gtggatttga tgagcagagg ctgagtgctg acagtgggta catcatcccc   3060
ctgcctgaca ttgaccctgt ttctgaagat gagcttggca aaaggaacag gcacagttcc   3120
cagacatctg aagagagtgc cattgaaacc ggttccagta gctctacctt tataaagaga   3180
gaggatgaga ccattgagga cattgacatg atggatgaca ttggaattga ctcctcggat   3240
cttgtagagg acagcttcct gtaa                                          3264
```

```
SEQ ID NO: 111        moltype = DNA  length = 3273
FEATURE               Location/Qualifiers
source                1..3273
                      mol_type = other DNA
                      organism = synthetic construct
SEQUENCE: 111
atgctctgtc cctctctgaa ggcatctctg cagctcctca tcctcactgg tctgctggag   60
gtaacgtctg gaggcagcgg gctgcacatc gaacctgaag atgctgagct cgtccttagg   120
ctccacagca ctttctccct cgtgtgctat ggggacggca cgctggtctg ggagcgggat   180
ggtcagcctc tcactgccgt gctggagcac agggacgggg tcttcatcag caacctcacc   240
ctcaggaacg tgacaggccg tcacacgggg gagtatgcgt gcttctacag ccctgaccag   300
gctccggagc gagcagagag gaaagccctt tacatctatg ttccagatcc ctccttagtt   360
tttctccccg caatcacttc tgaagagttc ttcatcttca tcacgggcta cacagaggcc   420
accatcccat gccgtgtgac caacccagag ctgcaggtga ccctctatga aagaaagtg   480
gagaatccca ttccagctac ttatgaccca caacagggct tcaaaggctt ctttgaggac   540
aagacctact actgccaggc aatcgtggat gaccaagagg tggattcaga caccttctat   600
gtctaccgga tccaggtctc atctgtgaac gtctccatca gcgcagtgca gaccgtagtg   660
cggcaggag aaaatgttac cctgatgtgc actgtcagtg gcaatgagct ggtcaatttc   720
aactgggatt atcccgcaa gcaggcaggg aaggctgtga gccagtgac cgatttcctg   780
cctggatcca cccatgacat ccgttccatc ctcatcatcc agaatgcaga gctagaggac   840
agtgggacct acgtctgcaa tgtctctgag ggctaccatg agaagacaga ccggaaagac   900
atcacggtcc aagtgatcga gcgtggcttt gtacgcttcc acacccacct ggccagcacg   960
gtgtatgctg aggtccacaa gagccacatc atccaggtgg atgtggaggc ctacccacag   1020
ccaaacattg tgtggctgaa gaacaacaag acattgacca tggagagcag cagcgagttc   1080
accatcacca acaggaacct gtcagaaacc aggtatcaga cgtctctggt cctggtgcgt   1140
gtgaagcagg aggaaggagg atattacacc atccgagctt ccaatgagga tgatgcacaa   1200
gagctgtcct tccatctgca gataaatgtg ccagccaaag tggtggatct caaggaaaac   1260
agcagtgcca gcagcgggga gcagactgta acgtgctctg ctgaagggat gcccagcca   1320
gagatcagtt ggtccacttg cagcaacatc aaatggtgtg gcagccaggg gcaacccacc   1380
cagctgctgg ggaacaactc tgcagagatt ggcctgcaca ctaatgctac gtaccatgca   1440
gagctgcagg tgtaccgtgt gaacagcacc ctgcagctgc acagggtgga tgaacccctg   1500
cttctgagat gcaccgtgca aaacttcctg ggctccaact cccaagacat cactctggtc   1560
ccaaatgcct tgccattcaa agtggtcatc atctccgtca tcctggctct gctggtcctc   1620
accgtcatct ccctgatcat cctgatcatc ctgtggcaga gaaacctcg ctatgagatc   1680
cgctggaagg tgatcgagtc agtgagctcc gatgggcacg agtacatcta cgtggatccc   1740
atgcagctcc cttatgactc cagctgggag gtgcccaggg acaagctggt gttaggacgc   1800
actcttggct ccggtgcctt tggacgcgtg gtggaggcaa cagcgcatgg cctgagccat   1860
tcacagtcca ccatgaaagt ggcagtcaag atgctcaagt ccactgcacg gagcagtgag   1920
aagcaagccc tcatgtctga gctgaagatc atgagccacc tgggacctca cctcaacatc   1980
gtcaacttgc tggggggctg caccaaagga gggcccatct atatcatcac cgagtactgc   2040
cgttatgggg acctggtgga ctacctgcac cgcaacaagc acaccttcct gcagtcctat   2100
ggcgagaagg cccgccggga ggcagagctg tatgggaata ccatcaagga ggaccacgtg   2160
cagagtcacc tctccttgtc tgtcgagagt gatggggct acatggacat gagcaaggat   2220
gagtctctgt attacgtgcc catgtctgac atgaaggtg aagtcaagta tgctgacatc   2280
gagtcttcta actatggcac cccatatgag ctggacagct attccccatc agctccggaa   2340
agaacagacc gggtgacact gataaatgaa tctccactcc tcagctacat ggacctggtg   2400
ggcttcagct tccaggtggc caatgggatg gagttcctgg cttccaaaaa ttgtgtgcat   2460
cgtgacctgg ctgccaggaa cgtcctcatc tgcgagggga gctggtgaa gatctgtgac   2520
tttggtctgg caagagacat catgagggat tccaactaca tctccaaagg cagtaccttc   2580
ttgcccctta agtggatggc cccagagagc atcttcaaca acctctacac cacccctaagt   2640
gatgtgtggt cctttgggat tcttctctgg gagatattca ctctaggagg gactccctac   2700
```

```
cctgaactgc ctatgaacga acagttctac aatgccatca aacgtggcta tcggatgtcc   2760
aaacctaccc atgcttctga tgaaatctac gatatcatgc agaagtgctg ggaggagaag   2820
tttgagatca gaccgtcctt ctcacagctg gtggtgctta tgggaaacct cttggtggac   2880
tgctacagaa agaggtacca acaggtagat gaagagttca tgaagagcga ccaccccgct   2940
gttgttcgca caagacccac catccccggg ctgaacaacg ccaggctccc tcccagctcc   3000
cccaccctct acacggctgt gcaccagaac gggggagaga acgactacat catccctctt   3060
cctgacccca agcctgatgc aatctgtgac ctccctcagg aggcctccgt cagccgtgcc   3120
agctctatgc tgaatgaagc caacacatca tctacaatat cctgtgacag ccccctgggc   3180
ccccggcagg acgaggagcc agaatgtgac ctgcagctgg gctgccagga gctggcccg   3240
ggtcaccacg aggtggagga gagctttctg tag                                3273
```

SEQ ID NO: 112          moltype = DNA  length = 3273
FEATURE                 Location/Qualifiers
source                  1..3273
                        mol_type = other DNA
                        organism = synthetic construct

SEQUENCE: 112

```
atgctctgtc cctctctgaa ggcatctctg cagctcctca tcctcactgg tctgctggag   60
gtaacgtctg gaggcagcgg gctgcacatc gaacctgaag atgctgagct cgtccttagg   120
ctccacagca ctttctccct cgtgtgctat ggggacggca cgctggtctg ggagcgggat   180
ggtcagcctc tcactgccgt gctggagcac agggacgggg tcttcatcag caacctcacc   240
ctcaggaacg tgacaggccg tcacacgggg gagtatgcgt gcttctacag ccctgaccag   300
gctccggagc gagcagagag gaaagccctt tacatctatg ttccagatcc ctccttagtt   360
tttctccccg caatcacttc tgaagagttc ttcatcttca tcacgggcta cacagaggcc   420
accatcccat gccgtgtgac caacccagag ctgcaggtga ccctctatga aaagaaagtg   480
gagaatccca ttccagctac ttatgaccca caacaggcgt tcaaaggctt ctttgaggac   540
aagacctact actgccaggc aatcgtggat gaccaagagg tggattcaga caccttctat   600
gtctaccgga tccaggtctc atctgtgaac gtctccatca gcgcagtgca gaccgtagtg   660
cggcagggag aaaatgttac cctgatgtgc actgtcagtg gcaatgagct ggtcaatttc   720
aactgggatt atccccgcaa gcaggcaggg aaggctgtga agcagtgac cgatttcctg   780
cctggatcca cccatgacat ccgttccatc ctcatcatcc agaatgcaga gctagaggac   840
agtgggacct acgtctgcaa tgtctctgag ggctaccatg agaagacaga ccggaaagac   900
atcacggtcc aagtgatcga gcgtggcttt gtacgcttcc acacccacct ggccagcacg   960
gtgtatgctg aggtccacaa gagccacatc atccaggtgg atgtggaggc ctacccacag   1020
ccaaacattg tgtggctgaa gaacaacaag acattgacca tggagagcag cagcgagttc   1080
accatcacca acaggaacct gtcagaaacc aggtatcaga cgtctctggt cctggtcgt   1140
gtgaagcagg aggaaggagg atattacacc atccgagctt ccaatgagga tgatgcacaa   1200
gagctgtcct tccatctgca gataaatgtg ccagccaaag tggtggatct caaggaaaac   1260
agcagtgcca gcagcgggga gcagactgta acgtgctctg ctgaagggat gccccagcca   1320
gagatcagtt ggtccacttg cagcaacatc aaatggtgtg gcagccaggg gcaacccacc   1380
cagctgctgg ggaacaactc tgcagagatt ggcctgcaca ctaatgctac gtaccatgca   1440
gagctgcagg tgtaccgtgt gaacagcacc ctgcagctgc acaggtgga tgaaccctg   1500
cttctgagat gcaccgtgca aaacttcctg ggctccaact cccaagacat cactctggtc   1560
ccaaatgcct tgccattcaa agtggtcatc atctccgtca tcctggctct gctggtcctc   1620
accgtcatct ccctgatcat cctgatcatc ctgtggcaga agaaacctcg ctatgagatc   1680
cgctggaagg tgatcgagtc agtgagctcc gatgggcacg agtacatcta cgtggatccc   1740
atgcagctcc cttatgactc cagctgggag gtgcccaggg acaagctggt gttaggacgc   1800
actcttggct ccggtgcctt tggacgcgtg gtggaggcaa cagcgcatgg cctgagccat   1860
tcacagtcca ccatgaaagt ggcagtcaag atgctcaagt ccactgcacg gagcagtgag   1920
aagcaagccc tcatgtctga gctgaagatc atgagccacc tgggacctca cctcaacatc   1980
gtcaacttgc tggggggctg caccaaagga gggcccatct atatcatcac cgagtactgc   2040
cgttatgggg acctggtgga ctacctgcac cgcaacaagc acaccttcct gcagtcctat   2100
ggcgagaagg cccgccggga ggcagagctg tatgggaata ccatcaagga ggaccacgtg   2160
cagagtcacc tctccttgtc tgtcgagagt gatggggct acatggacat gagcaaggat   2220
gagtctctgg attacgtgcc catgtctgac atgaaggtg aagtcaagta tgctgacatc   2280
gagtcttcta actatggcac cccatatgac ctggacagct attccccatc agctccggaa   2340
agaacagacc gggtgacact gataaatgaa tctccactcc tcagctacat ggacttggtg   2400
ggcttcagct tccaggtggc caatgggatg gagttcctgg cttccaaaaa ttgtgtgcat   2460
cgtgacctgg ctgccaggaa cgtcctcatc tgcgagggga agctggtgaa gatctgtgac   2520
tttggtctgg caagagacat catgaggaat tccaactaca tctccaaagg cagtaccttc   2580
ttgcccctta gtggatggc cccagagagc atcttcaaca acctctacac caccctaagt   2640
gatgtgtggt cctttgggat tcttctctgg gagatattca ctctaggagg gactccctac   2700
cctgaactgc ctatgaacga acagttctac aatgccatca aacgtggcta tcggatgtcc   2760
aaacctaccc atgcttctga tgaaatctac gatatcatgc agaagtgctg ggaggagaag   2820
tttgagatca gaccgtcctt ctcacagctg gtggtgctta tgggaaacct cttggtggac   2880
tgctacagaa agaggtacca acaggtagat gaagagttca tgaagagcga ccaccccgct   2940
gttgttcgca caagacccac catccccggg ctgaacaacg ccaggctccc tcccagctcc   3000
cccaccctct acacggctgt gcaccagaac gggggagaga acgactacat catccctctt   3060
cctgacccca agcctgatgc aatctgtgac ctccctcagg aggcctccgt cagccgtgcc   3120
agctctatgc tgaatgaagc caacacatca tctacaatat cctgtgacag cccccctgggc   3180
ccccggcagg acgaggagcc agaatgtgac ctgcagctgg gctgccagga gctggcccg   3240
ggtcaccacg aggtggagga gagctttctg tag                                3273
```

SEQ ID NO: 113          moltype = DNA  length = 3273
FEATURE                 Location/Qualifiers
source                  1..3273
                        mol_type = other DNA
                        organism = synthetic construct

SEQUENCE: 113

```
atgctctgtc cctctctgaa ggcatctctg cagctcctca tcctcactgg tctgctggag    60
gtaacgtctg gaggcagcgg gctgcacatc gaacctgaag atgctgagct cgtccttagg   120
ctccacagca ctttctccct cgtgtgctat ggggacggca cgctggtctg ggagcgggat   180
ggtcagcctc tcactgccgt gctggagcac agggacgggg tcttcatcag caacctcacc   240
ctcaggaacg tgacaggccg tcacacgggg gagtatgcgt gcttctacag ccctgaccag   300
gctccggagc gagcagagag gaaagccctt tacatctatg ttccagatcc ctccttagtt   360
tttctccccg caatcacttc tgaagagttc ttcatcttca tcacgggcta cacagaggcc   420
accatcccat gccgtgtgac caacccagag ctgcaggtga ccctctatga aaagaaagtg   480
gagaatccca ttccagctac ttatgaccca caacagggct tcaaaggctt ctttgaggac   540
aagacctact actgccaggc aatcgtggat gaccaagagg tggattcaga caccttctat   600
gtctaccgga tccaggtctc atctgtgaac gtctccatca gcgcagtgca gaccgtagtg   660
cggcaggagg aaaatgttac cctgatgtgc actgtcagtg gcaatgagct ggtcaatttc   720
aactgggatt atccccgcaa gcaggcaggg aaggctgtgg agccagtgac cgatttcctg   780
cctggatcca cccatgacat ccgttccatc ctcatcatcc agaatgcaga gctagaggac   840
agtgggacct acgtctgcaa tgtctctgag ggctaccatg agaagacaga ccggaaagac   900
atcacggtcc aagtgatcga gcgtggcttt gtacgcttcc acacccacct ggccagcacg   960
gtgtatgctg aggtccacaa gagccacatc atccaggtgg atgtggaggc ctacccacag  1020
ccaaacattg tgtggctgaa gaacaacaag acattgacca tggagagcag cagcgagttc  1080
accatcacca acaggaacct gtcagaaacc aggtatcaga cgtctctggt cctggtgcgt  1140
gtgaagcagg aggaaggagg atattacacc atccgagctt ccaatgagga tgatgcacaa  1200
gagctgtcct tccatctgca gataaatgtg ccagccaaag tggtggatct caaggaaaac  1260
agcagtgcca gcagcgggga gcagactgta acgtgctctg ctgaagggat gccccagcca  1320
gagatcagtt ggtccacttg cagcaacatc aaatggtgtg gcagccaggg gcaacccacc  1380
cagctgctgg ggaacaactc tgcagagatt ggcctgcaca ctaatgctac gtaccatgca  1440
gagctgcagg tgtaccgtgt gaacagcacc ctgcagctgc acagggtgga tgaaccctg   1500
cttctgagat gcaccgtgca aaacttcctg ggctccaact cccaagacat cactctggtc  1560
ccaaatgcct tgccattcaa agtggtcatc atctccgtca tcctggctct gctggtcctc  1620
accgtcatct ccctgatcat cctgatcatc ctgtggcaga agaaacctcg ctatgagatc  1680
cgctggaagg ccatcgagtc agtgagctcc gatgggcacg agtacatcta cgtggatccc  1740
atgcagctcc cttatgactc cagctgggag gtgcccaggg acaagctggt gttaggacgc  1800
actcttggct ccggtgcctt tggacgcgtg gtggaggcaa cagcgcatgg cctgagccat  1860
tcacagtcca ccatgaaagt ggcagtcaag atgctcaagt ccactgcacg gagcagtgag  1920
aagcaagccc tcatgtctga gctgaagatc atgagccacc tgggacctca cctcaacatc  1980
gtcaacttgc tgggggcctg caccaaagga gggccatcct atatcatcac cgagtactgc  2040
cgttatgggg acctggtgga ctacctgcac cgcaacaagc acaccttcct gcagtcctat  2100
ggcgagaagg cccgccggga ggcagagctg tatgggaata ccatcaagga ggaccacgtg  2160
cagagtcacc tctccttgtc tgtcgagagt gatggggct acatggacat gagcaaggat  2220
gagtctctgg attacgtgcc catgtctgac atgaaggtg aagtcaagta tgctgacatc  2280
gagtcttcta actatggcac cccatatgac ggacagctt attccccatc agctccggaa  2340
agaacagacc gggtgacact gataaatgaa tctccactcc tcagctacat ggacttggtg  2400
ggcttcagct tccaggtggc caatgggatg gagttcctgg cttccaaaaa ttgtgtgcat  2460
cgtgacctgg ctgccaggaa cgtcctcatc tgcgagggga agctggtgaa gatctgtgac  2520
tttggtctgg caagagacat catggggat tccaactaca tctccaaagg cagtaccttc  2580
ttgcccctta gtggatggc cccagagagc atcttcaaca acctctacac caccctaagt  2640
gatgtgtggt cctttgggat tcttctctgg gagatattca ctctaggagg gactccctac  2700
cctgaactgc ctatgaacga acagttctac aatgccatca aacgtggcta cggatgtcc   2760
aaacctaccc atgcttctga tgaaatctac gatatcatgc agaagtgctg ggaggagaag  2820
tttgagatca gaccgtcctt ctcacagctg gtggtgctta tgggaaacct cttggtggac  2880
tgctacagaa gaggtacca acaggtagat gaagagttca tgaagagcga ccacccccgct 2940
gttgttcgca agacccac catccccggg ctgaacaacg ccaggctccc tccagctcc    3000
cccaccctct acacggctgt gcaccagaac gggggagaga acgactacat catccctct   3060
cctgacccca gcctgatgc aatctgtgac ctccctcagg aggcctccgt cagccgtgcc  3120
agctctatgc tgaatgaagc caacacatca tctacaatat cctgtgacag cccccctgggc 3180
ccccggcagg acgaggagcc agaatgtgac ctgcagctgg gctgccagga gctggcccg   3240
ggtcaccacg aggtggagga gagctttctg tag                              3273
```

```
SEQ ID NO: 114        moltype = DNA   length = 3303
FEATURE               Location/Qualifiers
source                1..3303
                      mol_type = other DNA
                      organism = synthetic construct
SEQUENCE: 114
atggcgaaag gtggcataat cgtcgcgatc cttctcctta tcgttatgct tgctatagag    60
atattgcttt tgataactct tatcattgct gtaacgtctg gaggcagcgg gctgcacatc   120
gaacctgaag atgctgagct cgtccttagg ctccacagca ctttctccct cgtgtgctat   180
ggggacggca cgctggtctg ggagcgggat ggtcagcctc tcactgccgt gctggagcac   240
agggacgggg tcttcatcag caacctcacc ctcaggaacg tgacaggccg tcacacgggg   300
gagtatgcgt gcttctacag ccctgaccag gctccggagc gagcagagag gaaagccctt   360
tacatctatg ttccagatcc ctccttagtt tttctccccg caatcacttc tgaagagttc   420
ttcatcttca tcacgggcta cacagaggcc accatcccat gccgtgtgac caacccagag   480
ctgcaggtga ccctctatga aaagaaagtg gagaatccca ttccagctac ttatgaccca   540
caacagggct tcaaaggctt ctttgaggac aagacctact actgccaggc aatcgtggat   600
gaccaagagg tggattcaga caccttctat gtctaccgga tccaggtctc atctgtgaac   660
gtctccatca gcgcagtgca gaccgtagtg cggcaggagg aaaatgttac cctgatgtgc   720
actgtcagtg gcaatgagct ggtcaatttc aactgggatt atccccgcaa gcaggcaggg   780
aaggctgtgg agccagtgac cgatttcctg cctggatcca cccatgacat ccgttccatc   840
ctcatcatcc agaatgcaga gctagaggac agtgggacct acgtctgcaa tgtctctgag   900
ggctaccatg agaagacaga ccggaaagac atcacggtcc aagtgatcga gcgtggcttt   960
gtacgcttcc acacccacct ggccagcacg gtgtatgctg aggtccacaa gagccacatc  1020
```

```
atccaggtgg atgtggaggc ctacccacag ccaaacattg tgtggctgaa gaacaacaag 1080
acattgacca tggagagcag cagcgagttc accatcacca acaggaacct gtcagaaacc 1140
aggtatcaga cgtctctggt cctggtgcgt gtgaagcagg aggaaggagg atattacacc 1200
atccgagctt ccaatgagga tgatgcacaa gagctgtcct tccatctgca gataaatgtg 1260
ccagccaaag tggtggatct caaggaaaac agcagtgcca gcagcgggga gcagactgta 1320
acgtgctctg ctgaagggat gccccagcca gagatcagtt ggtccacttg cagcaacatc 1380
aaatggtgtg gcagccaggg gcaacccacc cagctgctgg ggaacaactc tgcagagatt 1440
ggcctgcaca ctaatgctac gtaccatgca gagctgcagg tgtaccgtgt gaacagcacc 1500
ctgcagctgc acagggtgga tgaacccctg cttctgagat gcaccgtgca aaacttcctg 1560
ggctccaact cccaagacat cactctggtc ccaaatgcct tgccattcaa agtggtcatc 1620
atctccgtca tcctggctct gctggtcctc accgtcatct ccctgatcat cctgatcatc 1680
ctgtggcaga agaaacctcg ctatgagatc cgctggaagg tgatcgagtc agtgagctcc 1740
gatgggcacg agtacatcta cgtggatccc atgcagctcc cttatgactc cagctgggag 1800
gtgcccaggg acaagctggt gttaggacgc actcttggct ccggtgcctt tggacgcgtg 1860
gtggaggcaa cagcgcatgg cctgagccat tcacagtcca ccatgaaagt ggcagtcaag 1920
atgctcaagt ccactgcacg gagcagtgag aagcaagccc tcatgtctga gctgaagatc 1980
atgagccacc tgggacctca cctcaacatc gtcaacttgc tgggggcctg caccaaagga 2040
gggcccatct atatcatcac cgagtactgc cgttatgggg acctggtgga ctacctgcac 2100
cgcaacaagc acaccttcct gcagtcctat ggcgagaagg cccgccggga ggcgagactg 2160
tatgggaata ccatcaagga ggaccacgtg cagagtcacc tctccttgtc tgtcgagagt 2220
gatgggggct acatggacat gagcaaggat gagtctctgg attacgtgcc catgtctgac 2280
atgaagggtg aagtcaagta tgctgacatc gagtcttcta actatggcac ccatatgag 2340
ctggacagct attccccatc agctccggaa agaacagacc gggtgacact gataaatgaa 2400
tctccactcc tcagctacat ggacttggtg ggcttcagct tccaggtggc caatgggatg 2460
gagttcctgg cttccaaaaa ttgtgtgcat cgtgacctgg ctgccaggaa cgtcctcatc 2520
tgcgagggaa agctggtgaa gatctgtgac tttggtctgg caagagacat catgagggat 2580
tccaactaca tctccaaagg cagtaccttc ttgcccctta agtggatggc cccagagagc 2640
atcttcaaca acctctacac caccctaagt gatgtgtggt cctttgggat tcttctctgg 2700
gagatattca ctctaggagg gactccctac cctgaactgc ctatgaacga acagttctac 2760
aatgccatca aacgtggcta tcggatgtcc aaacctacct atgcttctga tgaaatctac 2820
gatatcatgc agaagtgctg ggaggagaag tttgagatca gaccgtcctt ctcacagctg 2880
gtggtgctta tgggaaacct cttggtggac tgctacagaa agaggtacca acaggtagat 2940
gaagagttca tgaagagcga ccaccccgct gttgttcgca caagacccac catccccggg 3000
ctgaacaacg ccaggctccc tcccagctcc cccaccctct acaccgctgt gcaccgaaac 3060
ggggagagaa acgactacat catccctctt cctgacccca agcctgatgc aatctgtgac 3120
ctccctcagg aggcctccgt cagccgtgcc agctctatgc tgaatgaagc caacacatca 3180
tctacaatat cctgtgacag cccccctgggc ccccggcagg acgaggagcc agaatgtgac 3240
ctgcagctgg gctgccagga gctggccccg ggtcaccacg aggtggagga gagctttctg 3300
tag                                                                          3303
```

SEQ ID NO: 115           moltype = DNA  length = 3327
FEATURE                  Location/Qualifiers
source                   1..3327
                         mol_type = other DNA
                         organism = synthetic construct
SEQUENCE: 115

```
atggcggatt acaaggatga tgatgacaaa aaaggtggca taatcgtcgc gatccttctc 60
cttatcgtta tgcttgctat agagatattg cttttgataa ctcttatcat tgctgtaacg 120
tctggaggca gcgggctgca catcgaacct gaagatgctg agctcgtcct taggctccac 180
agcactttct ccctcgtgtg ctatggggac ggcacgctgg tctgggagcg ggatggtcag 240
cctctcactg ccgtgctgga gcacagggac ggggtcttca tcagcaacct caccctcagg 300
aacgtgacag gccgtcacac ggggggagtat gcgtgcttct acagccctga ccaggctccg 360
gagcgagcag agaggaaagc cctttacatc tatgttccag atccctcctt agttttttctc 420
cccgcaatca cttctgaaga gttcttcatc ttcatcacgg gctacacaga ggccaccatc 480
ccatgccgtg tgaccaaccc agagctgcag gtgaccctct atgaaaagaa agtggagaat 540
cccattccag ctacttatga cccacaacag ggcttcaaag gcttctttga ggacaagacc 600
tactactgcc aggcaatcgt ggatgaccaa gaggtggatt cagacacctt ctatgtctac 660
cggatccagg tctcatctgt gaacgtctcc atcagcgcag tgcagaccgt agtgcggcag 720
ggagaaaatg ttaccctgat gtgcactgtc agtggcaagg agctggtcaa tttcaactgg 780
gattatcccc gcaagcaggc agggaaggct gtggagccag tgaccgattt cctgcctgga 840
tccacccatg acatccgttc catcctcatc atccagaatg cagagctaga ggacagtggg 900
acctacgtct gcaatgtctc tgagggctac atgagaagaa cagaccggaa agacatcacg 960
gtccaagtga tcgagcgtgg cttttgtacgc ttccacaccc acctggccag cacggtgtat 1020
gctgaggtcc acaagagcca catcatccag gtggatgtga aggggtaccac acagccaaac 1080
attgtgtggc tgaagaacaa caagacattg accatggaga gcagcagcga gttcaccatc 1140
accaacagga acctgtcaga aaccaggtat cagacgtctc tggtcctggt gcgtgtgaag 1200
caggaggaag gaggatatta caccatccga gcttccaatg aggatgatgc acaagagctg 1260
tccttccatc tgcagataaa tgtgccagcc aaagtggtga tctcaaggaa aacagcagt 1320
gccagcagcg gggagcagac tgtaacgtgc tctgctgaag ggatgcccca gccagagatc 1380
agttggtcca cttgcagcaa catcaaatgg tgtggcagcc aggggcaacc cacccagctg 1440
ctggggaaca actctgcaga gattggcctg cacactaatg ctacgtacca tgcagagctg 1500
caggtgtacc gtgtgaacag caccctgcag ctgcacaggg tggatgaacc cctgcttctg 1560
agatgcaccg tgcaaaactt cctgggctcc aactcccaag acatcactct ggtcccaaat 1620
gccttgccat tcaaagtggt catcatctcc gtcatcctga t catcctgtgg cagaagaaac 1680
atctccctga tcatcctgat catcctgtgg cagaagaaac ctcgctatga gatccgctgg 1740
aaggtgatca gtcagtgag ctccgatggg cacgagtaca tctacgtgga tcccatgcag 1800
ctcccttatg actccagctg ggaggtgccc agggacaagc tggtgttagg acgcactctt 1860
ggctccggtc cctttggacg cgtggtggag gcaacagcgc atggcctgag ccattcacag 1920
tccaccatga aagtggcagt caagatgctc aagtccactg cacggagcag tgagaagcaa 1980
```

```
gccctcatgt ctgagctgaa gatcatgagc cacctgggac ctcacctcaa catcgtcaac   2040
ttgctggggg cctgcaccaa aggagggccc atctatatca tcaccgagta ctgccgttat   2100
ggggacctgg tggactacct gcaccgcaac aagcacacct tcctgcagtc ctatggcgag   2160
aaggcccgcc gggaggcaga gctgtatggg aataccatca aggaggacca cgtgcagagt   2220
cacctctcct tgtctgtcga gagtgatggg ggctacatgg acatgagcaa ggatgagtct   2280
ctggattacg tgcccatgtc tgacatgaag ggtgaagtca agtatgctga catcgagtct   2340
tctaactatg gcaccccata tgagctggac agctattccc catcagctcc ggaaagaaca   2400
gaccgggtga cactgataaa tgaatctcca ctcctcagct acatggactt ggtgggcttc   2460
agcttccagg tggccaatgg gatggagttc ctggcttcca aaaattgtgt gcatcgtgac   2520
ctggctgcca ggaacgtcct catctgcgag gggaagctgg tgaagatctg tgactttggt   2580
ctggcaagag acatcatgag ggattccaac tacatctcca aaggcagtac cttcttgccc   2640
cttaagtgga tggccccaga gagcatcttc aacaacctct acaccaccct aagtgatgtg   2700
tggtcctttg ggattcttct ctgggagata ttcactctag gagggactcc ctaccctgaa   2760
ctgcctatga acgaacagtt ctacaatgcc atcaaacgtg gctatcggat gccaaacct   2820
acccatgctt ctgatgaaat ctacgatatc atgcagaagt gctgggagga gaagtttgag   2880
atcagaccgt ccttctcaca gctggtggtg cttatgggaa acctcttggt ggactgctac   2940
agaaagaggt accaacaggt agatgaagag ttcatgaaga gcgaccaccc cgctgttgtt   3000
cgcacaagac ccaccatccc cgggctgaac aacgccaggc tccctcccag ctcccccacc   3060
ctctacacgg ctgtgcacca gaacggggga gagaacgact acatcatccc tcttcctgac   3120
cccaagcctg atgcaatctg tgacctccct caggaggcct ccgtcagccg tgccagctct   3180
atgctgaatg aagccaacac atcatctaca atatcctgtg acagccccct gggccccgg    3240
caggacgagg agccagaatg tgacctgcag ctgggctgcc aggagctggc cccgggtcac   3300
cacgaggtgg aggagagctt tctgtag                                       3327
```

```
SEQ ID NO: 116             moltype = DNA   length = 756
FEATURE                    Location/Qualifiers
source                     1..756
                           mol_type = other DNA
                           organism = synthetic construct
SEQUENCE: 116
atgtgcccgc agccggcaag gcttgaaccc ggcatgaatt tcggcgtggt cttcgccgtc   60
atcctctccc tgcccctggc ccgcctggag ggggacccca tacccgaaga tatttatgag   120
attttgggtg gcagctccgt gcgctccatc agtgacctcc agcgtgccct gcggatagac   180
tccgtagagg aggacagctc tagcctggac ctgaatgcaa ctcagcccag ccaaaaccat   240
gtgtccctgt ctcgagagag gcgaagcctt gatgctctgg cagcagcaga gccagctgtc   300
ctcgccgagt gcaagacacg gacggtggtc tttgagatct cccgtgacat ggtggacagc   360
accaatgcca acttcgtggt gtggccaccc tgcgtggagg tgcagcggtg ctccggctgc   420
tgcaacaacc gcaacgtgca gtgccgcccc atgcagattc gcgtccggca tgtccaggtg   480
aacaagattg agttttttcca gaggaagcca atattcaaaa aagtcatcgt gcctttggag   540
gaccacgtgc agtgccggtg cgaagtggtg tcccggccgc cacccaggag caaccgaccg   600
gcatcccgtg agcagagacg cttctcgccg tcattcacca cagccgccat ctcccagagg   660
aagcgggtac gccggccgcc agcacagaag agaaacacaa agaaatacaa gcatgtcaac   720
gataagaaag tgctgaaaga aatcctcata gcatag                             756
```

```
SEQ ID NO: 117             moltype = DNA   length = 660
FEATURE                    Location/Qualifiers
source                     1..660
                           mol_type = other DNA
                           organism = synthetic construct
SEQUENCE: 117
atgtgcccgc agccggcaag gcttgaaccc ggcatgaatt tcggcgtggt cttcgccgtc   60
atcctctccc tgcccctggc ccgcctggag ggggacccca tacccgaaga tatttatgag   120
attttgggtg gcagctccgt gcgctccatc agtgacctcc agcgtgccct gcggatagac   180
tccgtagagg aggacagctc tagcctggac ctgaatgcaa ctcagcccag ccaaaaccat   240
gtgtccctgt ctcgagagag gcgaagcctt gatgctctgg cagcagcaga gccagctgtc   300
ctcgccgagt gcaagacacg gacggtggtc tttgagatct cccgtgacat ggtggacagc   360
accaatgcca acttcgtggt gtggccaccc tgcgtggagg tgcagcggtg ctccggctgc   420
tgcaacaacc gcaacgtgca gtgccgcccc atgcagattc gcgtccggca tgtccaggtg   480
aacaagattg agttttttcca gaggaagcca atattcaaaa aagtcatcgt gcctttggag   540
gaccacgtgc agtgccggtg cgaagtggtg tcccggccgc cacccaggag caaccgaccg   600
gcatcccgtg agcagagacg cttctcgccg tcattcacca cagccgccat ctcccagtag   660
```

```
SEQ ID NO: 118             moltype = DNA   length = 114
FEATURE                    Location/Qualifiers
source                     1..114
                           mol_type = other DNA
                           organism = synthetic construct
SEQUENCE: 118
atggcgaaag gtggcataat cgtcgcgatc cttctcctta tcgttatgct tgctatagag   60
atattgcttt tgataactct tatcattgct gtaacgtctg gaggcagcgg gtag          114
```

```
SEQ ID NO: 119             moltype = DNA   length = 138
FEATURE                    Location/Qualifiers
source                     1..138
                           mol_type = other DNA
                           organism = synthetic construct
SEQUENCE: 119
atggcggatt acaaggatga tgatgacaaa aaaggtggca taatcgtcgc gatccttctc   60
cttatcgtta tgcttgctat agagatattg cttttgataa ctcttatcat tgctgtaacg   120
```

-continued

```
tctggaggca gcgggtag                                                        138

SEQ ID NO: 120          moltype = DNA  length = 5831
FEATURE                 Location/Qualifiers
source                  1..5831
                        mol_type = other DNA
                        organism = synthetic construct SEQUENCE: 120
gcccctgcag ccgaattata ttatttttgc caaataattt ttaacaaaag ctctgaagtc   60
ttcttcattt aaattcttag atgatacttc atctggaaaa ttgtcccaat tagtagcatc   120
acgctgtgag taagttctaa accatttttt tattgttgta ttatctctaa tcttactact   180
cgatgagttt tcggtattat ctctattttt aacttggagc aggttccatt cattgttttt   240
ttcatcatag tgaataaaat caactgcttt aacacttgtg cctgaacacc atatccatcc   300
ggcgtaatac gactcactat aggggagagcg gccgcgtcga catgcccgcc gtgaccgtcg   360
agaacccgct gacgctgccc cgcgtatccg cacccgccga cgccgtcgca cgtcccgtgc   420
tcaccgtgac caccgcgccc agcggtttcg agggcgaggg cttccggtg cgccgcgcgt   480
tcgccgggat caactaccgc cacctcgacc cgttcatcat gatggaccag atgggtgagg   540
tggagtacgc gcccggggag cccaagggca cgccctggca cccgcaccgc ggcttcgaga   600
ccgtgaccta catcgtcgac gcggccgcca gatcttccgg atggctcgag ttttttcagca   660
agatatgata agatacattg atgagtttgg acaaaccaca actagaatgc agtgaaaaaa   720
atgctttatt tgtgaaattt gtgatgctat tgctttattt gtaaccatta taagctgcaa   780
taaacaagtt tagttaacgc atgatacaaa ggcattaagc tgctatcc acatagcgta   840
aaaggagcaa catagttaag aataccagtc aatctttcac aaattttgta atccagaggt   900
tgatttcagg caccgggctt gcgggtcatg caccaggtgc gcggtccttc gggcacctcg   960
acgtcggcgg tgacggtgaa gccgagccgc tcgtagaagg ggaggttgcg gggcgcggag   1020
gtctccagga aggcgggcac cccggccgcg tcggccgcct ccactccggg agcacgacg   1080
gcgctgccca gacccttgcc ctggtggtcg ggcgagacgc cgacggtggc caggaaccac   1140
gcgggctcct tgggccggtg cggcgccagg aggccttcca tctgttgctg cgcggccagc   1200
cgggaaccgc tcaactcggc catgcgcggg ccgatctcgg cgaacaccgc ccccgcttcg   1260
acgctctccg gcgtggtcca gaccgccacc gcggcgccgt cgtccgcgac ccacaccttg   1320
ccgatgtcga gcccgacgcg cgtgaggaag agttcttgca gctcggtgac ccgctcgatg   1380
tggcggtccg gatcgacggt gtggcgcgtg gcggggtagt cggcgaacgc ggcggcgagg   1440
gtgcgtacgg ccctgggggac gtcgtcgcgg gtggcgaggc gcaccgtggg cttgtactcg   1500
gtcatagggc cgggattctc ctccacgtca ccgcatgtta gaagacttcc tctgccctcg   1560
cgagatccgg tggagccggg tccggcggtg ccgtccacgg cagaattgga cgactgagcg   1620
cgggatctgg cgaaggcgat gggggtcttg aaggcgtgct ggtactccac gatgcccagc   1680
tcggtgttgc tgtgcagctc ctccacgcgg cggaaggcga acatgggcc cccgttctgc   1740
aggatgctgc ggtggatggc gctcttgaag tgcatgtggc tgtccaccac gaagctgtag   1800
tagccgccgt cgcgcaggct gaaggtgcgg gcgaagctgc ccaccagcac gttatcgccc   1860
atggggtgca ggtgctccac ggtggcgttg ctgcggatga tcttgtcggt gaagatcacg   1920
ctgtcctcgg ggaagccggt gcccaccacc ttgaagtcgc cgatcacgcg gccggcctcg   1980
tagcggtagc tgaagctcac gtgcagcacg ccgccgtcct cgtacttctc gatgcgggtg   2040
ttggtgtagc cgccgttgtt gatggcgtgc aggaaggggt tctcgtagcc gctggggtag   2100
gtgccgaagt ggtagaagcc gtagcccatc acgtggctca gcaggtaggg ctgaaggtc   2160
agggcgcctt tggtgctctt catcttgttg gtcatgcggc cctgcttggg ggtgccctct   2220
ccgccgccca ccagctcgaa ctccacgccg ttcaggggtgc cggtgatgcg gcactcgatc   2280
tccatgacgg gcaggccgct ctcgtcgctc tccatggtgg cgtctagcgt aggcgccggt   2340
cacagcttgg atctgtaacg gcgcagaaca gaaaacgaaa caaagacgta gagttgagca   2400
agcagggtca ggcaaagcgt ggagagccgg ctgagtctag gtaggctcca agggagcgcc   2460
ggacaaaggc ccggtctcga cctgagcttt aaacttacct agacggcgga cgcagttcag   2520
gaggcaccac aggcgggagg cggcagacca cgactcaacc ggcgtggatg gcgggcctcag   2580
gtagggcggc gggcgcgtga aggagagatg cgagccctc gaagcttcag ctgtgttctg   2640
gcggcaaacc cgttgcgaaa aagaacgttc acggcgacta ctgcacttat atacggttct   2700
cccccaccct cgggaaaaag gcggagccag tacacgacat cactttccca gtttaccccg   2760
cgccaccttc tctaggcacc cgttcaattg ccgaccccct cccccaactt ctcggggact   2820
gtgggcgatg tgcgctctgc ccactgacgg gcaccggagc gatcgcagat ccttatcttt   2880
ctagaaattc taccgggtag gggaggcgct tttcccaagg cagtctggag catgcgcttt   2940
agcagccccc ctggcacttg gcgctacaca agtggcctct ggcctcgcac acattccaca   3000
tccaccggta gcgccaaccg gctccgttct ttggtggccc cttcgcgcca ccttctactc   3060
ctccctagt caggaagttc ccccccgccc cgcagctcgc gtcgtgcagg acgtgacaaa   3120
tggaagtagc acgtctcact agtctcgtgc agatggacag caccgctgag caatggaagc   3180
gggtaggcct ttggggcagc ggccaatagc agctttgctc cttcgctttc tgggctcagc   3240
agctgggaag ggtgggtccg ggggcgggct cagggcggg ctcaggggcg gggcgggcgc   3300
ccgaaggtcc tccggaggcc cggcattctg cacgcttcaa aagcgcacgt ctgccgcgct   3360
gttctcctct tcctcatctc cgggcctttc gacctggatc cgatatcggt accgctagca   3420
tcgatcagac atgataagat acattgatga gtttggacaa accacaacta gaatgcagtg   3480
aaaaaaatgt tttatttgtg aaatttgtga tgctattgct ttatttgtaa ccattataag   3540
ctgcaataaa caagttaaca acaacaattg cattcatttt atgtttcagg ttcagggggga   3600
ggtgtgggag gtttttttgtt taaacctcct gtgtgaaatt attatccgct cataattcca   3660
cacattatac gagccggaag cataaagtgt aaagcctggg gtgcctaatg agtgagctaa   3720
ctcacattaa ttgcgttgcg ctcactgcca attgctttcc agtcgggaaa cctgtcgtgc   3780
cagctgcatt aatgaatcgg ccaacgcgcg gggagaggcg gtttgcgtat gggcgctct   3840
tccgcttcct cgctcactga ctcgctgcgc tcggtcgttc ggctgcggcg agcggtatca   3900
gctcactcaa aggcggtaat acggttatcc acagaatcag gggataacgc aggaaagaac   3960
atgtgagcaa aaggccagca aaaggccagg aaccgtaaaa aggccgcgtt gctggcgttt   4020
ttccataggc tccgcccccc tgacgagcat cacaaaaatc gacgctcaag tcagaggtgg   4080
cgaaacccga caggactata aagataccag gcgtttcccc ctggaagctc cctcgtgcgc   4140
tctcctgttc cgaccctgcc gcttaccgga tacctgtccg cctttctccc ttcgggaagc   4200
gtggcgcttt ctcatagctc acgctgtagg tatctcagtt cggtgtaggt cgttcgctcc   4260
```

-continued

```
aagctgggct gtgtgcacga acccccgtt cagcccgacc gctgcgcctt atccggtaac    4320
tatcgtcttg agtccaaccc ggtaagacac gacttatcgc cactggcagc agccactggt    4380
aacaggatta gcagagcgag gtatgtaggc ggtgctacag agttcttgaa gtggtggcct    4440
aactacggct acactagaag aacagtattt ggtatctgcg ctctgctgaa gccagttacc    4500
ttcggaaaaa gagttggtag ctcttgatcc ggcaaacaaa ccaccgctgg tagcggtggt    4560
ttttttgttt gcaagcagca gattacgcgc agaaaaaaag gatctcaaga agatcctttg    4620
atcttttcta cggggtctga cgctcagtgg aacgaaaact cacgttaagg gattttggtc    4680
atgagattat caaaaaggat cttcacctag atccttttaa attaaaaatg aagttttaaa    4740
tcaatctaaa gtatatatga gtaaacttgg tctgacagtt accaatgctt aatcagtgag    4800
gcacctatct cagcgatctg tctatttcgt tcatccatag ttgcctgact ccccgtcgtg    4860
tagataacta cgatacggga gggcttacca tctggcccca gtgctgcaat gataccgcga    4920
gacccacgct caccggctcc agatttatca gcaataaacc agccagccgg aagggccgag    4980
cgcagaagtg gtcctgcaac tttatccgcc tccatccagt ctattaattg ttgccgggaa    5040
gctagagtaa gtagttcgcc agttaatagt ttgcgcaacg ttgttgccat tgctacaggc    5100
atcgtggtgt cacgctcgtc gtttggtatg gcttcattca gctccggttc ccaacgatca    5160
aggcgagtta catgatcccc catgttgtgc aaaaaagcgg ttagctcctt cggtcctccg    5220
atcgttgtca gaagtaagtt ggccgcagtg ttatcactca tggttatggc agcactgcat    5280
aattctctta ctgtcatgcc atccgtaaga tgcttttctg tgactggtga gtactcaacc    5340
aagtcattct gagaatagtg tatgcggcga ccgagttgct cttgcccggc gtcaatacgg    5400
gataataccg cgccacatag cagaacttta aaagtgctca tcattggaaa acgttcttcg    5460
gggcgaaaac tctcaaggat cttaccgctg ttgagatcca gttcgatgta acccactcgt    5520
gcacccaact gatcttcagc atcttttact ttcaccagcg tttctgggtg agcaaaaaca    5580
ggaaggcaaa atgccgcaaa aaagggaata agggcgacac ggaaatgttg aatactcata    5640
ctcttccttt ttcaatatta ttgaagcatt tatcagggtt attgtctcat gagcggatac    5700
atatttgaat gtatttagaa aaataaacaa ataggggttc cgcgcacatt tccccgaaaa    5760
gtgccacctg acgtctaaga aaccattatt atcatgacat taacctataa aaataggcgt    5820
atcacgaggc c                                                        5831
```

SEQ ID NO: 121          moltype = DNA   length = 6079
FEATURE                 Location/Qualifiers
source                  1..6079
                        mol_type = other DNA
                        organism = synthetic construct
SEQUENCE: 121

```
gcccctgcag ccgaattata ttattttttgc caaataattt ttaacaaaag ctctgaagtc    60
ttcttcattt aaattcttag atgatacttc atctggaaaa ttgtcccaat tagtagcatc    120
acgctgtgag taagttctaa accatttttt tattgttgta ttatctctaa tcttactact    180
cgatgagttt tcggtattat ctctattttt aacttggagc aggttccatt cattgttttt    240
ttcatcatag tgaataaaat caactgcttt aacacttgtg cctgaacacc atatccatcc    300
ggcgtaatac gactcactat agggagagc gccgccagat cttccggatg gctcgagttt    360
ttcagcaaga tcatgcctgc tattgtcttc ccaatcctcc cccttgctgt cctgccccac    420
cccaccccc agaatagaat gacacctact cagacaatgc gatgcaattt cctcatttta    480
ttaggaaagg acagtgggag tggcaccttc cagggtcaag gaaggcacgg gggagggca    540
aacaacagat ggctggcaac tagaaggcac agtcgcatat gtcaggcacc gggcttgcgg    600
gtcatgcacc aggtgcgcgg tccttcgggc acctcgacgt cggcggtgac ggtgaagccg    660
agccgctcgt agaaggggag gttgcggggc gcggatgtct ccaggaaggc gggcaccccg    720
gcgcgctcgg ccgcctccac tccggggagc acgacggcgc tgcccagacc cttgccctgg    780
tggtcgggcg agacgccgac ggtggccagg aaccacgcgg gctccttggg ccggtgcggc    840
gccaggaggc cttccatctg ttgctgcgcg gccagccggg aaccgctcaa ctcggccatg    900
cgcgggccga tctcggcgaa caccgccccc gcttcgacgc tctccggcgt ggtccagacc    960
gccaccgacg cgccgtcgtc cgcgacccac accttgccgg tgtcgagccc gacgcgcgtg   1020
aggaagagtt cttgcagctc ggtgacccgc tcgatgtggc ggtccggatc gacggtgtgg   1080
cgcgtggcgg ggtagtcggc gaacgcggcg gcgaggtgc gtacggccct ggggacgtcg   1140
tcgcgggtg cgaggcgcac cgtgggcttg tactcggtca taggaccggg gttttcttcc   1200
acgtctcctg cttgctttaa cagagagaag ttcgtggcac cggatcctcc agcgcctgtg   1260
ctatgtctgc cctcagctct ctcatattgt tccacgatgg tgtagtcccc attatggctg   1320
ataatgtcga gtttaaatatc agtcatgtag gcgccaggca gctgcacttg tttcttggcc   1380
ttgtaggttg ttttgacctc ggcatcgtag tgtcctccgt ctttgagttt cagtctcatt   1440
ttaatttcgc ctttcagagc gccatcctca ggatacattc ttcggtgga ggcttcccat   1500
cccattgttt tttttttgcat gacagggcca tcggagggga agttggttcc tctgagtttc   1560
acctataaa taaactctcc gtcctggagg gtgctatctt gtgtgactgt caccacgcct   1620
ccgtcctcga agttcatgaa tctctcccac ttgaagcctt cagggaagga gagcttcaga   1680
tagtcaggga tgtcggcagg gtgtttaaca taggctttgc ttccgtactg gaactgaggg   1740
ctcagaatat cccaggagaa gggggaggggt cctccttttg tgacccttgag cttagcggtt   1800
tgtgtgccct cgtaaggccg gccttctcct tctccctcaa tctcgaactc gtgtccgttg   1860
acgcttccct ccatcttgac cttaaatctc ataaactctt tgatgacatc ctcggagctg   1920
gccatggtgg cgatcgatag gtcgaaaggc ccggagatga ggaagaggag aacagcgcgg   1980
cagacgtgcg cttttgaagc gtgcagaatg ccgggcctcc ggaggacctt cgggcgcacc   2040
ccccgcccct gagcccgccc ctgagcccgc cccggaccc acccttccca gctgctgagc   2100
ccagaaagcg aaggagcaaa gctgctattg gccgctgccc caaaggccta cccgcttcca   2160
ttgctcagcg gtgctgtcca tctgcacgag actagtgaga cgtgctactt ccatttgtca   2220
cgtcctgcac gacgcgagct gcggggcggg ggggaacttc ctgactaggg gaggagtaga   2280
aggtggcgcg aaggggccac caaagaacgg agccggttgg cgctaccggt ggatgtggaa   2340
tgtgtgcgag gccagaggcc acttgtgtag cgccaagtgc ccaagtgctt gggctaaagc   2400
atgctccaga ctgccttggg aaaagcgcct ccctacccg gtagaattat ctttctagaa   2460
aggatctgcg atcgctccgg tgcccgtcag tgggcagagc gcacatcgcc cacagtcccc   2520
gagaagttgg ggggaggggt cggcaattga acgggtgcct agagaaggtg gcgcgggggta   2580
aactgggaaa gtgatgtcgt gtactggctc cgcctttttc ccgagggtgg gggagaaccg   2640
tatataagtg cagtagtcgc cgtgaacgtt ctttttcgca acgggtttgc cgccagaaca   2700
```

-continued

```
cagctgaagc ttcgagggg  tcgcatctct  ccttcacgcg  cccgccgccc  tacctgaggc  2760
cgccatccac gccggttgag  tcgcgttctg  ccgcctcccg  cctgtggtgc  ctcctgaact  2820
gcgtccgccg tctaggtaag  tttaaagctc  aggtcgagac  cgggcctttg  tccggcgctc  2880
ccttggagcc tacctagact  cagccggctc  tccacgcttt  gcctgaccct  gcttgctcaa  2940
ctctacgtct ttgtttcgtt  ttctgttctg  cgccgttaca  gatccaagct  gtgaccggcg  3000
cctacgaatt cgatatcggt  accgctagcc  ctaggacgcg  tcagacatga  taagatacat  3060
tgatgagttt ggacaaacca  caactagaat  gcagtgaaaa  aaatgcttta  tttgtgaaat  3120
ttgtgatgct attgctttat  ttgtaaccat  tataagctgc  aataaacaag  ttaacaacaa  3180
caattgcatt cattttatgt  ttcaggttca  gggggaggtg  tgggaggttt  tttatcgttc  3240
ttcttttatt ctctcaagat  tttcaggctg  tatattaaaa  cttatattaa  gaactatgct  3300
aaccacctca tcaggaaccg  ttgtaggtgg  cgtgggtttt  cttggcaatc  gactctcatg  3360
aaaactacga gctaaatatt  caatatgttc  ctcttgacca  actttattct  gcattttttt  3420
tgaacgaggt ttagagcaag  cttgtcgacg  atgtaggtca  cggtctcgaa  gccgcggtgc  3480
gggtgccagg gcgtgccctt  gggctccccg  ggcgcgtact  ccacctcacc  catctggtcc  3540
atcatgatga acgggtcgag  gtggcggtag  ttgatcccgg  cgaacgcgcg  gcgcaccggg  3600
aagccctcgc cctcgaaacc  gctgggcgcg  gtggtcacgg  tgagcacggg  acgtgcgacg  3660
gcgtcggcgg gtgcggatac  gcggggcagc  gtcagcgggt  tctcgacggt  cacggcgggc  3720
atgtcgacaa gcttcaggaa  actgagacag  gaattttatt  aaaaatttaa  attttgaaga  3780
aagttcaggg ttaatagcat  ccattttttg  ctttgcaagt  tcctcagcat  tcttaacaaa  3840
agacgtctct tttgacatgt  ttaaagttta  aacctcctgt  gtgaaattat  tatccgctca  3900
taattccaca cattatacga  gccggaagca  taaagtgtaa  agcctggggt  gcctaatgag  3960
tgagctaact cacattaatt  gcgttgcgct  cactgcccaat  tgctttccag  tcgggaaacc  4020
tgtcgtgcca gctgcattaa  tgaatcggcc  aacgcgcggg  gagaggcggt  ttgcgtattg  4080
ggcgctcttc cgcttcctcg  ctcactgact  cgctgcgctc  ggtcgttcgg  ctgcggcgag  4140
cggtatcagc tcactcaaag  gcggtaatac  ggttatccac  agaatcaggg  gataacgcag  4200
gaaagaacat gtgagcaaaa  ggccagcaaa  aggccaggaa  ccgtaaaaag  gccgcgttgc  4260
tggcgttttt ccataggctc  cgcccccctg  acgagcatca  caaaaatcga  cgctcaagtc  4320
agaggtggcg aaacccgaca  ggactataaa  gataccaggc  gtttccccct  ggaagctccc  4380
tcgtgcgctc tcctgttccg  accctgccgc  ttaccggata  cctgtccgcc  tttctccctt  4440
cgggaagcgt ggcgctttct  catagctcac  gctgtaggta  tctcagttcg  gtgtaggtcg  4500
ttcgctccaa gctgggctgt  gtgcacgaac  ccccgttca  gcccgaccgc  tgcgccttat  4560
ccggtaacta tcgtcttgag  tccaacccgg  taagacacga  cttatcgcca  ctggcagcag  4620
ccactggtaa caggattagc  agagcgaggt  atgtaggcgg  tgctacagag  ttcttgaagt  4680
ggtggcctaa ctacggctac  actagaagga  cagtatttgg  tatctgcgct  ctgctgaagc  4740
cagttacctt cggaaaaaga  gttggtagct  cttgatccgg  caaacaaacc  accgctggta  4800
gcggtggttt ttttgtttgc  aagcagcaga  ttacgcgcag  aaaaaaagga  tctcaagaag  4860
atcctttgat cttttctacg  gggtctgacg  ctcagtggaa  cgaaaactca  cgttaaggga  4920
ttttggtcat gagattatca  aaaaggatct  tcacctagat  cctttttaaat  taaaaatgaa  4980
gttttaaatc aatctaaagt  atatatgagt  aaacttggtc  tgacagttaa  caatgcttaa  5040
tcagtgaggc acctatctca  gcgatctgtc  tatttcgttc  atccatagtt  gcctgactcc  5100
ccgtcgtgta gataactacg  atacgggagg  gcttaccatc  tggccccagt  gctgcaatga  5160
taccgcgaga cccacgctca  ccggctccag  atttatcagc  aataaaccag  ccagccggaa  5220
gggccgagcg cagaagtggt  cctgcaactt  tatccgcctc  catccagtct  attaattgtt  5280
gccgggaagc tagagtaagt  agttcgccag  ttaatagttt  gcgcaacgtt  gttgccattg  5340
ctacaggcat cgtggtgtca  cgctcgtcgt  ttggtatggc  ttcattcagc  tccggttccc  5400
aacgatcaag gcgagttaca  tgatccccca  tgttgtgcaa  aaaagcggtt  agctccttcg  5460
gtcctccgat cgttgtcaga  agtaagttgg  ccgcagtgtt  atcactcatg  gttatggcag  5520
cactgcataa ttctcttact  gtcatgccat  ccgtaagatg  cttttctgtg  actggtgagt  5580
actcaaccaa gtcattctga  gaatagtgta  tgcggcgacc  gagttgctct  tgcccggcgt  5640
caatacggga taataccgcg  ccacatagca  gaactttaaa  agtgctcatc  attggaaaac  5700
gttcttcggg gcgaaaactc  tcaaggatct  taccgctgtt  gagatccagt  tcgatgtaac  5760
ccactcgtgc acccaactga  tcttcagcat  cttttactt  caccagcgtt  tctgggtgag  5820
caaaaacagg aaggcaaaat  gccgcaaaaa  agggaataag  ggcgacacgg  aaatgttgaa  5880
tactcatact cttcctttt  caatattatt  gaagcattta  tcagggttat  tgtctcatga  5940
gcggatacat atttgaatgt  atttagaaaa  ataaacaaat  aggggttccg  cgcacatttc  6000
cccgaaaagt gccacctgac  gtctaagaaa  ccattattat  catgacatta  acctataaaa  6060
ataggcgtat cacgaggcc                                                    6079
```

SEQ ID NO: 122        moltype = DNA  length = 6118
FEATURE               Location/Qualifiers
source                1..6118
                      mol_type = other DNA
                      organism = synthetic construct
SEQUENCE: 122

```
gcccctgcag ccgaattata  ttatttttgc  caaataattt  ttaacaaaag  ctctgaagtc  60
ttcttcattt aaattcttag  atgatacttc  atctggaaaa  ttgtcccaat  tagtagcatc  120
acgctgtgag taagttctaa  accatttttt  tattgttgta  ttatctctaa  tcttactact  180
cgatgagttt tcggtattat  ctctattttt  aacttggagc  aggttccatt  cattgttttt  240
ttcatcatag tgaataaaat  caactgcttt  aacacttgtg  cctgaacacc  atatccatcc  300
ggcgtaatac gactcactat  agggagagc  gccgccagat  cttccggatg  gctcgagttt  360
ttcagcaaga tcatgcctgc  tattgtcttc  ccaatcctcc  cccttgctgt  cctgcccac  420
cccaccccc  agaatagaat  gacacctact  cagacaatgc  gatgcaattt  cctcatttta  480
ttaggaaagg acagtgggag  tggcaccttc  agggtcaag  gaaggcacgg  gggaggggca  540
aacaacagat ggctggcaac  tagaaggcac  agtcgataat  gtcaggcaac  ggcgttgcgg  600
gtcatgcacc aggtgcgcgg  tccttcgggc  acctcgacgt  cggcggtgac  ggtgaagccg  660
agccgctcgt agaaggggag  gttgcgggc  gcggatgtct  ccaggaaggc  gggcaccccg  720
gcgcgctcgg ccgcctccac  tccggggagc  acgacgcgc  tgcccagacc  cttgccctgg  780
tggtcgggc  agacgccgac  ggtggccagg  aaccacgcg  gctccttggg  ccggtgcggc  840
gccaggaggc cttccatctg  ttgctgcgcg  gccagccggg  aaccgctcaa  ctcggccatg  900
```

-continued

```
cgcgggccga tctcggcgaa caccgcccc gcttcgacgc tctccggcgt ggtccagacc  960
gccaccgcgg cgccgtcgtc cgcgacccac accttgccga tgtcgagccc gacgcgcgtg 1020
aggaagagtt cttgcagctc ggtgacccgc tcgatgtggc ggtccggatc gacggtgtgg 1080
cgcgtggcgg ggtagtcggc gaacgcggcg gcgagggtgc gtacggccct ggggacgtcg 1140
tcgcgggtgg cgaggcgcac cgtgggcttg tactcggtca taggaccggg gttttcttcc 1200
acgtctcctg cttgctttaa cagagagaag ttcgtggcac cggatccctt gtacagctcg 1260
tccatgccga gagtgatccc ggcggcggtg cggaactcca gcaggaccat gtgatcgcgc 1320
ttctcgttgg ggtctttgct cagcacggac tgggtgctca ggtagtggct gtcgggcagc 1380
agcacggggc cgtcgccgat gggggtgttc tgctggtagt ggtcggcgag ctgcacgctg 1440
ccgtcctcca cgttgtggcg gatcttgaag ttcaccttga tgccgttctt ctgcttgacg 1500
gccatgatat agatgttgtg gctgttgaag ttgtactcca gcttgtgccc caggatgttg 1560
ccgtcctcct tgaagtcgac gcccttcagc tcgatgcggt tcactagggt gtcgccctcg 1620
aacttcacct cggcgcgggt cttgtaggtg ccgtcgtcct tgaagaagat ggtgcgctcc 1680
tggacgtagc cttcgggcat ggcggacttg aagaagtcgt gctgcttcat gtggtcgggg 1740
tagcgggcga agcactgcac gccgtggctc agggtggtca cgagggtggg ccagggcacg 1800
ggcagcttgc cggtggtgca gatgaacttc agggtcagct tgccgttggt ggcatcgccc 1860
tcgccctcgc ccctcacgct gaacttgtgg ccgtttacgt cgccgtccag ctcgaccagg 1920
atgggcacca ccccggtgaa cagctcctcg cccttgctca ccatggtggc gatcgatagg 1980
tcgaaaggcc cggagatgag gaagaggaga acagcgcggc agacgtgcgc ttttgaagcg 2040
tgcagaatgc cgggcctccg gaggaccttc gggcgcccgc cccgcccctg agcccgcccc 2100
tgagcccgcc cccggaccca cccttccag ctgctgagcc cagaaagcga aggagcaaag 2160
ctgctattgg ccgctgcccc aaaggcctac ccgcttccat tgctcagcgg tgctgtccat 2220
ctgcacgaga ctagtgagac gtgctacttc catttgtcac gtcctgcacg acgcgagctg 2280
cggggcgggg gggaacttcc tgactagggg aggagtagaa ggtggcgcga aggggccacc 2340
aaagaacgga gccggttggc gctaccggtg gatgtggaat gtgtgcgagg ccagaggcca 2400
cttgtgtagc gccaagtgcc agcggggctg ctaaagcgca tgtccagac tgccttggga 2460
aaagcgcctc ccctacccgg tagaattatc tttctagaaa ggatctgcga tcgctccggt 2520
gcccgtcagt gggcagagcg cacatcgccc acagtccccg agaagttggg gggaggggtc 2580
ggcaattgaa cgggtgccta gagaaggtgg cgcggggtaa actgggaaag tgatgtcgtg 2640
tactggctcc gccttttccc cgagggtggg ggagaaccgt atataagtgc agtagtcgcc 2700
gtgaacgttc tttttcgcaa cgggtttgcc gccagaacac agctgaagct tcgaggggct 2760
cgcatctctc cttcacgcgc ccgccgccct acctgaggcc gccatccacg ccggttgagt 2820
cgcgttctgc cgcctcccgc ctgtggtgcc tcctgaactg cgtccgccgt ctaggtaagt 2880
ttaaagctca ggtcgagacc gggcctttgt ccggcgctcc cttggagcct acctagactc 2940
agccggctct ccacgctttg cctgaccctg cttgctcaac tctacgtctt tgtttcgttt 3000
tctgttctgc gccgttacag atccaagctg tgaccggcgc ctacgaattc gatatcggta 3060
ccgctagccc taggacgcgt cagacatgat aagatacatt gatgagtttg gacaaaccac 3120
aactagaatg cagtgaaaaa aatgctttat ttgtgaaatt tgtgatgcta ttgctttatt 3180
tgtaaccatt ataagctgca ataaacaagt taacaacaac aattgcattc attttatgtt 3240
tcaggttcag ggggaggtgt gggaggtttt ttatcgttct tctttattc tctcaagatt 3300
ttcaggctgt atattaaaac ttatattaag aactatgcta accacctcat caggaaccgt 3360
tgtaggtggc gtgggttttc ttggcaatcg actctcatga aaactacgag ctaaatattc 3420
aatatgttcc tcttgaccaa cttttattctg cattttttt gaacgaggtt tagagcaagc 3480
ttgtcgacga tgtaggtcac ggtctcgaag ccgcggtgcg ggtccaggg cgtgcccttg 3540
ggctccccgg gcgcgtactc cacctcaccc atctggtcca tcatgatgaa cgggtcgagg 3600
tggcggtagt tgatcccggc gaacgcgcgg cgcaccggga agccctcgcc ctcgaaaccg 3660
ctgggcgcgg tggtcacggt gagcacggga cgtgcgaggg cgtcgggcgg tgcggatacg 3720
cggggcagcg tcagcgggtt ctcgacggtc acggcgggca tgtcgacaag cttcaggaaa 3780
ctgagacagg aattttatta aaaatttaaa ttttgaagaa agttcagggt taatagcatc 3840
cattttttgc tttgcaagtt cctcagcatt cttaacaaaa gacgtctctt ttgacatgtt 3900
taaagtttaa acctcctgtg tgaaattatt atccgctcat aattccacac attatacgag 3960
ccggaagcat aaagtgtaaa gcctggggtg cctaatgagt gagctaactc acattaattg 4020
cgttgcgctc actgccaatt gcttccagt cgggaaacct gtcgtgccag ctgcattaat 4080
gaatcggcca acgcgcgggg agaggcggtt tgcgtattgg gcgctcttcc gcttcctcgc 4140
tcactgactc gctgcgctcg gtcgttcggc tgcggcgagc ggtatcagct cactcaaagg 4200
cggtaatacg gttatccaca gaatcagggg ataacgcagg aaagaacatg tgagcaaaag 4260
gccagcaaaa ggccaggaac cgtaaaaagg ccgcgttgct ggcgtttttc cataggctcc 4320
gcccccctga cgagcatcac aaaaatcgac gctcaagtca gaggtggcga aacccgacag 4380
gactataaag ataccaggcg tttccccctg gaagctccct cgtgcgctct cctgttccga 4440
ccctgccgct taccggatac ctgtccgcct ttctcccttc gggaagcgtg gcgctttctc 4500
atagctcacg ctgtaggtat ctcagttcgg tgtaggtcgt tcgctccaag ctgggctgtg 4560
tgcacgaacc ccccgttcag cccgaccgct gcgccttatc cggtaactat cgtcttgagt 4620
ccaacccggt aagacacgac ttatcgccac tggcagcagc cactggtaac aggattagca 4680
gagcgaggta tgtaggcggt gctacagagt tcttgaagtg gtggcctaac tacggctaca 4740
ctagaaggac agtatttggt atctgcgctc tgctgaagcc agttaccttc ggaaaaagag 4800
ttggtagctc ttgatccggc aaacaaacca ccgctggtag cggtggtttt tttgtttgca 4860
agcagcagat tacgcgcaga aaaaaaggat ctcaagaaga tcctttgatc ttttctacgg 4920
ggtctgacgc tcagtggaac gaaaactcac gttaagggat tttggtcatg agattatcaa 4980
aaaggatctt cacctagatc ctttttaaatt aaaaatgaag ttttaaatca atctaaagta 5040
tatatgagta aacttggtct gacagttacc aatgcttaat cagtgaggca cctatctcag 5100
cgatctgtct atttcgttca tccatagttg cctgactccc cgtcgtgtag ataactacga 5160
tacgggaggg cttaccatct ggccccagtg ctgcaatgat accgcgagac ccacgctcac 5220
cggctccaga tttatcagca ataaaccagc cagccggaag ggccgagcgc agaagtggtc 5280
ctgcaacttt atccgcctcc atccagtcta ttaattgttg ccgggaagct agagtaagta 5340
gttcgccagt taatagtttg cgcaacgttg ttgccattgc tacaggcatc gtggtgtcac 5400
gctcgtcgtt tggtatggct tcattcagct ccggttccca acgatcaagg cgagttacat 5460
gatccccat gttgtgcaaa aaagcggtta gctccttcgg tcctccgatc gttgtcagaa 5520
gtaagttggc cgcagtgtta tcactcatgg ttatggcagc actgcataat tctcttactg 5580
tcatgccatc cgtaagatgc ttttctgtga ctggtgagta ctcaaccaag tcattctgag 5640
```

```
aatagtgtat gcggcgaccg agttgctctt gcccggcgtc aatacgggat aataccgcgc  5700
cacatagcag aactttaaaa gtgctcatca ttggaaaacg ttcttcgggg cgaaaactct  5760
caaggatctt accgctgttg agatccagtt cgatgtaacc cactcgtgca cccaactgat  5820
cttcagcatc ttttactttc accagcgttt ctgggtgagc aaaaacagga aggcaaaatg  5880
ccgcaaaaaa gggaataagg cgacacgga aatgttgaat actcatactc ttcctttttc  5940
aatattattg aagcatttat caggggttatt gtctcatgag cggatacata tttgaatgta  6000
tttagaaaaa taaacaaata ggggttccgc gcacatttcc ccgaaaagtg ccacctgacg  6060
tctaagaaac cattattatc atgacattaa cctataaaaa taggcgtatc acgaggcc    6118
```

SEQ ID NO: 123                    moltype = AA  length = 158
FEATURE                          Location/Qualifiers
source                           1..158
                                 mol_type = protein
                                 organism = synthetic construct
SEQUENCE: 123
MAAMAAGSIT TLPALPEDGG SGAFPPGHFK DPKRLYCKNG GFFLRIHPDG RVDGVREKSD    60
PHIKLQLQAE ERGVVSIKGV CANRYLAMKE DGRLLASKCA TDECFFFERL ESNNYNTYRS   120
RKYSSWYVAL KRTGQYKLGP KTGPGQKAIL FLPMSAKS                           158

SEQ ID NO: 124                    moltype = AA  length = 155
FEATURE                          Location/Qualifiers
source                           1..155
                                 mol_type = protein
                                 organism = synthetic construct
SEQUENCE: 124
MAAGSITTLP ALPEDGGSGA FPPGHFKDPK RLYCKNGGFF LRIHPDGRVD GVREKSDPHI    60
KLQLQAEERG VVSIKGVCAN RYLAMKEDGR LLASKCVTDE CFFFERLESN NYNTYRSRKY   120
TSWYVALKRT GQYKLGSKTG PGQKAILFLP MSAKS                              155

SEQ ID NO: 125                    moltype = AA  length = 70
FEATURE                          Location/Qualifiers
source                           1..70
                                 mol_type = protein
                                 organism = synthetic construct
SEQUENCE: 125
GPETLCGAEL VDALQFVCGD RGFYFSKPTG YGSSSRRLHH KGIVDECCFQ SCDLRRLEMY    60
CAPIKPPKSA                                                           70

SEQ ID NO: 126                    moltype = AA  length = 70
FEATURE                          Location/Qualifiers
source                           1..70
                                 mol_type = protein
                                 organism = synthetic construct
SEQUENCE: 126
GPETLCGAEL VDALQFVCGD RGFYFSKPTG YGSSSRRLHH KGIVDECCFQ SCDLRRLEMY    60
CAPIKPPKSA                                                           70

SEQ ID NO: 127                    moltype = AA  length = 70
FEATURE                          Location/Qualifiers
source                           1..70
                                 mol_type = protein
                                 organism = synthetic construct
SEQUENCE: 127
GPETLCGAEL VDALQFVCGD RGFYFSKPTG YGSSSRRLHH KGIVDECCFQ SCDLRRLEMY    60
CAPIKPPKSA                                                           70

SEQ ID NO: 128                    moltype = AA  length = 70
FEATURE                          Location/Qualifiers
source                           1..70
                                 mol_type = protein
                                 organism = synthetic construct
SEQUENCE: 128
GPETLCGAEL VDALQFVCGP RGFYFSKPTG YGSSIRRLHH KGIVDECCFQ SCDLRRLEMY    60
CAPIKPTKAA                                                           70

SEQ ID NO: 129                    moltype = AA  length = 251
FEATURE                          Location/Qualifiers
source                           1..251
                                 mol_type = protein
                                 organism = synthetic construct
SEQUENCE: 129
MCPQPARLEM NRCWALFLSL CCYLRLVSAE GDPIPEELYE MLSDHSIRSF DDLQRLLHGD    60
SVEEDGAELD LNXTRSHSGG ELESLSRGRR SLGSXTIAEP AVIAECKTRT EVFEISRRLI   120
DRTNANFLVW PPCVEVQRCS GCCNNRNVQC RPTQVQXRXV QVXKIEIVRK KPIFKKATVT   180
LEDHLACRCE TVXAXRPVTR XPGSSQEQRX AXTPQTRVTI RTVRVRRPPK GKHRKFKHTH   240
DKTALKETLG A                                                       251

SEQ ID NO: 130                    moltype = AA  length = 241
FEATURE                          Location/Qualifiers -continued

```
source                    1..241
                          mol_type = protein
                          organism = synthetic construct
SEQUENCE: 130
MNRCWALFLS LCCYLRLVSA EGDPIPEELY KMLSDHSIRS FDDLQRLLHG DSVDEDGAEL  60
DLNLTRSHSG GELESLSRGR RSLGSPTVAA EPAVIAECKT RTEVFEISRR LIDRTNANFL  120
VWPPCVEVQR CSGCCNNRNV QCRPTQVQDR KVQVKKIEIV RKKKIFKKAT VTLVDHLACR  180
CETVVARAVT RTPGSSQEQR ARTPQTRVTI RTVRVRRPPK GKHRKFKHTH DKTALKETLG  240
A                                                                 241

SEQ ID NO: 131            moltype = AA  length = 241
FEATURE                   Location/Qualifiers
source                    1..241
                          mol_type = protein
                          organism = synthetic construct
SEQUENCE: 131
MNRCWALFLS LCCYLRLVSA EGDPIPEELY EMLSDHSIRS FDDLQRLLHG DPGEEDGAEL  60
DLNMTRSHSG GELESLARGR RSLGSLTIAE PAMIAECKTR TEVFEISRRL IDRTNANFLV  120
WPPCVEVQRC SGCCNNRNVQ CRPTQVQLRP VQVRKIEIVR KKPIFKKATV TLEDHLACKC  180
ETVAAARPVT RSPGGSQEQR AKTPQTRVTI RTVRVRRPPK GKHRKFKHTH DKTALKETLG  240
A                                                                 241
```

ENGINEERING CELL LINES CAPABLE OF PROLIFERATION IN GROWTH FACTOR FREE MEDIA FORMULATIONS

1. CROSS-REFERENCE TO RELATED APPLICATIONS

This application claims the benefit of U.S. Provisional Application No. 63/349,865 filed Jun. 7, 2022, which is hereby incorporated in its entirety by reference.

2. SEQUENCE LISTING

The instant application contains a Sequence Listing with 131 sequences, which has been submitted via Patent Center and is hereby incorporated by reference in its entirety. Said XML copy, created on Jun. 7, 2023, is named 55926US-SequenceListing.xml, and is 252,422 bytes in size.

3. BACKGROUND

The mass production of cells remains limited by several factors, thus limiting final yields. Mass production of cells finds several downstream applications. For example, foods formulated from metazoan cells, cultured in vitro, have prospective advantages over their corporal-derived animal counterparts, including improved nutrition and safety. Production of these products have been projected to require fewer resources, convert biomass at a higher caloric efficiency and result in reduced environmental impacts relative to conventional in vivo methods. Together, metazoan cells, and their extracellular products, constitute a biomass that can potentially be harvested from a cultivation infrastructure for formulation of cell-based food products, such as cultured meat.

However, mass production of cells originating from cultured metazoan cells remains limited by several factors, for example, by the maximum culture density that can be conventionally achieved and the requirement for supplemented proteins, such as growth factors, which support the productivity of the cultivation process, thus limiting final yields. Provided herein are compositions and methods that address this and other related needs.

4. SUMMARY

This disclosure is based in part on the finding that introducing a polynucleotide comprising a coding sequence of a growth factor ligand and/or a coding sequence of a growth factor receptor into a cell line results in the cell line's reduced reliance on exogenous growth factors. For example, the Applicant found that introducing a polynucleotide comprising a coding sequence of a growth factor ligand and/or a coding sequence of a growth factor receptor into a cell line results in maintenance of cell proliferation rates similar to controls and an increase in the number of non-adherent cells (i.e., cells from anchorage-dependent growth) all while cells are grown in the absence of one or more exogenous growth factors (see FIG. 1).

Overall, this work demonstrated the ability to engineer cells to have reduced dependence on exogenous growth factors without compromising the cell's ability to proliferate or differentiate into myogenic cells. These findings are important because manufacturing cells suitable for consumption requires vast amounts of exogenous growth factors, which is both cost and time prohibitive (when factoring in supply chain). The engineered cells provided herein supply their own source of growth factor signaling—thereby bypassing or at least reducing the need to supplement the cultures with exogenous growth factors. Moreover, by promoting anchorage independent growth, which is currently essential for manufacturing cell based meats suitable for consumption, the engineered cell lines provided herein increase the efficiency by which cell based meats suitable for consumption can be produced.

In one aspect, this disclosure features a method for eliminating exogenous growth factor dependence of a culture comprising an avian or mammalian cell line, comprising: (a) introducing into the cell line one or more of: (i) a polynucleotide comprising a coding sequence of a growth factor ligand; (ii) a polynucleotide comprising a coding sequence of a growth factor receptor; or (iii) a polynucleotide comprising a coding sequence of an activated growth factor receptor; and (b) culturing the cell line in a cultivation infrastructure, wherein the cell line is capable of proliferating to a cell density higher than an initially seeded cell density over 72 hours of culture time without an addition of exogenous growth factors to the culture. In some embodiments, the polynucleotide sequence of (i), (ii), or (iii) are operably linked to a promoter sequence.

In some embodiments, the polynucleotide comprising a coding sequence of a growth factor ligand further comprises a coding sequence of an additional one or more growth factor ligands, wherein each of the additional growth factor ligands is selected from FGF2, IGF1, and PDGFb.

In some embodiments, the growth factor ligand is FGF2.

In some embodiments, the growth factor ligand is IGF1.

In some embodiments, the growth factor ligand is PDGFb.

In some embodiments, the coding sequence of the growth factor ligand includes a mutation for enhanced heat stability.

In some embodiments, the cell line is cultured in an absence of serum.

In some embodiments, the cell line cell density at least doubles from an initially seeded cell density.

In some embodiments, the cell line is cultured to a cell density of 1 million cells per milliliter or more.

In some embodiments, the growth factor ligand polynucleotide sequence further comprises a coding sequence of a signal peptide sequence, thereby providing a fusion protein sequence coding for a fusion protein having an increased secretion propensity relative to an endogenous growth factor.

In some embodiments,
  (a) the concentration of FGF2 in the culture medium is increased by at least 2.5% as compared to cell lines not engineered to include a polynucleotide encoding FGF2;
  (b) the concentration of IGF-1 in the culture medium is increased by at least 2.5% as compared to cell lines not engineered to include a polynucleotide encoding IGF1; and/or
  (c) the concentration of PDGFb in the culture medium is increased by at least 2.5% as compared to cell lines not engineered to include a polynucleotide encoding PDGFb.

In some embodiments, the polynucleotide comprising a coding sequence of a growth factor receptor further comprises a coding sequence of an additional one or more growth factor receptors, wherein each additional growth factor receptor is selected from FGFR, IGFR, and PDGFR.

In some embodiments, the growth factor receptor is an FGFR selected from FGFR1, FGFR2, FGFR3, and FGFR4.

In some embodiments, the growth factor receptor is IGF1R.

In some embodiments, the growth factor receptor is PDGFR.

In some embodiments, the cell line is derived from a chicken, duck, turkey, porcine, or bovine.

In some embodiments, the cell line is derived from chicken.

In some embodiments, the cells are myoblasts, myocytes, satellite cells, side population cells, muscle derived stem cells, mesenchymal stem cells, myogenic pericytes, mesoangioblasts, fibroblasts, stem cells, or are cells otherwise having myogenic or fibroblastic capacity.

In some embodiments, the step of forming a cell line into a cell-based food product suitable for consumption, wherein the cell line and a cell culture media used to grow the grown cell are edible.

In another aspect, this disclosure features a vector comprising a polynucleotide encoding a growth factor ligand or a fragment thereof, and a growth factor receptor or a fragment thereof.

In one aspect, this disclosure features method of engineering a cell line for reduced dependence on exogenous growth factors, comprising: (a) introducing into the cell line one or more of: (i) a polynucleotide comprising a coding sequence of a growth factor ligand; (ii) a polynucleotide comprising a coding sequence of a growth factor receptor; or (iii) a polynucleotide comprising a coding sequence of an activated downstream growth factor target; and (b) culturing the cell line in a cultivation infrastructure.

In one aspect, this disclosure features method of increasing the concentration of a growth factor ligand in culture medium of cells in culture, comprising: (a) introducing into a cell line one or more of: (i) a polynucleotide comprising a coding sequence of a growth factor ligand; and (ii) a polynucleotide comprising a coding sequence of a growth factor receptor; or (iii) a polynucleotide comprising a coding sequence of an activated downstream growth factor target; and (b) culturing the cell line in a cultivation infrastructure.

In one aspect, this disclosure features method for improving anchorage independent growth in a cell line, comprising: (a) introducing into the cell line one or more of: (i) a polynucleotide comprising a coding sequence of a growth factor ligand; and (ii) a polynucleotide comprising a coding sequence of a growth factor receptor; or (iii) a polynucleotide comprising a coding sequence of an activated downstream growth factor target; and (b) culturing the cell line in a cultivation infrastructure.

In one aspect, this disclosure features method for increasing the cell density of a culture comprising a cell line, comprising: (a) introducing into the cell line one or more of: (i) a polynucleotide comprising a coding sequence of a growth factor ligand; and (ii) a polynucleotide comprising a coding sequence of a growth factor receptor; or (iii) a polynucleotide comprising a coding sequence of an activated growth factor receptor; and (b) culturing the cell line in a cultivation infrastructure.

In some embodiments, the growth factor ligand is selected from basic fibroblast growth factor (FGF2), insulin-like growth factor 1 (IGF1), and platelet-derived growth factor subunit B (PDGFb).

In some embodiments, the polynucleotide comprising a coding sequence of a growth factor ligand further comprises an additional two or more growth factor ligands, wherein each of the additional growth factor ligands is selected from FGF2, IGF1, and PDGFb.

In some embodiments, the growth factor ligands is FGF2. In some embodiments, the FGF2 comprises an amino acid sequence having at least 80% sequence identity to a sequence selected from SEQ ID NO: 1-15.

In some embodiments, the growth factor ligands is IGF1. In some embodiments, the IGF1 comprises an amino acid sequence having at least 80% sequence identity to a sequence selected from SEQ ID NO: 16-17.

In some embodiments, the growth factor ligands is PDGFb. In some embodiments, the PDGFb comprises an amino acid sequence having at least 80% sequence identity to a sequence selected from SEQ ID NO: 18-21.

In some embodiments, the polynucleotide comprising a coding sequence of a growth factor ligand further comprises a coding sequence of a signal peptide located 5' to the coding sequence of the growth factor ligand, and wherein the signal sequence and the growth factor ligand are a fusion protein. In some embodiments, the signal sequence comprises an amino acid sequence having at least 80% sequence identity to a sequence selected from SEQ ID NO: 22-31.

In some embodiments, the polynucleotide comprising a coding sequence of a growth factor ligand further comprises a regulatory sequence operably linked to the coding sequence of the growth factor ligand and/or additional growth factor ligands.

In some embodiments, the regulatory sequence comprises a promoter selected from: an inducible promoter, a tissue specific promoter, and a constitutively active promoter.

In some embodiments, the promoter is selected from EF1alpha, PGK, CMV, RSV, and β-actin.

In some embodiments, the polynucleotide comprising a coding sequence of a growth factor ligand comprises a sequence encoding a polycistronic mRNA, wherein the polycistronic mRNA comprises the coding sequence of the growth factor ligand and the coding sequence one or more additional growth factor ligands.

In some embodiments, the polynucleotide comprising a coding sequence of a growth factor ligand comprises one or more sequences encoding a self-cleaving peptide, one or more internal ribosome entry sites (IRES), or a combination thereof.

In some embodiments, activity and/or expression of the growth factor ligand is controllable.

In some embodiments, activity and/or expression of the growth factor ligand is controlled using an inducible promoter, an inducible tag, or a degradation tag.

In some embodiments, expression of the growth factor ligands is controlled using an inducible promoter. In some embodiments, the coding sequence of the growth factor ligand is operably linked to the inducible promoter. In some embodiments, the method also includes: maintaining the engineered cell line in a culture medium comprising a molecule capable of controlling the inducible promoter, thereby enabling expression of the growth factor ligand.

In some embodiments, activity of the growth factor ligand is controlled using an inducible tag. In some embodiments, the polynucleotide comprising a coding sequence of a growth factor ligand further comprises a coding sequence of an inducible tag located 5' or 3' to the coding sequence of the growth factor ligand, and wherein the inducible tag and the growth factor ligand are a fusion protein. In some embodiments, the method also includes: maintaining the engineered cell line in a culture medium comprising a molecule capable of controlling the inducible tag, thereby inducing activity of the growth factor ligand/fusion protein.

In some embodiments, activity of the one or more growth factor ligands is controlled using a degradation tag. In some embodiments, the polynucleotide comprising a coding sequence of a growth factor ligand further comprises a coding sequence of a degradation tag located 5' or 3' to the coding sequence of the growth factor ligand, and wherein the degradation tag and the growth factor ligand are a fusion protein. In some embodiments, the method also includes: maintaining the engineered cell line in a culture medium comprising a molecule capable of controlling the degradation tag, thereby targeting the growth factor ligand/fusion protein for degradation.

In some embodiments, (a) the concentration of FGF2 in the culture medium is increased by at least 0.001 ng/mL as compared to cell lines not engineered to include a polynucleotide encoding FGF2; (b) the concentration of IGF-1 in the culture medium is increased by at least 0.001 ng/mL as compared to cell lines not engineered to include a polynucleotide encoding IGF1; and/or (c) the concentration of PDGFb in the culture medium is increased by at least 0.001 ng/mL as compared to cell lines not engineered to include a polynucleotide encoding PDGFb.

In some embodiments, (a) the concentration of FGF2 in the culture medium is increased by at least 2.5% as compared to cell lines not engineered to include a polynucleotide encoding FGF2; (b) the concentration of IGF-1 in the culture medium is increased by at least 2.5% as compared to cell lines not engineered to include a polynucleotide encoding IGF1; and/or (c) the concentration of PDGFb in the culture medium is increased by at least 2.5% as compared to cell lines not engineered to include a polynucleotide encoding PDGFb.

In some embodiments, the growth factor receptor is selected from fibroblast growth factor receptor (FGFR), insulin growth factor 1 receptor (IGF1R), and platelet-derived growth factor receptor (PDGFR).

In some embodiments, the polynucleotide comprising a coding sequence of a growth factor receptor further comprises an additional two or more growth factor receptors, wherein each additional growth factor receptor is selected from FGFR, IGFR, and PDGFR.

In some embodiments, the growth factor receptor is an FGFR selected from FGFR1, FGFR2, FGFR3, and FGFR4. In some embodiments, the FGFR comprises an amino acid sequence having at least 80% sequence identity to a sequence selected from SEQ ID NO: 32-49.

In some embodiments, the growth factor receptor is IGF1R. In some embodiments, the IGF1R comprises an amino acid sequence having at least 80% sequence identity to a sequence selected from SEQ ID NO: 50-51.

In some embodiments, the growth factor receptor is PDGFR. In some embodiments, the PDGFR comprises an amino acid sequence having at least 80% sequence identity to a sequence selected from SEQ ID NO: 52-58.

In some embodiments, the polynucleotide comprising a coding sequence of an activated downstream growth factor target comprises a growth factor receptor comprising one or more amino acid insertions, deletions, or substitutions that result in the receptor being constitutively activated.

In some embodiments, the polynucleotide comprising a coding sequence of a growth factor receptor comprises a regulatory sequence operably linked to the coding sequence of the growth factor receptor and/or the coding sequence of the additional growth factor receptors.

In some embodiments, the regulatory sequence comprises a promoter selected from: an inducible promoter, a tissue specific promoter, and a constitutively active promoter.

In some embodiments, the promoter is selected from EF1alpha, PGK, CMV, RSV, and β-actin.

In some embodiments, the polynucleotide comprising a coding sequence of a growth factor receptor comprises a sequence encoding a polycistronic mRNA, wherein the polycistronic mRNA comprises the coding sequence of the growth factor receptor and the coding sequence of the two or more additional growth factor receptors.

In some embodiments, the polynucleotide comprising a coding sequence of a growth factor receptor comprises one or more sequences encoding a self-cleaving peptide, one or more internal ribosome entry sites (IRES), or a combination thereof.

In some embodiments, activity and/or expression of the growth factor receptors is controllable.

In some embodiments, expression of the growth factor receptor is controlled using an inducible promoter, an inducible tag, and a degradation tag.

In some embodiments, expression of the growth factor receptor is controlled using an inducible promoter. In some embodiments, the coding sequence of the growth factor receptor is operably linked to the inducible promoter. In some embodiments, the method also includes: maintaining the engineered cell line in a culture medium comprising a molecule capable of controlling the inducible promoter, thereby enabling expression of the growth factor receptor.

In some embodiments, activity of the growth factor receptor is controlled using an inducible tag. In some embodiments, the polynucleotide comprising a coding sequence of a growth factor receptor further comprises a coding sequence of an inducible tag located 5' or 3' to the coding sequence of the growth factor receptor, and wherein the inducible tag and the growth factor receptor are a fusion protein.

In some embodiments, the method also includes: maintaining the engineered cell line in a culture medium comprising a molecule capable of controlling the inducible tag, thereby inducing activity of the growth factor receptor/fusion protein.

In some embodiments, activity of the one or more growth factor ligands is controlled using a degradation tag. In some embodiments, the polynucleotide comprising a coding sequence of a growth factor receptor further comprises a coding sequence of a degradation tag located 5' or 3' to the coding sequence of the growth factor receptor, and wherein the degradation tag and the growth factor receptor are a fusion protein.

In some embodiments, the method also includes: maintaining the engineered cell line in a culture medium comprising a molecule capable of controlling the degradation tag, thereby targeting the growth factor receptor/fusion protein for degradation.

In some embodiments, the method also includes introducing a polynucleotide sequence encoding an accessory protein.

In some embodiments, the polynucleotide comprising a coding sequence of a growth factor ligand and/or the polynucleotide comprising a coding sequence of a growth factor receptor further comprises a coding sequence of an accessory protein.

In some embodiments, the accessory protein is fibroblast growth factor binding protein (FGFBP). In some embodiments, the FGFBP comprises an amino acid sequence having at least 80% sequence identity to a sequence of SEQ ID NO: 59.

In some embodiments, the accessory protein is RASV12. In some embodiments, the RASV12 comprises an amino acid sequence having at least 80% sequence identity to a sequence of SEQ ID NO: 60.

In some embodiments, the method comprises introducing into the cell: (i) a polynucleotide comprising a coding sequence of FGF2, and a polynucleotide comprising a FGFR; (ii) a polynucleotide comprising a coding sequence of IGF1, and a polynucleotide comprising an IGF1R; (iii) a polynucleotide comprising a coding sequence of PDGF, and a polynucleotide comprising a PDGFR, or (iv) a combination selected from: (i) and (ii), (ii) and (iii), (ii) and iii), and (i), (ii), and (iii).

In some embodiments, the cell line is from a livestock, poultry, game or aquatic animal species. In some embodiments, the cell line is from a chicken, duck, or turkey. In some embodiments, the cell line is from a fish. In some embodiments, the cell line is from a livestock species. In some embodiments, the livestock species is porcine or bovine. In some embodiments, the cells are from any animal species intended for human or non-human dietary consumption.

In some embodiments, the cells are myogenic cells. In some embodiments, the myogenic cells are myoblasts, myocytes, satellite cells, side population cells, muscle derived stem cells, mesenchymal stem cells, myogenic pericytes, or mesoangioblasts.

In some embodiments, the cells are non-myogenic cells.

In some embodiments, the cells are fibroblasts, stem cells, or are cells otherwise having myogenic or fibroblastic capacity.

In another aspect, this disclosure features in vitro methods for producing cell-based meat suitable for consumption, comprising: (a) introducing into a cell one or more of: (i) a polynucleotide comprising a coding sequence of a growth factor; (ii) a polynucleotide comprising a coding sequence of a growth factor receptor; or (iii) a polynucleotide comprising a coding sequence of an activated downstream growth factor target; and (b) inducing myogenic specific differentiation, wherein the differentiated cells form myocytes and multinucleated myotubes; (c) culturing the myocytes and myotubes to generate skeletal muscle fibers, thereby producing a cell-based meat suitable for consumption.

In some embodiments, the cell line is avian or mammalian. In all embodiments, the cell line is non-human. In some embodiments, the cell line is from a livestock, poultry, game or aquatic animal species. In some embodiments, the cell line is from a chicken, duck, or turkey. In some embodiments, the cell line is from a fish. In some embodiments, the cell line is from a livestock species. In some embodiments, the livestock species is porcine or bovine.

In some embodiments, the cells are from any animal species intended for human or non-human dietary consumption.

In some embodiments, the cells are myogenic cells. In some embodiments, the myogenic cells are myoblasts, myocytes, satellite cells, side population cells, muscle derived stem cells, mesenchymal stem cells, myogenic pericytes, or mesoangioblasts.

In some embodiments, the cells are non-myogenic cells.

In some embodiments, the growth factor ligand is selected from basic fibroblast growth factor (FGF2), insulin-like growth factor 1 (IGF1), and platelet-derived growth factor subunit B (PDGFb).

In some embodiments, the polynucleotide comprising a coding sequence of a growth factor ligand further comprises an additional two or more growth factor ligands, wherein each of the additional growth factor ligands is selected from FGF2, IGF1, and PDGFb.

In some embodiments, the growth factor ligands is FGF2. In some embodiments, the FGF2 comprises an amino acid sequence having at least 80% sequence identity to a sequence selected from SEQ ID NO: 1-15.

In some embodiments, the growth factor ligands is IGF1. In some embodiments, the IGF1 comprises an amino acid sequence having at least 80% sequence identity to a sequence selected from SEQ ID NO: 16-17.

In some embodiments, the growth factor ligands is PDGFb. In some embodiments, the PDGFb comprises an amino acid sequence having at least 80% sequence identity to a sequence selected from SEQ ID NO: 18-21.

In some embodiments, the polynucleotide comprising a coding sequence of a growth factor ligand further comprises a coding sequence of a signal peptide located 5' to the coding sequence of the growth factor ligand, and wherein the signal sequence and the growth factor ligand are a fusion protein.

In some embodiments, the signal sequence comprises an amino acid sequence having at least 80% sequence identity to a sequence selected from SEQ ID NO: 22-31.

In some embodiments, the polynucleotide comprising a coding sequence of a growth factor ligand comprises a regulatory sequence operably linked to the coding sequence of the growth factor ligand and/or additional growth factor ligands.

In some embodiments, the regulatory sequence comprises a promoter selected from: an inducible promoter, a tissue specific promoter, and a constitutively active promoter.

In some embodiments, the promoter is selected from EF1alpha, PGK, CMV, RSV, and β-actin.

In some embodiments, the polynucleotide comprising a coding sequence of a growth factor ligand comprises a sequence encoding a polycistronic mRNA, wherein the polycistronic mRNA comprises the coding sequence of the growth factor ligand and the coding sequence one or more additional growth factor ligands.

In some embodiments, the polynucleotide comprising a coding sequence of a growth factor ligand further comprises one or more sequences encoding a self-cleaving peptide, one or more internal ribosome entry sites (IRES), or a combination thereof.

In some embodiments, activity and/or expression of the growth factor ligand is controllable.

In some embodiments, activity and/or expression of the growth factor ligand is controlled using an inducible promoter, an inducible tag, or a degradation tag.

In some embodiments, expression of the growth factor ligands is controlled using an inducible promoter. In some embodiments, the coding sequence of the growth factor ligand is operably linked to the inducible promoter. In some embodiments, the method also includes: maintaining the engineered cell line in a culture medium comprising a molecule capable of controlling the inducible promoter, thereby enabling expression of the growth factor ligand.

In some embodiments, activity of the growth factor ligand is controlled using an inducible tag. In some embodiments, the polynucleotide comprising a coding sequence of a growth factor ligand further comprises a coding sequence of an inducible tag located 5' or 3' to the coding sequence of the growth factor ligand, and wherein the inducible tag and the growth factor ligand are a fusion protein. In some embodiments, the method also includes: maintaining the engineered cell line in a culture medium comprising a molecule capable of controlling the inducible tag, thereby inducing activity of the growth factor ligand/fusion protein.

In some embodiments, activity of the one or more growth factor ligands is controlled using a degradation tag. In some embodiments, the polynucleotide comprising a coding sequence of a growth factor ligand further comprises a coding sequence of a degradation tag located 5' or 3' to the coding sequence of the growth factor ligand, and wherein the degradation tag and the growth factor ligand are a fusion protein. In some embodiments, the method also includes: maintaining the engineered cell line in a culture medium comprising a molecule capable of controlling the degradation tag, thereby targeting the growth factor ligand/fusion protein for degradation.

In some embodiments, the growth factor receptor is selected from fibroblast growth factor receptor (FGFR), insulin growth factor 1 receptor (IGF1R), and platelet-derived growth factor receptor (PDGFR).

In some embodiments, the polynucleotide comprising a coding sequence of a growth factor receptor further comprises an additional two or more growth factor receptors, wherein each additional growth factor receptor is selected from FGFR, IGFR, and PDGFR.

In some embodiments, the growth factor receptor is an FGFR selected from FGFR1, FGFR2, FGFR3, and FGFR4. In some embodiments, the FGFR comprises an amino acid sequence having at least 80% sequence identity to a sequence selected from SEQ ID NO: 32-49.

In some embodiments, the growth factor receptor is IGF1R. In some embodiments, the IGF1R comprises an amino acid sequence having at least 80% sequence identity to a sequence selected from SEQ ID NO: 50-51.

In some embodiments, the growth factor receptor is PDGFR. In some embodiments, the PDGFR comprises an amino acid sequence having at least 80% sequence identity to a sequence selected from SEQ ID NO: 52-58.

In some embodiments, the polynucleotide comprising a coding sequence of an activated downstream growth factor target comprises a growth factor receptor comprising one or more amino acid insertions, deletions, or substitutions that result in the receptor being constitutively activated.

In some embodiments, the polynucleotide comprising a coding sequence of a growth factor receptor comprises a regulatory sequence operably linked to the coding sequence of the growth factor receptor and/or the coding sequence of the additional growth factor receptors.

In some embodiments, the regulatory sequence comprises a promoter selected from: an inducible promoter, a tissue specific promoter, and a constitutively active promoter.

In some embodiments, the promoter is selected from EF1alpha, PGK, CMV, RSV, and β-actin.

In some embodiments, the polynucleotide comprising a coding sequence of a growth factor receptor comprises a sequence encoding a polycistronic mRNA, wherein the polycistronic mRNA comprises the coding sequence of the growth factor receptor and the coding sequence of the two or more additional growth factor receptors.

In some embodiments, the polynucleotide comprising a coding sequence of a growth factor receptor comprises one or more sequences encoding a self-cleaving peptide, one or more internal ribosome entry sites (IRES), or both.

In some embodiments, activity and/or expression of the growth factor receptors is controllable.

In some embodiments, expression of the growth factor receptor is controlled using an inducible promoter, an inducible tag, and a degradation tag.

In some embodiments, expression of the growth factor receptor is controlled using an inducible promoter. In some embodiments, the coding sequence of the growth factor receptor is operably linked to the inducible promoter. In some embodiments, the method also includes: maintaining the engineered cell line in a culture medium comprising a molecule capable of controlling the inducible promoter, thereby enabling expression of the growth factor receptor.

In some embodiments, activity of the growth factor receptor is controlled using an inducible tag. In some embodiments, the polynucleotide comprising a coding sequence of a growth factor receptor further comprises a coding sequence of an inducible tag located 5' or 3' to the coding sequence of the growth factor receptor, and wherein the inducible tag and the growth factor receptor are a fusion protein. In some embodiments, the method also includes: maintaining the engineered cell line in a culture medium comprising a molecule capable of controlling the inducible tag, thereby inducing activity of the growth factor receptor/fusion protein.

In some embodiments, activity of the one or more growth factor ligands is controlled using a degradation tag. In some embodiments, the polynucleotide comprising a coding sequence of a growth factor receptor further comprises a coding sequence of a degradation tag located 5' or 3' to the coding sequence of the growth factor receptor, and wherein the degradation tag and the growth factor receptor are a fusion protein. In some embodiments, the method also includes: maintaining the engineered cell line in a culture medium comprising a molecule capable of controlling the degradation tag, thereby targeting the growth factor receptor/fusion protein for degradation.

In some embodiments, the method also includes introducing a polynucleotide sequence encoding an accessory protein.

In some embodiments, the polynucleotide comprising a coding sequence of a growth factor ligand, the polynucleotide comprising a coding sequence of a growth factor receptor, or both, further comprises a coding sequence of an accessory protein.

In some embodiments, the accessory protein is fibroblast growth factor binding protein (FGFBP). In some embodiments, the FGFBP comprises an amino acid sequence having at least 80% sequence identity to a sequence of SEQ ID NO: 59.

In some embodiments, the accessory protein is RASV12. In some embodiments, the RASV12 comprises an amino acid sequence having at least 80% sequence identity to a sequence of SEQ ID NO: 60.

In some embodiments, the method comprises introducing into the cell: (i) a polynucleotide comprising a coding sequence of FGF2, and a polynucleotide comprising a coding sequence of FGFR; (ii) a polynucleotide comprising a coding sequence of IGF1, and a polynucleotide comprising a coding sequence of IGF1R; (iii) a polynucleotide comprising a coding sequence of PDGF, and a polynucleotide comprising a coding sequence of PDGFR, or (iv) a combination selected from: (i) and (ii), (ii) and (iii), (ii) and iii), and (i), (ii), and (iii).

In another aspect, this disclosure features a myogenic cell suitable for consumption comprising cells having increased expression of FGF2, IGF1, PDGFb, FGFR, IGF1R, or PDGFR, or a combination thereof.

In another aspect, this disclosure features a population of cells suitable for consumption comprising cells having increased expression of FGF2, IGF1, PDGFb, FGFR, IGF1R, or PDGFR, or a combination thereof.

In another aspect, this disclosure features a vector comprising a polynucleotide encoding a fusion protein comprising a coding sequence of a signaling sequence and a coding sequence of a growth factor ligand, and optionally a coding sequence of an inducible tag or a degradation tag.

In another aspect, this disclosure features a cell comprising a polynucleotide encoding a fusion protein comprising a coding sequence of a signaling sequence and a coding sequence of a growth factor ligand, and optionally a coding sequence of an inducible tag or a degradation tag.

In another aspect, this disclosure features a vector comprising a polynucleotide comprising a first coding sequence of a growth factor ligand, and a second coding sequence of growth factor receptor.

In another aspect, this disclosure features a cell comprising a polynucleotide comprising a coding sequence of a growth factor ligand or a fragment thereof, and a polynucleotide comprising a coding sequence of a growth factor receptor or a fragment thereof.

In another aspect, this disclosure features cell-based meat suitable for consumption produced using the any of the methods described herein.

5. BRIEF DESCRIPTION OF THE DRAWINGS

These and other features, aspects, and advantages of the present invention will become better understood with regard to the following description, and accompanying drawings, where:

These and other features, aspects, and advantages of the present invention will become better understood with regard to the following description, and accompanying drawings, where:

FIG. 1 shows illustration of three approaches to generate growth factor independent cell lines. Specific growth factors required for cell proliferation and/or tissue formation phenotypes are identified by conducting a growth factor screen and/or analysis for upregulated growth factor receptors. Growth factor-independent cell lines are generated with the following approaches: 1. Genetically engineer cells to overexpress native growth factor or growth factor variants with higher thermostability (heat stable), increased half-life, and/ or enhanced secretions. 2. Genetically engineer cells to overexpress native downstream growth factor targets such as growth factor receptors or growth factor receptor variants with constitutively active signaling. 3. Genetically engineer cells to overexpression both growth factor and activated downstream target.

FIG. 2C shows a sequence alignment of amino acid sequences for PDGFb from chicken, bovine, and human. Chicken PDGFb sequence has 53.5% and 53.1% identity with bovine and human sequences, respectively. Bovine and human PDGFb sequences share 90.5% identity.

Figures 3A, 3B:
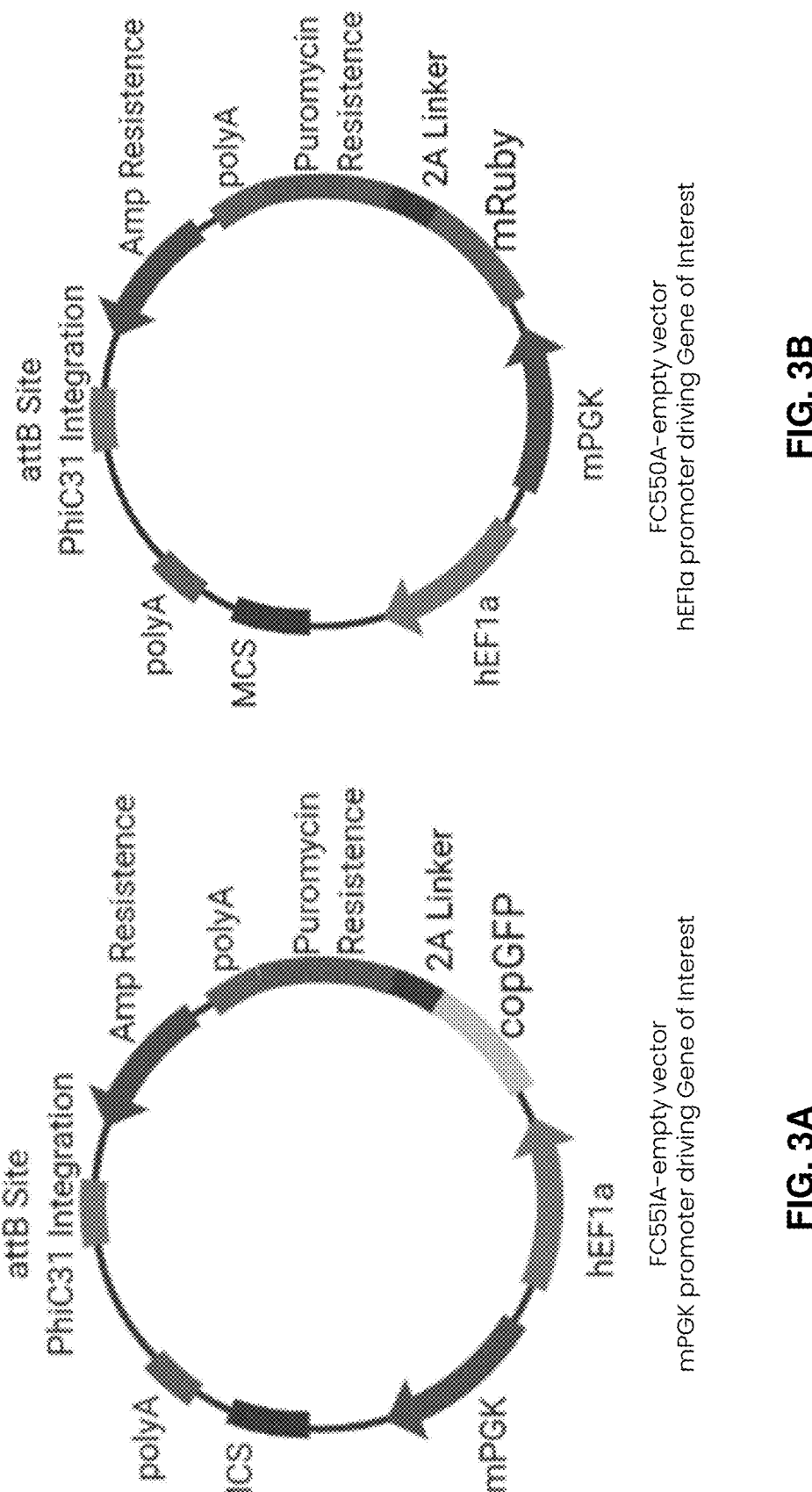

FIG. 3A shows a schematic of a vector used for promoter selection experiments. Gene of interest is expressed from a mouse PGK promoter.

FIG. 3B shows a schematic of a vector used for promoter selection experiments. Gene of interest is expressed from a human EF1alpha promoter.

Figure 4:
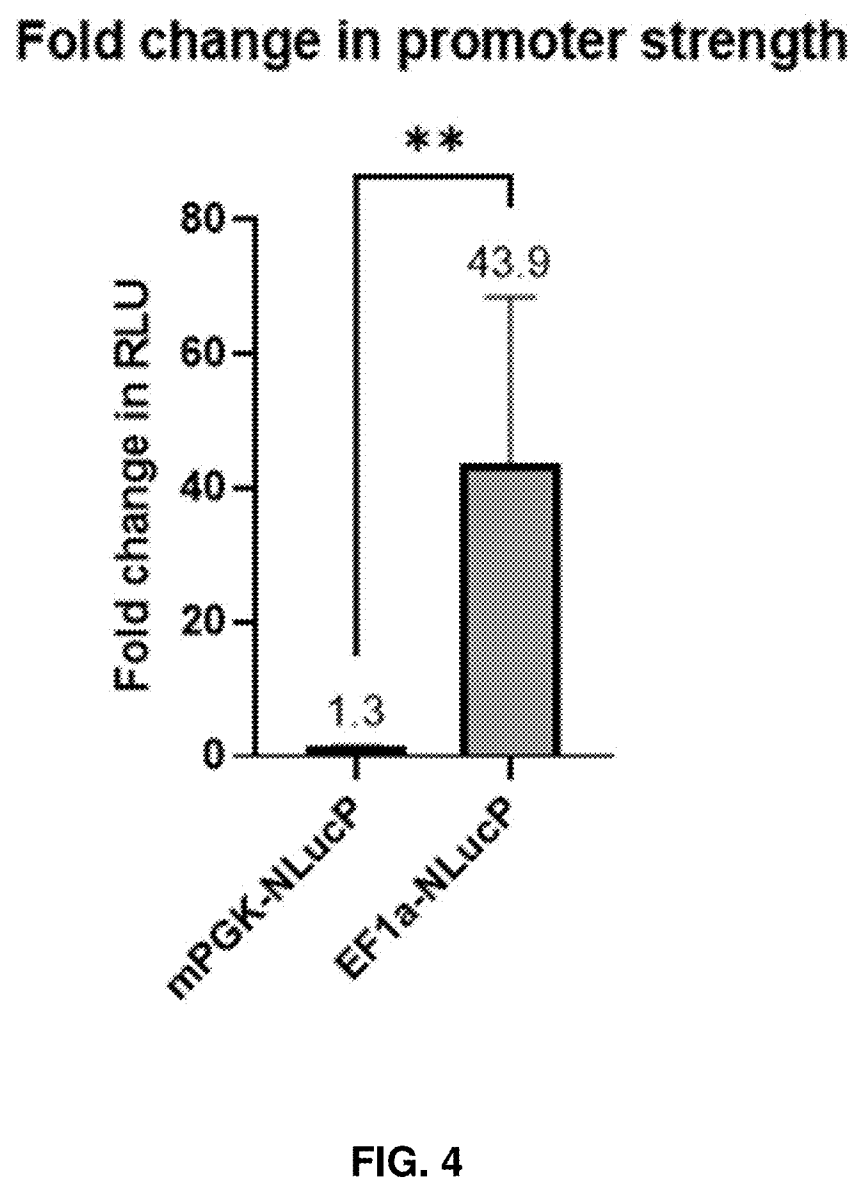

FIG. 4 is a bar graph showing the fold change (RLU) in expression for the promoter analysis performed in Example 1. Chicken cells were transiently transfected (n=3) with vectors expressing nano luciferase (NLucP) under control of a mouse PGK promoter or human EF1a promoter. After 24 hrs, luciferase expression was measured and depicted as relative light units (RLU). p<0.001 (**).

Figure 5:
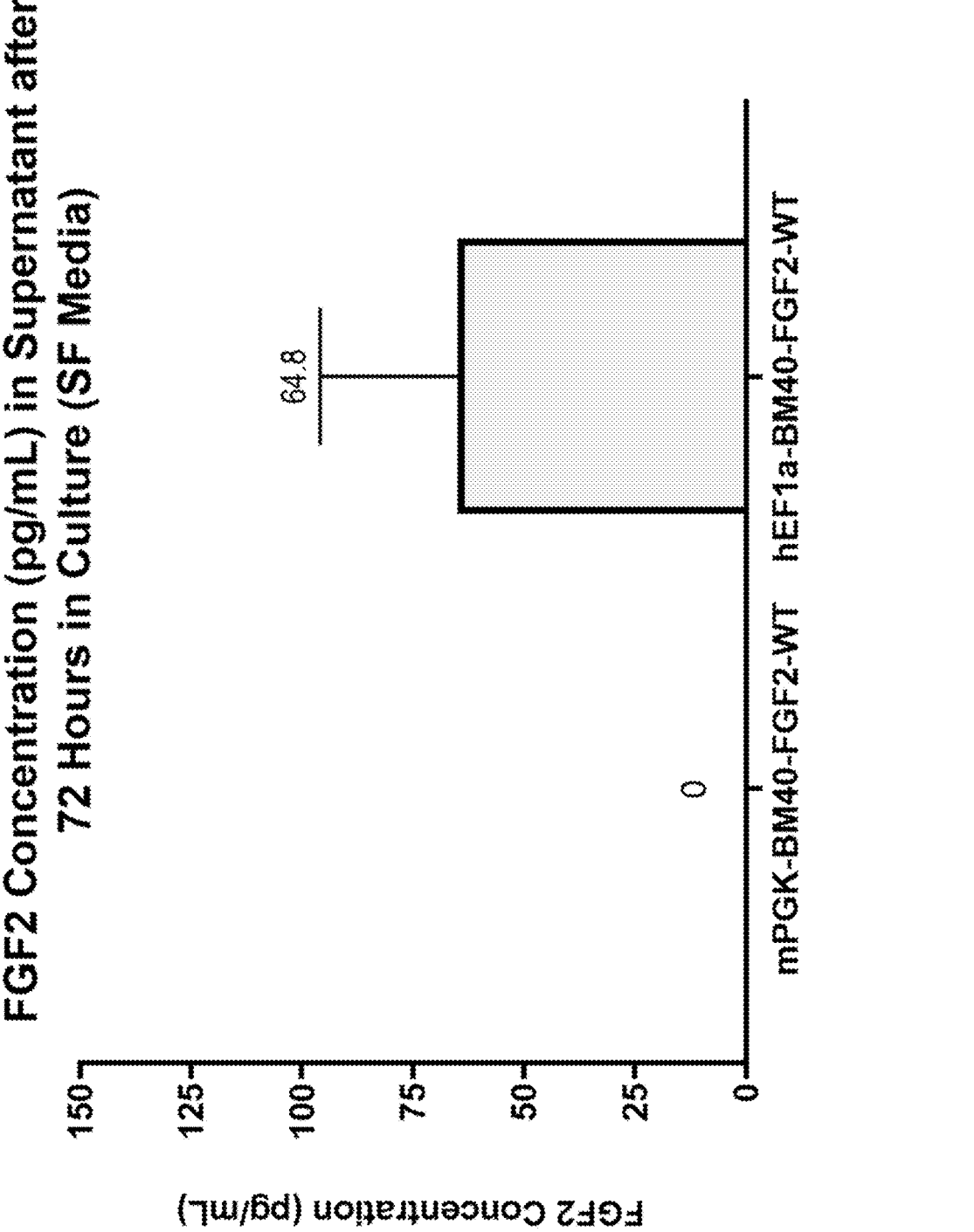

FIG. 5 is a bar graph showing FGF2 concentration in the supernatant after 72 hours in culture (serum-free) for cell lines expressing: mPGK-BM40-FGF2-WT and hEF1a-BM40-FGF2-WT. Abbreviations: PGK—PKG promoter, BM40—signal peptide; FGF2—growth factor ligand; and WT—wild type FGF2.

Figure 6:
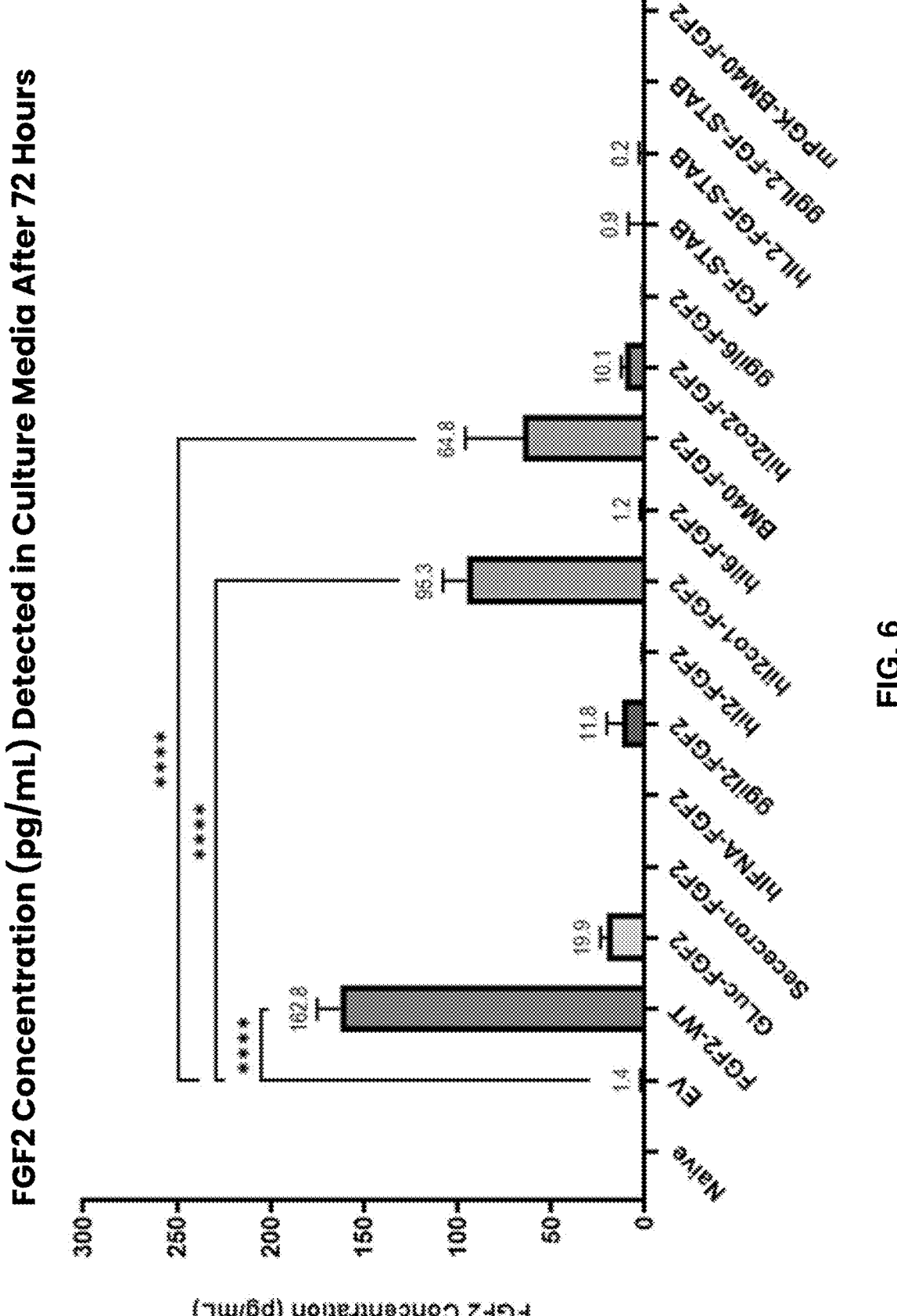

FIG. 6 is bar graph showing the FGF2 concentration in the supernatant in culture medium for the various transduction conditions. X-axis nomenclature: "signal peptide-growth factor ligand" (e.g., for "GLuc-FGF2" GLuc is signal peptide fused to FGF2).

Figure 7:
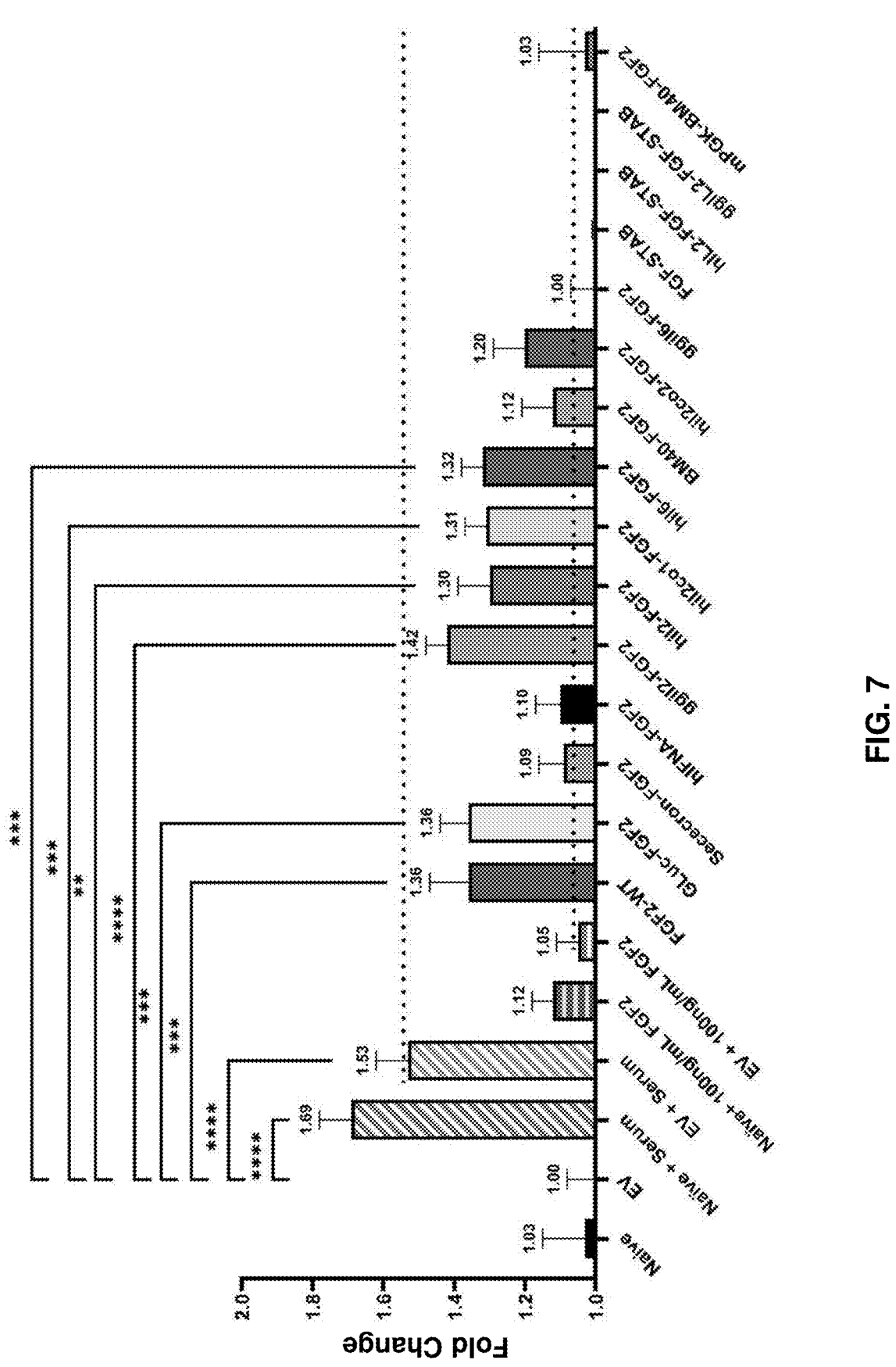

FIG. 7 is a bar graph showing cell proliferation as fold change for each of the various transduction conditions noted on the x-axis. Top dotted line indicates fold change for a serum containing positive control (i.e., cells transduced with empty vector (EV) and cultured in serum). Bottom dotted line indicates fold change for a serum containing positive control (i.e., cells transduced with empty vector) and grown in media include 100 ng/mL FGF2. X-axis nomenclature: "signal peptide-growth factor ligand" (e.g., for "GLuc-FGF2" GLuc is signal peptide fused to FGF2).

Figure 8:
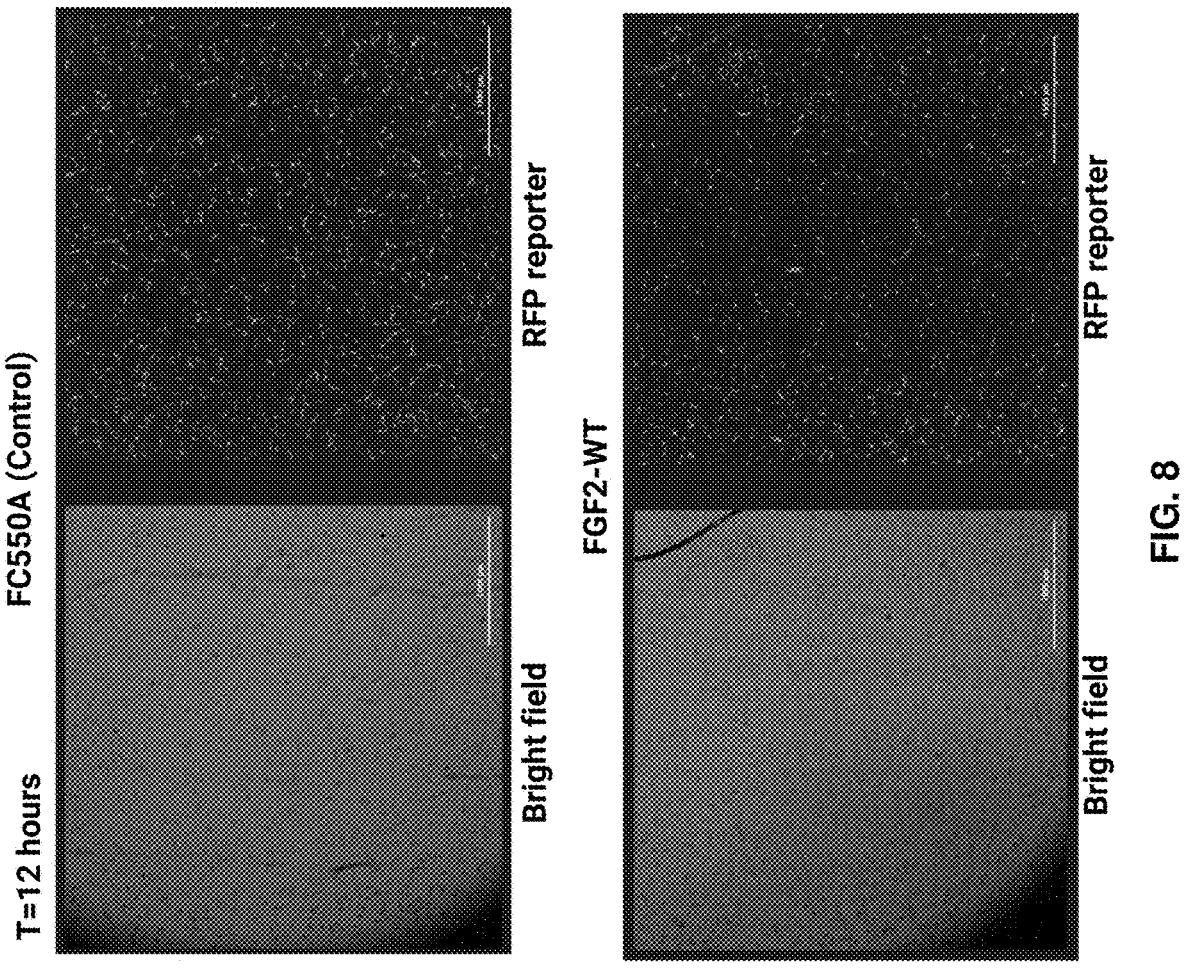

FIG. 8 shows representative images of control (FC550A) and FGF2-WT cells plated in serum free media not supplemented with FGF2. Images were taken 12 hours after initial seed at 4× magnification.

Figure 9:
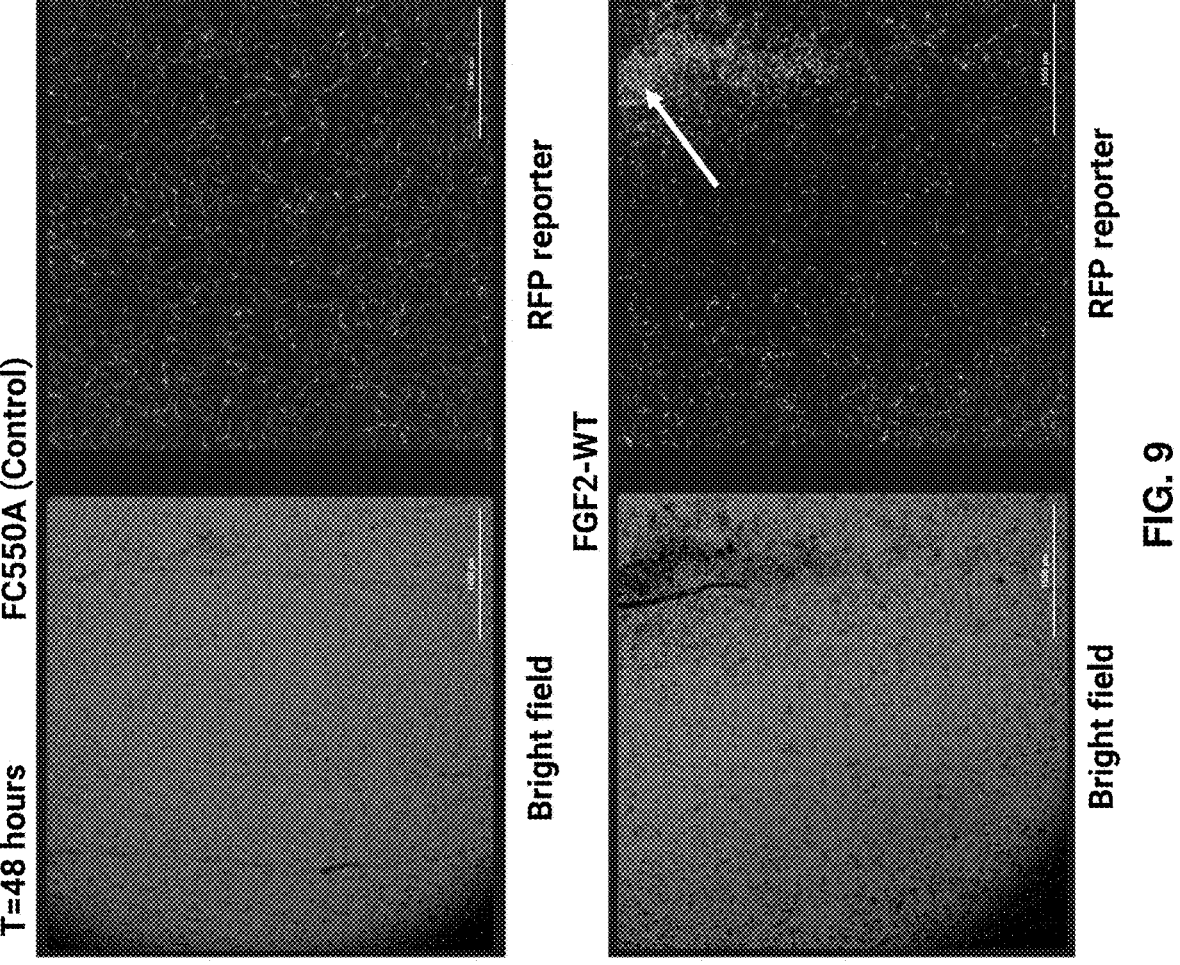

FIG. 9 shows representative images of control (FC550A) and FGF2-WT cells plated in serum free media not supplemented with FGF2. Images were taken 48 hours after initial seed at 4× magnification. Arrow indicates a secondary cell population that was not attached to the plate.

Figure 10:
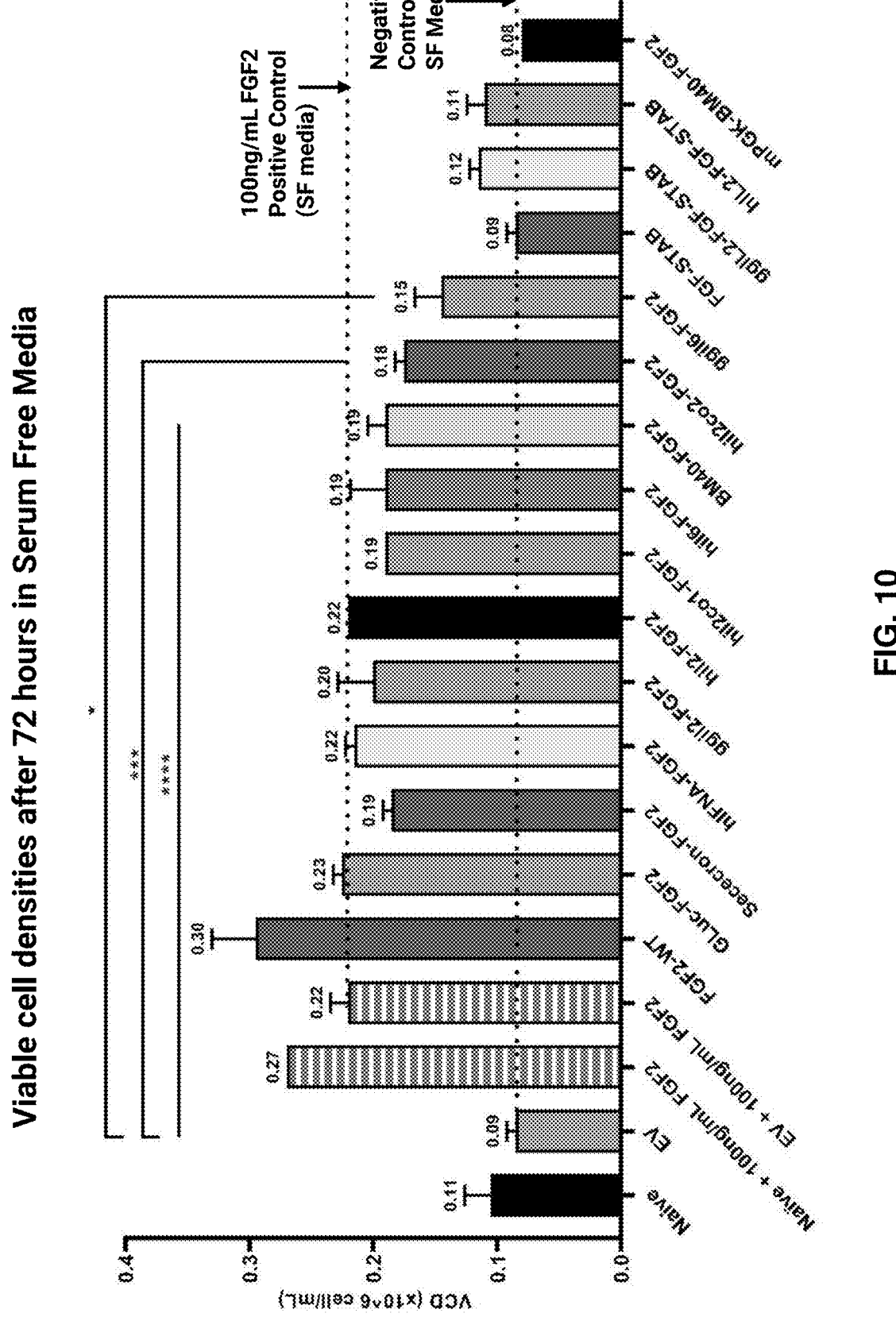

FIG. 10 is a bar graph showing Viable Cell Densities (VCD) for each of the various transduction conditions indicated on the x-axis. Top dotted line indices the VCD for a positive control (i.e., cells transduced with empty vector (EV) and cultured in media supplemented with 100 ng/mL FGF2). Bottom dotted line indicates the VCD for a negative control (i.e., cells transduced with empty vector (EV) and cultured in media not supplemented with FGF2). X-axis nomenclature: "signal peptide-growth factor ligand" (e.g., for "GLuc-FGF2" GLuc is signal peptide fused to FGF2).

Figure 11:
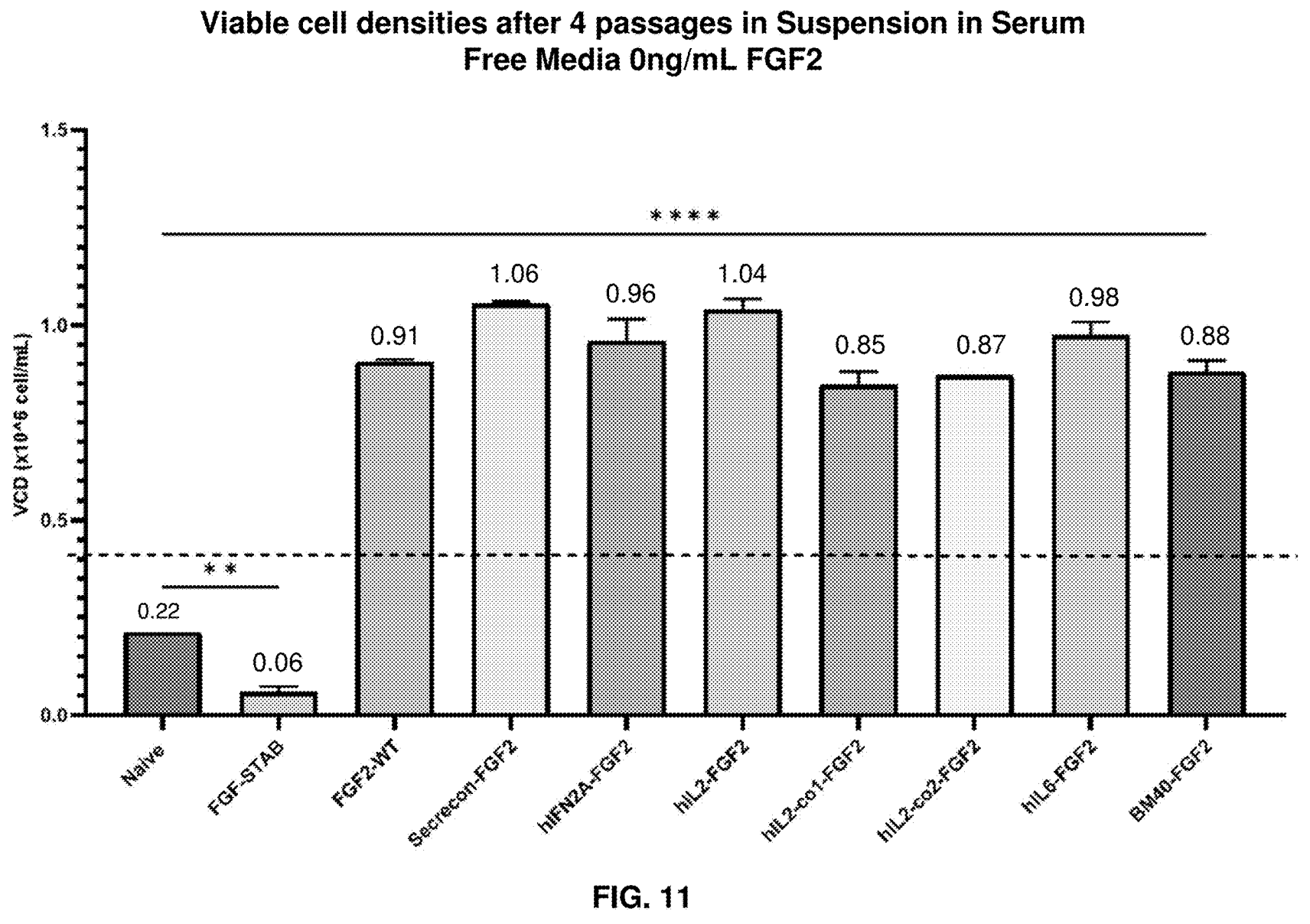

FIG. 11 is a bar graph showing Viable Cell Densities (VCD) for each of the various transduction conditions indicated on the x-axis. Dotted line indicates the seeding density of 0.4×10E6 cells/mL. X-axis nomenclature: "signal peptide-growth factor ligand" (e.g., for "GLuc-FGF2" GLuc is signal peptide fused to FGF2).

Figure 12:
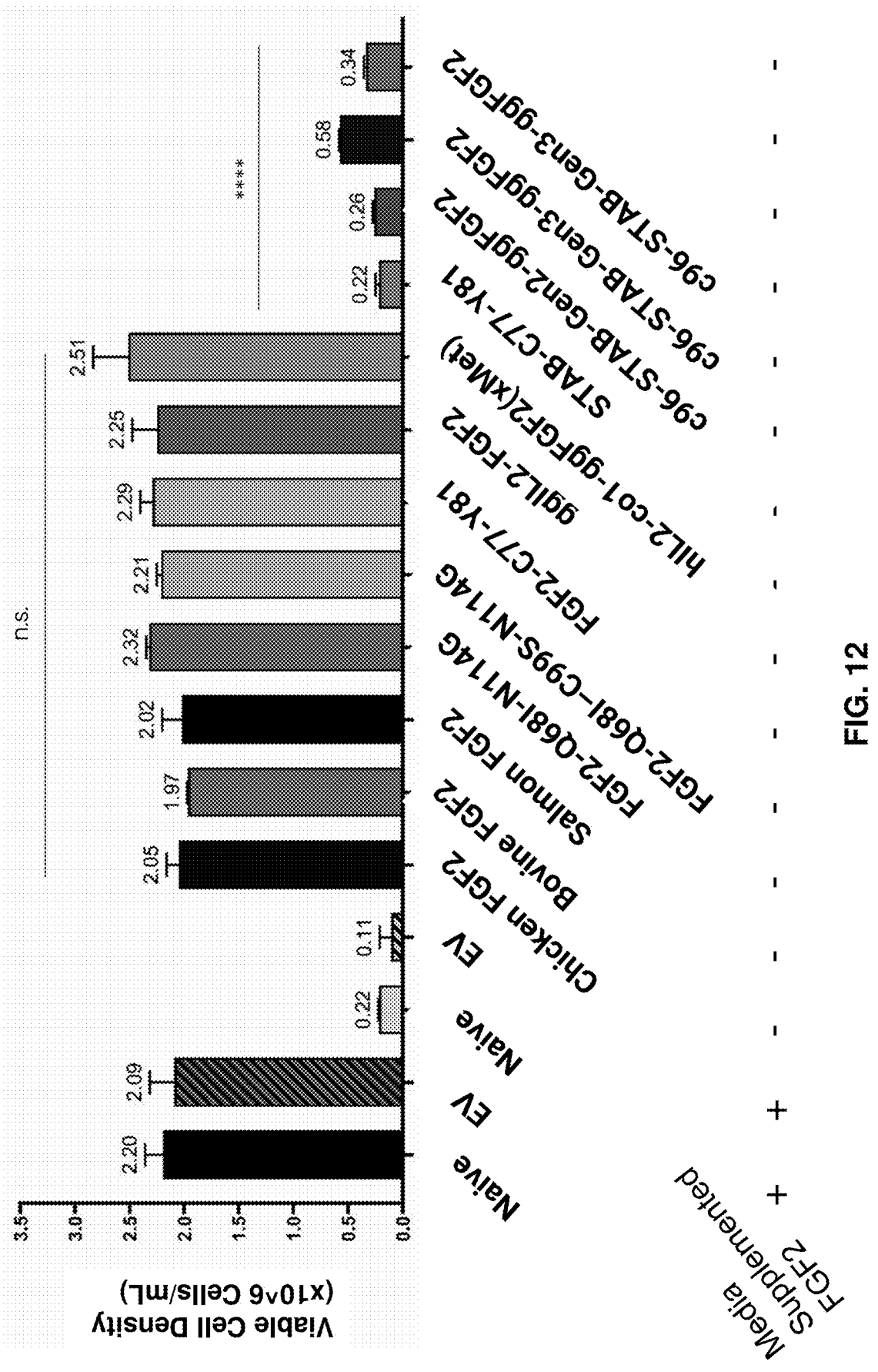

FIG. 12 is a bar graph showing Viable Cell Densities (VCD) for each of the cell lines indicated on the x-axis: chicken FGF2, bovine FGF2, salmon FGF2, heat stable variants of FGF2 (e.g., FGF2-Q68I-N114G and FGF2-Q68I-C99S-N114G), FGF2 having a secretion tags (e.g., ggIL2-FGF2 and hIL2-co1-ggFGF2(xMet)), FGF2 variants that preserve amino acid for non-canonical secretion (FGF2-C77-Y81), and FGF2-STAB variants (STAB-C77Y81, c96-STAB-Gen2-ggFGF2, STAB-Gen3-ggFGF2, and c96-STAB-Gen3-ggFGF2). VCD data was collected on day 2 of passage 4.

Figure 13:
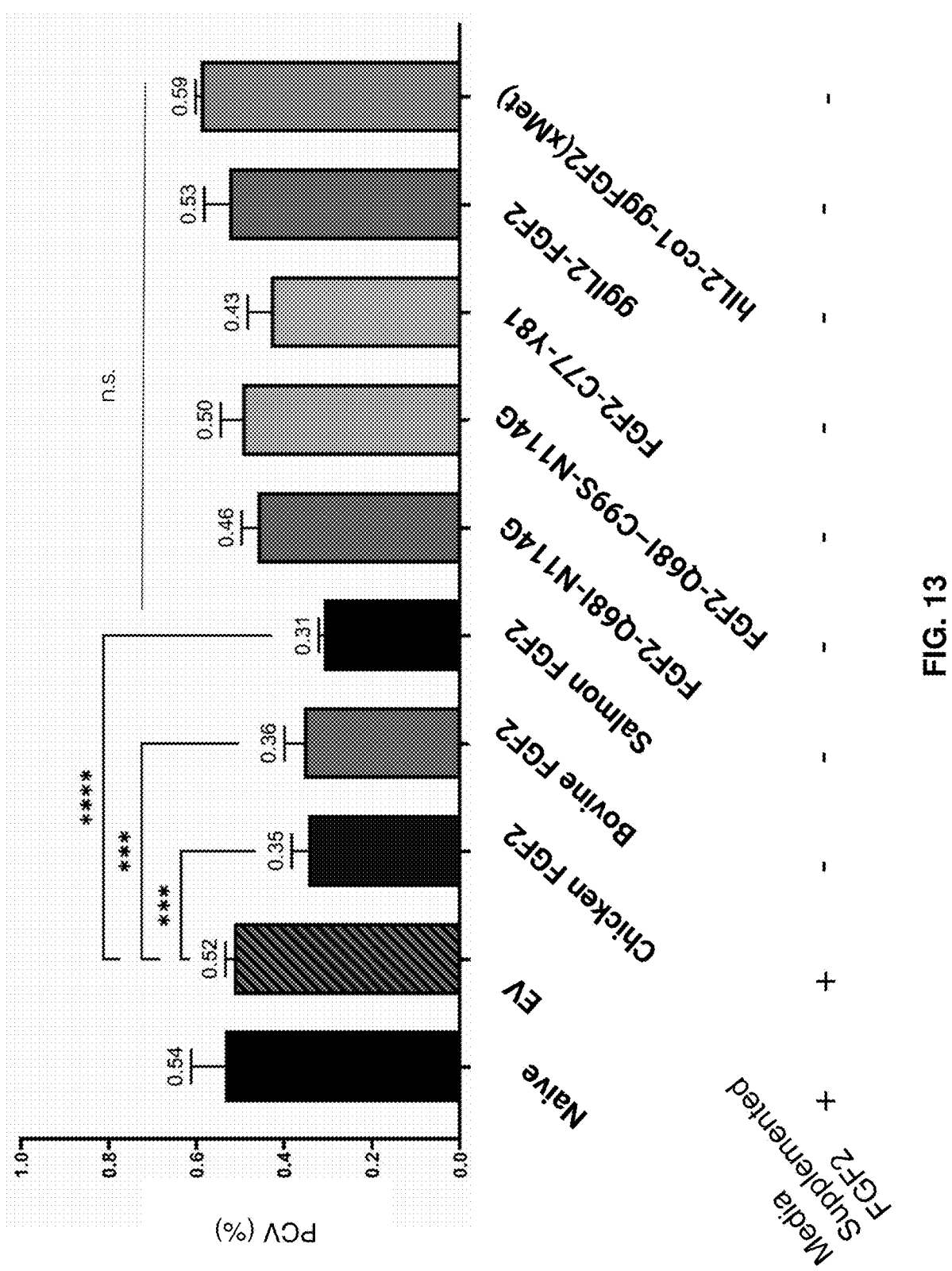

FIG. 13 is a bar graph showing percent (%) Packed Cell Volumes for each of the cell lines indicated on the x-axis: chicken FGF2, bovine FGF2, salmon FGF2, heat stable variants of FGF2 (e.g., FGF2-Q68I-N114G and FGF2-Q68I-C99S-N114G), FGF2 having a secretion tags (e.g., ggIL2-FGF2 and hIL2-co1-ggFGF2(xMet)), and FGF2 variants that preserve amino acid for non-canonical secretion (FGF2-C77-Y81). Percent packed cell volumes were assessed on day 2 of passage 5.

Figure 14:
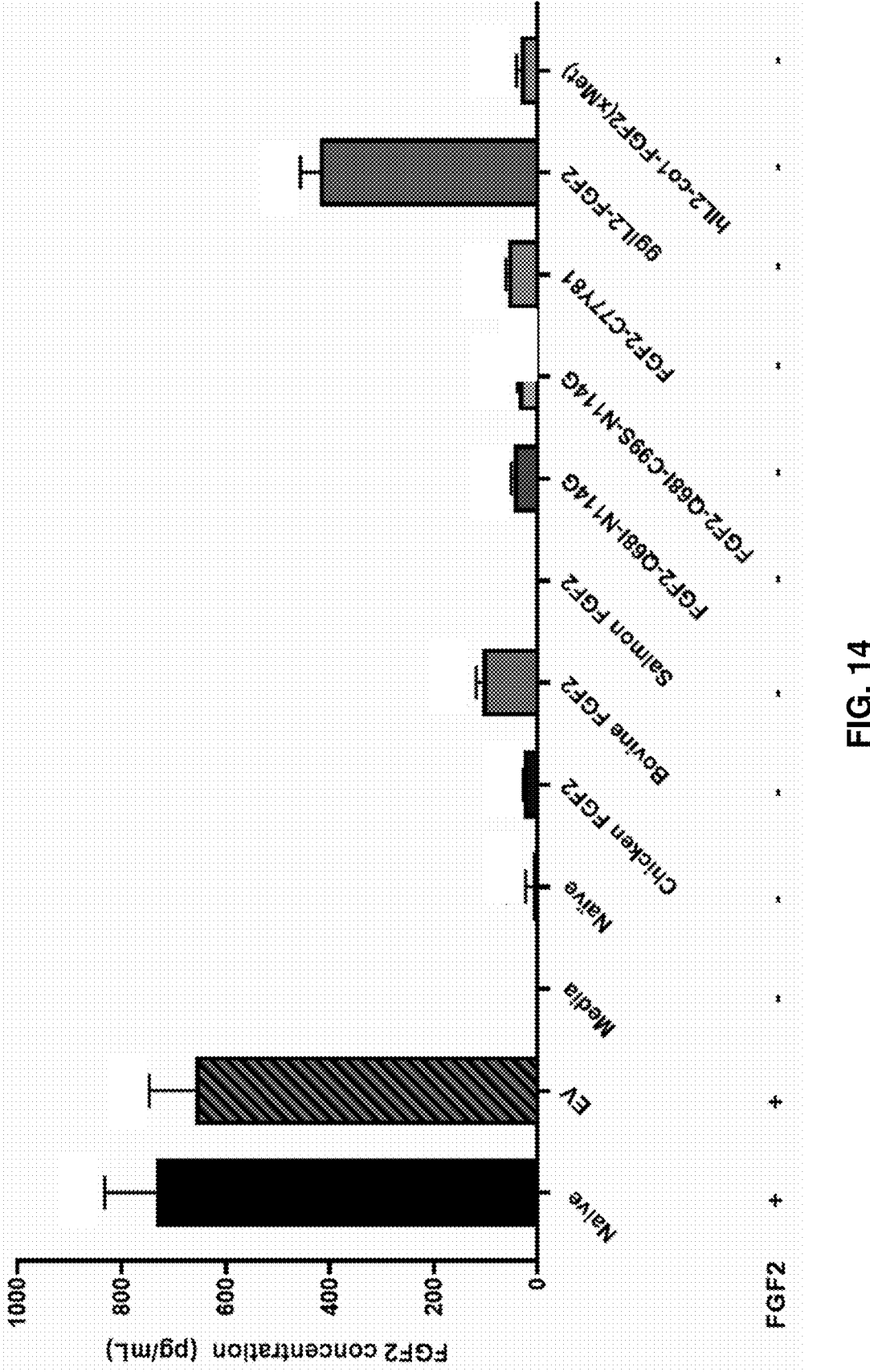

FIG. 14 is a bar graph of an ELISA showing FGF2 concentration in (pg/mL) in supernatants taken from the cultures indicated on the x-axis: chicken FGF2, bovine FGF2, salmon FGF2, heat stable variants of FGF2 (e.g., FGF2-Q68I-N114G and FGF2-Q68I-C99S-N114G), FGF2 having a secretion tags (e.g., ggIL2-FGF2 and hIL2-co1-ggFGF2(xMet)), and FGF2 variants that preserve amino acid for non-canonical secretion (FGF2-C77-Y81).

Figure 15:
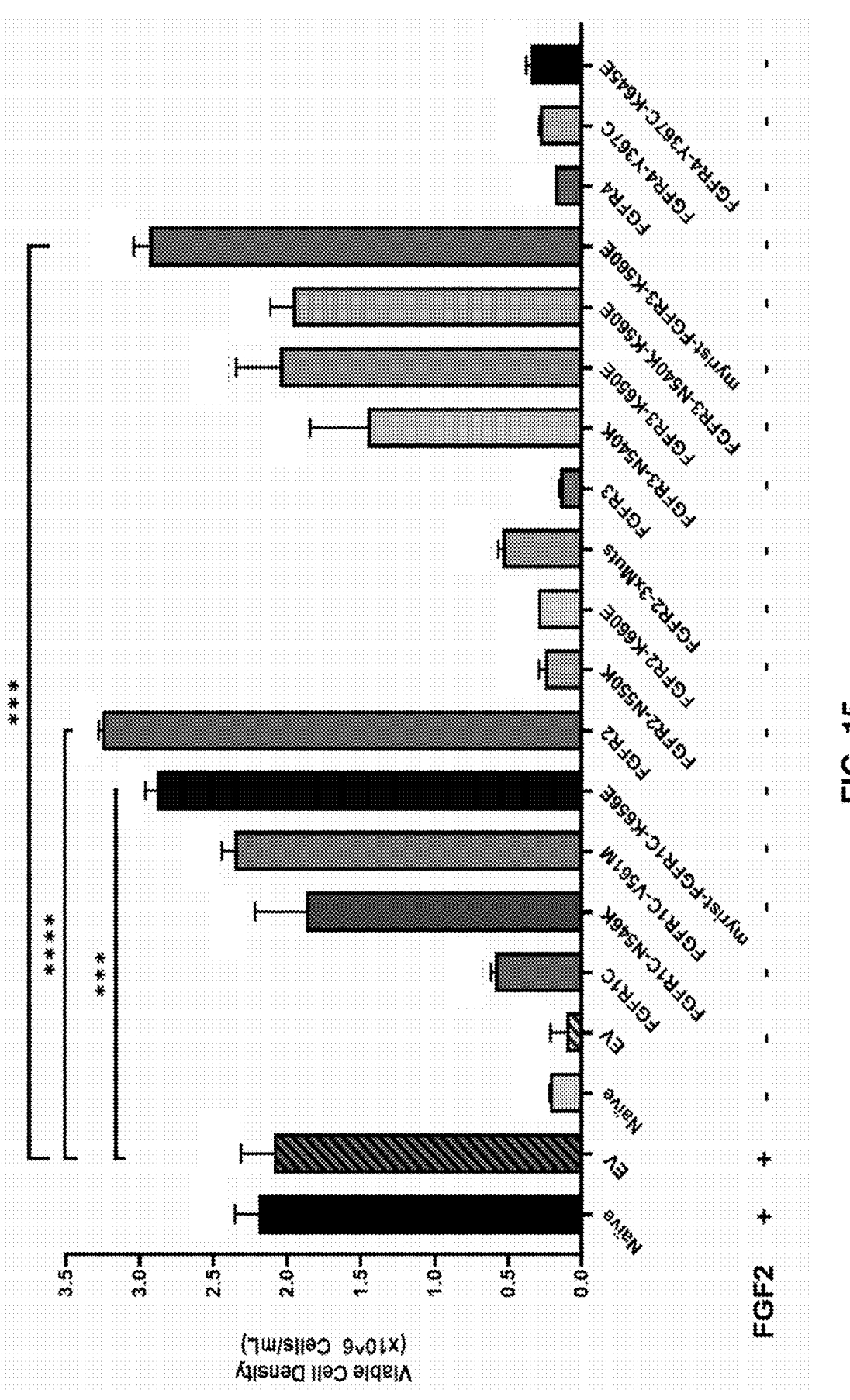

FIG. 15 is a bar graph of an ELISA showing Viable Cell Density (VCD) for each of the cell lines indicated on the x-axis. FGF1 receptors included: FGFR1C, FGFR1C-N546K, FGFR1C-V561M, and myrist-FGFR1C-K656E. FGF2 receptors included: FGFR2, FGFR2-N550K, FGFR2-K660E, and FGFR2-3xMuts. FGF3 receptors included: FGFR3, FGFR3-N540K, FGFR3-K560E, FGFR3-N540K-K560E, and myrist-FGF3R-K560E. FGF4 receptors included: FGF4R, FGF4R-Y367C, and FGF4R-Y367C-K654E.

Figure 16:
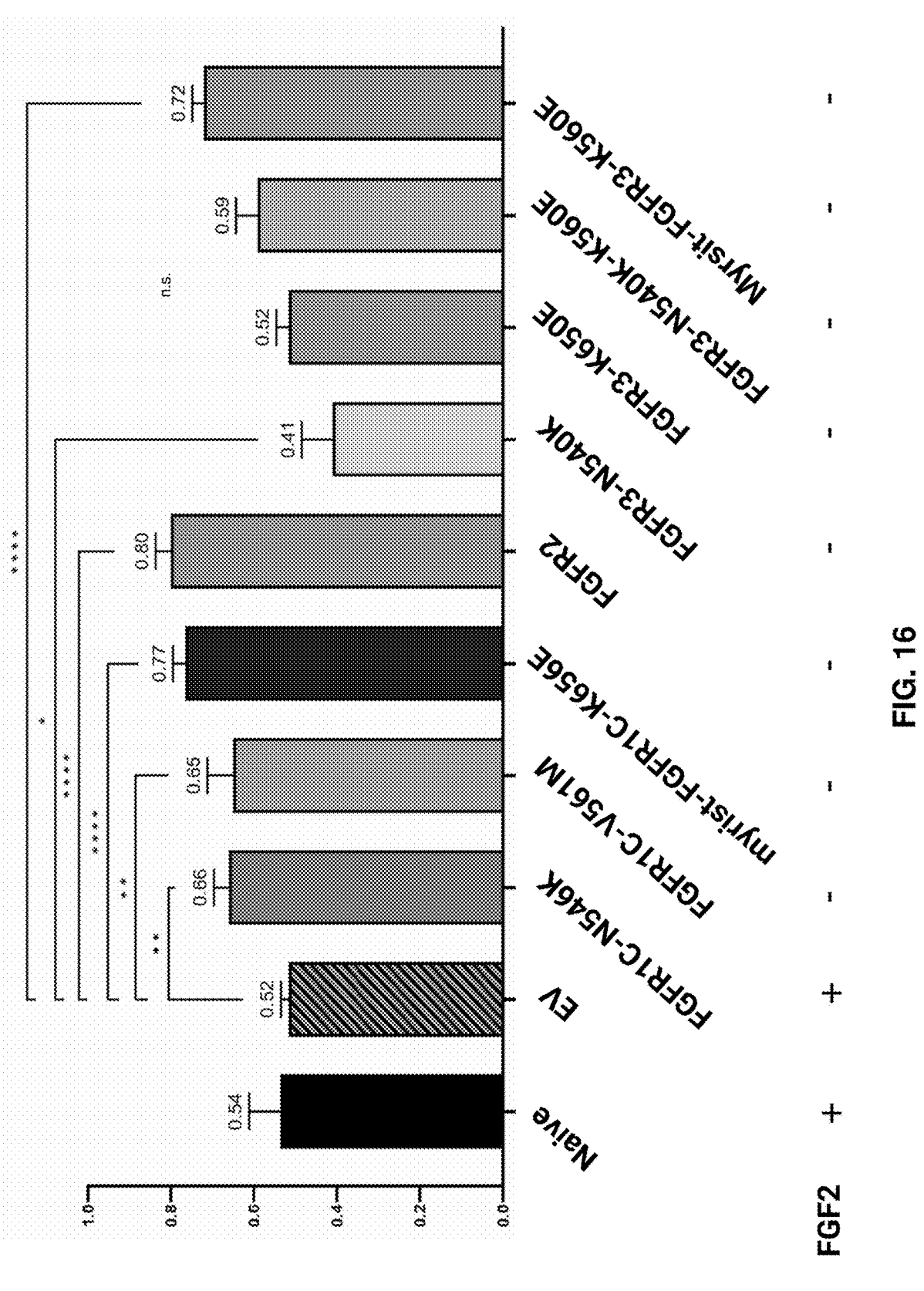

FIG. 16 is a bar graph showing percent (%) Packed Cell Volumes for each of the cell lines indicated on the x-axis. FGF1 receptors included: FGFR1C, FGFR1C-N546K, FGFR1C-V561M, and myrist-FGFR1C-K656E. FGF2 receptors included: FGFR2, FGFR2-N550K, FGFR2-K660E, and FGFR2-3xMuts. FGF3 receptors included: FGFR3, FGFR3-N540K, FGFR3-K560E, FGFR3-N540K-K560E, and myrist-FGF3R-K560E. FGF4 receptors included: FGF4R, FGF4R-Y367C, and FGF4R-Y367C-K654E.

Figure 17:
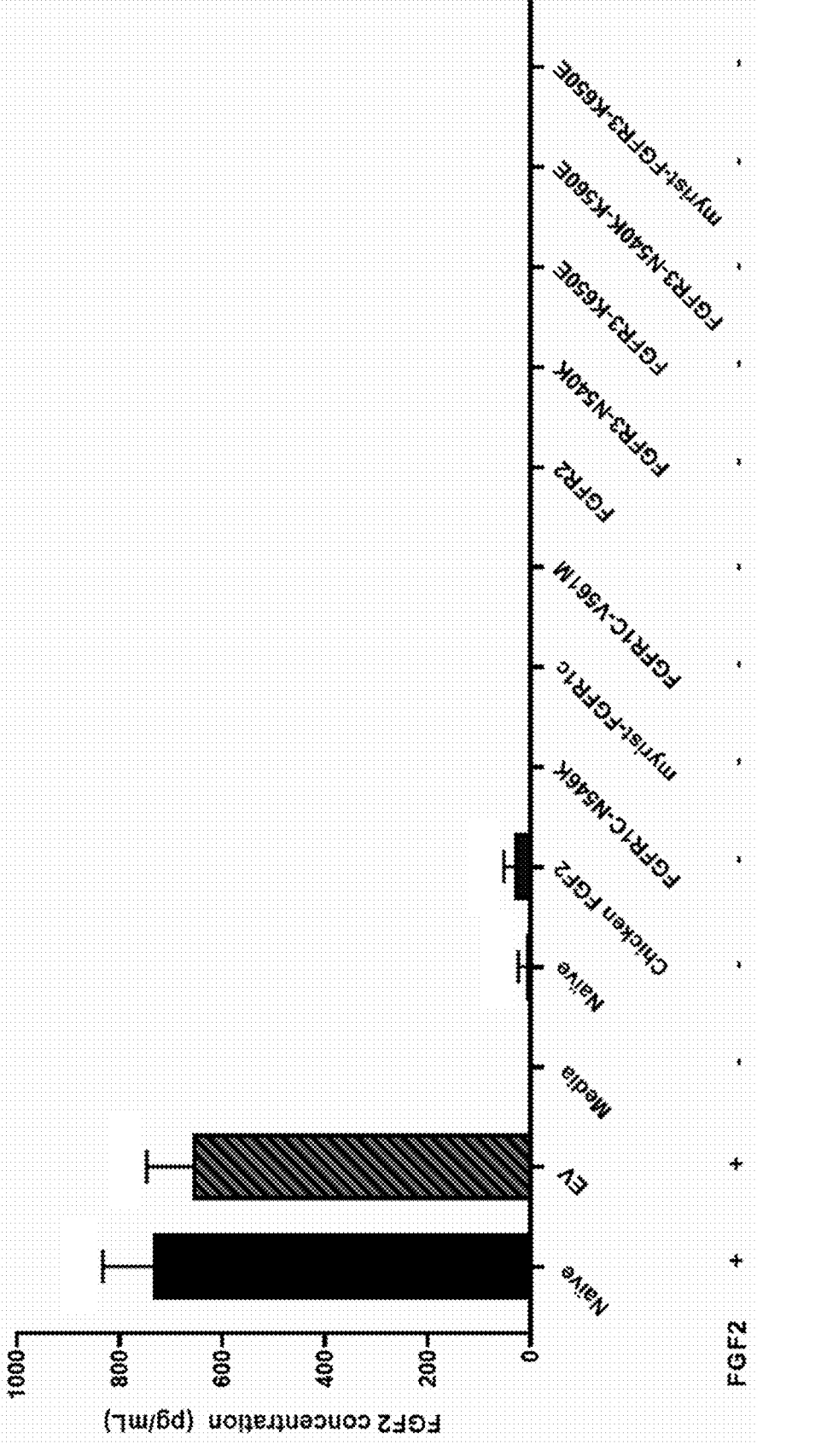

FIG. 17 is a bar graph of an ELISA showing FGF2 concentration in (pg/mL) in supernatants taken from the cultures indicated on the x-axis. FGF1 receptors included: FGFR1C, FGFR1C-N546K, FGFR1C-V561M, and myrist-FGFR1C-K656E. FGF2 receptors included: FGFR2, FGFR2-N550K, FGFR2-K660E, and FGFR2-3xMuts. FGF3 receptors included: FGFR3, FGFR3-N540K, FGFR3-K560E, FGFR3-N540K-K560E, and myrist-FGF3R-K560E. FGF4 receptors included: FGF4R, FGF4R-Y367C, and FGF4R-Y367C-K654E.

Figure 18:
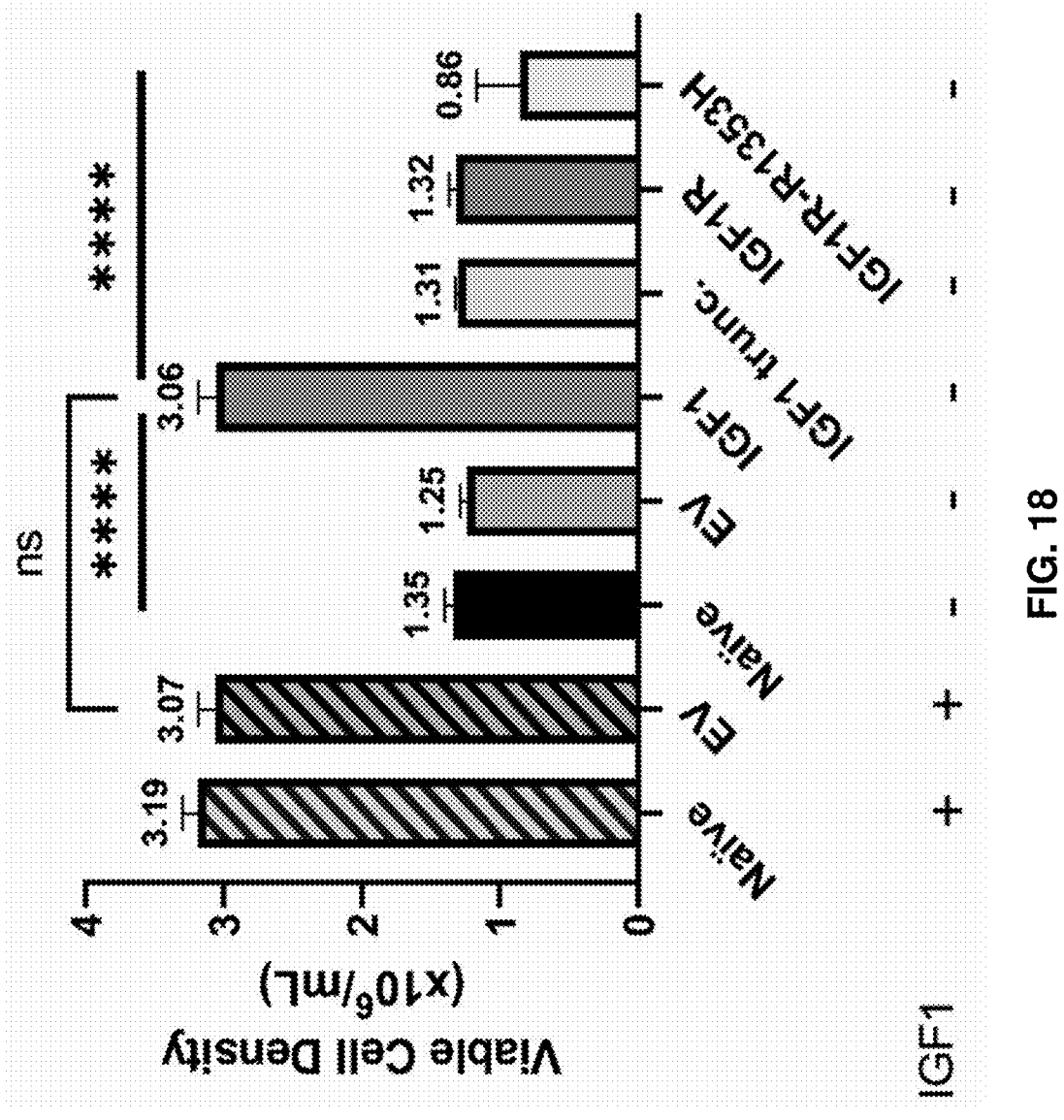

FIG. 18 is a bar graph showing viable cell density data for chicken cells engineered to express IGF1 (or variant) or IGF1 receptor (or variant).

Figure 19:
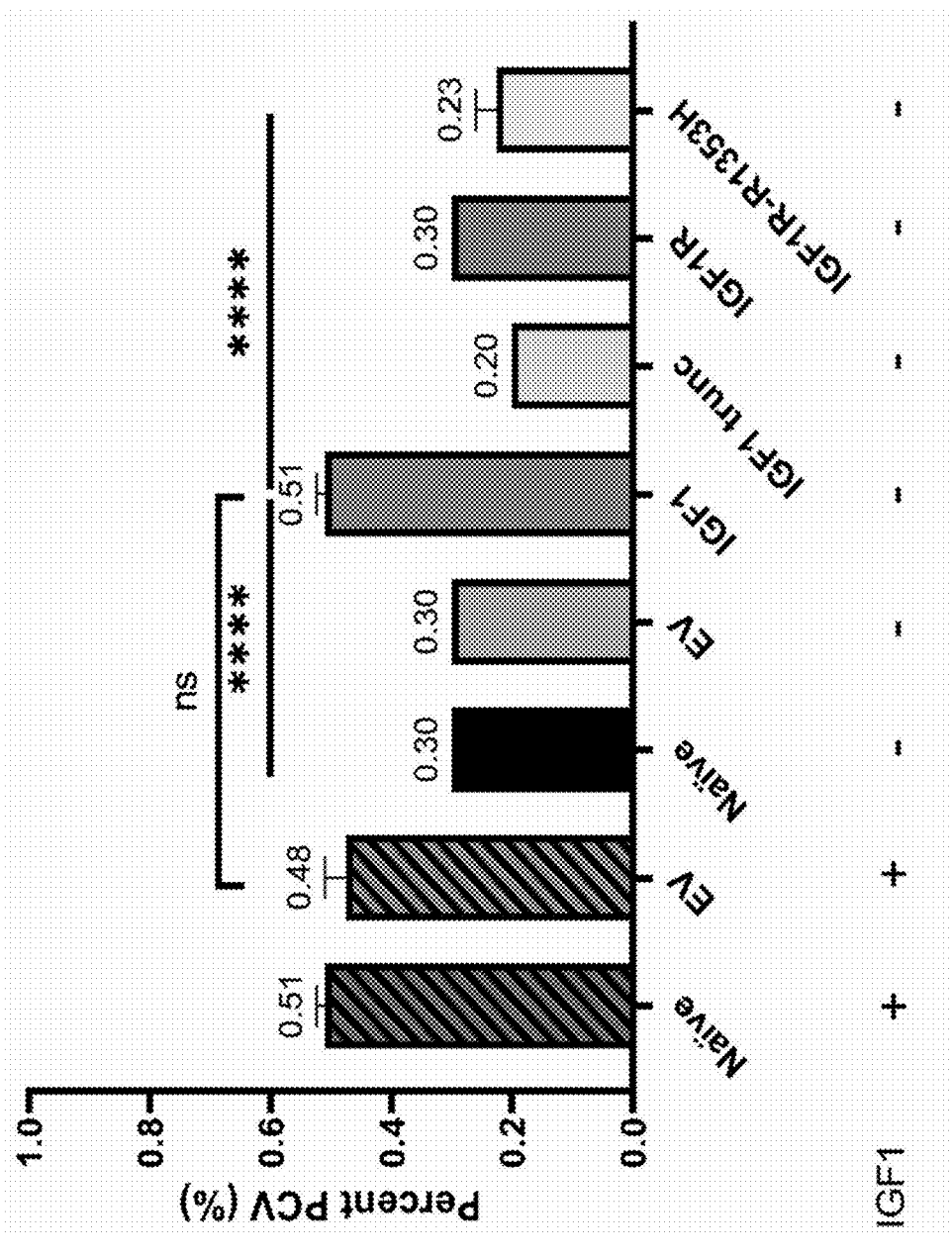

FIG. 19 is a bar graph showing packed cell volume data for chicken cells engineered to express IGF1 (or variant) or IGF1 receptor (or variant).

Figure 20A:
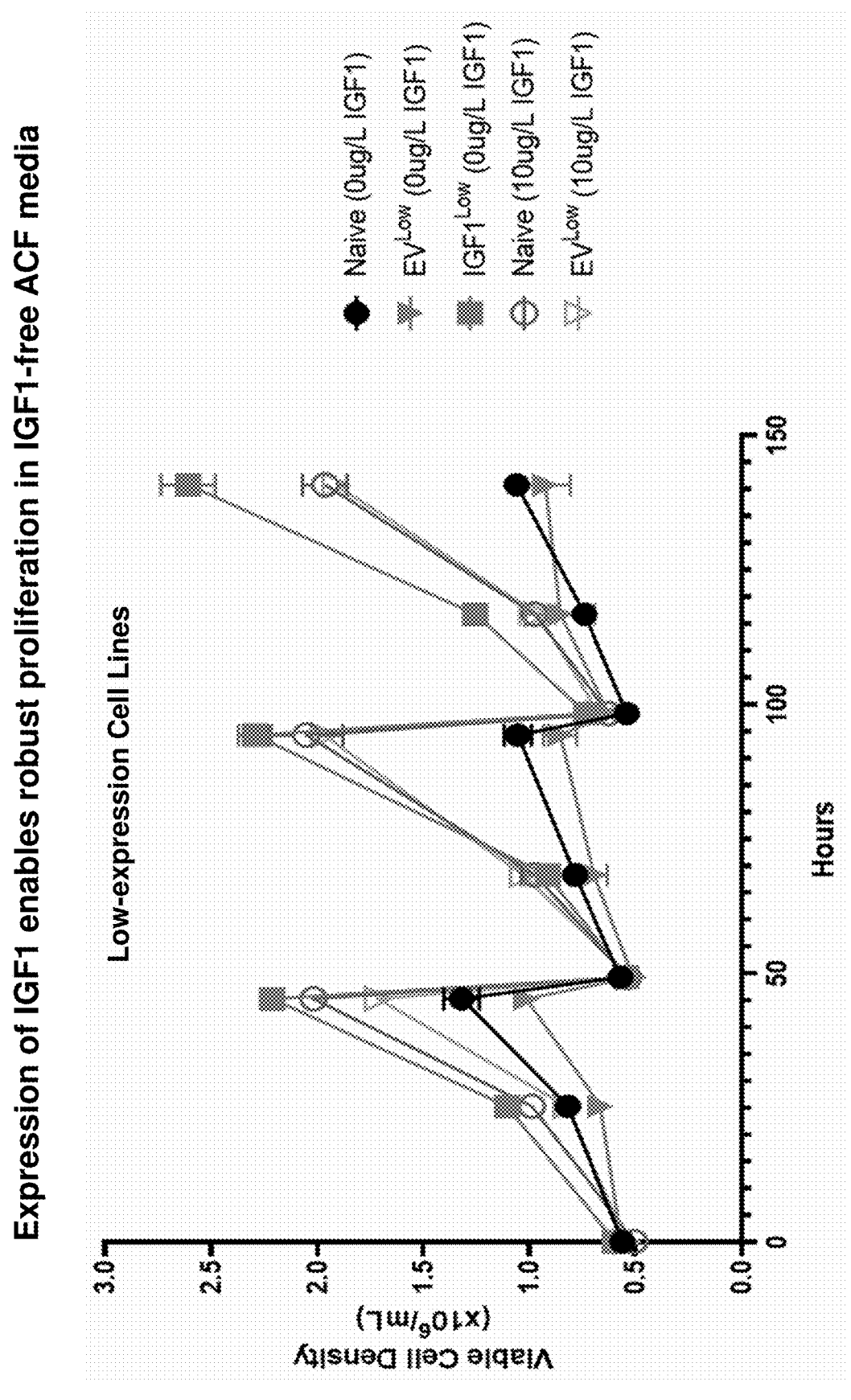
Figure 20B:
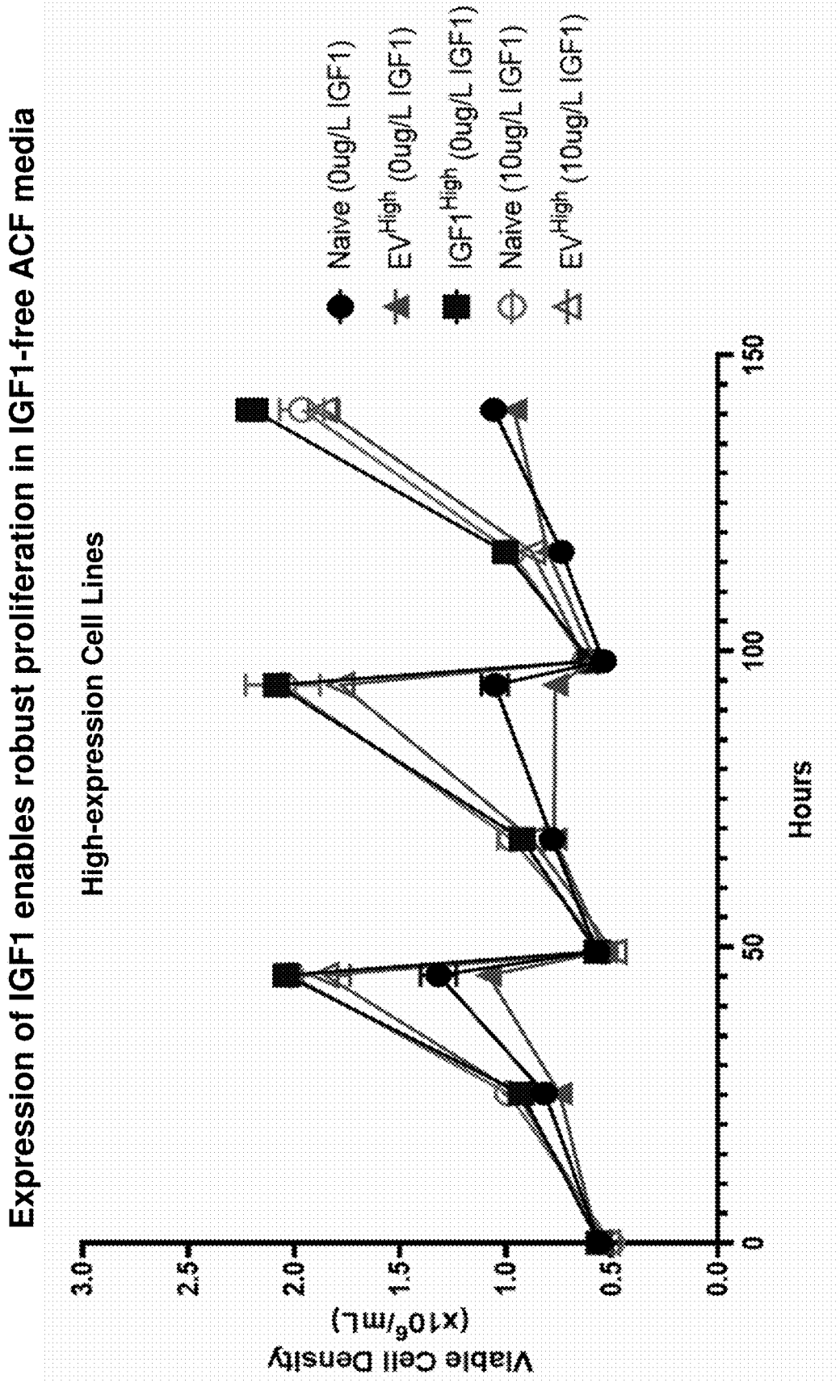

FIGS. 20A-20B are line graphs showing growth curves (Viable Cell Densities (VCD)) for controls (Naïve and empty vector (EV)) and IGF1 engineered cells. Cells are grown in media supplemented with either 0 µg/L IGF1 or 10 µg/L IGF1. FIG. 20A shows VCD data for cells engineered to express low levels of IGF1 (IGF1$^{Low}$) and controls with measurements taken every 24 hours and cells passaged on a 2-day cadence (e.g., about every 48 hours). FIG. 20B shows VCD data for cells engineered to express high levels of IGF1 (IGF1$^{High}$) and controls with measurements taken every 24 hours and cells passaged on a 2-day cadence (e.g., about every 48 hours).

Figure 21A:
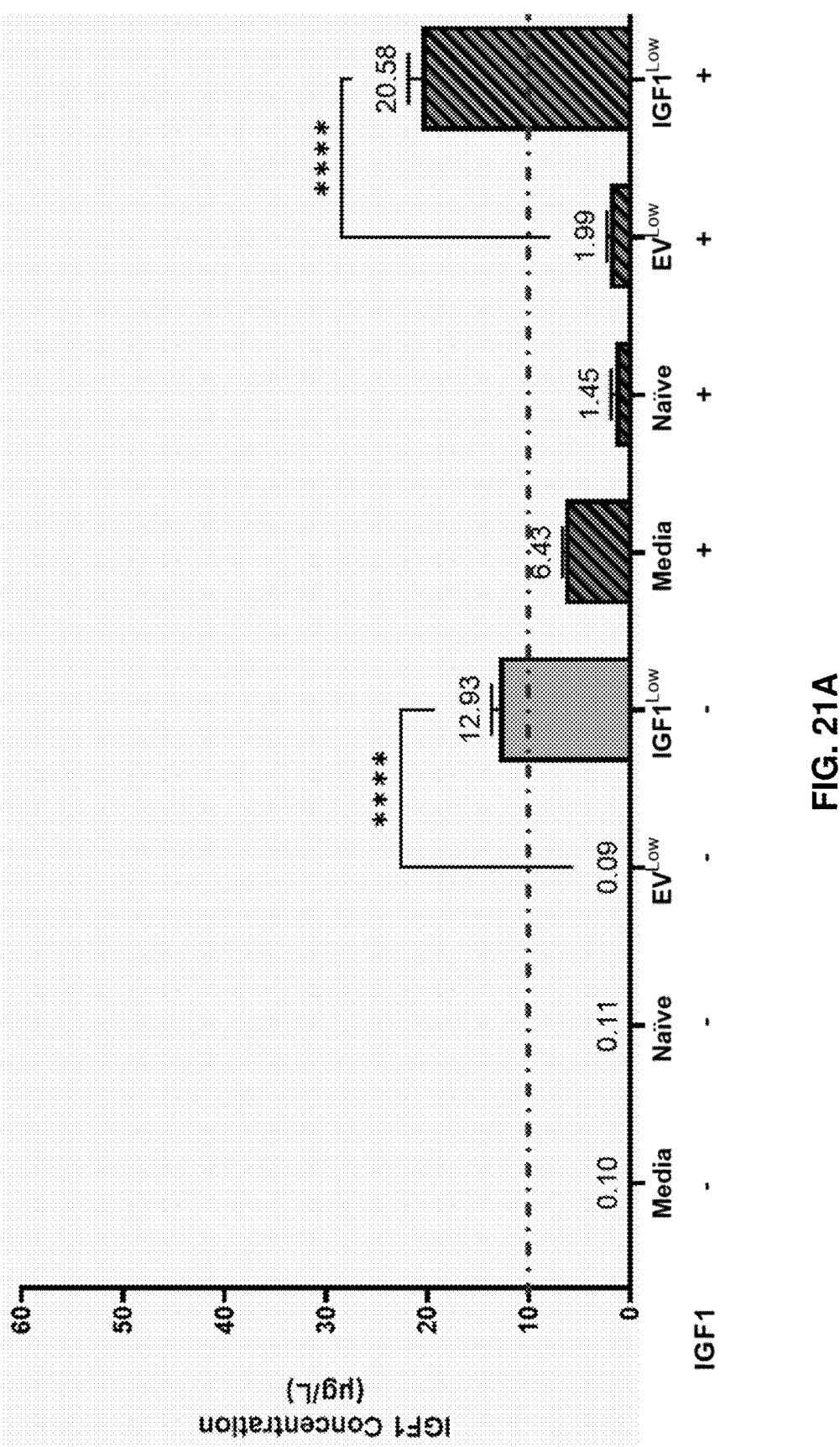
Figure 21B:
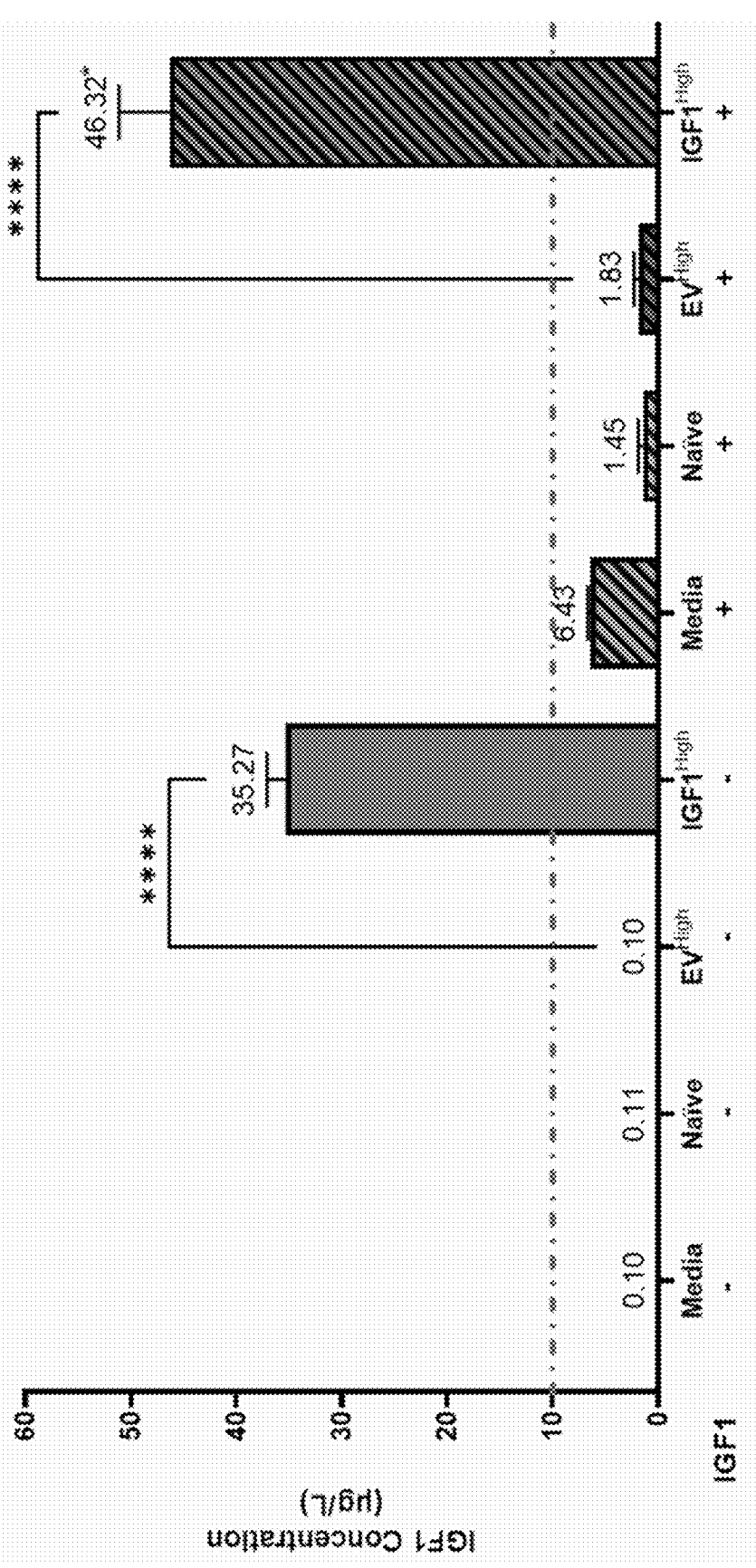

FIGS. 21A-21B are bar graphs showing data from an IGF1 ELISA for cells engineered to express IGF1$^{low}$ or IGF1$^{high}$. FIG. 21A shows IGF1 ELISA data for cells engineered to express IGF1$^{low}$. FIG. 21B shows IGF1 ELISA data for cells engineered to express IGF1$^{high}$.

Figure 22:
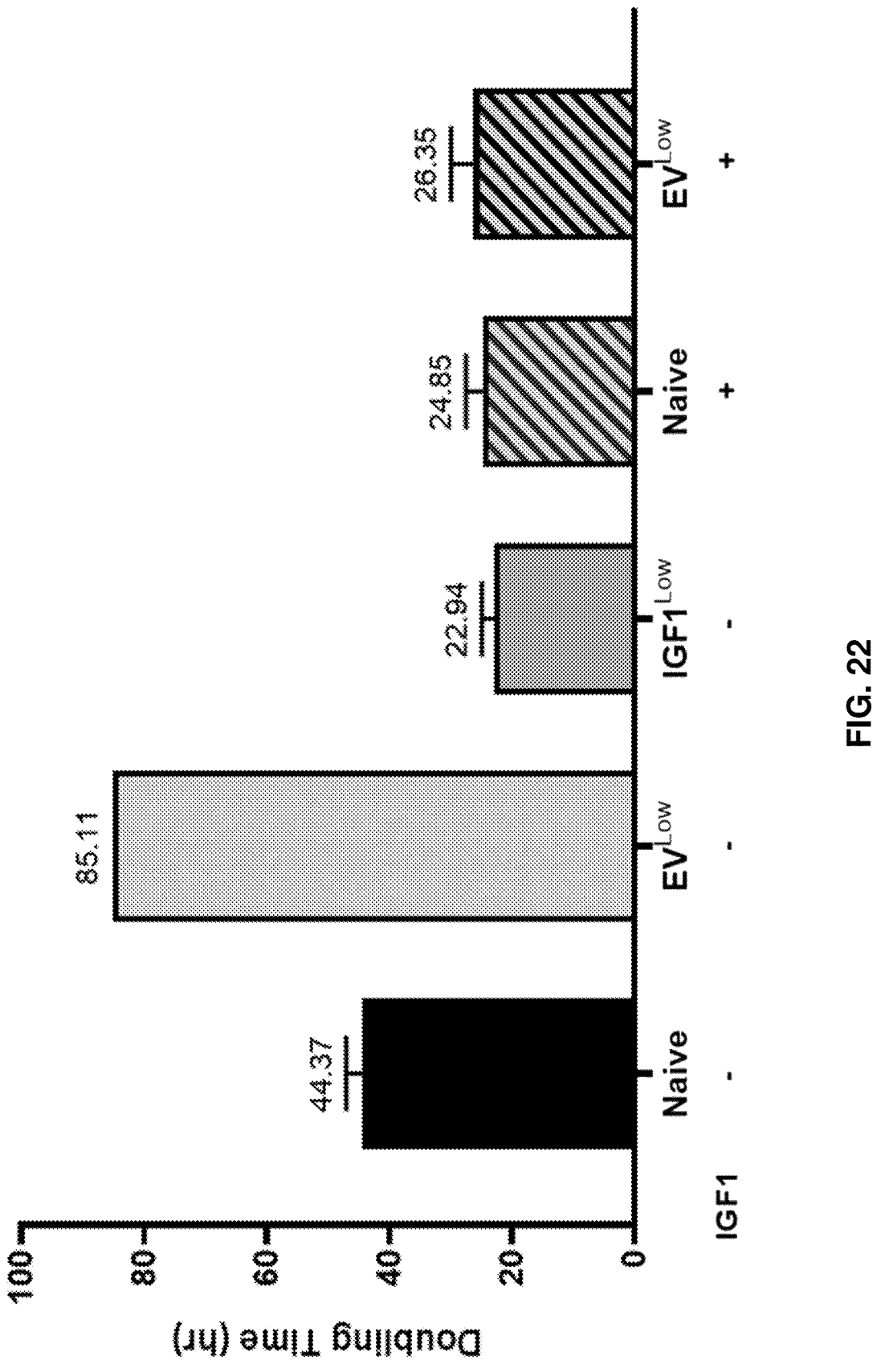

FIG. 22 are bar graphs showing doubling time (hours) data for cells engineered to express IGF1$^{low}$.

Figure 23A:
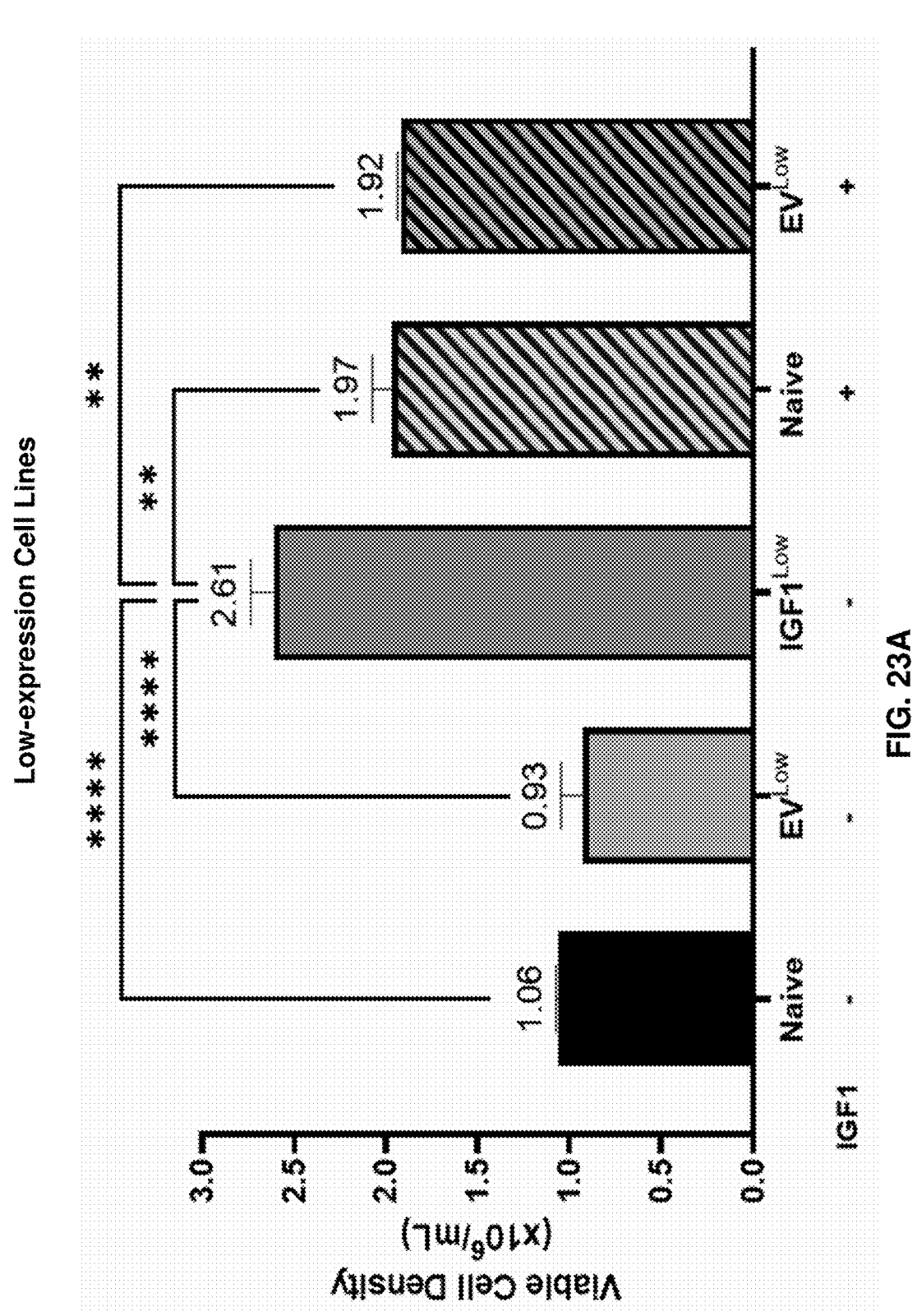
Figure 23B:
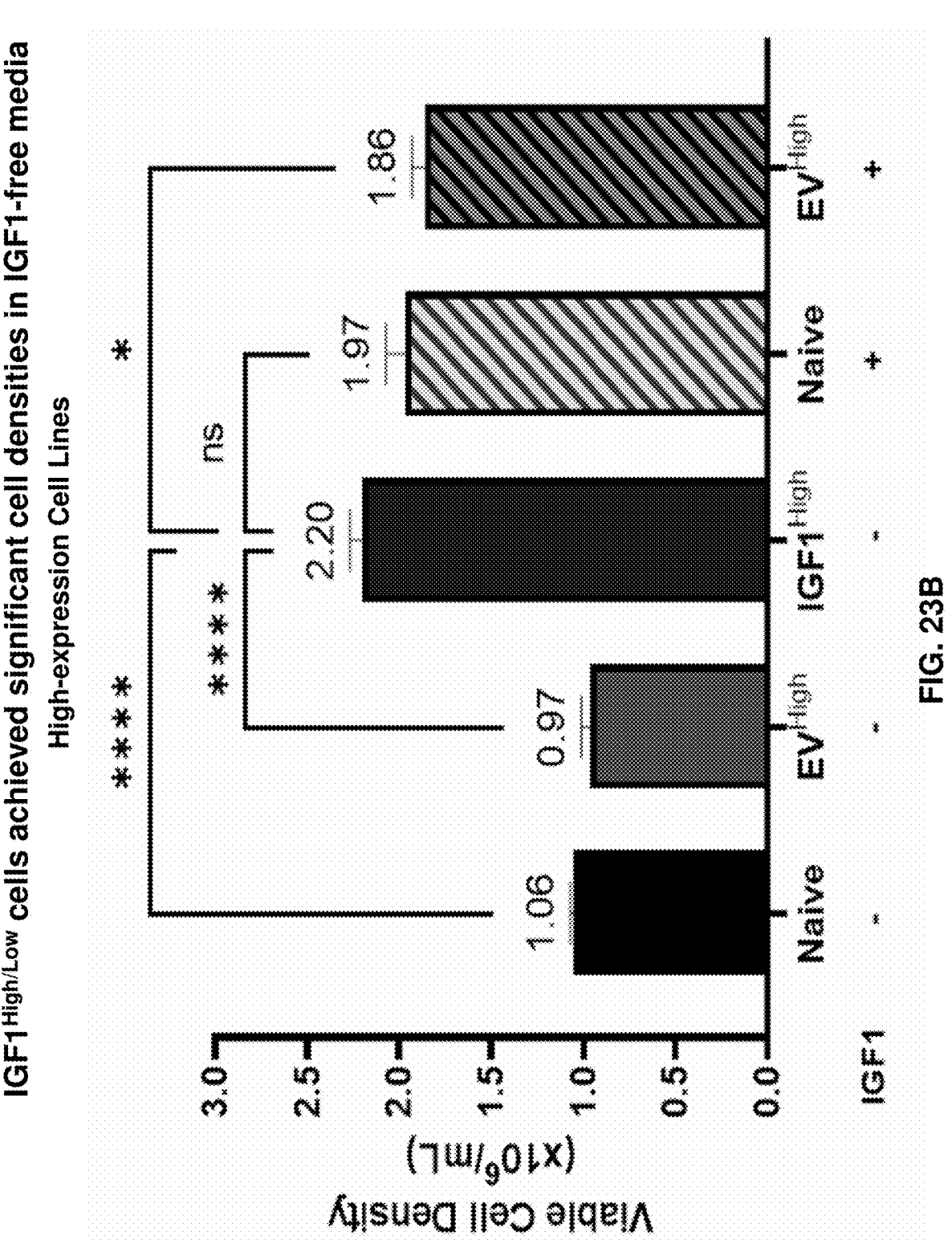

FIGS. 23A-23B are bar graphs showing Viable Cell Densities (VCD) for controls (Naïve and empty vector (EV)) and IGF1 engineered cells. Cells are grown in media supplemented with either 0 µg/L IGF1 or 10 µg/L IGF1. Cultures are analyzed at day 2 after the third passage. FIG. 23A shows VCD data for cells engineered to express low levels of IGF1 (IGF1$^{Low}$) and controls. FIG. 23B shows VCD data for cells engineered to express high levels of IGF1 (IGF1$^{High}$) and controls.

Figure 23C:
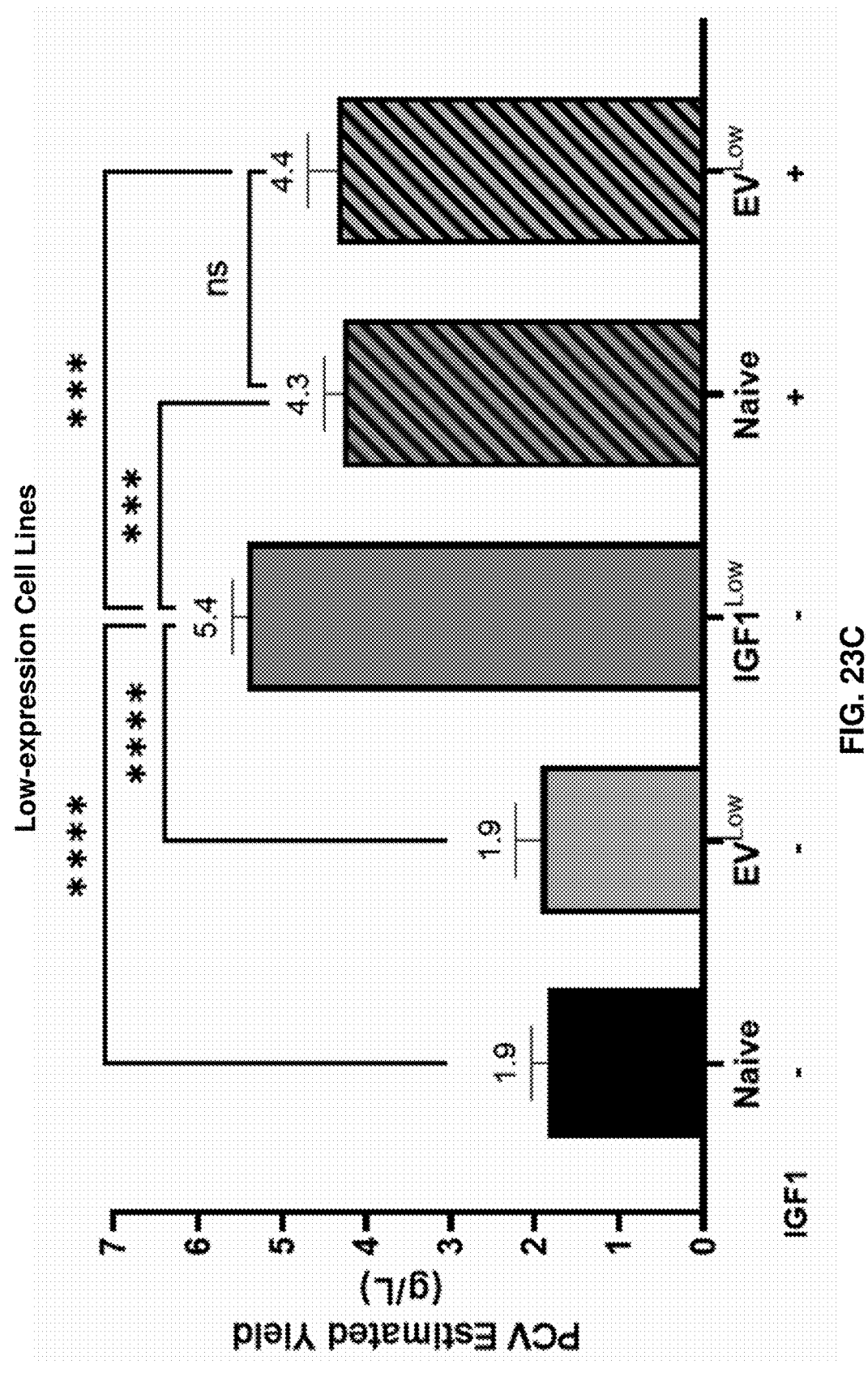
Figure 23D:
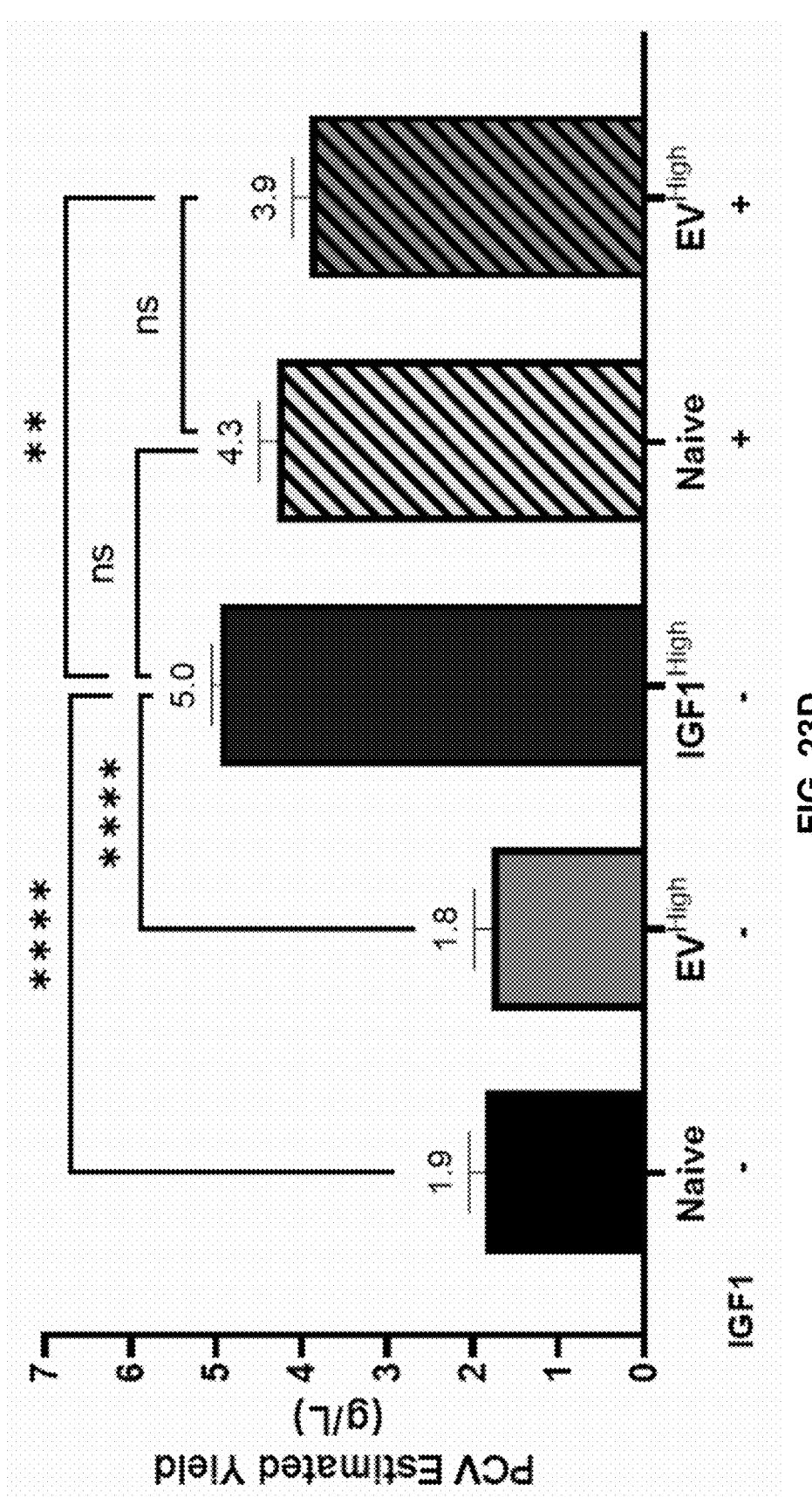

FIGS. 23C-23D are bar graphs showing Packed Cell Volumes (PCV) for controls (Naïve and empty vector (EV)) and IGF1 engineered cells. Cells are grown in media supplement with either 0 µg/L IGF1 or 10 µg/L IGF1. Cultures are analyzed at day 2 after the third passage. FIG. 23C shows PCV data for cells engineered to express low levels of IGF1 (IGF1$^{Low}$) and controls. FIG. 23D shows PCV data for cells engineered to express high levels of IGF1 (IGF1$^{High}$) and controls.

Figure 24:
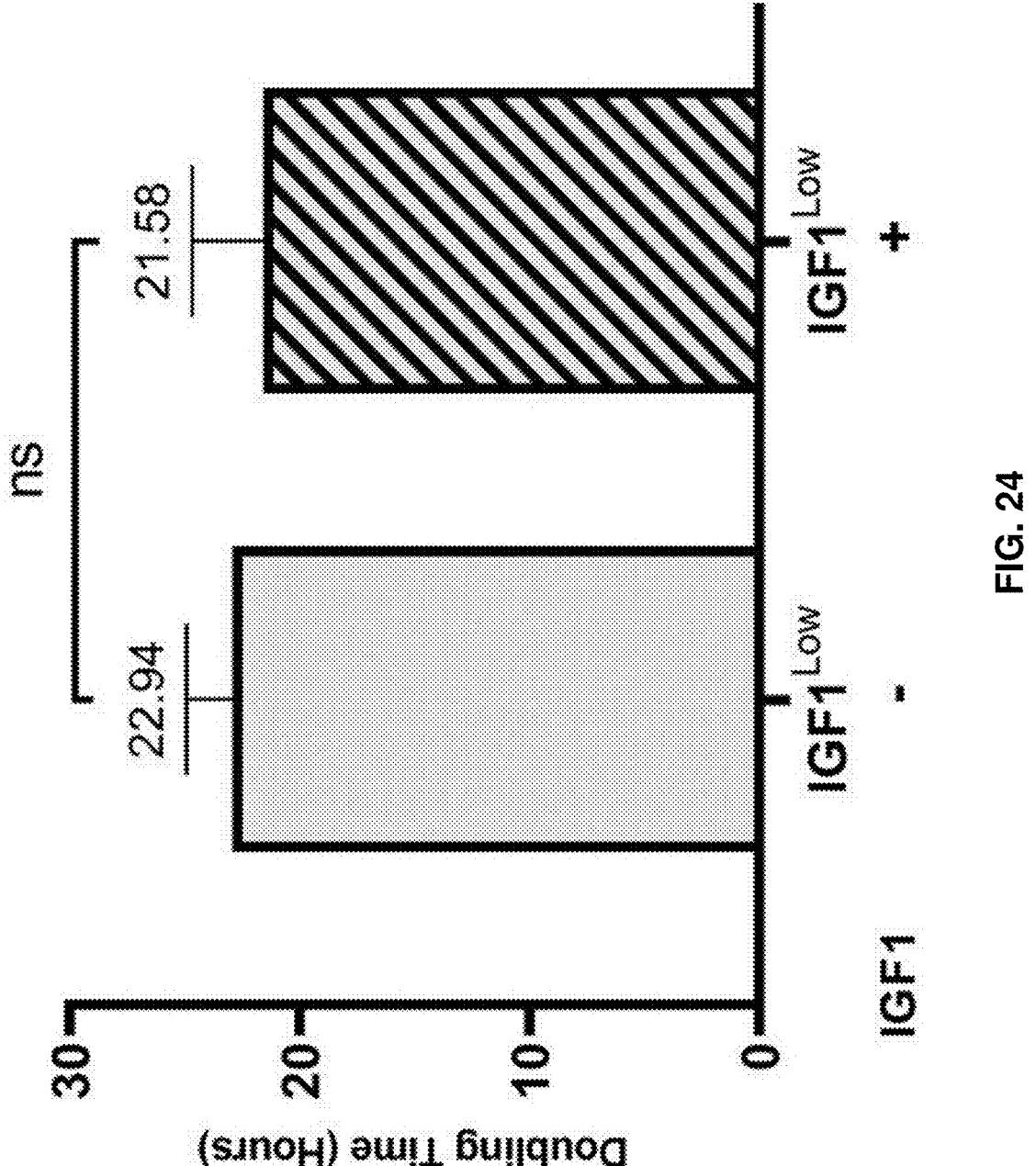

FIG. 24 shows doubling time (hours) for chicken for chicken cells engineered to express IGF1 (IGF1$^{low}$) grown in media supplement without ("−") and with ("+") IGF1.

Figure 25:
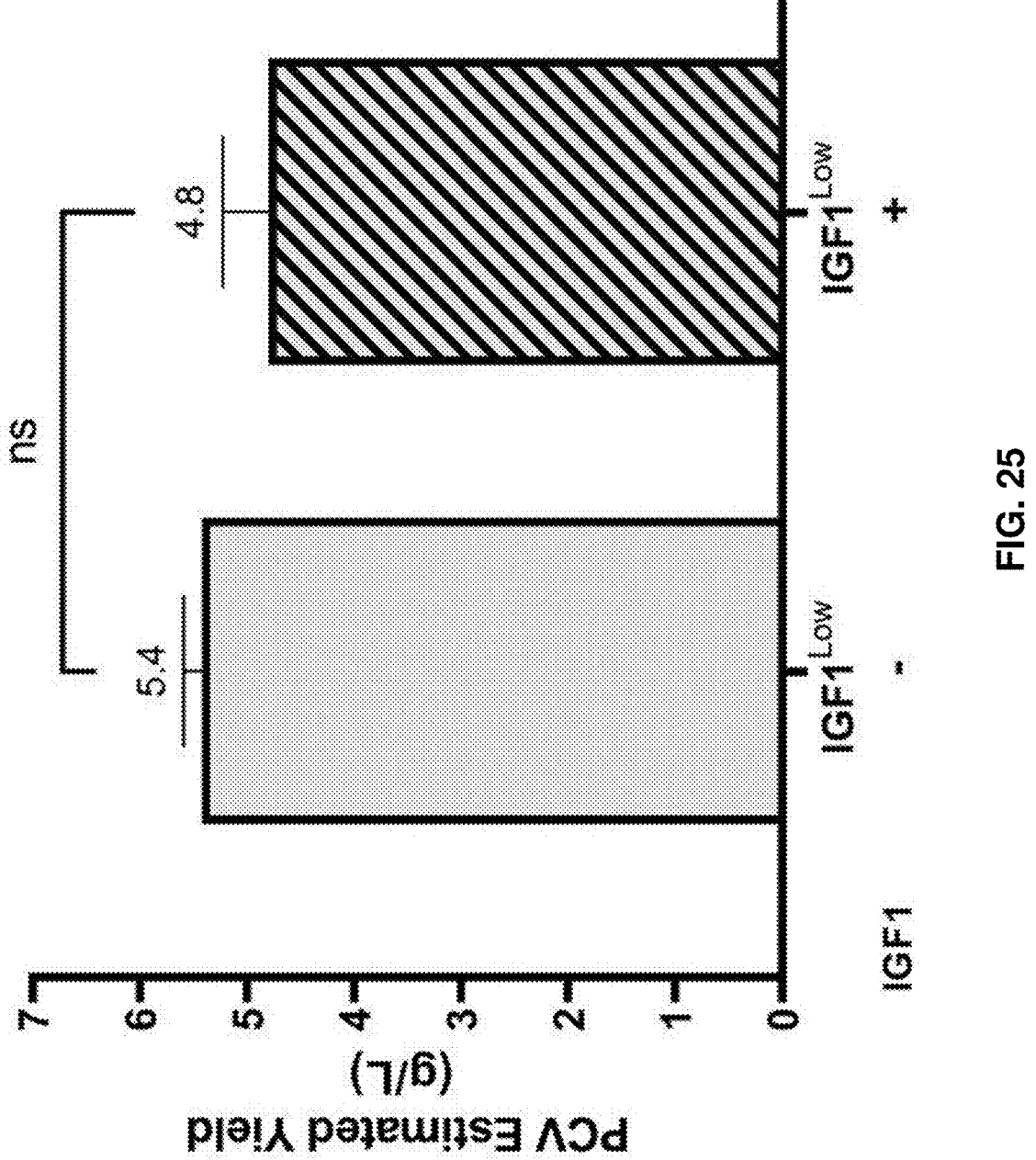

FIG. 25 shows packed cell volume estimated yield (g/L) for chicken cells engineered to express IGF1 (IGF1$^{low}$) grown in media supplement without ("−") and with ("+") IGF1.

Figure 26:
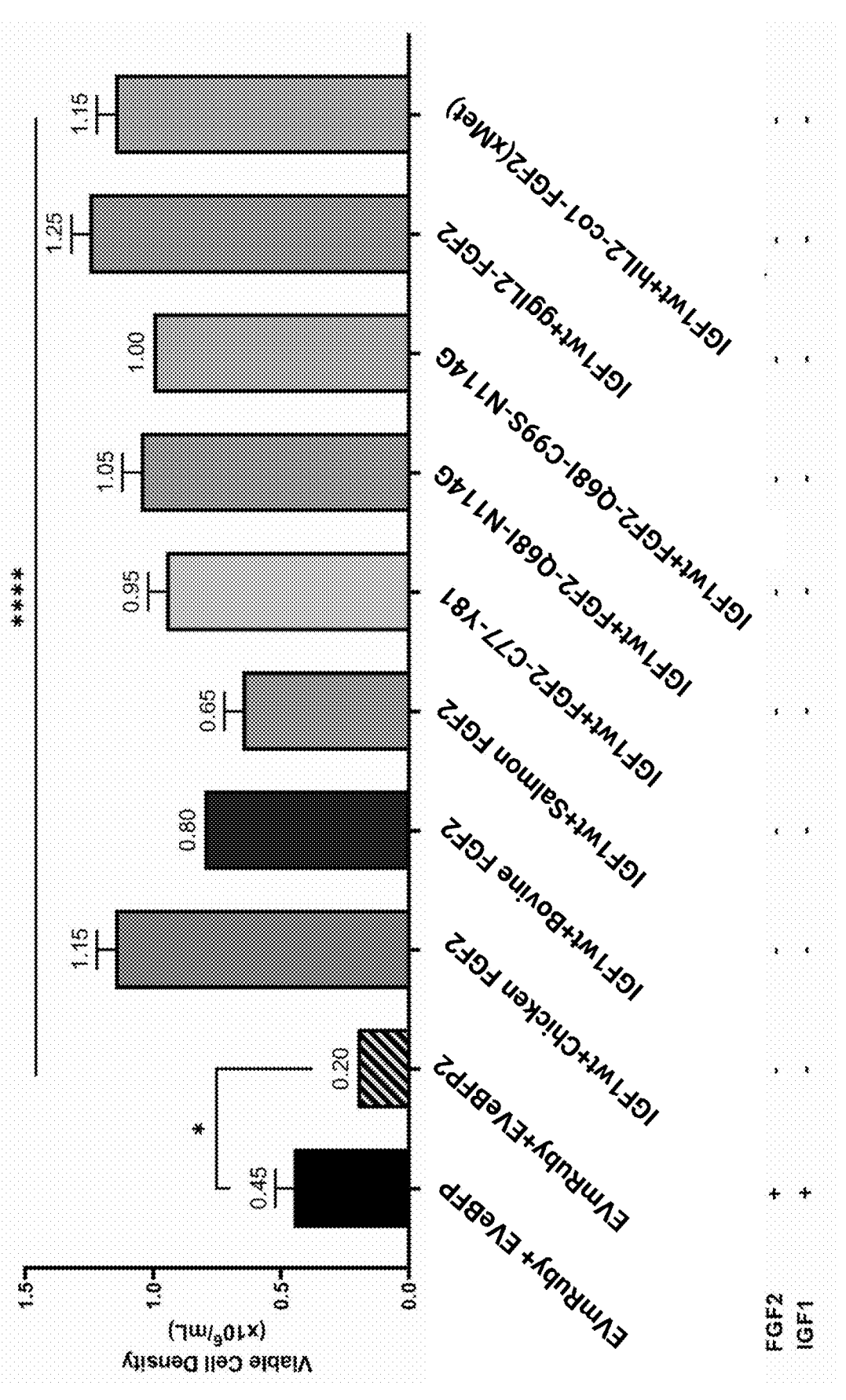

FIG. 26 shows viable cell density data for chicken cells engineered to express IGF1 and a FGF2 variant (chicken (Chicken FGF2), bovine (Bovine FGF2), salmon (Salmon FGF2), heat stable variants (FGF2-Q68I-N114G, FGF2-Q68I-C99S-N114G), secretion tagged variants (ggIL2-FGF2, hIL2-co1-ggFGF2(xMet)) or variant to preserve amino acid for non-canonical secretion (FGF2-C77Y81)). Controls grown with or without growth factors IGF1 (10 ug/L) and FGF2 (100 ug/L) consisted of dual empty vector (EVmRuby and EVeBFP2) that were used to construct IGF1 and FGF2 variants, respectively.

Figure 27:
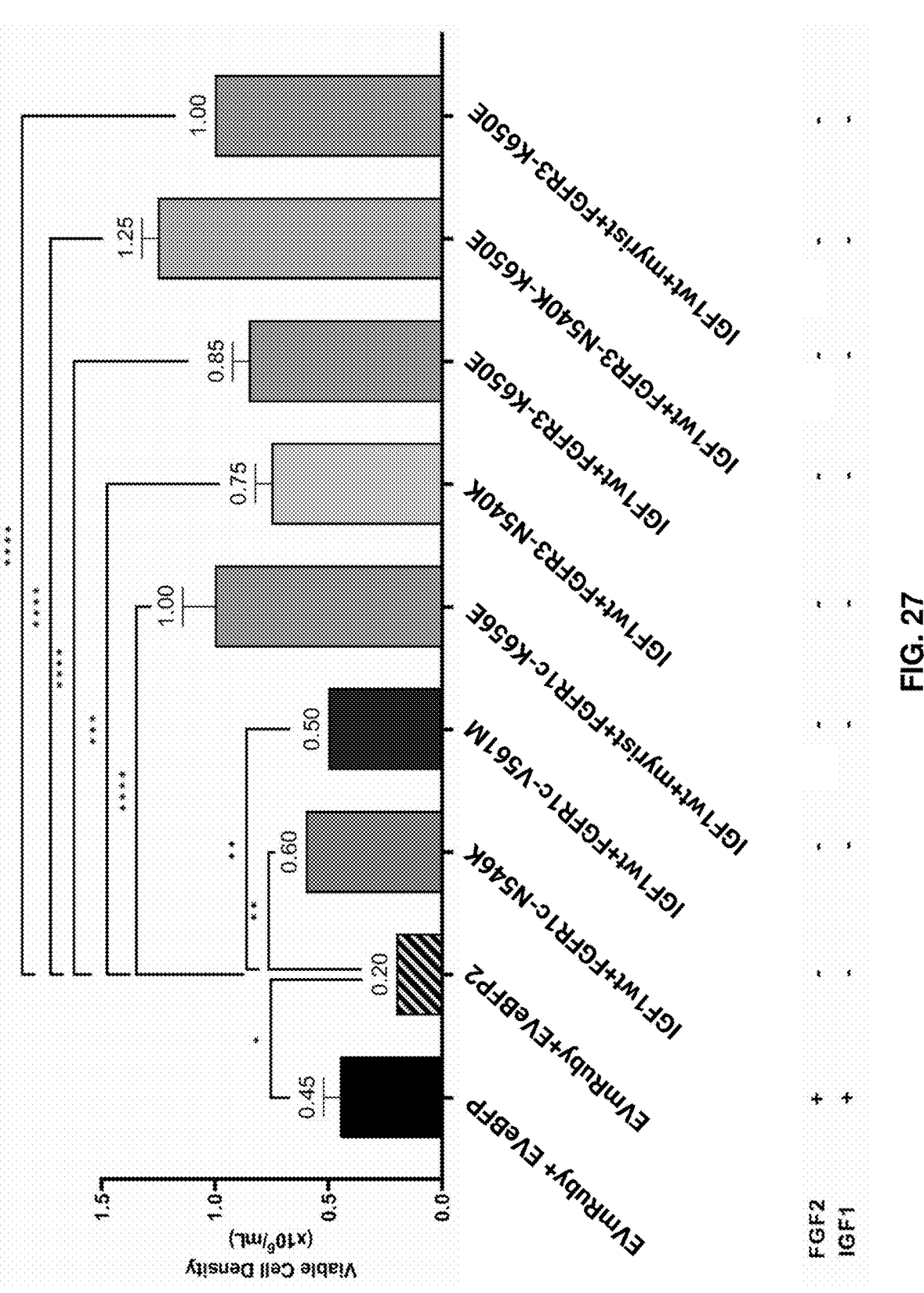

FIG. 27 shows that viable cell density data for chicken cells engineered to express IGF1 and a FGF receptor (FGFR1c-N546K, FGFR1c-V561M, myrist-FGFR1c-K656E, FGFR3-N540K, FGFR3-K650E, FGFR3-N540K-K650E, or myrist-FGFR3-K650E). Controls grown with or without growth factors IGF1 (10 ug/L) and FGF2 (100 ug/L) consisted of dual empty vector (EVmRuby and EVeBFP2) that were used to construct IGF1 and FGF receptor variants, respectively.

Figure 28:
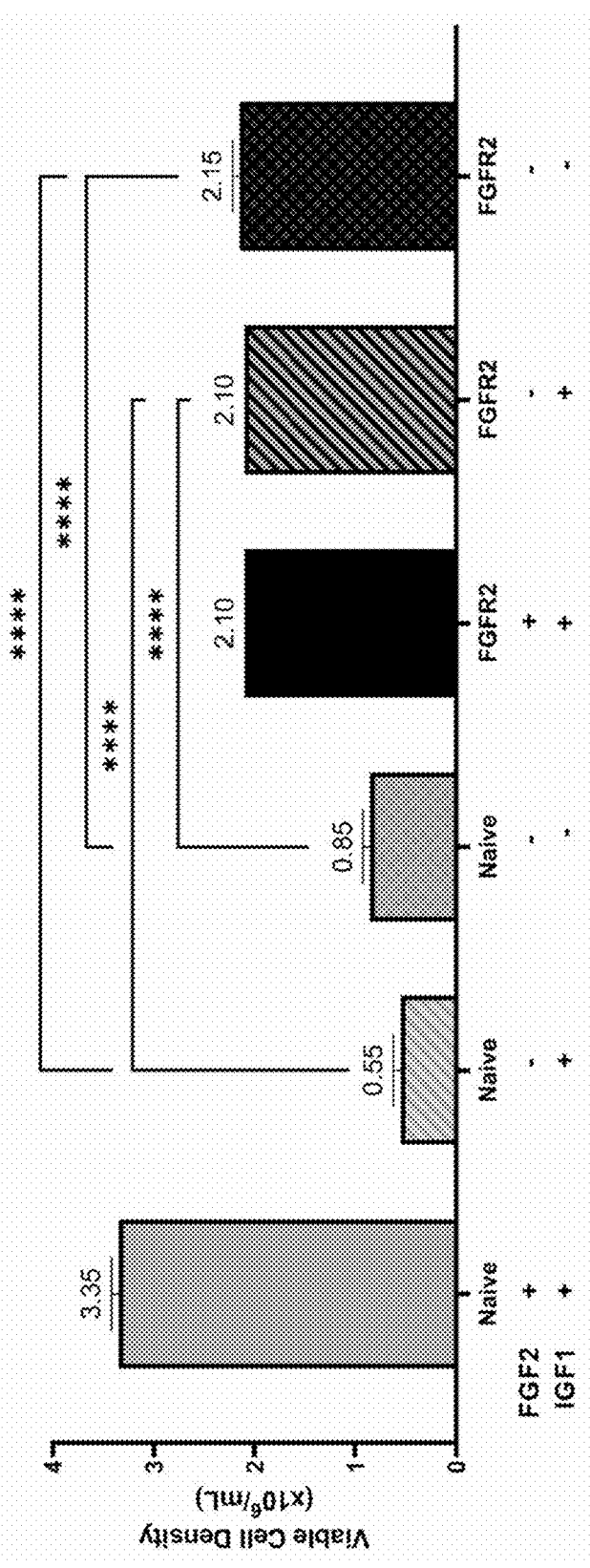

FIG. 28 shows that viable cell density data for chicken cells engineered to expressed FGFR2. Naïve chicken cells were used a controls.

Figure 29A:
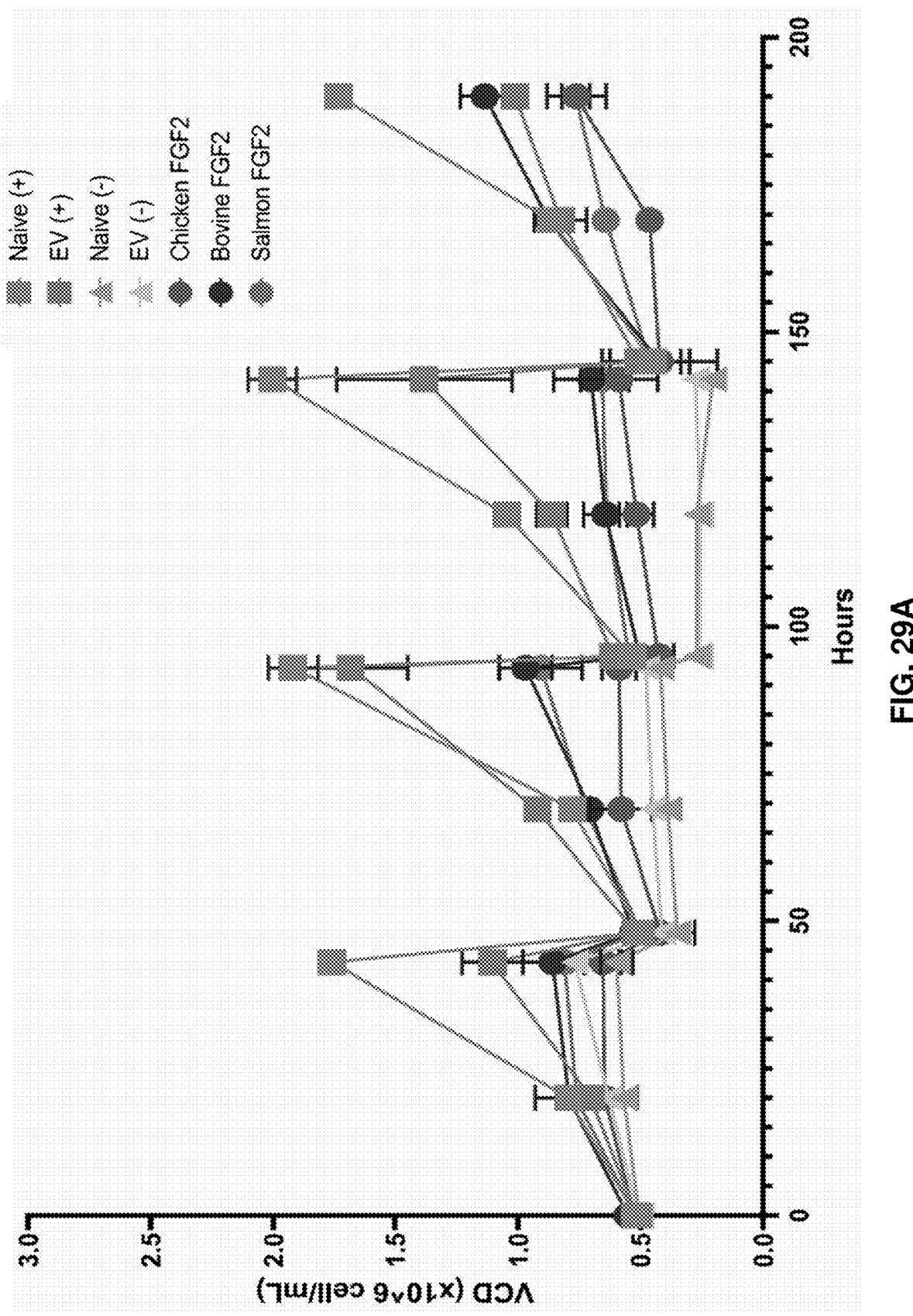
Figure 29B:
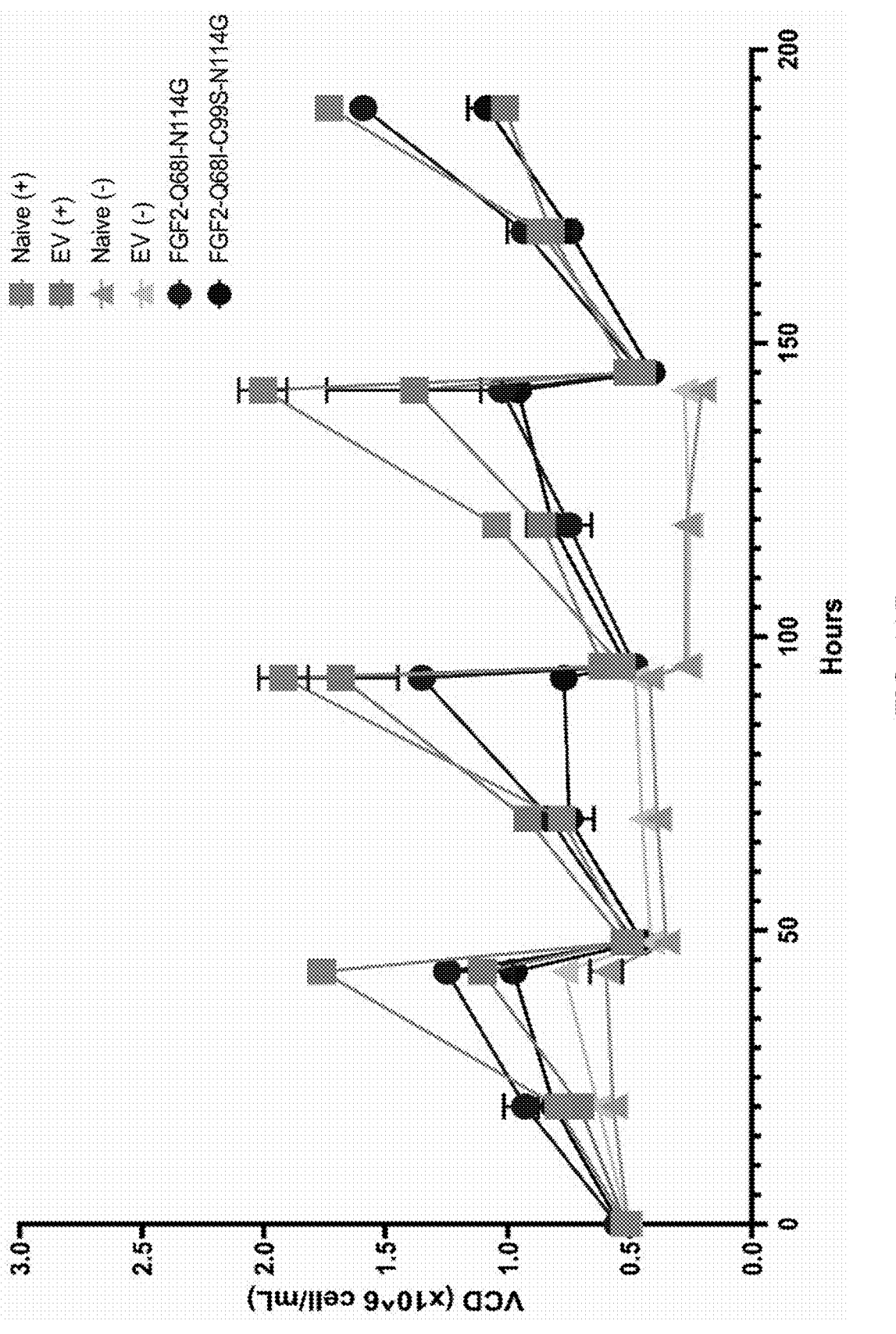
Figure 29C:
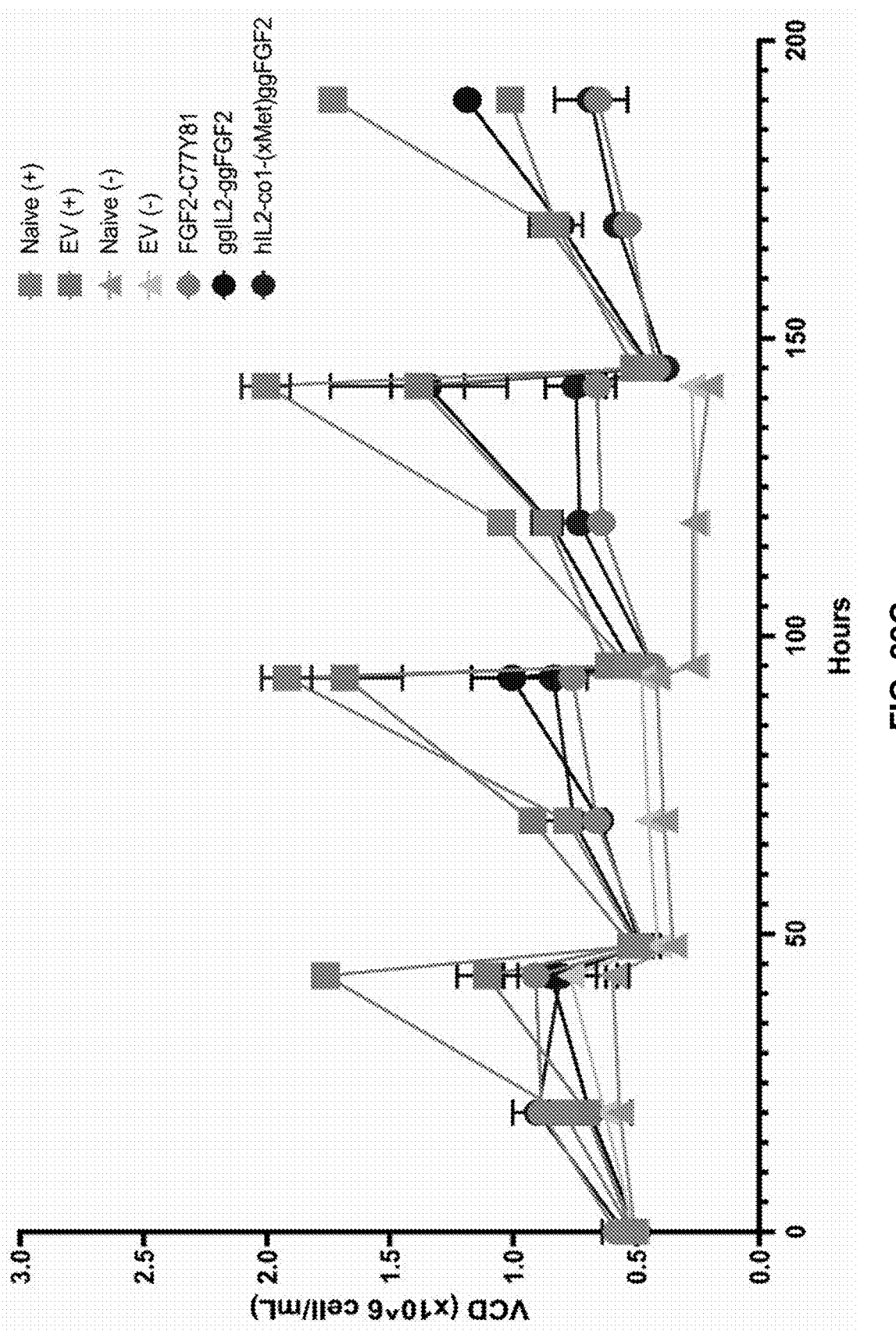

FIGS. 29A-29C show viable cell density (VCD) data over 200 hours in culture. FIG. 29A shows VCD data for chicken cells engineered to express FGF2 from different species (chicken, bovine, and salmon). FIG. 29B shows VCD data for chicken cells engineered to express FGF2 variants that have amino acid substitutions that increase heat stability. FIG. 29C shows VCD data for chicken cells engineered to express FGF2 designed with secretion signals or variants to preserve non-canonical secretion.

Figure 30:
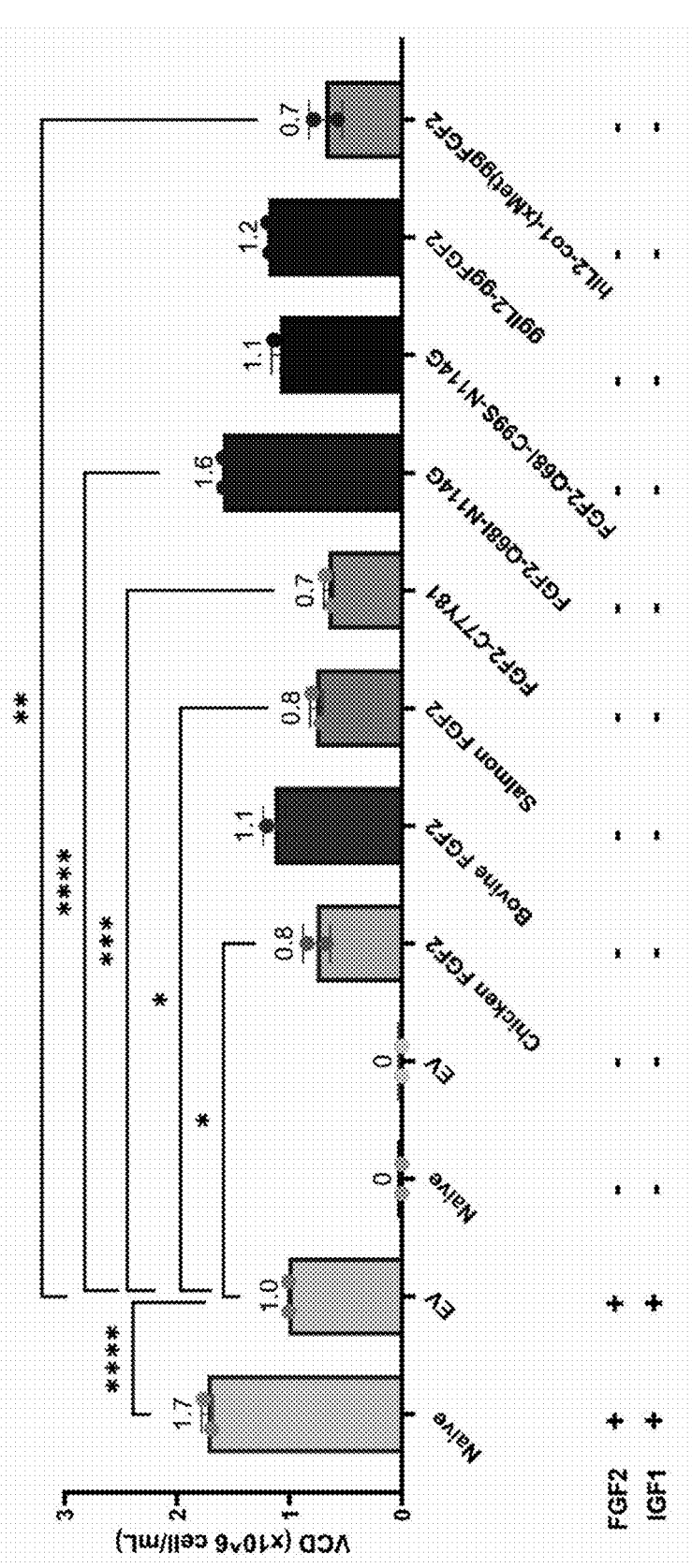

FIG. 30 show viable cell density (VCD) data summarizing FIGS. 29A-29C.

Figure 31A:
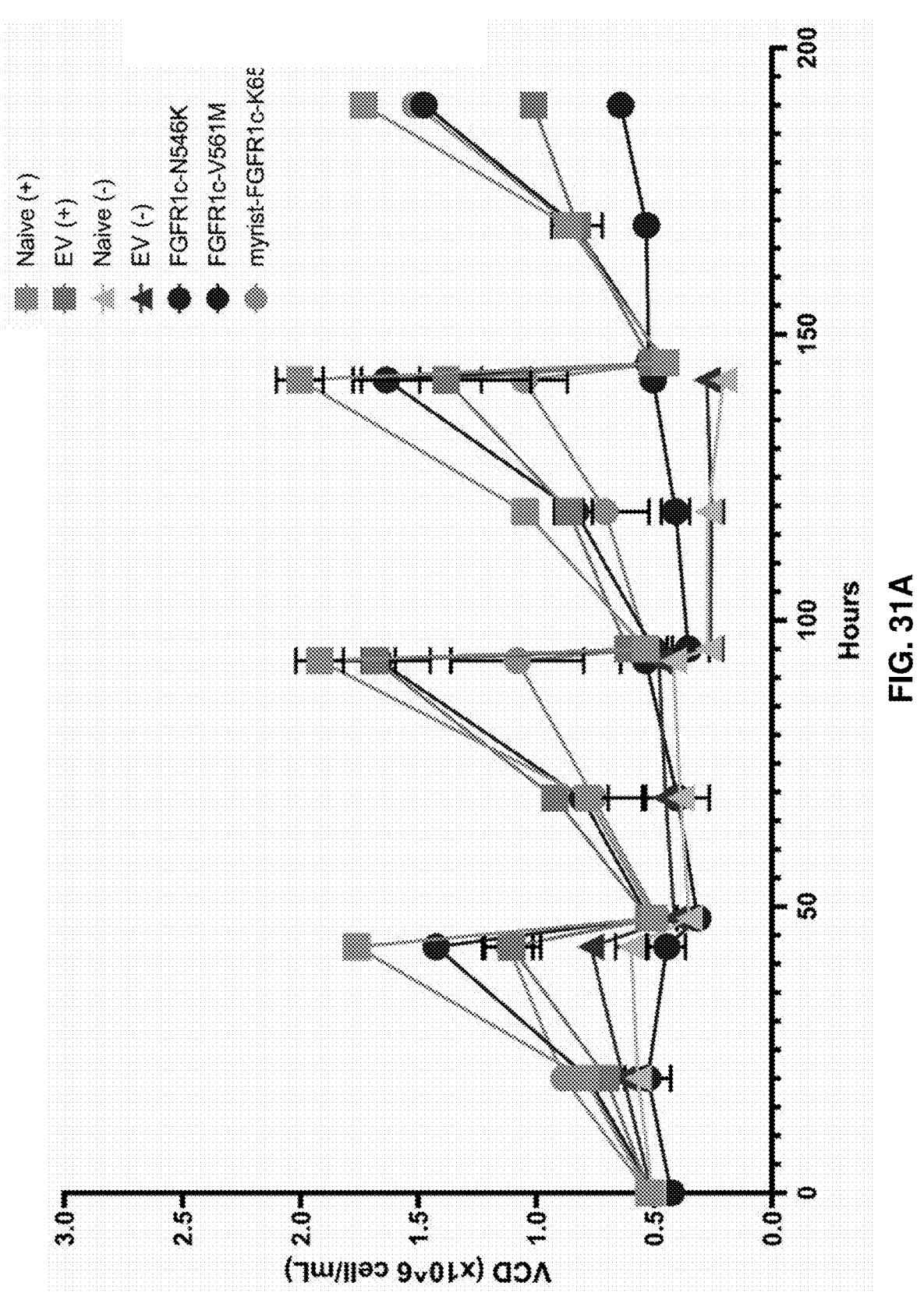
Figure 31B:
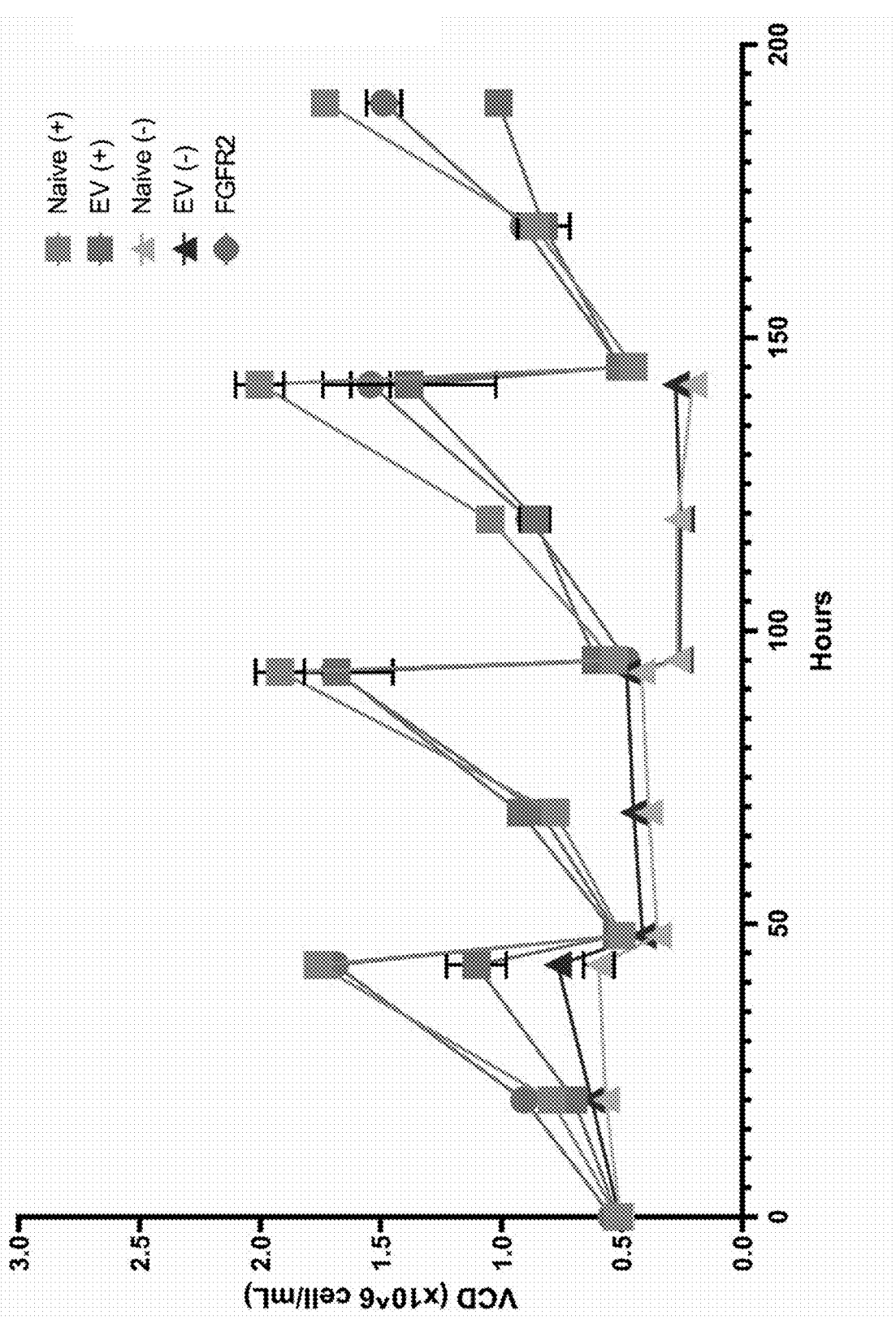
Figure 31C:
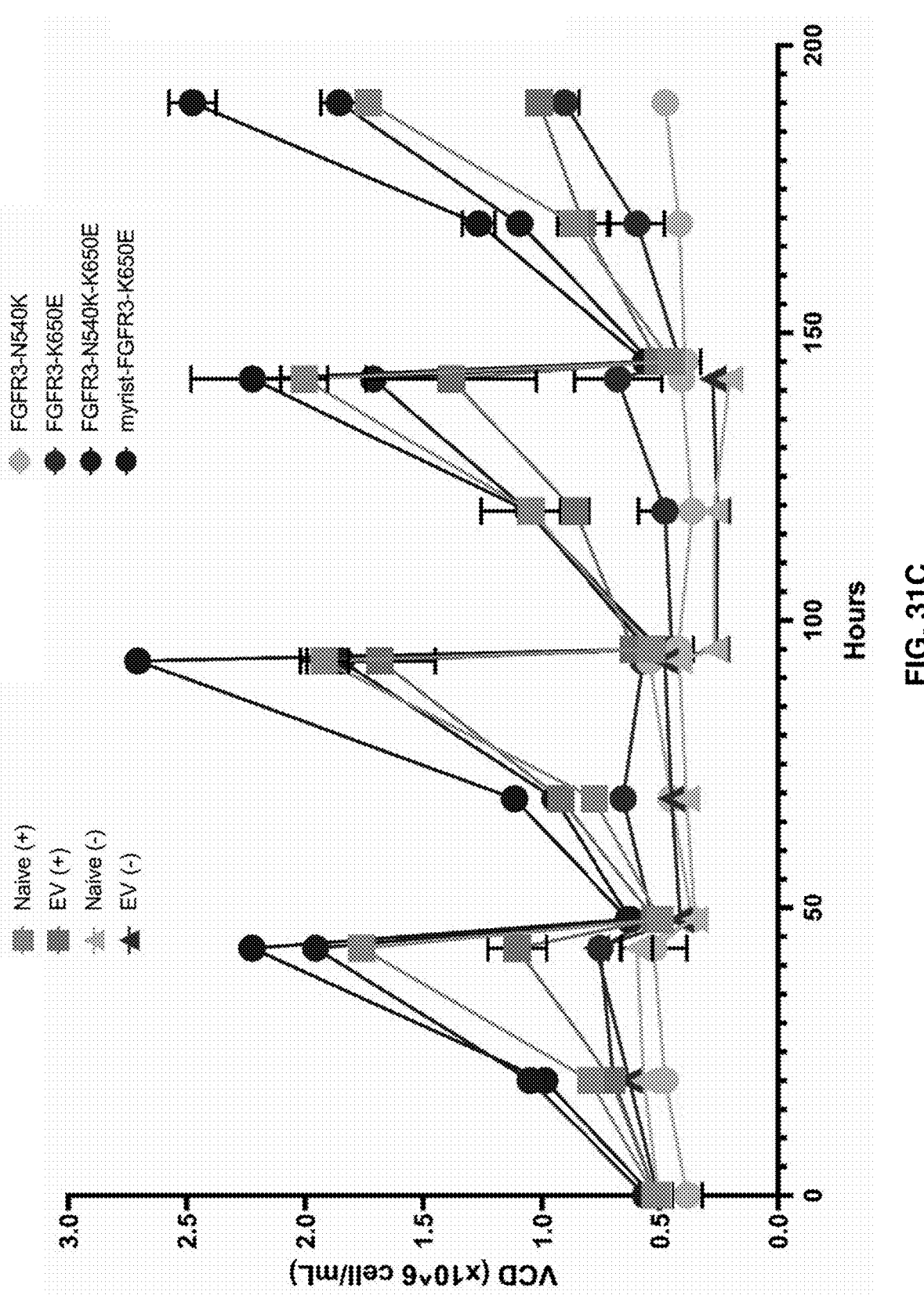

FIGS. 31A-31C show viable cell density (VCD) data over 200 hours in culture for chicken cells engineered to express the indicated FGF receptor variants. FIG. 31A shows VCD data for chicken cells engineered to express variants of FGFR1. FIG. 31B shows VCD data for chicken cells engineered to express FGFR2 variants. FIG. 31C shows VCD data for chicken cells engineered to express FGFR3 variants.

Figure 32:
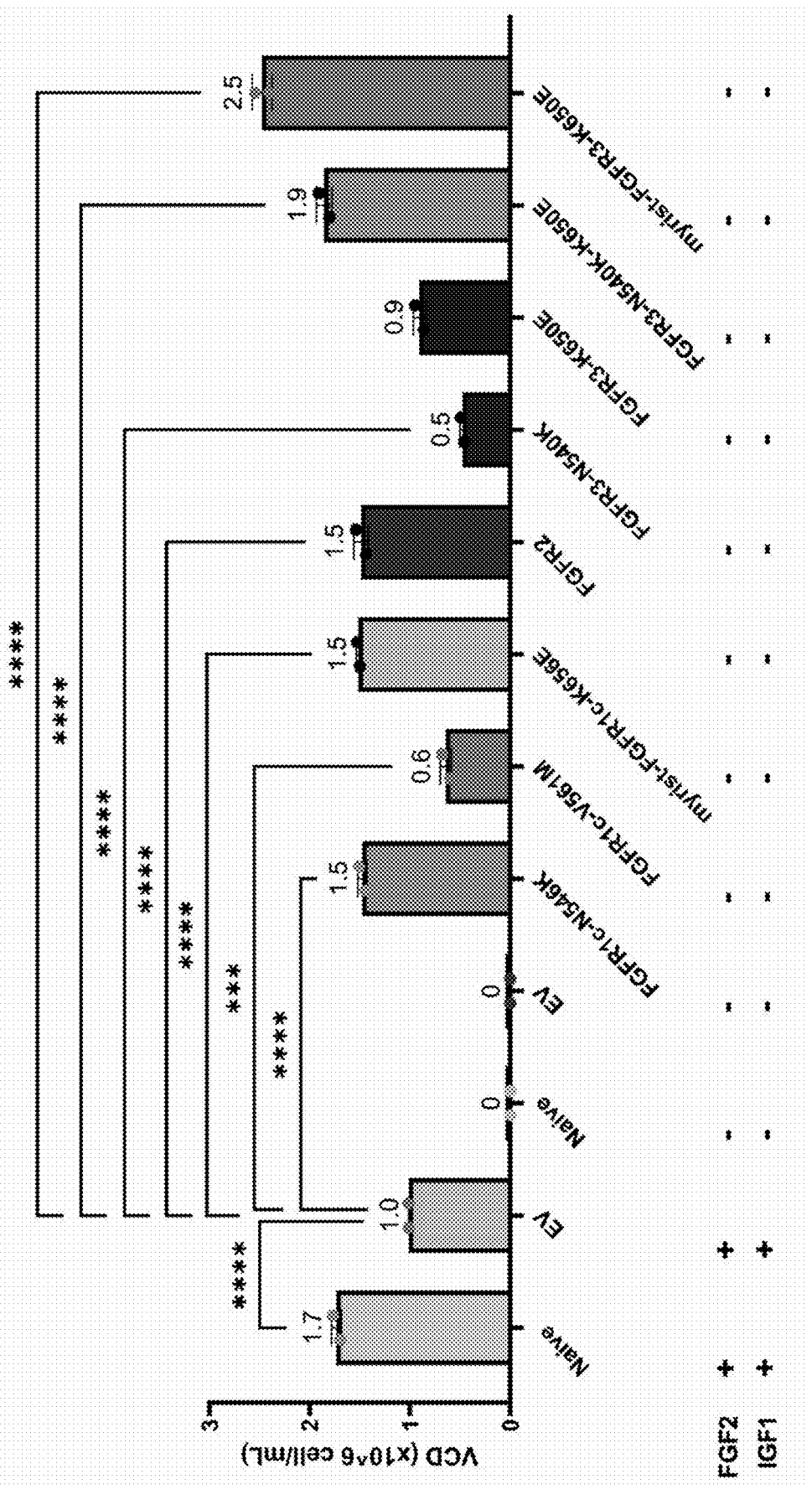

FIG. 32 shows viable cell density (VCD) data) for chicken cells engineered to express the indicated FGF receptor variants. One way ANOVA performed compared to empty vector control in growth factor containing media, Not significant (n.s.), p<0.05 (*), p<0.001 (), p<0.0001 (*) p<0.0001 (****).

Figure 33:
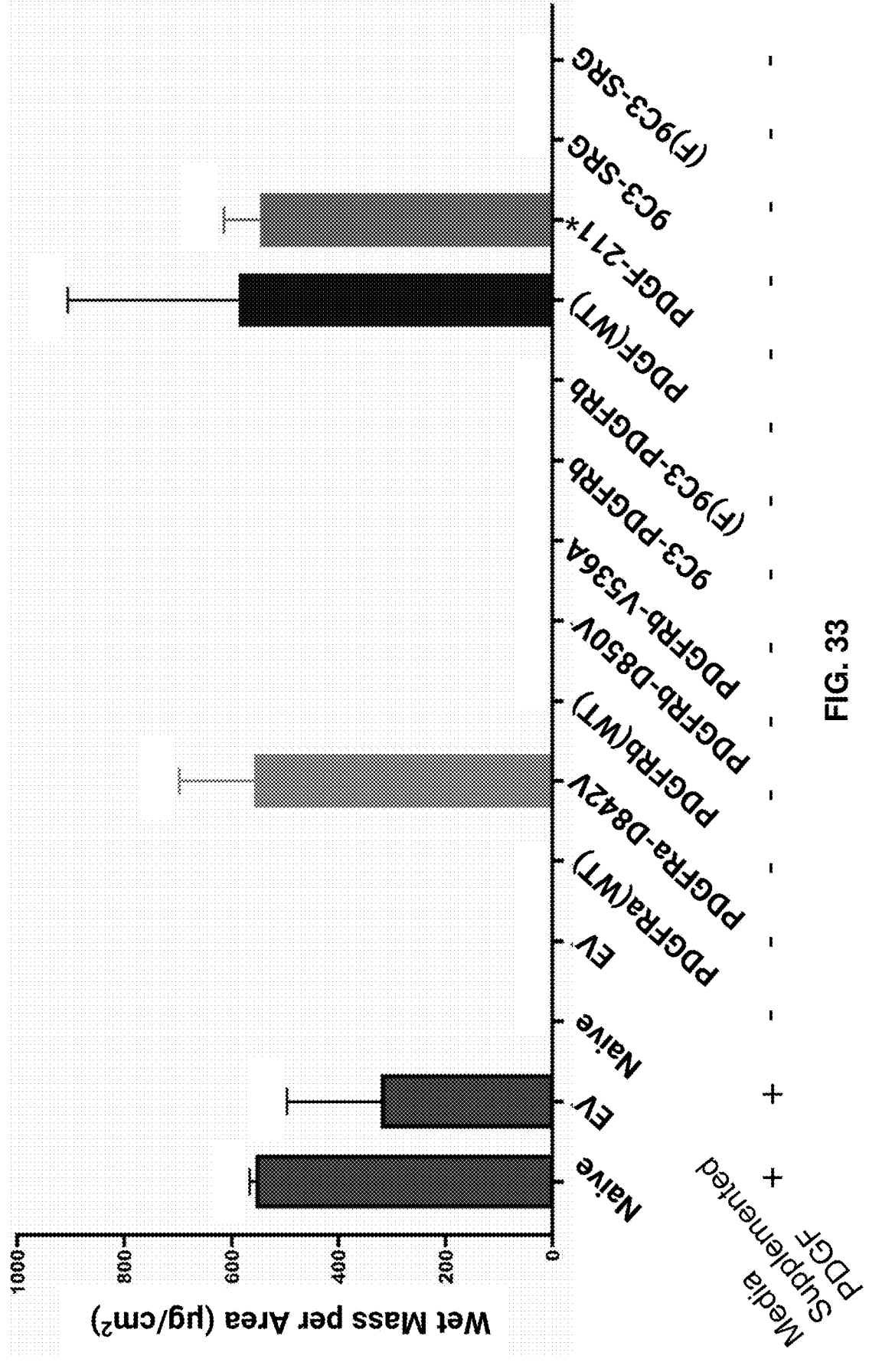

FIG. 33 shows Wet Mass per Area ($\mu g/cm^2$) for engineered cells and controls cultured in roller bottles over 14 day period in serum free media. Controls include Naive and empty vector (EV) cells grown with/without 50 ug/L PDGF (N=4). Chicken cells were engineered to express PDGFRa-D842V, PDGF(WT) or PDGF-211*.

Figure 34A:
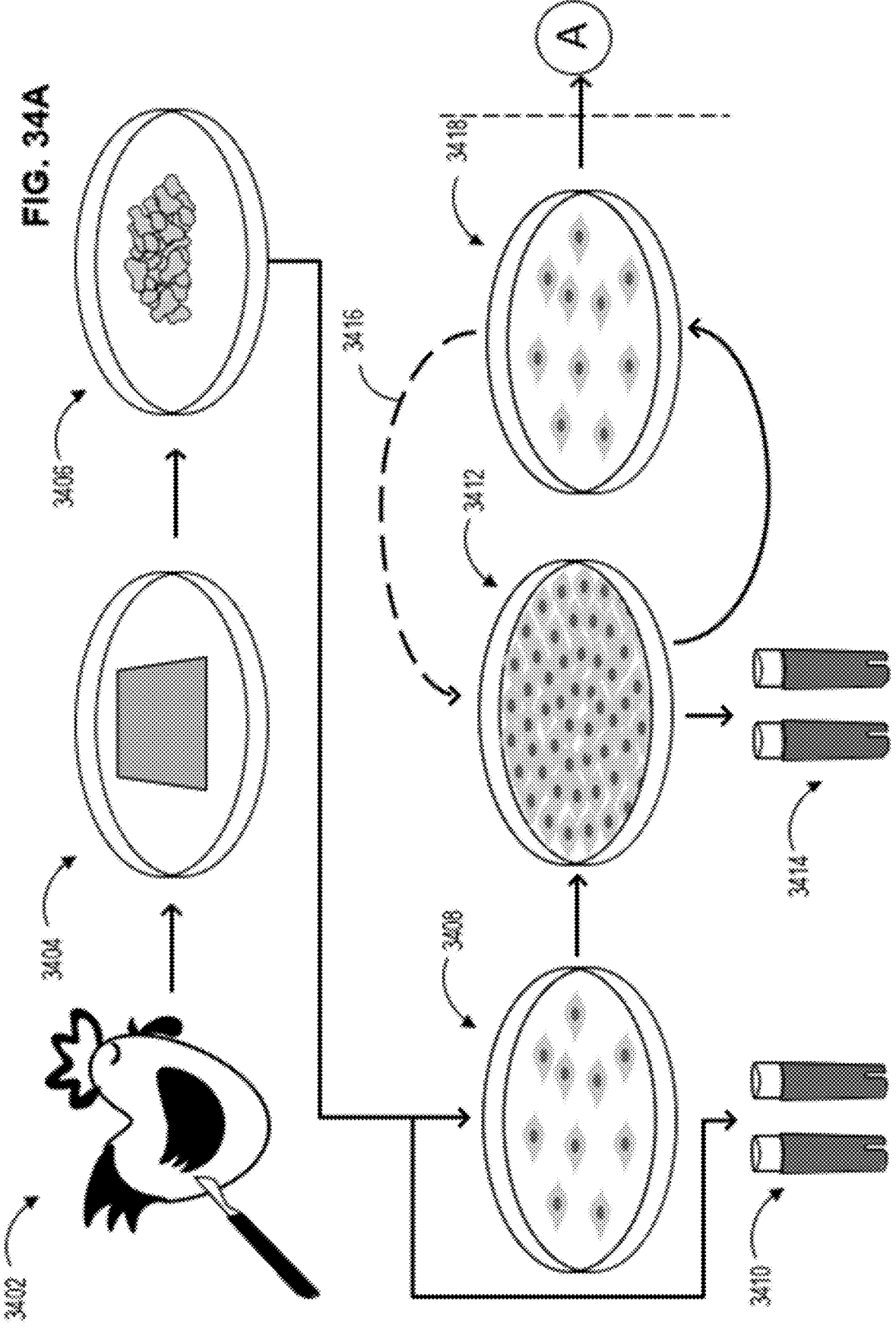
Figure 34B:
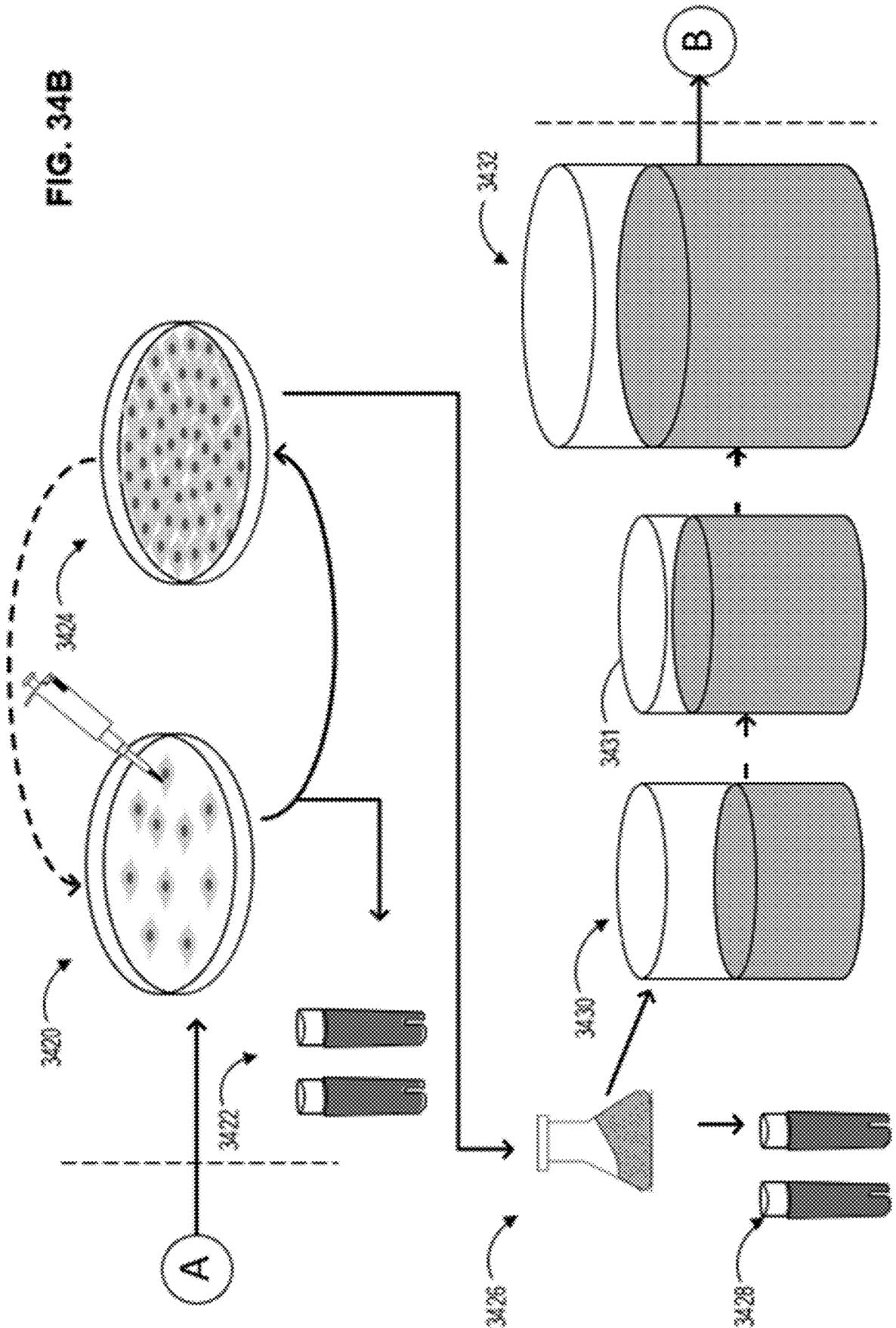
Figure 34C:
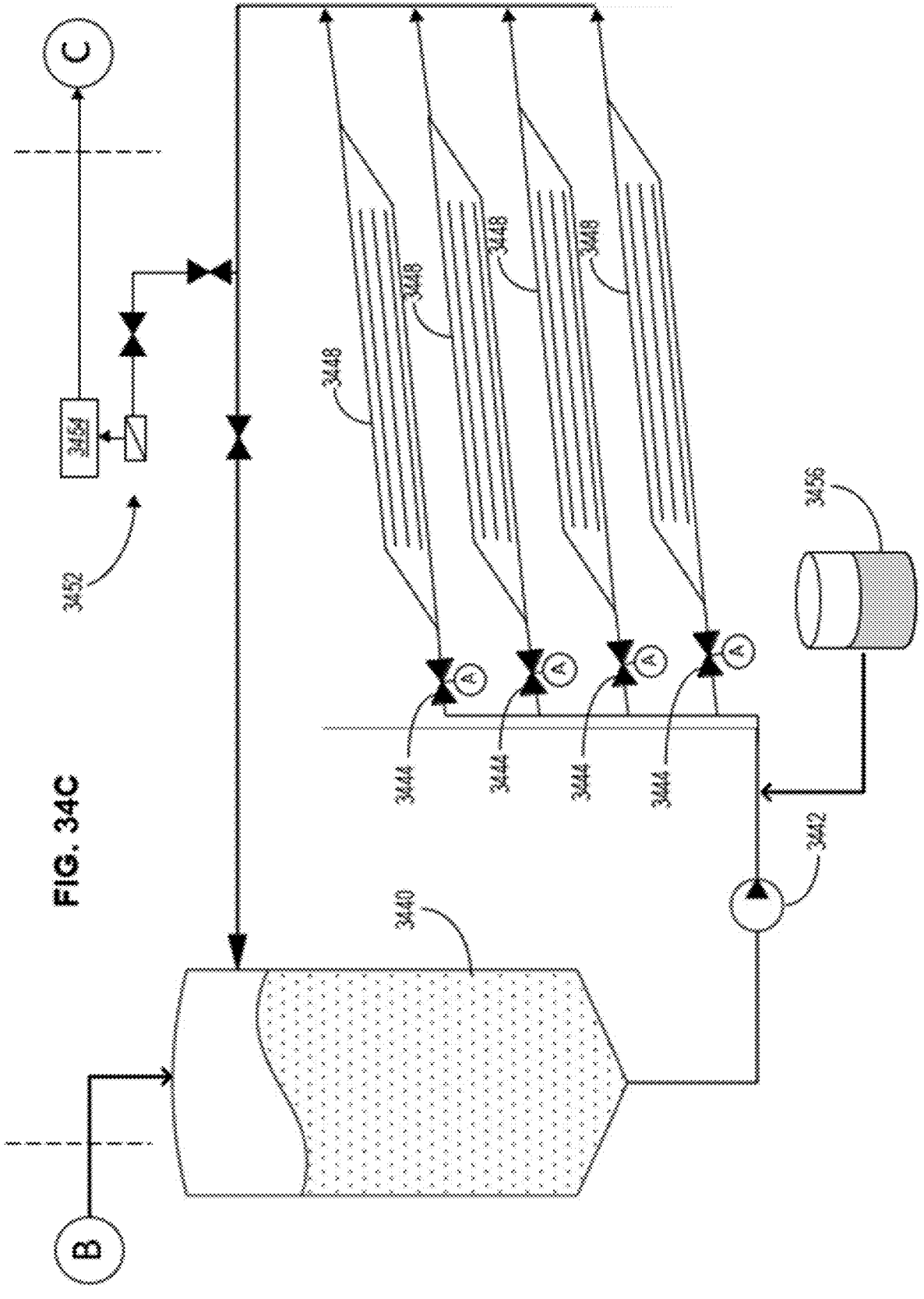
Figure 34D:
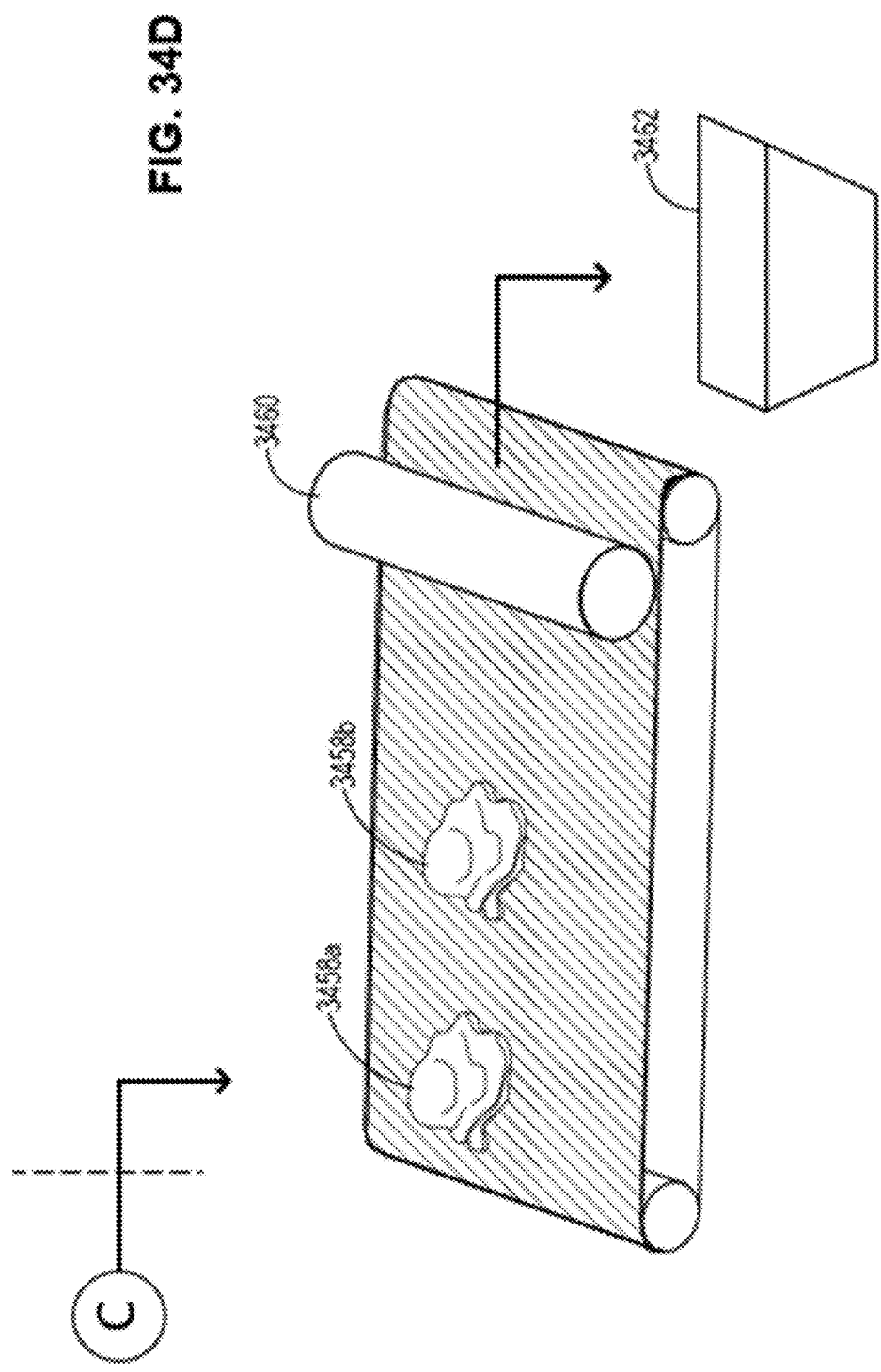

FIGS. 34A-34D show an overview diagram of growing and processing different types of cells in accordance with one or more embodiments of the present disclosure. FIG. 34A shows tissue collection, processing, culturing, and cryopreserving. FIG. 34B shows immortalizing, culturing until confluency, suspension culturing, cryopreserving, and expanding in larger culture vessels. FIG. 34C shows a bioreactor system. FIG. 34D shows a pressure apparatus that compresses cell masses.

6. DETAILED DESCRIPTION

6.1. Definitions

Unless defined otherwise, all technical and scientific terms used herein have the same meaning as is commonly understood by one of ordinary skill in the art to which this disclosure belongs. In the event that there is a plurality of definitions for terms cited herein, those in this section prevail unless otherwise stated.

Throughout this disclosure, the term "a" or "an" entity refers to one or more of that entity. As such, the terms "a" (or "an"), "one or more," and "at least one" can be used interchangeably herein. Furthermore, "and/or" as used in a phase such as "A and/or B" herein is intended to include "A and B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term "accessory protein" refers to a protein that modulates the actions or downstream signaling of a growth factor ligand or a growth factor receptor. Accessory proteins can modulate the actions of growth factor ligand and/or a growth factor receptor either directly (e.g., binding/interacting directly) or indirectly.

As used herein, the terms "comprising" and "including" or grammatical variants thereof are to be taken as specifying the stated features, integers, steps, or components but do not preclude the addition of one or more additional features, integers, steps, components, or groups thereof. This term encompasses the terms "consisting of" and "consisting essentially of".

As used herein, the terms "cell" and "cell line" are sometimes used interchangeably. As used herein, the term "cell" can refer to one or more cells originating from a cell line. As used herein, the term "cell line" can refer to a population of cells.

As used herein, the terms "cell surface" or "surface of the cell" when referring to a receptor refers to the presence of the receptor on the surface of the cell.

As used herein, the term "cultivation infrastructure" refers to the environment in which the cells, cell lines, myocytes, multinucleated myotubes, or skeletal muscle fibers are cultured.

As used herein, the term "differentiation capacity" refers to a cell's ability to differentiate to a particular cell lineage, stem cell, progenitor cell, or terminally differentiated cell.

As used herein, the term "exogenous," when referring to growth factors, refers to a growth factor derived from a source external to the culture and added (supplemented) to the culture medium.

As used herein, the term "fragment" or "portion" when referring to a protein or a polynucleotide refers to a protein that comprises a domain, portion, or fragment of a parent or reference protein or polypeptide. The term "portion" can be used interchangeably with the term "functional portion." The term "fragment" can be used interchangeably with the term "functional fragment." The terms "functional portion" or "functional fragment" refers to components that retain at least 50% activity associated with the domain, portion or fragment of the parent or reference compound, preferably at least 55%, 60%, 70%, 75%, 80%, 85%, 90%, 95%, 96%, 97%, 98%, 99%, 99.9%, or 100% level of activity of the parent protein or polypeptide, or provides a biological benefit. A "functional portion" or "functional fragment" of a protein or polypeptide has "similar binding" or "similar activity" when the functional portion or fragment displays no more than a 50% reduction in performance in a selected assay as compared to the parent or reference protein or polypeptide (preferably no more than 20% or 10%, or no more than a log difference as compared to the parent or reference with regard to affinity).

As used herein, the terms "growth factor ligand" refers to a secreted biologically active molecule that can affect the growth of cells, promote or inhibit mitosis, or affect cellular differentiation.

As used herein, the term "immortalized cell" refers to cells that are passaged or modified to proliferate indefinitely and evade normal cellular senescence.

As used herein, the term "myoblast" refers to mononucleated muscle cells. They are embryonic precursors of myocytes, also called muscle cells. Although myoblasts may be classified as skeletal muscle myoblasts, smooth muscle myoblasts, and cardiac muscle myoblasts depending on the type of muscle cell that they will differentiate into, in this specification the term myoblasts refer to skeletal muscle myoblasts.

As used herein, the term "myotube" refers to elongated structures, the result of differentiated myoblast. Upon differentiation, myoblasts fuse into one or more nucleated myotubes and express skeletal muscle markers.

As used herein the term "passaged cell" refers to the number of times the cells in the culture have been subcultured. This may occur without consideration of the inoculation densities or recoveries involved.

As used herein, the term "population doubling level (PDL)" refers to the total number of times the cells in the population have doubled since their primary isolation in vitro. Mathematically this is described as n=3.32 (log UCY−log l)+X, where n=the final PDL number at end of a given subculture, UCY=the cell yield at that point, l=the cell number used as inoculum to begin that subculture, and X=the doubling level of the inoculum used to initiate the subculture being quantitated.

As used herein, the term "substantially free of" or "substantially free from" means the amount (e.g., absolute number within a population or concentration/percentage within a population) of a cell or cell type is below a value where the cell or cell type, or any cell derived therefrom, could contribute to the population. For example, a population substantially free of a cell means that upon differentiation of the population the cell does not sustain progeny in the differentiated population. When referring to culture reagents, "substantially free of" or "substantially free from"

refer to the amount (e.g., concentration) of the reagent that is below a value where the cell culture reagent does not have a biological effect on the culture (i.e., the reagent is not capable of producing a biological effect at such low concentrations).

As used herein, the term "transdifferentiation" refers to the conversion of a cell type present in one tissue or organ into a cell type from another tissue or organ without going through a pluripotent cell state. Transdifferentiation between some cell types can occur naturally. In other cases, transdifferentiation can be induced using exogenous factors including small molecules, growth factors, and/or genetic engineering.

As used herein, the terms "transformed," "transduced," and "transfected" are used interchangeably unless otherwise noted. Each term refers to introduction of a nucleic acid sequence or polypeptide into a cell (e.g., an immortalized cell).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

6.2. Growth Factor Ligands

Figure 1:
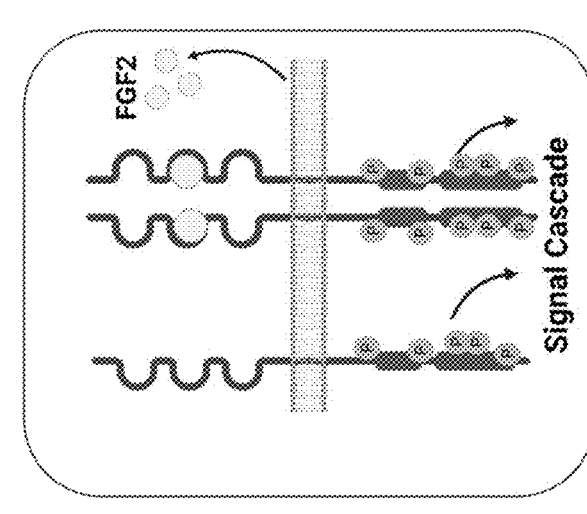
Figure 1:
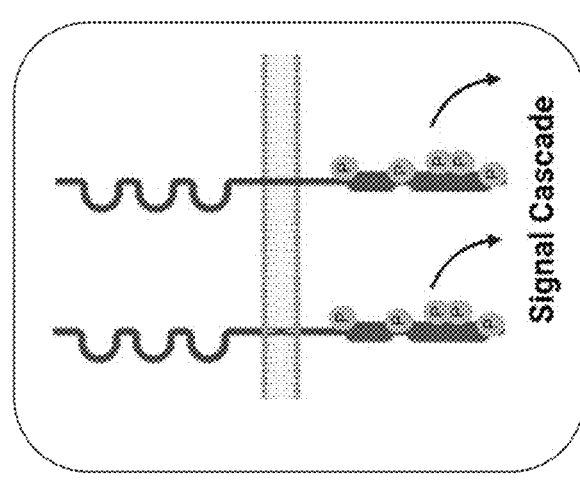
Figure 1:
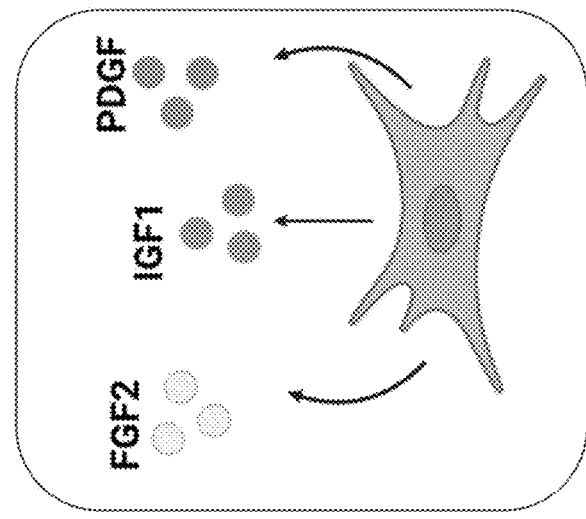

Provided herein are methods for introducing into a cell a polynucleotide comprising a coding sequence of a growth factor ligand (see FIG. 1). In some embodiments, introducing the polynucleotide comprising the coding sequence of the growth factor ligand into the cells results in the cells having reduced reliance on exogenous growth factors. In such cases, the cells are engineered to overexpress the coding sequence of the growth factor ligand. In some embodiments, the cells are genetically engineered to have stable integration of the one or more copies of a coding sequence for a growth factor ligand. In some embodiments, the cells overexpress the coding sequence of the growth factor ligand at levels sufficient to increase production and/or secretion of the growth factor ligands into the cell culture medium. In some embodiments, the growth factor ligand is selected from basic fibroblast growth factor (FGF2), insulin-like growth factor 1 (IGF1), insulin-like growth factor 2 (IGF2), and platelet-derived growth factor (PDGF). The FGF2, IGF1, IGF2, PDGF is selected from any metazoan species.

In some embodiments, the methods provided herein include introducing a polynucleotide comprising a coding sequence of FGF2, IGF1, IGF2, PDGF, or a combination thereof. For example, the polynucleotide comprises a coding sequence of FGF2, FGF2 and IGF1, FGF2 and PDGF, IGF1 and PDGF, or FGF2, IGF1 and PDGF.

6.2.1. Fibroblast Growth Factor 2

In some embodiments, the methods provided herein include introducing into a cell a polynucleotide comprising a coding sequence of fibroblast growth factor 2 (FGF2) or a fragment thereof. As used herein, "FGF2" refers to the fibroblast growth factor 2 (Fgf2) gene or FGF2 protein, which is a member of the fibroblast growth factor (FGF) family. FGF family members bind heparin and possess broad mitogenic and angiogenic activities. FGF2: acts as a ligand for FGFR1, FGFR2, FGFR3 and FGFR4; acts as an integrin ligand which is required for FGF2 signaling; binds to integrin ITGAV:ITGB3; plays an important role in the regulation of cell survival, cell division, cell differentiation and cell migration; functions as a potent mitogen in vitro; induces angiogenesis; and mediates phosphorylation of ERK1/2.

In some embodiments, the cells are modified to overexpress the coding sequence of an FGF2 protein. In some embodiments, the cells are genetically modified and carry stable integrations of one or more copies of an FGF2 coding sequence. In some embodiments, the cells overexpress the coding sequence of FGF2 protein at levels sufficient to increase production and/or secretion of FGF2 into the cell culture medium.

In some embodiments, the FGF2 coding sequence is selected from any metazoan species. In some embodiments, the FGF2 coding sequence is from any animal, such as vertebrate and invertebrate animal species. In some embodiments, the FGF2 coding sequence is from any vertebrate animal species such as mammals, reptiles, birds, amphibians, and the like. In some embodiments, the FGF2 coding sequence is from any mammalian species such as a human, murine, bovine, porcine, poultry, and the like. In some embodiments, the coding sequence of the FGF2 protein is derived from a species selected from any metazoan species, including without limitation, *Gallus gallus, Bos taurus, Sous scrofa, Meleagris gallopavo, Anas platyrynchos, Salmo salar, Thunnus thynnus, Ovis aries, Coturnix, Copra aegagrus hircus*, or *Homarus americanus*.

In some embodiments, increasing expression of FGF2 may be achieved using different approaches. In some embodiments, the expression is inducible. In some embodiments, the method comprises expressing polynucleotides comprising the coding sequence of FGF2. In some embodiments, the polynucleotides are ectopically expressed from constructs that are introduced into the cells, for example expressed from a plasmid, or other expression vector. In some embodiments, the constructs are integrated into the cell's genome, and the expression is driven in that manner (e.g., PhiC31 Integration Systems). In some embodiments, the expression of the FGF2 gene involves electroporating a DNA, delivering a DNA complexed with a transfection vehicle, using a viral vector (e.g. retrovirus, lentivirus, adenovirus, adeno-associated virus), and the like, or combinations thereof. In some embodiments, the expression is constitutive. In some embodiments, the expression is conditional (e.g. inducible).

In the methods described herein, a polynucleotide comprising a coding sequence of FGF2 may encode any homolog of FGF2, including FGF2 paralogs, such as FGF1, FGF3, FGF5, FGF9, and FGF16, or any other FGF2 paralogs, or an FGF2 protein translated from any splice variants of an FGF2 gene, or may comprise any mutations in the FGF2 gene sequence including, but not limited to nucleotide deletions, truncations, fusions, or substitutions. Mutations may be synthetic or naturally occurring.

Figure 2A:
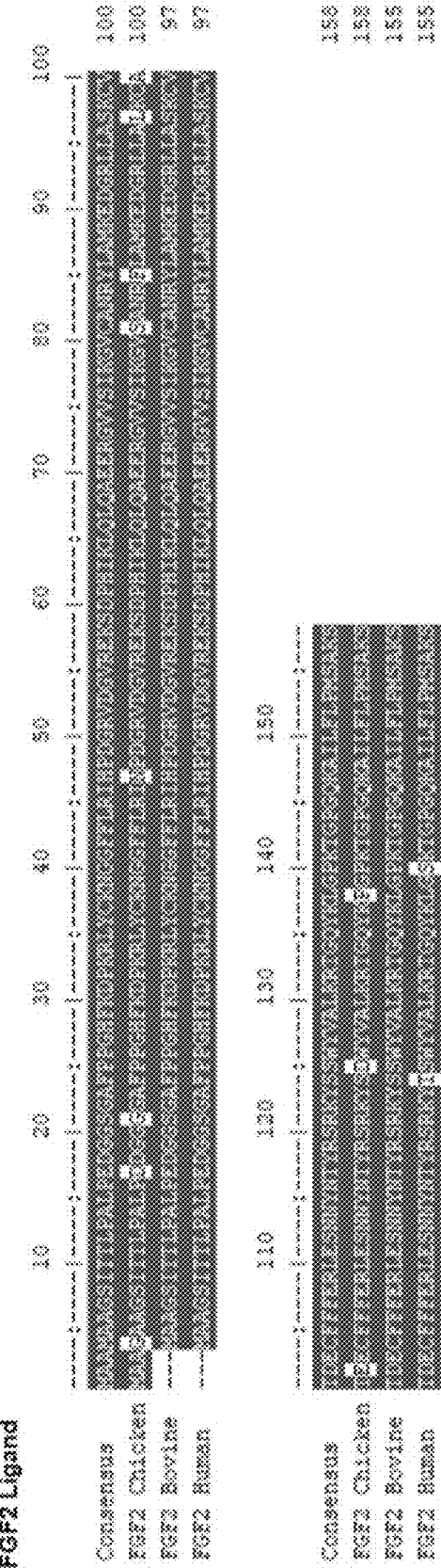
FIG. 2A shows sequence alignment of amino acid sequences for FGF2 from human, chicken, bovine, and salmon. Chicken FGF2 amino acid sequence has 91.6%, 92.9%, and 76.1% identity with human, bovine, and salmon FGF2 sequences, respectively.

In some embodiments, FGF2 refers to the Fgf2 gene or FGF2 protein, or fragment or variant thereof (e.g., a FGF2 protein having one or more (e.g., one, two, three, four, five, six, seven, eight, nine, ten, or more amino acid substitutions, deletions or insertions as compared to a wild type FGF2 protein)). FIG. 2A shows a sequence alignment for FGF2 from chicken, bovine and human. In some embodiments, FGF2 refers to a sequence listed in FIG. 2A.

In some embodiments, a FGF2 protein comprises an amino acid sequence having at least 80% (e.g., at least 85%, 90%, 95%, 96%, 97%, 98%, or 99%) sequence identity to a sequence selected from SEQ ID NOs: 1-15. In some embodiments, the FGF protein sequence comprises an amino acid sequence selected from SEQ ID NOs: 1-15.

In some embodiments, the FGF2 protein is a wild type (WT) chicken FGF2 (SEQ ID NO: 1). In some embodiments, the FGF2 is a stabilized version of wild type chicken FGF2 (SEQ ID NO: 2). In such embodiments, the FGF2 comprises one or more amino acid substitutions engineered to impart increased thermostability on the FGF2 protein (i.e., increase half-life in the culture medium). In some embodiments, a thermostable FGF2 is referred to as a STAB FGF2. In some embodiments, the one or more amino acid substitutions are selected from R31L, V52T, E54D, H59F, L92Y, S94I, C96N, S109E, T121P as compared to SEQ ID NO: 1.

In some embodiments, introducing the polynucleotide comprising the coding sequence of the FGF2 protein alone is not sufficient to confer reduced reliance on exogenous growth factors. In such embodiments, one or more additional growth factor ligands can be introduced into the cell line. For example, a polynucleotide comprising the coding sequence of a IGF1 protein or a PDGF protein can be introduced into the cell line to help confer reduced reliance on exogenous growth factors. In other embodiments, a polynucleotide comprising a coding sequence of a growth factor receptor can be introduced into the cell line to help confer reduced reliance on exogenous growth factors. In such embodiments, the growth factor receptor can be selected from a FGF2R, an IGF-1R, and a PDFGR. For example, in order to confer reduced reliance on exogenous growth factors on the cell line, a polynucleotide comprising a coding sequence of a growth factor ligand (e.g., FGF2) or a fragment thereof, and a polynucleotide comprising a coding sequence of a growth factor receptor (e.g., FGFR) are introduced into the cell line.

6.2.2. Insulin Growth Factor 1

In some embodiments, the methods provided herein include introducing into a cell a polynucleotide comprising a coding sequence of Insulin-like growth factor 1 (IGF1) or a fragment thereof. As used herein, "IGF1" refers to the insulin-like growth factor 1 (Igf1) gene or IGF1 protein that is gene similar to insulin in function and is a member of a family of proteins involved in mediating growth and development. Without wishing to be bound by theory, IGF1 acts as a ligand for insulin-like growth factor 1 receptor (IGF1R). IGF-1 binds to the alpha subunit of IGF1R, leading to the activation of the intrinsic tyrosine kinase activity which autophosphorylates tyrosine residues in the beta subunit thus initiating a cascade of down-stream signaling events leading to activation of the PI3K-AKT/PKB and the Ras-MAPK pathways. IGF1 can bind to integrins ITGAV:ITGB3 and ITGA6:ITGB4. Its binding to integrins and subsequent ternary complex formation with integrins and IGFR1 are important for IGF1 signaling. IGF1 induces the phosphorylation and activation of IGFR1, MAPK3/ERK1, MAPK1/ERK2 and AKT1.

In some embodiments, the cells are modified to overexpress the coding sequence of an IGF1 protein. In some embodiments, the cells are genetically modified and carry stable integrations of one or more copies of an IGF1 coding sequence. In some embodiments, the cells overexpress the coding sequence of IGF1 protein at levels sufficient to increase production and/or secretion of IGF1 into the cell culture medium.

In some embodiments, the IGF1 coding sequence is selected from any metazoan species. In some embodiments, the IGF1 coding sequence is from any animal, such as vertebrate and invertebrate animal species. In some embodiments, the IGF1 coding sequence is from any vertebrate animal species such as mammals, reptiles, birds, amphibians, and the like. In some embodiments, the IGF1 coding sequence is from any mammalian species such as a human, murine, bovine, porcine, poultry, and the like. In some embodiments, the coding sequence of the IGF1 protein is derived from a species selected from any metazoan species, including without limitation, *Gallus gallus, Bos taurus, Sous scrofa, Meleagris gallopavo, Anas platyrynchos, Salmo salar, Thunnus thynnus, Ovis aries, Coturnix coturnix, Copra aegagrus hircus*, or *Homarus americanus*.

In some embodiments, increasing expression of IGF1 may be achieved using different approaches. In some embodiments, the expression is inducible. In some embodiments, the method comprises expressing polynucleotides comprising the coding sequence of IGF1. In some embodiments, the polynucleotides are ectopically expressed from constructs that are introduced into the cells, for example expressed from a plasmid, or other expression vector. In some embodiments, the constructs are integrated into the cell's genome, and the expression is driven in that manner (e.g., PhiC31 Integration Systems). In some embodiments, the expression of the IGF1 gene involves electroporating a DNA, delivering a DNA complexed with a transfection vehicle, using a viral vector (e.g. retrovirus, lentivirus, adenovirus, adeno-associated virus), and the like, or combinations thereof. In some embodiments, the expression is constitutive. In some embodiments, the expression is conditional (e.g. inducible).

In the methods described herein, a polynucleotide comprising a coding sequence of IGF1 may encode any homolog of IGF1, including IGF1 paralogs, such as IGF2, INS, and INS-IGF2, or any other IGF1 paralogs, or an IGF1 protein translated from any splice variants of an IGF1 gene, or may comprise any mutations in the IGF1 gene sequence including, but not limited to nucleotide deletions, truncations, fusions, or substitutions. Mutations may be synthetic or naturally occurring.

Figure 2B:
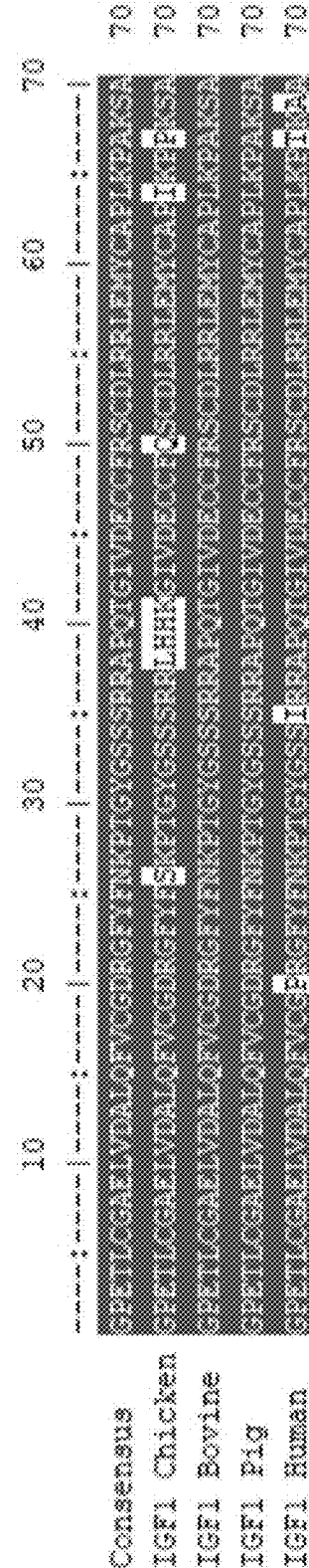
FIG. 2B shows a sequence alignment of amino acid sequences for IGF1 (truncated) from chicken, bovine (cow), pig, and human.
Figure 2C:
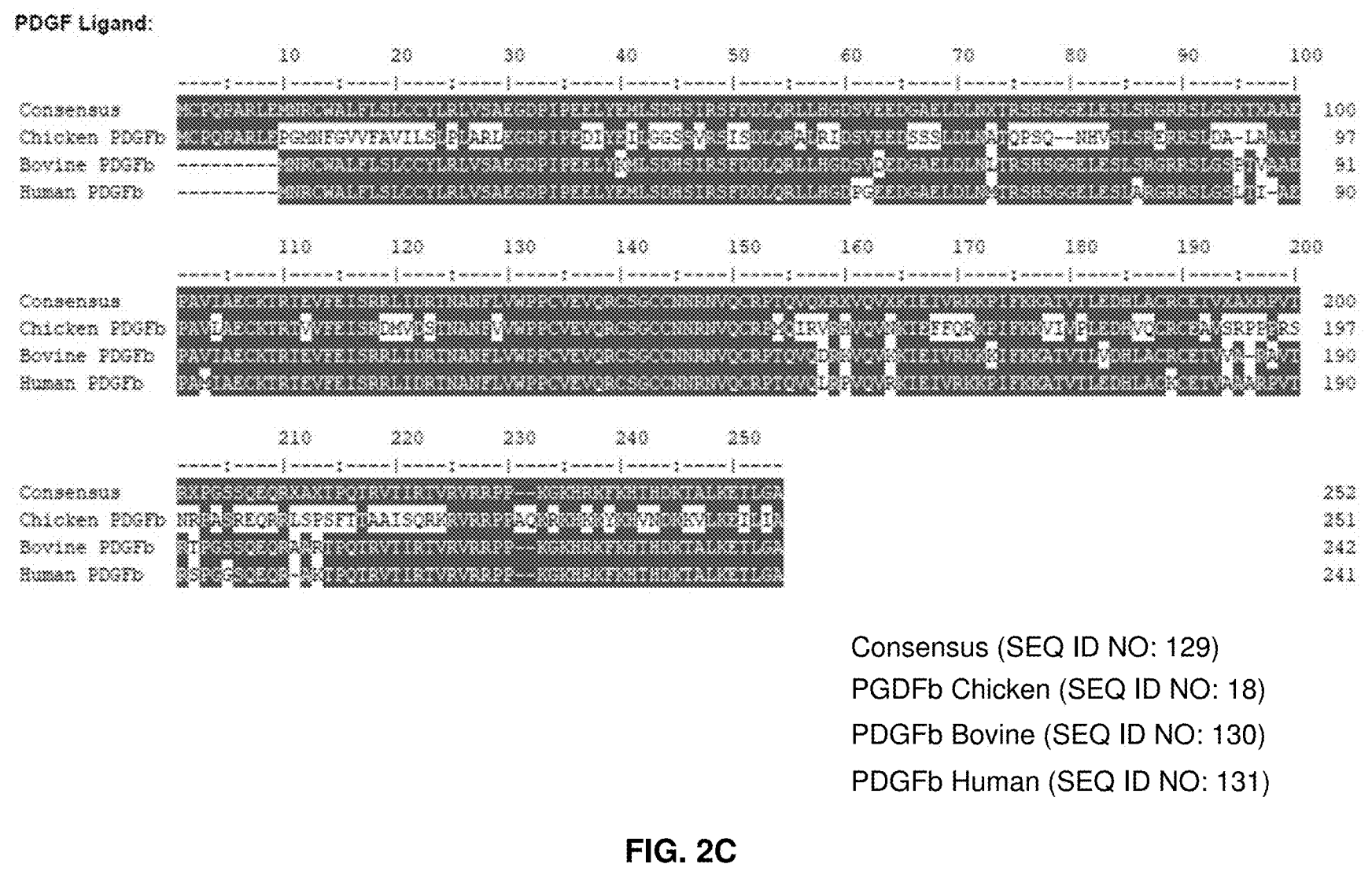

In some embodiments, IGF1 refers to the Igf1 gene or IGF1 protein, or fragment or variant thereof (e.g., a IGF1 protein having one or more (e.g., one, two, three, four, five, six, seven, eight, nine, ten, or more amino acid substitutions, deletions or insertions as compared to a wild type IGF1 protein)). FIG. 2B shows a sequence alignment for IGF1 from chicken, bovine, pig and human. In some embodiments, IGF1 refers to a sequence listed in FIG. 2B.

In some embodiments, an IGF1 protein comprises an amino acid sequence having at least 80% (e.g., at least 85%, 90%, 95%, 96%, 97%, 98%, or 99%) sequence identity to a sequence selected from SEQ ID NO: 16 or 17. In some embodiments, the FGF protein sequence comprises an amino acid sequence selected from SEQ ID NO: 16 or 17.

In some embodiments, introducing the polynucleotide comprising the coding sequence of the IGF-1 protein alone is not sufficient to confer reduced reliance on exogenous growth factors. In such embodiments, one or more additional growth factor ligands can be introduced into the cell line. For example, a polynucleotide comprising the coding sequence of a FGF2 protein or a PDGF protein can be introduced into the cell line to help confer reduced reliance on exogenous growth factors. In other embodiments, a polynucleotide (e.g., a second polynucleotide) comprising a coding sequence of a growth factor receptor can be introduced into the cell line to help confer reduced reliance on exogenous growth factors. In such embodiments, the growth factor receptor can be selected from a FGF2R, a IGF1R, and a PDFGR. For example, in order to confer reduced reliance on exogenous growth factors on the cell line, a polynucleotide comprising a coding sequence of a growth factor ligand (e.g., IGF1) or a fragment thereof, and a polynucleotide comprising a coding sequence of a growth factor receptor (e.g., IGF-1R) are introduced into the cell line.

6.2.3. Platelet Derived Growth Factor

In some embodiments, the methods provided herein include introducing into a cell a polynucleotide comprising a coding sequence of platelet derived growth factor (PDGF) or a fragment thereof. The PDGF family consists of PDGF-A, -B, -C and -D, which form either homo- or heterodimers (PDGF-AA, -AB, -BB, -CC, -DD). In some embodiments, the PDGF is PDGFA. In some embodiments, the PDGF is a PDGFB. In some embodiments, the PDGF is a PDGFC. In some embodiments, the PDGF is a PDGFD. As used herein, "PDGFb" refers to the platelet derived growth factor subunit b (Pdgfb) gene or PDGFb protein of the family comprised of both platelet-derived growth factors (PDGF) and vascular endothelial growth factors (VEGF). The encoded prepro-protein is proteolytically processed to generate platelet-derived growth factor subunit B, which can homodimerize, or alternatively, heterodimerize with the related platelet-derived growth factor subunit A. PDGFb can bind and activate PDGF receptor tyrosine kinases, which play a role in a wide range of developmental processes, angiogenesis, cell proliferation, and differentiation. PDGFb plays an essential role in the regulation of embryonic development, cell proliferation, cell migration, survival and chemotaxis. PDGFb is also a potent mitogen for cells of mesenchymal origin; required for normal proliferation and recruitment of pericytes and vascular smooth muscle cells in the central nervous system, skin, lung, heart and placenta; is required for normal blood vessel development, and for normal development of kidney glomeruli; plays an important role in wound healing.

In some embodiments, the cells are modified to overexpress the coding sequence of an PDGFb protein. In some embodiments, the cells are genetically modified and carry stable integrations of one or more copies of an PDGFb coding sequence. In some embodiments, the cells overexpress the coding sequence of PDGFb protein at levels sufficient to increase production and/or secretion of PDGFb into the cell culture medium.

In some embodiments, the PDGFb coding sequence is selected from any metazoan species. In some embodiments, the PDGFb coding sequence is from any animal, such as vertebrate and invertebrate animal species. In some embodiments, the PDGFb coding sequence is from any vertebrate animal species such as mammals, reptiles, birds, amphibians, and the like. In some embodiments, the PDGFb coding sequence is from any mammalian species such as a human, murine, bovine, porcine, poultry, and the like. In some embodiments, the coding sequence of the PDGFb protein is derived from a species selected from any metazoan species, including without limitation, *Gallus gallus, Bos taurus, Sous scrofa, Meleagris gallopavo, Anas platyrynchos, Salmo salar, Thunnus thynnus, Ovis aries, Coturnix coturnix, Copra aegagrus hircus*, or *Homarus americanus*.

In some embodiments, increasing expression of PDGFb may be achieved using different approaches. In some embodiments, the expression is inducible. In some embodiments, the method comprises expressing polynucleotides comprising the coding sequence of PDGFb. In some embodiments, the polynucleotides are ectopically expressed from constructs that are introduced into the cells, for example expressed from a plasmid, or other expression vector. In some embodiments, the constructs are integrated into the cell's genome, and the expression is driven in that manner (e.g., PhiC31 Integration Systems). In some embodiments, the expression of the PDGFb gene involves electroporating a DNA, delivering a DNA complexed with a transfection vehicle, using a viral vector (e.g. retrovirus, lentivirus, adenovirus, adeno-associated virus,), and the like, or combinations thereof. In some embodiments, the expression is constitutive. In some embodiments, the expression is conditional (e.g. inducible).

In the methods described herein, a polynucleotide comprising a coding sequence of PDGFb may encode any homolog of PDGFb, including PDGFb paralogs, such as PDGFa, or any other PDGFb paralogs, or an PDGFb protein translated from any splice variants of an PDGFb gene, or may comprise any mutations in the PDGFb gene sequence including, but not limited to nucleotide deletions, truncations, fusions, or substitutions. Mutations may be synthetic or naturally occurring.

In some embodiments, PDGFB refers to the Pdgfb gene or PDGFB protein, or fragment or variant thereof (e.g., a PDGFB protein having one or more (e.g., one, two, three, four, five, six, seven, eight, nine, ten, or more amino acid substitutions, deletions or insertions as compared to a wild type PDGFB polypeptide)). FIG. 2C shows a sequence alignment for PDGFb from chicken, bovine, and human. In some embodiments, PDGFb refers to a sequence listed in FIG. 2C.

In some embodiments, a PDGFb protein comprises an amino acid sequence having at least 80% (e.g., at least 85%, 90%, 95%, 96%, 97%, 98%, or 99%) sequence identity to a sequence selected from SEQ ID NOs: 18-21. In some embodiments, the PDGFb protein sequence comprises an amino acid sequence selected from SEQ ID NOs: 18-21.

In some embodiments, introducing the polynucleotide comprising the coding sequence of the PDGFb protein alone is not sufficient to confer reduced reliance on exogenous growth factors on the cell line. In such embodiments, one or more additional growth factor ligands can be introduced into the cell line. For example, a polynucleotide comprising the coding sequence of a FGF2 protein or an IGF-1 protein can be introduced into the cell line to help confer reduced reliance on exogenous growth factors. In other embodiments, a polynucleotide comprising a coding sequence of a growth factor receptor can be introduced into the cell line to help confer reduced reliance on exogenous growth factors. In such embodiments, the growth factor receptor can be selected from a FGF2R, an IGF1R, and a PDFGR. For example, in order to confer reduced reliance on exogenous growth factors on the cell line, a polynucleotide comprising a coding sequence of a growth factor ligand (e.g., PDGFb) or a fragment thereof, and a polynucleotide comprising a coding sequence of a growth factor receptor (e.g., PDGFR) are introduced into the cell line.

6.3. Growth Factor Receptors and Activated Downstream Targets

Provided herein are methods for introducing into a cell a polynucleotide comprising a coding sequence of a growth factor receptor and/or an activated downstream growth factor target. In some embodiments, introducing the polynucleotide comprising the coding sequence of the growth factor receptor (and/or an activated downstream growth factor target) into the cells results in the cells having reduced reliance on exogenous growth factors.

In some embodiments, the growth factor receptor is selected from fibroblast growth factor receptor (FGFR), insulin growth factor 1 receptor (IGF1R), and platelet-derived growth factor receptor (PDGFR). In some embodiments, the method include introducing an additional two or more growth factor receptors into the cell, wherein each additional growth factor receptor is selected from FGFR, IGF1R, and PDGFR.

In some embodiments, the methods provided herein include introducing into a cell a polynucleotide comprising a coding sequence of a growth factor ligand and a polynucleotide comprising a coding sequence of a growth factor receptor. In such cases, the cells are engineered to overexpress the coding sequence of the growth factor ligand, the growth factor receptor, or both. In some embodiments, the growth factor ligand and the growth factor receptor are components of the same signaling axis, for example, FGF2 and FGF1/2/3/4; IGF1 and IGF1R; or PDGFb and PDGFR. In such cases, the overexpressing the growth factor ligand and growth factor receptor results in a synergistic effect on the results described herein. Without wishing to be bound by theory, overexpressing both a growth factor ligand and a growth factor receptor enables a cell (or population of cells) to circumvent feedback mechanisms used by the cell to regulate signaling, thereby driving continued signaling within a cell. For example, the cell (or population of cells) can circumvent the feedback loop by expressing and secreting more growth factor ligands, expressing more receptors at the surface of the cell, or by expressing constitutively active receptors.

In some embodiments, the cells are engineered to overexpress the coding sequence of the growth factor receptor. In some embodiments, the cells are genetically engineered to have stable integration of the one or more copies of a coding sequence for a growth factor receptor. In some embodiments, the cells overexpress the coding sequence of the growth factor receptor at levels sufficient to reduce reliance on exogenous growth factors.

In some embodiments, introducing the polynucleotide comprising the coding sequence of the activated downstream growth factor target into the cells results in the cells having reduced reliance on exogenous growth factors. In some embodiments, the activated downstream growth factor target comprises a growth factor receptor comprising one or more amino acid insertions, deletions, or substitutions that result in the receptor being constitutively activated. In some embodiments, the activated downstream growth factor target includes a mutation in the intracellular portion or the growth factor receptor that triggers a signaling cascade (e.g., a phosphorylation cascade). In some embodiments, the activated downstream growth factor target comprises a gene and/or target associated with FGF signaling, IGF1 signaling, or PDGF signaling.

6.3.1. Fibroblast Growth Factor Receptor

In some embodiments, the methods provided herein include introducing into a cell a polynucleotide comprising a coding sequence of fibroblast growth factor receptor (FGFR). As used herein, the term "FGFR" refers to fibroblast growth factor receptor (Fgfr) gene or FGFR protein that is a family where amino acid sequence is highly conserved between members and throughout evolution. FGFR family members differ from one another in their ligand affinities and tissue distribution. The extracellular portion of the protein interacts with fibroblast growth factors, setting in motion a cascade of downstream signals, ultimately influencing mitogenesis and differentiation. The FGFR family include from FGFR1, FGFR2, FGFR3, and FGFR4.

In some embodiments, the cells are modified to overexpress the coding sequence of an FGFR. In some embodiments, the cells are genetically modified and carry stable integrations of one or more copies of an FGFR coding sequence. In some embodiments, the cells overexpress the coding sequence of FGFR protein at levels sufficient to increase expression of FGFR at the surface of the cell.

In some embodiments, the FGFR coding sequence is selected from any metazoan species. In some embodiments, the FGFR coding sequence is from any animal, such as vertebrate and invertebrate animal species. In some embodiments, the FGFR coding sequence is from any vertebrate animal species such as mammals, reptiles, birds, amphibians, and the like. In some embodiments, the FGFR coding sequence is from any mammalian species such as a human, murine, bovine, porcine, poultry, and the like. In some embodiments, the coding sequence of the FGFR is derived from a species selected from any metazoan species, including without limitation, *Gallus gallus, Bos taurus, Sous scrofa, Meleagris gallopavo, Anas platyrynchos, Salmo salar, Thunnus thynnus, Ovis aries, Coturnix coturnix, Copra aegagrus hircus,* or *Homarus americanus.*

In some embodiments, increasing expression of FGFR may be achieved using different approaches. In some embodiments, the expression is inducible. In some embodiments, the method comprises expressing polynucleotides comprising the coding sequence of FGFR. In some embodiments, the polynucleotides are ectopically expressed from constructs that are introduced into the cells, for example expressed from a plasmid, or other expression vector. In some embodiments, the constructs are integrated into the cell's genome, and the expression is driven in that manner (e.g., PhiC31 Integration Systems). In some embodiments, the expression of the FGFR gene involves electroporating a DNA, delivering a DNA complexed with a transfection vehicle, using a viral vector (e.g. retrovirus, lentivirus, adenovirus, adeno-associated virus), and the like, or combinations thereof. In some embodiments, the expression is constitutive. In some embodiments, the expression is conditional (e.g. inducible).

In some embodiments, a polynucleotide comprising a coding sequence of FGFR may encode any homolog of FGFR, including FGFR paralogs, such as FGFR1, FGFR2, FGFR3, and FGFR4, or any other FGFR paralogs, or an FGFR protein translated from any splice variants of an FGFR gene, or may comprise any mutations in the FGFR gene sequence including, but not limited to nucleotide deletions, truncations, fusions, or substitutions. Mutations may be synthetic or naturally occurring.

In some embodiments, FGFR refers to the FGFR protein, or fragment or variant thereof (e.g., a FGFR protein having one or more (e.g., one, two, three, four, five, six, seven, eight, nine, ten, or more amino acid substitutions, deletions or insertions as compared to a wild type FGFR protein)).

In some embodiments, a FGFR protein comprises an amino acid sequence having at least 80% (e.g., at least 85%, 90%, 95%, 96%, 97%, 98%, or 99%) sequence identity to a sequence selected from SEQ ID NOs: 32-49. In some embodiments, the FGFR protein sequence comprises an amino acid sequence selected from SEQ ID NOs: 32-49.

In some embodiments, introducing the polynucleotide comprising the coding sequence of the FGFR protein alone is not sufficient to confer reduced reliance on exogenous growth factors on the cell line. In such embodiments, one or more additional growth factor receptors can be introduced into the cell line. For example, a polynucleotide comprising the coding sequence of a PDGFR protein or an IGF-1R protein can be introduced into the cell line to help confer reduced reliance on exogenous growth factors. In other embodiments, a polynucleotide comprising a coding sequence of a growth factor ligand can be introduced into the cell line to help confer reduced reliance on exogenous growth factors. In such embodiments, the growth factor ligand can be selected from FGF2, IGF-1, and PDFG. For example, in order to confer reduced reliance on exogenous growth factors on the cell line, a polynucleotide sequence comprising a coding sequence of a growth factor receptor (e.g., FGFR) or a fragment thereof, and a polynucleotide comprising a coding sequence of a growth factor ligand (e.g., FGF2) are introduced into the cell line.

6.3.2. Insulin Growth Factor Receptor

In some embodiments, the methods provide herein include introducing into a cell a polynucleotide comprising a coding sequence of insulin-like growth factor receptor (IGFR). In some embodiments, the IGFR is an insulin like growth factor-1 receptor (IGF1R). As used herein, "IGFR1" refers to the insulin-like growth factor receptor (Igfr1) gene or IGF1R belonging to the class of tyrosine kinase receptors. IGF1R mediates the effects of IGF1, which is a polypeptide protein hormone similar in molecular structure to insulin.

In some embodiments, the cells are modified to overexpress the coding sequence of an IGF1R protein. In some embodiments, the cells are genetically modified and carry stable integrations of one or more copies of an IGF1R coding sequence. In some embodiments, the cells overexpress the coding sequence of IGF1R protein at levels sufficient to increase expression of IGF1R at the surface of the cell.

In some embodiments, the IGF1R coding sequence is selected from any metazoan species. In some embodiments, the IGF1R coding sequence is from any animal, such as vertebrate and invertebrate animal species. In some embodiments, the IGF1R coding sequence is from any vertebrate animal species such as mammals, reptiles, birds, amphibians, and the like. In some embodiments, the IGF1R coding sequence is from any mammalian species such as a human, murine, bovine, porcine, poultry, and the like. In some embodiments, the coding sequence of the IGF1R protein is derived from a species selected from any metazoan species, including without limitation, *Gallus gallus, Bos taurus, Sous scrofa, Meleagris gallopavo, Anas platyrynchos, Salmo salar, Thunnus thynnus, Ovis aries, Coturnix coturnix, Copra aegagrus hircus,* or *Homarus americanus.*

In some embodiments, increasing expression of IGF1R may be achieved using different approaches. In some embodiments, the expression is inducible. In some embodiments, the method comprises expressing polynucleotides comprising the coding sequence of IGF1R. In some embodiments, the polynucleotides are ectopically expressed from constructs that are introduced into the cells, for example expressed from a plasmid, or other expression vector. In some embodiments, the constructs are integrated into the cell's genome, and the expression is driven in that manner (e.g., PhiC31 Integration Systems). In some embodiments, the expression of the IGF1R gene involves electroporating a DNA, delivering a DNA complexed with a transfection vehicle, using a viral vector (e.g. retrovirus, lentivirus, adenovirus, adeno-associated virus), and the like, or combinations thereof. In some embodiments, the expression is constitutive. In some embodiments, the expression is conditional (e.g. inducible).

In the methods described herein, a polynucleotide comprising a coding sequence of IGFR may encode any homolog of IGF1R, including IGF1R paralogs, such as IGF1R, INSR, INSRR, ROS1, ERBB4, EPHA, or any other IGF1R paralogs, or an IGF1R protein translated from any splice variants of an IGF1 gene, or may comprise any mutations in the IGF1R gene sequence including, but not limited to nucleotide deletions, truncations, fusions, or substitutions. Mutations may be synthetic or naturally occurring.

In some embodiments, IGF1R refers to the IGF1R protein, or fragment or variant thereof (e.g., a IGF1R protein having one or more (e.g., one, two, three, four, five, six, seven, eight, nine, ten, or more amino acid substitutions, deletions or insertions as compared to a wild type IGF1R protein)).

In some embodiments, a IGF1R protein comprises an amino acid sequence having at least 80% (e.g., at least 85%, 90%, 95%, 96%, 97%, 98%, or 99%) sequence identity to a sequence selected from SEQ ID NOs: 50-51. In some embodiments, the IGF1R protein sequence comprises an amino acid sequence selected from SEQ ID NOs: 50-51.

In some embodiments, introducing the polynucleotide comprising the coding sequence of the IGF1R protein alone is not sufficient to confer reduced reliance on exogenous growth factors on the cell line. In such embodiments, one or more additional growth factor receptors can be introduced into the cell line. For example, a polynucleotide comprising the coding sequence of a FGFR protein or an PDGFR protein can be introduced into the cell line to help confer reduced reliance on exogenous growth factors. In other embodiments, a polynucleotide comprising a coding sequence of a growth factor ligand can be introduced into the cell line to help confer reduced reliance on exogenous growth factors. In such embodiments, the growth factor ligand can be selected from FGF2, IGF1, and PDFG. For example, in order to confer reduced reliance on exogenous growth factors on the cell line, a polynucleotide sequence comprising a coding sequence of a growth factor receptor (e.g., IGF1R) or a fragment thereof; and a polynucleotide comprising a coding sequence of a growth factor ligand (e.g., IGF1) are introduced into the cell line.

6.3.3. Platelet Derived Growth Factor Receptor

In some embodiments, the methods provide herein include introducing into a cell a polynucleotide comprising a coding sequence of platelet derived growth factor receptor (PDGFR). As used herein, "PDGFR" refers to the platelet derived growth factor receptor (Pdgfr) gene or PDGFR protein of the protein family comprised of both platelet-derived growth factors (PDGF) and vascular endothelial growth factors (VEGF). PDGFRs are catalytic receptors that have intracellular tyrosine kinase activity. PDGFR have roles in the regulation of many biological processes including embryonic development, angiogenesis, cell proliferation and differentiation.

In some embodiments, the cells are modified to overexpress the coding sequence of an PDGFR protein. In some embodiments, the cells are genetically modified and carry stable integrations of one or more copies of an PDGFR coding sequence. In some embodiments, the cells overexpress the coding sequence of PDGFR protein at levels sufficient to increase expression of FGFR at the surface of the cell.

In some embodiments, the PDGFR coding sequence is selected from any metazoan species. In some embodiments, the PDGFR coding sequence is from any animal, such as vertebrate and invertebrate animal species. In some embodiments, the PDGFR coding sequence is from any vertebrate animal species such as mammals, reptiles, birds, amphibians, and the like. In some embodiments, the PDGFR coding sequence is from any mammalian species such as a human, murine, bovine, porcine, poultry, and the like. In some embodiments, the coding sequence of the PDGFR protein is derived from a species selected from any metazoan species, including without limitation, *Gallus gallus, Bos taurus, Sous scrofa, Meleagris gallopavo, Anas platyrynchos, Salmo salar, Thunnus thynnus, Ovis aries, Coturnix coturnix, Copra aegagrus hircus,* or *Homarus americanus.*

In some embodiments, increasing expression of PDGFR may be achieved using different approaches. In some embodiments, the expression is inducible. In some embodiments, the method comprises expressing polynucleotides comprising the coding sequence of PDGFR. In some embodiments, the polynucleotides are ectopically expressed from constructs that are introduced into the cells, for example expressed from a plasmid, or other expression vector. In some embodiments, the constructs are integrated into the cell's genome, and the expression is driven in that manner (e.g., PhiC31 Integration Systems). In some embodiments, the expression of the PDGFR gene involves electroporating a DNA, delivering a DNA complexed with a transfection vehicle, using a viral vector (e.g. retrovirus, lentivirus, adenovirus, adeno-associated virus), and the like, or combinations thereof. In some embodiments, the expression is constitutive. In some embodiments, the expression is conditional (e.g. inducible).

In the methods described herein, a polynucleotide comprising a coding sequence of PDGFR may encode any homolog of PDGFR, including PDGFR paralogs, such as PDGFRA and PDGFRB, or any other PDGFR paralogs, or an PDGFR protein translated from any splice variants of an PDGFR gene, or may comprise any mutations in the PDGFR gene sequence including, but not limited to nucleotide deletions, truncations, fusions, or substitutions. Mutations may be synthetic or naturally occurring.

In some embodiments, PDGFR refers to the PDGFR protein, or fragment or variant thereof (e.g., a PDGFR protein having one or more (e.g., one, two, three, four, five, six, seven, eight, nine, ten, or more amino acid substitutions, deletions or insertions as compared to a wild type PDGFR protein)).

In some embodiments, a PDGFR protein comprises an amino acid sequence having at least 80% (e.g., at least 85%, 90%, 95%, 96%, 97%, 98%, or 99%) sequence identity to a sequence selected from SEQ ID NOs: 52-58. In some embodiments, the PDGFR protein sequence comprises an amino acid sequence selected from SEQ ID NOs: 52-58.

In some embodiments, introducing the polynucleotide comprising the coding sequence of the PDGFRB protein alone is not sufficient to confer reduced reliance on exogenous growth factors on the cell line. In such embodiments, one or more additional growth factor receptors can be introduced into the cell line. For example, a polynucleotide comprising the coding sequence of a FGFR protein or an IGF1R protein can be introduced into the cell line to help confer reduced reliance on exogenous growth factors. In other embodiments, a polynucleotide comprising a coding sequence of a growth factor ligand can be introduced into the cell line to help confer reduced reliance on exogenous growth factors. In such embodiments, the growth factor ligand can be selected from FGF2, IGF1, and PDFG. For example, in order to confer reduced reliance on exogenous growth factors on the cell line, a polynucleotide sequence comprising a coding sequence of a growth factor receptor (e.g., PDGFRB) or a fragment thereof, and a polynucleotide comprising a coding sequence of a growth factor ligand (e.g., PDGF) are introduced into the cell line.

6.4. Accessory Proteins

In some embodiments, the methods provided herein include introducing into a cell a polynucleotide comprising a coding sequence of an accessory protein.

6.4.1. Fibroblast Growth Factor Binding Protein

In some embodiments, accessory protein refers to a fibroblast growth factor binding protein (FGFBP). As used herein, "FGFBP" refers to the fibroblast growth factor binding protein (Fgfbp) gene or FGFBP protein, which belongs to a family of fibroblast growth factor carrier proteins. Family members include, without limitation, FGFBP1, FGFBP2, and FGFBP3. FGFBPs play a role in cell proliferation, differentiation and migration by binding to fibroblast growth factors and potentiating their biological effects on target cells.

In some embodiments, the FGFBP is FGBP1 or a fragment thereof. In some embodiments, FGFBP1 enhances FGF2 signaling.

In some embodiments, FGFBP1 refers to the Fgfbp1 gene or FGFBP1 protein, or fragment or variant thereof (e.g., a FGFBP1 protein having one or more (e.g., one, two, three, four, five, six, seven, eight, nine, ten, or more amino acid substitutions, deletions or insertions as compared to a wild type FGFBP1 polypeptide)).

In some embodiments, a FGFBP1 protein comprises an amino acid sequence having at least 80% (e.g., at least 85%, 90%, 95%, 96%, 97%, 98%, or 99%) sequence identity to a sequence selected from SEQ ID NOs: 59. In some embodiments, the FGFBP1 protein sequence comprises an amino acid sequence selected from SEQ ID NOs: 59.

6.4.2. RASV12

In some embodiments, accessory protein refers to a H-RasV12 or RASV12. As used herein, "RASV12" refers to the H-RasV12 protein or RASV12 protein. RASV12 is involved in the activation of Ras protein signal transduction and binds GDP/GTP and possess intrinsic GTPase activity.

In some embodiments, RASV12 refers to the RASV12 protein, or fragment or variant thereof (e.g., a RASV12 protein having one or more (e.g., one, two, three, four, five, six, seven, eight, nine, ten, or more amino acid substitutions, deletions or insertions as compared to a wild type RASH or RASV12 polypeptide)).

In some embodiments, a RASV12 protein comprises an amino acid sequence having at least 80% (e.g., at least 85%, 90%, 95%, 96%, 97%, 98%, or 99%) sequence identity to a sequence selected from SEQ ID NOs: 60. In some embodiments, the RASV12 protein sequence comprises an amino acid sequence selected from SEQ ID NOs: 60.

6.5. Signal Peptides

In some embodiments, the methods provided herein include introducing into a cell a polynucleotide comprising a coding sequence of a growth factor ligand, where the growth factor ligand is fused to a signal peptide. In some embodiments, the polynucleotide includes a sequence encoding a signal peptide located 5' to the coding sequence of the growth factor ligand, and wherein the signal sequence and the growth factor ligand are a fusion protein. In some embodiments, the polynucleotide includes a sequence encoding a signal peptide located 3' to the coding sequence of the growth factor ligand, and wherein the signal sequence and the growth factor ligand are a fusion protein. Non-limiting examples of signal peptides having at least 80% (e.g., at least 85%, 90%, 95%, 96%, 97%, 98%, or 99%) sequence identity to a sequence selected from SEQ ID NOs: 22-31.

6.6. Method for Increasing Concentration of a Growth Factor in Culture Medium Provided herein are methods of increasing the concentration of a growth factor ligand in culture medium of cells in culture where the method includes introducing one or more of a coding sequence of any of the growth factor ligands described herein, a coding sequence of any of the growth factor receptors described herein, a coding sequence of any of the activated downstream growth factors described herein, a coding sequence of any of the accessory proteins described herein, or a combination thereof, into the cell line; and culturing the cell line in a cultivation infrastructure.

In some embodiments, introducing a polynucleotide comprising a coding sequence of FGF2 into a cell line and culturing the cells in a cultivating infrastructure results in an increase of FGF2 in the medium of the cells in culture.

In some embodiments, the concentration of FGF2 in the culture medium is increased by at least 0.00001 ng/mL, (e.g., at least 0.000025 ng/mL, at least 0.000075 ng/mL, by at least 0.0005 ng/mL, at least 0.001 ng/mL, at least 0.005 ng/mL, at least 0.01 ng/mL, at least 0.05 ng/mL, at least 0.1 ng/mL, at least 0.5 ng/mL, at least 1.0 ng/mL, at least 2.5 ng/mL, at least 5.0 ng/mL, at least 7.5 ng/mL, at least 10 ng/mL, at least 15 ng/mL, at least 20 ng/mL, at least 25 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 150 ng/mL, at least 200 ng/mL, at least 200 ng/mL, at least 250 ng/mL, at least 300 ng/mL, at least 350 ng/mL, at least 400 ng/mL, at least 450 ng/mL, at least 500 ng/mL, at least 550 ng/mL, at least 600 ng/mL, at least 650 ng/mL, at least 700 ng/mL, at least 750 ng/mL, at least 800 ng/mL, at least 850 ng/mL, at least 900 ng/mL, at least 950 ng/mL, or at least 1000 ng/mL) as compared to a cell line not engineered to include a polynucleotide comprising a coding sequence of FGF2.

In some embodiments, the concentration of FGF2 in the culture medium is increased by at least 0.01% (e.g., at least 0.05%, at least 0.1%, at least 0.5%, at least 1.0%, at least 1.5%, at least 2.0%, at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or at least 10,000%) as compared to a cell line not engineered to include a polynucleotide encoding FGF2.

In some embodiments, introducing a polynucleotide comprising a coding sequence of IGF1 into a cell line and culturing the cells in a cultivating infrastructure results in an increase of IGF1 in the medium of the cells in culture.

In some embodiments, the concentration of IGF1 in the culture medium is increased by at least 0.00001 ng/mL, (e.g., at least 0.000025 ng/mL, at least 0.000075 ng/mL, at least 0.0005 ng/mL, at least 0.001 ng/mL, at least 0.005 ng/mL, at least 0.01 ng/mL, at least 0.05 ng/mL, at least 0.1 ng/mL, at least 0.5 ng/mL, at least 1.0 ng/mL, at least 2.5 ng/mL, at least 5.0 ng/mL, at least 7.5 ng/mL, at least 10 ng/mL, at least 15 ng/mL, at least 20 ng/mL, at least 25 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 150 ng/mL, at least 200 ng/mL, at least 200 ng/mL, at least 250 ng/mL, at least 300 ng/mL, at least 350 ng/mL, at least 400 ng/mL, at least 450 ng/mL, at least 500 ng/mL, at least 550 ng/mL, at least 600 ng/mL, at least 650 ng/mL, at least 700 ng/mL, at least 750 ng/mL, at least 800 ng/mL, at least 850 ng/mL, at least 900 ng/mL, at least 950 ng/mL, or at least 1000 ng/mL) as compared to a cell line not engineered to include a polynucleotide encoding IGF-1.

In some embodiments, the concentration of IGF1 in the culture medium is increased by at least 0.01% (e.g., at least 0.05%, at least 0.1%, at least 0.5%, at least 1.0%, at least 1.5%, at least 2.0%, least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or by at least 10,000%) as compared to a cell line not engineered to include a polynucleotide encoding IGF1.

In some embodiments, introducing a polynucleotide comprising a coding sequence of PDGFb into a cell line and culturing the cells in a cultivating infrastructure results in an increase of PDGFb in the medium of the cells in culture.

In some embodiments, the concentration of PDGFb in the culture medium is increased by at least 0.00001 ng/mL, (e.g., at least 0.000025 ng/mL, at least 0.000075 ng/mL, at least 0.0005 ng/mL, at least 0.001 ng/mL, at least 0.005 ng/mL, at least 0.01 ng/mL, at least 0.05 ng/mL, at least 0.1 ng/mL, at least 0.5 ng/mL, at least 1.0 ng/mL, at least 2.5 ng/mL, at least 5.0 ng/mL, at least 7.5 ng/mL, at least 10 ng/mL, at least 15 ng/mL, at least 20 ng/mL, at least 25 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 150 ng/mL, at least 200 ng/mL, at least 200 ng/mL, at least 250 ng/mL, at least 300 ng/mL, at least 350 ng/mL, at least 400 ng/mL, at least 450 ng/mL, at least 500 ng/mL, at least 550 ng/mL, at least 600 ng/mL, at least 650 ng/mL, at least 700 ng/mL, at least 750 ng/mL, at least 800 ng/mL, at least 850 ng/mL, at least 900 ng/mL, at least 950 ng/mL, or at least 1000 ng/mL) as compared to a cell line not engineered to include a polynucleotide encoding PDGFb.

In some embodiments, the concentration of PDGFb in the culture medium is increased by at least 0.01% (e.g., at least 0.05%, at least 0.1%, at least 0.5%, at least 1.0%, at least 1.5%, at least 2.0%, least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 9 50%, at least 1000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or at least 10,000%) as compared to a cell line not engineered to include a polynucleotide encoding PDGFb.

The methods of the present disclosure advantageously enable selection of transfected cells using only the absence of growth factors, thereby obviating the need for antibiotic and cre-lox selection protocols, which are less desirable when creating a food product since they are not recognized as generally acceptable for consumption.

6.7. Method of Increasing Cell Density

Provided herein are methods of increasing the cell density of a culture where the method includes introducing one or more of a coding sequence of any of the growth factor ligands described herein, a coding sequence of any of the growth factor receptors described herein, a coding sequence of any of the activated downstream growth factor targets described herein, a coding sequence of any of the accessory proteins described herein, or a combination thereof, into the cell line; and culturing the cell line in a cultivation infrastructure.

In some embodiments, an increase in the cell density of a culture (e.g., suspension culture) using the methods described herein is about 1.025 fold, 1.05 fold, 1.10-fold, 1.15-fold, 1.20-fold, 1.25-fold, 1.30 fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or about 200-fold, compared to the density of a culture comprising cells that do not include a coding sequence of any of the growth factor ligands described herein, a coding sequence of any of the growth factor receptors described herein, a coding sequence of any of the accessory proteins described herein, or a combination thereof.

In some embodiments, an increase in the density of cells in a culture (e.g., suspension culture) using the methods described herein is at least 10%, at least 15%, at least 20%, at least 25%, at least 30%, at least 35%), at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 8 50%, at least 900%, at least 9 50%, at least 1000%, compared to the density of a culture comprising cells that do not include a coding sequence of any of the growth factor ligands described herein, a coding sequence of any of the growth factor receptors described herein, a coding sequence of any of the accessory proteins described herein, or a combination thereof.

In some embodiments, methods described herein increase the density of cells in a culture (e.g., suspension culture) by increasing the rate of proliferation of cells in the culture. In some embodiments, the increase in the rate of cell proliferation is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, or at least 1000%), including values and ranges therebetween, compared to the density of a culture comprising cells that do not include a coding sequence of any of the growth factor ligands described herein, a coding sequence of any of the growth factor receptors described herein, a coding sequence of any of the accessory proteins described herein, or a combination thereof. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to the density of a culture comprising cells that do not include a coding sequence of any of the growth factor ligands described herein, a coding sequence of any of the growth factor receptors described herein, a coding sequence of any of the accessory proteins described herein, or a combination thereof.

In some embodiments, methods described herein increase the cell density of a culture (e.g., suspension culture) by decreasing cell death within the cellular biomass. In some embodiments, the decrease in cell death is at least 2.5%, at least 5%, at least 10%>, at least 15%, at least 20%, at least 25%, at least 30%), at least 35%, at least 40%, at least 45%, at least 50%, at least 55%, at least 60%, at least 65%, at least 70%, at least 75%, at least 80%, at least 85%, at least 90%, at least 95%, at least 100%), including values and ranges therebetween, compared to the density of a culture comprising cells that do not include a coding sequence of any of the growth factor ligands described herein, a coding sequence of any of the growth factor receptors described herein, a coding sequence of any of the accessory proteins described herein, or a combination thereof. In some embodiments, a decrease in the rate of cell death within the cellular biomass is about 2.5-10%, about 2.5-75%, about 2.5-50%, about 5.0-100%, about 5.0-75%, about 5.0-50%, about 10-100%, about 10-75%, or about 10-50%, including values and ranges therebetween, compared to the density of a culture comprising cells that do not include a coding sequence of any of the growth factor ligands described herein, a coding sequence of any of the growth factor receptors described herein, a coding sequence of any of the accessory proteins described herein, or a combination thereof.

In some embodiments, using the methods described herein, the density of cells in a culture may reach about 1E4 cells/mL, about 1E5 cells/mL, about 1E6 cells/mL, about 1E7 cells/mL, about 1E8 cells/mL, about 1E9 cells/mL, about 1E10 cells/mL, about 1E11 cells/mL, about 1E12 cells/mL, or about 1E13 cells/mL (cells in suspension culture or cells in the cellular biomass/mL of cultivation infrastructure), including values and ranges therebetween.

In some embodiments, using the methods described herein, the density of cells in a culture (e.g., suspension culture) may reach about 1 g/L, 5 g/L, 10 g/L, 25 g/L, 50 g/L, 75 g/L, 100 g/L, 150 g/L, 200 g/L, 250 g/L, 300 g/L, 350 g/L, 400 g/L, 450 g/L, 500 g/L, 550 g/L, 600 g/L, 650 g/L, 700 g/L, 750 g/L, 800 g/L, 850 g/L, 900 g/L, or 1000 g/L (g of cellular biomass/L of cultivation infrastructure), including values and ranges therebetween. In some embodiments, the density of cells in a culture (e.g., suspension culture) may range from about 1 g/L to about 5 g/L, about 1 g/L to about 750 g/L, about 1 g/L to about 500 g/L, about 1 g/L to about 250 g/L, about 1 g/L to about 100 g/L, about 1 g/L to about 50 g/L, about 5 g/L to about 1000 g/L, about 5 g/L to about 750 g/L, about 5 g/L to about 500 g/L, about 5 g/L to about 250 g/L, about 5 g/L to about 100 g/L, about 5 g/L to about 50 g/L, about 25 g/L to about 1000 g/L, about 25 g/L to about 750 g/L, about 25 g/L to about 500 g/L, about 25 g/L to about 300 g/L, about 25 g/L to about 250 g/L, about 25 g/L to about 100 g/L, about 50 g/L to about 1000 g/L, about 50 g/L to about 750 g/L, about 50 g/L to about 500 g/L, about 50 g/L to about 300 g/L, about 50 g/L to about 250 g/L, about 100 g/L to about 1000 g/L, about 100 g/L to about 750 g/L, about 100 g/L to about 500 g/L, about 200 g/L to about 1000 g/L, about 200 g/L to about 750 g/L, about 200 g/L to about 500 g/L, about 300 g/L to about 1000 g/L, about 300 g/L to about 800 g/L, about 400 g/L to about 1000 g/L, or about 500 g/L to about 1000 g/L including values and ranges therebetween.

6.8. Method for Improving Anchorage Independent Growth

Provided herein are methods of improving anchorage independent growth in a cell line where the method includes introducing a coding sequence of any of the growth factor ligands described herein, a coding sequence of any of the growth factor receptors described herein, a coding sequence of any of the accessory protein described herein, or a combination thereof, into the cell line; and culturing the cell line in a cultivation infrastructure.

In some embodiments, a cell line's ability to grow as a non-adherent, anchorage independent cell line can be modulated by culturing the cell line with FGF2 and/or IGF1 growth factors. In some embodiments, introducing a polynucleotide comprising a coding sequence of FGF2 and/or IGF1 into a cell line results in a cell line with at least a portion of the cell line having anchorage independent growth. In some embodiments, introducing a polynucleotide comprising a coding sequence of an FGFR and/or an IGFR results in a cell line with at least a portion of the cell line having anchorage independent growth.

In some embodiments, introducing a polynucleotide comprising a coding sequence of FGF2 or a fragment thereof and/or a coding sequence of IGF1 or a fragment thereof results in an increase in the rate of cell proliferation and decrease in cell death, which promotes the cell line (e.g., an adherent cell line) to transition to a non-adherent form (e.g., a non-adherent cell line). In some embodiments, an increase in the rate of cell proliferation and decrease in cell death promotes transition to anchorage-independent growth from anchorage-dependent growth.

In some embodiments, increase in the rate of cell proliferation is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, including values and ranges therebetween, compared to a cell line not including a polynucleotide comprising a coding sequence of FGF2 and/or a coding sequence of IGF1. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to a cell line not including a polynucleotide comprising a coding sequence of FGF2 and/or a coding sequence of IGF1.

In some embodiments, the methods provided herein that include introducing a polynucleotide comprising a coding sequence of FGF2 or a fragment thereof and/or a coding sequence of IGF1 or a fragment thereof into a cell line promote anchorage-independent growth of the cell line by decreasing cell-to-cell contact inhibition. In some embodiments, the decrease in contact inhibition provided by the present methods is about 10%, 20%, 30%, 40%, 50%, 60%, 70%, 80%, 90%, or 100%, including values and ranges therebetween, compared to a cell line not including a polynucleotide comprising a coding sequence of FGF2 or a coding sequence of IGF1.

In some embodiments, the methods provided herein that include introducing a polynucleotide comprising a coding sequence of FGF2 or a fragment thereof and/or a coding sequence of IGF1 or a fragment thereof into a cell line promote anchorage-independent growth of the cell line by decreasing cell death. In some embodiments, the decrease in cell death provided by the present methods is about 2.5%, 5%, 10%, 20%, 30%, 40%, 50%, 60%, 70%, 80%, 90%, or 100%, including values and ranges therebetween, compared to a cell line not including a polynucleotide comprising a coding sequence of FGF2 or a coding sequence of IGF1.

In some embodiments, introducing a polynucleotide comprising a coding sequence of FGFR or a fragment thereof or a coding sequence of an IGF1R or a fragment thereof results in an increase in the rate of cell proliferation and decrease in cell death, which promotes cell line (e.g., an adherent cell line) to transition to a non-adherent form (e.g., a non-adherent cell line). In some embodiments, an increase in the rate of cell proliferation and decrease in cell death promotes transition to anchorage-independent growth from anchorage-dependent growth.

In some embodiments, increase in the rate of cell proliferation is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, including values and ranges therebetween, compared to a cell line not including a polynucleotide comprising a coding sequence of IGF1. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to a cell line not including a polynucleotide comprising a coding sequence of FGFR or a coding sequence of IGF1R.

In some embodiments, the methods provided herein that include introducing a polynucleotide comprising a coding sequence of FGFR or a fragment thereof or a coding sequence of an IGFR or a fragment thereof into a cell line promote anchorage-independent growth of the cell line by decreasing cell-to-cell contact inhibition. In some embodiments, the decrease in contact inhibition provided by the present methods is about 10%, 20%, 30%, 40%, 50%, 60%, 70%, 80%, 90%, or 100%, including values and ranges therebetween, compared to a cell line not including a polynucleotide comprising a coding sequence of FGFR or a coding sequence of IGF1R.

In some embodiments, the methods provided herein that include introducing a polynucleotide comprising a coding sequence of FGFR or a fragment thereof or a coding sequence of an IGFR or a fragment thereof into a cell line promote anchorage-independent growth of the cell line by decreasing cell death. In some embodiments, the decrease in cell death provided by the present methods is about 2.5%, 5%, 10%, 20%, 30%, 40%, 50%, 60%, 70%, 80%, 90%, or 100%, including values and ranges therebetween, compared to a cell line not including a polynucleotide comprising a coding sequence of FGFR or a coding sequence IGF1R.

6.9. Methods for Producing Cell-Based Meat Suitable for Consumption

Provided herein are in vitro methods for producing cell-based meat suitable for consumption, comprising: (a) introducing into a cell line one or more of a polynucleotide comprising a coding sequence of a growth factor ligand or a fragment thereof, a polynucleotide comprising a coding sequence of a growth factor receptor, a polynucleotide comprising a coding sequence of an activated downstream growth factor target; (b) inducing myogenic specific differentiation, wherein the differentiated cells form myotubes and multinucleated myotubes; (c) culturing the myocytes and myotubes to generate skeletal muscle fibers, thereby producing a cell-based meat suitable for consumption. In some embodiments, the in vitro method for producing cell-based meat suitable for consumption includes a step of adapting the cells to be grown in suspension. In some embodiments, the in vitro method for producing cell-based meat suitable for consumption includes a step of culturing the cells in a cultivation infrastructure.

In some embodiments, provided herein is cell-based meat suitable for consumption produced by the in vitro methods described herein.

In some embodiments, the in vitro method for producing cell-based meat suitable for consumption includes maintaining the engineered cell line in a culture medium comprising a molecule capable of controlling an inducible promoter, thereby enabling expression of the growth factor ligand (e.g., any of the growth factor ligands described herein), growth factor receptor (e.g., any of the growth factor receptors described herein), or a combination thereof, at specified times during the in vitro method. In some embodiments of the in vitro method, the engineered cell line is maintained in culture medium comprising a molecule capable of controlling an inducible promoter prior, contemporaneously with, or after the step of inducing myogenic specific differentiation. In some embodiments of the in vitro method, the engineered cell line is maintained in culture medium comprising a molecule capable of controlling an inducible promoter prior to the step of inducing myogenic specific differentiation. In such cases, the expression of the growth factor ligand, growth factor receptor, or a combination thereof, can be decreased or eliminated prior to the inducing of myogenic specific differentiation.

In some embodiments, the in vitro method for producing cell-based meat suitable for consumption includes maintaining the engineered cell line in a culture medium comprising a molecule capable of controlling the inducible tag, thereby inducing activity of the growth factor ligand/fusion protein (e.g., any of the growth factor ligands described herein), growth factor receptor/fusion protein (e.g., any of the growth factor receptors described herein), or a combination thereof, at specified times during the in vitro method. In some embodiments of the in vitro method, the engineered cell line is maintained in culture medium comprising a molecule capable of controlling an inducible tag prior, contemporaneously with, or after the step of inducing myogenic specific differentiation. In some embodiments of the in vitro method, the engineered cell line is maintained in culture medium comprising a molecule capable of controlling an inducible tag prior to the step of inducing myogenic specific differentiation. In such cases, the activity of the growth factor ligand, growth factor receptor, or a combination thereof, can be reduced or inhibited prior to the inducing of myogenic specific differentiation.

In some embodiments, the in vitro method for producing cell-based meat suitable for consumption includes maintaining the engineered cell line in a culture medium comprising a molecule controlling the degradation tag, thereby targeting the growth factor ligand/fusion protein (e.g., any of the growth factor ligands described herein), growth factor receptor/fusion protein (e.g., any of the growth factor receptors described herein), or a combination thereof, for degradation at specific times during the in vitro method. In some embodiments of the in vitro method, the engineered cell line is maintained in culture medium comprising a molecule capable of controlling a degradation tag prior, contemporaneously with, or after the step of inducing myogenic specific differentiation. In some embodiments of the in vitro method, the engineered cell line is maintained in culture medium comprising a molecule capable of controlling a degradation tag contemporaneously with or after the step of inducing myogenic specific differentiation. In such cases, the activity of the growth factor ligand, growth factor receptor, or combination thereof, can be reduced or inhibited in the same step as or shortly after beginning the inducing of myogenic specific differentiation.

In some embodiments, the cell line is from a livestock, poultry, game or aquatic animal species. In some embodiments, the cell line is from a chicken, duck, or turkey. In some embodiments, the cell line is from a fish. In some embodiments, the cell line is from a livestock species. In some embodiments, the livestock species is porcine or bovine. In some embodiments, the cells are from any animal species intended for human or non-human dietary consumption. In some embodiments, the cells are myogenic cells. In some embodiments, the myogenic cells are myoblasts, myocytes, satellite cells, side population cells, muscle derived stem cells, mesenchymal stem cells, myogenic pericytes, or mesoangioblasts. In some embodiments, the cells are non-myogenic cells.

Non-limiting examples of myogenic differentiation are as described in WO2019014652A1 and WO2015066377A1, both of which are herein incorporated by reference in their entireties.

In some embodiments, the myogenic cells and/or skeletal muscle produced according to the methods described herein can be processed as a raw, uncooked food product (cultured meat) or as a cooked food product or as a cooked/uncooked food ingredient. In some embodiments, processing comprises withdrawal of the culture medium that supports the viability, survival, growth or expansion (e.g., increase in total protein content of the non-naturally occurring myogenic cells) and differentiation of the myogenic cells. Withdrawal may comprise physical removal of the culture medium or altering the composition of the culture medium, for example, by addition of components that would reduce or prevent further expansion and/or differentiation of the cell line or cells-derived from the cell line or by depletion of components that support expansion and/or differentiation of the cell line or cells derived from the cell line.

6.9.1. Inducible Promoter, Inducible Tag, and Degradation Tag

In some embodiments, activity and/or expression of the growth factor ligand (e.g., any of the growth factor ligands described herein), growth factor receptor (e.g., any of the growth factor receptors described herein), or a combination thereof, is controllable. In some embodiments, control of the activity and/or expression of the growth factor ligand, growth factor receptor, or a combination thereof, is controlled using an inducible promoter, an inducible tag, and/or a degradation tag.

In some embodiments, expression of a growth factor ligand or a fragment thereof, growth factor receptor or a fragment thereof, or a combination thereof, is controlled using an inducible promoter where expression is induced in the presence of a molecule capable of inducing the inducible promoter. In some embodiments, the promoter is a positive inducible promoter (e.g., addition of a controllable molecule induces binding to the promoter thereby activating transcription). In some embodiments, the promoter is a negative inducible promoter (e.g., addition of a controllable molecule removes a repressor from the promoter thereby allowing transcriptional machinery to bind and activate transcription). Inducible promoters include, without limitation, chemically inducible promoters (e.g., tetracycline inducible (tetracycline response elements (TRE)/tetracycline activator), cumate inducible (cumate operator (CuO)/cumate activator), alcohol inducible (AlcA promoter/AlcR activator), and steroid-inducible (e.g., LexA promoter/XVE (synthetic) activator)); temperature inducible promoters (e.g., heat shock inducible (e.g., hsp70, hsp90), and light inducible promoters (e.g., FixK2 promoter/blue-light sensing protein YFI; Vivid (VVD)/light oxygen voltage (LOV)).

In some embodiments, the coding sequence of the growth factor ligand or a fragment thereof, growth factor receptor or a fragment thereof, or both are operably linked to the inducible promoter. To induce expression of the growth factor ligand, the growth factor receptor, or a combination thereof, the engineered cell line is maintained in a culture medium comprising a molecule capable of controlling the inducible promoter.

In some embodiments, activity of a growth factor ligand or a fragment thereof, a growth factor receptor or a fragment thereof, or a combination thereof, is controlled using an inducible tag where activity of the growth factor ligand and/or growth factor receptor is controlled by the presence or absence of a molecule capable of capable of controlling the inducible tag. In such embodiments, the polynucleotide includes a coding sequence of an inducible tag located 5' or 3' to the coding sequence of the growth factor ligand, and wherein the inducible tag and the growth factor ligand are a fusion protein. In such cases, the inducible tag prevents growth factor ligand activity in the absence of the controllable molecule. To enable activity of the growth factor ligand, the engineered cell line is maintained in a culture medium comprising a molecule capable of controlling the inducible tag, thereby controlling the activity of the fusion protein.

In some embodiments, the inducible tag is a ESR1 ligand binding domain that is activated in the presence of the ESR1 agonist (e.g., 17-β Estradiol (E2)), thereby allowing the growth factor ligand to bind to its receptor and facilitate downstream signaling. In some embodiments, the inducible tag is an estrogen receptor binding domain that is activated in the presence of tamoxifen, thereby allowing the growth factor ligand to bind to its receptor and facilitate downstream signaling.

In some embodiments, the activity of a growth factor ligand or a fragment thereof, a growth factor receptor or a fragment thereof, or a combination thereof, is controlled using a degradation tag, where activity of the growth factor ligand and/or growth factor receptor is controlled by the presence or absence of a molecule capable of controlling the degradation tag. In some embodiments, the polynucleotide includes a coding sequence of the degradation tag located 5' or 3' to the coding sequence of the growth factor ligand, and wherein the degradation tag and the growth factor ligand are a fusion protein. In such cases, the degradation tag targets the growth factor ligand for degradation upon addition of a molecule capable of controlling the degradation tag to the culture medium.

Non-limiting examples of degradation tags include: Anchor away (e.g., the FKBP12-rapamycin-binding-domain of FRAP (FRB) is fused to a specific protein of interest, while the FKBP12 is fused to the anchor protein, rapamycin bridges between the POI and the anchor protein, allowing functional inhibition of the target protein); auxin-inducible degron system; and dTag system (i.e., three major components: an FKBP12F36V-fused protein of interest, a small synthetic molecule, a defined degrader, and the endogenous E3 ligase complex).

6.10. Cultivation Infrastructure

In some embodiments, a cultivation infrastructure may be a tube, a cylinder, a flask, a petri-dish, a multi-well plate, a dish, a vat, a roller bottle, an incubator, a bioreactor, an industrial fermenter and the like.

In some embodiments, a cultivation infrastructure can be of any scale, and support any volume of cellular biomass and culturing reagents. In some embodiments, the cultivation infrastructure ranges from about 10 μL to about 100,000 L. In some embodiments, the cultivation infrastructure is about 10 μL, about 100 μL, about 1 mL, about 10 mL, about 100 mL, about 1 L, about 10 L, about 100 L, about 1000 L, about 10,000 L, or even about 100,000 L.

In some embodiments, the cultivation infrastructure comprises a substrate. In some embodiments, a cultivation infrastructure may comprise a permeable substrate (e.g. permeable to physiological solutions) or an impermeable substrate (e.g. impermeable to physiological solutions).

In some embodiments, the cultivation infrastructure comprises a primary substrate, which can be a flat, concave, or convex substrate. In some embodiments, the cultivation infrastructure further comprises a secondary substrate, either introduced, or autologous, to direct cellular growth between the substrates, e.g. to direct attachment, proliferation and hypertrophy of cells on a plane perpendicular to the primary substrate.

In some embodiments, the cultivation infrastructure comprises a hydrogel, a liquid cell culture media, or soft agar. In some embodiments, the cultivation infrastructure does not comprise a substrate to which cells can adhere. In some embodiments, the cultivation infrastructure comprises a suspension culture, e.g. supporting the growth of a self-adhering biomass, or single-cell suspension in a liquid medium.

In some embodiments, the cultivation infrastructure comprises adherent cells (i.e. those cells that adhere to a substrate). In some embodiments, the cultivation infrastructure comprises non-adherent cells (i.e. those cells that do not adhere to a substrate). In some embodiments, the cultivation infrastructure comprises both adherent and non-adherent cells.

6.11. Immortalization

In some embodiments, the method provided herein include a cell line immortalized prior, contemporaneously therewith, or after introducing into the cell any of the polynucleotides described herein.

In some embodiments, immortalization comprises transforming a cell with a telomerase reverse transcriptase (TERT) gene. As used herein, "TERT" refers to telomerase reverse transcriptase (TERT) gene or TERT polypeptide that is a ribonucleoprotein polymerase that maintains telomere ends by addition of the telomere repeat TTAGGG. Telomerase expression plays a role in cellular senescence, as it is normally repressed in postnatal somatic cells resulting in progressive shortening of telomeres. In some embodiments, cells ectopically express the TERT polynucleotide. In some embodiments, the cells are genetically modified and carry stable integrations of one or more copies of the TERT polynucleotide. Exemplary methods for immortalizing a cell line are as described in WO2019014652A1, which is herein incorporated by reference in its entirety.

In some embodiments, increased expression of TERT may be achieved using different approaches. In some embodiments, increased expression of TERT may be achieved by ectopically expressing TERT. In some embodiments, increased expression of TERT may be achieved by introducing targeted mutations in the TERT promoter. In some embodiments, increased expression of TERT may be achieved by activating endogenous TERT expression by an engineered transcriptional activator. In some embodiments, increased expression of TERT may be achieved by transiently transfecting TERT mRNA.

The polynucleotide encoding TERT can be from any organism. The TERT polynucleotide can be from bacteria, plants, fungi, and archaea. The TERT polynucleotide can be from any animal, such as vertebrate and invertebrate animal species. The TERT polynucleotide can be from any vertebrate animal species such as mammals, reptiles, birds, amphibians, and the like. The TERT polynucleotide can be from any mammalian species, such as a human, murine, bovine, porcine, and the like.

In some embodiments, immortalization comprises transforming a cell with a polynucleotide encoding a cyclin-dependent kinase 4 ("CDK4") protein. In some embodiments, immortalization comprises inactivating a gene encoding an inhibitor of cyclin-dependent kinase 4 (CDK4). Exemplary methods for immortalizing a cell line are as described in WO2017124100A1, which is herein incorporated by reference in its entirety.

6.12. Nucleic Acids/Vectors

Also provided herein are polynucleotides comprising coding sequences of any of the growth factor ligands described herein, any of the growth factor receptors described herein, any of the accessory proteins described herein, or a combination thereof.

Also provided herein is a construct (i.e., a vector) that includes any of the polynucleotides described herein. In some embodiments, any of the vectors described herein can be an expression vector. In some embodiments, an expression vector can include one or more promoter sequences (e.g., any of the promoter sequences described herein) operably linked to a coding sequence of any of the growth factor ligands described herein, any of the growth factor receptors described herein, any of the accessory proteins described herein, or a combination thereof. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. In some embodiments, a vector includes sufficient cis-acting elements that supplement expression where the remaining elements needed for expression can be supplied by the host cell (e.g., the cell line).

In some embodiments, a vector includes a polynucleotide comprising a coding sequence of a single growth factor ligand or fragment thereof. In some embodiments, a vector includes a polynucleotide comprising a first coding sequence of a first growth factor ligand and a second coding sequence of a second growth factor ligand. In some embodiments, a vector (e.g., a construct) includes a polynucleotide comprising a first coding sequence of a first growth factor ligand, a second coding sequence of a second growth factor ligand, and a third coding sequence of a third growth factor ligand. In such embodiments where the construct includes coding sequences for two or more growth factor ligands, each of the two or more coding sequences are operably linked to a promoter sequence or to another coding sequence via a self-cleaving polypeptide or IRES. As used herein, the term "operably linked" is well known in the art and refers to genetic components that are combined such that they carry out their normal functions. For example, a coding sequence is operably linked to a promoter when its transcription is under the control of the promoter. In another example, a coding sequence can be operably linked to other coding sequences by a self-cleaving 2A polypeptide or an internal ribosome entry site (IRES). In such cases, the self-cleaving 2A polypeptide allows the second coding sequence to be under the control of the promoter operably linked to the first coding sequence. In some cases, the coding sequences described herein can be operably linked to any other coding sequence described herein using a self-cleaving 2A polypeptide or IRES.

In some embodiments, a vector includes a polynucleotide comprising a coding sequence of a single growth factor receptor or fragment thereof. In some embodiments, a vector includes a polynucleotide comprising a first coding sequence of a first growth factor receptor and a second coding sequence of a second growth factor receptor. In some embodiments, a vector (e.g., a construct) includes a polynucleotide comprising a first coding sequence of a first growth factor receptor, a second coding sequence of a second growth factor receptor, and a third coding sequence of a third growth factor receptor. In such embodiments where the construct includes coding sequences for two or more growth factor receptors, each of the two or more coding sequences are operably linked to a promoter sequence or to another coding sequence via a self-cleaving polypeptide or IRES. In another example, a coding sequence can be operably linked to other coding sequences by a self-cleaving 2A polypeptide or an internal ribosome entry site (IRES). In such cases, the self-cleaving 2A polypeptide allows the second coding sequence to be under the control of the promoter operably linked to the first coding sequence. In some cases, the coding sequences described herein can be operably linked to any other coding sequence described herein using a self-cleaving 2A polypeptide or IRES.

In some embodiments, a single construct comprises a coding sequence of FGF2 or a fragment thereof, and a coding sequence of any of the FGFR described herein or a fragment thereof, and includes a self-cleaving 2A polypeptide or an IRES to operably link the coding sequences. In some embodiments, a single construct comprises a coding sequence of IGF1 or a fragment thereof, and a coding sequence of IGF1R or a fragment thereof, and includes a self-cleaving 2A polypeptide or an IRES to operably link the coding sequences. In some embodiments, a single construct comprises a coding sequence of PDGF or a fragment thereof, and a coding sequence of PDGFR or a fragment thereof, and includes a self-cleaving 2A polypeptide or an IRES to operably link the coding sequences.

Also provided herein are a set of vectors that include two or more vectors. For example, the set of vectors include a first vector comprising a coding sequence of FGF2 or a fragment thereof, and a second vector comprising a coding sequence of FGFR (e.g., any of the FGFRs described herein) or a fragment thereof. In another example, the set of vectors include a first vector comprising a coding sequence of IGF1 or a fragment thereof, and a second vector comprising a coding sequence of IGF1R or a fragment thereof. In yet another example, the set of vectors include a first vector comprising a coding sequence of PDGF (e.g., PDGFB) or a fragment thereof, and a second vector comprising a coding sequence of IGF-1R or a fragment thereof.

In some embodiments, a coding sequence of any one or more of the growth factor ligands described herein, any one or more of the growth factor ligands described herein, any of the accessory protein described herein, or a combination thereof, is operably linked to a promoter. In some embodiments, the promoter is a tissue-specific promoter. In some embodiments, the tissue-specific promoter is a muscle-specific promoter. In some embodiments, the muscle-specific promoter is selected from the group consisting of: skeletal β-action, myosin light chain 2a, dystrophin, SPc-512, muscle creatine kinase, and synthetic muscle promoters. In some embodiments, the promoter is a constitutively active promoter. In some embodiments, the promoter is selected from the group consisting of: EF1 (e.g., EF1alpha), PGK, CMV, RSV, and β-actin. In some embodiments, the promoter is a EF1 (e.g., EF1alpha) promoter. In some embodiments, the promoter is a PGK promoter. In some embodiments, the vector comprises a selectable marker (e.g., puromycin).

In some embodiments, a vector comprises a polynucleotide comprising a first coding sequence (e.g., a coding sequence of any of the growth factor ligands, growth factor receptors, or accessory proteins described herein) operably linked to a first promoter and a polynucleotide comprising a second coding sequence (e.g., a coding sequence of any of the growth factor ligands, growth factor receptors, or accessory proteins described herein) operably linked to a second promoter.

In some embodiments, a vector system is used to integrate a polynucleotide comprising a coding sequence of any one or more of the growth factor ligands described herein, any one or more of the growth factor ligands described herein, any of the accessory protein described herein, or a combination thereof, into the genome of a cell line (e.g., any of the cell lines described herein). In some embodiments, the vector system used for integration is a vector phiC31 Integrase Vector System. Additional non-limiting examples of vectors systems that can be used to integrate a coding sequence of any one or more of the growth factor ligands described herein, any one or more of the growth factor ligands described herein, any of the accessory protein described herein, or a combination thereof, into the genome of a cell line (e.g., any of the cell lines described herein) include: a sleeping beauty transposon system (as described in U.S. Pat. No. 7,985,739), a piggyBac transposition system (as described in US20090042297), CRISPR/Cas-mediated knockin, TALEN-mediated knockin, and viral vector-mediated integration. In such embodiments where integration is mediated via a viral vector, non-limiting examples of viral vectors include adenovirus, adeno-associated virus, lentivirus, retrovirus (e.g., a gamma-retrovirus), or sendai virus.

SEQ ID NOs: 120-122 represent exemplary vector backbones used in this study: Sequences listed in SEQ ID NO: 61-119 were cloned into any one of vectors in SEQ ID NOs: 120-122 using EcoRI and KpnI restriction sites with a kozak sequence GCCACC inserted ahead of ATG start site. FC550A-eBFP2 was created by replacing mRuby sequence in FC550A-empty vector (EVmRuby) with eBFP2. In some embodiments, the polynucleotide sequence includes a sequence having at least 80% (e.g., at least 85%, 90%, 95%, 96%, 97%, 98%, or 99%) sequence identity to a sequence selected from SEQ ID NOs: 61-119.

6.13. Methods of Transducing Cells

Methods of introducing nucleic acids and expression vectors into a cell (e.g., an immortalized cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral, retroviral, and lentiviral transduction), lipid nanoparticle (LNP) transfection, and nanoparticle transfection.

6.14. Kits

Also provided herein are kits comprising any of the cell lines, any of the cells derived from the cell lines, any of the polynucleotides described herein (e.g., any of the coding sequence of any one or more of the growth factor ligands described herein, any one or more of the growth factor ligands described herein, any of the accessory protein described herein, or a combination thereof). In some embodiments, the kit includes instructions for performing any of the methods described herein.

6.15. Cells/Cell Lines

Also provided herein are cell line(s) for cultured food production. In some embodiments, the cell line(s) are capable of self-renewal. In some embodiments, the cell line(s) are immortalized cell line(s). In some embodiments, the cell lines are then differentiated to cell types of interest (e.g., myogenic cells).

Also provided herein are immortalized cells (e.g., any of the immortalized cells described herein). In some embodiments, the immortalized cells are fibroblasts. In some embodiments, the immortalized cells comprise any of the nucleic acids described herein that encode any of the myogenic regulatory factors described herein. In some embodiments, an immortalized cell is immortalized prior to performing the methods described herein. In some embodiments, the methods provided herein include a step of immortalizing a cell. In some embodiments, a cell is immortalized by transforming the cell with TERT.

Also provided herein are cells comprising any of the polynucleotides described herein that include any of the growth factor ligands described herein, any of the growth factor receptors described herein, any of the accessory proteins described herein, or a combination thereof.

Also provided herein are cells derived from the cell line(s). Non-limiting examples of cells derived from the immortalized cells (e.g., using the methods described herein) include myoblasts, myotubes, multinucleated myotubes, satellite cells, skeletal muscle fibers, or any combination thereof.

In some embodiments, the cell line is from a livestock, poultry, game or aquatic animal species. In some embodiments, the cell line or immortalized cell line are from a chicken, duck, or turkey. In some embodiments, the cell line or immortalized cell line are from a fish. In some embodiments, the cell line or immortalized cell line are from a livestock species. In some embodiments, the livestock species is porcine or bovine.

In some embodiments, the cell line is selected from any metazoan species. In some embodiments, the cell line is from any animal, such as vertebrate and invertebrate animal species. In some embodiments, the cell line is from any vertebrate animal species such as mammals, reptiles, birds, amphibians, and the like. In some embodiments, the cell line is from any mammalian species such as a human, murine, bovine, porcine, poultry, and the like. In some embodiments, the cell line is derived from a species selected from including without limitation, *Gallus gallus, Bos taurus, Sous scrofa, Meleagris gallopavo, Anas platyrynchos, Salmo salar, Thunnus thynnus, Ovis aries, Coturnix coturnix, Copra aegagrus hircus,* or *Homarus americanus.*

In some embodiments, the cell line (e.g., a cell line that is ultimately immortalized) is isolated from *Gallus gallus* (chicken). In some embodiments, the cell is isolated from chicken skin. In some embodiments, the cell is isolated from chicken muscle. In some embodiment, the cell is isolated from a chicken (e.g., chicken skin or chicken muscle) and cultured until a monoculture of cells is established (e.g., a monoculture of fibroblasts originating from the isolated chicken cells).

In some embodiments, the cell line (e.g., a cell line that is ultimately immortalized) is selected from the group consisting of: a myoblast, an immortalized myoblast, an immortalized primary myoblast, a muscle satellite cell, and a muscle stem cell. In some embodiments, the immortalized cell is an immortalized myoblast or an immortalized primary myoblast.

In some embodiments, the cell line (e.g., a cell line that is ultimately immortalized) is a fibroblast. For example, the cell is an immortalized fibroblast.

In some embodiments, skeletal muscle satellite cells are isolated from a chicken. In adults these are quiescent mononucleated myogenic cells that act as a reserve population of cells, able to proliferate and/or differentiate upon stimulation and give rise to regenerated muscle and to more satellite cells.

In some embodiments, an immortalized cell is not a stem cell (e.g., a muscle stem cell or a muscle satellite cell). In some embodiments, an immortalized cell is not a pluripotent stem cell (e.g., an embryonic stem cell or an induced pluripotent stem cell).

Also provided herein are cell banks comprising immortalized cell lines (e.g., immortalized fibroblast cells lines) generated according to the methods described herein.

Also provided herein is cell-based meat suitable for consumption.

7. ADDITIONAL EMBODIMENTS

Embodiment 1. A method of engineering a cell line for reduced dependence on exogenous growth factors, comprising: (a) introducing into the cell line one or more of: (i) a polynucleotide comprising a coding sequence of a growth factor ligand; (ii) a polynucleotide comprising a coding sequence of a growth factor receptor; or (iii) a polynucleotide comprising a coding sequence of an activated downstream growth factor target; and (b) culturing the cell line in a cultivation infrastructure.

Embodiment 2. A method of increasing the concentration of a growth factor ligand in culture medium of cells in culture, comprising: (a) introducing into a cell line one or more of: (i) a polynucleotide comprising a coding sequence of a growth factor ligand; and (ii) a polynucleotide comprising a coding sequence of a growth factor receptor; or (iii) a polynucleotide comprising a coding sequence of an activated downstream growth factor target; and (b) culturing the cell line in a cultivation infrastructure.

Embodiment 3. A method for improving anchorage independent growth in a cell line, comprising: (a) introducing into the cell line one or more of: (i) a polynucleotide comprising a coding sequence of a growth factor ligand; and (ii) a polynucleotide comprising a coding sequence of a growth factor receptor; or (iii) a polynucleotide comprising a coding sequence of an activated downstream growth factor target; and (b) culturing the cell line in a cultivation infrastructure.

Embodiment 4. A method for increasing the cell density of a culture comprising a cell line, comprising: (a) introducing into the cell line one or more of: (i) a polynucleotide comprising a coding sequence of a growth factor ligand; and (ii) a polynucleotide comprising a coding sequence of a growth factor receptor; or (iii) a polynucleotide comprising a coding sequence of an activated growth factor receptor; and (b) culturing the cell line in a cultivation infrastructure.

Embodiment 5. The method of any one of embodiments 1-4, wherein the growth factor ligand is selected from basic fibroblast growth factor (FGF2), insulin-like growth factor 1 (IGF1), and platelet-derived growth factor subunit B (PDGFb).

Embodiment 6. The method of any one of embodiments 1-5, wherein the polynucleotide comprising a coding sequence of a growth factor ligand further comprises an additional two or more growth factor ligands, wherein each of the additional growth factor ligands is selected from FGF2, IGF1, and PDGFb.

Embodiment 7. The method of embodiment 5 or 6, wherein the growth factor ligand is FGF2.

Embodiment 8. The method of embodiment 7, wherein the FGF2 comprises an amino acid sequence having at least 80% sequence identity to a sequence selected from SEQ ID NO: 1-15.

Embodiment 9. The method of embodiment 5, wherein the growth factor ligand is IGF1.

Embodiment 10. The method of embodiment 9, wherein the IGF1 comprises an amino acid sequence having at least 80% sequence identity to a sequence selected from SEQ ID NO: 16-17.

Embodiment 11. The method of embodiment 5 or 6, wherein the growth factor ligand is PDGFb.

Embodiment 12. The method of embodiment 11, wherein the PDGFb comprises an amino acid sequence having at least 80% sequence identity to a sequence selected from SEQ ID NO: 18-21.

Embodiment 13. The method of any one of embodiments 1-12, wherein the polynucleotide comprising a coding sequence of a growth factor ligand further comprises a coding sequence of a signal peptide located 5' to the coding sequence of the growth factor ligand, and wherein the signal sequence and the growth factor ligand are a fusion protein.

Embodiment 14. The method of embodiment 13, wherein the signal sequence comprises an amino acid sequence having at least 80% sequence identity to a sequence selected from SEQ ID NO: 22-31.

Embodiment 15. The method of any one of embodiments 1-14, wherein the polynucleotide comprising a coding sequence of a growth factor ligand further comprises a regulatory sequence operably linked to the coding sequence of the growth factor ligand and/or additional growth factor ligands.

Embodiment 16. The method of embodiment 15, wherein the regulatory sequence comprises a promoter selected from: an inducible promoter, a tissue specific promoter, and a constitutively active promoter.

Embodiment 17. The method of embodiment 15 or 16, wherein the promoter is selected from EF1alpha, PGK, CMV, RSV, and β-actin.

Embodiment 18. The method of any one of embodiments 1-17, wherein the polynucleotide comprising a coding sequence of a growth factor ligand comprises a sequence encoding a polycistronic mRNA, wherein the polycistronic mRNA comprises the coding sequence of the growth factor ligand and the coding sequence one or more additional growth factor ligands.

Embodiment 19. The method of embodiment 18, wherein the polynucleotide comprising a coding sequence of a growth factor ligand comprises one or more sequences encoding a self-cleaving peptide, one or more internal ribosome entry sites (IRES), or a combination thereof.

Embodiment 20. The method of any one of embodiment 1-19, wherein activity and/or expression of the growth factor ligand is controllable.

Embodiment 21. The method of embodiment 20, where activity and/or expression of the growth factor ligand is controlled using an inducible promoter, an inducible tag, or a degradation tag.

Embodiment 22. The method of embodiment 21, wherein expression of the growth factor ligands is controlled using an inducible promoter.

Embodiment 23. The method of embodiment 22, wherein the coding sequence of the growth factor ligand is operably linked to the inducible promoter.

Embodiment 24. The method of embodiment 22 or 23, further comprising:
maintaining the engineered cell line in a culture medium comprising a molecule capable of controlling the inducible promoter, thereby enabling expression of the growth factor ligand.

Embodiment 25. The method of embodiment 21, wherein activity of the growth factor ligand is controlled using an inducible tag.

Embodiment 26. The method of embodiment 25, wherein the polynucleotide comprising a coding sequence of a growth factor ligand further comprises a coding sequence of an inducible tag located 5' or 3' to the coding sequence of the growth factor ligand, and wherein the inducible tag and the growth factor ligand are a fusion protein.

Embodiment 27. The method of embodiment 25 or 26, further comprising: maintaining the engineered cell line in a culture medium comprising a molecule capable of controlling the inducible tag, thereby inducing activity of the growth factor ligand/fusion protein.

Embodiment 28. The method of embodiment 21, wherein activity of the one or more growth factor ligands is controlled using a degradation tag.

Embodiment 29. The method of any one of embodiments 28, wherein the polynucleotide comprising a coding sequence of a growth factor ligand further comprises a coding sequence of a degradation tag located 5' or 3' to the coding sequence of the growth factor ligand, and wherein the degradation tag and the growth factor ligand are a fusion protein.

Embodiment 30. The method of embodiment 28 or 29, further comprising: maintaining the engineered cell line in a culture medium comprising a molecule capable of controlling the degradation tag, thereby targeting the growth factor ligand/fusion protein for degradation.

Embodiment 31. The method of any one of embodiments 1-30, wherein (a) the concentration of FGF2 in the culture medium is increased by at least 0.001 ng/mL as compared to cell lines not engineered to include a polynucleotide encoding FGF2; (b) the concentration of IGF-1 in the culture medium is increased by at least 0.001 ng/mL as compared to cell lines not engineered to include a polynucleotide encoding IGF1; and/or (c) the concentration of PDGFb in the culture medium is increased by at least 0.001 ng/mL as compared to cell lines not engineered to include a polynucleotide encoding PDGFb.

Embodiment 32. The method of any one of embodiments 1-30, wherein (a) the concentration of FGF2 in the culture medium is increased by at least 2.5% as compared to cell lines not engineered to include a polynucleotide encoding FGF2; (b) the concentration of IGF-1 in the culture medium is increased by at least 2.5% as compared to cell lines not engineered to include a polynucleotide encoding IGF1; and/or (c) the concentration of PDGFb in the culture medium is increased by at least 2.5% as compared to cell lines not engineered to include a polynucleotide encoding PDGFb.

Embodiment 33. The method of any one of embodiments 1-32, wherein the growth factor receptor is selected from fibroblast growth factor receptor (FGFR), insulin growth factor 1 receptor (IGF1R), and platelet-derived growth factor receptor (PDGFR).

Embodiment 34. The method of embodiment 33, wherein the polynucleotide comprising a coding sequence of a growth factor receptor further comprises an additional two or more growth factor receptors, wherein each additional growth factor receptor is selected from FGFR, IGFR, and PDGFR.

Embodiment 35. The method of embodiment 33 or 34, wherein the growth factor receptor is an FGFR selected from FGFR1, FGFR2, FGFR3, and FGFR4.

Embodiment 36. The method of embodiment 35, wherein the FGFR comprises an amino acid sequence having at least 80% sequence identity to a sequence selected from SEQ ID NO: 32-49.

Embodiment 37. The method of embodiment 33 or 34, wherein the growth factor receptor is IGF1R.

Embodiment 38. The method of embodiment 37, wherein the IGF1R comprises an amino acid sequence having at least 80% sequence identity to a sequence selected from SEQ ID NO: 50-51.

Embodiment 39. The method of embodiment 33 or 34, wherein the growth factor receptor is PDGFR.

Embodiment 40. The method of embodiment 39, wherein the PDGFR comprises an amino acid sequence having at least 80% sequence identity to a sequence selected from SEQ ID NO: 52-58.

Embodiment 41. The method of any one of embodiments 1-40, wherein the polynucleotide comprising a coding sequence of an activated downstream growth factor target comprises a growth factor receptor comprising one or more amino acid insertions, deletions, or substitutions that result in the receptor being constitutively activated.

Embodiment 42. The method of any one of embodiments 33-41, wherein the polynucleotide comprising a coding sequence of a growth factor receptor comprises a regulatory sequence operably linked to the coding sequence of the growth factor receptor and/or the coding sequence of the additional growth factor receptors.

Embodiment 43. The method of embodiment 42, wherein the regulatory sequence comprises a promoter selected from: an inducible promoter, a tissue specific promoter, and a constitutively active promoter.

Embodiment 44. The method of embodiment 42 or 43, wherein the promoter is selected from EF1alpha, PGK, CMV, RSV, and β-actin.

Embodiment 45. The method of any one of embodiments 1-44, wherein the polynucleotide comprising a coding sequence of a growth factor receptor comprises a sequence encoding a polycistronic mRNA, wherein the polycistronic mRNA comprises the coding sequence of the growth factor receptor and the coding sequence of the two or more additional growth factor receptors.

Embodiment 46. The method of embodiment 45, wherein the polynucleotide comprising a coding sequence of a growth factor receptor comprises one or more sequences encoding a self-cleaving peptide, one or more internal ribosome entry sites (IRES), or a combination thereof.

Embodiment 47. The method of any one of embodiment 1-46, wherein activity and/or expression of the growth factor receptors is controllable.

Embodiment 48. The method of embodiment 47, wherein expression of the growth factor receptor is controlled using an inducible promoter, an inducible tag, and a degradation tag.

Embodiment 49. The method of embodiment 48, wherein expression of the growth factor receptor is controlled using an inducible promoter.

Embodiment 50. The method of embodiment 49, wherein the coding sequence of the growth factor receptor is operably linked to the inducible promoter.

Embodiment 51. The method of embodiment 49 or 50, further comprising: maintaining the engineered cell line in a culture medium comprising a molecule capable of controlling the inducible promoter, thereby enabling expression of the growth factor receptor.

Embodiment 52. The method of embodiment 48, wherein activity of the growth factor receptor is controlled using an inducible tag.

Embodiment 53. The method of embodiment 52, wherein the polynucleotide comprising a coding sequence of a growth factor receptor further comprises a coding sequence of an inducible tag located 5' or 3' to the coding sequence of the growth factor receptor, and wherein the inducible tag and the growth factor receptor are a fusion protein.

Embodiment 54. The method of embodiment 52 or 53, further comprising: maintaining the engineered cell line in a culture medium comprising a molecule capable of controlling the inducible tag, thereby inducing activity of the growth factor receptor/fusion protein.

Embodiment 55. The method of embodiment 48, wherein activity of the one or more growth factor ligands is controlled using a degradation tag.

Embodiment 56. The method of embodiment 55, wherein the polynucleotide comprising a coding sequence of a growth factor receptor further comprises a coding sequence of a degradation tag located 5' or 3' to the coding sequence of the growth factor receptor, and wherein the degradation tag and the growth factor receptor are a fusion protein.

Embodiment 57. The method of embodiment 55 or 56, further comprising: maintaining the engineered cell line in a culture medium comprising a molecule capable of controlling the degradation tag, thereby targeting the growth factor receptor/fusion protein for degradation.

Embodiment 58. The method of any one of embodiments 1-57, further comprising introducing a polynucleotide sequence encoding an accessory protein.

Embodiment 59. The method of any one of embodiments 1-58, wherein the polynucleotide comprising a coding sequence of a growth factor ligand and/or the polynucleotide comprising a coding sequence of a growth factor receptor further comprises a coding sequence of an accessory protein.

Embodiment 60. The method of embodiment 58 or 59, wherein the accessory protein is fibroblast growth factor binding protein (FGFBP).

Embodiment 61. The method of embodiment 60, wherein the FGFBP comprises an amino acid sequence having at least 80% sequence identity to a sequence of SEQ ID NO: 59.

Embodiment 62. The method of embodiment 58 or 59, wherein the accessory protein is RASV12.

Embodiment 63. The method of embodiment 62, wherein the RASV12 comprises an amino acid sequence having at least 80% sequence identity to a sequence of SEQ ID NO: 60.

Embodiment 64. The method of any one of embodiments 1-63, wherein the method comprises introducing into the cell: (i) a polynucleotide comprising a coding sequence of FGF2, and a polynucleotide comprising a FGFR; (ii) a polynucleotide comprising a coding sequence of IGF1, and a polynucleotide comprising an IGF1R; (iii) a polynucleotide comprising a coding sequence of PDGF, and a polynucleotide comprising a PDGFR, or (iv) a combination selected from: (i) and (ii), (ii) and (iii), (ii) and iii), and (i), (ii), and (iii).

Embodiment 65. The method of any one of embodiments 1-64, wherein the cell line is from a livestock, poultry, game or aquatic animal species.

Embodiment 66. The method of embodiment 65, wherein the cell line is from a chicken, duck, or turkey.

Embodiment 67. The method of embodiment 65, wherein the cell line is from a fish.

Embodiment 68. The method of embodiment 65, wherein the cell line is from a livestock species.

Embodiment 69. The method of embodiment 65, wherein the livestock species is porcine or bovine.

Embodiment 70. The method of any one of embodiments 1-64, wherein the cells are from any animal species intended for human or non-human dietary consumption.

Embodiment 71. The method of any one of embodiments 1-70, wherein the cells are myogenic cells.

Embodiment 72. The method of embodiment 71, wherein the myogenic cells are myoblasts, myocytes, satellite cells, side population cells, muscle derived stem cells, mesenchymal stem cells, myogenic pericytes, or mesoangioblasts.

Embodiment 73. The method of any one of embodiments 1-72, wherein the cells are non-myogenic cells.

Embodiment 74. An in vitro method for producing cell-based meat suitable for consumption, comprising: (a) introducing into a cell one or more of: (i) a polynucleotide comprising a coding sequence of a growth factor; (ii) a polynucleotide comprising a coding sequence of a growth factor receptor; or (iii) a polynucleotide comprising a coding sequence of an activated downstream growth factor target; and (b) inducing myogenic specific differentiation, wherein the differentiated cells form myocytes and multinucleated myotubes; (c) culturing the myocytes and myotubes to generate skeletal muscle fibers, thereby producing a cell-based meat suitable for consumption.

Embodiment 75. The method of embodiment 74, wherein the cell line is from a livestock, poultry, game or aquatic animal species.

Embodiment 76. The method of embodiment 75, wherein the cell line is from a chicken, duck, or turkey.

Embodiment 77. The method of embodiment 75, wherein the cell line is from a fish.

Embodiment 78. The method of embodiment 75, wherein the cell line is from a livestock species.

Embodiment 79. The method of embodiment 75, wherein the livestock species is porcine or bovine.

Embodiment 80. The method of embodiment 74, wherein the cells are from any animal species intended for human or non-human dietary consumption.

Embodiment 81. The method of any one of embodiments 74-80, wherein the cells are myogenic cells.

Embodiment 82. The method of embodiment 81, wherein the myogenic cells are myoblasts, myocytes, satellite cells, side population cells, muscle derived stem cells, mesenchymal stem cells, myogenic pericytes, or mesoangioblasts.

Embodiment 83. The method of any one of embodiments 74-82, wherein the cells are non-myogenic cells.

Embodiment 84. The method of any one of embodiments 74-83, wherein the growth factor ligand is selected from basic fibroblast growth factor (FGF2), insulin-like growth factor 1 (IGF1), and platelet-derived growth factor subunit B (PDGFb).

Embodiment 85. The method of embodiment 84, wherein the polynucleotide comprising a coding sequence of a growth factor ligand further comprises an additional two or more growth factor ligands, wherein each of the additional growth factor ligands is selected from FGF2, IGF1, and PDGFb.

Embodiment 86. The method of embodiment 84 or 85, wherein the growth factor ligands is FGF2.

Embodiment 87. The method of embodiment 86, wherein the FGF2 comprises an amino acid sequence having at least 80% sequence identity to a sequence selected from SEQ ID NO: 1-15.

Embodiment 88. The method of embodiment 84 or 85, wherein the growth factor ligands is IGF1.

Embodiment 89. The method of embodiment 88, wherein the IGF1 comprises an amino acid sequence having at least 80% sequence identity to a sequence selected from SEQ ID NO: 16-17.

Embodiment 90. The method of embodiment 84 or 85, wherein the growth factor ligands is PDGFb.

Embodiment 91. The method of embodiment 90, wherein the PDGFb comprises an amino acid sequence having at least 80% sequence identity to a sequence selected from SEQ ID NO: 18-21.

Embodiment 92. The method of any one of embodiments 74-91, wherein the polynucleotide comprising a coding sequence of a growth factor ligand further comprises a coding sequence of a signal peptide located 5' to the coding sequence of the growth factor ligand, and wherein the signal sequence and the growth factor ligand are a fusion protein.

Embodiment 93. The method of embodiment 92, wherein the signal sequence comprises an amino acid sequence having at least 80% sequence identity to a sequence selected from SEQ ID NO: 22-31.

Embodiment 94. The method of any one of embodiments 74-93, wherein the polynucleotide comprising a coding sequence of a growth factor ligand comprises a regulatory sequence operably linked to the coding sequence of the growth factor ligand and/or additional growth factor ligands.

Embodiment 95. The method of embodiment 94, wherein the regulatory sequence comprises a promoter selected from: an inducible promoter, a tissue specific promoter, and a constitutively active promoter.

Embodiment 96. The method of embodiment 94 or 95, wherein the promoter is selected from EF1alpha, PGK, CMV, RSV, and β-actin.

Embodiment 97. The method of any one of embodiments 74-96, wherein the polynucleotide comprising a coding sequence of a growth factor ligand comprises a sequence encoding a polycistronic mRNA, wherein the polycistronic mRNA comprises the coding sequence of the growth factor ligand and the coding sequence one or more additional growth factor ligands.

Embodiment 98. The method of embodiment 97, wherein the polynucleotide comprising a coding sequence of a growth factor ligand further comprises one or more sequences encoding a self-cleaving peptide, one or more internal ribosome entry sites (IRES), or a combination thereof.

Embodiment 99. The method of any one of embodiment 74-99, wherein activity and/or expression of the growth factor ligand is controllable.

Embodiment 100. The method of embodiment 99, wherein activity and/or expression of the growth factor ligand is controlled using an inducible promoter, an inducible tag, or a degradation tag.

Embodiment 101. The method of embodiment 100, wherein expression of the growth factor ligands is controlled using an inducible promoter.

Embodiment 102. The method of embodiment 101, wherein the coding sequence of the growth factor ligand is operably linked to the inducible promoter.

Embodiment 103. The method of embodiment 101 or 102, further comprising: maintaining the engineered cell line in a culture medium comprising a molecule capable of controlling the inducible promoter, thereby enabling expression of the growth factor ligand.

Embodiment 104. The method of embodiment 100, wherein activity of the growth factor ligand is controlled using an inducible tag.

Embodiment 105. The method of embodiment 104, wherein the polynucleotide comprising a coding sequence of a growth factor ligand further comprises a coding sequence of an inducible tag located 5' or 3' to the coding sequence of the growth factor ligand, and wherein the inducible tag and the growth factor ligand are a fusion protein.

Embodiment 106. The method of embodiment 104 or 105, further comprising: maintaining the engineered cell line in a culture medium comprising a molecule capable of controlling the inducible tag, thereby inducing activity of the growth factor ligand/fusion protein.

Embodiment 107. The method of embodiment 100, wherein activity of the one or more growth factor ligands is controlled using a degradation tag.

Embodiment 108. The method of any one of embodiments 107, wherein the polynucleotide comprising a coding sequence of a growth factor ligand further comprises a coding sequence of a degradation tag located 5' or 3' to the coding sequence of the growth factor ligand, and wherein the degradation tag and the growth factor ligand are a fusion protein.

Embodiment 109. The method of embodiment 107 or 108, further comprising: maintaining the engineered cell line in a culture medium comprising a molecule capable of controlling the degradation tag, thereby targeting the growth factor ligand/fusion protein for degradation.

Embodiment 110. The method of any one of embodiments 74-109, wherein the growth factor receptor is selected from fibroblast growth factor receptor (FGFR), insulin growth factor 1 receptor (IGF1R), and platelet-derived growth factor receptor (PDGFR).

Embodiment 111. The method of embodiment 110, wherein the polynucleotide comprising a coding sequence of a growth factor receptor further comprises an additional two or more growth factor receptors, wherein each additional growth factor receptor is selected from FGFR, IGFR, and PDGFR.

Embodiment 112. The method of embodiment 110 or 111, wherein the growth factor receptor is an FGFR selected from FGFR1, FGFR2, FGFR3, and FGFR4.

Embodiment 113. The method of embodiment 112, wherein the FGFR comprises an amino acid sequence having at least 80% sequence identity to a sequence selected from SEQ ID NO: 32-49.

Embodiment 114. The method of embodiment 110 or 111, wherein the growth factor receptor is IGF1R.

Embodiment 115. The method of embodiment 114, wherein the IGF1R comprises an amino acid sequence having at least 80% sequence identity to a sequence selected from SEQ ID NO: 50-51.

Embodiment 116. The method of embodiment 110 or 111, wherein the growth factor receptor is PDGFR.

Embodiment 117. The method of embodiment 116, wherein the PDGFR comprises an amino acid sequence having at least 80% sequence identity to a sequence selected from SEQ ID NO: 52-58.

Embodiment 118. The method of any one of embodiments 74-117, wherein the polynucleotide comprising a coding sequence of an activated downstream growth factor target comprises a growth factor receptor comprising one or more amino acid insertions, deletions, or substitutions that result in the receptor being constitutively activated.

Embodiment 119. The method of any one of embodiments 110-118, wherein the polynucleotide comprising a coding sequence of a growth factor receptor comprises a regulatory sequence operably linked to the coding sequence of the growth factor receptor and/or the coding sequence of the additional growth factor receptors.

Embodiment 120. The method of embodiment 119, wherein the regulatory sequence comprises a promoter selected from: an inducible promoter, a tissue specific promoter, and a constitutively active promoter.

Embodiment 121. The method of embodiment 119 or 120, wherein the promoter is selected from EF1alpha, PGK, CMV, RSV, and β-actin.

Embodiment 122. The method of any one of embodiments 74-121, wherein the polynucleotide comprising a coding sequence of a growth factor receptor comprises a sequence encoding a polycistronic mRNA, wherein the polycistronic mRNA comprises the coding sequence of the growth factor receptor and the coding sequence of the two or more additional growth factor receptors.

Embodiment 123. The method of embodiment 122, wherein the polynucleotide comprising a coding sequence of a growth factor receptor comprises one or more sequences encoding a self-cleaving peptide, one or more internal ribosome entry sites (IRES), or both.

Embodiment 124. The method of any one of embodiment 74-123, wherein activity and/or expression of the growth factor receptors is controllable.

Embodiment 125. The method of embodiment 124, where expression of the growth factor receptor is controlled using an inducible promoter, an inducible tag, and a degradation tag.

Embodiment 126. The method of embodiment 125, wherein expression of the growth factor receptor is controlled using an inducible promoter.

Embodiment 127. The method of embodiment 126, wherein the coding sequence of the growth factor receptor is operably linked to the inducible promoter.

Embodiment 128. The method of embodiment 126 or 127, further comprising:

maintaining the engineered cell line in a culture medium comprising a molecule capable of controlling the inducible promoter, thereby enabling expression of the growth factor receptor.

Embodiment 129. The method of embodiment 125, wherein activity of the growth factor receptor is controlled using an inducible tag.

Embodiment 130. The method of embodiment 129, wherein the polynucleotide comprising a coding sequence of a growth factor receptor further comprises a coding sequence of an inducible tag located 5' or 3' to the coding sequence of the growth factor receptor, and wherein the inducible tag and the growth factor receptor are a fusion protein.

Embodiment 131. The method of embodiment 129 or 130, further comprising: maintaining the engineered cell line in a culture medium comprising a molecule capable of controlling the inducible tag, thereby inducing activity of the growth factor receptor/fusion protein.

Embodiment 132. The method of embodiment 125, wherein activity of the one or more growth factor ligands is controlled using a degradation tag.

Embodiment 133. The method of embodiment 132, wherein the polynucleotide comprising a coding sequence of a growth factor receptor further comprises a coding sequence of a degradation tag located 5' or 3' to the coding sequence of the growth factor receptor, and wherein the degradation tag and the growth factor receptor are a fusion protein.

Embodiment 134. The method of embodiment 132 or 133, further comprising: maintaining the engineered cell line in a culture medium comprising a molecule capable of controlling the degradation tag, thereby targeting the growth factor receptor/fusion protein for degradation.

Embodiment 135. The method of any one of embodiments 74-134, further comprising introducing a polynucleotide sequence encoding an accessory protein.

Embodiment 136. The method of any one of embodiment 74-134, wherein the polynucleotide comprising a coding sequence of a growth factor ligand, the polynucleotide comprising a coding sequence of a growth factor receptor, or both, further comprises a coding sequence of an accessory protein.

Embodiment 137. The method of embodiment 135 or 136, wherein the accessory protein is fibroblast growth factor binding protein (FGFBP).

Embodiment 138. The method of embodiment 137, wherein the FGFBP comprises an amino acid sequence having at least 80% sequence identity to a sequence of SEQ ID NO: 59.

Embodiment 139. The method of embodiment 135 or 136, wherein the accessory protein is RASV12.

Embodiment 140. The method of embodiment 139, wherein the RASV12 comprises an amino acid sequence having at least 80% sequence identity to a sequence of SEQ ID NO: 60.

Embodiment 141. The method of any one of embodiments 74-140, wherein the method comprises introducing into the cell:

(i) a polynucleotide comprising a coding sequence of FGF2, and a polynucleotide comprising a coding sequence of FGFR;

(ii) a polynucleotide comprising a coding sequence of IGF1, and a polynucleotide comprising a coding sequence of IGF1R;

(iii) a polynucleotide comprising a coding sequence of PDGF, and a polynucleotide comprising a coding sequence of PDGFR, or (iv) a combination selected from: (i) and (ii), (ii) and (iii), (ii) and iii), and (i), (ii), and (iii).

Embodiment 142. A myogenic cell suitable for consumption comprising cells having increased expression of FGF2, IGF1, PDGFb, FGFR, IGF1R, or PDGFR, or a combination thereof.

Embodiment 143. A population of cells suitable for consumption comprising cells having increased expression of FGF2, IGF1, PDGFb, FGFR, IGF1R, or PDGFR, or a combination thereof.

Embodiment 144. A vector comprising a polynucleotide encoding a fusion protein comprising a coding sequence of a signaling sequence and a coding sequence of a growth factor ligand, and optionally a coding sequence of an inducible tag or a degradation tag.

Embodiment 145. A cell comprising a polynucleotide encoding a fusion protein comprising a coding sequence of a signaling sequence and a coding sequence of a growth factor ligand, and optionally a coding sequence of an inducible tag or a degradation tag.

Embodiment 146. A vector comprising a polynucleotide comprising a first coding sequence of a growth factor ligand or a fragment thereof, and a second coding sequence of growth factor receptor or a fragment thereof.

Embodiment 147. A cell comprising a polynucleotide comprising a coding sequence of a growth factor ligand or a fragment thereof, and a polynucleotide comprising a coding sequence of a growth factor receptor or a fragment thereof.

Embodiment 148. A cell-based meat suitable for consumption produced using the methods of any one of embodiments 74-141.

8. EXAMPLES

8.1. Summary of Experimental Observations

Applicant evaluated cell lines harboring a polynucleotide comprising a coding sequence of FGF2, IGF1, and/or PDGF for cell proliferation, impact on adherence, and amount of FGF2, IGF1, PDGF secreted into the culture medium. Applicant evaluated whether cells engineered to express and secrete FGF2, IGF1, and/or PDGF ligands could be grown in serum-free media (serum is known to contain an assortment of growth factors) in the absence of exogenous growth factors (i.e., media not supplemented with FGF2, IGF1, and/or PDGF). Applicant further evaluated whether cells engineered to express FGF2, IGF1, and/or PDGF receptors could be grown in serum-free media in the absence of exogenous growth factors. Applicant additionally evaluated whether cells engineered with specific promoters to drive expression of the exogenous polynucleotides or signaling peptides fused to the FGF2, IGF1, and/or PDG ligands could be grown in serum-free media in the absence of exogenous growth factors and increase growth factor secretion, respectively. Applicant demonstrated that introducing the polynucleotide comprising a coding sequence of an FGF2, IGF1, and/or PDGF ligand, receptor, or activated receptor into an immortalized cell line and culturing the cell line in serum free media resulted in cell proliferation and packed cell volumes similar to positive control cell lines grown in serum and/or in culture medium supplemented with exogenous growth factors. As a negative control, cell lines grown without being engineered to express an exogenous polynucleotide, without serum, and without exogenous growth factors failed to proliferate over 72 hours and also exhibited decreases in population doubling times. Additionally, Applicant found that specific promoters further improved cell line performance when introducing the polynucleotide comprising a coding sequence of an FGF2, IGF1, and/or PDGF ligand, receptor, or activated receptor into an immortalized cell line and culturing the cell line in serum free media without any addition of exogenous growth factors. In addition, Applicant demonstrated that cell lines harboring the polynucleotide comprising a coding sequence of an FGF2, IGF1, and/or PDGF ligand secreted these growth factors into the serum-free media and this secretion was increased further when a polynucleotide comprising a coding sequence for a signaling peptide was combined with a polynucleotide comprising a coding sequence for growth factor to provide a fusion protein coding sequence. Applicant has further found that species to species and cell to cell variability impacts the efficacy of this approach and of these gene targets. For instance, Applicant found that introduction of polynucleotides comprising coding sequences for FGF2 ligands (of salmon, chicken, and bovine varieties) into bovine cell lines failed to generate a growth factor independent cell line. Application further notes that, even within the same species, cells of a different type often respond differently to any given growth factor and may require different growth factor targets.

Applicant further tested the cell lines harboring a polynucleotide comprising a coding sequence of FGF2 for impact on anchorage-dependent growth. Applicant demonstrated that introducing the polynucleotide comprising a coding sequence of FGF2 into an immortalized cell line resulted in an increase in the number of non-adherent cells capable of anchorage-independent growth.

Applicant also evaluated cell lines harboring a polynucleotide comprising a coding sequence of IGF1 for cell proliferation rate (e.g., viable cell density (VCD)) and packed cell volumes (PCV), where PCV is used as a proxy for cell biomass. In particular, Applicant demonstrated that introducing the polynucleotide comprising a coding sequence of IGF1 into an immortalized cell line and culturing the cell line in serum-free media in the absence of exogenous IGF1 resulted in increased viable cell densities as compared to the controls. Applicant also showed the cells engineered to express IGF1 had greater PCVs as compared to controls.

Applicant also evaluated cell lines harboring a polynucleotide comprising a coding sequence of IGF1 and a polynucleotide encoding an FGF2 for cell proliferation rate (e.g., viable cell density (VCD)) and packed cell volumes (PCV), where PCV is used as a proxy for cell biomass. Applicant demonstrated that introducing the polynucleotide comprising a coding sequence of IGF1 and a polynucleotide sequence encoding an FGF2 into an immortalized cell line and culturing the cell line in serum-free media in the absence of growth factors resulted in increased viable cell densities and PCVs as compared to controls.

Applicant also evaluated cell lines harboring a polynucleotide comprising a coding sequence of IGF1 and a polynucleotide encoding an FGF2 receptor for cell proliferation rate (e.g., viable cell density (VCD)) and packed cell volumes (PCV. Applicant demonstrated that introducing the polynucleotide comprising a coding sequence of IGF1 and a polynucleotide sequence encoding an FGF2 receptor into a cell line and culturing the cell line in serum-free media in the absence of growth factors resulted in increased viable cell densities and PCVs as compared to controls.

Lastly, Applicant also evaluated cell lines harboring a polynucleotide comprising a coding sequence of PDGF or a polynucleotide encoding an PDGF receptor for cell proliferation rate (e.g., viable cell density (VCD)) and packed cell volumes (PCV. Applicant demonstrated that introducing the polynucleotide comprising a coding sequence of PDGF or a polynucleotide sequence encoding an PDGF receptor into a cell line and culturing the cell line in serum-free media in the absence of growth factors resulted in increased viable cell densities and PCVs as compared to controls.

Overall, this work demonstrated the ability to engineer cells to have reduced dependence on exogenous growth factors without compromising the cell's ability to proliferate or differentiate into myogenic cells. In particular, this work demonstrated that engineering cells to express growth factor ligands and/or growth factor receptors results in engineered cells that (i) maintain cell proliferation rates similar to positive controls, (ii) have an increase in the number of non-adherent cells (i.e., cells that exhibit anchorage-independent growth) as compared to controls, and (iii) have an increase in packed cell volumes as compared to both positive and negative controls, all while cells are grown in the absence of one or more exogenous growth factors. These findings are important because manufacturing cells suitable for consumption requires vast amounts of exogenous growth factor ligands in order to sufficiently expand the cells and adapt them to the appropriate culture formats (e.g., suspension culture). The engineered cells provided herein supply their own source of growth factor signaling-thereby bypassing or at least reducing the need to supplement the cultures with exogenous growth factors. Moreover, by promoting anchorage independent growth, which is currently essential for manufacturing cell-based meats suitable for consumption, the engineered cell lines provided herein increase the efficiency by which cell based meats suitable for consumption can be produced.

8.2. Methods 8.2.1. Cell Line Production.

In order to generate cell lines with integrated polynucleotides, a PhiC31 Integrase Expression Plasmid system was used (System Biosciences). Briefly, coding sequences of genes of interest (e.g., coding sequence of FGF2 or coding sequence of IGF1) were cloned into a PhiC31 dual promoter expression plasmid (System Biosciences, Cat No. FC550A-1). Cell lines were transfected with the plasmid containing the coding sequences of the gene(s) of interest (e.g., FGF2 or IGF1) and a plasmid containing an integrase (PhiC31 integrase, System Biosciences, Cat No. FC200PA-1) to integrate the coding sequences into the genome. In some cases, the Phi31 plasmids also included a red fluorescent protein as a reporter. Cell lines with integrated plasmids were selected using puromycin and assessed for transgene expression and/or fluorescent marker expression. Cell lines exhibiting stable expression were selected for further analysis.

8.2.2. Assessment of Secreted FGF2 or Secreted IGF1

Engineered cells were serum starved and plated into serum free media (no FGF2) for 72 hours. FGF2 ELISA (DFB50 (R&D Biosystems QuantikineIM ELISA kit for Human FGF basic) was used to determine the concentration of FGF2 in the supernatant.

Engineered cells were serum starved and plated into serum free media (no IGF1) for 72 hours. IGF1 ELISA ((R&D Biosystems) was used to determine the concentration of IGF1 in the supernatant.

8.2.3. Assessment of Cell Proliferation

A colorimetric assay (WST-1 based) was used to assess cell proliferation (Roche, Cat. No. 05 015 944 001). WST-1 assay used to measure cell proliferation based on the cleavage of tetrazolium salt (WST-1) to formazan by cellular mitochondrial dehydrogenases. Through a colorimetric measurement, the proliferation fold change can be calculated and utilized to determine which cell lines grew significantly more than the negative control, FC550A (grown in serum free media). Cells were serum starved and plated in adherent plates with serum free media. WST-1 measured after 48 hours in culture.

8.2.4. Assessment of Myogenicity

Using qRT-PCR (real-time quantitative reverse transcription). Messenger RNA (mRNA) is isolated from cells to examine gene expression with probes specifically designed to amplify select target genes to characterize cell lines. Identical quantity of mRNA is reverse transcribed to generate cDNA. Each cDNA is submitted to quantitative PCR (qPCR) to assess the expression of myogenic factors relative to a housekeeping gene. Expression of MyoD, MyoG, and/or MyHC1e indicate myogenic cells. Additionally, high levels of MyHC1e are indicative of cells that can mature to form myotubes.

Using immunohistochemistry. Cells are seeded in a 96-well plate at a low density (5000-10,000 cells/cm2) to allow cells to grow in the presence or absence of different small molecule combinations. After 2 days of media exposure, cells are fixed with 4% paraformaldehyde (PFA) and washed. Cells are permeabilized with 0.05% PBS-T (triton-x), blocked with normal goat serum (Millipore Sigma) and are incubated with antibodies, and subsequently with secondary antibodies.

8.3. Example 1: Promoter Screen Identified hEF1α as Potent Promoter for Driving Expression of Growth Factor Ligand This experiment was designed to evaluate promoters for their ability to drive expression of the growth factor ligands (and growth factor receptors).

For these experiments, vectors having bi-directional promoters were used (see, e.g., FIGS. 3A and 3B) to assess each promoter's ability to drive expression of FGF2. In particular, the constructs included hEF1alpha and mPGK promoter sequences and a coding sequence of FGF2 or a luciferase reporter gene downstream of the promoter sequences. The vectors shown in FIG. 3A and FIG. 3B were transfected into chicken fibroblast cells. Promoter strength (i.e., the promoter's ability to drive expression of a luciferase reporter gene) was assessed by measuring relative light unit (RLU) fold change relative to mPGK-NLucP control (see FIG. 4). Promoter strength for driving expression of FGF2 was measured by determining the FGF2 concentration in the supernatant after 72 hours in culture.

Surprisingly, as shown in FIG. 4, the hEF1alpha promoter produced statistically significantly greater levels of luciferase reporter gene expression. In particular, the hEF1alpha promoter produced 43.9× higher expression of the luciferase reporter gene than the mPGK promoter. Statistically significant differences between the means were determined by a t-test with P-values indicated with asterisks. N=5. ** p<0.01.

As shown in FIG. 5, the hEF1alpha promoter resulted in a mean of 64.8 pg/mL of FGF2 in the supernatant following 72 hours in culture compared to 0 pg/mL of FGF2 in the supernatant when expression of FGF2 was linked to the mPGK promoter.

This data showed that the hEF1alpha promoter resulted in greater than 60-fold increase in expression compared to the mPGK promoter. For at least these reasons, the hEF1alpha promoter was selected for use in the following experiments.

8.4. Example 2: Cells Engineered to Express FGF2 Secrete FGF2 into Culture Media This experiment was designed to assess performance of different FGF2 variants by measuring FGF2 concentration in the culture media 72 hours post transduction. For these experiments, chicken 1312 cells were transfected, selected using a cell sorter, and expanded prior to assessing FGF2 concentration in the cell culture media.

In particular, chicken 1312 cells seeded in a 6-well plate were transfected using Lipofectamine™ 3000 Transfection Reagent using a 1:1 ratio of diluted Lipofectamine™ 3000 mixture (e.g., 125 µL Opti-Mem™ and 3.75 µL Lipofectamine™) to diluted DNA plasmid mixture (e.g., 125 µL Opti-MemIM+5 µL of P3000 reagent+2.5 µg of DNA plasmid). After 48-72 hours, cells were assessed for expression levels using microscopy and flow cytometry (data not shown).

A cell sorter was used to sort the mRuby$^+$ cells, which served as a proxy for FGF2 expressing cells. Gates for sorting mRuby$^+$ cells were set up using Naïve transfection (no transfection control) (data not shown).

Following sorting, cells were grown in a tissue culture treated 12 well plates. When cells reach 80-90% confluence, the cells were trypsinized and passaged. Cells were maintained in maintenance media (DMEM/F12 and 10% FBS and 1-2% chicken serum).

After the cells recovered from cell sorting, the cells were re-adapted to suspension culture and grown in 50 mL TPP tubes or shake flasks. Cells were seeded at a density of 0.25 1E6 cells/mL and passaged every 3 days. Serum free and ACF media formulation (100 ng/mL FGF2 and 10 ng/mL IGF1) was added to the cultures for continuous growth.

To assess FGF2 concentration in the culture media, an ELISA (enzyme-linked immunoassay) was used. In particular, chicken 1312 cells transduced and sorted according to the above methods were plated in 48-well plates in replicate (N=2) at 60,000 cells/well in 400 µL Serum Free media supplemented with 5 µg/mL Fibronectin. Cells were left to grow at 39° C. for about 72 hours. Supernatant was removed, spun at 300 rcf for 5 minutes and moved to a clean Eppendorf™ centrifuge tube. 100 µL of each supernatant was assessed for each well—biological replicates were expanded to technical duplicates resulting in a final N=4 per condition. The results of the FGF2 ELISA are shown in FIG. 6.

Applicant also assessed whether secretion signal peptides (SSPs) could be used to enhance secretion of FGF2. Wild type FGF2 is secreted by a non-conventional secretion mechanism, which does not rely on SSPs. Therefore, Applicant hypothesized that using a SSP fused to the N-terminus of FGF-2 would enhance FGF2 secretion by using conventional secretion pathways (e.g., through the endoplasmic reticulum and golgi apparatus).

As shown in FIG. 6, cells engineered to express FGF2 wild type (FGF2-wt) or engineered to express FGF2 with an N-terminal secretion signal peptide (cohIL2col-FGF2 and BM40-FGF2) secreted statistically significantly levels of FGF2 into the media after 72 hours. Statistically significant differences between the means were determined by an ANOVA one-way test with Dunnett's exclusion (post hoc) with P-values indicated with asterisks. * p<0.05;  p<0.001; * p<0.0005; **** p<0.0001; and ns=not significant.

To assess proliferation of the chicken 1312 cells following transduction and sorting (according to the above methods), a WST-1 assay was used. The WST-1 assay used to measure cell proliferation based on the cleavage of tetrazolium salt (WST-1) to formazan by cellular mitochondrial dehydrogenases. Through a colorimetric measurement, the proliferation fold change can be calculated and utilized to determine which cell lines grew significantly more than the negative control, FC550A (grown in serum free media). Cells were serum starved and plated in adherent plates with serum free media. WST-1 measured after 48 hours in culture.

In particular, transfected and sorted chicken 1312 cells were plated in triplicate in 96-well plates in seeding media comprising Serum Free Media (no FGF2). As controls, transfected and sorted chicken 1312 cells were also plated in serum containing media and serum free media having 100 ng/mL FGF2 (i.e., supplemental FGF2). Cells were grown for 48 hours in a stationary incubator at 39° C. N=3 additional wells with a media only were set up as negative controls. Following the 48-hour incubation, 10 μL/well of WST-1 substrate (Roche scientific) was added to each well. Plates were incubated in a stationary incubator for 3 hours. Following incubation, plates were placed on a shaker to ensure mixing for 1 minute. Plates were read on a Cyation™ Cell Imaging Reader to determine absorbance (colorimetric output) at 450 nm (630 nm for wavelength correction).

As shown in FIG. 7, ggIL2-FGF2, containing a chicken IL2 secretion signal, had the highest fold change in proliferation compared to FC550A empty vector control (1.42). Statistically significant increases in proliferation were observed for FGF2-WT, Gluc-FGF2, ggIL2-FGF2, hIL2-FGF2, hIL2col-FGF2, and hIL6-FGF2. Controls grown in serum containing media resulted in the highest fold change (positive control). Statistically significant differences between the means were determined by an ANOVA one-way test with Dunnett's exclusion (post hoc) with P-values indicated with asterisks. * p<0.05;  p<0.001; * p<0.0005; **** p<0.0001; and ns=not significant.

Taken together, this data showed that cell lines engineered to express FGF2 result in robust production of FGF2, as measured by the concentration of FGF2 in the culture media (FIG. 6). Additionally, the data showed that cell lines engineered to express FGF2 can be grown in serum-free media without the need for supplementing the media with exogenous sources of FGF2 (FIG. 7).

8.5. Example 3: Cells Engineered to Express FGF2 Exhibit Significantly Improved Cell Density This experiment was designed to assess the impact of each FGF2 variant on cell density in adherent, serum-free cultures.

In particular, chicken cells transduced and sorted according to the methods described in Example 2 were plated in 48-well plates in replicates (N=2 wells) at 75,000 cells/well in 400 μL serum-free media supplemented with 5 ug/mL fibronectin. Additional controls included: cell lines not transfected and cell lines transfected with an FC550A empty vector; where the control cell lines were grown in serum-free media supplemented with 100 ng/mL FGF2.

Cells were serum-starved and left to grow at 39° C. for about 72 hours and Biospa imaging was performed every 12 hours to count cells. Cells were then harvested at the end of the experiment and final cell counts were analyzed using a ViCell BLU cell counter.

FIG. 8 shows representative images taken at 12 hours after initial seeding of control (FC550A) and FGF2-WT cells plated in serum free media with no exogenous FGF2. FIG. 9 shows representative images taken at 48 hours after initial seeding of control (FC550A) and FGF2-WT cells plated in serum free media with no exogenous FGF2.

As shown in FIG. 9, after 48 hours, multiple cell lines engineered to express FGF2 developed a secondary cell population that was not attached to the plate (identified by the Arrow in FIG. 9) while the FC550A empty vector control consisted only of cells that were adherent.

At the end of the 72-hour period, the cells were harvested and viable cell densities were calculated for each condition. As shown in FIG. 10, FGF2-WT transfected cells grew significantly better than the negative controls and similar to positive controls grown in serum free media with 100 ng/mL FGF2. Many FGF-expressing lines were able to grow significantly better than the FC550A empty vector control (Blue bar). Interestingly, all FGF-STAB expressing cell lines were not significant. Statistically significant differences between the means were determined by an ANOVA one-way test with Dunnett's exclusion (post hoc) with P-values indicated with asterisks. * p<0.05;  p<0.001; * p<0.0005; **** p<0.0001; and ns=not significant.

This data showed that cell lines engineered to express FGF2 result in cell densities comparable to positive controls, indicating that these cell lines are suitable sources for generating cell-based meat.

8.5.1. Further Assessment of Impact on Cell Density

In another experiment, to test impact on cell density, naïve cells (none transfected controls) and cells engineered to express FGF2-WT or FGF2-WT with a secretion tag (e.g., a secretion tag selected from Secrecon, human IGN2A, human IL2, human IL2 variation 1, human IL2 variation 2, human IL6, BM40) were adapted into suspension format and seeded into a 4 passage proliferation study. Cells were grown in serum free, ACF media for 4 passages on a 2 day passaging cadence (seeding density ~400K/mL) as biological replicates. (N=2). Serum free, ACF media contained 10 ng/mL IGF1 and 0 ng/mL FGF2. VCDs measurements were taken on Day 0 and Day 2 for each passage to determine doubling times and maximum VCDs. Naïve and FGF-STAB variants were used as controls. As shown in FIG. 11, after 4 passages, each of the FGF2 variants tested showed statistically significant increases in VCD as compared to the controls. This data established that engineered cells (FGF2 and FGF2 with a secretion tag) were able to grow in suspension without media-supplemented with FGF2. Notably, cells engineered to express thermostable FGF-STAB sequences and naive cells did not proliferate. FIG. 11 shows Viable Cell Density (VCD) of day 2, passage 4. One way ANOVA was performed with significance indicated as P<0.0001 (**) and P<0.001 () compared to naive control.

8.6. Example 4: Cells Engineered to Express FGF2 Variants Enabled Cell Proliferation without Media-Supplemented FGF2

Chicken cells were engineered to express chicken FGF2, bovine FGF2, salmon FGF2, heat stable variants of FGF2 (e.g., FGF2-Q68I-N114G and FGF2-Q68I-C99S-N114G), FGF2 having a secretion tag (e.g., ggTL2-FGF2 and hIL2-col-ggFGF2(xMet)), FGF2 variants that preserve amino acids for non-canonical secretion (FGF2-C77-Y81), and FGF2-STAB variants (STAB-C77Y81, c96-STAB-Gen2-ggFGF2, STAB-Gen3-ggFGF2, and c96-STAB-Gen3-ggFGF2). Controls include cells transduced with an empty vector (EV) and untransfected controls (Naïve).

In a first set of experiments, cells engineered to express FGF2 and FGF2 variants described above were assessed for their ability to proliferate and enable biomass production in media not supplemented with FGF2.

For assessment of impact on proliferation, naïve and engineered cells were grown in suspension in ACF media (10 ug/L IGF1) for 4 passages on a 2 day passaging cadence (initial seeding density 0.5 Mcells/mL) as biological replicates (N=2). Positive controls included naive and empty vector (EV) engineer cells grown with media supplemented FGF2. Statistics: One way ANOVA was performed to compare test groups against empty vector (EV) grown in FGF2-containing media (100 µg/L): not significant (n.s.), p<0.05 (*), p<0.001 (), p<0.0001 (*), and p<0.0001 (****).

FIG. 12 shows viable cell density data shown for cultures on day 2 of passage 4. This data showed that thermostable FGF2 sequence variations based on computationally designed STAB sequence were unable to promote cell growth in FGF2-free media (FIG. 14). In contrast, each of the other variants of FGF2 resulted in VCDs similar to the controls.

For assessment of impact on biomass production, naïve and engineered cells were grown in suspension for 5 passages on a 2 day passaging cadence in media containing IGF1 (10 µg/L). Seeding density at each passage was 0.5M cells/mL; N=2. Naive and empty vector negative controls grown without media-supplemented FGF2 and did not survive to passage 5 (data not shown). On Day 2 of passage 5, packed cell volume (PCV) was taken by spinning 500 µL of culture at 1000×g for 5 minutes and collecting a PCV reading. The PCV reading can be converted to percent PCV by the following formula: % PCV=(PCV reading/sample volume)*100. Statistics: One way ANOVA was performed to compare test groups against empty vector (EV) grown in FGF2-containing media (100 µg/L): Not significant (n.s.), p<0.05 (*), p<0.001 (), p<0.0001 (*)p<0.0001 (****). Biomass production data (i.e., percent packed cell volumes) is shown in FIG. 13.

FIG. 13 shows percent packed cell volume for cultures on day 2 of passage 5. FIG. 13 shows that media supplemented with FGF2 was not required for the eight engineered cell lines to achieve packed cell volumes similar to the controls. The lower PCV's observed for chicken, bovine, and salmon FGF2 cell lines may be attributed to variations in the polyclonal population.

The engineered cells lines were assessed for their ability to secrete FGF2. An ELISA was performed on spent media (supernatants) from cell lines grown in suspension media (10 µg/L IGF1) with/without media supplemented FGF2 (100 µg/L); biological replicates N=2. Positive controls included spent media from naive and empty vector (EV) cells grown in FGF2 supplemented media. Negative controls included base media (Media) and spent media from naive cells grown in media not supplemented with FGF2. On Day 2 of Passage 5, cells were spun at 300×g for 5 minutes and the supernatant was removed for use in FGF2-ELISA kit to evaluate the concentration of FGF2 in the supernatant. For each condition, biological replicates (N=2) and technical replicates (N=4) were analyzed. FIG. 14 shows FGF2 concentration (pg/mL) in supernatants collected from the controls and the engineered cells.

Overall, this data showed that cells engineered to express FGF2 or variants of FGF2 could be grown in the absence of FGF2, exhibit robust growth as compared to controls, thereby showing that the engineered cells can be grown in culture media not supplemented with FGF2. Therefore, these cells lines are ideal for use in cell based meat products suitable for consumption because they can endure the requisite culture conditions (i.e., extensive passaging) needed to make these products all while reducing the costs associated with using the vast amounts of exogenous growth factors traditionally needed to make these products.

8.7. Example 5: Cell Lines Engineered to Express FGF Receptor Variants Proliferate without Media Supplemented FGF2

Chicken cells were engineered to express FGF receptors, including FGF1 receptors, FGF2 receptors, FGF3 receptors, and FGF4 receptors. FGF1 receptors included: FGFR1C, FGFR1C-N546K, FGFR1C-V561M, and myrist-FGFR1C-K656E. FGF2 receptors included: FGFR2, FGFR2-N550K, FGFR2-K660E, and FGFR2-3xMuts. FGF3 receptors included: FGFR3, FGFR3-N540K, FGFR3-K560E, FGFR3-N540K-K560E, and myrist-FGF3R-K560E. FGF4 receptors included: FGF4R, FGF4R-Y367C, and FGF4R-Y367C-K654E.

For assessment of impact the FGF receptors on proliferation, cells were grown over 4 passages in suspension culture with ACF media containing IGF1 (10 ug/L) and with/without FGF2 (100 ug/L) on a 2 day passaging cadence (seeding density 0.5 Mcells/mL) as biological replicates (N=2). Viable Cell Density (VCD) was taken on day 2 of passage 4 of culture (see FIG. 15). One way ANOVA was performed to compare test groups against empty Vector (EV) grown in FGF2-containing media (100 ug/L), Not significant (n.s.), p<0.05 (*), p<0.001 (), p<0.0001 (*), and p<0.0001 (****).

As shown in FIG. 15, three cell lines including myrist-FGFR1C-K656E, FGFR2 (wild type), myrist-FGFR3-K560E achieved higher viable cell densities in FGF2-free media than positive controls grown with FGF2. Multiple conditions archived growth comparable to Positive Controls including FGFR1C-N546K, FGFR1C-V561M, FGFR3-N540K, FGFR2-K650E, and FGFR3-N540K-K560E.

For assessment of impact of the FGF receptors on biomass production, cells were grown in suspension for 5 passages on a 2 day passaging cadence in media containing IGF1 (10 µg/L). Seeding density at each passage was 0.5M cells/mL; N=2. Naive and empty vector negative controls grown without media-supplemented with FGF2 did not survive to passage 5 (data not shown). On Day 2 of passage 5, packed cell volume (PCV) was taken by spinning 500 µL of culture at 1000×g for 5 minutes and collecting a PCV reading. The PCV reading can be converted to percent PCV by the following formula: % PCV=(PCV reading/sample volume)*100. One way ANOVA was performed to compare test groups against empty Vector (EV) grown in FGF2-containing media (100 ug/L), Not significant (n.s.), p<0.05 (*), p<0.001 (), p<0.0001 (*), and p<0.0001 (****).

As shown in FIG. 16, shows that media supplemented with FGF2 was not required for the eight engineered cell lines to achieve packed cell volumes similar to the controls.

The engineered cells lines were assessed for their ability to secrete FGF2. An ELISA was performed on spent media (supernatants) from cell lines grown in suspension media (10 µg/L IGF1) with/without media supplemented FGF2 (100 µg/L); biological replicates N=2. Positive controls included spent media from naive and empty vector (EV) cells grown in FGF2 supplemented media. Negative controls included base media (Media) and spent media from naive cells grown in media not supplemented with FGF2. On Day 2 of Passage 5, cells were spun at 300×g for 5 minutes and the supernatant was removed for use in FGF2-ELISA kit to evaluate the concentration of FGF2 in the supernatant. For each condition, biological replicates (N=2) and technical replicates (N=4) were analyzed. FIG. 17 shows FGF2 concentration (pg/mL) in supernatants collected from the controls and the engineered cells.

Overall, this data showed that cells engineered to express FGF1 receptor, FGF2 receptors, FGF3 receptors, or FGFR4 receptors (or variants thereof) could be grown in the absence of FGF2, exhibit robust growth as compared to controls, thereby showing that the engineered cells can be grown in culture media not supplemented with FGF2. Therefore, these cells lines are ideal for use in cell-based meat products and cell-based food products suitable for consumption because they can endure the requisite culture conditions (i.e., extensive passaging) needed to make these products all while reducing the costs associated with using the vast amounts of exogenous growth factors traditionally needed to make these products.

8.8. Summary of Examples 2-5

Overall, this data suggests that cell lines engineered to express FGF2-WT, or cells engineered to express FGF2-WT with various secretion signals, and grown in the absence of FGF2, exhibit robust growth as compared to controls, thereby showing that the engineered cells can be grown in culture media not supplemented with FGF2. Therefore, these cells lines are ideal for use in cell-based meat products and cell-based food products suitable for consumption because they can endure the requisite culture conditions (i.e., extensive passaging) needed to make these products all while reducing the costs associated with using the vast amounts of exogenous growth factors traditionally needed to make these products.

8.9. Example 6: Cells Engineered to Express IGF1 and IGF1 Receptors (or Variants Thereof) Significantly Improve Cell Density and Packed Cell Volumes This example was designed to assess how expression of exogenous IGF1 impacted cell density and packed cell volume. This experiment was also designed to assess how cells characterized as IGF1$^{low}$ or IGF1$^{high}$ contributed to cell density and packed cell volume.

8.9.1. Assessment of IGF1 and IGF1 Receptor Variants

In a first set of experiments, Chicken cells were engineered to express IGF1 WT (SEQ ID NO: 16), IGF1-trunc., IGF1R, or IGF1R-R1353H. These cells were grown in suspension with ACF media (100 ug/L FGF2) without media supplemented IGF1. Cells were seeded at 0.5E6 cells/mL (N=2) and passaged every 2 days over 4 passages. Viable cell density (FIG. 18) and packed cell volume (PCV (FIG. 19) were assessed to help determine how the engineered cells performed compared to controls.

Viable Cell Density (VCD) of day 2, passage 4 is provided in FIG. 18. One way ANOVA performed compared to IGF1 expressing cell line grown in IGF1-free media, Not significant (n.s.), p<0.05 (*), p<0.001 (), p<0.000 1 (*), and p<0.0001 (****). As shown in FIG. 18, expression of IGF1 receptor variations or truncated IGF1 was not able to boost cell growth in IGF1-free media. In contrast, cells engineered to express wild type IGF-1 produced VCD similar to the controls (FIG. 18).

Packed cell volume (PCV) of day 2, passage 3 is provided in FIG. 19. PCV determined by spinning 500 μL of culture at 1000×g for 5 minutes and collecting a PCV reading. The PCV reading was converted to percent PCV by the following formula: % PCV=(PCV reading/sample volume)*100. One way ANOVA performed compared to IGF1 expressing cell line grown in IGF1-free media, Not significant (n.s.), p<0.05 (*), p<0.001 (), p<0.000 1 (*), and p<0.0001 (****). As shown in FIG. 19, expression of IGF1 receptor variations or truncated IGF1 was not able to boost cell growth in IGF1-free media. In contrast, cells engineered to express wild type IGF-1 produced PCV similar to the controls (FIG. 19).

This data showed that chicken cells engineered to express IGF1 yield produced the most favorable cell density and packed cell volume among the conditions tested. Chicken cells engineered to express IGF1 were selected for additional analysis.

8.9.2. Assessment of IGF1$^{low}$ and IGF1$^{high}$ Cells

In another set of experiments, chicken cells were engineered to express either an FC550A empty vector ("EV") control or a Phi31 vector containing an IGF1 wild type (IGF1-WT) sequence (SEQ ID NO: 16). Transduced cells were sorted into "low" expressing cells and "high" expressing cells based on RFP expression. RFP expression served as a proxy for IGF1 expression. "Low-expression" cells and "high-expression" cells were separately plated in suspension format in TPP tubes. Controls included: cell lines not transfected ("Naïve") and the EV control; where the control cell lines were grown in serum-free media supplemented with and without IGF1.

FIGS. 20A-20B shows growth curves over 3 passages for cell lines grown in ACF media supplemented with 0 μg/L or 10 μg/L IGF1. Here, cells were seeded at 0.5E6 cells/mL and passaged on a 2-day cadence. Cell counts were taken daily using ViCell BLU. Each condition was grown as a biological replicate (N=2).

As shown in FIG. 20A, cells engineered to expressed low levels of IGF1 (IGF1$^{Low}$) grown in 0 μg/L IGF1 had robust growth curves as compared to controls (i.e., Naïve and EV) not grown in the presence of IGF1. In fact, the cells engineered to express IGF1 (IGF1$^{Low}$) had growth curves similar to the controls (i.e., Naïve and EV) grown in 10 μg/L IGF1 (see FIG. 20A). This data suggests that IGF1$^{Low}$ cells are able to produce enough of IGF1 such that supplementing the culture media with IGF1 is not required.

FIG. 20B show cells engineered to expressed high levels of IGF1 (IGF1$^{High}$) grown in 0 μg/L IGF1 had robust growth curves as compared to controls (i.e., Naïve and EV) not grown in the presence of IGF1. Similar to the IGF1$^{Low}$ cells, the cells engineered to express high levels of IGF1 (IGF1$^{High}$) had growth curves similar to the controls (i.e., Naïve and EV) grown in 10 μg/L IGF1 (see FIG. 20B). This data suggests that IGF1$^{high}$ cells are able to produce enough of IGF1 such that supplementing the culture media with IGF1 is not necessary.

The IGF1$^{low}$ and IGF1$^{high}$ cultures were assessed for their ability to secrete IGF1 into the culture medium. For these experiments, an ELISA was performed on spent media (supernatants) from cell lines grown in ACF media (100 ug/L FGF2) with/without media supplemented IGF1 (10 μg/L). Positive controls included spent media from Naïve cells, empty vector (EV) cells grown in IGF1 supplemented media, and EV cells grown in base media (100 ug/L FGF2). Negative controls included base media (Media) and spent media from naive cells grown without IGF1. On Day 2 of Passage 3, cells were spun at 300×g for 5 minutes and the supernatant was removed for use in IGF1-ELISA kit to evaluate the concentration of IGF1 in the supernatant. For each condition, biological replicates (N=2) and technical replicates (N=4) were analyzed. One way ANOVA was performed to compare to IGF1 expressing cell lines to empty vector (EV) controls: not significant (n.s.), p<0.05 (*), p<0.001 (), p<0.000 1 (*)p<0.0001 (****).

FIG. 21A shows IGF1 ELISA data for IGF1$^{low}$ cells. Supernatants from IGF1$^{low}$ cells had 12.93 μg/L of IGF1 when grown in media not supplemented with IGF1 and 20.58 μg/L of IGF1 when grown in media supplemented with IGF1 (see FIG. 21A). FIG. 21B shows IGF1 ELISA data for IGF1$^{high}$ cells. Supernatants from IGF1$^{high}$ cells had 35.27 μg/L of IGF1 when grown in media not supplemented with IGF1 and 45.32 μg/L of IGF1 when grown in media supplemented with IGF1 (see FIG. 21B). Overall, this data showed robust IGF1 secretion into the culture media by the engineered cells, and the results were as expected with IGF1$^{low}$ secreting lower amounts of IGF1 than IFG1$^{high}$.

IGF1$^{low}$ cells were assessed for population doubling time (FIG. 22), viable cell density (FIG. 23A) and packed cell volume (FIG. 23C). IGF1$^{high}$ cells were assessed for viable cell density (FIG. 23B) and packed cell volume (FIG. 23D).

FIG. 22 shows doubling time (hours) for chicken cells engineered to express IGF1 (IGF1$^{low}$) grown in media supplement without ("−") and with ("+") IGF1. Cells were grown with or without 10 μg/L IGF1 in ACF media (100 ug/L FGF2) over 3 passages. Cells seeded at 0.5E6 cells/mL and passaged on a 2-day cadence (N=2). Doubling time was calculated by applying exponential growth equation Y=Y0*exp(k*x) to proliferation profiles obtained on the third passage. Where Y0 is the starting population, k is the rate constant, and Doubling Time (hr) is the time need for the population to double, calculated as ln(2)/k. Where Y0 is the starting population, k is the rate constant, and Doubling Time (hr) is the time need for the population to double, calculated as ln(2)/k. One way ANOVA was performed: not significant (n.s.), $p<0.05$ (*), $p<0.001$ (), $p<0.0001$ (*), and $p<0.0001$ (****). As shown in FIG. 22, the addition of media-supplemented IGF1 to IGF1$^{Low}$ culture did not impact cell doubling time.

Further analysis of the suspension cultures at day 2 during the third passage revealed that both IGF1$^{low}$ cells (FIG. 23A) and IGF1$^{high}$ cells (FIG. 23B) had statistically significant differences in viable cell densities (VCD) as compared to the controls. In particular, IGF1$^{Low}$ cells had statistically significant greater VCDs as compared to controls (i.e., Naïve and EV) grown in either 0 μg/L IGF1 or 10 μg/L IGF1 (see FIG. 23A). Similarly, IGF1$^{high}$ cells had statistically significant greater VCDs as compared to both controls (i.e., Naïve and EV) grown in 0 μg/L IGF1 but was only statistically significant as compared to the EV control when controls were grown in 10 μg/L IGF1 (see FIG. 23B). Statistically significant differences between the means were determined by an ANOVA one-way test with Dunnett's exclusion with P-values indicated with asterisks. * $p<0.05$;  $p<0.001$; * $p<0.0005$; **** $p<0.0001$; and ns=not significant.

Applicant then looked at Pack Cell Volumes (PCV), which is a proxy for cell biomass. PCV analysis for the suspension cultures at day 3 during the third passage revealed that both IGF1$^{low}$ cells (FIG. 23C) and IGF1$^{high}$ cells (FIG. 23D) had statistically significant differences in PCV as compared to the controls. To measure PCV, 500 μL of culture volume was collected in a small PCV tube and centrifuged at 1000×g for 5 minutes. Each condition was measured in duplicate (biological replicates with technical replicates N=4).

As shown in FIG. 23C, IGF1$^{low}$ cells had statistically significant greater PCVs as compared to controls (i.e., Naïve and EV) grown in either 0 μg/L IGF1 or 10 μg/L IGF1. IGF1$^{high}$ cells had statistically significant greater PCVs as compared to both controls (i.e., Naïve and EV) grown in 0 μg/L IGF1 but was only statistically significant as compared to the EV control when controls were grown in 10 μg/L IGF1 (see FIG. 23D). Statistically significant differences between the means were determined by an ANOVA one-way test with Dunnett's exclusion with P-values indicated with asterisks. * $p<0.05$;  $p<0.001$; * $p<0.0005$; **** $p<0.0001$; and ns=not significant.

Overall, FIGS. 23C-23D show that cells engineered to express IGF1 (e.g., IGF1$^{Low}$ and IGF1$^{High}$) actually outperformed (i.e., enable greater PCV) cells grown in the presence of IGF1. As PCV is a proxy for cell biomass, this data suggest that the engineered cells are ideal for use in cell-based meat products and cell-based food products suitable for consumption because they produce the amounts of cell biomass needed for these products and can do so in the absence of exogenous IGF1.

8.9.3. Assessment of Impact of Media Supplemented IGF1 on IGF1$^{low}$ Cultures

FIG. 26 shows doubling time (hours) for chicken cells engineered to express IGF-1 (IGF1$^{low}$) grown in media supplement without ("−") and with ("+") IGF1. Cells were grown with or without 10 μg/L IGF1 in ACF media (100 ug/L FGF2) over 3 passages. Cells seeded at 0.5E6 cells/mL and passaged on a 2-day cadence (N=2). Doubling time was calculated by applying exponential growth equation Y=Y0*exp(k*x) to proliferation profiles obtained on the third passage. Where Y0 is the starting population, k is the rate constant, and Doubling Time (hr) is the time need for the population to double, calculated as ln(2)/k. Where Y0 is the starting population, k is the rate constant, and Doubling Time (hr) is the time need for the population to double, calculated as ln(2)/k. One way ANOVA was performed: not significant (n.s.), $p<0.05$ (*), $p<0.001$ (), $p<0.0001$ (*), and $p<0.0001$ (****). As shown in FIG. 24, the addition of media-supplemented IGF1 to IGF1$^{Low}$ culture did not impact cell doubling time.

FIG. 25 shows biomass (as PCV (g/L)) for chicken cells engineered to express IGF-1 (IGF1$^{low}$) grown in media supplement without ("−") and with ("+") IGF1. Cells were grown with or without 10 μg/L IGF1 in ACF media (100 ug/L FGF2) over 3 passages. Cells seeded at 0.5E6 cells/mL and passaged on a 2-day cadence (N=2). PCV was measured on Day 2 of Passage 3 using 500 μL of culture volume and centrifuged at 1000×g for 5 minutes. One way ANOVA performed, Not significant (n.s.), $p<0.05$ (*), $p<0.001$ (), $p<0.0001$ (*), $p<0.0001$ (****). One way ANOVA was performed: Not significant (n.s.), $p<0.05$ (*), $p<0.001$ (), $p<0.0001$ (*)$p<0.0001$ (****). As shown in FIG. 25, the addition of media-supplemented IGF1 to IGF1$^{Low}$ culture did not impact PCV.

Taken together, FIGS. 20A-20B, FIG. 21A-21B, FIG. 22, FIGS. 23A-23D, FIG. 24, and FIG. 25 show that IGF1$^{Low}$ and IGF1$^{High}$ cells not only exhibit robust growth independent of exogenous IGF1 (i.e., media supplemented with IGF1) but also outperform (i.e., produce higher VCD) cells grown in the presence of IGF1. This data suggests these cells lines are ideal for use in cell-based meat products and cell-based food products suitable for consumption because they can endure the requisite culture conditions (i.e., extensive passage) needed to make these products—all while reducing the costs associated with using the vast amounts of exogenous growth factors traditionally needed to make these products.

8.10. Example 7: Cells Engineered for Complete Growth Factor-Independence Using IGF1 and FGF2

In this example chicken cells were engineered to assess whether expression of IGF1 WT and an FGF2 variant enables growth-factor independence (no requirement for growth factors in culture media).

Chicken cells engineered to express IGF1 WT (IGF1 amino acid sequence of were engineered with an FC550A empty vector ("EV") control or a Phi31 vector containing one or more FGF2 variants, including chicken (Chicken FGF2), bovine (Bovine FGF2), salmon (Salmon FGF2), heat stable variants (FGF2-Q68I-N114G, FGF2-Q68I-C99S-N114G), secretion tagged variants (ggIL2-FGF2, hIL2-co1-ggFGF2(xMet)) or variants that preserve amino acids for non-canonical secretion (FGF2-C77-Y81)). Controls consisted of dual empty vector (EVmRuby and EVeBFP2) that were used to construct the IGF1 and FGF2 variants, respectively, and were grown with or without growth factors IGF1 (10 μg/L) and FGF2 (100 μg/L) (see FIG. 26). Cells were grown in suspension over 4 passages using a 2 day passaging cadence at initial seeding density of 0.5E6 cells/mL (N=2). One way ANOVA performed compared to EV control in growth factor-free media, Not significant (n.s.), p<0.05 (*), p<0.001 (), p<0.0001 (*), and p<0.0001 (****).

As shown in FIG. 26, each cell line expressing IGF1 WT and a FGF2 variant resulted in increased viable cell density as compared to the controls. Overall, this data showed that cell lines engineered to express IGF1 WT and a FGF2 variant significantly increased the viable cell density as compared to controls.

8.11. Example 8: Cells Engineered for Complete Growth Factor-Independence Using IGF1 and a FGF2 Receptor In this example chicken cells were engineered to assess whether expression of IGF1 WT and an FGF2 receptor variant enables growth-factor independence (no requirement for growth factors in culture media).

Chicken cells engineered to express IGF1 WT (IGF1 amino acid sequence of were transduced with an FC550A empty vector ("EV") control or a Phi31 vector containing one or more of: FGFR1c-N546K, FGFR1c-V561M, myrist-FGFR1c-K656E, FGFR3-N540K, FGFR3-K650E, FGFR3-N540K-K650E, or myrist-FGFR3-K650E. Controls consisted of dual empty vector (EVmRuby and EVeBFP2) that were used to construct the IGF1 and FGF2 variants, respectively, and were grown with or without growth factors IGF1 (10 μg/L) and FGF2 (100 μg/L) (see FIG. 27). Cells were grown in suspension over 3 passages using a 2 day passaging cadence at initial seeding density of 0.5E6 cells/mL (N=2). One way ANOVA was performed compared to EV control in growth factor-free media: not significant (n.s.), p<0.05 (*), p<0.001 (), p<0.0001 (*), and p<0.0001 (****).

As shown in FIG. 27, each cell line expressing IGF1 WT and a FGF receptor variant resulted in increased viable cell density as compared to the controls. Overall, this data showed that cell lines engineered to express IGF1 WT and a FGF receptor variant significantly increased the viable cell density as compared to controls.

8.12. Example 9: Cells Engineered for Complete Growth Factor-Independence Using FGF2 Receptors In this example chicken cells were engineered to assess whether expression of an FGF2 receptor alone was sufficient to enable growth-factor independence (no requirement for growth factors in culture media).

Chicken cells were engineered to expressed FGFR2 and were grown in suspension in a 3 passage proliferation study on a 2-day passaging cadence and initial seeding density of 0.5E6 cells/mL (N=2). Cells were grown in media with or without IGF1 (10 ug/L) and FGF2 (100 ug/L) (see FIG. 28). Naïve (no transduced chicken cells) were used as controls. FIG. 28 shows viable cell density at day 2 of passage 3. One way ANOVA performed compared to Naive controls, Not significant (n.s.), p<0.05 (*), p<0.001 (), p<0.000 1 (*) p<0.0001 (****).

As shown in FIG. 28, engineering the chicken cells to express FGFR alone was, to Applicant's surprise, sufficient to enable both FGF2 and IGF independent proliferation, albeit at slight lower levels than the naïve chicken cells grown in the presence of FGF2 and IGF1.

8.13. Example 10: Cells Engineered for Complete Growth Factor-Independence Using FGF2

In this example chicken cells were engineered to assess whether expression of an FGF2 variant alone was sufficient to enable growth-factor independence (no requirement for growth factors in culture media).

Chicken cells were engineered to express: FGF2 (wild type (FIG. 31A): chicken FGF2, bovine FGF2, salmon FGF2; heat stability point mutations (FIG. 31B): chicken FGF2-Q68I-N114G or chicken FGF2-Q68I-C99S-N114G; and FGF2 with a secretion signal or variant to preserve amino acid for non-canonical secretion (FIG. 31C): chicken FGF2-C77Y8a, ggIL2-ggFGF2, and hIL2-co1-(xMet) ggFGF2). These cells were grown in growth factor-free media (ACF media) over 4 passages on 2 day passaging cadence with initial seeding density of 0.5E6 cells/mL (N=2). Naive and empty vector (EV) controls were grown in growth factor containing media (10 μg/L IGF1 and 100 μg/L FGF2) or growth factor-free media (0 μg/L IGF1 and 0 μg/L FGF2). FIGS. 29A-29C shows viable cell density measurements taken over the course of about 200 hours in culture. Notably, controls grown in growth factor free media died by passage 3 (see FIGS. 29A-29C). FIG. 30 shows summary of VCD data from FIGS. 29A-29C at passage 4 day 2 (N=2). One way ANOVA was performed compared to empty vector control in growth factor containing media: not significant (n.s.), p<0.05 (*), p<0.001 (), p<0.0001 (*), and p<0.0001 (****).

Overall, this data showed that chicken cells engineered to express FGF2 from different species (chicken, bovine, and salmon) can be used to maintain VCD (viable cell density) over 200 hours in culture as compared to controls, and in some instances, increase VCD compared to controls (FIG. 29A and FIG. 30). This data also showed that chicken cells engineered to express FGF2 variants that have amino acid substitutions that increase heat stability can be used to maintain VCD (viable cell density) over 200 hours in cultures as compared to controls, and in some instances, increase VCD compared to controls (FIG. 29B and FIG. 30). Lastly, this data showed that chicken cells engineered to express FGF2 designed with secretion signals or variants to preserve non-canonical secretion could be used to maintain VCD (viable cell density) over 200 hours in cultures as compared to controls, and in some instances, increase VCD compared to controls (FIG. 29C and FIG. 30).

8.14. Example 11: Cells Engineered for Complete Growth Factor-Independence Using FGF2 Receptors Alone In this example chicken cells were engineered to assess whether expression of an FGF2 receptor variant alone was sufficient to enable growth-factor independence (no requirement for growth factors in culture media) (see FIGS. 31A-31C and FIG. 32).

In a first set of experiments, chicken cells were engineered to express an FGFR1c-N546K, FGF1Rc-V561M, and myrist-FGF1Rc-K656E and were grown in growth factor-free media over 4 passages on 2 day passaging cadence with initial seeding density of 0.5E6 cells/mL (N=2) (see FIG. 31A). Naive and empty vector (EV) controls were grown in growth factor containing media (10 μg/L IGF1 and 100 μg/L FGF2) or growth factor-free media (0 μg/L IGF1 and 0 μg/L FGF2).

FIG. 31A and FIG. 32 show viable cell density (VCD) for chicken cells engineered to express an FGFR1c-N546K, FGF1Rc-V561M, and myrist-FGF1Rc-K656E over 4 passages. Controls grown in growth factor free media died by passage 3 (see FIG. 31A). FIG. 31A shows daily viable cell densities over 4 passages in ACF media. Overall, this data showed that chicken cells engineered to express these FGFR1c variants can be used to maintain VCD (viable cell density) over 200 hours similar to controls, and in some instances, increase VCD compared to controls.

In a second set of experiments, chicken cells were engineered to express FGFR2 and were grown in growth factor-free media over 4 passages on 2 day passaging cadence with initial seeding density of 0.5E6 cells/mL (N=2) (see FIG. 31B). Naive and empty vector (EV) controls were grown in growth factor containing media (10 μg/L IGF1 and 100 μg/L FGF2) or growth factor-free media (0 μg/L IGF1 and 0 μg/L FGF2).

FIG. 31B and FIG. 32 show viable cell density (VCD) for chicken cells engineered to express an FGFR2 over 4 passages. Controls grown in growth factor free media died by passage 3 (see FIG. 31B). Overall, this data showed that chicken cells engineered to express FGFR2 can be used to maintain VCD (viable cell density) over 200 hours in culture similar to controls, and in some instances, increase VCD compared to controls.

In a third set of experiments, chicken cells were engineered to express FGFR3-N540K, FGFR3-K650E, FGFR3-N540K-K560E, or myrist-FGFR3-K650E and were grown in growth factor-free media over 4 passages on 2 day passaging cadence with initial seeding density of 0.5E6 cells/mL (N=2) (see FIG. 31C). Naive and empty vector (EV) controls were grown in growth factor containing media (10 μg/L IGF1 and 100 μg/L FGF2) or growth factor-free media (0 μg/L IGF1 and 0 μg/L FGF2).

FIG. 31C and FIG. 32 show viable cell density (VCD) for chicken cells engineered to express these FGFR3 variants over 4 passages. Controls grown in growth factor free media died by passage 3 (see FIG. 31C). Overall, this data showed that chicken cells engineered to express FGFR3 (or variants thereof) can be used to maintain VCD (viable cell density) over 200 hours in culture similar to controls, and in some instances, increase VCD compared to controls.

To Applicant's surprise, expression of FGF2R receptors alone enabled the serum free proliferation of chicken cells without the need for IGF1 and FGF2 exogenous supplementation. Cell growth is typically limited in the absence of IGF1 and is needed to achieve robust cell proliferation and high cell densities.

8.15. Example 12: Cells Engineered to Express PDGF (or Variants Thereof) or PDGF Receptor (or Variants Thereof) Enabled Tissue Formation in Growth Factor-Free Media This experiment was designed to assess how expressing PDGF (or PDGF variants) or PDGF receptor (or PDGF receptor variants) enabled tissue formation (as measured by Wet Mass per Area (μg/cm2) (see FIG. 33)).

In particular, chicken cells were transduced with either an FC550A empty vector ("EV") control or a Phi31 vector containing PDGFRa-D842V, PDGF(WT) or PDGF-211*. Controls included: cell lines not transfected ("Naïve") and the EV control. Engineered cells and controls were cultured in roller bottles over 14 day period in serum free media. Controls were grown with or without 50 μg/L PDGF (N=4). Tissue was harvested after 14 days culture and weighed for wet mass and normalized to growth area.

FIG. 33 shows chicken cells engineered to express PDG-FRa-D842V, PDGF(WT) or PDGF-211* formed tissue without media supplemented growth factors and was comparable to positive controls. Overall, this data showed that chicken cells engineered to express PDGF (or a variant thereof) or a PDGF receptor (or a variant thereof) formed tissue when grown in media not supplemented with growth factors and did so in comparable volume to positive controls. Therefore, these cells lines are ideal for use in cell-based meat products and cell-based food products suitable for consumption because they can endure the requisite culture conditions (i.e., extensive passaging) needed to make these products all while reducing the costs associated with using the vast amounts of exogenous growth factors traditionally needed to make these products.

8.16. Example 13: Methods for Producing Cell-Based Meat Suitable for Consumption The manufacturing of cultured muscle cells suitable for consumption, in one exemplary protocol, can comprise:

In exemplary first step, cells are engineered to express the coding sequence of a growth factor ligand (e.g., FGF2, IGF1, PDGF, or a combination thereof), a growth factor receptor or activated growth factor receptor (e.g., a FGFR, an IGF1R, or an PDGFR), where the cells are from a livestock, poultry, game, or an aquatic animal species. Engineered cells are adapted to suspension culture and cultured in a cultivation infrastructure (e.g., any of the cultivation infrastructures described herein), seeded onto a substrate consisting of peptide-coated tissue-culture treated plastic in a standard growth medium at a density of $7.5 \times 10^3$ cells/cm² and cultured at 37° C. under 5% CO2 atmospheric conditions. As cultures approach 80% confluence, cells are enzymatically dissociated and the cells are expanded. This process is repeated until the total number of cells harvested following dissociation exceeds about $1.0 \times 10^8$ cells, or more. The engineered cells are cryopreserved and stored in a cryopreserved cell bank. Cells harvested in quantities equal to or exceeding $1.0 \times 10^8$ cells.

In an exemplary second step, the cryopreserved cells are seeded and cultivated in a cultivation infrastructure. In accordance with the cultivation scale desired, one or more vials from the master cell bank is rapidly thawed to room temperature. The cryopreservation medium is removed from the cells by a 5-minute, 300×g centrifugation step. Cells are suspended in standard growth medium and seeded onto a gelatin-coated cultivation substrate in standard growth medium as before, except that, on the final passage prior to harvest, the cells are permitted to proliferate to 100% confluence on the cell culture substrate. The cells are adapted for suspension culture in growth media to facilitate expansion of the cells. Following expansion, the cells are adapted to adherent culture in a cultivation infrastructure. The growth medium is exchanged for differentiation medium, thereby inducing myogenic differentiation where the differentiated cells form myocytes and multinucleated myotubes; and the myocytes and myotubes are cultured to generate skeletal muscle fibers.

In an exemplary fourth step, the engineered cells are harvested for dietary consumption. After the cells have proliferated to confluence, the culture medium is removed, and the adherent cell cultures are rinsed with phosphate buffered saline. Next, the confluent biomass of adherent cells are mechanically, fluidically, enzymatically, or metabolically dissociated from the substrate by means of a scraping device, pressurized fluid, or a harvest media. The dissociated biomass is collected into centrifuge tubes, pelleted to remove excess liquid, and processed for food product preparation.

8.17. Example 14: Procurement of Engineered Cells and Growth of Cells into a Cell Mass FIGS. 34A-34D and the following accompanying paragraphs describe procurement of cells and growth of cells into a cell mass in accordance with one or more embodiments. Generally, FIGS. 34A-34D illustrate a process of collecting cells from an animal, growing cells in a favorable environment, banking successful cells, and collecting cells into a cell mass followed by de-wetting and/or other treatments.

As illustrated by step 3402 in FIG. 34A, tissue is collected from a living animal via biopsy. In particular, stem cells, mesenchymal progeny, ectoderm lineage, and/or endoderm lineages can be isolated from the removed tissue. In some implementations of the present disclosure, tissue, such as fat and others, are processed to isolate stem cells, mesenchymal, ectoderm, and/or endoderm progeny or lineage cells. As illustrated, tissue 3404 is removed from an animal. In some examples, the tissue 3404 is removed from a living animal by taking a skin sample from the living animal. For instance, skin or muscle samples may be taken from a chicken, cow, fish, shellfish or another animal.

Cells may be extracted from the tissue 3404 that was removed from the animal. More specifically, the tissue 3404 is broken down by enzymatic and/or mechanical means. To illustrate, FIG. 34A includes digested tissue 3406 that comprises the cells to be grown in cultivation.

Cells in the digested tissue 3406 may be proliferated under appropriate conditions to begin a primary culture. As illustrated in FIG. 34A, cells 3408 from the digested tissue 3406 are spread on a surface or substrate and proliferated until they reach confluence. As shown in FIG. 34A, in some cases, cells 3412 have reached confluence when they start contacting other cells in the vessel, and/or have occupied all the available surface or substrate.

In some examples, cells are stored and frozen (i.e., banked) at different steps along the cell culture process. Cryopreservation generally comprises freezing cells for preservation and long-term storage. In some implementations, tissue and/or cells are removed from a surface or substrate, centrifuged to remove moisture content, and treated with a protective agent for cryopreservation. For example, as part of cryopreservation, tissues and cells are stored at temperatures at or below −80 C. The protective agent may comprise dimethyl sulfoxide (DMSO) or glycerol.

Cells stored through cryopreservation may be used to replenish working cell stock. For instance, while a portion of the digested tissue 3406 is used as the cells 3408 spread on a surface or substrate, the remaining or excess digested tissue 3406 is transferred to cryovials 3410 for storage.

Furthermore, the cells 3412 may be banked once reaching confluence and stored in cryovials 3414.

Once the cells 3412 have reached confluence, or just before the cells 3412 have reached confluence (e.g., occupation of about 80% of the substrate), the disclosed process comprises a series of cell passage steps. During cell passage, the cells 3412 are divided into one or more new culture vessels for continued proliferation. To illustrate, the cells 3412 may be diluted or spread on one or more surfaces or substrates to form the cells 3418. The cells 3418 are then grown 3416 to confluence, or just before confluence.

The cycle of dividing the cells 3412 into the cells 3418 for continued proliferation in new culture vessels may be repeated for a determined number of cycles. Typically, cell lines derived from primary cultures have a finite life span. Passaging the cells allows cells with the highest growth capacity to predominate. In one example, cells are passaged for five cycles to meet a desired genotypic and phenotypic uniformity in the cell population.

In some implementations, the disclosed method comprises immortalizing cells that have been grown and passaged for the determined number of cycles. For instance, the cells 3418 may be immortalized. As shown in FIG. 34B, cells 3420 have demonstrated a preferred growth capacity to proceed to immortalization. To achieve immortalization, the disclosed process transfects the cells 3420 with genes of interest. In one example telomerase reverse transcriptase (TERT) is introduced to the cells 3420. In some embodiments, the cells may be subjected to a selection process as known by those skilled in the art. The cells 3420 may then be passaged for a predetermined set of passaging cycles. In one example passaging cycle, the cells 3420 are grown to (or near) confluence 3424, then they are reseeded in new growth vessels, preserved in vials 3422, or some combination of both. The disclosed process may include any number of passaging cycles to ensure that the cells have reached immortality (e.g., can passage 60+ times without senescing), a target growth capacity, and/or a target quantity for banking. For example, cells may be passaged until they have reached a passage level of 100 (e.g., have been passaged for 100 passaging cycles). In another example, cells are passaged until they reach a population doubling level of 100.

Cells that have reached immortality or a target growth capacity by living through a target passage level may be adapted to suspension culture. In one example, a suspension culture media and agitation of cells in this suspension environment help cells to adapt and start proliferating in the new growth environment. The cells adapted to suspension 3426 may be stored in cryovials 3428 for cryopreservation and banking. Cells in suspension 3426 will begin to proliferate and the process begins a series of dilute and expand steps.

During dilution and expansion, cells are moved from growth vessels into newer, and progressively larger, growth vessels. For example, cells in suspension 3426 may begin in a single tube. The cells will proliferate and increase in cellular density. Once the cells have reached a target cell number (i.e., viable cell density (VCD) at desired volume), they are diluted and moved to a larger growth vessel. Optionally, the cells are banked in cryovials throughout expansion. For example, once cells in suspension reach a maximum VCD, the cells may begin to leave exponential growth due to overcrowding. After reaching a target density, the suspension cells may be transferred to a larger vessel 3430 and diluted with additional media. The dilute-and-expand steps are repeated using progressively larger vessels (e.g., the vessel 3431 and the vessel 3432) and/or progressive dilution until the cells reach a production-ready volume. For example, cells may be production ready at about a 1,000-100,000 liter scale at 5 million cells per mL. The cells may be banked in cryovials at any of the dilution and expansion cycles.

As part of preparing cells to form cell-based-meat products, the disclosed process comprises growing the cells as an adherent culture. Generally, cells that are grown attached to a substrate form a texture that more closely resembles tissue found in conventional meat. Thus, the cells may be transferred from growth in suspension to growth in an adherent reactor. For example, the cells grown in suspension in the vessel 3432 may be transferred to growth on a substrate. FIG. 34C illustrates a bioreactor system comprising a plurality of adherent bioreactors 3448 connecting in parallel to a media vessel 3440. The media vessel 3440 holds the cells grown in suspension media. In some implementations, cells from the vessel 3432 are transferred directly to a cell culture media (or just "media") vessel 3440. In one example, the media vessel 3440 comprises the vessel 3432. The adherent bioreactors 3448 may comprise pipe-based bioreactors. As shown, a plurality of valves 3444 is secured to the plurality of adherent bioreactors 3448 to enable individual use and access of each of the adherent bioreactors 3448. For instance, to limit flow to only a first bioreactor of the plurality of adherent bioreactors 3448, the valve 3444 of the first bioreactor is opened while the remaining valves 3444 are closed. Furthermore, the bioreactor system can include a directional valve 3442 for changing between flow directions.

In some implementations, and as illustrated in FIG. 34C, cells (e.g., adherent cells or suspension adapted cells) are prepared by flowing cells suspended in media (e.g., cell culture media) across substrates in the plurality of adherent bioreactors 3448. More particularly, cells from the media vessel 3440 may contact or land on the substrates in the plurality of adherent bioreactors 3448. Cells and media that flowed through the adherent bioreactors 3448 are cycled back to the media vessel 3440. The media and cells can be cycled through the adherent bioreactors 3448 until a target adherent cell density is reached. For instance, in some implementations, the disclosed method comprises measuring a cell density of outflow from the adherent bioreactors 3448 to infer an adherent cell density.

The cells grow into adherent tissue within the adherent bioreactors 3448. Once they have grown to a target density, either according to a learned timing or according to a measured fluctuation in cell metabolism of components such as glucose and oxygen, then the adherent tissue is ready for removal. The removal process of the disclosed method uses a high-pressure flow to shear the adherent tissue off the substrate surfaces. In one example, wash buffer from a wash tank 3456 is flowed across the substrates in the adherent bioreactors 3448. The wash buffer and cell mixture are flowed through a filter 3452 where the cells are collected into one or more cell masses 3454.

The cell masses 3454 may be further processed to adjust moisture content. FIG. 34D illustrates an example apparatus for reducing moisture content in the cells. In particular, FIG. 34D illustrates a pressure apparatus 3460 that compresses the cell masses 3458a and 3458b. While FIG. 34D illustrates a mechanical method for adjusting moisture content of the cell masses 3458a and 3458b, other methods may be used to adjust moisture content. For example, the cell masses 3458a and 3458b may be mixed with a drying agent, vacuum dried, centrifuged, or otherwise dried. A moisture-adjusted-cell mass may be transferred to a container 3462 for additional processing. For example, the cell mass 3458a or 3458b may be removed from the container 3462 to be formed into a cell-based-meat product.

9. SEQUENCE APPENDIX

| SEQ ID NO: | Description | Sequence |
|---|---|---|
| 1 | ggFGF2-Wild Type (chicken) | MAAGAAGSITTLPALPDDGGGGAFPPGHFKDPKRLYCKNGGFFLRINPDGRVD GVREKSDPHIKLQLQAEERGVVSIKGVSANRFLAMKEDGRLLALKCATEECFFF ERLESNNYNTYRSRKYSDWYVALKRTGQYKPGPKTGPGQKAILFLPMSAKS* |
| 2 | ggFGF2STAB (Thermal Stabilized) | MAAGAAGSITTLPALPDDGGGGAFPPGHFKDPKRLYCKNGGFFLLINPDGRVD GTREKSDPFIKLQLQAEERGVVSIKGVSANRFLAMKEDGRLYALKYATEECFFF ERLEENNYNTYRSRKYSDWYVALKRTGQYKPGPKTGPGQKAILFLPMSAKS* |
| 3 | BM40sp-ggFGF2 | MRAWIFFLLCLAGRALAMAAGAAGSITTLPALPDDGGGGAFPPGHFKDPKRLY CKNGGFFLRINPDGRVDGVREKSDPHIKLQLQAEERGVVSIKGVSANRFLAMK EDGRLLALKCATEECFFFERLESNNYNTYRSRKYSDWYVALKRTGQYKPGPKT GPGQKAILFLPMSAKS* |
| 4 | ggIL2-ggFGF2 | MMCKVLIFGCISVAMLMTTAYMAAGAAGSITTLPALPDDGGGGAFPPGHFKDP KRLYCKNGGFFLRINPDGRVDGVREKSDPHIKLQLQAEERGVVSIKGVSANRFL AMKEDGRLLALKCATEECFFFERLESNNYNTYRSRKYSDWYVALKRTGQYKP GPKTGPGQKAILFLPMSAKS* |
| 5 | Gluc-ggFGF2 | MGVKVLFALICIAVAEAMAAGAAGSITTLPALPDDGGGGAFPPGHFKDPKRLY CKNGGFFLRINPDGRVDGVREKSDPHIKLQLQAEERGVVSIKGVSANRFLAMK EDGRLLALKCATEECFFFERLESNNYNTYRSRKYSDWYVALKRTGQYKPGPKT GPGQKAILFLPMSAKS* |
| 6 | cohIL2-ggFGF2 | MYRMQLLSCIALSLALVTNSMAAGAAGSITTLPALPDDGGGGAFPPGHFKDPK RLYCKNGGFFLRINPDGRVDGVREKSDPHIKLQLQAEERGVVSIKGVSANRFLA MKEDGRLLALKCATEECFFFERLESNNYNTYRSRKYSDWYVALKRTGQYKPG PKTGPGQKAILFLPMSAKS* |
| 7 | cohIL2col-ggFGF2 | MRMQLLLLIALSLALVTNSMAAGAAGSITTLPALPDDGGGGAFPPGHFKDPKR LYCKNGGFFLRINPDGRVDGVREKSDPHIKLQLQAEERGVVSIKGVSANRFLA |

9. SEQUENCE APPENDIX

| SEQ ID NO: | Description | Sequence |
|---|---|---|
| | | MKEDGRLLALKCATEECFFFERLESNNYNTYRSRKYSDWYVALKRTGQYKPG PKTGPGQKAILFLPMSAKS* |
| 8 | cohIL2co2-ggFGF2 | MRRMQLLLLIALSLALVTNSMAAGAAGSITTLPALPDDGGGGAFPPGHFKDPK RLYCKNGGFFLRINPDGRVDGVREKSDPHIKLQLQAEERGVVSIKGVSANRFLA MKEDGRLLALKCATEECFFFERLESNNYNTYRSRKYSDWYVALKRTGQYKPG PKTGPGQKAILFLPMSAKS* |
| 9 | ggIL2-FGF2STAB | MMCKVLIFGCISVAMLMTTAYMAAGAAGSITTLPALPDDGGGGAFPPGHFKDP KRLYCKNGGFFLLINPDGRVDGTREKSDPFIKLQLQAEERGVVSIKGVSANRFL AMKEDGRLYALKYATEECFFFERLEENNYNTYRSRKYSDWYVALKRTGQYKP GPKTGPGQKAILFLPMSAKS* |
| 10 | hIL2-ggFGF2STAB | MYRMQLLSCIALSLALVTNSMAAGAAGSITTLPALPDDGGGGAFPPGHFKDPK RLYCKNGGFFLLINPDGRVDGTREKSDPFIKLQLQAEERGVVSIKGVSANRFLA MKEDGRLYALKYATEECFFFERLEENNYNTYRSRKYSDWYVALKRTGQYKPG PKTGPGQKAILFLPMSAKS* |
| 11 | ggIL6-ggFGF2 | MNFTEGCEATGRRPGSAGSRRRRAPRPGPVALLPLLLPLLLPPAAAVPLPMAAG AAGSITTLPALPDDGGGGAFPPGHFKDPKRLYCKNGGFFLRINPDGRVDGVREK SDPHIKLQLQAEERGVVSIKGVSANRFLAMKEDGRLLALKCATEECFFFERLES NNYNTYRSRKYSDWYVALKRTGQYKPGPKTGPGQKAILFLPMSAKS* |
| 12 | hIL2-ggFGF2 | MNSFSTSAFGPVAFSLGLLLVLPAAFPAPMAAGAAGSITTLPALPDDGGGGAFP PGHFKDPKRLYCKNGGFFLRINPDGRVDGVREKSDPHIKLQLQAEERGVVSIKG VSANRFLAMKEDGRLLALKCATEECFFFERLESNNYNTYRSRKYSDWYVALK RTGQYKPGPKTGPGQKAILFLPMSAKS* |
| 13 | hIL2-ggFGF2 | MYRMQLLSCIALSLALVTNSMAAGAAGSITTLPALPDDGGGGAFPPGHFKDPK RLYCKNGGFFLLINPDGRVDGTREKSDPFIKLQLQAEERGVVSIKGVSANRFLA MKEDGRLYALKYATEECFFFERLEENNYNTYRSRKYSDWYVALKRTGQYKPG PKTGPGQKAILFLPMSAKS* |
| 14 | hIFNa2-ggFGF2 | MALTFALLVALLVLSCKSSCSVGMVSKMAAGAAGSITTLPALPDDGGGGAFPP GHFKDPKRLYCKNGGFFLRINPDGRVDGVREKSDPHIKLQLQAEERGVVSIKG VSANRFLAMKEDGRLLALKCATEECFFFERLESNNYNTYRSRKYSDWYVALK RTGQYKPGPKTGPGQKAILFLPMSAKS* |
| 15 | secrecon-ggFGF2 | MWWRLWWLLLLLLLLLWPMVWAMAAGAAGSITTLPALPDDGGGGAFPPGHF KDPKRLYCKNGGFFLRINPDGRVDGVREKSDPHIKLQLQAEERGVVSIKGVSA NRFLAMKEDGRLLALKCATEECFFFERLESNNYNTYRSRKYSDWYVALKRTG QYKPGPKTGPGQKAILFLPMSAKS* |
| 16 | ggIGF1-WT | MEKINSLSTQLVKCCFCDFLKVKMHTVSYIHFFYLGLCLLTLTSSAAAGPETLC GAELVDALQFVCGDRGFYFSKPTGYGSSSRRLHHKGIVDECCFQSCDLRRLEM YCAPIKPPKSARSVRAQRHTDMPKAQKEVHLKNTSRGNTGNRNYRM* |
| 17 | ggIGF1-truncated | MGPETLCGAELVDALQFVCGDRGFYFSKPTGYGSSSRRLHHKGIVDECCFQSC DLRRLEMYCAPIKPPKSA* |
| 18 | ggPDGFb | MCPQPARLEPGMNFGVVFAVILSLPLARLEGDPIPEDIYEILGGSSVRSISDLQRA LRIDSVEEDSSSLDLNATQPSQNHVSLSRERRSLDALAAAEPAVLAECKTRTVV FEISRDMVDSTNANFVVWPPCVEVQRCSGCCNNRNVQCRPMQIRVRHVQVNK IEFFQRKPIFKKVIVPLEDHVQCRCEVVSRPPPRSNRPASREQRRFSPSFTTAAISQ RKRVRRPPAQKRKHKKYKHVNDKKVLKEILIA* |
| 19 | ggPDGFb-211STOP | MCPQPARLEPGMNFGVVFAVILSLPLARLEGDPIPEDIYEILGGSSVRSISDLQRA LRIDSVEEDSSSLDLNATQPSQNHVSLSRERRSLDALAAAEPAVLAECKTRTVV FEISRDMVDSTNANFVVWPPCVEVQRCSGCCNNRNVQCRPMQIRVRHVQVNK IEFFQRKPIFKKVIVPLEDHVQCRCEVVSRPPPRSNRPASREQRRFSPSFTTAAISQ * |
| 20 | F-9C-SRG | MADYKDDDDKKGGIIVAILLLIVMLAIEILLLITLIIAVTSGGSG* |
| 21 | 9C-SRG | MAKGGIIVAILLLIVMLAIEILLLITLIIAVTSGGSG* |
| 22 | IL2 (human) ("hil2" or "hIL2") Signal peptide | MYRMQLLSCIALSLALVTNS |
| 23 | IL2-CO1 (human) | MRMQLLLLIALSLALVTNS |

9. SEQUENCE APPENDIX

| SEQ ID NO: | Description | Sequence |
|---|---|---|
| | ("hil2col1") Signal peptide | |
| 24 | IL2-CO2 (human) ("hil2col2") Signal peptide | MRRMQLLLLIALSLALVTNS |
| 25 | IL2 (chicken) ("ggil2" or "ggIL2") Signal peptide | MMCKVLIFGCISVAMLMTTAY |
| 26 | IFNa (human) ("hIFNA") Signal peptide | MALTFALLVALLVLSCKSSCSVGMVSK |
| 27 | IL6 (human) ("hil6") Signal peptide | MNSFSTSAFGPVAFSLGLLLVLPAAFPAP |
| 28 | IL6 (chicken) ("ggil6") Signal peptide | MNFTEGCEATGRRPGSAGSRRRRAPRPGPVALLPLLLPLLLPPAAAVPLP |
| 29 | Gaussia Luciferase ("GLuc") Signal peptide | MGVKVLFALICIAVAEA |
| 30 | Secrecon Signal peptide | MWWRLWWLLLLLLLLWPMVWA |
| 31 | BM40 signal peptide Signal peptide | MRAWIFFLLCLAGRALA |
| 32 | FGFR1-WT | MFTWRCLILWAVLVTATLSAARPAPTLPDQALPKANIEVESHSAHPGDLLQLR CRLRDDVQSINWVRDGVQLPENNRTRITGEEVEVRDAVPEDSGLYACMTNSPS GSETTYFSVNVSDALPSAEDDDDEDDSSSEEKEADNTKPNQAVAPYWTYPEKM EKKLHAVPAAKTVKFKCPSGGTPNPTLRWLKNGKEFKPDHRIGGYKVRYATW SIIMDSVVPSDKGNYTCIVENKYGSINHTYQLDVVERSPHRPILQAGLPANKTV ALGSNVEFVCKVYSDPQPHIQWLKHIEVNGSKIGPDNLPYVQILKTAGVNTTDK EMEVLHLRNVSFEDAGEYTCLAGNSIGISHHSAWLTVLEATEQSPAMMTSPLY LEIIIYCTGAFLISCMVVTVIIYKMKSTTKKTDFNSQLAVHKLAKSIPLRRQVTVS ADSSSSMNSGVMLVRPSRLSSSGTPMLAGVSEYELPEDPRWELPRDRLILGKPL GEGCFGQVVLAEAIGLDKDKPNRVTKVAVKMLKSDATEKDLSDLISEMEMMK MIGKHKNIINLLGACTQDGPLYVIVEYASKGNLREYLQARRPPGMEYCYNPTRI PEEQLSFKDLVSCAYQVARGMEYLASKKCIHRDLAARNVLVTEDNVMKIADF GLARDIHHIDYYKKTTNGRLPVKWMAPEALFDRIYTHQSDVWSFGVLLWEIFT LGGSPYPGVPVEELFKLLKEGHRMDKPSNCTNELYMMMRDCWHAVPSQRPTF KQLVEDLDRIVAMTSNQEYLDLSVPLDQYSPGFPATRSSTCSSGEDSVFSHDPLP DEPCLPRCPPHSHGALKRH* |
| 33 | FGFR1-N546K | MFTWRCLILWAVLVTATLSAARPAPTLPDQALPKANIEVESHSAHPGDLLQLR CRLRDDVQSINWVRDGVQLPENNRTRITGEEVEVRDAVPEDSGLYACMTNSPS GSETTYFSVNVSDALPSAEDDDDEDDSSSEEKEADNTKPNQAVAPYWTYPEKM EKKLHAVPAAKTVKFKCPSGGTPNPTLRWLKNGKEFKPDHRIGGYKVRYATW SIIMDSVVPSDKGNYTCIVENKYGSINHTYQLDVVERSPHRPILQAGLPANKTV ALGSNVEFVCKVYSDPQPHIQWLKHIEVNGSKIGPDNLPYVQILKTAGVNTTDK EMEVLHLRNVSFEDAGEYTCLAGNSIGISHHSAWLTVLEATEQSPAMMTSPLY LEIIIYCTGAFLISCMVVTVIIYKMKSTTKKTDFNSQLAVHKLAKSIPLRRQVTVS ADSSSSMNSGVMLVRPSRLSSSGTPMLAGVSEYELPEDPRWELPRDRLILGKPL GEGCFGQVVLAEAIGLDKDKPNRVTKVAVKMLKSDATEKDLSDLISEMEMMK MIGKHKNIIKLLGACTQDGPLYVIVEYASKGNLREYLQARRPPGMEYCYNPTRI PEEQLSFKDLVSCAYQVARGMEYLASKKCIHRDLAARNVLVTEDNVMKIADF GLARDIHHIDYYKKTTNGRLPVKWMAPEALFDRIYTHQSDVWSFGVLLWEIFT LGGSPYPGVPVEELFKLLKEGHRMDKPSNCTNELYMMMRDCWHAVPSQRPTF KQLVEDLDRIVAMTSNQEYLDLSVPLDQYSPGFPATRSSTCSSGEDSVFSHDPLP DEPCLPRCPPHSHGALKRH* |

9. SEQUENCE APPENDIX

| SEQ ID NO: | Description | Sequence |
|---|---|---|
| 34 | FGFR1-K656E | MFTWRCLILWAVLVTATLSAARPAPTLPDQALPKANIEVESHSAHPGDLLQLR CRLRDDVQSINWVRDGVQLPENNRTRITGEEVEVRDAVPEDSGLYACMTNSPS GSETTYFSVNVSDALPSAEDDDDEDDSSSEEKEADNTKPNQAVAPYWTYPEKM EKKLHAVPAAKTVKFKCPSGGTPNPTLRWLKNGKEFKPDHRIGGYKVRYATW SIIMDSVVPSDKGNYTCIVENKYGSINHTYQLDVVERSPHRPILQAGLPANKTV ALGSNVEFVCKVYSDPQPHIQWLKHIEVNGSKIGPDNLPYVQILKTAGVNTTDK EMEVLHLRNVSFEDAGEYTCLAGNSIGISHHSAWLTVLEATEQSPAMMTSPLY LEIIIYCTGAFLISCMVVTVIIYKMKSTTKKTDFNSQLAVHKLAKSIPLRRQVTVS ADSSSSMNSGVMLVRPSRLSSSGTPMLAGVSEYELPEDPRWELPRDRLILGKPL GEGCFGQVVLAEAIGLDKDKPNRVTKVAVKMLKSDATEKDLSDLISEMEMMK MIGKHKNIINLLGACTQDGPLYVIVEYASKGNLREYLQARRPPGMEYCYNPTRI PEEQLSFKDLVSCAYQVARGMEYLASKKCIHRDLAARNVLVTEDNVMKIADF GLARDIHHIDYYKETTNGRLPVKWMAPEALFDRIYTHQSDVWSFGVLLWEIFT LGGSPYPGVPVEELFKLLKEGHRMDKPSNCTNELYMMMRDCWHAVPSQRPTF KQLVEDLDRIVAMTSNQEYLDLSVPLDQYSPGFPATRSSTCSSGEDSVFSHDPLP DEPCLPRCPPHSHGALKRH* |
| 35 | FGFR1-N546K-K656E-S780A | MFTWRCLILWAVLVTATLSAARPAPTLPDQALPKANIEVESHSAHPGDLLQLR CRLRDDVQSINWVRDGVQLPENNRTRITGEEVEVRDAVPEDSGLYACMTNSPS GSETTYFSVNVSDALPSAEDDDDEDDSSSEEKEADNTKPNQAVAPYWTYPEKM EKKLHAVPAAKTVKFKCPSGGTPNPTLRWLKNGKEFKPDHRIGGYKVRYATW SIIMDSVVPSDKGNYTCIVENKYGSINHTYQLDVVERSPHRPILQAGLPANKTV ALGSNVEFVCKVYSDPQPHIQWLKHIEVNGSKIGPDNLPYVQILKTAGVNTTDK EMEVLHLRNVSFEDAGEYTCLAGNSIGISHHSAWLTVLEATEQSPAMMTSPLY LEIIIYCTGAFLISCMVVTVIIYKMKSTTKKTDFNSQLAVHKLAKSIPLRRQVTVS ADSSSSMNSGVMLVRPSRLSSSGTPMLAGVSEYELPEDPRWELPRDRLILGKPL GEGCFGQVVLAEAIGLDKDKPNRVTKVAVKMLKSDATEKDLSDLISEMEMMK MIGKHKNIIKLLGACTQDGPLYVIVEYASKGNLREYLQARRPPGMEYCYNPTRI PEEQLSFKDLVSCAYQVARGMEYLASKKCIHRDLAARNVLVTEDNVMKIADF GLARDIHHIDYYKETTNGRLPVKWMAPEALFDRIYTHQSDVWSFGVLLWEIFT LGGSPYPGVPVEELFKLLKEGHRMDKPSNCTNELYMMMRDCWHAVPSQRPTF KQLVEDLDRIVAMTSNQEYLDLSVPLDQYAPGFPATRSSTCSSGEDSVFSHDPL PDEPCLPRCPPHSHGALKRH* |
| 36 | FGFR1-myrist-K656E | MGSSKSKPKDPSQRKMKSTTKKTDFNSQLAVHKLAKSIPLRRQVTVSADSSSS MNSGVMLVRPSRLSSSGTPMLAGVSEYELPEDPRWELPRDRLILGKPLGEGCFG QVVLAEAIGLDKDKPNRVTKVAVKMLKSDATEKDLSDLISEMEMMKMIGKHK NIINLLGACTQDGPLYVIVEYASKGNLREYLQARRPPGMEYCYNPTRIPEEQLSF KDLVSCAYQVARGMEYLASKKCIHRDLAARNVLVTEDNVMKIADFGLARDIH HIDYYKETTNGRLPVKWMAPEALFDRIYTHQSDVWSFGVLLWEIFTLGGSPYP GVPVEELFKLLKEGHRMDKPSNCTNELYMMMRDCWHAVPSQRPTFKQLVED LDRIVAMTSNQEYLDLSVPLDQYSPGFPATRSSTCSSGEDSVFSHDPLPDEPCLP RCPPHSHGALKRH* |
| 37 | FGF2-WT | MGLKSTWRYGNGPGTYSKKMVSWDSGCLICLVVVTMAGLSLARPSFNLVVED ATLEPEEPPTKYQISQPDVHSALPGEPLELRCQLKDAVMISWTKDGVPLGPDNR TVIIGEYLQIKDASPRDSGLYACTAIRTLDSDTLYFIVNVTDALSSGDDEDDNDG SEDFVNDSNQMRAPYWTHTDKMEKRLHAVPAANTVKFRCPAMGNPTPTMRW LKNGKEFKQEHRIGGYKVRNQHWSLIMESVVPSDKGNYTCIVENQYGSINHTY HLDVVERSPHRPILQAGLPANASAVVGGDVEFVCKVYSDAQPHIQWIKHVERN GSKYGPDGLPYLQVLKAAGVNTTDKEIEVLYIRNVTFEDAGEYTCLAGNSIGIS FHTAWLTVLPAPEKEKEFPTSPDYLEIAIYCIGVFLIACMVLTVILCRMKNTTKK PDFSSQPAVHKLTKRIPLRRQVSADSSSSMNSNTPLVRITTRLSSTADAPMLAGV SEYELPEDPKWEFPRDKLTLGKPLGEGCFGQVVMAEAVGIDKDRPKEAVTVAV KMLKDDATEKDLSDLVSEMEMMKMIGKHKNIINLLGACTQDGPLYVIVEYAS KGNLREYLRARRPPGMEYSFDINRVPEEQMTFKDLVSCTYQLARGMEYLASQK CIHRDLAARNVLVTENNVMKIADFGLARDINNIDYYKKTTNGRLPVKWMAPE ALFDRVYTHQSDVWSFGVLMWEIFTLGGSPYPGIPVEELFKLLKEGHRMDKPA NCTNELYMMMRDCWQAVPSQRPTFKQLVEDLDRILTLTTNEEYLDLSGPLEQY SPSYPDTRSSCSSGDDSVFSPDPMPYEPCLPKYQHMNGSVKT* |
| 38 | FGF2-N550K | MGLKSTWRYGNGPGTYSKKMVSWDSGCLICLVVVTMAGLSLARPSFNLVVED ATLEPEEPPTKYQISQPDVHSALPGEPLELRCQLKDAVMISWTKDGVPLGPDNR TVIIGEYLQIKDASPRDSGLYACTAIRTLDSDTLYFIVNVTDALSSGDDEDDNDG SEDFVNDSNQMRAPYWTHTDKMEKRLHAVPAANTVKFRCPAMGNPTPTMRW LKNGKEFKQEHRIGGYKVRNQHWSLIMESVVPSDKGNYTCIVENQYGSINHTY HLDVVERSPHRPILQAGLPANASAVVGGDVEFVCKVYSDAQPHIQWIKHVERN GSKYGPDGLPYLQVLKAAGVNTTDKEIEVLYIRNVTFEDAGEYTCLAGNSIGIS FHTAWLTVLPAPEKEKEFPTSPDYLEIAIYCIGVFLIACMVLTVILCRMKNTTKK PDFSSQPAVHKLTKRIPLRRQVSADSSSSMNSNTPLVRITTRLSSTADAPMLAGV SEYELPEDPKWEFPRDKLTLGKPLGEGCFGQVVMAEAVGIDKDRPKEAVTVAV KMLKDDATEKDLSDLVSEMEMMKMIGKHKNIIKLLGACTQDGPLYVIVEYAS |

-continued

9. SEQUENCE APPENDIX

| SEQ ID NO: | Description | Sequence |
|---|---|---|
| | | KGNLREYLRARRPPGMEYSFDINRVPEEQMTFKDLVSCTYQLARGMEYLASQK CIHRDLAARNVLVTENNVMKIADFGLARDINNIDYYKKTTNGRLPVKWMAPE ALFDRVYTHQSDVWSFGVLMWEIFTLGGSPYPGIPVEELFKLLKEGHRMDKPA NCTNELYMMMRDCWQAVPSQRPTFKQLVEDLDRILTLTTNEEYLDLSGPLEQY SPSYPDTRSSCSSGDDSVFSPDMPYEPCLPKYQHMNGSVKT* |
| 39 | FGF2-K660E | MGLKSTWRYGNGPGTYSKKMVSWDSGCLICLVVVTMAGLSLARPSFNLVVED ATLEPEEPPTKYQISQPDVHSALPGEPLELRCQLKDAVMISWTKDGVPLGPDNR TVIIGEYLQIKDASPRDSGLYACTAIRTLDSDTLYFIVNVTDALSSGDDEDDNDG SEDFVNDSNQMRAPYWTHTDKMEKRLHAVPAANTVKFRCPAMGNPTPTMRW LKNGKEFKQEHRIGGYKVRNQHWSLIMESVVPSDKGNYTCIVENQYGSINHTY HLDVVERSPHRPILQAGLPANASAVVGGDVEFVCKVYSDAQPHIQWIKHVERN GSKYGPDGLPYLQVLKAAGVNTTDKEIEVLYIRNVTFEDAGEYTCLAGNSIGIS FHTAWLTVLPAPEKEKEFPTSPDYLEIAIYCIGVFLIACMVLTVILCRMKNTTKK PDFSSQPAVHKLTKRIPLRRQVSADSSSSMNSNTPLVRITTRLSSTADAPMLAGV SEYELPEDPKWEFPRDKLTLGKPLGEGCFGQVVMAEAVGIDKDRPKEAVTVAV KMLKDDATEKDLSDLVSEMEMMKMIGKHKNIINLLGACTQDGPLYVIVEYAS KGNLREYLRARRPPGMEYSFDINRVPEEQMTFKDLVSCTYQLARGMEYLASQK CIHRDLAARNVLVTENNVMKIADFGLARDINNIDYYKETTNGRLPVKWMAPE ALFDRVYTHQSDVWSFGVLMWEIFTLGGSPYPGIPVEELFKLLKEGHRMDKPA NCTNELYMMMRDCWQAVPSQRPTFKQLVEDLDRILTLTTNEEYLDLSGPLEQY SPSYPDTRSSCSSGDDSVFSPDMPYEPCLPKYQHMNGSVKT* |
| 40 | FGF2-N550K-N660E-S780A | MGLKSTWRYGNGPGTYSKKMVSWDSGCLICLVVVTMAGLSLARPSFNLVVED ATLEPEEPPTKYQISQPDVHSALPGEPLELRCQLKDAVMISWTKDGVPLGPDNR TVIIGEYLQIKDASPRDSGLYACTAIRTLDSDTLYFIVNVTDALSSGDDEDDNDG SEDFVNDSNQMRAPYWTHTDKMEKRLHAVPAANTVKFRCPAMGNPTPTMRW LKNGKEFKQEHRIGGYKVRNQHWSLIMESVVPSDKGNYTCIVENQYGSINHTY HLDVVERSPHRPILQAGLPANASAVVGGDVEFVCKVYSDAQPHIQWIKHVERN GSKYGPDGLPYLQVLKAAGVNTTDKEIEVLYIRNVTFEDAGEYTCLAGNSIGIS FHTAWLTVLPAPEKEKEFPTSPDYLEIAIYCIGVFLIACMVLTVILCRMKNTTKK PDFSSQPAVHKLTKRIPLRRQVSADSSSSMNSNTPLVRITTRLSSTADAPMLAGV SEYELPEDPKWEFPRDKLTLGKPLGEGCFGQVVMAEAVGIDKDRPKEAVTVAV KMLKDDATEKDLSDLVSEMEMMKMIGKHKNIIKLLGACTQDGPLYVIVEYAS KGNLREYLRARRPPGMEYSFDINRVPEEQMTFKDLVSCTYQLARGMEYLASQK CIHRDLAARNVLVTENNVMKIADFGLARDINNIDYYKETTNGRLPVKWMAPE ALFDRVYTHQSDVWSFGVLMWEIFTLGGSPYPGIPVEELFKLLKEGHRMDKPA NCTNELYMMMRDCWQAVPSQRPTFKQLVEDLDRILTLTTNEEYLDLSGPLEQY APSYPDTRSSCSSGDDSVFSPDMPYEPCLPKYQHMNGSVKT* |
| 41 | FGFR3-WT | MSEAGGGAAAAASLPRSRAGGMRAAWGSVWCLCLAAAVGALPAARRRGAE RSGGQAAEYLRSETAFLEELVFGSGDTIELSCNTQSSSVSVFWFKDGIGIAPSNR THIGQKLLKIINVSYDDSGLYSCKPRHSNEVLGNFTVRVTGVPFWTRPDKMEK KLLAVPAANTVRFRCPAGGNPTPTIYWLKNGKEFKGEHRIGGIKLRHQQWSLV MESVVPSDRGNYTCVVENKYGNIRHTYQLDVLERSPHRPILQAGLPANQTVVV GSNVEFHCKVYSDAQPHIQWLKHVEVNGSKYGPDGTPYVTVLKSWISKNAEA DANLNLFNVTEQDEGEYLCRANNFVGIAEKPFWLHIRKPKPAEELMEMDDSGS VYAGILSYGTGLVLFILVLVIVIICRMKMPNKKAMNTTTVQKVSKFPLKRQVTV SLESNSSMNSNTPLVRITRLSSSDGPMLANVSELELPPDPKWELARSRLTLGKPL GEGCFGQVVMAEAIGIDKDKPNKAITVAVKMLKDDATDKDLSDLVSEMEMM KMIGKHKNIINLLGACTQDGPLYVLVEYASKGNLREYLRARRPPGMDYSFDTC KLPEEQLTFKDLVSCAYQVARGMEYLASQKCIHRDLAARNVLVTEDNVMKIA DFGLARDVHNIDYYKKTTNGRLPVKWMAPEALFDRVYTHQSDVWSFGVLLW EIFTLGGSPYPGIPVEELFKLLKEGHRMDKPANCTHDLYMIMRECWHAVPSQRP TFKQLVEDLDRVLTMSTDEYLDLSVPFEQYSPAGQDTHSTCSSGDDSVFAHD LLPDEPCLPKHVPCNGVIRT* |
| 42 | FGFR3-N540K | MSEAGGGAAAAASLPRSRAGGMRAAWGSVWCLCLAAAVGALPAARRRGAE RSGGQAAEYLRSETAFLEELVFGSGDTIELSCNTQSSSVSVFWFKDGIGIAPSNR THIGQKLLKIINVSYDDSGLYSCKPRHSNEVLGNFTVRVTGVPFWTRPDKMEK KLLAVPAANTVRFRCPAGGNPTPTIYWLKNGKEFKGEHRIGGIKLRHQQWSLV MESVVPSDRGNYTCVVENKYGNIRHTYQLDVLERSPHRPILQAGLPANQTVVV GSNVEFHCKVYSDAQPHIQWLKHVEVNGSKYGPDGTPYVTVLKSWISKNAEA DANLNLFNVTEQDEGEYLCRANNFVGIAEKPFWLHIRKPKPAEELMEMDDSGS VYAGILSYGTGLVLFILVLVIVIICRMKMPNKKAMNTTTVQKVSKFPLKRQVTV SLESNSSMNSNTPLVRITRLSSSDGPMLANVSELELPPDPKWELARSRLTLGKPL GEGCFGQVVMAEAIGIDKDKPNKAITVAVKMLKDDATDKDLSDLVSEMEMM KMIGKHKNIIKLLGACTQDGPLYVLVEYASKGNLREYLRARRPPGMDYSFDTC KLPEEQLTFKDLVSCAYQVARGMEYLASQKCIHRDLAARNVLVTEDNVMKIA DFGLARDVHNIDYYKKTTNGRLPVKWMAPEALFDRVYTHQSDVWSFGVLLW EIFTLGGSPYPGIPVEELFKLLKEGHRMDKPANCTHDLYMIMRECWHAVPSQRP TFKQLVEDLDRVLTMSTDEYLDLSVPFEQYSPAGQDTHSTCSSGDDSVFAHD LLPDEPCLPKHVPCNGVIRT* |

9. SEQUENCE APPENDIX

| SEQ ID NO: | Description | Sequence |
|---|---|---|
| 43 | FGFR3-K650E | MSEAGGGAAAAASLPRSRAGGMRAAWGSVWCLCLAAAVGALPAARRRGAE RSGGGQAAEYLRSETAFLEELVFGSGDTIELSCNTQSSSVSVFWFKDGIGIAPSNR THIGQKLLKIINVSYDDSGLYSCKPRHSNEVLGNFTVRVTGVPFWTRPDKMEK KLLAVPAANTVRFRCPAGGNPTPTIYWLKNGKEFKGEHRIGGIKLRHQQWSLV MESVVPSDRGNYTCVVENKYGNIRHTYQLDVLERSPHRPILQAGLPANQTVVV GSNVEFHCKVYSDAQPHIQWLKHVEVNGSKYGPDGTPYVTVLKSWISKNAEA DANLNLFNVTEQDEGEYLCRANNFVGIAEKPFWLHIRKPKPAEELMEMDDSGS VYAGILSYGTGLVLFILVLVIVIICRMKMPNKKAMNTTTVQKVSKFPLKRQVTV SLESNSSMNSNTPLVRITRLSSSDGPMLANVSELELPPDPKWELARSRLTLGKPL GEGCFGQVVMAEAIGIDKDKPNKAITVAVKMLKDDATDKDLSDLVSEMEMM KMIGKHKNIINLLGACTQDGPLYVLVEYASKGNLREYLRARRPPGMDYSFDTC KLPEEQLTFKDLVSCAYQVARGMEYLASQKCIHRDLAARNVLVTEDNVMKIA DFGLARDVHNIDYYKETTNGRLPVKWMAPEALFDRVYTHQSDVWSFGVLLW EIFTLGGSPYPGIPVEELFKLLKEGHRMDKPANCTHDLYMIMRECWHAVPSQRP TFKQLVEDLDRVLTMTSTDEYLDLSVPFEQYSPAGQDTHSTCSSGDDSVFAHD LLPDEPCLPKHVPCNGVIRT* |
| 44 | FGFR3-N540K-K650E | MSEAGGGAAAAASLPRSRAGGMRAAWGSVWCLCLAAAVGALPAARRRGAE RSGGGQAAEYLRSETAFLEELVFGSGDTIELSCNTQSSSVSVFWFKDGIGIAPSNR THIGQKLLKIINVSYDDSGLYSCKPRHSNEVLGNFTVRVTGVPFWTRPDKMEK KLLAVPAANTVRFRCPAGGNPTPTIYWLKNGKEFKGEHRIGGIKLRHQQWSLV MESVVPSDRGNYTCVVENKYGNIRHTYQLDVLERSPHRPILQAGLPANQTVVV GSNVEFHCKVYSDAQPHIQWLKHVEVNGSKYGPDGTPYVTVLKSWISKNAEA DANLNLFNVTEQDEGEYLCRANNFVGIAEKPFWLHIRKPKPAEELMEMDDSGS VYAGILSYGTGLVLFILVLVIVIICRMKMPNKKAMNTTTVQKVSKFPLKRQVTV SLESNSSMNSNTPLVRITRLSSSDGPMLANVSELELPPDPKWELARSRLTLGKPL GEGCFGQVVMAEAIGIDKDKPNKAITVAVKMLKDDATDKDLSDLVSEMEMM KMIGKHKNIIKLLGACTQDGPLYVLVEYASKGNLREYLRARRPPGMDYSFDTC KLPEEQLTFKDLVSCAYQVARGMEYLASQKCIHRDLAARNVLVTEDNVMKIA DFGLARDVHNIDYYKETTNGRLPVKWMAPEALFDRVYTHQSDVWSFGVLLW EIFTLGGSPYPGIPVEELFKLLKEGHRMDKPANCTHDLYMIMRECWHAVPSQRP TFKQLVEDLDRVLTMTSTDEYLDLSVPFEQYSPAGQDTHSTCSSGDDSVFAHD LLPDEPCLPKHVPCNGVIRT* |
| 45 | FGFR3-myrist-K650E | MGSSKSKPKDPSQRRMKMPNKKAMNTTTVQKVSKFPLKRQVTVSLESNSSMN SNTPLVRITRLSSSDGPMLANVSELELPPDPKWELARSRLTLGKPLGEGCFGQV VMAEAIGIDKDKPNKAITVAVKMLKDDATDKDLSDLVSEMEMMKMIGKHKNI INLLGACTQDGPLYVLVEYASKGNLREYLRARRPPGMDYSFDTCKLPEEQLTF KDLVSCAYQVARGMEYLASQKCIHRDLAARNVLVTEDNVMKIADFGLARDV HNIDYYKETTNGRLPVKWMAPEALFDRVYTHQSDVWSFGVLLWEIFTLGGSP YPGIPVEELFKLLKEGHRMDKPANCTHDLYMIMRECWHAVPSQRPTFKQLVED LDRVLTMTSTDEYLDLSVPFEQYSPAGQDTHSTCSSGDDSVFAHDLLPDEPCLP KHVPCNGVIRT* |
| 46 | FGFR4-WT | MLPLRLVLAGLLVAAGSAASHRGEMEPELFESPLLESEEEHLLLDPGNALKLYC DVNQSGASVVWYKESRPLLPGPRVRLQQSVLEIAEVAYEDSGLYVCRARGTGE VLRNFTISVVDSLASGDDDEDSDGDGPHGDRSEEPVYVHRAPYWTHPHRMDK KLYAVPAGNTVKFRCPASGSPSPSIRWFKNGREFRGEHRIGGIRLRHQHWSLVM ESVVPSDRGNYTCLVENRFGSIRYSYLLDVLERSPHRPILQAGLPANTTALVGSD VEFFCKVYSDAQPHIQWLKHIEVNGSSYGPDGVPYVQVLKTADINSSEVEVLYL RNVTMEDAGEYTCLAGNSIGLSYQSAWLTVLPEELVHEAEAPEAKYTDIIIYTS GSLAVAMALIIVVLCRMQTSSKQPLEPMAVHKLSKFPLIRQFSLDSSSSGKSST SLMRVTRLSSSCAPMLAGVVELDLPLDSKWEFPREKLVLGKPLGEGCFGQVVR AEAYGIDRQWPDRAVTVAVKMLKDNATDKDLADLISEMEMMKLMDKHKNII NLLGVCTQDGPLYVIVEFAAKGNLREYLRARRPPMPDYTFDITELHEEQLCFKD LVSCVYQVARGMEYLESRRCIHRDLAARNVLVTAENVMKIADFGLARDVHDI DYYKKTSNGRLPVKWMAPEALFDRVYTHQSDVWSFGILMWEIFTLGGSPYPGI PVEELFKLLKEGHRMDCPSNCTHELYMLMRECWHAVPSQRPTFKQLVEGLDKI LAAISEEYLDLSMPFEQYSPSCEDTTSTCSSDDSVFTHDPLPLAPCLFACPSGRT* |
| 47 | FGFR4-Y367C | MLPLRLVLAGLLVAAGSAASHRGEMEPELFESPLLESEEEHLLLDPGNALKLYC DVNQSGASVVWYKESRPLLPGPRVRLQQSVLEIAEVAYEDSGLYVCRARGTGE VLRNFTISVVDSLASGDDDEDSDGDGPHGDRSEEPVYVHRAPYWTHPHRMDK KLYAVPAGNTVKFRCPASGSPSPSIRWFKNGREFRGEHRIGGIRLRHQHWSLVM ESVVPSDRGNYTCLVENRFGSIRYSYLLDVLERSPHRPILQAGLPANTTALVGSD VEFFCKVYSDAQPHIQWLKHIEVNGSSYGPDGVPYVQVLKTADINSSEVEVLYL RNVTMEDAGEYTCLAGNSIGLSYQSAWLTVLPEELVHEAEAPEAKCTDIIIYTS GSLAVAMALIIVVLCRMQTSSKQPLEPMAVHKLSKFPLIRQFSLDSSSSGKSST SLMRVTRLSSSCAPMLAGVVELDLPLDSKWEFPREKLVLGKPLGEGCFGQVVR AEAYGIDRQWPDRAVTVAVKMLKDNATDKDLADLISEMEMMKLMDKHKNII NLLGVCTQDGPLYVIVEFAAKGNLREYLRARRPPMPDYTFDITELHEEQLCFKD LVSCVYQVARGMEYLESRRCIHRDLAARNVLVTAENVMKIADFGLARDVHDI |

-continued

9. SEQUENCE APPENDIX

| SEQ ID NO: | Description | Sequence |
|---|---|---|
| | | DYYKKTSNGRLPVKWMAPEALFDRVYTHQSDVWSFGILMWEIFTLGGSPYPGI PVEELFKLLKEGHRMDCPSNCTHELYMLMRECWHAVPSQRPTFKQLVEGLDKI LAAISEEYLDLSMPFEQYSPSCEDTTSTCSSDDSVFTHDPLPLAPCLFACPSGRT* |
| 48 | FGFR4-K645E | MLPLRLVLAGLLVAAGSAASHRGEMEPELFESPLLESEEEHLLLDPGNALKLYC DVNQSGASVVWYKESRPLLPGPRVRLQQSVLEIAEVAYEDSGLYVCRARGTGE VLRNFTISVVDSLASGDDDEDSDGDGPHGDRSEEPVYVHRAPYWTHPHRMDK KLYAVPAGNTVKFRCPASGSPSPSIRWFKNGREFRGEHRIGGIRLRHQHWSLVM ESVVPSDRGNYTCLVENRFGSIRYSYLLDVLERSPHRPILQAGLPANTTALVGSD VEFFCKVYSDAQPHIQWLKHIEVNGSSYGPDGVPYVQVLKTADINSSEVEVLYL RNVTMEDAGEYTCLAGNSIGLSYQSAWLTVLPEELVHEAEAPEAKYTDIIIYTS GSLAVAMALIIVVLCRMQTQSSKQPLEPMAVHKLSKFPLIRQFSLDSSSSGKSST SLMRVTRLSSSCAPMLAGVVELDLPLDSKWEFPREKLVLGKPLGEGCFGQVVR AEAYGIDRQWPDRAVTVAVKMLKDNATDKDLADLISEMEMMKLMDKHKNII NLLGVCTQDGPLYVIVEFAAKGNLREYLRARRPPMPDYTFDITELHEEQLCFKD LVSCVYQVARGMEYLESRRCIHRDLAARNVLVTAENVMKIADFGLARDVHDI DYYKETSNGRLPVKWMAPEALFDRVYTHQSDVWSFGILMWEIFTLGGSPYPGI PVEELFKLLKEGHRMDCPSNCTHELYMLMRECWHAVPSQRPTFKQLVEGLDKI LAAISEEYLDLSMPFEQYSPSCEDTTSTCSSDDSVFTHDPLPLAPCLFACPSGRT* |
| 49 | FGFR4-Y367C-K645E | MLPLRLVLAGLLVAAGSAASHRGEMEPELFESPLLESEEEHLLLDPGNALKLYC DVNQSGASVVWYKESRPLLPGPRVRLQQSVLEIAEVAYEDSGLYVCRARGTGE VLRNFTISVVDSLASGDDDEDSDGDGPHGDRSEEPVYVHRAPYWTHPHRMDK KLYAVPAGNTVKFRCPASGSPSPSIRWFKNGREFRGEHRIGGIRLRHQHWSLVM ESVVPSDRGNYTCLVENRFGSIRYSYLLDVLERSPHRPILQAGLPANTTALVGSD VEFFCKVYSDAQPHIQWLKHIEVNGSSYGPDGVPYVQVLKTADINSSEVEVLYL RNVTMEDAGEYTCLAGNSIGLSYQSAWLTVLPEELVHEAEAPEAKCTDIIIYTS GSLAVAMALIIVVLCRMQTQSSKQPLEPMAVHKLSKFPLIRQFSLDSSSSGKSST SLMRVTRLSSSCAPMLAGVVELDLPLDSKWEFPREKLVLGKPLGEGCFGQVVR AEAYGIDRQWPDRAVTVAVKMLKDNATDKDLADLISEMEMMKLMDKHKNII NLLGVCTQDGPLYVIVEFAAKGNLREYLRARRPPMPDYTFDITELHEEQLCFKD LVSCVYQVARGMEYLESRRCIHRDLAARNVLVTAENVMKIADFGLARDVHDI DYYKETSNGRLPVKWMAPEALFDRVYTHQSDVWSFGILMWEIFTLGGSPYPGI PVEELFKLLKEGHRMDCPSNCTHELYMLMRECWHAVPSQRPTFKQLVEGLDKI LAAISEEYLDLSMPFEQYSPSCEDTTSTCSSDDSVFTHDPLPLAPCLFACPSGRT* |
| 50 | ggIGFR1-WT | MKSGAGGGTLAVFCGLLLAFAALCLCPTNGEICGPNVDIRNDIHELKRLENCTV VEGFLQILLISKAEDYRNFRFPKLTVITDYLLLFRVAGLESLSDLFPNLTVIRGRN LFYNYALVIFEMTNLKEIGLHNLRNITRGAIRIEKNSDLCYLSTVDWSLILDAVS NNYIVGNKPPKECGDLCPGTMEEKPLCEKTSINNEYNYRCWTTNHCQKMCPSS CGKRACTDQNECCHPECLGSCTAPDNNTACVACRNYYYEGVCMPTCPPNTYK FEGWRCVTKEFCSKVPATETSDYERFVIHNDECMAECPSGFIRNGSQSMFCSPC EGPCPKICEDGKTKTIDSVTSAQMLQGCTILKGNLLINIRRGNNIASELENFMGLI ETVTGYVKIRHSHALVSLSFLKNLRYILGEEQVDGNYSFYVLDNHNLQQLWD WNHHNLTIKEGKMYFAFNPKLCVSEIYRMEEVSGTKGRQSKGDINPRNNGERA SCEESHILRFVSNTTLKNRIKLTWERYRPPDYRDLISFTVYYKEAPFKNVTEYDGQ DACGSNSWNMVDVDLPPNKENDPGILLQGLKPWTQYAIYVKAVTLTMMENH HIHGAKSEIVYIRTNAAVPSIPLDVISASNSSSQLIVKWNPPSLPNGNLSYYIVRW QQQPQDSYLYRHNYCSKDKVPIRRYADGTIDTEEATEPTKPEGCGGEKGPCCA CPKTEAEKQAEKEEAEYRKVFENFLHNSIFVPRPDRKRRDVFRIANATLATRNR NITGADHFTNASDAEESEVEYPFFETKVDGKERTVISHLQPFTLYRIDIHSCNHE ADTLGCSASNFVFARTMPSEGADNIPGTVAWEAKEENTVYLKWLEPTNPNGLI LMYEIKYGQHGEEKRECVSRQEYKKLGGAKLTHLNPGNYSARVQATSLAGNG SWTEPVSFYVQPKSANYDNFLHLIIVLPIAFLLIIGGLLIMLYVFNKKRNSDRLGN GVLYASVNPEYFSASDVYVPDEWEVPREKITMCRELGQGSFGMVYEGIAKGV VKDEPETRVAIKTVNESASMRERIEFLNEASVMKEFNCHHVVRLLGVVSQGQP TLVIMELMTRGDLKSYLRSLRPDTESNPGQAPPTLKKMIQMAGEIADGMAYLN ANKFVHRDLAARNCMVAEDFTVKIGDFGMTRDIYETDYYRKGGKGLLPVRW MSPESLKDGVFTTHSDVWSFGVVLWEIATLAEQPYQGMTNEQVLRFVMEGGL LEKPDNCPDMLFELMRMCWQYNPKMRPSFLEIISSIKDELDPAFKEVSFFYSEE NKPPDTEELDLETENMESIPLDPSSTLQPTDKHSGHKAENGPGVVVLRASFEER QPYAHMNGGRKNERALPLPQSSAC* |
| 51 | ggIGFR1-H1353H | MKSGAGGGTLAVFCGLLLAFAALCLCPTNGEICGPNVDIRNDIHELKRLENCTV VEGFLQILLISKAEDYRNFRFPKLTVITDYLLLFRVAGLESLSDLFPNLTVIRGRN LFYNYALVIFEMTNLKEIGLHNLRNITRGAIRIEKNSDLCYLSTVDWSLILDAVS NNYIVGNKPPKECGDLCPGTMEEKPLCEKTSINNEYNYRCWTTNHCQKMCPSS CGKRACTDQNECCHPECLGSCTAPDNNTACVACRNYYYEGVCMPTCPPNTYK FEGWRCVTKEFCSKVPATETSDYERFVIHNDECMAECPSGFIRNGSQSMFCSPC EGPCPKICEDGKTKTIDSVTSAQMLQGCTILKGNLLINIRRGNNIASELENFMGLI ETVTGYVKIRHSHALVSLSFLKNLRYILGEEQVDGNYSFYVLDNHNLQQLWD WNHHNLTIKEGKMYFAFNPKLCVSEIYRMEEVSGTKGRQSKGDINPRNNGERA SCEESHILRFVSNTTLKNRIKLTWERYRPPDYRDLISFTVYYKEAPFKNVTEYDGQ |

-continued

---

9. SEQUENCE APPENDIX

---

| SEQ ID NO: | Description | Sequence |
|---|---|---|
| | | DACGSNSWNMVDVDLPPNKENDPGILLQGLKPWTQYAIYVKAVTLTMMENH HIHGAKSEIVYIRTNAAVPSIPLDVISASNSSSQLIVKWNPPSLPNGNLSYYIVRW QQQPQDSYLYRHNYCSKDKVPIRRYADGTIDTEEATEPTKPEGCGGEKGPCCA CPKTEAEKQAEKEEAEYRKVFENFLHNSIFVPRPDRKRRDVFRIANATLATRNR NITGADHFTNASDAEESEVEYPFFETKVDGKERTVISHLQPFTLYRIDIHSCNHE ADTLGCSASNFVFARTMPSEGADNIPGTVAWEAKEENTVYLKWLEPTNPNGLI LMYEIKYGQHGEEKRECVSRQEYKKLGGAKLTHLNPGNYSARVQATSLAGNG SWTEPVSFYVQPKSANYDNFLHLIIVLPIAFLLIIGGLLIMLYVFNKKRNSDRLGN GVLYASVNPEYFSASDVYVPDEWEVPREKITMCRELGQGSFGMVYEGIAKGV VKDEPETRVAIKTVNESASMRERIEFLNEASVMKEFNCHHVVRLLGVVSQGQP TLVIMELMTRGDLKSYLRSLRPDTESNPGQAPPTLKKMIQMAGEIADGMAYLN ANKFVHRDLAARNCMVAEDFTVKIGDFGMTRDIYETDYYRKGGKGLLPVRW MSPESLKDGVFTTHSDVWSFGVVLWEIATLAEQPYQGMTNEQVLRFVMEGGL LEKPDNCPDMLFELMRMCWQYNPKMRPSFLEIISSIKDELDPAFKEVSFFYSEE NKPPDTEELDLETENMESIPLDPSSTLQPTDKHSGHKAENGPGVVVLRASFEER QPYAHMNGGRKNEHALPLPQSSAC* |
| 52 | gPDGFRA-WT | MGTPPRTFLILGCFLTGPLLTLCQLPLPTIVPNRNEMVVQLNSNFTLKCSGDSEV SWQYPVTEGSHRIDIRHEENNSGLFVTVLEVGNASAAHTGMYVCYYNHTQVE DGEVEGKDIYIYVPDPDMPFVPSLPEDQFILVEEGDPTVIPCRTSDPSAEVTLVNS LDKPVYAFYDSKQGFVGNFLAGPYTCKTMVKGVEFKSDEFLIYILRATSQLPVE IEALKTVYKTGETIVVTCVVFDNEVVNLQWNYPGKVKEKGLIKLDDIKVPSQK LVYTLTIPDASVKDTGDYECTARHATKEVKENKKVVITVHDKGFIHLEPQFSPL EAVNLHEVKNFVVDVQAYPAPKMYWLKDNVTLIENLTEIVTSSNRVQETRFQS VLKLIRAKEEDSGYYTLVAENEDEIKRYTFSLLIQVPALILDLMDDHQGSAGRQ TVRCLAEGTPLPDVEWLVCKDIKKCSNDTSWTLLTNNISDIHMEAHLDERNMV ESQVTFQKVEETLAVRCVARNDLGAVTRELKLVAPTLRSELTVAAAVLVLLVI VIISLIVLVIIWKQKPRYEIRWRVIESISPDGHEYIYVDPMQLPYDSRWEFPRDGL VLGRILGSGAFGKVVEGTAYGLSRSQPVMKVAVKMLKPTARSSEKQALMSEL KIMTHLGPHLNIVNLLGACTKSGPIYIITEYCFYGDLVNYLHKNRDNFLSRHPEK PKKDLDIFGMNPADESTRSYVILSFENTGEYMDMKQADTTQYVPMLERKEGSK YSDIQRSVYDRPASYKKKSLSESEVKNLLSDDGSEGLSLLDLLSFTYQVARGME FLASKNCVHRDLAARNVLLAQGKIVKICDFGLARDIMHDSNYVSKGSTFLPVK WMAPESIFDNLYTTLSDVWSYGILLWEIFSLGGTPYPGMMVDSTFYNKIKSGYR MAKPDHATNEVYEIMVKCWNSEPEKRPSFYHLSEIVESLLPGEYKKSYEKIHLD FLKSDHPAVTRMRGDCDNAYIGVTYKNEDKIKDRESGFDEQRLSADSGYIIPLP DIDPVSEDELGKRNRHSSQTSEESAIETGSSSSTFIKREDETIEDIDMMDDIGIDSS DLVEDSFL* |
| 53 | ggPDGFRA-D842V | MGTPPRTFLILGCFLTGPLLTLCQLPLPTIVPNRNEMVVQLNSNFTLKCSGDSEV SWQYPVTEGSHRIDIRHEENNSGLFVTVLEVGNASAAHTGMYVCYYNHTQVE DGEVEGKDIYIYVPDPDMPFVPSLPEDQFILVEEGDPTVIPCRTSDPSAEVTLVNS LDKPVYAFYDSKQGFVGNFLAGPYTCKTMVKGVEFKSDEFLIYILRATSQLPVE IEALKTVYKTGETIVVTCVVFDNEVVNLQWNYPGKVKEKGLIKLDDIKVPSQK LVYTLTIPDASVKDTGDYECTARHATKEVKENKKVVITVHDKGFIHLEPQFSPL EAVNLHEVKNFVVDVQAYPAPKMYWLKDNVTLIENLTEIVTSSNRVQETRFQS VLKLIRAKEEDSGYYTLVAENEDEIKRYTFSLLIQVPALILDLMDDHQGSAGRQ TVRCLAEGTPLPDVEWLVCKDIKKCSNDTSWTLLTNNISDIHMEAHLDERNMV ESQVTFQKVEETLAVRCVARNDLGAVTRELKLVAPTLRSELTVAAAVLVLLVI VIISLIVLVIIWKQKPRYEIRWRVIESISPDGHEYIYVDPMQLPYDSRWEFPRDGL VLGRILGSGAFGKVVEGTAYGLSRSQPVMKVAVKMLKPTARSSEKQALMSEL KIMTHLGPHLNIVNLLGACTKSGPIYIITEYCFYGDLVNYLHKNRDNFLSRHPEK PKKDLDIFGMNPADESTRSYVILSFENTGEYMDMKQADTTQYVPMLERKEGSK YSDIQRSVYDRPASYKKKSLSESEVKNLLSDDGSEGLSLLDLLSFTYQVARGME FLASKNCVHRDLAARNVLLAQGKIVKICDFGLARVIMHDSNYVSKGSTFLPVK WMAPESIFDNLYTTLSDVWSYGILLWEIFSLGGTPYPGMMVDSTFYNKIKSGYR MAKPDHATNEVYEIMVKCWNSEPEKRPSFYHLSEIVESLLPGEYKKSYEKIHLD FLKSDHPAVTRMRGDCDNAYIGVTYKNEDKIKDRESGFDEQRLSADSGYIIPLP DIDPVSEDELGKRNRHSSQTSEESAIETGSSSSTFIKREDETIEDIDMMDDIGIDSS DLVEDSFL* |
| 54 | ggPDGFRBWT | MLCPSLKASLQLLILTGLLEVTSGGSGLHIEPEDAELVLRLHSTFSLVCYGDGTL VWERDGQPLTAVLEHRDGVFISNLTLRNVTGRHTGEYACFYSPDQAPERAERK ALYIYVPDPSLVFLPAITSEEFFIFITGYTEATIPCRVTNPELQVTLYEKKVENPIP ATYDPQQGFKGFFEDKTYYCQAIVDDQEVDSDTFYVYRIQVSSVNVSISAVQT VVRQGENVTLMCTVSGNELVNFNWDYPRKQAGKAVEPVTDFLPGSTHDIRSIL IIQNAELEDSGTYVCNVSEGYHEKTDRKDITVQVIERGFVRFHTHLASTVYAEV HKSHIIQVDVEAYPQPNIVWLKNNKTLTMESSSEFTITNRNLSETRYQTSLVLVR VKQEEGGYYTIRASNEDDAQELSFHLQINVPAKVVDLKENSSASSGEQTVTCSA EGMPQPEISWSTCSNIKWCGSQGQPTQLLGNNSAEIGLHTNATYHAELQVYRV NSTLQLHRVDEPLLLRCTVQNFLGSNSQDITLVPNALPFKVVIISVILALLVLTVI SLIILIILWQKKPRYEIRWKVIESVSSDGHEYIYVDPMQLPYDSSWEVPRDKLVL GRTLGSGAFGRVVEATAHGLSHSQSTMKVAVKMLKSTARSSEKQALMSELKI |

9. SEQUENCE APPENDIX

| SEQ ID NO: | Description | Sequence |
|---|---|---|
| | | MSHLGPHLNIVNLLGACTKGGPIYIITEYCRYGDLVDYLHRNKHTFLQSYGEKA RREAELYGNTIKEDHVQSHLSLSVESDGGYMDMSKDESLDYVPMSDMKGEVK YADIESSNYGTPYELDSYSPSAPERTDRVTLINESPLLSYMDLVGFSFQVANGM EFLASKNCVHRDLAARNVLICEGKLVKICDFGLARDIMRDSNYISKGSTFLPLK WMAPESIFNNLYTTLSDVWSFGILLWEIFTLGGTPYPELPMNEQFYNAIKRGYR MSKPTHASDEIYDIMQKCWEEKFEIRPSFSQLVVLMGNLLVDCYRKRYQQVDE EFMKSDHPAVVRTRPTIPGLNNARLPPSSPTLYTAVHQNGGENDYIIPLPDPKPD AICDLPQEASVSRASSMLNEANTSSTISCDSPLGPRQDEEPECDLQLGCQELAPG HHEVEESFL* |
| 55 | ggPDGFRB- V536A | MLCPSLKASLQLLILTGLLEVTSGGSGLHIEPEDAELVLRLHSTFSLVCYGDGTL VWERDGQPLTAVLEHRDGVFISNLTLRNVTGRHTGEYACFYSPDQAPERAERK ALYIYVPDPSLVFLPAITSEEFFIFITGYTEATIPCRVTNPELQVTLYEKKVENPIP ATYDPQQGFKGFFEDKTYYCQAIVDDQEVDSDTFYVYRIQVSSVNVSISAVQT VVRQGENVTLMCTVSGNELVNFNWDYPRKQAGKAVEPVTDFLPGSTHDIRSIL IIQNAELEDSGTYVCNVSEGYHEKTDRKDITVQVIERGFVRFHTHLASTVYAEV HKSHIIQVDVEAYPQPNIVWLKNNKTLTMESSSEFTITNRNLSETRYQTSLVLVR VKQEEGGYYTIRASNEDDAQELSFHLQINVPAKVVDLKENSSASSGEQTVTCSA EGMPQPEISWSTCSNIKWCGSQGQPTQLLGNNSAEIGLHTNATYHAELQVYRV NSTLQLHRVDEPLLLRCTVQNFLGSNSQDITLVPNALPFKVVIISVILALLVLTVI SLIILIILWQKKPRYEIRWKAIESVSSDGHEYIYVDPMQLPYDSSWEVPRDKLVL GRTLGSGAFGRVVEATAHGLSHSQSTMKVAVKMLKSTARSSEKQALMSELKI MSHLGPHLNIVNLLGACTKGGPIYIITEYCRYGDLVDYLHRNKHTFLQSYGEKA RREAELYGNTIKEDHVQSHLSLSVESDGGYMDMSKDESLDYVPMSDMKGEVK YADIESSNYGTPYELDSYSPSAPERTDRVTLINESPLLSYMDLVGFSFQVANGM EFLASKNCVHRDLAARNVLICEGKLVKICDFGLARDIMRDSNYISKGSTFLPLK WMAPESIFNNLYTTLSDVWSFGILLWEIFTLGGTPYPELPMNEQFYNAIKRGYR MSKPTHASDEIYDIMQKCWEEKFEIRPSFSQLVVLMGNLLVDCYRKRYQQVDE EFMKSDHPAVVRTRPTIPGLNNARLPPSSPTLYTAVHQNGGENDYIIPLPDPKPD AICDLPQEASVSRASSMLNEANTSSTISCDSPLGPRQDEEPECDLQLGCQELAPG HHEVEESFL* |
| 56 | ggPDGFRB- D850V | MLCPSLKASLQLLILTGLLEVTSGGSGLHIEPEDAELVLRLHSTFSLVCYGDGTL VWERDGQPLTAVLEHRDGVFISNLTLRNVTGRHTGEYACFYSPDQAPERAERK ALYIYVPDPSLVFLPAITSEEFFIFITGYTEATIPCRVTNPELQVTLYEKKVENPIP ATYDPQQGFKGFFEDKTYYCQAIVDDQEVDSDTFYVYRIQVSSVNVSISAVQT VVRQGENVTLMCTVSGNELVNFNWDYPRKQAGKAVEPVTDFLPGSTHDIRSIL IIQNAELEDSGTYVCNVSEGYHEKTDRKDITVQVIERGFVRFHTHLASTVYAEV HKSHIIQVDVEAYPQPNIVWLKNNKTLTMESSSEFTITNRNLSETRYQTSLVLVR VKQEEGGYYTIRASNEDDAQELSFHLQINVPAKVVDLKENSSASSGEQTVTCSA EGMPQPEISWSTCSNIKWCGSQGQPTQLLGNNSAEIGLHTNATYHAELQVYRV NSTLQLHRVDEPLLLRCTVQNFLGSNSQDITLVPNALPFKVVIISVILALLVLTVI SLIILIILWQKKPRYEIRWKVIESVSSDGHEYIYVDPMQLPYDSSWEVPRDKLVL GRTLGSGAFGRVVEATAHGLSHSQSTMKVAVKMLKSTARSSEKQALMSELKI MSHLGPHLNIVNLLGACTKGGPIYIITEYCRYGDLVDYLHRNKHTFLQSYGEKA RREAELYGNTIKEDHVQSHLSLSVESDGGYMDMSKDESLDYVPMSDMKGEVK YADIESSNYGTPYELDSYSPSAPERTDRVTLINESPLLSYMDLVGFSFQVANGM EFLASKNCVHRDLAARNVLICEGKLVKICDFGLARDIMRNSNYISKGSTFLPLK WMAPESIFNNLYTTLSDVWSFGILLWEIFTLGGTPYPELPMNEQFYNAIKRGYR MSKPTHASDEIYDIMQKCWEEKFEIRPSFSQLVVLMGNLLVDCYRKRYQQVDE EFMKSDHPAVVRTRPTIPGLNNARLPPSSPTLYTAVHQNGGENDYIIPLPDPKPD AICDLPQEASVSRASSMLNEANTSSTISCDSPLGPRQDEEPECDLQLGCQELAPG HHEVEESFL* |
| 57 | F-9C- PRggPDGFRB | MADYKDDDDKKGGIIVAILLLIVMLAIEILLLITLIIAVTSGGSGLHIEPEDAELVL RLHSTFSLVCYGDGTLVWERDGQPLTAVLEHRDGVFISNLTLRNVTGRHTGEY ACFYSPDQAPERAERKALYIYVPDPSLVFLPAITSEEFFIFITGYTEATIPCRVTNP ELQVTLYEKKVENPIPATYDPQQGFKGFFEDKTYYCQAIVDDQEVDSDTFYVY RIQVSSVNVSISAVQTVVRQGENVTLMCTVSGNELVNFNWDYPRKQAGKAVE PVTDFLPGSTHDIRSILIIQNAELEDSGTYVCNVSEGYHEKTDRKDITVQVIERGF VRFHTHLASTVYAEVHKSHIIQVDVEAYPQPNIVWLKNNKTLTMESSSEFTITN RNLSETRYQTSLVLVRVKQEEGGYYTIRASNEDDAQELSFHLQINVPAKVVDL KENSSASSGEQTVTCSAEGMPQPEISWSTCSNIKWCGSQGQPTQLLGNNSAEIG LHTNATYHAELQVYRVNSTLQLHRVDEPLLLRCTVQNFLGSNSQDITLVPNALP FKVVIISVILALLVLTVISLIILIILWQKKPRYEIRWKVIESVSSDGHEYIYVDPMQ LPYDSSWEVPRDKLVLGRTLGSGAFGRVVEATAHGLSHSQSTMKVAVKMLKS TARSSEKQALMSELKIMSHLGPHLNIVNLLGACTKGGPIYIITEYCRYGDLVDYL HRNKHTFLQSYGEKARREAELYGNTIKEDHVQSHLSLSVESDGGYMDMSKDE SLDYVPMSDMKGEVKYADIESSNYGTPYELDSYSPSAPERTDRVTLINESPLLS YMDLVGFSFQVANGMEFLASKNCVHRDLAARNVLICEGKLVKICDFGLARDI MRDSNYISKGSTFLPLKWMAPESIFNNLYTTLSDVWSFGILLWEIFTLGGTPYPE LPMNEQFYNAIKRGYRMSKPTHASDEIYDIMQKCWEEKFEIRPSFSQLVVLMG NLLVDCYRKRYQQVDEEFMKSDHPAVVRTRPTIPGLNNARLPPSSPTLYTAVH |

9. SEQUENCE APPENDIX

| SEQ ID NO: | Description | Sequence |
|---|---|---|
| | | QNGGENDYIIPLPDPKPDAICDLPQEASVSRASSMLNEANTSSTISCDSPLGPRQD<br>EEPECDLQLGCQELAPGHHEVEESFL* |
| 58 | 9C-PRggPDGFRB | MAKGGIIVAILLLIVMLAIEILLLITLIIAVTSGGSGLHIEPEDAELVLRLHSTFSLV<br>CYGDGTLVWERDGQPLTAVLEHRDGVFISNLTLRNVTGRHTGEYACFYSPDQA<br>PERAERKALYIYVPDPSLVFLPAITSEEFFIFITGYTEATIPCRVTNPELQVTLYEK<br>KVENPIPATYDPQQGFKGFFEDKTYYCQAIVDDQEVDSDTFYVYRIQVSSVNVS<br>ISAVQTVVRQGENVTLMCTVSGNELVNFNWDYPRKQAGKAVEPVTDFLPGST<br>HDIRSILIIQNAELEDSGTYVCNVSEGYHEKTDRKDITVQVIERGFVRFHTHLAS<br>TVYAEVHKSHIIQVDVEAYPQPNIVWLKNNKTLTMESSSEFTITNRNLSETRYQ<br>TSLVLVRVKQEEGGYYTIRASNEDDAQELSFHLQINVPAKVVDLKENSSASSGE<br>QTVTCSAEGMPQPEISWSTCSNIKWCGSQGQPTQLLGNNSAEIGLHTNATYHAE<br>LQVYRVNSTLQLHRVDEPLLLRCTVQNFLGSNSQDITLVPNALPFKVVIISVILA<br>LLVLTVISLIILIILWQKKPRYEIRWKVIESVSSDGHEYIYVDPMQLPYDSSWEVP<br>RDKLVLGRTLGSGAFGRVVEATAHGLSHSQSTMKVAVKMLKSTARSSEKQAL<br>MSELKIMSHLGPHLNIVNLLGACTKGGPIYIITEYCRYGDLVDYLHRNKHTFLQ<br>SYGEKARREAELYGNTIKEDHVQSHLSLSVESDGGYMDMSKDESLDYVPMSD<br>MKGEVKYADIESSNYGTPYELDSYSPSAPERTDRVTLINESPLLSYMDLVGFSF<br>QVANGMEFLASKNCVHRDLAARNVLICEGKLVKICDFGLARDIMRDSNYISKG<br>STFLPLKWMAPESIFNNLYTTLSDVWSFGILLWEIFTLGGTPYPELPMNEQFYNA<br>IKRGYRMSKPTHASDEIYDIMQKCWEEKFEIRPSFSQLVVLMGNLLVDCYRKR<br>YQQVDEEFMKSDHPAVVRTRPTIPGLNNARLPPSSPTLYTAVHQNGGENDYIIP<br>LPDPKPDAICDLPQEASVSRASSMLNEANTSSTISCDSPLGPRQDEEPECDLQLG<br>CQELAPGHHEVEESFL* |
| 59 | FGFBP | MWIKNVGLLCVLILVSQMLLASCERQKERRRGKQGIEHGGKKQAESNPEREKG<br>RKPKGGKASPKGKFKSKENADCSWAVTDMSAATVHIECRNGDSAFWCEFSGD<br>PSACPHYAANQKSYWKQVSRSLKKQKQICQDPRSILKPKICRKGPRGAHLKLT<br>RSSLLAAVDPAKGHPAHHAAEDAQGPAASETGKQPEHSPPDCVEDVDYIDQRK<br>VAEEYCPESLLSLCNFFITMVQDKKC |
| 60 | RASV12 | MTEYKLVVVGAVGVGKSALTIQLIQNHFVDEYDPTIEDSYRKQVVIDGETCLL<br>DILDTAGQEEYSAMRDQYMRTGEGFLCVFAINNTKSFEDIHQYREQIKRVKDS<br>DDVPMVLVGNKCDLPARTVETRQAQDLARSYGIPYIETSAKTRQGVEDAFYTL<br>VREIRQHKLRKLNPPDESGPGCMNCKCVIS* |
| 61 | Chicken FGF2 or FGF2-WT | ATGGCGGCAGGAGCAGCTGGTTCCATAACCACATTGCCCGCCCTCCCAGAC<br>GATGGGGGCGGAGGCGCATTTCCTCCAGGTCATTTCAAGGACCCCAAAAGG<br>CTGTACTGTAAGAATGGTGGTTTTTTCCTGAGGATAAACCCTGACGGACGG<br>GTGGACGGCGTACGCGAGAAATCAGATCCACATATCAAGCTGCAGTTGCAA<br>GCCGAGGAACGCGGGGTAGTCTCTATAAAAGGGGTTAGCGCTAACAGATTT<br>TTGGCAATGAAGGAAGACGGTAGGCTCCTCGCGCTTAAGTGTGCCACCGAG<br>GAGTGCTTCTTCTTCGAACGGCTCGAATCTAACAACTACAACACGTACCGCT<br>CTCGCAAATACTCTGACTGGTACGTCGCACTCAAACGCACTGGGCAGTATA<br>AACCGGGGCCAAAGACGGGTCCGGGGCAGAAAGCTATCCTGTTCCTTCCAA<br>TGTCCGCCAAGAGTTAG |
| 62 | BM40-FGF2 | ATGGCGGCAGGAGCAGCTGGTTCCATAACCACATTGCCCGCCCTCCCAGAC<br>GATGGGGGCGGAGGCGCATTTCCTCCAGGTCATTTCAAGGACCCCAAAAGG<br>CTGTACTGTAAGAATGGTGGTTTTTTCCTGAGGATAAACCCTGACGGACGG<br>GTGGACGGCGTACGCGAGAAATCAGATCCACATATCAAGCTGCAGTTGCAA<br>GCCGAGGAACGCGGGGTAGTCTCTATAAAAGGGGTTAGCGCTAACAGATTT<br>TTGGCAATGAAGGAAGACGGTAGGCTCCTCGCGCTTAAGTGTGCCACCGAG<br>GAGTGCTTCTTCTTCGAACGGCTCGAATCTAACAACTACAACACGTACCGCT<br>CTCGCAAATACTCTGACTGGTACGTCGCACTCAAACGCACTGGGCAGTATA<br>AACCGGGGCCAAAGACGGGTCCGGGGCAGAAAGCTATCCTGTTCCTTCCAA<br>TGTCCGCCAAGAGTTAG |
| 63 | ggIL2-FGF2 | ATGATGTGTAAAGTTCTTATCTTCGGATGCATCTCCGTAGCAATGCTCATGA<br>CTACAGCTTACATGGCGGCAGGAGCAGCTGGTTCCATAACCACATTGCCCG<br>CCCTCCCAGACGATGGGGGCGGAGGCGCATTTCCTCCAGGTCATTTCAAGG<br>ACCCCAAAAGGCTGTACTGTAAGAATGGTGGTTTTTTCCTGAGGATAAACC<br>CTGACGGACGGGTGGACGGCGTACGCGAGAAATCAGATCCACATATCAAGC<br>TGCAGTTGCAAGCCGAGGAACGCGGGGTAGTCTCTATAAAAGGGGTTAGCG<br>CTAACAGATTTTTGGCAATGAAGGAAGACGGTAGGCTCCTCGCGCTTAAGT<br>GTGCCACCGAGGAGTGCTTCTTCTTCGAACGGCTCGAATCTAACAACTACA<br>ACACGTACCGCTCTCGCAAATACTCTGACTGGTACGTCGCACTCAAACGCA<br>CTGGGCAGTATAAACCGGGGCCAAAGACGGGTCCGGGGCAGAAAGCTATC<br>CTGTTCCTTCCAATGTCCGCCAAGAGTTAG |
| 64 | GLuc-FGF2 | ATGGGGGTCAAAGTGCTGTTTGCCTTGATCTGTATTGCTGTGGCCGAGGCAA<br>TGGCGGCAGGAGCAGCTGGTTCCATAACCACATTGCCCGCCCTCCCAGACG<br>ATGGGGGCGGAGGCGCATTTCCTCCAGGTCATTTCAAGGACCCCAAAAGGC |

-continued

9. SEQUENCE APPENDIX

| SEQ ID NO: | Description | Sequence |
|---|---|---|

TGTACTGTAAGAATGGTGGTTTTTTCCTGAGGATAAACCCTGACGGACGGGT
GGACGGCGTACGCGAGAAATCAGATCCACATATCAAGCTGCAGTTGCAAGC
CGAGGAACGCGGGGTAGTCTCTATAAAAGGGGTTAGCGCTAACAGATTTTT
GGCAATGAAGGAAGACGGTAGGCTCCTCGCGCTTAAGTGTGCCACCGAGGA
GTGCTTCTTCTTCGAACGGCTCGAATCTAACAACTACAACACGTACCGCTCT
CGCAAATACTCTGACTGGTACGTCGCACTCAAACGCACTGGGCAGTATAAA
CCGGGGCCAAAGACGGGTCCGGGGCAGAAAGCTATCCTGTTCCTTCCAATG
TCCGCCAAGAGTTAG 65   hIL2-FGF2   ATGTATCGCATGCAACTGCTTTCATGCATTGCTCTTAGCCTGGCGCTGGTCA
CGAACTCTATGGCGGCAGGAGCAGCTGGTTCCATAACCACATTGCCCGCCC
TCCCAGACGATGGGGGCGGAGGCGCATTTCCTCCAGGTCATTTCAAGGACC
CCAAAAGGCTGTACTGTAAGAATGGTGGTTTTTTCCTGAGGATAAACCCTG
ACGGACGGGTGGACGGCGTACGCGAGAAATCAGATCCACATATCAAGCTGC
AGTTGCAAGCCGAGGAACGCGGGGTAGTCTCTATAAAAGGGGTTAGCGCTA
ACAGATTTTTGGCAATGAAGGAAGACGGTAGGCTCCTCGCGCTTAAGTGTG
CCACCGAGGAGTGCTTCTTCTTCGAACGGCTCGAATCTAACAACTACAACA
CGTACCGCTCTCGCAAATACTCTGACTGGTACGTCGCACTCAAACGCACTGG
GCAGTATAAACCGGGGCCAAAGACGGGTCCGGGGCAGAAAGCTATCCTGTT
CCTTCCAATGTCCGCCAAGAGTTAG 66   hIL2co1-FGF2   ATGAGAATGCAACTGCTCCTGCTTATAGCGCTCAGTTTGGCTCTCGTGACCA
ACTCAATGGCGGCAGGAGCAGCTGGTTCCATAACCACATTGCCCGCCCTCC
CAGACGATGGGGGCGGAGGCGCATTTCCTCCAGGTCATTTCAAGGACCCCA
AAAGGCTGTACTGTAAGAATGGTGGTTTTTTCCTGAGGATAAACCCTGACG
GACGGGTGGACGGCGTACGCGAGAAATCAGATCCACATATCAAGCTGCAGT
TGCAAGCCGAGGAACGCGGGGTAGTCTCTATAAAAGGGGTTAGCGCTAACA
GATTTTTGGCAATGAAGGAAGACGGTAGGCTCCTCGCGCTTAAGTGTGCCA
CCGAGGAGTGCTTCTTCTTCGAACGGCTCGAATCTAACAACTACAACACGT
ACCGCTCTCGCAAATACTCTGACTGGTACGTCGCACTCAAACGCACTGGGC
AGTATAAACCGGGGCCAAAGACGGGTCCGGGGCAGAAAGCTATCCTGTTCC
TTCCAATGTCCGCCAAGAGTTAG 67   hIL2co2-FGF2   ATGAGGCGGATGCAATTGCTGCTGTTGATCGCACTCTCTCTGGCACTTGTCA
CTAATAGTATGGCGGCAGGAGCAGCTGGTTCCATAACCACATTGCCCGCCC
TCCCAGACGATGGGGGCGGAGGCGCATTTCCTCCAGGTCATTTCAAGGACC
CCAAAAGGCTGTACTGTAAGAATGGTGGTTTTTTCCTGAGGATAAACCCTG
ACGGACGGGTGGACGGCGTACGCGAGAAATCAGATCCACATATCAAGCTGC
AGTTGCAAGCCGAGGAACGCGGGGTAGTCTCTATAAAAGGGGTTAGCGCTA
ACAGATTTTTGGCAATGAAGGAAGACGGTAGGCTCCTCGCGCTTAAGTGTG
CCACCGAGGAGTGCTTCTTCTTCGAACGGCTCGAATCTAACAACTACAACA
CGTACCGCTCTCGCAAATACTCTGACTGGTACGTCGCACTCAAACGCACTGG
GCAGTATAAACCGGGGCCAAAGACGGGTCCGGGGCAGAAAGCTATCCTGTT
CCTTCCAATGTCCGCCAAGAGTTAG 68   ggIL6-FGF2   ATGAATTTTACAGAAGGGTGTGAAGCGACTGGCAGGAGACCAGGATCCGCC
GGGTCAAGGAGAAGAAGGGCCCCCCGGCCTGGGCCTGTCGCGCTTCTTCCC
CTGTTGCTTCCGCTGTTGCTTCCACCGGCAGCTGCGGTTCCCTTGCCCATGG
CGGCAGGAGCAGCTGGTTCCATAACCACATTGCCCGCCCTCCCAGACGATG
GGGGCGGAGGCGCATTTCCTCCAGGTCATTTCAAGGACCCCAAAAGGCTGT
ACTGTAAGAATGGTGGTTTTTTCCTGAGGATAAACCCTGACGGACGGGTGG
ACGGCGTACGCGAGAAATCAGATCCACATATCAAGCTGCAGTTGCAAGCCG
AGGAACGCGGGGTAGTCTCTATAAAAGGGGTTAGCGCTAACAGATTTTTGG
CAATGAAGGAAGACGGTAGGCTCCTCGCGCTTAAGTGTGCCACCGAGGAGT
GCTTCTTCTTCGAACGGCTCGAATCTAACAACTACAACACGTACCGCTCTCG
CAAATACTCTGACTGGTACGTCGCACTCAAACGCACTGGGCAGTATAAACC
GGGGCCAAAGACGGGTCCGGGGCAGAAAGCTATCCTGTTCCTTCCAATGTC
CGCCAAGAGTTAG 69   hIFN2A-
     ggFGF2   ATGGCGCTCACGTTTGCCCTCTTGGTTGCGCTTCTCGTTCTTTCCTGCAAGAG
TAGCTGTTCCGTGGGAATGGTATCCAAGATGGCGGCAGGAGCAGCTGGTTC
CATAACCACATTGCCCGCCCTCCCAGACGATGGGGGCGGAGGCGCATTTCC
TCCAGGTCATTTCAAGGACCCCAAAAGGCTGTACTGTAAGAATGGTGGTTTT
TTCCTGAGGATAAACCCTGACGGACGGGTGGACGGCGTACGCGAGAAATCA
GATCCACATATCAAGCTGCAGTTGCAAGCCGAGGAACGCGGGGTAGTCTCT
ATAAAAGGGGTTAGCGCTAACAGATTTTTGGCAATGAAGGAAGACGGTAGG
CTCCTCGCGCTTAAGTGTGCCACCGAGGAGTGCTTCTTCTTCGAACGGCTCG
AATCTAACAACTACAACACGTACCGCTCTCGCAAATACTCTGACTGGTACGT
CGCACTCAAACGCACTGGGCAGTATAAACCGGGGCCAAAGACGGGTCCGG
GGCAGAAAGCTATCCTGTTCCTTCCAATGTCCGCCAAGAGTTAG 70   secrecon-
     FGF2   ATGTGGTGGCGCTTGTGGTGGTTGCTGTTGTTGTTGCTGCTGTTGTGGCCTAT
GGTCTGGGCAATGGCGGCAGGAGCAGCTGGTTCCATAACCACATTGCCCGC

| | | |
|---|---|---|
| | | 9. SEQUENCE APPENDIX |

| SEQ ID NO: | Description | Sequence |
|---|---|---|
| | | CCTCCCAGACGATGGGGGCGGAGGCGCATTTCCTCCAGGTCATTTCAAGGA CCCCAAAAGGCTGTACTGTAAGAATGGTGGTTTTTTCCTGAGGATAAACCCT GACGGACGGGTGGACGGCGTACGCGAGAAATCAGATCCACATATCAAGCT GCAGTTGCAAGCCGAGGAACGCGGGGTAGTCTCTATAAAAGGGGTTAGCGC TAACAGATTTTTGGCAATGAAGGAAGACGGTAGGCTCCTCGCGCTTAAGTG TGCCACCGAGGAGTGCTTCTTCTTCGAACGGCTCGAATCTAACAACTACAAC ACGTACCGCTCTCGCAAATACTCTGACTGGTACGTCGCACTCAAACGCACTG GGCAGTATAAACCGGGGCCAAAGACGGGTCCGGGGCAGAAAGCTATCCTG TTCCTTCCAATGTCCGCCAAGAGTTAG |
| 71 | hIL6-FGF2 | ATGAATAGCTTCAGTACGTCTGCGTTCGGACCTGTGGCTTTTAGCCTCGGAC TGCTGCTCGTGCTGCCGGCGGCGTTTCCGGCACCCATGGCGGCAGGAGCAG CTGGTTCCATAACCACATTGCCCGCCCTCCCAGACGATGGGGGCGGAGGCG CATTTCCTCCAGGTCATTTCAAGGACCCCAAAAGGCTGTACTGTAAGAATG GTGGTTTTTTCCTGAGGATAAACCCTGACGGACGGGTGGACGGCGTACGCG AGAAATCAGATCCACATATCAAGCTGCAGTTGCAAGCCGAGGAACGCGGG GTAGTCTCTATAAAAGGGGTTAGCGCTAACAGATTTTTGGCAATGAAGGAA GACGGTAGGCTCCTCGCGCTTAAGTGTGCCACCGAGGAGTGCTTCTTCTTCG AACGGCTCGAATCTAACAACTACAACACGTACCGCTCTCGCAAATACTCTG ACTGGTACGTCGCACTCAAACGCACTGGGCAGTATAAACCGGGGCCAAAGA CGGGTCCGGGGCAGAAAGCTATCCTGTTCCTTCCAATGTCCGCCAAGAGTT AG |
| 72 | FGF2-Q68I- N114G-FGF2 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGAGGATAAACCCTGACGGACGG GTGGACGGCGTACGCGAGAAATCAGATCCACATATCAAGCTGCAGTTGATA GCCGAGGAACGCGGGGTAGTCTCTATAAAAGGGGTTAGCGCTAACAGATTT TTGGCAATGAAGGAAGACGGTAGGCTCCTCGCGCTTAAGTGTGCCACCGAG GAGTGCTTCTTCTTCGAACGGCTCGAATCTAACGGCTACAACACGTACCGCT CTCGCAAATACTCTGACTGGTACGTCGCACTCAAACGCACTGGGCAGTATA AACCGGGGCCAAAGACGGGTCCGGGGCAGAAAGCTATCCTGTTCCTTCCAA TGTCCGCCAAGAGTTAG |
| 73 | FGF2-Q68I- N114G-C99S- FGF2 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGAGGATAAACCCTGACGGACGG GTGGACGGCGTACGCGAGAAATCAGATCCACATATCAAGCTGCAGTTGATA GCCGAGGAACGCGGGGTAGTCTCTATAAAAGGGGTTAGCGCTAACAGATTT TTGGCAATGAAGGAAGACGGTAGGCTCCTCGCGCTTAAGTCTGCCACCGAG GAGTGCTTCTTCTTCGAACGGCTCGAATCTAACGGCTACAACACGTACCGCT CTCGCAAATACTCTGACTGGTACGTCGCACTCAAACGCACTGGGCAGTATA AACCGGGGCCAAAGACGGGTCCGGGGCAGAAAGCTATCCTGTTCCTTCCAA TGTCCGCCAAGAGTTAG |
| 74 | hIL2- colggFGF2 (xMet) | ATGAGAATGCAACTGCTCCTGCTTATAGCGCTCAGTTTGGCTCTCGTGACCA ACTCAGCGGCAGGAGCAGCTGGTTCCATAACCACATTGCCCGCCCTCCCAG ACGATGGGGGCGGAGGCGCATTTCCTCCAGGTCATTTCAAGGACCCCAAAA GGCTGTACTGTAAGAATGGTGGTTTTTTCCTGAGGATAAACCCTGACGGAC GGGTGGACGGCGTACGCGAGAAATCAGATCCACATATCAAGCTGCAGTTGC AAGCCGAGGAACGCGGGGTAGTCTCTATAAAAGGGGTTAGCGCTAACAGAT TTTTGGCAATGAAGGAAGACGGTAGGCTCCTCGCGCTTAAGTGTGCCACCG AGGAGTGCTTCTTCTTCGAACGGCTCGAATCTAACAACTACAACACGTACC GCTCTCGCAAATACTCTGACTGGTACGTCGCACTCAAACGCACTGGGCAGT ATAAACCGGGGCCAAAGACGGGTCCGGGGCAGAAAGCTATCCTGTTCCTTC CAATGTCCGCCAAGAGTTAG |
| 75 | FGF2-C77Y81 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGAGGATAAACCCTGACGGACGG GTGGACGGCGTACGCGAGAAATCAGATCCACATATCAAGCTGCAGTTGCAA GCCGAGGAACGCGGGGTAGTCTCTATAAAAGGGGTTTGCGCTAACAGATAT TTGGCAATGAAGGAAGACGGTAGGCTCCTCGCGCTTAAGTGTGCCACCGAG GAGTGCTTCTTCTTCGAACGGCTCGAATCTAACAACTACAACACGTACCGCT CTCGCAAATACTCTGACTGGTACGTCGCACTCAAACGCACTGGGCAGTATA AACCGGGGCCAAAGACGGGTCCGGGGCAGAAAGCTATCCTGTTCCTTCCAA TGTCCGCCAAGAGTTAG |
| 76 | FGF-STAB | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGCTGATAAACCCTGACGGACGGG TGGACGGCACCCGCGAGAAATCAGATCCATTCATCAAGCTGCAGTTGCAAG CCGAGGAACGCGGGGTAGTCTCTATAAAAGGGGGTTAGCGCTAACAGATTTT |

-continued

9. SEQUENCE APPENDIX

| SEQ ID NO: | Description | Sequence |
|---|---|---|
| | | TGGCAATGAAGGAAGACGGTAGGCTCTACGCGCTTAAGTATGCCACCGAGG AGTGCTTCTTCTTCGAACGGCTCGAAGAGAACAACTACAACACGTACCGCT CTCGCAAATACTCTGACTGGTACGTCGCACTCAAACGCACTGGGCAGTATA AACCGGGGCCAAAGACGGGTCCGGGGCAGAAAGCTATCCTGTTCCTTCCAA TGTCCGCCAAGAGTTAG |
| 77 | ggIL2-FGF-STAB | ATGATGTGTAAAGTTCTTATCTTCGGATGCATCTCCGTAGCAATGCTCATGA CTACAGCTTACATGGCGGCAGGAGCAGCTGGTTCCATAACCACATTGCCCG CCCTCCCAGACGATGGGGGCGGAGGCGCATTTCCTCCAGGTCATTTCAAGG ACCCCAAAAGGCTGTACTGTAAGAATGGTGGTTTTTTCCTGCTGATAAACCC TGACGGACGGGTGGACGGCACCCGCGAGAAATCAGATCCATTCATCAAGCT GCAGTTGCAAGCCGAGGAACGCGGGGTAGTCTCTATAAAAGGGGTTAGCGC TAACAGATTTTTGGCAATGAAGGAAGACGGTAGGCTCTACGCGCTTAAGTA TGCCACCGAGGAGTGCTTCTTCTTCGAACGGCTCGAAGAGAACAACTACAA CACGTACCGCTCTCGCAAATACTCTGACTGGTACGTCGCACTCAAACGCACT GGGCAGTATAAACCGGGGCCAAAGACGGGTCCGGGGCAGAAAGCTATCCT GTTCCTTCCAATGTCCGCCAAGAGTTAG |
| 78 | hIL2-FGF-STAB | ATGTATCGCATGCAACTGCTTTCATGCATTGCTCTTAGCCTGGCGCTGGTCA CGAACTCTATGGCGGCAGGAGCAGCTGGTTCCATAACCACATTGCCCGCCC TCCCAGACGATGGGGGCGGAGGCGCATTTCCTCCAGGTCATTTCAAGGACC CCAAAAGGCTGTACTGTAAGAATGGTGGTTTTTTCCTGCTGATAAACCCTGA CGGACGGGTGGACGGCACCCGCGAGAAATCAGATCCATTCATCAAGCTGCA GTTGCAAGCCGAGGAACGCGGGGTAGTCTCTATAAAAGGGGTTAGCGCTAA CAGATTTTTGGCAATGAAGGAAGACGGTAGGCTCTACGCGCTTAAGTATGC CACCGAGGAGTGCTTCTTCTTCGAACGGCTCGAAGAGAACAACTACAACAC GTACCGCTCTCGCAAATACTCTGACTGGTACGTCGCACTCAAACGCACTGG GCAGTATAAACCGGGGCCAAAGACGGGTCCGGGGCAGAAAGCTATCCTGTT CCTTCCAATGTCCGCCAAGAGTTAG |
| 79 | STAB-C77Y81 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGAGGATAAACCCTGACGGACGG GTGGACGGCGTACGCGAGAAATCAGATCCACATATCAAGCTGCAGTTGCAA GCCGAGGAACGCGGGGTAGTCTCTATAAAAGGGGTTTGCGCTAACAGATAT TTGGCAATGAAGGAAGACGGTAGGCTCCTCGCGCTTAAGTGTGCCACCGAG GAGTGCTTCTTCTTCGAACGGCTCGAATCTAACAACTACAACACGTACCGCT CTCGCAAATACTCTGACTGGTACGTCGCACTCAAACGCACTGGGCAGTATA AACCGGGGCCAAAGACGGGTCCGGGGCAGAAAGCTATCCTGTTCCTTCCAA TGTCCGCCAAGAGTTAG |
| 80 | c96-STAB-Gen2-ggFGF2 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGCTGATAAACCCTGACGGACGGG TGGACGGCACCCGCGAGAAATCAGATCCATTCATCAAGCTGCAGTTGCAAG CCGAGGAACGCGGGGTAGTCTCTATAAAAGGGGTTAGCGCTAACAGATTTT TGGCAATGAAGGAAGACGGTAGGCTCTACGCGCTTAAGTGTGCCACCGAGG AGTGCTTCTTCTTCGAACGGCTCGAAGAGAACAACTACAACACGTACCGCT CTCGCAAATACTCTGACTGGTACGTCGCACTCAAACGCACTGGGCAGTATA AACCGGGGCCAAAGACGGGTCCGGGGCAGAAAGCTATCCTGTTCCTTCCAA TGTCCGCCAAGAGTTAG |
| 81 | STAB-Gen3-ggFGF2 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGCTGATAAACCCTGACGGACGGG TGGACGGCACCCGCGACAAATCAGATCCATTCATCAAGCTGCAGTTGCAAG CCGAGGAACGCGGGGTAGTCTCTATAAAAGGGGTTAGCGCTAACAGATTTT TGGCAATGAAGGAAGACGGTAGGCTCTACGCGATAAAGAATGCCACCGAG GAGTGCTTCTTCTTCGAACGGCTCGAAGAGAACAACTACAACACGTACCGC TCTCGCAAATACCCTGACTGGTACGTCGCACTCAAACGCACTGGGCAGTAT AAACCGGGGCCAAAGACGGGTCCGGGGCAGAAAGCTATCCTGTTCCTTCCA ATGTCCGCCAAGAGTTAG |
| 82 | c96-STAB-Gen3-ggFGF2 | ATGGCGGCAGGAGCAGCTGGTTCCATAACCACATTGCCCGCCCTCCCAGAC GATGGGGGCGGAGGCGCATTTCCTCCAGGTCATTTCAAGGACCCCAAAAGG CTGTACTGTAAGAATGGTGGTTTTTTCCTGCTGATAAACCCTGACGGACGGG TGGACGGCACCCGCGACAAATCAGATCCATTCATCAAGCTGCAGTTGCAAG CCGAGGAACGCGGGGTAGTCTCTATAAAAGGGGTTAGCGCTAACAGATTTT TGGCAATGAAGGAAGACGGTAGGCTCTACGCGATAAAGTGTGCCACCGAG GAGTGCTTCTTCTTCGAACGGCTCGAAGAGAACAACTACAACACGTACCGC TCTCGCAAATACCCTGACTGGTACGTCGCACTCAAACGCACTGGGCAGTAT AAACCGGGGCCAAAGACGGGTCCGGGGCAGAAAGCTATCCTGTTCCTTCCA ATGTCCGCCAAGAGTTAG |

-continued

| | | 9. SEQUENCE APPENDIX |
|---|---|---|

| SEQ ID NO: | Description | Sequence |
|---|---|---|
| 83 | Bovine FGF2 | ATGGCCGCCGGGAGCATCACCACGCTGCCAGCCCTGCCGGAGGACGGCGGC AGCGGCGCTTTCCCGCCGGGGCCACTTCAAGGACCCCAAGCGGCTGTACTGC AAGAACGGGGGCTTCTTCCTGCGCATCCACCCCGACGGCCGAGTGGACGGG GTCCGCGAGAAGAGCGACCCACACATCAAACTACAACTTCAAGCAGAAGA GAGAGGGGTTGTGTCTATCAAAGGAGTGTGTGCAAACCGTTACCTTGCTAT GAAAGAAGATGGAAGATTACTAGCTTCTAAATGTGTTACAGACGAGTGTTT CTTTTTTGAACGATTGGAGTCTAATAACTACAATACTTACCGGTCAAGGAAA TACTCCAGTTGGTATGTGGCACTGAAACGAACTGGGCAGTATAAACTTGGA CCCAAAACAGGACCTGGGCAGAAAGCTATACTTTTTCTTCCAATGTCTGCTA AGAGCTGA |
| 84 | Salmon FGF2 | ATGGCCACAGGAGAAATCACCACTCTACCCGCCACACCTGAAGATGGAGGC AGTGGCGGCTTCCCTCCAGGAAACTTTAAGGATCCCAAGAGGCTGTACTGT AAAAACGGGGGCTACTTCTTGAGAATAAACTCTAATGGAAGCGTGGACGGG ATCCGAGAGAAGAACGACCCCCACATCAAGCTTCAACTCCAGGCGACCTCA GTAGGGGAGGTAGTGATCAAAGGGGTCTCAGCCAACCGTTATCTGGCCATG AATGGAGATGGAAGACTGTTTGGAACGAGACGGACAACAGATGAATGCTA CTTCATGGAGAGGCTGGAGAGTAACAACTACAACACCTACCGCTCACGGAA GTACCCTGACATGTATGTGGCGCTGAAAAGGACTGGCCAGTACAAGTCAGG ATCCAAAACTGGACCGGGCCAAAAAGCCATTCTCTTTCTCCCCATGTCAGCC AGACGCTGA |
| 85 | RASv12 | ATGACCGAGTACAAGCTGGTGGTAGTGGGAGCTGTAGGTGTCGGGAAGAGC GCTTTGACGATACAGCTCATTCAGAACCATTTTGTTGATGAGTACGACCCCA CAATAGAGGATTCCTACAGAAAGCAAGTCGTCATCGATGGAGAGACCTGTT TGCTGGACATCCTGGATACGGCGGGGCAGGAGGAGTACAGTGCCATGCGAG ACCAGTACATGAGAACGGGGGAAGGATTCCTGTGCGTCTTTGCCATTAACA ACACCAAGTCCTTTGAGGACATCCACCAGTACAGGGAGCAGATCAAGAGGG TGAAAGACTCAGATGATGTCCCCATGGTGCTGGTGGGAAATAAATGTGATC TGCCAGCACGGACAGTGGAGACCCGGCAAGCGCAGGACCTGGCCCGGAGT TACGGGATCCCCTACATAGAAACGTCGGCCAAAACCAGACAGGGCGTCGAA GATGCCTTCTATACCTTAGTGCGGGAGATCCGTCAGCATAAACTGCGCAAG CTGAACCCACCAGATGAGAGTGGCCCTGGCTGCATGAACTGTAAATGCGTG ATATCGTGA |
| 86 | FGFR1-WT | ATGTTCACGTGGAGATGTCTCATCCTGTGGGCGGTACTGGTTACCGCAACGT TGAGCGCAGCTAGGCCCGCCCCCACGCTGCCTGACCAGGCTCTCCCTAAGG CGAATATAGAAGTAGAATCACATTCTGCACATCCAGGAGACTTGTTGCAAT TGCGGTGCCGCTTGAGAGACGATGTCCAATCAATCAATTGGGTCAGGGACG GGGTCCAACTTCCGGAGAATAACCGGACAAGGATTACTGGAGAGGAGGTTG AAGTCAGGGACGCTGTTCCCGAAGATAGCGGCTTGTACGCTTGCATGACTA ATTCCCCGTCAGGGTCAGAAACCACGTATTTTTTCTGTAAACGTTAGCGATGC TCTTCCGAGTGCTGAAGACGATGATGATGAAGACGATAGCAGCTCCGAAGA GAAAGAGGCGGATAATACTAAACCAAATCAAGCTGTTGCACCATATTGGAC CTACCCCGAAAAAATGGAGAAAAAGTTGCATGCTGTTCCGGCAGCCAAAAC CGTAAAATTCAAGTGCCCCTCCGGCGGTACCCCTAATCCAACTCTGAGATG GTTGAAGAACGGTAAGGAGTTCAAACCGGATCACCGGATAGGTGGATATAA AGTTCGGTATGCGACCTGGTCCATTATTATGGACTCTGTCGTGCCCTCCGAC AAAGGTAACTACACTTGTATCGTCGAGAACAAGTACGGCAGCATCAATCAT ACGTACCAACTGGACGTGGTAGAACGCAGTCCACACCGCCCCATCCTCCAG GCCGGACTCCCTGCCAACAAAACAGTTGCGCTCGGCTCTAATGTTGAATTTG TGTGCAAAGTTTACTCAGACCCTCAACCTCATATCCAATGGCTTAAACATAT CGAAGTCAACGGTAGTAAGATAGGTCCCGACAACCTGCCGTATGTCCAGAT CCTTAAAACTGCGGGGGTAAATACCACTGACAAGGAAATGGAGGTCTTGCA TCTTCGCAACGTGAGCTTTGAAGATGCAGGTGAGTATACTTGTTTGGCAGGT AATAGCATCGGAATCTCCCACCATTCCGCCTGGCTGACAGTGCTGGAGGCC ACGGAACAAAGTCCGGCCATGATGACCAGTCCGTTGTATCTGGAAATTATC ATTTACTGTACAGGGGCCTTTCTCATATCATGCATGGTCGTAACCGTGATTA TATATAAAATGAAGAGCACAACGAAGAAGACTGATTTTAATTCACAACTGG CGGTACATAAACTCGCAAAATCTATCCCATTGAGGCGGCAGGTTACAGTCT CCGCCGACAGCTCCAGCAGCATGAACTCAGGAGTGATGCTTGTTCGCCCCA GCAGACTGAGTTCTAGTGGGACTCCGATGCTTGCTGGAGTCAGTGAATACG AATTGCCGGAGGATCCGCGGTGGGAACTTCCTAGGGACCGCCTTATATTGG GCAAACCCCTCGGTGAGGGCTGTTTCGGACAGGTCGTGCTCGCAGAGGCCA TCGGCCTTGACAAAGATAAGCCGAATAGAGTGACCAAGGTGGCGGTTAAA TGCTGAAATCAGACGCTACGGAAAAGGACCTCTCAGACCTCATCAGTGAAA TGGAAATGATGAAAATGATAGGGAAGCACAAAAAACATCATCAATTTGCTCG GAGCTTGTACCCAGGACGGTCCCCTCTACGTGATCGTAGAATACGCTTCCAA AGGTAATCTGCGCGAATATCTGCAAGCTCGGAGGCCGCCAGGTATGGAATA CTGTTATAATCCGACACGGATTCCCGAGGAACAGCTCTCTTTTAAAGATTTG GTTTCATGCGCGTATCAAGTGGCGAGGGGCATGGAGTATCTGGCGTCCAAG AAGTGCATTCATAGGGACTTGGCTGCAAGAAATGTCTTGGTAACAGAAGAC |

9. SEQUENCE APPENDIX

| SEQ ID NO: | Description | Sequence |
|---|---|---|

AACGTCATGAAGATCGCCGACTTCGGCCTTGCACGGGATATTCATCACATC
GACTATTACAAAAAGACGACGAACGGCCGCCTCCCAGTTAAGTGGATGGCC
CCCGAAGCCCTGTTCGATCGGATTTACACGCATCAATCCGACGTGTGGTCTT
TCGGTGTCCTGCTTTGGGAGATATTTACACTCGGGGGATCACCCTACCCCGG
AGTACCGGTGGAGGAGTTGTTCAAACTTCTTAAAGAAGGTCACAGAATGGA
CAAACCCAGTAACTGCACTAACGAGCTGTATATGATGATGCGCGATTGCTG
GCACGCTGTTCCGTCACAACGGCCCACTTTTAAACAGCTCGTGGAGGATCTT
GACAGAATCGTCGCGATGACTAGCAACCAAGAGTATTTGGATTTGTCAGTC
CCGCTTGACCAATATTCCCCCGGTTTTCCGGCTACCCGCTCTTCTACTTGTTC
CAGCGGTGAGGATAGTGTATTTTCTCATGACCCACTTCCAGATGAGCCGTGC
TTGCCTCGGTGTCCTCCCCACTCCCATGGAGCGCTCAAACGCCACTGA

87  FGFR1C-N546K

ATGTTCACGTGGAGATGTCTCATCCTGTGGGCGGTACTGGTTACCGCAACGT
TGAGCGCAGCTAGGCCCGCCCCCACGCTGCCTGACCAGGCTCTCCCTAAGG
CGAATATAGAAGTAGAATCACATTCTGCACATCCAGGAGACTTGTTGCAAT
TGCGGTGCCGCTTGAGAGACGATGTCCAATCAATCAATTGGGTCAGGGACG
GGGTCCAACTTCCGGAGAATAACCGGACAAGGATTACTGGAGAGGAGGTTG
AAGTCAGGGACGCTGTTCCCGAAGATAGCGGCTTGTACGCTTGCATGACTA
ATTCCCCGTCAGGGTCAGAAACCACGTATTTTTCTGTAAACGTTAGCGATGC
TCTTCCGAGTGCTGAAGACGATGATGATGAAGACGATAGCAGCTCCGAAGA
GAAAGAGGCGGATAATACTAAACCAAATCAAGCTGTTGCACCATATTGGAC
CTACCCCGAAAAAATGGAGAAAAAGTTGCATGCTGTTCCGGCAGCCAAAAC
CGTAAAATTCAAGTGCCCCTCCGGCGGTACCCCTAATCCAACTCTGAGATG
GTTGAAGAACGGTAAGGAGTTCAAACCGGATCACCGGATAGGTGGATATAA
AGTTCGGTATGCGACCTGGTCCATTATTATGGACTCTGTCGTGCCCTCCGAC
AAAGGTAACTACACTTGTATCGTCGAGAACAAGTACGGCAGCATCAATCAT
ACGTACCAACTGGACGTGGTAGAACGCAGTCCACACCGCCCCATCCTCCAG
GCCGGACTCCCTGCCAACAAAACAGTTGCGCTCGGCTCTAATGTTGAATTTG
TGTGCAAAGTTTACTCAGACCCTCAACCTCATATCCAATGGCTTAAACATAT
CGAAGTCAACGGTAGTAAGATAGGTCCCGACAACCTGCCGTATGTCCAGAT
CCTTAAAACTGCGGGGGTAAATACCACTGACAAGGAAATGGAGGTCTTGCA
TCTTCGCAACGTGAGCTTTGAAGATGCAGGTGAGTATACTTGTTTGGCAGGT
AATAGCATCGGAATCTCCCACCATTCCGCCTGGCTGACAGTGCTGGAGGCC
ACGGAACAAAGTCCGGCCATGATGACCAGTCCGTTGTATCTGGAAATTATC
ATTTACTGTACAGGGGCCTTTCTCATATCATGCATGGTCGTAACCGTGATTA
TATATAAAATGAAGAGCACAACGAAGAAGACTGATTTTAATTCACAACTGG
CGGTACATAAACTCGCAAAATCTATCCCATTGAGGCGGCAGGTTACAGTCT
CCGCCGACAGCTCCAGCAGCATGAACTCAGGAGTGATGCTTGTTCGCCCCA
GCAGACTGAGTTCTAGTGGGACTCCGATGCTTGCTGGAGTCAGTGAATACG
AATTGCCGGAGGATCCGCGGTGGGAACTTCCTAGGGACCGCCTTATATTGG
GCAAACCCCTCGGTGAGGGCTGTTTCGGACAGGTCGTGCTCGCAGAGGCCA
TCGGCCTTGACAAAGATAAGCCGAATAGAGTGACCAAGGTGGCGGTTAAAA
TGCTGAAATCAGACGCTACGGAAAAGGACCTCTCAGACCTCATCAGTGAAA
TGGAAATGATGAAAATGATAGGGAAGCACAAAAACATCATCAAGTTGCTCG
GAGCTTGTACCCAGGACGGTCCCCTCTACGTGATCGTAGAATACGCTTCCAA
AGGTAATCTGCGCGAATATCTGCAAGCTCGGAGGCCGCCAGGTATGGAATA
CTGTTATAATCCGACACGGATTCCCGAGGAACAGCTCTCTTTTAAAGATTTG
GTTTCATGCGCGTATCAAGTGGCGAGGGGCATGGAGTATCTGGCGTCCAAG
AAGTGCATTCATAGGGACTTGGCTGCAAGAAATGTCTTGGTAACAGAAGAC
AACGTCATGAAGATCGCCGACTTCGGCCTTGCACGGGATATTCATCACATC
GACTATTACAAAAAGACGACGAACGGCCGCCTCCCAGTTAAGTGGATGGCC
CCCGAAGCCCTGTTCGATCGGATTTACACGCATCAATCCGACGTGTGGTCTT
TCGGTGTCCTGCTTTGGGAGATATTTACACTCGGGGGATCACCCTACCCCGG
AGTACCGGTGGAGGAGTTGTTCAAACTTCTTAAAGAAGGTCACAGAATGGA
CAAACCCAGTAACTGCACTAACGAGCTGTATATGATGATGCGCGATTGCTG
GCACGCTGTTCCGTCACAACGGCCCACTTTTAAACAGCTCGTGGAGGATCTT
GACAGAATCGTCGCGATGACTAGCAACCAAGAGTATTTGGATTTGTCAGTC
CCGCTTGACCAATATTCCCCCGGTTTTCCGGCTACCCGCTCTTCTACTTGTTC
CAGCGGTGAGGATAGTGTATTTTCTCATGACCCACTTCCAGATGAGCCGTGC
TTGCCTCGGTGTCCTCCCCACTCCCATGGAGCGCTCAAACGCCACTGA

88  FGFR1C-V561M

GCCGCCACCATGTTCACGTGGAGATGTCTCATCCTGTGGGCGGTACTGGTTA
CCGCAACGTTGAGCGCAGCTAGGCCCGCCCCCACGCTGCCTGACCAGGCTC
TCCCTAAGGCGAATATAGAAGTAGAATCACATTCTGCACATCCAGGAGACT
TGTTGCAATTGCGGTGCCGCTTGAGAGACGATGTCCAATCAATCAATTGGGT
CAGGGACGGGGTCCAACTTCCGGAGAATAACCGGACAAGGATTACTGGAG
AGGAGGTTGAAGTCAGGGACGCTGTTCCCGAAGATAGCGGCTTGTACGCTT
GCATGACTAATTCCCCGTCAGGGTCAGAAACCACGTATTTTTCTGTAAACGT
TAGCGATGCTCTTCCGAGTGCTGAAGACGATGATGATGAAGACGATAGCAG
CTCCGAAGAGAAAGAGGCGGATAATACTAAACCAAATCAAGCTGTTGCACC
ATATTGGACCTACCCCGAAAAAATGGAGAAAAAGTTGCATGCTGTTCCGGC
AGCCAAAACCGTAAAATTCAAGTGCCCCTCCGGCGGTACCCCTAATCCAAC
TCTGAGATGGTTGAAGAACGGTAAGGAGTTCAAACCGGATCACCGGATAGG

-continued

---

9. SEQUENCE APPENDIX

| SEQ ID NO: | Description | Sequence |
|---|---|---|
| | | TGGATATAAAGTTCGGTATGCGACCTGGTCCATTATTATGGACTCTGTCGTG |
| | | CCCTCCGACAAAGGTAACTACACTTGTATCGTCGAGAACAAGTACGGCAGC |
| | | ATCAATCATACGTACCAACTGGACGTGGTAGAACGCAGTCCACACCGCCCC |
| | | ATCCTCCAGGCCGGACTCCCTGCCAACAAAACAGTTGCGCTCGGCTCTAAT |
| | | GTTGAATTTGTGTGCAAAGTTTACTCAGACCCTCAACCTCATATCCAATGGC |
| | | TTAAACATATCGAAGTCAACGGTAGTAAGATAGGTCCCGACAACCTGCCGT |
| | | ATGTCCAGATCCTTAAAACTGCGGGGGTAAATACCACTGACAAGGAAATGG |
| | | AGGTCTTGCATCTTCGCAACGTGAGCTTTGAAGATGCAGGTGAGTATACTTG |
| | | TTTGGCAGGTAATAGCATCGGAATCTCCCACCATTCCGCCTGGCTGACAGTG |
| | | CTGGAGGCCACGGAACAAAGTCCGGCCATGATGACCAGTCCGTTGTATCTG |
| | | GAAATTATCATTTACTGTACAGGGGCCTTTCTCATATCATGCATGGTCGTAA |
| | | CCGTGATTATATATAAAATGAAGAGCACAACGAAGAAGACTGATTTTAATT |
| | | CACAACTGGCGGTACATAAACTCGCAAAATCTATCCCATTGAGGCGGCAGG |
| | | TTACAGTCTCCGCCGACAGCTCCAGCAGCATGAACTCAGGAGTGATGCTTG |
| | | TTCGCCCCAGCAGACTGAGTTCTAGTGGGACTCCGATGCTTGCTGGAGTCAG |
| | | TGAATACGAATTGCCGGAGGATCCGCGGTGGGAACTTCCTAGGGACCGCCT |
| | | TATATTGGGCAAACCCCTCGGTGAGGGCTGTTTCGGACAGGTCGTGCTCGC |
| | | AGAGGCCATCGGCCTTGACAAAGATAAGCCGAATAGAGTGACCAAGGTGG |
| | | CGGTTAAAATGCTGAAATCAGACGCTACGGAAAAGGACCTCTCAGACCTCA |
| | | TCAGTGAAATGGAAATGATGAAAATGATAGGGAAGCACAAAAACATCATC |
| | | AATTTGCTCGGAGCTTGTACCCAGGACGGTCCCCTCTACGTGATCATGGAAT |
| | | ACGCTTCCAAAGGTAATCTGCGCGAATATCTGCAAGCTCGGAGGCCGCCAG |
| | | GTATGGAATACTGTTATAATCCGACACGGATTCCCGAGGAACAGCTCTCTTT |
| | | TAAAGATTTGGTTTCATGCGCGTATCAAGTGGCGAGGGGCATGGAGTATCT |
| | | GGCGTCCAAGAAGTGCATTCATAGGGACTTGGCTGCAAGAAATGTCTTGGT |
| | | AACAGAAGACAACGTCATGAAGATCGCCGACTTCGGCCTTGCACGGGATAT |
| | | TCATCACATCGACTATTACAAAAAGACGACGAACGGCCGCCTCCCAGTTAA |
| | | GTGGATGGCCCCCGAAGCCCTGTTCGATCGGATTTACACGCATCAATCCGA |
| | | CGTGTGGTCTTTCGGTGTCCTGCTTTGGGAGATATTTACACTCGGGGGATCA |
| | | CCCTACCCCGGAGTACCGGTGGAGGAGTTGTTCAAACTTCTTAAAGAAGGT |
| | | CACAGAATGGACAAACCCAGTAACTGCACTAACGAGCTGTATATGATGATG |
| | | CGCGATTGCTGGCACGCTGTTCCGTCACAACGGCCCACTTTTAAACAGCTCG |
| | | TGGAGGATCTTGACAGAATCGTCGCGATGACTAGCAACCAAGAGTATTTGG |
| | | ATTTGTCAGTCCCGCTTGACCAATATTCCCCCGGTTTTCCGGCTACCCGCTCT |
| | | TCTACTTGTTCCAGCGGTGAGGATAGTGTATTTTCTCATGACCCACTTCCAG |
| | | ATGAGCCGTGCTTGCCTCGGTGTCCTCCCCACTCCCATGGAGCGCTCAAACG |
| | | CCACTGA |
| 89 | FGFR1C-K656E | ATGTTCACGTGGAGATGTCTCATCCTGTGGGCGGTACTGGTTACCGCAACGT |
| | | TGAGCGCAGCTAGGCCCGCCCCCACGCTGCCTGACCAGGCTCTCCCTAAGG |
| | | CGAATATAGAAGTAGAATCACATTCTGCACATCCAGGAGACTTGGTGCAAT |
| | | TGCGGTGCCGCTTGAGAGACGATGTCCAATCAATCAATTGGGTCAGGGACG |
| | | GGGTCCAACTTCCGGAGAATAACCGGACAAGGATTACTGGAGAGGAGGTTG |
| | | AAGTCAGGGACGCTGTTCCCGAAGATAGCGGCTTGTACGCTTGCATGACTA |
| | | ATTCCCCGTCAGGGTCAGAAACCACGTATTTTTTCTGTAAACGTTAGCGATGC |
| | | TCTTCCGAGTGCTGAAGACGATGATGATGAAGACGATAGCAGCTCCGAAGA |
| | | GAAAGAGGCGGATAATACTAAACCAAATCAAGCTGTTGCACCATATTGGAC |
| | | CTACCCCGAAAAAATGGAGAAAAAGTTGCATGCTGTTCCGGCAGCCAAAAC |
| | | CGTAAAATTCAAGTGCCCCTCCGGCGGTACCCCTAATCCAACTCTGAGATG |
| | | GTTGAAGAACGGTAAGGAGTTCAAACCGGATCACCGGATAGGTGGATATAA |
| | | AGTTCGGTATGCGACCTGGTCCATTATTATGGACTCTGTCGTGCCCTCCGAC |
| | | AAAGGTAACTACACTTGTATCGTCGAGAACAAGTACGGCAGCATCAATCAT |
| | | ACGTACCAACTGGACGTGGTAGAACGCAGTCCACACCGCCCCATCCTCCAG |
| | | GCCGGACTCCCTGCCAACAAAACAGTTGCGCTCGGCTCTAATGTTGAATTTG |
| | | TGTGCAAAGTTTACTCAGACCCTCAACCTCATATCCAATGGCTTAAACATAT |
| | | CGAAGTCAACGGTAGTAAGATAGGTCCCGACAACCTGCCGTATGTCCAGAT |
| | | CCTTAAAACTGCGGGGGTAAATACCACTGACAAGGAAATGGAGGTCTTGCA |
| | | TCTTCGCAACGTGAGCTTTGAAGATGCAGGTGAGTATACTTGTTTGGCAGGT |
| | | AATAGCATCGGAATCTCCCACCATTCCGCCTGGCTGACAGTGCTGGAGGCC |
| | | ACGGAACAAAGTCCGGCCATGATGACCAGTCCGTTGTATCTGGAAATTATC |
| | | ATTTACTGTACAGGGGCCTTTCTCATATCATGCATGGTCGTAACCGTGATTA |
| | | TATATAAAATGAAGAGCACAACGAAGAAGACTGATTTTAATTCACAACTGG |
| | | CGGTACATAAACTCGCAAAATCTATCCCATTGAGGCGGCAGGTTACAGTCT |
| | | CCGCCGACAGCTCCAGCAGCATGAACTCAGGAGTGATGCTTGTTCGCCCCA |
| | | GCAGACTGAGTTCTAGTGGGACTCCGATGCTTGCTGGAGTCAGTGAATACG |
| | | AATTGCCGGAGGATCCGCGGTGGGAACTTCCTAGGGACCGCCTTATATTGG |
| | | GCAAACCCCTCGGTGAGGGCTGTTTCGGACAGGTCGTGCTCGCAGAGGCCA |
| | | TCGGCCTTGACAAAGATAAGCCGAATAGAGTGACCAAGGTGGCGGTTAAAA |
| | | TGCTGAAATCAGACGCTACGGAAAAGGACCTCTCAGACCTCATCAGTGAAA |
| | | TGGAAATGATGAAAATGATAGGGAAGCACAAAAACATCATCAATTTGCTCG |
| | | GAGCTTGTACCCAGGACGGTCCCCTCTACGTGATCGTAGAATACGCTTCCAA |
| | | AGGTAATCTGCGCGAATATCTGCAAGCTCGGAGGCCGCCAGGTATGGAATA |
| | | CTGTTATAATCCGACACGGATTCCCGAGGAACAGCTCTCTTTTAAAGATTTG |

-continued

| 9. SEQUENCE APPENDIX |
| --- |

SEQ
ID
NO:    Description       Sequence

|  |  | GTTTCATGCGCGTATCAAGTGGCGAGGGGCATGGAGTATCTGGCGTCCAAG<br>AAGTGCATTCATAGGGACTTGGCTGCAAGAAATGTCTTGGTAACAGAAGAC<br>AACGTCATGAAGATCGCCGACTTCGGCCTTGCACGGGATATTCATCACATC<br>GACTATTACAAAGAGACGACGAACGGCCGCCTCCCAGTTAAGTGGATGGCC<br>CCCGAAGCCCTGTTCGATCGGATTTACACGCATCAATCCGACGTGTGGTCTT<br>TCGGTGTCCTGCTTTGGGAGATATTTACACTCGGGGGATCACCCTACCCCGG<br>AGTACCGGTGGAGGAGTTGTTCAAACTTCTTAAAGAAGGTCACAGAATGGA<br>CAAACCCAGTAACTGCACTAACGAGCTGTATATGATGATGCGCGATTGCTG<br>GCACGCTGTTCCGTCACAACGGCCCACTTTTAAACAGCTCGTGGAGGATCTT<br>GACAGAATCGTCGCGATGACTAGCAACCAAGAGTATTTGGATTTGTCAGTC<br>CCGCTTGACCAATATTCCCCCGGTTTTCCGGCTACCCGCTCTTCTACTTGTTC<br>CAGCGGTGAGGATAGTGTATTTTCTCATGACCCACTTCCAGATGAGCCGTGC<br>TTGCCTCGGTGTCCTCCCCACTCCCATGGAGCGCTCAAACGCCACTGA |
| 90 | FGFR1-<br>N546K-<br>K656E-S780A | ATGTTCACGTGGAGATGTCTCATCCTGTGGGCGGTACTGGTTACCGCAACGT<br>TGAGCGCAGCTAGGCCCGCCCCCACGCTGCCTGACCAGGCTCTCCCTAAGG<br>CGAATATAGAAGTAGAATCACATTCTGCACATCCAGGAGACTTGTTGCAAT<br>TGCGGTGCCGCTTGAGAGACGATGTCCAATCAATCAATTGGGTCAGGGACG<br>GGGTCCAACTTCCGGAGAATAACCGGACAAGGATTACTGGAGAGGAGGTTG<br>AAGTCAGGGACGCTGTTCCCGAAGATAGCGGCTTGTACGCTTGCATGACTA<br>ATTCCCCGTCAGGGTCAGAAACCACGTATTTTTCTGTAAACGTTAGCGATGC<br>TCTTCCGAGTGCTGAAGACGATGATGATGAAGACGATAGCAGCTCCGAAGA<br>GAAAGAGGCGGATAATACTAAACCAAATCAAGCTGTTGCACCATATTGGAC<br>CTACCCCGAAAAAATGGAGAAAAAGTTGCATGCTGTTCCGGCAGCCAAAAC<br>CGTAAAATTCAAGTGCCCCTCCGGCGGTACTCCTAATCCAACTCTGAGATGG<br>TTGAAGAACGGTAAGGAGTTCAAACCGGATCACCGGATAGGTGGATATAAA<br>GTTCGGTATGCGACCTGGTCCATTATTATGGACTCTGTCGTGCCCTCCGACA<br>AAGGTAACTACACTTGTATCGTCGAGAACAAGTACGGCAGCATCAATCATA<br>CGTACCAACTGGACGTGGTAGAACGCAGTCCACACCGCCCCATCCTCCAGG<br>CCGGACTCCCTGCCAACAAAACAGTTGCGCTCGGCTCTAATGTTGAATTTGT<br>GTGCAAAGTTTACTCAGACCCTCAACCTCATATCCAATGGCTTAAACATATC<br>GAAGTCAACGGTAGTAAGATAGGTCCCGACAACCTGCCGTATGTCCAGATC<br>CTTAAAACTGCGGGGGTAAATACCACTGACAAGGAAATGGAGGTCTTGCAT<br>CTTCGCAACGTGAGCTTTGAAGATGCAGGTGAGTATACTTGTTTGGCAGGTA<br>ATAGCATCGGAATCTCCCCACCATTCCGCCTGGCTGACAGTGCTGGAGGCCA<br>CGGAACAAAGTCCGGCCATGATGACCAGTCCGTTGTATCTGGAAATTATCA<br>TTTACTGTACAGGGGCCTTTCTCATATCATGCATGGTCGTAACCGTGATTAT<br>ATATAAAATGAAGAGCACAACGAAGAAGACTGATTTTAATTCACAACTGGC<br>GGTACATAAACTCGCAAAATCTATCCCATTGAGGCGGCAGGTTACAGTCTC<br>CGCCGACAGCTCCAGCAGCATGAACTCAGGAGTGATGCTTGTTCGCCCCAG<br>CAGACTGAGTTCTAGTGGGACTCCGATGCTTGCTGGAGTCAGTGAATACGA<br>ATTGCCGGAGGATCCGCGGTGGGAACTTCCTAGGGACCGCCTTATATTGGG<br>CAAACCCCTCGGTGAGGGCTGTTTCGGACAGGTCGTGCTCGCAGAGGCCAT<br>CGGCCTTGACAAAGATAAGCCGAATAGAGTGACCAAGGTGGCGGTTAAAAT<br>GCTGAAATCAGACGCTACGGAAAAGGACCTCTCAGACCTCATCAGTGAAAT<br>GGAAATGATGAAAATGATAGGGAAGCACAAAAACATCATCAAGTTGCTCG<br>GAGCTTGTACCCAGGACGGTCCCCTCTACGTGATCGTAGAATACGCTTCCAA<br>AGGTAATCTGCGCGAATATCTGCAAGCTCGGAGGCCGCCAGGTATGGAATA<br>CTGTTATAATCCGACACGGATTCCCGAGGAACAGCTCTCTTTTAAAGATTTG<br>GTTTCATGCGCGTATCAAGTGGCGAGGGGCATGGAGTATCTGGCGTCCAAG<br>AAGTGCATTCATAGGGACTTGGCTGCAAGAAATGTCTTGGTAACAGAAGAC<br>AACGTCATGAAGATCGCCGACTTCGGCCTTGCACGGGATATTCATCACATC<br>GACTATTACAAAGAGACGACGAACGGCCGCCTCCCAGTTAAGTGGATGGCC<br>CCCGAAGCCCTGTTCGATCGGATTTACACGCATCAATCCGACGTGTGGTCTT<br>TCGGTGTCCTGCTTTGGGAGATATTTACACTCGGGGGATCACCCTACCCCGG<br>AGTACCGGTGGAGGAGTTGTTCAAACTTCTTAAAGAAGGTCACAGAATGGA<br>CAAACCCAGTAACTGCACTAACGAGCTGTATATGATGATGCGCGATTGCTG<br>GCACGCTGTTCCGTCACAACGGCCCACTTTTAAACAGCTCGTGGAGGATCTT<br>GACAGAATCGTCGCGATGACTAGCAACCAAGAGTATTTGGATTTGTCAGTC<br>CCGCTTGACCAATATGCCCCCGGTTTTCCGGCTACCCGCTCTTCTACTTGTTC<br>CAGCGGTGAGGATAGTGTATTTTCTCATGACCCACTTCCAGATGAGCCGTGC<br>TTGCCTCGGTGTCCTCCCCACTCCCATGGAGCGCTCAAACGCCACTGA |
| 91 | myrist-<br>FGFR1C-<br>K656E | ATGGGATCATCCAAGTCAAAACCGAAAGACCCGTCACAGAGAAAAATGAA<br>GAGCACAACGAAGAAGACTGATTTTAATTCACAACTGGCGGTACATAAACT<br>CGCAAAATCTATCCCATTGAGGCGGCAGGTTACAGTCTCCGCCGACAGCTC<br>CAGCAGCATGAACTCAGGAGTGATGCTTGTTCGCCCCAGCAGACTGAGTTC<br>TAGTGGGACTCCGATGCTTGCTGGAGTCAGTGAATACGAATTGCCGGAGGA<br>TCCGCGGTGGGAACTTCCTAGGGACCGCCTTATATTGGGCAAACCCCTCGGT<br>GAGGGCTGTTTCGGACAGGTCGTGCTCGCAGAGGCCATCGGCCTTGACAAA<br>GATAAGCCGAATAGAGTGACCAAGGTGGCGGTTAAAATGCTGAAATCAGA<br>CGCTACGGAAAAGGACCTCTCAGACCTCATCAGTGAAATGGAAATGATGAA<br>AATGATAGGGAAGCACAAAAACATCATCAATTTGCTCGGAGCTTGTACCCA |

| SEQ ID NO: | Description | Sequence |
|---|---|---|
| | | GGACGGTCCCCTCTACGTGATCGTAGAATACGCTTCCAAAGGTAATCTGCG<br>CGAATATCTGCAAGCTCGGAGGCCGCCAGGTATGGAATACTGTTATAATCC<br>GACACGGATTCCCGAGGAACAGCTCTCTTTTAAAGATTTGGTTTCATGCGCG<br>TATCAAGTGGCGAGGGGCATGGAGTATCTGGCGTCCAAGAAGTGCATTCAT<br>AGGGGACTTGGCTGCAAGAAATGTCTTGGTAACAGAAGACAACGTCATGAAG<br>ATCGCCGACTTCGGCCTTGCACGGGATATTCATCACATCGACTATTACAAAG<br>AGACGACGAACGGCCGCCTCCCAGTTAAGTGGATGGCCCCCGAAGCCCTGT<br>TCGATCGGATTTACACGCATCAATCCGACGTGTGGTCTTTCGGTGTCCTGCT<br>TTGGGAGATATTTACACTCGGGGGATCACCCTACCCCGGAGTACCGGTGGA<br>GGAGTTGTTCAAACTTCTTAAAGAAGGTCACAGAATGGACAAACCCAGTAA<br>CTGCACTAACGAGCTGTATATGATGATGCGCGATTGCTGGCACGCTGTTCCG<br>TCACAACGGCCCACTTTTAAACAGCTCGTGGAGGATCTTGACAGAATCGTC<br>GCGATGACTAGCAACCAAGAGTATTTGGATTTGTCAGTCCCGCTTGACCAAT<br>ATTCCCCCGGTTTTCCGGCTACCCGCTCTTCTACTTGTTCCAGCGGTGAGGA<br>TAGTGTATTTTCTCATGACCCACTTCCAGATGAGCCGTGCTTGCCTCGGTGT<br>CCTCCCCACTCCCATGGAGCGCTCAAACGCCACTGA |
| 92 | FGFR2-WT | ATGGGCCTTAAGTCAACTTGGAGATACGGCAATGGCCCGGGTACGTACTCC<br>AAGAAAATGGTATCTTGGGATTCCGGTTGTCTCATTTGTCTGGTAGTGGTTA<br>CCATGGCGGGCCTGAGTCTGGCGAGACCCTCTTTTAATCTGGTAGTTGAAGA<br>CGCTACCTTGGAGCCAGAAGAGCCGCCCACTAAGTATCAGATAAGTCAGCC<br>TGATGTGCACTCCGCGCTTCCGGGAGAACCTCTCGAGTTGCGCTGTCAACTC<br>AAGGATGCCGTGATGATCAGCTGGACGAAAGATGGAGTGCCTCTTGGACCA<br>GATAATCGCACTGTTATCATTGGTGAATACTTGCAAATTAAAGATGCATCAC<br>CACGGGATTCTGGCCTTTACGCGTGCACAGCTATCAGGACGCTCGACTCCG<br>ATACACTCTATTTATAGTCAACGTTACCGATGCGTTGTCAAGCGGGGATGA<br>TGAGGACGACAACGACGGGTCAGAAGACTTCGTTAACGATTCCAATCAGAT<br>GAGAGCTCCCTATTGGACCCACACTGACAAAATGGAAAAAAGGCTCCACGC<br>TGTCCCGGCTGCGAATACTGTGAAGTTTAGATGTCCCGCAATGGGCAACCC<br>CACGCCAACAATGCGGTGGTTGAAAAATGGTAAAGAGTTCAAACAGGAGC<br>ATCGGATAGGTGGGTATAAAGTGAGAAATCAACATTGGAGCTTGATCATGG<br>AGTCTGTAGTTCCTTCAGATAAAGGAAATTATACATGCATCGTCGAGAATC<br>AATACGGCTCTATTAACCATACATATCACCTGGACGTCGTAGAGAGGAGTC<br>CCCACAGGCCTATCCTGCAAGCGGGACTGCCGGCAAATGCTTCTGCAGTCG<br>TGGGCGGTGACGTTGAGTTCGTCTGTAAGGTGTACAGCGACGCACAACCAC<br>ACATCCAATGGATAAAGCATGTTGAGAGAAATGGTTCAAAATATGGCCCGG<br>ACGGCTTGCCCTACCTTCAGGTGCTCAAAGCTGCGGGAGTCAACACTACTG<br>ATAAGGAAATCGAGGTGCTCTATATTAGGAACGTTACCTTTGAAGACGCCG<br>GCGAATACACCTGTCTCGCGGGAAACTCTATCGGTATCTCATTTCACACCGC<br>ATGGTTGACTGTGCTTCCAGCTCCGGAGAAAGAGAAGGAGTTTCCGACCTC<br>CCCTGATTACCTCGAAATAGCGATCTATTGCATCGGAGTTTTTCTCATCGCG<br>TGCATGGTTCTTACTGTGATACTTTGTAGAATGAAGAACACCACCAAGAAA<br>CCGGATTTTTCCTCCCAACCGGCCGTCCACAAGTTGACGAAACGGATCCCAT<br>TGAGGCGCCAGGTGAGTGCTGACAGCTCAAGTTCAATGAACAGTAACACGC<br>CGCTCGTGAGGATCACTACTCGGCTGAGCTCTACCGCGGATGCGCCAATGTT<br>GGCAGGGGTCAGTGAGTACGAACTCCCGGAAGATCCGAAGTGGGAGTTTCC<br>GCGCGACAAACTCACTCTTGGAAAACCGCTTGGAGAGGGATGCTTCGGACA<br>GGTCGTAATGGCCGAGGCGGTTGGTATAGACAAAGATAGACCCAAAGAAG<br>CTGTCACAGTAGCTGTAAAAATGCTTAAGGATGATGCCACTGAAAAAGATT<br>TGAGCGACCTCGTAAGCGAGATGGAAATGATGAAAATGATAGGGAAGCAC<br>AAAAATATAATTAACCTCCTGGGGGCCTGCACACAGGACGGCCCGTTGTAT<br>GTCATCGTCGAATATGCCTCCAAAGGGAACCTCAGGGAGTACCTTAGAGCG<br>CGCAGACCGCCGGGGATGGAGTATTCATTTGACATCAATCGGGTCCCCGAA<br>GAACAAATGACTTTCAAAGACCTTGTCTCCTGTACCTATCAACTCGCCCGCG<br>GAATGGAATATTTGGCTAGTCAAAAATGCATTCACCGCGATCTTGCTGCAC<br>GGAACGTACTCGTCACTGAGAATAACGTTATGAAAATAGCGGATTTCGGCC<br>TCGCAAGGGACATAAACAACATCGACTACTACAAAAAAACCACGAATGGC<br>AGACTGCCAGTCAAGTGGATGGCGCCAGAAGCCCTTTTTGATAGAGTCTAC<br>ACGCACCAGTCAGACGTGTGGTCCTTTGGAGTGCTCATGTGGGAAATCTTTA<br>CGCTGGGTGGTAGCCCTTACCCGGGGATTCCCGTGGAAGAACTTTTCAAGCT<br>GTTGAAAGAGGGCCATCGGATGGACAAACCCGCAAATTGCACAAATGAATT<br>GTATATGATGATGCGCGACTGTTGGCAAGCCGTGCCTTCACAGAGACCTAC<br>ATTCAAGCAGTTGGTCGAAGACCTCGACCGGATCCTGACGCTTACAACGAA<br>CGAAGAATACCTGGACTTGTCTGGTCCCTTGGAGCAATACTCACCAAGCTA<br>CCCCGATACTCGGTCATCTTGCTCTAGTGGCGACGATAGTGTCTTTTCACCT<br>GATCCAATGCCCTACGAACCGTGTCTGCCAAAGTACCAACACATGAACGGT<br>TCAGTAAAGACCTGA |
| 93 | FGFR2-<br>N550K | ATGGGCCTTAAGTCAACTTGGAGATACGGCAATGGCCCGGGTACGTACTCC<br>AAGAAAATGGTATCTTGGGATTCCGGTTGTCTCATTTGTCTGGTAGTGGTTA<br>CCATGGCGGGCCTGAGTCTGGCGAGACCCTCTTTTAATCTGGTAGTTGAAGA<br>CGCTACCTTGGAGCCAGAAGAGCCGCCCACTAAGTATCAGATAAGTCAGCC<br>TGATGTGCACTCCGCGCTTCCGGGAGAACCTCTCGAGTTGCGCTGTCAACTC |

9. SEQUENCE APPENDIX

| SEQ ID NO: | Description | Sequence |
|---|---|---|
| | | AAGGATGCCGTGATGATCAGCTGGACGAAAGATGGAGTGCCTCTTGGACCA<br>GATAATCGCACTGTTATCATTGGTGAATACTTGCAAATTAAAGATGCATCAC<br>CACGGGATTCTGGCCTTTACGCGTGCACAGCTATCAGGACGCTCGACTCCG<br>ATACACTCTATTTTATAGTCAACGTTACCGATGCGTTGTCAAGCGGGGATGA<br>TGAGGACGACAACGACGGGTCAGAAGACTTCGTTAACGATTCCAATCAGAT<br>GAGAGCTCCCTATTGGACCCACACTGACAAAATGGAAAAAAGGCTCCACGC<br>TGTCCCGGCTGCGAATACTGTGAAGTTTAGATGTCCCGCAATGGGCAACCC<br>CACGCCAACAATGCGGTGGTTGAAAAATGGTAAAGAGTTCAAACAGGAGC<br>ATCGGATAGGTGGGTATAAAGTGAGAAATCAACATTGGAGCTTGATCATGG<br>AGTCTGTAGTTCCTTCAGATAAAGGAAATTATACATGCATCGTCGAGAATC<br>AATACGGCTCTATTAACCATACATATCACCTGGACGTCGTAGAGAGGAGTC<br>CCCACAGGCCTATCCTGCAAGCGGGACTGCCGGCAAATGCTTCTGCAGTCG<br>TGGGCGGTGACGTTGAGTTCGTCTGTAAGGTGTACAGCGACGCACAACCAC<br>ACATCCAATGGATAAAGCATGTTGAGAGAAATGGTTCAAAATATGGCCCGG<br>ACGGCTTGCCCTACCTTCAGGTGCTCAAAGCTGCGGGAGTCAACACTACTG<br>ATAAGGAAATCGAGGTGCTCTATATTAGGAACGTTACCTTTGAAGACGCCG<br>GCGAATACACCTGTCTCGCGGGAAACTCTATCGGTATCTCATTTCACACCGC<br>ATGGTTGACTGTGCTTCCAGCTCCGGAGAAAGAGAAGGAGTTTCCGACCTC<br>CCCTGATTACCTCGAAATAGCGATCTATTGCATCGGAGTTTTTTCTCATCGCG<br>TGCATGGTTCTTACTGTGATACTTTGTAGAATGAAGAACACCACCAAGAAA<br>CCGGATTTTTCCTCCCAACCGGCCGTCCACAAGTTGACGAAACGGATCCCAT<br>TGAGGCGCCAGGTGAGTGCTGACAGCTCAAGTTCAATGAACAGTAACACGC<br>CGCTCGTGAGGATCACTACTCGGCTGAGCTCTACCGCGGATGCGCCAATGTT<br>GGCAGGGGTCAGTGAGTACGAACTCCCGGAAGATCCGAAGTGGGAGTTTCC<br>GCGCGACAAACTCACTCTTGGAAAACCGCTTGGAGAGGGATGCTTCGGACA<br>GGTCGTAATGGCCGAGGCGGTTGGTATAGACAAAGATAGACCCAAAGAAG<br>CTGTCACAGTAGCTGTAAAAATGCTTAAGGATGATGCCACTGAAAAAGATT<br>TGAGCGACCTCGTAAGCGAGATGGAAATGATGAAAATGATAGGGAAGCAC<br>AAAAATATAATTAAGCTCCTGGGGGCCTGCACACAGGACGGCCCGTTGTAT<br>GTCATCGTCGAATATGCCTCCAAAGGGAACCTCAGGGAGTACCTTAGAGCG<br>CGCAGACCGCCGGGGATGGAGTATTCATTTGACATCAATCGGGTCCCCGAA<br>GAACAAATGACTTTCAAAGACCTTGTCTCCTGTACCTATCAACTCGCCCGCG<br>GAATGGAATATTTGGCTAGTCAAAAATGCATTCACCGCGATCTTGCTGCAC<br>GGAACGTACTCGTCACTGAGAATAACGTTATGAAAATAGCGGATTTCGGCC<br>TCGCAAGGGACATAAACAACATCGACTACTACAAAAAAACCACGAATGGC<br>AGACTGCCAGTCAAGTGGATGGCGCCAGAAGCCCTTTTTGATAGAGTCTAC<br>ACGCACCAGTCAGACGTGTGGTCCTTTGGAGTGCTCATGTGGGAAATCTTTA<br>CGCTGGGTGGTAGCCCTTACCCGGGGATTCCCGTGGAAGAACTTTTCAAGCT<br>GTTGAAAGAGGGCCATCGGATGGACAAACCCGCAAATTGCACAAATGAATT<br>GTATATGATGATGCGCGACTGTTGGCAAGCCGTGCCTTCACAGAGACCTAC<br>ATTCAAGCAGTTGGTCGAAGACCTCGACCGGATCCTGACGCTTACAACGAA<br>CGAAGAATACCTGGACTTGTCTGGTCCCTTGGAGCAATACTCACCAAGCTA<br>CCCCGATACTCGGTCATCTTGCTCTAGTGGCGACGATAGTGTCTTTTCACCT<br>GATCCAATGCCCTACGAACCGTGTCTGCCAAAGTACCAACACATGAACGGT<br>TCAGTAAAGACCTGA |
| 94 | FGFR2-<br>K660E | ATGGGCCTTAAGTCAACTTGGAGATACGGCAATGGCCCGGGTACGTACTCC<br>AAGAAAATGGTATCTTGGGATTCCGGTTGTCTCATTTGTCTGGTAGTGGTTA<br>CCATGGCGGGCCTGAGTCTGGCGAGACCCTCTTTTAATCTGGTAGTTGAAGA<br>CGCTACCTTGGAGCCAGAAGAGCCGCCCACTAAGTATCAGATAAGTCAGCC<br>TGATGTGCACTCCGCGCTTCCGGGAGAACCTCTCGAGTTGCGCTGTCAACTC<br>AAGGATGCCGTGATGATCAGCTGGACGAAAGATGGAGTGCCTCTTGGACCA<br>GATAATCGCACTGTTATCATTGGTGAATACTTGCAAATTAAAGATGCATCAC<br>CACGGGATTCTGGCCTTTACGCGTGCACAGCTATCAGGACGCTCGACTCCG<br>ATACACTCTATTTTATAGTCAACGTTACCGATGCGTTGTCAAGCGGGGATGA<br>TGAGGACGACAACGACGGGTCAGAAGACTTCGTTAACGATTCCAATCAGAT<br>GAGAGCTCCCTATTGGACCCACACTGACAAAATGGAAAAAAGGCTCCACGC<br>TGTCCCGGCTGCGAATACTGTGAAGTTTAGATGTCCCGCAATGGGCAACCC<br>CACGCCAACAATGCGGTGGTTGAAAAATGGTAAAGAGTTCAAACAGGAGC<br>ATCGGATAGGTGGGTATAAAGTGAGAAATCAACATTGGAGCTTGATCATGG<br>AGTCTGTAGTTCCTTCAGATAAAGGAAATTATACATGCATCGTCGAGAATC<br>AATACGGCTCTATTAACCATACATATCACCTGGACGTCGTAGAGAGGAGTC<br>CCCACAGGCCTATCCTGCAAGCGGGACTGCCGGCAAATGCTTCTGCAGTCG<br>TGGGCGGTGACGTTGAGTTCGTCTGTAAGGTGTACAGCGACGCACAACCAC<br>ACATCCAATGGATAAAGCATGTTGAGAGAAATGGTTCAAAATATGGCCCGG<br>ACGGCTTGCCCTACCTTCAGGTGCTCAAAGCTGCGGGAGTCAACACTACTG<br>ATAAGGAAATCGAGGTGCTCTATATTAGGAACGTTACCTTTGAAGACGCCG<br>GCGAATACACCTGTCTCGCGGGAAACTCTATCGGTATCTCATTTCACACCGC<br>ATGGTTGACTGTGCTTCCAGCTCCGGAGAAAGAGAAGGAGTTTCCGACCTC<br>CCCTGATTACCTCGAAATAGCGATCTATTGCATCGGAGTTTTTTCTCATCGCG<br>TGCATGGTTCTTACTGTGATACTTTGTAGAATGAAGAACACCACCAAGAAA<br>CCGGATTTTTCCTCCCAACCGGCCGTCCACAAGTTGACGAAACGGATCCCAT<br>TGAGGCGCCAGGTGAGTGCTGACAGCTCAAGTTCAATGAACAGTAACACGC |

| 9. SEQUENCE APPENDIX | | |
|---|---|---|

| SEQ ID NO: | Description | Sequence |
|---|---|---|
| | | CGCTCGTGAGGATCACTACTCGGCTGAGCTCTACCGCGGATGCGCCAATGTT<br>GGCAGGGGTCAGTGAGTACGAACTCCCGGAAGATCCGAAGTGGGAGTTTCC<br>GCGCGACAAACTCACTCTTGGAAAACCGCTTGGAGAGGGATGCTTCGGACA<br>GGTCGTAATGGCCGAGGCGGTTGGTATAGACAAAGATAGACCCAAAGAAG<br>CTGTCACAGTAGCTGTAAAAATGCTTAAGGATGATGCCACTGAAAAAGATT<br>TGAGCGACCTCGTAAGCGAGATGGAAATGATGAAAATGATAGGGAAGCAC<br>AAAAAATATAATTAACCTCCTGGGGGCCTGCACACAGGACGGCCCGTTGTAT<br>GTCATCGTCGAATATGCCTCCAAAGGGAACCTCAGGGAGTACCTTAGAGCG<br>CGCAGACCGCCGGGGATGGAGTATTCATTTGACATCAATCGGGTCCCCGAA<br>GAACAAATGACTTTCAAAGACCTTGTCTCCTGTACCTATCAACTCGCCCGCG<br>GAATGGAATATTTGGCTAGTCAAAAATGCATTCACCGCGATCTTGCTGCAC<br>GGAACGTACTCGTCACTGAGAATAACGTTATGAAAATAGCGGATTTCGGCC<br>TCGCAAGGGACATAAACAACATCGACTACTACAAAGAAACCACGAATGGC<br>AGACTGCCAGTCAAGTGGATGGCGCCAGAAGCCCTTTTTGATAGAGTCTAC<br>ACGCACCAGTCAGACGTGTGGTCCTTTGGAGTGCTCATGTGGGAAATCTTTA<br>CGCTGGGTGGTAGCCCTTACCCGGGGATTCCCGTGGAAGAACTTTTCAAGCT<br>GTTGAAAGAGGGCCATCGGATGGACAAACCCGCAAATTGCACAAATGAATT<br>GTATATGATGATGCGCGACTGTTGGCAAGCCGTGCCTTCACAGAGACCTAC<br>ATTCAAGCAGTTGGTCGAAGACCTCGACCGGATCCTGACGCTTACAACGAA<br>CGAAGAATACCTGGACTTGTCTGGTCCCTTGGAGCAATACTCACCAAGCTA<br>CCCCGATACTCGGTCATCTTGCTCTAGTGGCGACGATAGTGTCTTTTCACCT<br>GATCCAATGCCCTACGAACCGTGTCTGCCAAAGTACCAACACATGAACGGT<br>TCAGTAAAGACCTGA |
| 95 | FGFR2-<br>N550K-<br>N660E-S780A | ATGGGCCTTAAGTCAACTTGGAGATACGGCAATGGCCCGGGTACGTACTCC<br>AAGAAAATGGTATCTTGGGATTCCGGTTGTCTCATTTGTCTGGTAGTGGTTA<br>CCATGGCGGGCCTGAGTCTGGCGAGACCCTCTTTTAATCTGGTAGTTGAAGA<br>CGCTACCTTGGAGCCAGAAGAGCCGCCCACTAAGTATCAGATAAGTCAGCC<br>TGATGTGCACTCCGCGCTTCCGGGAGAACCTCTCGAGTTGCGCTGTCAACTC<br>AAGGATGCCGTGATGATCAGCTGGACGAAAGATGGAGTGCCTCTTGGACCA<br>GATAATCGCACTGTTATCATTGGTGAATACTTGCAAATTAAAGATGCATCAC<br>CACGGGATTCTGGCCTTTACGCGTGCACAGCTATCAGGACGCTCGACTCCG<br>ATACACTCTATTTTATAGTCAACGTTACCGATGCGTTGTCAAGCGGGGATGA<br>TGAGGACGACAACGACGGGTCAGAAGACTTCGTTAACGATTCCAATCAGAT<br>GAGAGCTCCCTATTGGACCCACACTGACAAAATGGAAAAAAGGCTCCACGC<br>TGTCCCGGCTGCGAATACTGTGAAGTTTAGATGTCCCGCAATGGGCAACCC<br>CACGCCAACAATGCGGTGGTTGAAAAATGGTAAAGAGTTCAAACAGGAGC<br>ATCGGATAGGTGGGTATAAAGTGAGAAATCAACATTGGAGCTTGATCATGG<br>AGTCTGTAGTTCCTTCAGATAAAGGAAATTATACATGCATCGTCGAGAATC<br>AATACGGCTCTATTAACCATACATATCACCTGGACGTCGTAGAGAGGAGTC<br>CCCACAGGCCTATCCTGCAAGCGGGACTGCCGGCAAATGCTTCTGCAGTCG<br>TGGGCGGTGACGTTGAGTTCGTCTGTAAGGTGTACAGCGACGCACAACCAC<br>ACATCCAATGGATAAAGCATGTTGAGAGAAATGGTTCAAAATATGGCCCGG<br>ACGGCTTGCCCTACCTTCAGGTGCTCAAAGCTGCGGGAGTCAACACTACTG<br>ATAAGGAAATCGAGGTGCTCTATATTAGGAACGTTACCTTTGAAGACGCCG<br>GCGAATACACCTGTCTCGCGGGAAACTCTATCGGTATCTCATTTCACACCGC<br>ATGGTTGACTGTGCTTCCAGCTCCGGAGAAAGAGAAGGAGTTTCCGACCTC<br>CCCTGATTACCTCGAAATAGCGATCTATTGCATCGGAGTTTTTTCTCATCGCG<br>TGCATGGTTCTTACTGTGATACTTTGTAGAATGAAGAACACCACCAAGAAA<br>CCGGATTTTTCCTCCCAACCGGCCGTCCACAAGTTGACGAAACGGATCCCAT<br>TGAGGCGCCAGGTGAGTGCTGACAGCTCAAGTTCAATGAACAGTAACACGC<br>CGCTCGTGAGGATCACTACTCGGCTGAGCTCTACCGCGGATGCGCCAATGTT<br>GGCAGGGGTCAGTGAGTACGAACTCCCGGAAGATCCGAAGTGGGAGTTTCC<br>GCGCGACAAACTCACTCTTGGAAAACCGCTTGGAGAGGGATGCTTCGGACA<br>GGTCGTAATGGCCGAGGCGGTTGGTATAGACAAAGATAGACCCAAAGAAG<br>CTGTCACAGTAGCTGTAAAAATGCTTAAGGATGATGCCACTGAAAAAGATT<br>TGAGCGACCTCGTAAGCGAGATGGAAATGATGAAAATGATAGGGAAGCAC<br>AAAAAATATAATTAAGCTCCTGGGGGCCTGCACACAGGACGGCCCGTTGTAT<br>GTCATCGTCGAATATGCCTCCAAAGGGAACCTCAGGGAGTACCTTAGAGCG<br>CGCAGACCGCCGGGGATGGAGTATTCATTTGACATCAATCGGGTCCCCGAA<br>GAACAAATGACTTTCAAAGACCTTGTCTCCTGTACCTATCAACTCGCCCGCG<br>GAATGGAATATTTGGCTAGTCAAAAATGCATTCACCGCGATCTTGCTGCAC<br>GGAACGTACTCGTCACTGAGAATAACGTTATGAAAATAGCGGATTTCGGCC<br>TCGCAAGGGACATAAACAACATCGACTACTACAAAGAAACCACGAATGGC<br>AGACTGCCAGTCAAGTGGATGGCGCCAGAAGCCCTTTTTGATAGAGTCTAC<br>ACGCACCAGTCAGACGTGTGGTCCTTTGGAGTGCTCATGTGGGAAATCTTTA<br>CGCTGGGTGGTAGCCCTTACCCGGGGATTCCCGTGGAAGAACTTTTCAAGCT<br>GTTGAAAGAGGGCCATCGGATGGACAAACCCGCAAATTGCACAAATGAATT<br>GTATATGATGATGCGCGACTGTTGGCAAGCCGTGCCTTCACAGAGACCTAC<br>ATTCAAGCAGTTGGTCGAAGACCTCGACCGGATCCTGACGCTTACAACGAA<br>CGAAGAATACCTGGACTTGTCTGGTCCCTTGGAGCAATACGCACCAAGCTA<br>CCCCGATACTCGGTCATCTTGCTCTAGTGGCGACGATAGTGTCTTTTCACCT |

| 9. SEQUENCE APPENDIX | | |
|---|---|---|

| SEQ ID NO: | Description | Sequence |
|---|---|---|
|  |  | GATCCAATGCCCTACGAACCGTGTCTGCCAAAGTACCAACACATGAACGGT<br>TCAGTAAAGACCTGA |
| 96 | FGFR3-WT | ATGTCAGAAGCTGGTGGCGGCGCCGCTGCCGCAGCCTCACTCCCGAGATCA<br>AGGGCCGGTGGCATGCGCGCGGCATGGGGATCCGTGTGGTGTTTGTGCCTC<br>GCGGCGGCTGTCGGAGCTCTGCCGGCTGCAAGGCGCAGGGGAGCGGAACG<br>GAGCGGTGGCCAGGCGGCGGAGTATCTCCGGAGTGAAACTGCATTTCTTGA<br>GGAGCTTGTTTTCGGTTCAGGGGATACCATCGAGCTTTCCTGTAACACACAA<br>TCTTCAAGTGTAAGCGTATTCTGGTTCAAAGATGGTATAGGCATTGCGCCCA<br>GTAATAGAACACACATCGGGCAGAAACTTTTGAAGATCATCAACGTTTCAT<br>ATGATGATTCCGGACTGTACTCATGTAAGCCAAGGCACAGTAACGAGGTGC<br>TTGGGAACTTCACAGTCAGGGTTACAGGCGTACCATTCTGGACGAGGCCCG<br>ATAAGATGGAAAAAAAACTTTTGGCAGTGCCCGCAGCCAATACAGTGCGGT<br>TCCGCTGCCCCGCAGGTGGGAATCCGACGCCCACAATTTATTGGCTGAAGA<br>ATGGCAAGGAGTTCAAAGGAGAACATAGGATCGGCGGAATCAAACTGAGG<br>CACCAGCAATGGTCTCTGGTGATGGAATCAGTAGTCCCATCTGACCGCGGT<br>AACTACACGTGCGTAGTAGAAAACAAGTATGGGAATATTCGGCATACCTAC<br>CAGCTCGATGTGCTCGAGAGATCTCCTCACAGGCCTATCTTGCAGGCTGGAC<br>TGCCAGCTAATCAAACAGTAGTTGTCGGATCTAACGTGGAGTTCCACTGCA<br>AAGTTTACTCAGACGCCCAACCGCACATTCAATGGCTTAAACACGTGGAGG<br>TTAACGGTAGCAAGTATGGACCTGATGGGACTCCCTATGTGACAGTCCTTA<br>AGAGTTGGATTTCTAAGAATGCCGAGGCGGATGCGAACTTGAACCTGTTTA<br>ACGTAACCGAGCAGGACGAGGGCGAATATCTTTGTCGCGCTAACAACTTCG<br>TTGGAATAGCGGAGAAGCCCTTCTGGCTGCATATACGGAAGCCAAAGCCGG<br>CGGAGGAGTTGATGGAGATGGATGACTCCGGTTCCGTATACGCCGGAATCC<br>TTAGCTACGGAACCGGGCTGGTGCTGTTTATCCTCGTTTTGGTTATTGTTATT<br>ATATGCCGCATGAAGATGCCAAACAAAAAGGCAATGAATACTACAACTGTG<br>CAGAAAGTGTCAAAATTCCCACTTAAACGGCAAGTCACTGTCTCACTCGAA<br>TCTAACTCTTCCATGAACTCCAACACTCCGTTGGTGCGGATTACCAGATTGT<br>CCTCATCCGACGGTCCCATGTTGGCAAATGTCAGTGAGCTGGAATTGCCGCC<br>CGATCCCAAATGGGAACTTGCAAGATCCCGGCTTACTCTCGGTAAGCCCCT<br>GGGCGAAGGTTGCTTTGGACAAGTCGTCATGGCCGAAGCGATTGGAATCGA<br>TAAAGACAAACCCAACAAGGCTATAACGGTCGCAGTAAAAATGTTGAAAG<br>ATGACGCGACCGACAAGGACCTGTCAGATCTGGTCTCAGAGATGGAAATGA<br>TGAAGATGATTGGTAAACACAAGAATATAATCAACTTGCTTGGAGCATGTA<br>CGCAAGACGGCCCTCTCTACGTTCTCGTGGAGTATGCCTCTAAGGGCAATTT<br>GAGGGAGTACCTGAGAGCTCGCAGACCTCCGGGCATGGATTATAGTTTCGA<br>CACTTGTAAGCTGCCGGAGGAGCAACTTACCTTCAAGGATCTTGTAAGTTGC<br>GCGTACCAGGTTGCAAGGGGGATGGAATACCTCGCCAGTCAAAAGTGCATA<br>CATAGAGATTTGGCAGCGAGGAACGTGCTCGTGACTGAGGACAACGTCATG<br>AAAATTGCGGACTTTGGGCTTGCACGGGATGTTCATAACATCGATTACTACA<br>AGAAAACTACTAACGGACGGCTCCCTGTGAAGTGGATGGCTCCAGAAGCGC<br>TTTTTGATAGAGTTTACACACATCAAAGTGACGTATGGAGTTTTGGAGTATT<br>GCTCTGGGAGATTTTCACCTTGGGAGGGTCTCCTTACCCTGGAATACCCGTC<br>GAAGAGCTCTTTAAGCTGCTTAAAGAAGGCCACAGGATGGACAAGCCGGCG<br>AACTGCACTCATGATCTGTACATGATAATGAGAGAGTGCTGGCACGCCGTT<br>CCCTCCCAGCGGCCGACATTCAAGCAGCTGGTGAAGACCTTGATAGGGTA<br>CTCACTATGACGTCCACCGATGAGTATCTGGACTTGTCTGTTCCATTCGAAC<br>AATACTCTCCGGCCGGTCAGGATACGCATTCCACTTGCTCCAGTGGTGATGA<br>TTCTGTCTTTGCACACGATCTTCTCCCAGACGAACCCTGTCTTCCTAAACAC<br>GTACCGTGTAACGGTGTCATAAGGACATAG |
| 97 | FGFR3-<br>N540K | ATGTCAGAAGCTGGTGGCGGCGCCGCTGCCGCAGCCTCACTCCCGAGATCA<br>AGGGCCGGTGGCATGCGCGCGGCATGGGGATCCGTGTGGTGTTTGTGCCTC<br>GCGGCGGCTGTCGGAGCTCTGCCGGCTGCAAGGCGCAGGGGAGCGGAACG<br>GAGCGGTGGCCAGGCGGCGGAGTATCTCCGGAGTGAAACTGCATTTCTTGA<br>GGAGCTTGTTTTCGGTTCAGGGGATACCATCGAGCTTTCCTGTAACACACAA<br>TCTTCAAGTGTAAGCGTATTCTGGTTCAAAGATGGTATAGGCATTGCGCCCA<br>GTAATAGAACACACATCGGGCAGAAACTTTTGAAGATCATCAACGTTTCAT<br>ATGATGATTCCGGACTGTACTCATGTAAGCCAAGGCACAGTAACGAGGTGC<br>TTGGGAACTTCACAGTCAGGGTTACAGGCGTACCATTCTGGACGAGGCCCG<br>ATAAGATGGAAAAAAAACTTTTGGCAGTGCCCGCAGCCAATACAGTGCGGT<br>TCCGCTGCCCCGCAGGTGGGAATCCGACGCCCACAATTTATTGGCTGAAGA<br>ATGGCAAGGAGTTCAAAGGAGAACATAGGATCGGCGGAATCAAACTGAGG<br>CACCAGCAATGGTCTCTGGTGATGGAATCAGTAGTCCCATCTGACCGCGGT<br>AACTACACGTGCGTAGTAGAAAACAAGTATGGGAATATTCGGCATACCTAC<br>CAGCTCGATGTGCTCGAGAGATCTCCTCACAGGCCTATCTTGCAGGCTGGAC<br>TGCCAGCTAATCAAACAGTAGTTGTCGGATCTAACGTGGAGTTCCACTGCA<br>AAGTTTACTCAGACGCCCAACCGCACATTCAATGGCTTAAACACGTGGAGG<br>TTAACGGTAGCAAGTATGGACCTGATGGGACTCCCTATGTGACAGTCCTTA<br>AGAGTTGGATTTCTAAGAATGCCGAGGCGGATGCGAACTTGAACCTGTTTA<br>ACGTAACCGAGCAGGACGAGGGCGAATATCTTTGTCGCGCTAACAACTTCG<br>TTGGAATAGCGGAGAAGCCCTTCTGGCTGCATATACGGAAGCCAAAGCCGG |

9. SEQUENCE APPENDIX

| SEQ ID NO: | Description | Sequence |
|---|---|---|
| | | CGGAGGAGTTGATGGAGATGGATGACTCCGGTTCCGTATACGCCGGAATCC<br>TTAGCTACGGAACCGGGCTGGTGCTGTTTATCCTCGTTTTGGTTATTGTTATT<br>ATATGCCGCATGAAGATGCCAAACAAAAAGGCAATGAATACTACAACTGTG<br>CAGAAAGTGTCAAAATTCCCACTTAAACGGCAAGTCACTGTCTCACTCGAA<br>TCTAACTCTTCCATGAACTCCAACACTCCGTTGGTGCGGATTACCAGATTGT<br>CCTCATCCGACGGTCCCATGTTGGCAAATGTCAGTGAGCTGGAATTGCCGCC<br>CGATCCCAAATGGGAACTTGCAAGATCCCGGCTTACTCTCGGTAAGCCCCT<br>GGGCGAAGGTTGCTTTGGACAAGTCGTCATGGCCGAAGCGATTGGAATCGA<br>TAAAGACAAACCCAACAAGGCTATAACGGTCGCAGTAAAAATGTTGAAAG<br>ATGACGCGACCGACAAGGACCTGTCAGATCTGGTCTCAGAGATGGAAATGA<br>TGAAGATGATTGGTAAACACAAGAATATAATCAAGTTGCTTGGAGCATGTA<br>CGCAAGACGGCCCTCTCTACGTTCTCGTGGAGTATGCCTCTAAGGGCAATTT<br>GAGGGAGTACCTGAGAGCTCGCAGACCTCCGGGCATGGATTATAGTTTCGA<br>CACTTGTAAGCTGCCGGAGGAGCAACTTACCTTCAAGGATCTTGTAAGTTGC<br>GCGTACCAGGTTGCAAGGGGGATGGAATACCTCGCCAGTCAAAAGTGCATA<br>CATAGAGATTTGGCAGCGAGGAACGTGCTCGTGACTGAGGACAACGTCATG<br>AAAATTGCGGACTTTGGGCTTGCACGGGATGTTCATAACATCGATTACTACA<br>AGAAAACTACTAACGGACGGCTCCCTGTGAAGTGGATGGCTCCAGAAGCGC<br>TTTTTGATAGAGTTTACACACATCAAAGTGACGTATGGAGTTTTGGAGTATT<br>GCTCTGGGAGATTTTCACCTTGGGAGGGTCTCCTTACCCTGGAATACCCGTC<br>GAAGAGCTCTTTAAGCTGCTTAAAGAAGGCCACAGGATGGACAAGCCGGCG<br>AACTGCACTCATGATCTGTACATGATAATGAGAGAGTGCTGGCACGCCGTT<br>CCCTCCCAGCGGCCGACATTCAAGCAGCTGGTGGAAGACCTTGATAGGGTA<br>CTCACTATGACGTCCACCGATGAGTATCTGGACTTGTCTGTTCCATTCGAAC<br>AATACTCTCCGGCCGGTCAGGATACGCATTCCACTTGCTCCAGTGGTGATGA<br>TTCTGTCTTTGCACACGATCTTCTCCCAGACGAACCCTGTCTTCCTAAACAC<br>GTACCGTGTAACGGTGTCATAAGGACATAG |
| 98 | FGFR3-<br>K650E | ATGTCAGAAGCTGGTGGCGGCGCCGCTGCCGCAGCCTCACTCCCGAGATCA<br>AGGGCCGGTGGCATGCGCGCGGCATGGGGATCCGTGTGGTGTTTGTGCCTC<br>GCGGCGGCTGTCGGAGCTCTGCCGGCTGCAAGGCGCAGGGGAGCGGAACG<br>GAGCGGTGGCCAGGCGGCGGAGTATCTCCGGAGTGAAACTGCATTTCTTGA<br>GGAGCTTGTTTTCGGTTCAGGGGATACCATCGAGCTTTCCTGTAACACACAA<br>TCTTCAAGTGTAAGCGTATTCTGGTTCAAAGATGGTATAGGCATTGCGCCCA<br>GTAATAGAACACACATCGGGCAGAAACTTTTGAAGATCATCAACGTTTCAT<br>ATGATGATTCCGGACTGTACTCATGTAAGCCAAGGCACAGTAACGAGGTGC<br>TTGGGAACTTCACAGTCAGGGTTACAGGCGTACCATTCTGGACGAGGCCCG<br>ATAAGATGGAAAAAAAACTTTTGGCAGTGCCCGCAGCCAATACAGTGCGGT<br>TCCGCTGCCCCGCAGGTGGGAATCCGACGCCCACAATTTATTGGCTGAAGA<br>ATGGCAAGGAGTTCAAAGGAGAACATAGGATCGGCGGAATCAAACTGAGG<br>CACCAGCAATGGTCTCTGGTGATGGAATCAGTAGTCCCATCTGACCGCGGT<br>AACTACACGTGCGTAGTAGAAAACAAGTATGGGAATATTCGGCATACCTAC<br>CAGCTCGATGTGCTCGAGAGATCTCCTCACAGGCCTATCTTGCAGGCTGGAC<br>TGCCAGCTAATCAAACAGTAGTTGTCGGATCTAACGTGGAGTTCCACTGCA<br>AAGTTTACTCAGACGCCCAACCGCACATTCAATGGCTTAAACACGTGGAGG<br>TTAACGGTAGCAAGTATGGACCTGATGGGACTCCCTATGTGACAGTCCTTA<br>AGAGTTGGATTTCTAAGAATGCCGAGGCGGATGCGAACTTGAACCTGTTTA<br>ACGTAACCGAGCAGGACGAGGGCGAATATCTTTGTCGCGCTAACAACTTCG<br>TTGGAATAGCGGAGAAGCCCTTCTGGCTGCATATACGGAAGCCAAAGCCGG<br>CGGAGGAGTTGATGGAGATGGATGACTCCGGTTCCGTATACGCCGGAATCC<br>TTAGCTACGGAACCGGGCTGGTGCTGTTTATCCTCGTTTTGGTTATTGTTATT<br>ATATGCCGCATGAAGATGCCAAACAAAAAGGCAATGAATACTACAACTGTG<br>CAGAAAGTGTCAAAATTCCCACTTAAACGGCAAGTCACTGTCTCACTCGAA<br>TCTAACTCTTCCATGAACTCCAACACTCCGTTGGTGCGGATTACCAGATTGT<br>CCTCATCCGACGGTCCCATGTTGGCAAATGTCAGTGAGCTGGAATTGCCGCC<br>CGATCCCAAATGGGAACTTGCAAGATCCCGGCTTACTCTCGGTAAGCCCCT<br>GGGCGAAGGTTGCTTTGGACAAGTCGTCATGGCCGAAGCGATTGGAATCGA<br>TAAAGACAAACCCAACAAGGCTATAACGGTCGCAGTAAAAATGTTGAAAG<br>ATGACGCGACCGACAAGGACCTGTCAGATCTGGTCTCAGAGATGGAAATGA<br>TGAAGATGATTGGTAAACACAAGAATATAATCAACTTGCTTGGAGCATGTA<br>CGCAAGACGGCCCTCTCTACGTTCTCGTGGAGTATGCCTCTAAGGGCAATTT<br>GAGGGAGTACCTGAGAGCTCGCAGACCTCCGGGCATGGATTATAGTTTCGA<br>CACTTGTAAGCTGCCGGAGGAGCAACTTACCTTCAAGGATCTTGTAAGTTGC<br>GCGTACCAGGTTGCAAGGGGGATGGAATACCTCGCCAGTCAAAAGTGCATA<br>CATAGAGATTTGGCAGCGAGGAACGTGCTCGTGACTGAGGACAACGTCATG<br>AAAATTGCGGACTTTGGGCTTGCACGGGATGTTCATAACATCGATTACTACA<br>AGGAAACTACTAACGGACGGCTCCCTGTGAAGTGGATGGCTCCAGAAGCGC<br>TTTTTGATAGAGTTTACACACATCAAAGTGACGTATGGAGTTTTGGAGTATT<br>GCTCTGGGAGATTTTCACCTTGGGAGGGTCTCCTTACCCTGGAATACCCGTC<br>GAAGAGCTCTTTAAGCTGCTTAAAGAAGGCCACAGGATGGACAAGCCGGCG<br>AACTGCACTCATGATCTGTACATGATAATGAGAGAGTGCTGGCACGCCGTT<br>CCCTCCCAGCGGCCGACATTCAAGCAGCTGGTGGAAGACCTTGATAGGGTA<br>CTCACTATGACGTCCACCGATGAGTATCTGGACTTGTCTGTTCCATTCGAAC |

9. SEQUENCE APPENDIX

| SEQ ID NO: | Description | Sequence |
|---|---|---|
| | | AATACTCTCCGGCCGGTCAGGATACGCATTCCACTTGCTCCAGTGGTGATGA TTCTGTCTTTGCACACGATCTTCTCCCAGACGAACCCTGTCTTCCTAAACAC GTACCGTGTAACGGTGTCATAAGGACATAG |
| 99 | FGFR3-N540K-K650E | ATGTCAGAAGCTGGTGGCGGCGCCGCTGCCGCAGCCTCACTCCCGAGATCA AGGGCCGGTGGCATGCGCGCGGCATGGGGATCCGTGTGGTGTTTGTGCCTC GCGGCGGCTGTCGGAGCTCTGCCGGCTGCAAGGCGCAGGGGAGCGGAACG GAGCGGTGGCCAGGCGGCGGAGTATCTCCGGAGTGAAACTGCATTTCTTGA GGAGCTTGTTTTCGGTTCAGGGGATACCATCGAGCTTTCCTGTAACACACAA TCTTCAAGTGTAAGCGTATTCTGGTTCAAAGATGGTATAGGCATTGCGCCCA GTAATAGAACACACATCGGGCAGAAACTTTTGAAGATCATCAACGTTTCAT ATGATGATTCCGGACTGTACTCATGTAAGCCAAGGCACAGTAACGAGGTGC TTGGGAACTTCACAGTCAGGGTTACAGGCGTACCATTCTGGACGAGGCCCG ATAAGATGGAAAAAAAACTTTTGGCAGTGCCCGCAGCCAATACAGTGCGGT TCCGCTGCCCCGCAGGTGGGAATCCGACGCCCACAATTTATTGGCTGAAGA ATGGCAAGGAGTTCAAAGGAGAACATAGGATCGGCGGAATCAAACTGAGG CACCAGCAATGGTCTCTGGTGATGGAATCAGTAGTCCCATCTGACCGCGGT AACTACACGTGCGTAGTAGAAAACAAGTATGGGAATATTCGGCATACCTAC CAGCTCGATGTGCTCGAGAGATCTCCTCACAGGCCTATCTTGCAGGCTGGAC TGCCAGCTAATCAAACAGTAGTTGTCGGATCTAACGTGGAGTTCCACTGCA AAGTTTACTCAGACGCCCAACCGCACATTCAATGGCTTAAACACGTGGAGG TTAACGGTAGCAAGTATGGACCTGATGGGACTCCCTATGTGACAGTCCTTA AGAGTTGGATTTCTAAGAATGCCGAGGCGGATGCGAACTTGAACCTGTTTA ACGTAACCGAGCAGGACGAGGGCGAATATCTTTGTCGCGCTAACAACTTCG TTGGAATAGCGGAGAAGCCCTTCTGGCTGCATATACGGAAGCCAAAGCCGG CGGAGGAGTTGATGGAGATGGATGACTCCGGTTCCGTATACGCCGGAATCC TTAGCTACGGAACCGGGCTGGTGCTGTTTATCCTCGTTTTGGTTATTGTTATT ATATGCCGCATGAAGATGCCAAACAAAAAGGCAATGAATACTACAACTGTG CAGAAAGTGTCAAAATTCCCACTTAAACGGCAAGTCACTGTCTCACTCGAA TCTAACTCTTCCATGAACTCCAACACTCCGTTGGTGCGGATTACCAGATTGT CCTCATCCGACGGTCCCATGTTGGCAAATGTCAGTGAGCTGGAATTGCCGCC CGATCCCAAATGGGAACTTGCAAGATCCCGGCTTACTCTCGGTAAGCCCCT GGGCGAAGGTTGCTTTGGACAAGTCGTCATGGCCGAAGCGATTGGAATCGA TAAAGACAAACCCAACAAGGCTATAACGGTCGCAGTAAAAATGTTGAAAG ATGACGCGACCGACAAGGACCTGTCAGATCTGGTCTCAGAGATGGAAATGA TGAAGATGATTGGTAAACACAAGAATATAATCAAGTTGCTTGGAGCATGTA CGCAAGACGGCCCTCTCTACGTTCTCGTGGAGTATGCCTCTAAGGGCAATTT GAGGGAGTACCTGAGAGCTCGCAGACCTCCGGGCATGGATTATAGTTTCGA CACTTGTAAGCTGCCGGAGGAGCAACTTACCTTCAAGGATCTTGTAAGTTGC GCGTACCAGGTTGCAAGGGGGATGGAATACCTCGCCAGTCAAAAGTGCATA CATAGAGATTTGGCAGCGAGGAACGTGCTCGTGACTGAGGACAACGTCATG AAAATTGCGGACTTTGGGCTTGCACGGGATGTTCATAACATCGATTACTACA AGGAAACTACTAACGGACGGCTCCCTGTGAAGTGGATGGCTCCAGAAGCGC TTTTTGATAGAGTTTACACACATCAAAGTGACGTATGGAGTTTTGGAGTATT GCTCTGGGAGATTTTCACCTTGGGAGGGTCTCCTTACCCTGGAATACCCGTC GAAGAGCTCTTTAAGCTGCTTAAAGAAGGCCACAGGATGGACAAGCCGGCG AACTGCACTCATGATCTGTACATGATAATGAGAGAGTGCTGGCACGCCGTT CCCTCCCAGCGGCCGACATTCAAGCAGCTGGTGGAAGACCTTGATAGGGTA CTCACTATGACGTCCACCGATGAGTATCTGGACTTGTCTGTTCCATTCGAAC AATACTCTCCGGCCGGTCAGGATACGCATTCCACTTGCTCCAGTGGTGATGA TTCTGTCTTTGCACACGATCTTCTCCCAGACGAACCCTGTCTTCCTAAACAC GTACCGTGTAACGGTGTCATAAGGACATAG |
| 100 | myrist-FGFR3-K650E | ATGGGATCATCCAAGTCAAAACCGAAAGACCCGTCACAGAGACGCATGAA GATGCCAAACAAAAAGGCAATGAATACTACAACTGTGCAGAAAGTGTCAA AATTCCCACTTAAACGGCAAGTCACTGTCTCACTCGAATCTAACTCTTCCAT GAACTCCAACACTCCGTTGGTGCGGATTACCAGATTGTCCTCATCCGACGGT CCCATGTTGGCAAATGTCAGTGAGCTGGAATTGCCGCCCGATCCCAAATGG GAACTTGCAAGATCCCGGCTTACTCTCGGTAAGCCCCTGGGCGAAGGTTGC TTTGGACAAGTCGTCATGGCCGAAGCGATTGGAATCGATAAAGACAAACCC AACAAGGCTATAACGGTCGCAGTAAAAATGTTGAAAGATGACGCGACCGA CAAGGACCTGTCAGATCTGGTCTCAGAGATGGAAATGATGAAGATGATTGG TAAACACAAGAATATAATCAACTTGCTTGGAGCATGTACGCAAGACGGCCC TCTCTACGTTCTCGTGGAGTATGCCTCTAAGGGCAATTTGAGGGAGTACCTG AGAGCTCGCAGACCTCCGGGCATGGATTATAGTTTCGACACTTGTAAGCTG CCGGAGGAGCAACTTACCTTCAAGGATCTTGTAAGTTGCGCGTACCAGGTT GCAAGGGGGATGGAATACCTCGCCAGTCAAAAGTGCATACATAGAGATTTG GCAGCGAGGAACGTGCTCGTGACTGAGGACAACGTCATGAAAATTGCGGAC TTTGGGCTTGCACGGGATGTTCATAACATCGATTACTACAAGGAAACTACTA ACGGACGGCTCCCTGTGAAGTGGATGGCTCCAGAAGCGCTTTTTGATAGAG TTTACACACATCAAAGTGACGTATGGAGTTTTGGAGTATTGCTCTGGGAGAT TTTCACCTTGGGAGGGTCTCCTTACCCTGGAATACCCGTCGAAGAGCTCTTT AAGCTGCTTAAAGAAGGCCACAGGATGGACAAGCCGGCGAACTGCACTCAT |

9. SEQUENCE APPENDIX

| SEQ ID NO: | Description | Sequence |
|---|---|---|
| | | GATCTGTACATGATAATGAGAGAGTGCTGGCACGCCGTTCCCTCCCAGCGG<br>CCGACATTCAAGCAGCTGGTGGAAGACCTTGATAGGGTACTCACTATGACG<br>TCCACCGATGAGTATCTGGACTTGTCTGTTCCATTCGAACAATACTCTCCGG<br>CCGGTCAGGATACGCATTCCACTTGCTCCAGTGGTGATGATTCTGTCTTTGC<br>ACACGATCTTCTCCCAGACGAACCCTGTCTTCCTAAACACGTACCGTGTAAC<br>GGTGTCATAAGGACATAG |
| 101 | FGFR4-WT | ATGCTTCCTCTGCGCCTGGTTCTCGCTGGCCTCTTGGTCGCAGCGGGTTCAG<br>CGGCGAGTCATAGGGGAGAAATGGAGCCGGAACTCTTTGAGTCTCCACTCT<br>TGGAATCCGAAGAAGAACACCTCCTTCTGGACCCAGGAAACGCATTGAAAC<br>TCTATTGTGACGTAAACCAGTCCGGAGCTAGTGTGGTTTGGTATAAGGAGA<br>GTAGACCTCTGCTGCCAGGGCCCCGCGTCAGATTGCAACAAAGCGTTCTTG<br>AAATAGCGGAAGTAGCTTACGAGGATTCCGGCCTCTACGTCTGTAGAGCTC<br>GCGGAACCGGTGAGGTCCTTAGGAACTTCACCATATCAGTTGTAGATTCACT<br>TGCCTCAGGCGATGACGATGAAGACAGCGATGGGGATGGTCCACATGGAG<br>ACCGCTCTGAAGAACCAGTATACGTTCACAGAGCACCTTATTGGACCCATC<br>CACACAGGATGGATAAAAAACTCTACGCTGTTCCTGCGGGCAATACCGTGA<br>AATTCCGCTGTCCAGCGAGTGGGTCTCCAAGCCCGTCCATTAGATGGTTTAA<br>GAATGGCAGAGAGTTTCGCGGGGAGCACAGAATAGGGGGCATTAGGCTCC<br>GGCATCAGCATTGGTCACTCGTTATGGAGTCAGTCGTGCCGTCTGATAGGG<br>GGAATTACACCTGCTTGGTAGAGAACCGGTTTGGTTCAATCCGCTATAGTTA<br>TCTGCTGGATGTCCTCGAACGCTCCCCACACAGACCCATCTTGCAAGCTGGA<br>CTTCCAGCTAACACAACAGCTCTGGTAGGTTCAGATGTGGAATTTTTCTGCA<br>AGGTATACTCTGATGCTCAACCGCACATACAGTGGTTGAAACACATTGAAG<br>TTAACGGGTCCTCATATGGGCCAGACGGTGTACCCTACGTGCAGGTACTGA<br>AGACGGCCGACATTAATTCATCTGAGGTTGAGGTGCTGTATTTGCGGAACG<br>TCACAATGGAAGACGCCGGGGAGTATACTTGTCTTGCCGGTAATAGTATTG<br>GGCTGTCCTATCAGTCCGCGTGGCTCACCGTCCTGCCAGAGAGAGCTGGTTCA<br>TGAGGCTGAGGCACCTGAGGCGAAATACACCGACATCATAATTTACACTTC<br>CGGATCATTGGCCGTGGCAATGGCTCTTATCATCGTCGTTCTGTGTAGGATG<br>CAAACTCAGAGCTCTAAACAACCCCTTGAACCCATGGCAGTACACAAATTG<br>AGCAAATTTCCTCTTATTAGACAGTTTTCCCTTGACTCAAGTAGCTCAGGGA<br>AATCTAGCACATCACTTATGCGGGTGACGAGACTGTCTTCCAGCTGCGCGCC<br>CATGTTGGCTGGGGTGGTGGAACTTGATCTGCCTCTGGACAGCAAGTGGGA<br>ATTTCCGAGGGAGAAACTGGTTCTTGGGAAGCCGCTCGGCGAAGGCTGTTT<br>TGGTCAGGTGGTCAGGGCGGAAGCGTACGGGATCGACAGACAGTGGCCTG<br>ATCGCGCAGTTACTGTCGCAGTAAAAATGCTGAAAGACAACGCTACTGATA<br>AGGATCTGGCAGACCTGATAAGTGAAATGGAGATGATGAAACTGATGGAC<br>AAACACAAGAACATCATTAATCTCTTGGGTGTATGTACACAAGATGGGCCT<br>CTGTATGTTATAGTAGAGTTTGCGGCCAAAGGCAACCTTCGGGAGTATCTTC<br>GCGCTAGAAGACCGCCAATGCCCGACTACACGTTCGATATTACAGAACTCC<br>ATGAGGAACAACTTTGTTTTAAGGATCTTGTTAGCTGTGTGTATCAAGTCGC<br>CCGGGGGATGGAGTATCTGGAATCAAGACGGTGTATACACCGCGACCTCGC<br>TGCCAGAAACGTTCTCGTCACGGCGGAAAATGTGATGAAGATCGCCGACTT<br>CGGACTTGCCAGGGATGTCCATGATATAGACTATTACAAAAAAACATCTAA<br>TGGGCGGCTCCCTGTCAAGTGGATGGCGCCCGAAGCACTGTTTGACAGAGT<br>ATACACGCACCAGTCTGACGTGTGGTCATTTGGCATACTGATGTGGGAAATT<br>TTTACACTCGGTGGTTCACCTTATCCTGGCATCCCTGTTGAGGAGCTTTTTAA<br>ATTGCTCAAAGAGGGCCACAGAATGGACTGTCCTAGTAACTGCACCCATGA<br>GCTGTATATGCTCATGCGCGAGTGCTGGCATGCGGTGCCTAGTCAAAGGCC<br>AACCTTCAAACAGCTCGTCGAAGGCCTGGACAAGATTCTTGCTGCAATAAG<br>CGAGGAGTACCTCGACTTGTCTATGCCATTCGAGCAATACTCACCTTCTTGT<br>GAAGACACGACGAGTACATGCAGCAGCGACGACTCTGTATTTACACACGAC<br>CCTTTGCCCCTTGCTCCTTGCCTGTTTGCCTGTCCTAGTGGCCGCACCTAG |
| 102 | FGFR4-<br>Y367C | ATGCTTCCTCTGCGCCTGGTTCTCGCTGGCCTCTTGGTCGCAGCGGGTTCAG<br>CGGCGAGTCATAGGGGAGAAATGGAGCCGGAACTCTTTGAGTCTCCACTCT<br>TGGAATCCGAAGAAGAACACCTCCTTCTGGACCCAGGAAACGCATTGAAAC<br>TCTATTGTGACGTAAACCAGTCCGGAGCTAGTGTGGTTTGGTATAAGGAGA<br>GTAGACCTCTGCTGCCAGGGCCCCGCGTCAGATTGCAACAAAGCGTTCTTG<br>AAATAGCGGAAGTAGCTTACGAGGATTCCGGCCTCTACGTCTGTAGAGCTC<br>GCGGAACCGGTGAGGTCCTTAGGAACTTCACCATATCAGTTGTAGATTCACT<br>TGCCTCAGGCGATGACGATGAAGACAGCGATGGGGATGGTCCACATGGAG<br>ACCGCTCTGAAGAACCAGTATACGTTCACAGAGCACCTTATTGGACCCATC<br>CACACAGGATGGATAAAAAACTCTACGCTGTTCCTGCGGGCAATACCGTGA<br>AATTCCGCTGTCCAGCGAGTGGGTCTCCAAGCCCGTCCATTAGATGGTTTAA<br>GAATGGCAGAGAGTTTCGCGGGGAGCACAGAATAGGGGGCATTAGGCTCC<br>GGCATCAGCATTGGTCACTCGTTATGGAGTCAGTCGTGCCGTCTGATAGGG<br>GGAATTACACCTGCTTGGTAGAGAACCGGTTTGGTTCAATCCGCTATAGTTA<br>TCTGCTGGATGTCCTCGAACGCTCCCCACACAGACCCATCTTGCAAGCTGGA<br>CTTCCAGCTAACACAACAGCTCTGGTAGGTTCAGATGTGGAATTTTTCTGCA<br>AGGTATACTCTGATGCTCAACCGCACATACAGTGGTTGAAACACATTGAAG<br>TTAACGGGTCCTCATATGGGCCAGACGGTGTACCCTACGTGCAGGTACTGA |

| 9. SEQUENCE APPENDIX | | |
| --- | --- | --- |

| SEQ ID NO: | Description | Sequence |
| --- | --- | --- |
|  |  | AGACGGCCGACATTAATTCATCTGAGGTTGAGGTGCTGTATTTGCGGAACG TCACAATGGAAGACGCCGGGGAGTATACTTGTCTTGCCGGTAATAGTATTG GGCTGTCCTATCAGTCCGCGTGGCTCACCGTCCTGCCAGAAGAGCTGGTTCA TGAGGCTGAGGCACCTGAGGCGAAATGTACCGACATCATAATTTACACTTC CGGATCATTGGCCGTGGCAATGGCTCTTATCATCGTCGTTCTGTGTAGGATG CAAACTCAGAGCTCTAAACAACCCCTTGAACCCATGGCAGTACACAAATTG AGCAAATTTCCTCTTATTAGACAGTTTTCCCTTGACTCAAGTAGCTCAGGGA AATCTAGCACATCACTTATGCGGGTGACGAGACTGTCTTCCAGCTGCGCGCC CATGTTGGCTGGGGTGGTGGAACTTGATCTGCCTCTGGACAGCAAGTGGGA ATTTCCGAGGGAGAAACTGGTTCTTGGGAAGCCGCTCGGCGAAGGCTGTTT TGGTCAGGTGGTCAGGGCGGAAGCGTACGGGATCGACAGACAGTGGCCTG ATCGCGCAGTTACTGTCGCAGTAAAAATGCTGAAAGACAACGCTACTGATA AGGATCTGGCAGACCTGATAAGTGAAATGGAGATGATGAAACTGATGGAC AAACACAAGAACATCATTAATCTCTTGGGTGTATGTACACAAGATGGGCCT CTGTATGTTATAGTAGAGTTTGCGGCCAAAGGCAACCTTCGGGAGTATCTTC GCGCTAGAAGACCGCCAATGCCCGACTACACGTTCGATATTACAGAACTCC ATGAGGAACAACTTTGTTTTAAGGATCTTGTTAGCTGTGTGTATCAAGTCGC CCGGGGGATGGAGTATCTGGAATCAAGACGGTGTATACACCGCGACCTCGC TGCCAGAAACGTTCTCGTCACGGCGGAAAATGTGATGAAGATCGCCGACTT CGGACTTGCCAGGGATGTCCATGATATAGACTATTACAAAAAAACATCTAA TGGGCGGCTCCCTGTCAAGTGGATGGCGCCCGAAGCACTGTTTGACAGAGT ATACACGCACCAGTCTGACGTGTGGTCATTTGGCATACTGATGTGGGAAATT TTTACACTCGGTGGTTCACCTTATCCTGGCATCCCTGTTGAGGAGCTTTTTAA ATTGCTCAAAGAGGGCCACAGAATGGACTGTCCTAGTAACTGCACCCATGA GCTGTATATGCTCATGCGCGAGTGCTGGCATGCGGTGCCTAGTCAAAGGCC AACCTTCAAACAGCTCGTCGAAGGCCTGGACAAGATTCTTGCTGCAATAAG CGAGGAGTACCTCGACTTGTCTATGCCATTCGAGCAATACTCACCTTCTTGT GAAGACACGACGAGTACATGCAGCAGCGACGACTCTGTATTTACACACGAC CCTTTGCCCCTTGCTCCTTGCCTGTTTGCCTGTCCTAGTGGCCGCACCTAG |
| 103 | FGFR4-K645E | ATGCTTCCTCTGCGCCTGGTTCTCGCTGGCCTCTTGGTCGCAGCGGGTTCAG CGGCGAGTCATAGGGGAGAAATGGAGCCGGAACTCTTTGAGTCTCCACTCT TGGAATCCGAAGAAGAACACCTCCTTCTGGACCCAGGAAACGCATTGAAAC TCTATTGTGACGTAAACCAGTCCGGAGCTAGTGTGGTTTGGTATAAGGAGA GTAGACCTCTGCTGCCAGGGCCCCGCGTCAGATTGCAACAAAGCGTTCTTG AAATAGCGGAAGTAGCTTACGAGGATTCCGGCCTCTACGTCTGTAGAGCTC GCGGAACCGGTGAGGTCCTTAGGAACTTCACCATATCAGTTGTAGATTCACT TGCCTCAGGCGATGACGATGAAGACAGCGATGGGGATGGTCCACATGGAG ACCGCTCTGAAGAACCAGTATACGTTCACAGAGCACCTTATTGGACCCATC CACACAGGATGGATAAAAAAACTCTACGCTGTTCCTGCGGGCAATACCGTGA AATTCCGCTGTCCAGCGAGTGGGTCTCCAAGCCCGTCCATTAGATGGTTTAA GAATGGCAGAGAGTTTCGCGGGGAGCACAGAATAGGGGGCATTAGGCTCC GGCATCAGCATTGGTCACTCGTTATGGAGTCAGTCGTGCCGTCTGATAGGG GGAATTACACCTGCTTGGTAGAGAACCGGTTTGGTTCAATCCGCTATAGTTA TCTGCTGGATGTCCTCGAACGCTCCCCACACAGACCCATCTTGCAAGCTGGA CTTCCAGCTAACACAACAGCTCTGGTAGGTTCAGATGTGGAATTTTTCTGCA AGGTATACTCTGATGCTCAACCGCACATACAGTGGTTGAAACACATTGAAG TTAACGGGTCCTCATATGGGCCAGACGGTGTACCCTACGTGCAGGTACTGA AGACGGCCGACATTAATTCATCTGAGGTTGAGGTGCTGTATTTGCGGAACG TCACAATGGAAGACGCCGGGGAGTATACTTGTCTTGCCGGTAATAGTATTG GGCTGTCCTATCAGTCCGCGTGGCTCACCGTCCTGCCAGAAGAGCTGGTTCA TGAGGCTGAGGCACCTGAGGCGAAATACACCGACATCATAATTTACACTTC CGGATCATTGGCCGTGGCAATGGCTCTTATCATCGTCGTTCTGTGTAGGATG CAAACTCAGAGCTCTAAACAACCCCTTGAACCCATGGCAGTACACAAATTG AGCAAATTTCCTCTTATTAGACAGTTTTCCCTTGACTCAAGTAGCTCAGGGA AATCTAGCACATCACTTATGCGGGTGACGAGACTGTCTTCCAGCTGCGCGCC CATGTTGGCTGGGGTGGTGGAACTTGATCTGCCTCTGGACAGCAAGTGGGA ATTTCCGAGGGAGAAACTGGTTCTTGGGAAGCCGCTCGGCGAAGGCTGTTT TGGTCAGGTGGTCAGGGCGGAAGCGTACGGGATCGACAGACAGTGGCCTG ATCGCGCAGTTACTGTCGCAGTAAAAATGCTGAAAGACAACGCTACTGATA AGGATCTGGCAGACCTGATAAGTGAAATGGAGATGATGAAACTGATGGAC AAACACAAGAACATCATTAATCTCTTGGGTGTATGTACACAAGATGGGCCT CTGTATGTTATAGTAGAGTTTGCGGCCAAAGGCAACCTTCGGGAGTATCTTC GCGCTAGAAGACCGCCAATGCCCGACTACACGTTCGATATTACAGAACTCC ATGAGGAACAACTTTGTTTTAAGGATCTTGTTAGCTGTGTGTATCAAGTCGC CCGGGGGATGGAGTATCTGGAATCAAGACGGTGTATACACCGCGACCTCGC TGCCAGAAACGTTCTCGTCACGGCGGAAAATGTGATGAAGATCGCCGACTT CGGACTTGCCAGGGATGTCCATGATATAGACTATTACAAAGAAACATCTAA TGGGCGGCTCCCTGTCAAGTGGATGGCGCCCGAAGCACTGTTTGACAGAGT ATACACGCACCAGTCTGACGTGTGGTCATTTGGCATACTGATGTGGGAAATT TTTACACTCGGTGGTTCACCTTATCCTGGCATCCCTGTTGAGGAGCTTTTTAA ATTGCTCAAAGAGGGCCACAGAATGGACTGTCCTAGTAACTGCACCCATGA GCTGTATATGCTCATGCGCGAGTGCTGGCATGCGGTGCCTAGTCAAAGGCC |

| 9. SEQUENCE APPENDIX | | |
|---|---|---|
| SEQ ID NO: | Description | Sequence |

|  |  | AACCTTCAAACAGCTCGTCGAAGGCCTGGACAAGATTCTTGCTGCAATAAG<br>CGAGGAGTACCTCGACTTGTCTATGCCATTCGAGCAATACTCACCTTCTTGT<br>GAAGACACGACGAGTACATGCAGCAGCGACGACTCTGTATTTACACACGAC<br>CCTTTGCCCCTTGCTCCTTGCCTGTTTGCCTGTCCTAGTGGCCGCACCTAG |
|---|---|---|
| 104 | FGFR4-<br>Y367C-K645E | ATGCTTCCTCTGCGCCTGGTTCTCGCTGGCCTCTTGGTCGCAGCGGGTTCAG<br>CGGCGAGTCATAGGGGAGAAATGGAGCCGGAACTCTTTGAGTCTCCACTCT<br>TGGAATCCGAAGAAGAACACCTCCTTCTGGACCCAGGAAACGCATTGAAAC<br>TCTATTGTGACGTAAACCAGTCCGGAGCTAGTGTGGTTTGGTATAAGGAGA<br>GTAGACCTCTGCTGCCAGGGCCCCGCGTCAGATTGCAACAAAGCGTTCTTG<br>AAATAGCGGAAGTAGCTTACGAGGATTCCGGCCTCTACGTCTGTAGAGCTC<br>GCGGAACCGGTGAGGTCCTTAGGAACTTCACCATATCAGTTGTAGATTCACT<br>TGCCTCAGGCGATGACGATGAAGACAGCGATGGGGATGGTCCACATGGAG<br>ACCGCTCTGAAGAACCAGTATACGTTCACAGAGCACCTTATTGGACCCATC<br>CACACAGGATGGATAAAAAACTCTACGCTGTTCCTGCGGGCAATACCGTGA<br>AATTCCGCTGTCCAGCGAGTGGGTCTCCAAGCCCGTCCATTAGATGGTTTAA<br>GAATGGCAGAGAGTTTCGCGGGGAGCACAGAATAGGGGGCATTAGGCTCC<br>GGCATCAGCATTGGTCACTCGTTATGGAGTCAGTCGTGCCGTCTGATAGGG<br>GGAATTACACCTGCTTGGTAGAGAACCGGTTTGGTTCAATCCGCTATAGTTA<br>TCTGCTGGATGTCCTCGAACGCTCCCCACACAGACCCATCTTGCAAGCTGGA<br>CTTCCAGCTAACACAACAGCTCTGGTAGGTTCAGATGTGGAATTTTTCTGCA<br>AGGTATACTCTGATGCTCAACCGCACATACAGTGGTTGAAACACATTGAAG<br>TTAACGGGTCCTCATATGGGCCAGACGGTGTACCCTACGTGCAGGTACTGA<br>AGACGGCCGACATTAATTCATCTGAGGTTGAGGTGCTGTATTTGCGGAACG<br>TCACAATGGAAGACGCCGGGGAGTATACTTGTCTTGCCGGTAATAGTATTG<br>GGCTGTCCTATCAGTCCGCGTGGCTCACCGTCCTGCCAGAAGAGCTGGTTCA<br>TGAGGCTGAGGCACCTGAGGCGAAATGTACCGACATCATAATTTACACTTC<br>CGGATCATTGGCCGTGGCAATGGCTCTTATCATCGTCGTTCTGTGTAGGATG<br>CAAACTCAGAGCTCTAAACAACCCCTTGAACCCATGGCAGTACACAAATTG<br>AGCAAATTTCCTCTTATTAGACAGTTTTCCCTTGACTCAAGTAGCTCAGGGA<br>AATCTAGCACATCACTTATGCGGGTGACGAGACTGTCTTCCAGCTGCGCGCC<br>CATGTTGGCTGGGGTGGTGGAACTTGATCTGCCTCTGGACAGCAAGTGGGA<br>ATTTCCGAGGGAGAAACTGGTTCTTGGGAAGCCGCTCGGCGAAGGCTGTTT<br>TGGTCAGGTGGTCAGGGCGGAAGCGTACGGGATCGACAGACAGTGGCCTG<br>ATCGCGCAGTTACTGTCGCAGTAAAAATGCTGAAAGACAACGCTACTGATA<br>AGGATCTGGCAGACCTGATAAGTGAAATGGAGATGATGAAACTGATGGAC<br>AAACACAAGAACATCATTAATCTCTTGGGTGTATGTACACAAGATGGGCCT<br>CTGTATGTTATAGAAGAGTTTGCGGCCAAAGGCAACCTTCGGGAGTATCTTC<br>GCGCTAGAAGACCGCCAATGCCCGACTACACGTTCGATATTACAGAACTCC<br>ATGAGGAACAACTTTGTTTTAAGGATCTTGTTAGCTGTGTGTATCAAGTCGC<br>CCGGGGGATGGAGTATCTGGAATCAAGACGGTGTATACACCGCGACCTCGC<br>TGCCAGAAACGTTCTCGTCACGGCGGAAAATGTGATGAAGATCGCCGACTT<br>CGGACTTGCCAGGGATGTCCATGATATAGACTATTACAAAAAAAACATCTAA<br>TGGGCGGCTCCCTGTCAAGTGGATGGCGCCCGAAGCACTGTTTGACAGAGT<br>ATACACGCACCAGTCTGACGTGTGGTCATTTGGCATACTGATGTGTGGGAAATT<br>TTTACACTCGGTGGTTCACCTTATCCTGGCATCCCTGTTGAGGAGCTTTTTAA<br>ATTGCTCAAAGAGGGCCACAGAATGGACTGTCCTAGTAACTGCACCCATGA<br>GCTGTATATGCTCATGCGCGAGTGCTGGCATGCGGTGCCTAGTCAAAGGCC<br>AACCTTCAAACAGCTCGTCGAAGGCCTGGACAAGATTCTTGCTGCAATAAG<br>CGAGGAGTACCTCGACTTGTCTATGCCATTCGAGCAATACTCACCTTCTTGT<br>GAAGACACGACGAGTACATGCAGCAGCGACGACTCTGTATTTACACACGAC<br>CCTTTGCCCCTTGCTCCTTGCCTGTTTGCCTGTCCTAGTGGCCGCACCTAG |
|---|---|---|
| 105 | IGF1(WT) | ATGGAAAAAATCAACAGTCTTTCAACACAATTAGTTAAGTGCTGCTTTTGTG<br>ATTTCTTGAAGGTGAAGATGCACACTGTGTCCTACATTCATTTCTTCTACCTT<br>GGCCTGTGTTTGCTTACCTTAACCAGTTCTGCTGCTGCCGGCCCAGAAACAC<br>TGTGTGGTGCTGAGCTGGTTGATGCTCTTCAGTTCGTATGTGGAGACAGAGG<br>CTTCTACTTCAGTAAGCCTACAGGGTATGGATCCAGCAGTAGACGCTTACAC<br>CACAAGGGAATAGTGGATGAGTGCTGCTTCCAGAGTTGTGACCTGAGGAGG<br>CTGGAGATGTACTGTGCTCCAATAAAGCCACCTAAATCTGCACGCTCTGTAC<br>GTGCTCAGCGCCACACTGATATGCCAAAAGCACAAAAGGAAGTGCATTTGA<br>AGAATACAAGTAGAGGGAACACAGGAAACAGAAACTACAGAATGTAA |
| 106 | IGF1 Trunc<br>(truncated) | GGCCCAGAAACACTGTGTGGTGCTGAGCTGGTTGATGCTCTTCAGTTCGTAT<br>GTGGAGACAGAGGCTTCTACTTCAGTAAGCCTACAGGGTATGGATCCAGCA<br>GTAGACGCTTACACCACAAGGGAATAGTGGATGAGTGCTGCTTCCAGAGTT<br>GTGACCTGAGGAGGCTGGAGATGTACTGTGCTCCAATAAAGCCACCTAAAT<br>CTGCATAA |
| 107 | IGF1R | ATGAAATCTGGGGCTGGGGGAGGGGACCCTCGCCGTATTCTGTGGGCTTTTGT<br>TGGCGTTCGCCGCACTCTGTCTCTGTCCGACCAATGGTGAAATATGCGGCCC<br>GAATGTGGATATTAGAAACGATATTCACGAGCTCAAGAGGCTCGAAAATTG<br>TACTGTAGTGGAGGGGTTTCTGCAAATACTGCTTATCAGTAAGGCGGAAGA |

-continued

9. SEQUENCE APPENDIX

| SEQ ID NO: | Description | Sequence |
|---|---|---|
| | | TTACCGCAACTTCCGCTTTCCTAAGCTGACTGTGATCACAGACTATCTCCTG |
| | | CTGTTCAGAGTTGCCGGACTTGAATCCCTCTCAGATCTGTTTCCTAACCTCA |
| | | CAGTGATCAGGGGTAGAAACCTGTTCTACAACTATGCTCTCGTAATATTTGA |
| | | GATGACGAACCTTAAGGAGATTGGACTCCACAATCTTCGCAACATAACCAG |
| | | GGGTGCTATAAGGATCGAAAAAAATAGCGACCTGTGCTATCTTTCTACAGT |
| | | AGACTGGAGTCTCATATTGGACGCAGTATCCAACAACTATATAGTTGGCAA |
| | | CAAGCCTCCCAAAGAATGCGGTGATCTCTGTCCTGGAACTATGGAGGAAAA |
| | | ACCTCTCTGCGAAAAGACTAGTATAAACAACGAGTACAACTATAGGTGTTG |
| | | GACTACCAACCACTGCCAGAAGATGTGCCCGAGCAGCTGCGGCAAGCGCGC |
| | | GTGCACCGATCAGAATGAATGCTGCCACCCCGAATGTCTTGGTAGCTGTAC |
| | | GGCTCCCGACAATAACACAGCCTGCGTTGCGTGTCGCAATTACTATTATGAG |
| | | GGTGTCTGTATGCCTACCTGTCCGCCTAACACATATAAGTTCGAGGGGTGGC |
| | | GCTGCGTGACAAAAGAATTTTGTTCCAAGGTCCCAGCAACGGAGACGTCTG |
| | | ACTATGAAAGGTTTGTAATTCATAATGATGAATGTATGGCGGAATGCCCAT |
| | | CTGGATTTATCAGGAACGGTAGTCAGAGCATGTTTTGCTCCCCATGTGAAGG |
| | | CCCATGTCCCAAAATTTGTGAAGACGGGAAGACGAAGACAATAGATAGCGT |
| | | CACTTCTGCTCAAATGCTTCAGGGATGTACCATCTTGAAAGGAAATCTCTTG |
| | | ATTAACATTCGCCGGGGTAATAATATAGCAAGTGAGCTTGAAAACTTTATG |
| | | GGGCTCATAGAAACGGTAACTGGGTATGTCAAGATCCGCCATAGTCATGCA |
| | | CTCGTGTCACTTTCATTCTTGAAGAATCTCCGCTATATACTCGGCGAAGAGC |
| | | AAGTTGACGGCAACTACTCATTTTACGTTCTCGATAATCATAATTTGCAGCA |
| | | GCTTTGGGACTGGAATCACCACAACTTGACCATTAAAGAAGGAAAGATGTA |
| | | CTTCGCTTTCAATCCGAAACTTTGTGTATCCGAAATTTACCGCATGGAAGAG |
| | | GTGTCTGGAACTAAAGGACGCCAGTCAAAAGGAGATATAAATCCCAGGAAT |
| | | AATGGAGAAAGGGCGTCCTGTGAGAGCCATATATTGAGATTCGTGAGCAAT |
| | | ACCACGCTGAAGAACCGGATAAAACTCACCTGGGAGAGATACAGGCCCCC |
| | | GGATTACCGGGACCTCATCTCTTTCACGGTTTATTACAAGGAGGCCCCCTTC |
| | | AAAAACGTCACAGAGTACGATGGGCAAGATGCCTGCGGCTCCAACTCTTGG |
| | | AACATGGTCGACGTAGACTTGCCCCCTAACAAAGAGAATGACCCTGGTATA |
| | | TTGCTTCAAGGACTTAAACCTTGGACGCAGTACGCCATATACGTCAAAGCC |
| | | GTGACCCTTACAATGATGGAAAACCACCACATCCACGGGGCTAAATCCGAG |
| | | ATTGTTTATATAAGGACAAATGCAGCCGTCCCCAGCATACCTCTCGACGTAA |
| | | TATCTGCCTCTAATAGCAGCAGCCAGCTCATTGTGAAGTGGAATCCTCCTTC |
| | | ACTTCCCAACGGGAATCTGTCTTATTACATTGTCCGCTGGCAACAACAACCT |
| | | CAGGATTCTTATTTGTATCGGCATAACTACTGTAGTAAAGACAAGGTGCCG |
| | | ATTCGCCGGTACGCGGACGGTACTATTGACACGGAAGAAGCAACAGAGCCA |
| | | ACAAAACCCGAAGGATGCGGCGGTGAAAAAGGTCCGTGTTGTGCGTGCCCT |
| | | AAGACCGAAGCTGAGAAGCAAGCTGAAAAGGAAGAAGCTGAATACCGCAA |
| | | GGTGTTTGAGAACTTCCTGCATAACTCCATCTTCGTTCCTCGCCCGGATAGA |
| | | AAGAGGCGCGACGTGTTCAGGATTGCTAACGCCACGCTCGCTACGAGGAAT |
| | | CGGAACATTACTGGTGCGGATCACTTCACCAATGCATCCGATGCGGAAGAG |
| | | TCCGAAGTAGAGTACCCATTTTTTGAGACGAAAGTCGACGGGAAGGAGAGA |
| | | ACGGTAATATCTCATTTGCAGCCTTTTACCCTTTATAGAATAGATATCCACA |
| | | GCTGCAATCACGAAGCAGACACCCTTGGTTGTAGTGCTTCTAACTTCGTGTT |
| | | TGCCCGCACGATGCCCTCTGAAGGCGCTGACAATATACCCGGAACCGTAGC |
| | | ATGGGAAGCGAAGGAGGAGAACACGGTTTATCTTAAATGGTTGGAACCCAC |
| | | CAACCCTAACGGACTTATCTTGATGTACGAGATTAAATATGGACAACACGG |
| | | GGAGGAAAAGAGGGAGTGTGTCAGTAGGCAAGAATACAAAAAACTTGGTG |
| | | GCGCCAAATTGACACACTTGAACCCTGGTAATTACAGCGCGCGCGTGCAGG |
| | | CGACTAGCTTGGCAGGTAATGGTTCTTGGACTGAACCCGTCTCCTTCTATGT |
| | | TCAGCCCAAATCCGCAAATTACGACAACTTTCTCCATTTGATAATAGTCCTT |
| | | CCAATAGCCTTCCTGTTGATAATAGGTGGCCTCCTCATTATGTTGTACGTCTT |
| | | TAATAAGAAACGGAACTCTGACCGGCTCGGAAATGGTGTTCTGTATGCAAG |
| | | TGTTAATCCAGAATATTTCTCTGCATCAGACGTTTATGTGCCGGACGAGTGG |
| | | GAAGTGCCAAGGGAGAAAATTACAATGTGCAGAGAACTCGGACAGGGTTC |
| | | TTTTGGCATGGTTTACGAGGGCATCGCAAAAGGCGTGGTGAAGGACGAACC |
| | | CGAGACGAGAGTTGCTATCAAAACAGTCAATGAGTCAGCTTCTATGCGCGA |
| | | ACGGATTGAGTTTTTGAATGAGGCCAGTGTAATGAAGGAGTTTAACTGCCA |
| | | CCACGTCGTACGGTTGCTTGGCGTCGTGTCTCAAGGACAGCCCACCCTCGTT |
| | | ATTATGGAGTTGATGACCCGGGGGGGATCTCAAGTCCTACTTGAGGTCTCTTC |
| | | GCCCTGACACTGAGTCAAACCCAGGGCAGGCACCTCCTACGCTGAAAAAAA |
| | | TGATACAAATGGCTGGAGAAATCGCCGATGGGATGGCGTATCTCAACGCTA |
| | | ATAAGTTTGTACACCGCGATCTGGCCGCAAGAAATTGTATGGTCGCAGAGG |
| | | ATTTTACTGTCAAGATCGGCGATTTCGGCATGACACGCGACATCTATGAGAC |
| | | CGACTACTATAGGAAGGGGGGGAAGGGTTTGCTCCCAGTAAGGTGGATGTC |
| | | ACCGGAGAGCCTCAAGGATGGGGTGTTCACGACTCACAGCGATGTCTGGTC |
| | | TTTTGGAGTTGTACTCTGGGAAATAGCTACACTGGCAGAGCAACCCTACCA |
| | | AGGAATGACAAATGAACAAGTCCTCCGCTTTGTAATGGAAGGGGGTCTTCT |
| | | CGAAAAACCGGACAACTGCCCAGACATGCTTTTCGAGCTGATGCGCATGTG |
| | | CTGGCAGTACAATCCCAAAATGCGCCCGTCTTTTCTTGAAATAATCTCAAGC |
| | | ATCAAGGATGAACTTGACCCGGCCTTTAAAGAAGTATCATTTTTCTATTCCG |
| | | AAGAAAATAAACCGCAGATACAGAAGAACTCGACCTTGAGACAGAAAAC |
| | | ATGGAAAGTATTCCTCTCGATCCTTCCTCAACTTTGCAGCCGACGGATAAAC |

9. SEQUENCE APPENDIX

| SEQ ID NO: | Description | Sequence |
|---|---|---|
| | | ATTCTGGCCACAAGGCGGAAAATGGCCCGGGGGTTGTAGTACTCAGGGCAT CATTTGAAGAAAGGCAGCCATACGCACATATGAATGGGGGTCGCAAGAAC GAGCGGGCTTTGCCTCTTCCCCAATCTTCTGCATGCTAG |
| 108 | IGFR-R1353H | GAATTCATGAAATCTGGGGCTGGGGGAGGGACCCTCGCCGTATTCTGTGGG CTTTTGTTGGCGTTCGCCGCACTCTGTCTCTGTCCGACCAATGGTGAAATAT GCGGCCCGAATGTGGATATTAGAAACGATATTCACGAGCTCAAGAGGCTCG AAAATTGTACTGTAGTGGAGGGGTTTCTGCAAATACTGCTTATCAGTAAGG CGGAAGATTACCGCAACTTCCGCTTTCCTAAGCTGACTGTGATCACAGACTA TCTCCTGCTGTTCAGAGTTGCCGGACTTGAATCCCTCTCAGATCTGTTTCCTA ACCTCACAGTGATCAGGGGTAGAAACCTGTTCTACAACTATGCTCTCGTAAT ATTTGAGATGACGAACCTTAAGGAGATTGGACTCCACAATCTTCGCAACAT AACCAGGGGTGCTATAAGGATCGAAAAAAATAGCGACCTGTGCTATCTTTC TACAGTAGACTGGAGTCTCATATTGGACGCAGTATCCAACAACTATATAGTT GGCAACAAGCCTCCCAAAGAATGCGGTGATCTCTGTCCTGGAACTATGGAG GAAAAACCTCTCTGCGAAAAGACTAGTATAAACAACGAGTACAACTATAGG TGTTGGACTACCAACCACTGCCAGAAGATGTGCCCGAGCAGCTGCGGCAAG CGCGCGTGCACCGATCAGAATGAATGCTGCCACCCCGAATGTCTTGGTAGC TGTACGGCTCCCGACAATAACACAGCCTGCGTTGCGTGTCGCAATTACTATT ATGAGGGTGTCTGTATGCCTACCTGTCCGCCTAACACATATAAGTTCGAGGG GTGGCGCTGCGTGACAAAAGAATTTTGTTCCAAGGTCCCAGCAACGGAGAC GTCTGACTATGAAAGGTTTGTAATTCATAATGATGAATGTATGGCGGAATG CCCATCTGGATTTATCAGGAACGGTAGTCAGAGCATGTTTTGCTCCCCATGT GAAGGCCCATGTCCCAAAATTTGTGAAGACGGGAAGACGAAGACAATAGA TAGCGTCACTTCTGCTCAAATGCTTCAGGGATGTACCATCTTGAAAGGAAAT CTCTTGATTAACATTCGCCGGGGTAATAATATAGCAAGTGAGCTTGAAAAC TTTATGGGGCTCATAGAAACGGTAACTGGGTATGTCAAGATCCGCCATAGT CATGCACTCGTGTCACTTTCATTCTTGAAGAATCTCCGCTATATACTCGGCG AAGAGCAAGTTGACGGCAACTACTCATTTTACGTTCTCGATAATCATAATTT GCAGCAGCTTTGGGACTGGAATCACCACAACTTGACCATTAAAGAAGGAA GATGTACTTCGCTTTCAATCCGAAACTTTGTGTATCCGAAATTTACCGCATG GAAGAGGTGTCTGGAACTAAAGGACGCCAGTCAAAAGGAGATATAAATCC CAGGAATAATGGAGAAAGGGCGTCCTGTGAGAGCCATATATTGAGATTCGT GAGCAATACCACGCTGAAGAACCGGATAAAACTCACCTGGGAGAGATACA GGCCCCCGGATTACCGGGACCTCATCTCTTTCACGGTTTATTACAAGGAGGC CCCCTTCAAAAACGTCACAGAGTACGATGGGCAAGATGCCTGCGGCTCCAA CTCTTGGAAACATGGTCGACGTAGACTTGCCCCCTAACAAAGAGAATGACCC TGGTATATTGCTTCAAGGACTTAAACCTTGGACGCAGTACGCCATATACGTC AAAGCCGTGACCCTTACAATGATGGAAAACCACCACATCCACGGGGCTAAA TCCGAGATTGTTTATATAAGGACAAATGCAGCCGTCCCCAGCATACCTCTCG ACGTAATATCTGCCTCTAATAGCAGCAGCCAGCTCATTGTGAAGTGGAATC CTCCTTCACTTCCCAACGGGAATCTGTCTTATTACATTGTCCGCTGGCAACA ACAACCTCAGGATTCTTATTTGTATCGGCATAACTACTGTAGTAAAGACAAG GTGCCGATTCGCCGGTACGCGGACGGTACTATTGACACGGAAGAAGCAACA GAGCCAACAAAACCCGAAGGATGCGGCGGTGAAAAAGGTCCGTGTTGTGC GTGCCCTAAGACCGAAGCTGAGAAGCAAGCTGAAAAGGAAGAAGCTGAAT ACCGCAAGGTGTTTGAGAACTTCCTGCATAACTCCATCTTCGTTCCTCGCCC GGATAGAAAGAGGCGCGACGTGTTCAGGATTGCTAACGCCACGCTCGCTAC GAGGAATCGGAACATTACTGGTGCGGATCACTTCACCAATGCATCCGATGC GGAAGAGTCCGAAGTAGAGTACCCATTTTTTGAGACGAAAGTCGACGGGAA GGAGAGAACGGTAATATCTCATTTGCAGCCTTTTACCCTTTATAGAATAGAT ATCCACAGCTGCAATCACGAAGCAGACACCCTTGGTTGTAGTGCTTCTAACT TCGTGTTTGCCCGCACGATGCCCTCTGAAGGCGCTGACAATATACCCGGAA CCGTAGCATGGGAAGCGAAGGAGGAGAACACGGTTTATCTTAAATGGTTGG AACCCACCAACCCTAACGGACTTATCTTGATGTACGAGATTAAATATGGAC AACACGGGGAGGAAAAGAGGGAGTGTGTCAGTAGGCAAGAATACAAAAAA CTTGGTGGCGCCAAATTGACACACTTGAACCCTGGTAATTACAGCGCGCGC GTGCAGGCGACTAGCTTGGCAGGTAATGGTTCTTGGACTGAACCCGTCTCCT TCTATGTTCAGCCCAAATCCGCAAATTACGACAACTTTCTCCATTTGATAAT AGTCCTTCCAATAGCCTTCCTGTTGATAATAGGTGGCCTCCTCATTATGTTGT ACGTCTTTAATAAGAAACGGAACTCTGACCGGCTCGGAAATGGTGTTCTGT ATGCAAGTGTTAATCCAGAATATTTCTCTGCATCAGACGTTTATGTGCCGGA CGAGTGGGAAGTGCCAAGGGAGAAAATTACAATGTGCAGAGAACTCGGAC AGGGTTCTTTTGGCATGGTTTACGAGGGCATCGCAAAAGGCGTGGTGAAGG ACGAACCCGAGACGAGAGTTGCTATCAAAACAGTCAATGAGTCAGCTTCTA TGCGCGAACGGATTGAGTTTTTGAATGAGGCCAGTGTAATGAAGGAGTTTA ACTGCCACCACGTCGTACGGTTGCTTGGCGTCGTGTCTCAAGGACAGCCCAC CCTCGTTATTATGGAGTTGATGACCCGGGGGGGATCTCAAGTCCTACTTGAGG TCTCTTCGCCCTGACACTGAGTCAAACCCAGGGCAGGCACCTCCTACGCTGA AAAAAATGATACAAATGGCTGGAGAAATCGCCGATGGGATGGCGTATCTCA ACGCTAATAAGTTTGTACACCGCGATCTGGCCGCAAGAAATTGTATGGTCG CAGAGGATTTTACTGTCAAGATCGGCGATTTCGGCATGACACGCGACATCT ATGAGACCGACTACTATAGGAAGGGGGGGAAGGGTTTGCTCCCAGTAAGGT |

9. SEQUENCE APPENDIX

| SEQ ID NO: | Description | Sequence |
|---|---|---|
| | | GGATGTCACCGGAGAGCCTCAAGGATGGGGTGTTCACGACTCACAGCGATG<br>TCTGGTCTTTTGGAGTTGTACTCTGGGAAATAGCTACACTGGCAGAGCAACC<br>CTACCAAGGAATGACAAATGAACAAGTCCTCCGCTTTGTAATGGAAGGGGG<br>TCTTCTCGAAAAACCGGACAACTGCCCAGACATGCTTTTCGAGCTGATGCGC<br>ATGTGCTGGCAGTACAATCCCAAAATGCGCCCGTCTTTTCTTGAAATAATCT<br>CAAGCATCAAGGATGAACTTGACCCGGCCTTTAAAGAAGTATCATTTTTCTA<br>TTCCGAAGAAAATAAACCGCCAGATACAGAAGAACTCGACCTTGAGACAG<br>AAAACATGGAAAGTATTCCTCTCGATCCTTCCTCAACTTTGCAGCCGACGGA<br>TAAACATTCTGGCCACAAGGCGGAAATGGCCCGGGGGTTGTAGTACTCAG<br>GGCATCATTTGAAGAAAGGCAGCCATACGCACATATGAATGGGGGTCGCAA<br>GAACGAGCATGCTTTGCCTCTTCCCCAATCTTCTGCATGCTAG |
| 109 | PDGFRa(WT) | ATGGGTACTCCCCCAAGGACGTTCCTGATCCTGGGATGTTTTCTCACAGGAC<br>CGCTCCTAACACTTTGCCAGCTTCCTCTGCCGACTATTGTTCCCAATAGAAA<br>TGAGATGGTTGTACAGCTGAATTCCAATTTCACACTCAAATGCTCTGGAGAC<br>AGCGAAGTGAGCTGGCAGTACCCAGTGACCGAGGGAAGCCACAGGATAGA<br>CATCAGACACGAGGAGAACAACAGTGGCCTCTTCGTGACAGTGCTTGAAGT<br>CGGAAATGCCTCAGCCGCTCACACGGGCATGTATGTTTGCTATTATAACCAC<br>ACGCAAGTGGAGGATGGGGAAGTCGAGGGGAAGGACATCTACATCTATGT<br>GCCTGACCCAGACATGCCTTTCGTTCCTTCCTTACCAGAAGACCAGTTCATC<br>CTAGTAGAAGAAGGTGATCCCACTGTTATCCCTTGTCGGACAAGTGACCCA<br>AGTGCTGAAGTGACTTTAGTTAACAGTTTAGACAAGCCTGTCTATGCTTTCT<br>ATGACAGCAAACAGGGCTTCGTAGGGAACTTCCTTGCAGGACCATACACAT<br>GCAAACAATGGTTAAAGGCGTGGAGTTCAAGTCCGATGAGTTCCTCATCT<br>ATATTTTAAGAGCTACTTCACAGCTGCCGGTTGAAATTGAAGCTCTGAAAAC<br>TGTCTACAAAACAGGCGAGACCATCGTAGTAACTTGTGTGGTCTTTGACAAT<br>GAGGTGGTTAATTTACAGTGGAATTATCCCGGGAAAGTGAAAGAAAAAGGT<br>CTGATAAAACTTGATGATATCAAAGTCCCATCACAGAAGTTGGTTTACACGT<br>TGACCATACCTGACGCATCAGTGAAAGACACAGGGGATTATGAATGTACTG<br>CCCGACATGCAACCAAGGAGGTTAAGGAAAATAAGAAAGTAGTCATTACA<br>GTTCATGACAAAGGGTTCATTCATCTAGAGCCTCAATTTAGCCCTTTGGAAG<br>CTGTCAATCTACATGAAGTCAAAAATTTTGTCGTCGATGTGCAGGCGTACCC<br>CGCTCCAAAAATGTACTGGTTGAAGGATAATGTGACTCTGATTGAAAACCT<br>TACTGAGATTGTTACTAGTTCAAACAGAGTCCAGGAAACACGGTTTCAAAG<br>TGTACTAAAATTGATCCGGGCCAAGGAAGAAGACAGTGGGTACTATACTTT<br>GGTTGCTGAAAATGAAGATGAGATTAAGAGATACACCTTCTCGTTGCTAAT<br>ACAAGTTCCAGCCTTGATCTTAGACCTCATGGACGACCACCAAGGCTCTGCT<br>GGCAGGCAGACGGTGAGGTGCTTGGCTGAAGGTACCCCGCTTCCTGATGTG<br>GAATGGTTGGTTTGCAAGGACATTAAAAAAATGCAGCAATGACACTTCCTGG<br>ACTCTTCTGACTAACAATATCTCTGATATACACATGGAAGCCCACCTGGATG<br>AGAGGAATATGGTGGAAAGCCAGGTGACCTTCCAGAAGGTAGAAGAAACC<br>CTGGCTGTGAGATGTGTAGCAAGAAACGACCTTGGAGCTGTTACTCGGGAA<br>CTGAAACTTGTGGCTCCCACCTTGCGATCAGAACTGACGGTGGCTGCTGCTG<br>TCTTAGTACTGCTGGTGATTGTGATAATTTCACTGATTGTCCTGGTCATCATC<br>TGGAAACAGAAGCCAAGATATGAGATAAGATGGAGAGTCATTGAGTCTATC<br>AGCCCCGATGGCCATGAATACATTTATGTGGACCCAATGCAGCTACCTTATG<br>ACTCCAGATGGGAGTTTCCTCGAGATGGGTTAGTGCTTGGTCGAATCCTTGG<br>TTCTGGTGCATTTGGAAAAGTGGTGGAAGGGACAGCATATGGATTGAGTCG<br>TTCTCAACCTGTGATGAAAGTAGCCGTGAAAATGCTGAAACCTACAGCTAG<br>ATCCAGTGAAAAACAGGCGCTCATGTCTGAACTGAAGATAATGACACATCT<br>TGGGCCCCACCTGAATATTGTGAACCTGCTTGGAGCTTGTACGAAATCAGGT<br>CCTATTTACATAATCACTGAATACTGCTTTTACGGTGATTTGGTGAACTATC<br>TGCACAAGAACAGGGACAACTTCCTCAGCCGACATCCAGAGAAACCAAAG<br>AAAGATCTGGATATTTTTGGGATGAACCCAGCTGATGAAAGCACAAGAAGC<br>TATGTGATTTTATCATTTGAAAACACCGGAGAATATATGGATATGAAACAA<br>GCTGATACCACTCAGTATGTGCCAATGCTGGAAAGGAAGGAGGGGATCTAAA<br>TACTCTGATATTCAGAGATCTGTATATGATCGACCTGCTTCATATAAGAAGA<br>AATCTTTGTCAGAATCAGAAGTAAAAAACCTTCTTTCAGATGACGGTTCGG<br>AGGGTCTAAGCCTACTGGATTTGCTAAGCTTCACCTACCAGGTTGCACGGG<br>GAATGGAATTCTTGGCTTCTAAAAATTGCGTACACCGTGACTTGGCAGCTCG<br>TAATGTCCTTCTGGCTCAAGGCAAATCGTGAAGATCTGCGACTTTGGGTTG<br>GCTAGAGACATCATGCATGATTCCAACTATGTCTCCAAGGGCAGCACCTTCC<br>TCCCAGTAAAATGGATGGCACCTGAAAGCATTTTTGACAATCTGTACACAA<br>CATTAAGTGATGTCTGGTCTTATGGCATTCTGCTGTGGGAAATATTTTCTCTT<br>GGTGGCACACCATATCCTGGCATGATGGTCGACTCCACCTTCTACAATAAG<br>ATAAAGAGTGGCTACCGAATGGCAAAACCTGATCATGCTACCAATGAAGTG<br>TATGAGATCATGGTAAAGTGCTGGAACAGTGAACCAGAGAAAAGACCTTCG<br>TTTTACCATCTGAGTGAAATTGTGGAGAGCTTGTTGCCTGGAGAGTACAAA<br>AAGAGCTACGAGAAGATTCACCTGGACTTCCTGAAAAGCGATCACCCAGCT<br>GTCACTCGAATGAGAGGGGACTGTGACAATGCTTACATTGGTGTCACCTAC<br>AAGAATGAAGACAAGATAAAGGATAGAGAGAGTGGATTTGATGAGCAGAG<br>GCTGAGTGCTGACAGTGGGTACATCATCCCCCTGCCTGACATTGACCCTGTT<br>TCTGAAGATGAGCTTGGCAAAAGGAACAGGCACAGTTCCCAGACATCTGAA |

-continued

9. SEQUENCE APPENDIX

| SEQ ID NO: | Description | Sequence |
|---|---|---|
| | | GAGAGTGCCATTGAAACCGGTTCCAGTAGCTCTACCTTTATAAAGAGAGAG<br>GATGAGACCATTGAGGACATTGACATGATGGATGACATTGGAATTGACTCC<br>TCGGATCTTGTAGAGGACAGCTTCCTGTAA |
| 110 | PDGFRa-<br>D842V | ATGGGTACTCCCCCAAGGACGTTCCTGATCCTGGGATGTTTTCTCACAGGAC<br>CGCTCCTAACACTTTGCCAGCTTCCTCTGCCGACTATTGTTCCCAATAGAAA<br>TGAGATGGTTGTACAGCTGAATTCCAATTTCACACTCAAATGCTCTGGAGAC<br>AGCGAAGTGAGCTGGCAGTACCCAGTGACCGAGGGAAGCCACAGGATAGA<br>CATCAGACACGAGGAGAACAACAGTGGCCTCTTCGTGACAGTGCTTGAAGT<br>CGGAAATGCCTCAGCCGCTCACACGGGCATGTATGTTTGCTATTATAACCAC<br>ACGCAAGTGGAGGATGGGGAAGTCGAGGGGAAGGACATCTACATCTATGT<br>GCCTGACCCAGACATGCCTTTCGTTCCTTCCTTACCAGAAGACCAGTTCATC<br>CTAGTAGAAGAAGGTGATCCCACTGTTATCCCTTGTCGGACAAGTGACCCA<br>AGTGCTGAAGTGACTTTAGTTAACAGTTTAGACAAGCCTGTCTATGCTTTCT<br>ATGACAGCAAACAGGGCTTCGTAGGGAACTTCCTTGCAGGACCATACACAT<br>GCAAAACAATGGTTAAAGGCGTGGAGTTCAAGTCCGATGAGTTCCTCATCT<br>ATATTTTAAGAGCTACTTCACAGCTGCCGGTTGAAATTGAAGCTCTGAAAAC<br>TGTCTACAAAACAGGCGAGACCATCGTAGTAACTTGTGTGGTCTTTGACAAT<br>GAGGTGGTTAATTTACAGTGGAATTATCCCGGGAAAGTGAAAGAAAAAGGT<br>CTGATAAAACTTGATGATATCAAAGTCCCATCACAGAAGTTGGTTTACACGT<br>TGACCATACCTGACGCATCAGTGAAAGACACAGGGGATTATGAATGTACTG<br>CCCGACATGCAACCAAGGAGGTTAAGGAAAATAAGAAAGTAGTCATTACA<br>GTTCATGACAAAGGGTTCATTCATCTAGAGCCTCAATTTAGCCCTTTGGAAG<br>CTGTCAATCTACATGAAGTCAAAAATTTTGTCGTCGATGTGCAGGCGTACCC<br>CGCTCCAAAAATGTACTGGTTGAAGGATAATGTGACTCTGATTGAAAACCT<br>TACTGAGATTGTTACTAGTTCAAACAGAGTCCAGGAAACACGGTTTCAAAG<br>TGTACTAAAATTGATCCGGGCCAAGGAAGAAGACAGTGGGTACTATACTTT<br>GGTTGCTGAAAATGAAGATGAGATTAAGAGATACACCTTCTCGTTGCTAAT<br>ACAAGTTCCAGCCTTGATCTTAGACCTCATGGACGACCACCAAGGCTCTGCT<br>GGCAGGCAGACGGTGAGGTGCTTGGCTGAAGGTACCCCGCTTCCTGATGTG<br>GAATGGTTGGTTTGCAAGGACATTAAAAAAATGCAGCAATGACACTTCCTGG<br>ACTCTTCTGACTAACAATATCTCTGATATACACATGGAAGCCCACCTGGATG<br>AGAGGAATATGGTGGAAAGCCAGGTGACCTTCCAGAAGGTAGAAGAAACC<br>CTGGCTGTGAGATGTGTAGCAAGAAACGACCTTGGAGCTGTTACTCGGGAA<br>CTGAAACTTGTGGCTCCCACCTTGCGATCAGAACTGACGGTGGCTGCTGCTG<br>TCTTAGTACTGCTGGTGATTGTGATAATTTCACTGATTGTCCTGGTCATCATC<br>TGGAAACAGAAGCCAAGATATGAGATAAGATGGAGAGTCATTGAGTCTATC<br>AGCCCCGATGGCCATGAATACATTTATGTGGACCCAATGCAGCTACCTTATG<br>ACTCCAGATGGGAGTTTCCTCGAGATGGGTTAGTGCTTGGTCGAATCCTTGG<br>TTCTGGTGCATTTGGAAAAGTGGTGGAAGGGACAGCATATGGATTGAGTCG<br>TTCTCAACCTGTGATGAAAGTAGCCGTGAAAATGCTGAAACCTACAGCTAG<br>ATCCAGTGAAAAACAGGCGCTCATGTCTGAACTGAAGATAATGACACATCT<br>TGGGCCCCACCTGAATATTGTGAACCTGCTTGGAGCTTGTACGAAATCAGGT<br>CCTATTTACATAATCACTGAATACTGCTTTTACGGTGATTTGGTGAACTATC<br>TGCACAAGAACAGGGACAACTTCCTCAGCCGACATCCAGAGAAACCAAAG<br>AAAGATCTGGATATTTTTGGGATGAACCCAGCTGATGAAAGCACAAGAAGC<br>TATGTGATTTTATCATTTGAAAACACCGGAGAATATATGGATATGAAACAA<br>GCTGATACCACTCAGTATGTGCCAATGCTGGAAAGGAAGGAGGGGATCTAAA<br>TACTCTGATATTCAGAGATCTGTATATGATCGACCTGCTTCATATAAGAAGA<br>AATCTTTGTCAGAATCAGAAGTAAAAAACCTTCTTTCAGATGACGGTTCGG<br>AGGGTCTAAGCCTACTGGATTTGCTAAGCTTCACCTACCAGGTTGCACGGG<br>GAATGGAATTCTTGGCTTCTAAAAATTGCGTACACCGTGACTTGGCAGCTCG<br>TAATGTCCTTCTGGCTCAAGGCAAAATCGTGAAGATCTGCGACTTTGGGTTG<br>GCTAGAGTCATCATGCATGATTCCAACTATGTCTCCAAGGGCAGCACCTTCC<br>TCCCAGTAAAATGGATGGCACCTGAAAGCATTTTTGACAATCTGTACACAA<br>CATTAAGTGATGTCTGGTCTTATGGCATTCTGCTGTGGGAAATATTTTCTCTT<br>GGTGGCACACCATATCCTGGCATGATGGTCGACTCCACCTTCTACAATAAG<br>ATAAAGAGTGGCTACCGAATGGCAAAACCTGATCATGCTACCAATGAAGTG<br>TATGAGATCATGGTAAAGTGCTGGAACAGTGAACCAGAGAAAAGACCTTCG<br>TTTTACCATCTGAGTGAAATTGTGGAGAGCTTGTTGCCTGGAGAGTACAAA<br>AAGAGCTACGAGAAGATTCACCTGGACTTCCTGAAAAGCGATCACCCAGCT<br>GTCACTCGAATGAGAGGGGACTGTGACAATGCTTACATTGGTGTCACCTAC<br>AAGAATGAAGACAAGATAAAGGATAGAGAGAGTGGATTTGATGAGCAGAG<br>GCTGAGTGCTGACAGTGGGTACATCATCCCCCTGCCTGACATTGACCCTGTT<br>TCTGAAGATGAGCTTGGCAAAAGGAACAGGCACAGTTCCCAGCACATCTGAA<br>GAGAGTGCCATTGAAACCGGTTCCAGTAGCTCTACCTTTATAAAGAGAGAG<br>GATGAGACCATTGAGGACATTGACATGATGGATGACATTGGAATTGACTCC<br>TCGGATCTTGTAGAGGACAGCTTCCTGTAA |
| 111 | PDGFRb(WT) | ATGCTCTGTCCCTCTCTGAAGGCATCTCTGCAGCTCCTCATCCTCACTGGTCT<br>GCTGGAGGTAACGTCTGGAGGCAGCGGGCTGCACATCGAACCTGAAGATGC<br>TGAGCTCGTCCTTAGGCTCCACAGCACTTTCTCCCTCGTGTGCTATGGGGAC<br>GGCACGCTGGTCTGGGAGCGGGATGGTCAGCCTCTCACTGCCGTGCTGGAG |

-continued

9. SEQUENCE APPENDIX

| SEQ ID NO: | Description | Sequence |
|---|---|---|
| | | CACAGGGACGGGGTCTTCATCAGCAACCTCACCCTCAGGAACGTGACAGGC<br>CGTCACACGGGGGAGTATGCGTGCTTCTACAGCCCTGACCAGGCTCCGGAG<br>CGAGCAGAGAGGAAAGCCCTTTACATCTATGTTCCAGATCCCTCCTTAGTTT<br>TTCTCCCCGCAATCACTTCTGAAGAGTTCTTCATCTTCATCACGGGCTACAC<br>AGAGGCCACCATCCCATGCCGTGTGACCAACCCAGAGCTGCAGGTGACCCT<br>CTATGAAAAGAAAGTGGAGAATCCCATTCCAGCTACTTATGACCCACAACA<br>GGGCTTCAAAGGCTTCTTTGAGGACAAGACCTACTACTGCCAGGCAATCGT<br>GGATGACCAAGAGGTGGATTCAGACACCTTCTATGTCTACCGGATCCAGGT<br>CTCATCTGTGAACGTCTCCATCAGCGCAGTGCAGACCGTAGTGCGGCAGGG<br>AGAAAATGTTACCCTGATGTGCACTGTCAGTGGCAATGAGCTGGTCAATTTC<br>AACTGGGATTATCCCCGCAAGCAGGCAGGGAAGGCTGTGGAGCCAGTGACC<br>GATTTCCTGCCTGGATCCACCCATGACATCCGTTCCATCCTCATCATCCAGA<br>ATGCAGAGCTAGAGGACAGTGGGACCTACGTCTGCAATGTCTCTGAGGGCT<br>ACCATGAGAAGACAGACCGGAAAGACATCACGGTCCAAGTGATCGAGCGT<br>GGCTTTGTACGCTTCCACACCCACCTGGCCAGCACGGTGTATGCTGAGGTCC<br>ACAAGAGCCACATCATCCAGGTGGATGTGGAGGCCTACCCACAGCCAAACA<br>TTGTGTGGCTGAAGAACAACAAGACATTGACCATGGAGAGCAGCAGCGAGT<br>TCACCATCACCAACAGGAACCTGTCAGAAACCAGGTATCAGACGTCTCTGG<br>TCCTGGTGCGTGTGAAGCAGGAGGAAGGAGGATATTACACCATCCGAGCTT<br>CCAATGAGGATGATGCACAAGAGCTGTCCTTCCATCTGCAGATAAATGTGC<br>CAGCCAAAGTGGTGGATCTCAAGGAAAACAGCAGTGCCAGCAGCGGGGAG<br>CAGACTGTAACGTGCTCTGCTGAAGGGATGCCCCAGCCAGAGATCAGTTGG<br>TCCACTTGCAGCAACATCAAATGGTGTGGCAGCCAGGGGCAACCCACCCAG<br>CTGCTGGGGAACAACTCTGCAGAGATTGGCCTGCACACTAATGCTACGTAC<br>CATGCAGAGCTGCAGGTGTACCGTGTGAACAGCACCCTGCAGCTGCACAGG<br>GTGGATGAACCCCTGCTTCTGAGATGCACCGTGCAAAACTTCCTGGGCTCCA<br>ACTCCCAAGACATCACTCTGGTCCCAAATGCCTTGCCATTCAAAGTGGTCAT<br>CATCTCCGTCATCCTGGCTCTGCTGGTCCTCACCGTCATCTCCCTGATCATCC<br>TGATCATCCTGTGGCAGAAGAAACCTCGCTATGAGATCCGCTGGAAGGTGA<br>TCGAGTCAGTGAGCTCCGATGGGCACGAGTACATCTACGTGGATCCCATGC<br>AGCTCCCTTATGACTCCAGCTGGGAGGTGCCCAGGGACAAGCTGGTGTTAG<br>GACGCACTCTTGGCTCCGGTGCCTTTGGACGCGTGGTGGAGGCAACAGCGC<br>ATGGCCTGAGCCATTCACAGTCCACCATGAAAGTGGCAGTCAAGATGCTCA<br>AGTCCACTGCACGGAGCAGTGAGAAGCAAGCCCTCATGTCTGAGCTGAAGA<br>TCATGAGCCACCTGGGACCTCACCTCAACATCGTCAACTTGCTGGGGGCCTG<br>CACCAAAGGAGGGCCCATCTATATCATCACCGAGTACTGCCGTTATGGGGA<br>CCTGGTGGACTACCTGCACCGCAACAAGCACACCTTCCTGCAGTCCTATGGC<br>GAGAAGGCCCGCGGGAGGCAGAGCTGTATGGGAATACCATCAAGGAGGA<br>CCACGTGCAGAGTCACCTCTCCTTGTCTGTCGAGAGTGATGGGGGCTACATG<br>GACATGAGCAAGGATGAGTCTCTGGATTACGTGCCCATGTCTGACATGAAG<br>GGTGAAGTCAAGTATGCTGACATCGAGTCTTCTAACTATGGCACCCCATATG<br>AGCTGGACAGCTATTCCCCATCAGCTCCGGAAAGAACAGACCGGGTGACAC<br>TGATAAATGAATCTCCACTCCTCAGCTACATGGACTTGGTGGGCTTCAGCTT<br>CCAGGTGGCCAATGGGATGGAGTTCCTGGCTTCCAAAAATTGTGTGCATCG<br>TGACCTGGCTGCCAGGAACGTCCTCATCTGCGAGGGGAAGCTGGTGAAGAT<br>CTGTGACTTTGGTCTGGCAAGAGACATCATGAGGGATTCCAACTACATCTCC<br>AAAGGCAGTACCTTCTTGCCCCTTAAGTGGATGGCCCCAGAGAGCATCTTC<br>AACAACCTCTACACCACCCTAAGTGATGTGTGGTCCTTTGGGATTCTTCTCT<br>GGGAGATATTCACTCTAGGAGGGACTCCCTACCCTGAACTGCCTATGAACG<br>AACAGTTCTACAATGCCATCAAACGTGGCTATCGGATGTCCAAACCTACCC<br>ATGCTTCTGATGAAATCTACGATATCATGCAGAAGTGCTGGGAGGAGAAGT<br>TTGAGATCAGACCGTCCTTCTCACAGCTGGTGGTGCTTATGGGAAACCTCTT<br>GGTGGACTGCTACAGAAAGAGGTACCAACAGGTAGATGAAGAGTTCATGA<br>AGAGCGACCACCCCGCTGTTGTTCGCACAAGACCCACCATCCCCGGGCTGA<br>ACAACGCCAGGCTCCCTCCCAGCTCCCCCACCCTCTACACGGCTGTGCACCA<br>GAACGGGGGAGAGAACGACTACATCATCCCTCTTCCTGACCCCAAGCCTGA<br>TGCAATCTGTGACCTCCCTCAGGAGGCCTCCGTCAGCCGTGCCAGCTCTATG<br>CTGAATGAAGCCAACACATCATCTACAATATCCTGTGACAGCCCCCTGGGC<br>CCCCGGCAGGACGAGGAGCCAGAATGTGACCTGCAGCTGGGCTGCCAGGA<br>GCTGGCCCCGGGTCACCACGAGGTGGAGGAGAGCTTTCTGTAG |
| 112 | PDGFRb-<br>D850V | ATGCTCTGTCCCTCTCTGAAGGCATCTCTGCAGCTCCTCATCCTCACTGGTCT<br>GCTGGAGGTAACGTCTGGAGGCAGCGGGCTGCACATCGAACCTGAAGATGC<br>TGAGCTCGTCCTTAGGCTCCACAGCACTTTCTCCCTCGTGTGCTATGGGGAC<br>GGCACGCTGGTCTGGGAGCGGGATGGTCAGCCTCTCACTGCCGTGCTGGAG<br>CACAGGGACGGGGTCTTCATCAGCAACCTCACCCTCAGGAACGTGACAGGC<br>CGTCACACGGGGGAGTATGCGTGCTTCTACAGCCCTGACCAGGCTCCGGAG<br>CGAGCAGAGAGGAAAGCCCTTTACATCTATGTTCCAGATCCCTCCTTAGTTT<br>TTCTCCCCGCAATCACTTCTGAAGAGTTCTTCATCTTCATCACGGGCTACAC<br>AGAGGCCACCATCCCATGCCGTGTGACCAACCCAGAGCTGCAGGTGACCCT<br>CTATGAAAAGAAAGTGGAGAATCCCATTCCAGCTACTTATGACCCACAACA<br>GGGCTTCAAAGGCTTCTTTGAGGACAAGACCTACTACTGCCAGGCAATCGT<br>GGATGACCAAGAGGTGGATTCAGACACCTTCTATGTCTACCGGATCCAGGT |

9. SEQUENCE APPENDIX

| SEQ ID NO: | Description | Sequence |
|---|---|---|
|  |  | CTCATCTGTGAACGTCTCCATCAGCGCAGTGCAGACCGTAGTGCGGCAGGG |
|  |  | AGAAAATGTTACCCTGATGTGCACTGTCAGTGGCAATGAGCTGGTCAATTTC |
|  |  | AACTGGGATTATCCCCGCAAGCAGGCAGGGAAGGCTGTGGAGCCAGTGACC |
|  |  | GATTTCCTGCCTGGATCCACCCATGACATCCGTTCCATCCTCATCATCCAGA |
|  |  | ATGCAGAGCTAGAGGACAGTGGGACCTACGTCTGCAATGTCTCTGAGGGCT |
|  |  | ACCATGAGAAGACAGACCGGAAAGACATCACGGTCCAAGTGATCGAGCGT |
|  |  | GGCTTTGTACGCTTCCACACCCACCTGGCCAGCACGGTGTATGCTGAGGTCC |
|  |  | ACAAGAGCCACATCATCCAGGTGGATGTGGAGGCCTACCCACAGCCAAACA |
|  |  | TTGTGTGGCTGAAGAACAACAAGACATTGACCATGGAGAGCAGCAGCGAGT |
|  |  | TCACCATCACCAACAGGAACCTGTCAGAAACCAGGTATCAGACGTCTCTGG |
|  |  | TCCTGGTGCGTGTGAAGCAGGAGGAAGGAGGATATTACACCATCCGAGCTT |
|  |  | CCAATGAGGATGATGCACAAGAGCTGTCCTTCCATCTGCAGATAAATGTGC |
|  |  | CAGCCAAAGTGGTGGATCTCAAGGAAAACAGCAGTGCCAGCAGCGGGGAG |
|  |  | CAGACTGTAACGTGCTCTGCTGAAGGGATGCCCCAGCCAGAGATCAGTTGG |
|  |  | TCCACTTGCAGCAACATCAAATGGTGTGGCAGCCAGGGGCAACCCACCCAG |
|  |  | CTGCTGGGGAACAACTCTGCAGAGATTGGCCTGCACACTAATGCTACGTAC |
|  |  | CATGCAGAGCTGCAGGTGTACCGTGTGAACAGCACCCTGCAGCTGCACAGG |
|  |  | GTGGATGAACCCCTGCTTCTGAGATGCACCGTGCAAAACTTCCTGGGCTCCA |
|  |  | ACTCCCAAGACATCACTCTGGTCCCAAATGCCTTGCCATTCAAAGTGGTCAT |
|  |  | CATCTCCGTCATCCTGGCTCTGCTGGTCCTCACCGTCATCTCCCTGATCATCC |
|  |  | TGATCATCCTGTGGCAGAAGAAACCTCGCTATGAGATCCGCTGGAAGGTGA |
|  |  | TCGAGTCAGTGAGCTCCGATGGGCACGAGTACATCTACGTGGATCCCATGC |
|  |  | AGCTCCCTTATGACTCCAGCTGGGAGGTGCCCAGGGACAAGCTGGTGTTAG |
|  |  | GACGCACTCTTGGCTCCGGTGCCTTTGGACGCGTGGTGAGGCAACAGCGC |
|  |  | ATGGCCTGAGCCATTCACAGTCCACCATGAAAGTGGCAGTCAAGATGCTCA |
|  |  | AGTCCACTGCACGGAGCAGTGAGAAGCAAGCCCTCATGTCTGAGCTGAAGA |
|  |  | TCATGAGCCACCTGGGACCTCACCTCAACATCGTCAACTTGCTGGGGGGCCTG |
|  |  | CACCAAAGGAGGGCCCATCTATATCATCACCGAGTACTGCCGTTATGGGGA |
|  |  | CCTGGTGGACTACCTGCACCGCAACAAGCACACCTTCCTGCAGTCCTATGGC |
|  |  | GAGAAGGCCCGCGGGAGGCAGAGCTGTATGGGAATACCATCAAGGAGGA |
|  |  | CCACGTGCAGAGTCACCTCTCCTTGTCTGTCGAGAGTGATGGGGGCTACATG |
|  |  | GACATGAGCAAGGATGAGTCTCTGGATTACGTGCCCATGTCTGACATGAAG |
|  |  | GGTGAAGTCAAGTATGCTGACATCGAGTCTTCTAACTATGGCACCCCATATG |
|  |  | AGCTGGACAGCTATTCCCCATCAGCTCCGGAAAGAACAGACCGGGTGACAC |
|  |  | TGATAAATGAATCTCCACTCCTCAGCTACATGGACTTGGTGGGCTTCAGCTT |
|  |  | CCAGGTGGCCAATGGGATGGAGTTCCTGGCTTCCAAAAATTGTGTGCATCG |
|  |  | TGACCTGGCTGCCAGGAACGTCCTCATCTGCGAGGGGAAGCTGGTGAAGAT |
|  |  | CTGTGACTTTGGTCTGGCAAGAGACATCATGAGGAATTCCAACTACATCTCC |
|  |  | AAAGGCAGTACCTTCTTGCCCCTTAAGTGGATGGCCCCAGAGAGCATCTTC |
|  |  | AACAACCTCTACACCACCCTAAGTGATGTGTGGTCCTTTGGGATTCTTCTCT |
|  |  | GGGAGATATTCACTCTAGGAGGGACTCCCTACCCTGAACTGCCTATGAACG |
|  |  | AACAGTTCTACAATGCCATCAAACGTGGCTATCGGATGTCCAAACCTACCC |
|  |  | ATGCTTCTGATGAAATCTACGATATCATGCAGAAGTGCTGGGAGGAGAAGT |
|  |  | TTGAGATCAGACCGTCCTTCTCACAGCTGGTGGTGCTTATGGGAAACCTCTT |
|  |  | GGTGGACTGCTACAGAAAGAGGTACCAACAGGTAGATGAAGAGTTCATGA |
|  |  | AGAGCGACCACCCCGCTGTTGTTCGCACAAGACCCACCATCCCCGGGCTGA |
|  |  | ACAACGCCAGGCTCCCTCCCAGCTCCCCACCCTCTACACGGCTGTGCACCA |
|  |  | GAACGGGGGAGAGAACGACTACATCATCCCTCTTCCTGACCCCAAGCCTGA |
|  |  | TGCAATCTGTGACCTCCCTCAGGAGGCCTCCGTCAGCCGTGCCAGCTCTATG |
|  |  | CTGAATGAAGCCAACACATCATCTACAATATCCTGTGACAGCCCCCTGGGC |
|  |  | CCCCGGCAGGACGAGGAGCCAGAATGTGACCTGCAGCTGGGCTGCCAGGA |
|  |  | GCTGGCCCCGGGTCACCACGAGGTGGAGGAGAGCTTTCTGTAG |
| 113 | PDGFRb-V536A | ATGCTCTGTCCCTCTCTGAAGGCATCTCTGCAGCTCCTCATCCTCACTGGTCT |
|  |  | GCTGGAGGTAACGTCTGGAGGCAGCGGGCTGCACATCGAACCTGAAGATGC |
|  |  | TGAGCTCGTCCTTAGGCTCCACAGCACTTTCTCCCTCGTGTGCTATGGGGAC |
|  |  | GGCACGCTGGTCTGGGAGCGGGATGGTCAGCCTCTCACTGCCGTGCTGGAG |
|  |  | CACAGGGACGGGGTCTTCATCAGCAACCTCACCCTCAGGAACGTGACAGGC |
|  |  | CGTCACACGGGGGAGTATGCGTGCTTCTACAGCCCTGACCAGGCTCCGGAG |
|  |  | CGAGCAGAGAGGAAAGCCCTTTACATCTATGTTCCAGATCCCTCCTTAGTTT |
|  |  | TTCTCCCCGCAATCACTTCTGAAGAGTTCTTCATCTTCATCACGGGCTACAC |
|  |  | AGAGGCCACCATCCCATGCCGTGTGACCAACCCAGAGCTGCAGGTGACCCT |
|  |  | CTATGAAAAGAAAGTGGAGAATCCCATTCCAGCTACTTATGACCCACAACA |
|  |  | GGGCTTCAAAGGCTTCTTTGAGGACAAGACCTACTACTGCCAGGCAATCGT |
|  |  | GGATGACCAAGAGGTGGATTCAGACACCTTCTATGTCTACCGGATCCAGGT |
|  |  | CTCATCTGTGAACGTCTCCATCAGCGCAGTGCAGACCGTAGTGCGGCAGGG |
|  |  | AGAAAATGTTACCCTGATGTGCACTGTCAGTGGCAATGAGCTGGTCAATTTC |
|  |  | AACTGGGATTATCCCCGCAAGCAGGCAGGGAAGGCTGTGGAGCCAGTGACC |
|  |  | GATTTCCTGCCTGGATCCACCCATGACATCCGTTCCATCCTCATCATCCAGA |
|  |  | ATGCAGAGCTAGAGGACAGTGGGACCTACGTCTGCAATGTCTCTGAGGGCT |
|  |  | ACCATGAGAAGACAGACCGGAAAGACATCACGGTCCAAGTGATCGAGCGT |
|  |  | GGCTTTGTACGCTTCCACACCCACCTGGCCAGCACGGTGTATGCTGAGGTCC |
|  |  | ACAAGAGCCACATCATCCAGGTGGATGTGGAGGCCTACCCACAGCCAAACA |

9. SEQUENCE APPENDIX

| SEQ ID NO: | Description | Sequence |
|---|---|---|
| | | TTGTGTGGCTGAAGAACAACAAGACATTGACCATGGAGAGCAGCAGCGAGT<br>TCACCATCACCAACAGGAACCTGTCAGAAACCAGGTATCAGACGTCTCTGG<br>TCCTGGTGCGTGTGAAGCAGGAGGAAGGAGGATATTACACCATCCGAGCTT<br>CCAATGAGGATGATGCACAAGAGCTGTCCTTCCATCTGCAGATAAATGTGC<br>CAGCCAAAGTGGTGGATCTCAAGGAAAACAGCAGTGCCAGCAGCGGGGAG<br>CAGACTGTAACGTGCTCTGCTGAAGGGATGCCCCAGCCAGAGATCAGTTGG<br>TCCACTTGCAGCAACATCAAATGGTGTGGCAGCCAGGGGCAACCCACCCAG<br>CTGCTGGGGAACAACTCTGCAGAGATTGGCCTGCACACTAATGCTACGTAC<br>CATGCAGAGCTGCAGGTGTACCGTGTGAACAGCACCCTGCAGCTGCACAGG<br>GTGGATGAACCCCTGCTTCTGAGATGCACCGTGCAAAACTTCCTGGGCTCCA<br>ACTCCCAAGACATCACTCTGGTCCCAAATGCCTTGCCATTCAAAGTGGTCAT<br>CATCTCCGTCATCCTGGCTCTGCTGGTCCTCACCGTCATCTCCCTGATCATCC<br>TGATCATCCTGTGGCAGAAGAAACCTCGCTATGAGATCCGCTGGAAGGCCA<br>TCGAGTCAGTGAGCTCCGATGGGCACGAGTACATCTACGTGGATCCCATGC<br>AGCTCCCTTATGACTCCAGCTGGGAGGTGCCCAGGGACAAGCTGGTGTTAG<br>GACGCACTCTTGGCTCCGGTGCCTTTGGACGCGTGGTGGAGGCAACAGCGC<br>ATGGCCTGAGCCATTCACAGTCCACCATGAAAGTGGCAGTCAAGATGCTCA<br>AGTCCACTGCACGGAGCAGTGAGAAGCAAGCCCTCATGTCTGAGCTGAAGA<br>TCATGAGCCACCTGGGACCTCACCTCAACATCGTCAACTTGCTGGGGGCCTG<br>CACCAAAGGAGGGCCCATCTATATCATCACCGAGTACTGCCGTTATGGGGA<br>CCTGGTGGACTACCTGCACCGCAACAAGCACACCTTCCTGCAGTCCTATGGC<br>GAGAAGGCCCGCCGGGAGGCAGAGCTGTATGGGAATACCATCAAGGAGGA<br>CCACGTGCAGAGTCACCTCTCCTTGTCTGTCGAGAGTGATGGGGGCTACATG<br>GACATGAGCAAGGATGAGTCTCTGGATTACGTGCCCATGTCTGACATGAAG<br>GGTGAAGTCAAGTATGCTGACATCGAGTCTTCTAACTATGGCACCCCATATG<br>AGCTGGACAGCTATTCCCCATCAGCTCCGGAAAGAACAGACCGGGTGACAC<br>TGATAAATGAATCTCCACTCCTCAGCTACATGGACTTGGTGGGCTTCAGCTT<br>CCAGGTGGCCAATGGGATGGAGTTCCTGGCTTCCAAAAATTGTGTGCATCG<br>TGACCTGGCTGCCAGGAACGTCCTCATCTGCGAGGGGAAGCTGGTGAAGAT<br>CTGTGACTTTGGTCTGGCAAGAGACATCATGAGGGATTCCAACTACATCTCC<br>AAAGGCAGTACCTTCTTGCCCCTTAAGTGGATGGCCCCAGAGAGCATCTTC<br>AACAACCTCTACACCACCCTAAGTGATGTGTGGTCCTTTGGGATTCTTCTCT<br>GGGAGATATTCACTCTAGGAGGGACTCCCTACCCTGAACTGCCTATGAACG<br>AACAGTTCTACAATGCCATCAAACGTGGCTATCGGATGTCCAAACCTACCC<br>ATGCTTCTGATGAAATCTACGATATCATGCAGAAGTGCTGGGAGGAGAAGT<br>TTGAGATCAGACCGTCCTTCTCACAGCTGGTGGTGCTTATGGGAAACCTCTT<br>GGTGGACTGCTACAGAAAGAGGTACCAACAGGTAGATGAAGAGTTCATGA<br>AGAGCGACCACCCCGCTGTTGTTCGCACAAGACCCACCATCCCCGGGCTGA<br>ACAACGCCAGGCTCCCTCCCAGCTCCCCCACCCTCTACACGGCTGTGCACCA<br>GAACGGGGGAGAGAACGACTACATCATCCCTCTTCCTGACCCCAAGCCTGA<br>TGCAATCTGTGACCTCCCTCAGGAGGCCTCCGTCAGCCGTGCCAGCTCTATG<br>CTGAATGAAGCCAACACATCATCTACAATATCCTGTGACAGCCCCCTGGGC<br>CCCCGGCAGGACGAGGAGCCAGAATGTGACCTGCAGCTGGGCTGCCAGGA<br>GCTGGCCCCGGGTCACCACGAGGTGGAGGAGAGCTTTCTGTAG |
| 114 | 9C3-PDGFRb | ATGGCGAAAGGTGGCATAATCGTCGCGATCCTTCTCCTTATCGTTATGCTTG<br>CTATAGAGATATTGCTTTTGATAACTCTTATCATTGCTGTAACGTCTGGAGG<br>CAGCGGGCTGCACATCGAACCTGAAGATGCTGAGCTCGTCCTTAGGCTCCA<br>CAGCACTTTCTCCCTCGTGTGCTATGGGGACGGCACGCTGGTCTGGGAGCG<br>GGATGGTCAGCCTCTCACTGCCGTGCTGGAGCACAGGGACGGGGTCTTCAT<br>CAGCAACCTCACCCTCAGGAACGTGACAGGCCGTCACACGGGGGAGTATGC<br>GTGCTTCTACAGCCCTGACCAGGCTCCGGAGCGAGCAGAGAGGAAAGCCCT<br>TTACATCTATGTTCCAGATCCCTCCTTAGTTTTTCTCCCCGCAATCACTTCTG<br>AAGAGTTCTTCATCTTCATCACGGGCTACACAGAGGCCACCATCCCATGCCG<br>TGTGACCAACCCAGAGCTGCAGGTGACCCTCTATGAAAAGAAAGTGGAGAA<br>TCCCATTCCAGCTACTTATGACCCACAACAGGGCTTCAAAGGCTTCTTTGAG<br>GACAAGACCTACTACTGCCAGGCAATCGTGGATGACCAAGAGGTGGATTCA<br>GACACCTTCTATGTCTACCGGATCCAGGTCTCATCTGTGAACGTCTCCATCA<br>GCGCAGTGCAGACCGTAGTGCGGCAGGGAGAAAATGTTACCCTGATGTGCA<br>CTGTCAGTGGCAATGAGCTGGTCAATTTCAACTGGGATTATCCCCGCAAGC<br>AGGCAGGGAAGGCTGTGGAGCCAGTGACCGATTTCCTGCCTGGATCCACCC<br>ATGACATCCGTTCCATCCTCATCATCCAGAATGCAGAGCTAGAGGACAGTG<br>GGACCTACGTCTGCAATGTCTCTGAGGGCTACCATGAGAAGACAGACCGGA<br>AAGACATCACGGTCCAAGTGATCGAGCGTGGCTTTGTACGCTTCCACACCC<br>ACCTGGCCAGCACGGTGTATGCTGAGGTCCACAAGAGCCACATCATCCAGG<br>TGGATGTGGAGGCCTACCCACAGCCAAACATTGTGTGGCTGAAGAACAACA<br>AGACATTGACCATGGAGAGCAGCAGCGAGTTCACCATCACCAACAGGAACC<br>TGTCAGAAACCAGGTATCAGACGTCTCTGGTCCTGGTGCGTGTGAAGCAGG<br>AGGAAGGAGGATATTACACCATCCGAGCTTCCAATGAGGATGATGCACAAG<br>AGCTGTCCTTCCATCTGCAGATAAATGTGCCAGCCAAAGTGGTGGATCTCA<br>AGGAAAACAGCAGTGCCAGCAGCGGGGAGCAGACTGTAACGTGCTCTGCT<br>GAAGGGATGCCCCAGCCAGAGATCAGTTGGTCCACTTGCAGCAACATCAAA<br>TGGTGTGGCAGCCAGGGGCAACCCACCCAGCTGCTGGGGAACAACTCTGCA |

9. SEQUENCE APPENDIX

| SEQ ID NO: | Description | Sequence |
|---|---|---|
|  |  | GAGATTGGCCTGCACACTAATGCTACGTACCATGCAGAGCTGCAGGTGTAC |
|  |  | CGTGTGAACAGCACCCTGCAGCTGCACAGGGTGGATGAACCCCTGCTTCTG |
|  |  | AGATGCACCGTGCAAAACTTCCTGGGCTCCAACTCCCAAGACATCACTCTG |
|  |  | GTCCCAAATGCCTTGCCATTCAAAGTGGTCATCATCTCCGTCATCCTGGCTC |
|  |  | TGCTGGTCCTCACCGTCATCTCCCTGATCATCCTGATCATCCTGTGGCAGAA |
|  |  | GAAACCTCGCTATGAGATCCGCTGGAAGGTGATCGAGTCAGTGAGCTCCGA |
|  |  | TGGGCACGAGTACATCTACGTGGATCCCATGCAGCTCCCTTATGACTCCAGC |
|  |  | TGGGAGGTGCCCAGGGACAAGCTGGTGTTAGGACGCACTCTTGGCTCCGGT |
|  |  | GCCTTTGGACGCGTGGTGGAGGCAACAGCGCATGGCCTGAGCCATTCACAG |
|  |  | TCCACCATGAAAGTGGCAGTCAAGATGCTCAAGTCCACTGCACGGAGCAGT |
|  |  | GAGAAGCAAGCCCTCATGTCTGAGCTGAAGATCATGAGCCACCTGGGACCT |
|  |  | CACCTCAACATCGTCAACTTGCTGGGGGCCTGCACCAAAGGAGGGCCCATC |
|  |  | TATATCATCACCGAGTACTGCCGTTATGGGGACCTGGTGGACTACCTGCACC |
|  |  | GCAACAAGCACACCTTCCTGCAGTCCTATGGCGAGAAGGCCCGCCGGGAGG |
|  |  | CAGAGCTGTATGGGAATACCATCAAGGAGGACCACGTGCAGAGTCACCTCT |
|  |  | CCTTGTCTGTCGAGAGTGATGGGGGCTACATGGACATGAGCAAGGATGAGT |
|  |  | CTCTGGATTACGTGCCCATGTCTGACATGAAGGGTGAAGTCAAGTATGCTG |
|  |  | ACATCGAGTCTTCTAACTATGGCACCCCATATGAGCTGGACAGCTATTCCCC |
|  |  | ATCAGCTCCGGAAAGAACAGACCGGGTGACACTGATAAATGAATCTCCACT |
|  |  | CCTCAGCTACATGGACTTGGTGGGCTTCAGCTTCCAGGTGGCCAATGGGAT |
|  |  | GGAGTTCCTGGCTTCCAAAAATTGTGTGCATCGTGACCTGGCTGCCAGGAA |
|  |  | CGTCCTCATCTGCGAGGGGAAGCTGGTGAAGATCTGTGACTTTGGTCTGGC |
|  |  | AAGAGACATCATGAGGGATTCCAACTACATCTCCAAAGGCAGTACCTTCTT |
|  |  | GCCCCTTAAGTGGATGGCCCCAGAGAGCATCTTCAACAACCTCTACACCAC |
|  |  | CCTAAGTGATGTGTGGTCCTTTGGGATTCTTCTCTGGGAGATATTCACTCTA |
|  |  | GGAGGGACTCCCTACCCTGAACTGCCTATGAACGAACAGTTCTACAATGCC |
|  |  | ATCAAACGTGGCTATCGGATGTCCAAACCTACCCATGCTTCTGATGAAATCT |
|  |  | ACGATATCATGCAGAAGTGCTGGGAGGAGAAGTTTGAGATCAGACCGTCCT |
|  |  | TCTCACAGCTGGTGGTGCTTATGGGAAACCTCTTGGTGGACTGCTACAGAA |
|  |  | AGAGGTACCAACAGGTAGATGAAGAGTTCATGAAGAGCGACCACCCCGCT |
|  |  | GTTGTTCGCACAAGACCCACCATCCCCGGGCTGAACAACGCCAGGCTCCCT |
|  |  | CCCAGCTCCCCCACCCTCTACACGGCTGTGCACCAGAACGGGGGAGAGAAC |
|  |  | GACTACATCATCCCTCTTCCTGACCCCAAGCCTGATGCAATCTGTGACCTCC |
|  |  | CTCAGGAGGCCTCCGTCAGCCGTGCCAGCTCTATGCTGAATGAAGCCAACA |
|  |  | CATCATCTACAATATCCTGTGACAGCCCCCTGGGCCCCCGGCAGGACGAGG |
|  |  | AGCCAGAATGTGACCTGCAGCTGGGCTGCCAGGAGCTGGCCCCGGGTCACC |
|  |  | ACGAGGTGGAGGAGAGCTTTCTGTAG |
| 115 | (F)-9C3-PDGFRb | ATGGCGGATTACAAGGATGATGATGACAAAAAAGGTGGCATAATCGTCGCG |
|  |  | ATCCTTCTCCTTATCGTTATGCTTGCTATAGAGATATTGCTTTTGATAACTCT |
|  |  | TATCATTGCTGTAACGTCTGGAGGCAGCGGGCTGCACATCGAACCTGAAGA |
|  |  | TGCTGAGCTCGTCCTTAGGCTCCACAGCACTTTCTCCCTCGTGTGCTATGGG |
|  |  | GACGGCACGCTGGTCTGGGAGCGGGATGGTCAGCCTCTCACTGCCGTGCTG |
|  |  | GAGCACAGGGACGGGGTCTTCATCAGCAACCTCACCCTCAGGAACGTGACA |
|  |  | GGCCGTCACACGGGGGAGTATGCGTGCTTCTACAGCCCTGACCAGGCTCCG |
|  |  | GAGCGAGCAGAGAGGAAAGCCCTTTACATCTATGTTCCAGATCCCTCCTTA |
|  |  | GTTTTTCTCCCCGCAATCACTTCTGAAGAGTTCTTCATCTTCATCACGGGCTA |
|  |  | CACAGAGGCCACCATCCCATGCCGTGTGACCAACCCAGAGCTGCAGGTGAC |
|  |  | CCTCTATGAAAGAAAGTGGAGAATCCCATTCCAGCTACTTATGACCCACA |
|  |  | ACAGGGCTTCAAAGGCTTCTTTGAGGACAAGACCTACTACTGCCAGGCAAT |
|  |  | CGTGGATGACCAAGAGGTGGATTCAGACACCTTCTATGTCTACCGGATCCA |
|  |  | GGTCTCATCTGTGAACGTCTCCATCAGCGCAGTGCAGACCGTAGTGCGGCA |
|  |  | GGGAGAAAATGTTACCCTGATGTGCACTGTCAGTGGCAATGAGCTGGTCAA |
|  |  | TTTCAACTGGGATTATCCCCGCAAGCAGGCAGGGAAGGCTGTGGAGCCAGT |
|  |  | GACCGATTTCCTGCCTGGATCCACCCATGACATCCGTTCCATCCTCATCATC |
|  |  | CAGAATGCAGAGCTAGAGGACAGTGGGACCTACGTCTGCAATGTCTCTGAG |
|  |  | GGCTACCATGAGAAGACAGACCGGAAAGACATCACGGTCCAAGTGATCGA |
|  |  | GCGTGGCTTTGTACGCTTCCACACCCACCTGGCCAGCACGGTGTATGCTGAG |
|  |  | GTCCACAAGAGCCACATCATCCAGGTGGATGTGGAGGCCTACCCACAGCCA |
|  |  | AACATTGTGTGGCTGAAGAACAACAAGACATTGACCATGGAGAGCAGCAG |
|  |  | CGAGTTCACCATCACCAACAGGAACCTGTCAGAAACCAGGTATCAGACGTC |
|  |  | TCTGGTCCTGGTGCGTGTGAAGCAGGAGGAAGGAGGATATTACACCATCCG |
|  |  | AGCTTCCAATGAGGATGATGCACAAGAGCTGTCCTTCCATCTGCAGATAAA |
|  |  | TGTGCCAGCCAAAGTGGTGGATCTCAAGGAAAACAGCAGTGCCAGCAGCG |
|  |  | GGGAGCAGACTGTAACGTGCTCTGCTGAAGGGATGCCCCAGCCAGAGATCA |
|  |  | GTTGGTCCACTTGCAGCAACATCAAATGGTGTGGCAGCCAGGGGCAACCCA |
|  |  | CCCAGCTGCTGGGGAACAACTCTGCAGAGATTGGCCTGCACACTAATGCTA |
|  |  | CGTACCATGCAGAGCTGCAGGTGTACCGTGTGAACAGCACCCTGCAGCTGC |
|  |  | ACAGGGTGGATGAACCCCTGCTTCTGAGATGCACCGTGCAAAACTTCCTGG |
|  |  | GCTCCAACTCCCAAGACATCACTCTGGTCCCAAATGCCTTGCCATTCAAAGT |
|  |  | GGTCATCATCTCCGTCATCCTGGCTCTGCTGGTCCTCACCGTCATCTCCCTGA |
|  |  | TCATCCTGATCATCCTGTGGCAGAAGAAACCTCGCTATGAGATCCGCTGGA |
|  |  | AGGTGATCGAGTCAGTGAGCTCCGATGGGCACGAGTACATCTACGTGGATC |

-continued

---

9. SEQUENCE APPENDIX

---

| SEQ ID NO: | Description | Sequence |
|---|---|---|
| | | CCATGCAGCTCCCTTATGACTCCAGCTGGGAGGTGCCCAGGGACAAGCTGG<br>TGTTAGGACGCACTCTTGGCTCCGGTGCCTTTGGACGCGTGGTGGAGGCAA<br>CAGCGCATGGCCTGAGCCATTCACAGTCCACCATGAAAGTGGCAGTCAAGA<br>TGCTCAAGTCCACTGCACGGAGCAGTGAGAAGCAAGCCCTCATGTCTGAGC<br>TGAAGATCATGAGCCACCTGGGACCTCACCTCAACATCGTCAACTTGCTGG<br>GGGCCTGCACCAAAGGAGGGCCCATCTATATCATCACCGAGTACTGCCGTT<br>ATGGGGACCTGGTGGACTACCTGCACCGCAACAAGCACACCTTCCTGCAGT<br>CCTATGGCGAGAAGGCCCGCCGGGAGGCAGAGCTGTATGGGAATACCATCA<br>AGGAGGACCACGTGCAGAGTCACCTCTCCTTGTCTGTCGAGAGTGATGGGG<br>GCTACATGGACATGAGCAAGGATGAGTCTCTGGATTACGTGCCCATGTCTG<br>ACATGAAGGGTGAAGTCAAGTATGCTGACATCGAGTCTTCTAACTATGGCA<br>CCCCATATGAGCTGGACAGCTATTCCCCATCAGCTCCGGAAAGAACAGACC<br>GGGTGACACTGATAAATGAATCTCCACTCCTCAGCTACATGGACTTGGTGG<br>GCTTCAGCTTCCAGGTGGCCAATGGGATGGAGTTCCTGGCTTCCAAAAATTG<br>TGTGCATCGTGACCTGGCTGCCAGGAACGTCCTCATCTGCGAGGGGAAGCT<br>GGTGAAGATCTGTGACTTTGGTCTGGCAAGAGACATCATGAGGGATTCCAA<br>CTACATCTCCAAAGGCAGTACCTTCTTGCCCCTTAAGTGGATGGCCCCAGAG<br>AGCATCTTCAACAACCTCTACACCACCCTAAGTGATGTGTGGTCCTTTGGGA<br>TTCTTCTCTGGGAGATATTCACTCTAGGAGGGACTCCCTACCCTGAACTGCC<br>TATGAACGAACAGTTCTACAATGCCATCAAACGTGGCTATCGGATGTCCAA<br>ACCTACCCATGCTTCTGATGAAATCTACGATATCATGCAGAAGTGCTGGGA<br>GGAGAAGTTTGAGATCAGACCGTCCTTCTCACAGCTGGTGGTGCTTATGGG<br>AAACCTCTTGGTGGACTGCTACAGAAAGAGGTACCAACAGGTAGATGAAGA<br>GTTCATGAAGAGCGACCACCCCGCTGTTGTTCGCACAAGACCCACCATCCC<br>CGGGCTGAACAACGCCAGGCTCCCTCCCAGCTCCCCCACCCTCTACACGGCT<br>GTGCACCAGAACGGGGGAGAGAACGACTACATCATCCCTCTTCCTGACCCC<br>AAGCCTGATGCAATCTGTGACCTCCCTCAGGAGGCCTCCGTCAGCCGTGCC<br>AGCTCTATGCTGAATGAAGCCAACACATCATCTACAATATCCTGTGACAGC<br>CCCCTGGGCCCCCGGCAGGACGAGGAGCCAGAATGTGACCTGCAGCTGGGC<br>TGCCAGGAGCTGGCCCCGGGTCACCACGAGGTGGAGGAGAGCTTTCTGTAG |
| 116 | PDGF(WT) | ATGTGCCCGCAGCCGGCAAGGCTTGAACCCGGCATGAATTTCGGCGTGGTC<br>TTCGCCGTCATCCTCTCCCTGCCCCTGGCCCGCCTGGAGGGGGGACCCCATAC<br>CCGAAGATATTTATGAGATTTTGGGTGGCAGCTCCGTGCGCTCCATCAGTGA<br>CCTCCAGCGTGCCCTGCGGATAGACTCCGTAGAGGAGGACAGCTCTAGCCT<br>GGACCTGAATGCAACTCAGCCCAGCCAAAACCATGTGTCCCTGTCTCGAGA<br>GAGGCGAAGCCTTGATGCTCTGGCAGCAGCAGAGCCAGCTGTCCTCGCCGA<br>GTGCAAGACACGGACGGTGGTCTTTGAGATCTCCCGTGACATGGTGGACAG<br>CACCAATGCCAACTTCGTGGTGTGGCCACCCTGCGTGGAGGTGCAGCGGTG<br>CTCCGGCTGCTGCAACAACCGCAACGTGCAGTGCCGCCCCATGCAGATTCG<br>CGTCCGGCATGTCCAGGTGAACAAGATTGAGTTTTTCCAGAGGAAGCCAAT<br>ATTCAAAAAAGTCATCGTGCCTTTGGAGGACCACGTGCAGTGCCGGTGCGA<br>AGTGGTGTCCCGGCCGCCACCCAGGAGCAACCGACCGGCATCCCGTGAGCA<br>GAGACGCTTCTCGCCGTCATTCACCACAGCCGCCATCTCCCAGAGGAAGCG<br>GGTACGCCGGCCGCCAGCACAGAAGAGAAAACACAAGAAATACAAGCATG<br>TCAACGATAAGAAAGTGCTGAAAGAAATCCTCATAGCATAG |
| 117 | PDGF-211* | ATGTGCCCGCAGCCGGCAAGGCTTGAACCCGGCATGAATTTCGGCGTGGTC<br>TTCGCCGTCATCCTCTCCCTGCCCCTGGCCCGCCTGGAGGGGGGACCCCATAC<br>CCGAAGATATTTATGAGATTTTGGGTGGCAGCTCCGTGCGCTCCATCAGTGA<br>CCTCCAGCGTGCCCTGCGGATAGACTCCGTAGAGGAGGACAGCTCTAGCCT<br>GGACCTGAATGCAACTCAGCCCAGCCAAAACCATGTGTCCCTGTCTCGAGA<br>GAGGCGAAGCCTTGATGCTCTGGCAGCAGCAGAGCCAGCTGTCCTCGCCGA<br>GTGCAAGACACGGACGGTGGTCTTTGAGATCTCCCGTGACATGGTGGACAG<br>CACCAATGCCAACTTCGTGGTGTGGCCACCCTGCGTGGAGGTGCAGCGGTG<br>CTCCGGCTGCTGCAACAACCGCAACGTGCAGTGCCGCCCCATGCAGATTCG<br>CGTCCGGCATGTCCAGGTGAACAAGATTGAGTTTTTCCAGAGGAAGCCAAT<br>ATTCAAAAAAGTCATCGTGCCTTTGGAGGACCACGTGCAGTGCCGGTGCGA<br>AGTGGTGTCCCGGCCGCCACCCAGGAGCAACCGACCGGCATCCCGTGAGCA<br>GAGACGCTTCTCGCCGTCATTCACCACAGCCGCCATCTCCCAGTAG |
| 118 | 9C3-SRG | ATGGCGAAAGGTGGCATAATCGTCGCGATCCTTCTCCTTATCGTTATGCTTG<br>CTATAGAGATATTGCTTTTGATAACTCTTATCATTGCTGTAACGTCTGGAGG<br>CAGCGGGTAG |
| 119 | (F)9C3-SRG | ATGGCGGATTACAAGGATGATGATGACAAAAAAGGTGGCATAATCGTCGCG<br>ATCCTTCTCCTTATCGTTATGCTTGCTATAGAGATATTGCTTTTGATAACTCT<br>TATCATTGCTGTAACGTCTGGAGGCAGCGGGTAG |
| 120 | FC551A-empty vector | GCCCCTGCAGCCGAATTATATTATTTTTGCCAAATAATTTTTAACAAAAGCT<br>CTGAAGTCTTCTTCATTTAAATTCTTAGATGATACTTCATCTGGAAAATTGTC<br>CCAATTAGTAGCATCACGCTGTGAGTAAGTTCTAAACCATTTTTTTATTGTT<br>GTATTATCTCTAATCTTACTACTCGATGAGTTTTCGGTATTATCTCTATTTTT |

9. SEQUENCE APPENDIX

| SEQ ID NO: | Description | Sequence |
|---|---|---|

AACTTGGAGCAGGTTCCATTCATTGTTTTTTTCATCATAGTGAATAAAATCA
ACTGCTTTAACACTTGTGCCTGAACACCATATCCATCCGGCGTAATACGACT
CACTATAGGGAGAGCGGCCGCGTCGACATGCCCGCCGTGACCGTCGAGAAC
CCGCTGACGCTGCCCCGCGTATCCGCACCCGCCGACGCCGTCGCACGTCCC
GTGCTCACCGTGACCACCGCGCCCAGCGGTTTCGAGGGCGAGGGCTTCCCG
GTGCGCCGCGCGTTCGCCGGGATCAACTACCGCCACCTCGACCCGTTCATCA
TGATGGACCAGATGGGTGAGGTGGAGTACGCGCCCGGGGAGCCCAAGGGC
ACGCCCTGGCACCCGCACCGCGGCTTCGAGACCGTGACCTACATCGTCGAC
GCGGCCGCCAGATCTTCCGGATGGCTCGAGTTTTTCAGCAAGATATGATAA
GATACATTGATGAGTTTGGACAAACCACAACTAGAATGCAGTGAAAAAAAT
GCTTTATTTGTGAAATTTGTGATGCTATTGCTTTATTTGTAACCATTATAAGC
TGCAATAAACAAGTTTAGTTAACGCATGATACAAAGGCATTAAAGCAGCGT
ATCCACATAGCGTAAAAGGAGCAACATAGTTAAGAATACCAGTCAATCTTT
CACAAATTTTGTAATCCAGAGGTTGATTTCAGGCACCGGGCTTGCGGGTCAT
GCACCAGGTGCGCGGTCCTTCGGGCACCTCGACGTCGGCGGTGACGGTGAA
GCCGAGCCGCTCGTAGAAGGGGAGGTTGCGGGGCGCGGAGGTCTCCAGGA
AGGCGGGCACCCCGGCGCGCTCGGCCGCCTCCACTCCGGGGAGCACGACGG
CGCTGCCCAGACCCTTGCCCTGGTGGTCGGGCGAGACGCCGACGGTGGCCA
GGAACCACGCGGGCTCCTTGGGCCGGTGCGGCGCCAGGAGGCCTTCCATCT
GTTGCTGCGCGGCCAGCCGGGAACCGCTCAACTCGGCCATGCGCGGGCCGA
TCTCGGCGAACACCGCCCCCGCTTCGACGCTCTCCGGCGTGGTCCAGACCGC
CACCGCGGCGCCGTCGTCCGCGACCCACACCTTGCCGATGTCGAGCCCGAC
GCGCGTGAGGAAGAGTTCTTGCAGCTCGGTGACCCGCTCGATGTGGCGGTC
CGGATCGACGGTGTGGCGCGTGGCGGGGTAGTCGGCGAACGCGGCGGCGA
GGGTGCGTACGGCCCTGGGGACGTCGTCGCGGGTGGCGAGGCGCACCGTGG
GCTTGTACTCGGTCATAGGGCCGGGATTCTCCTCCACGTCACCGCATGTTAG
AAGACTTCCTCTGCCCTCGCGAGATCCGGTGGAGCCGGGTCCGGCGGTGCC
GTCCACGGCAGAATTGGACGACTGAGCGCGGGATCTGGCGAAGGCGATGG
GGGTCTTGAAGGCGTGCTGGTACTCCACGATGCCCAGCTCGGTGTTGCTGTG
CAGCTCCTCCACGCGGCGGAAGGCGAACATGGGGCCCCCGTTCTGCAGGAT
GCTGGGGTGGATGGCGCTCTTGAAGTGCATGTGGCTGTCCACCACGAAGCT
GTAGTAGCCGCCGTCGCGCAGGCTGAAGGTGCGGGCGAAGCTGCCCACCAG
CACGTTATCGCCCATGGGGTGCAGGTGCTCCACGGTGGCGTTGCTGCGGAT
GATCTTGTCGGTGAAGATCACGCTGTCCTCGGGGAAGCCGGTGCCCACCAC
CTTGAAGTCGCCGATCACGCGGCCGGCCTCGTAGCGGTAGCTGAAGCTCAC
GTGCAGCACGCCGCCGTCCTCGTACTTCTCGATGCGGGTGTTGGTGTAGCCG
CCGTTGTTGATGGCGTGCAGGAAGGGGTTCTCGTAGCCGCTGGGGTAGGTG
CCGAAGTGGTAGAAGCCGTAGCCCATCACGTGGCTCAGCAGGTAGGGGCTG
AAGGTCAGGGCGCCTTTGGTGCTCTTCATCTTGTTGGTCATGCGGCCCTGCT
TGGGGGGTGCCCTCTCCGCCGCCCACCAGCTCGAACTCCACGCCGTTCAGGGT
GCCGGTGATGCGGCACTCGATCTCCATGGCGGGCAGGCCGCTCTCGTCGCT
CTCCATGGTGGCGTCTAGCGTAGGCGCCGGTCACAGCTTGGATCTGTAACG
GCGCAGAACAGAAAACGAAACAAAGACGTAGAGTTGAGCAAGCAGGGTCA
GGCAAAGCGTGGAGAGCCGGCTGAGTCTAGGTAGGCTCCAAGGGAGCGCC
GGACAAAGGCCCGGTCTCGACCTGAGCTTTAAACTTACCTAGACGGCGGAC
GCAGTTCAGGAGGCACCACAGGCGGGAGGCGGCAGAACGCGACTCAACCG
GCGTGGATGGCGGCCTCAGGTAGGGCGGCGGGCGCGTGAAGGAGAGATGC
GAGCCCCTCGAAGCTTCAGCTGTGTTCTGGCGGCAAACCCGTTGCGAAAAA
GAACGTTCACGGCGACTACTGCACTTATATACGGTTCTCCCCCACCCTCGGG
AAAAAGGCGGAGCCAGTACACGACATCACTTTCCCAGTTTACCCCGCGCCA
CCTTCTCTAGGCACCCGTTCAATTGCCGACCCCTCCCCCCAACTTCTCGGGG
ACTGTGGGCGATGTGCGCTCTGCCCACTGACGGGCACCGGAGCGATCGCAG
ATCCTTATCTTTCTAGAAATTCTACCGGGTAGGGGAGGCGCTTTTCCCAAGG
CAGTCTGGAGCATGCGCTTTAGCAGCCCCGCTGGCACTTGGCGCTACACAA
GTGGCCTCTGGCCTCGCACACATTCCACATCCACCGGTAGCGCCAACCGGCT
CCGTTCTTTGGTGGCCCCTTCGCGCCACCTTCTACTCCTCCCCTAGTCAGGA
AGTTCCCCCCCGCCCCGCAGCTCGCGTCGTGCAGGACGTGACAAATGGAAG
TAGCACGTCTCACTAGTCTCGTGCAGATGGACAGCACCGCTGAGCAATGGA
AGCGGGTAGGCCTTTGGGGCAGCGGCCAATAGCAGCTTTGCTCCTTCGCTTT
CTGGGCTCAGCAGCTGGGAAGGGTGGGTCCGGGGGCGGGCTCAGGGGCGG
GCTCAGGGGCGGGGGGGCGCCCGAAGGTCCTCCGGAGGCCCGGCATTCTG
CACGCTTCAAAAGCGCACGTCTGCCGCGCTGTTCTCCTCTTCCTCATCTCCG
GGCCTTTCGACCTGGATCCGATATCGGTACCGCTAGCATCGATCAGACATG
ATAAGATACATTGATGAGTTTGGACAAACCACAACTAGAATGCAGTGAAAA
AAATGCTTTATTTGTGAAATTTGTGATGCTATTGCTTTATTTGTAACCATTAT
AAGCTGCAATAAACAAGTTAACAACAACAATTGCATTCATTTTATGTTTCAG
GTTCAGGGGGAGGTGTGGGAGGTTTTTTGTTTAAACCTCCTGTGTGAAATTA
TTATCCGCTCATAATTCCACACATTATACGAGCCGGAAGCATAAAGTGTAA
AGCCTGGGGTGCCTAATGAGTGAGCTAACTCACATTAATTGCGTTGCGCTCA
CTGCCAATTGCTTTCCAGTCGGGAAACCTGTCGTGCCAGCTGCATTAATGAA
TCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGC

9. SEQUENCE APPENDIX

| SEQ ID NO: | Description | Sequence |
|---|---|---|
| | | AGGAAAGAACATGTGAGCAAAAGGCCAGCAAAAGGCCAGGAACCGTAAAA<br>AGGCCGCGTTGCTGGCGTTTTTCCATAGGCTCCGCCCCCCTGACGAGCATCA<br>CAAAAATCGACGCTCAAGTCAGAGGTGGCGAAACCCGACAGGACTATAAA<br>GATACCAGGCGTTTCCCCCTGGAAGCTCCCTCGTGCGCTCTCCTGTTCCGAC<br>CCTGCCGCTTACCGGATACCTGTCCGCCTTTCTCCCTTCGGGAAGCGTGGCG<br>CTTTCTCATAGCTCACGCTGTAGGTATCTCAGTTCGGTGTAGGTCGTTCGCT<br>CCAAGCTGGGCTGTGTGCACGAACCCCCCGTTCAGCCCGACCGCTGCGCCTT<br>ATCCGGTAACTATCGTCTTGAGTCCAACCCGGTAAGACACGACTTATCGCCA<br>CTGGCAGCAGCCACTGGTAACAGGATTAGCAGAGCGAGGTATGTAGGCGGT<br>GCTACAGAGTTCTTGAAGTGGTGGCCTAACTACGGCTACACTAGAAGAACA<br>GTATTTGGTATCTGCGCTCTGCTGAAGCCAGTTACCTTCGGAAAAAGAGTTG<br>GTAGCTCTTGATCCGGCAAACAAACCACCGCTGGTAGCGGTGGTTTTTTTGT<br>TTGCAAGCAGCAGATTACGCGCAGAAAAAAAGGATCTCAAGAAGATCCTTT<br>GATCTTTTCTACGGGGTCTGACGCTCAGTGGAACGAAAACTCACGTTAAGG<br>GATTTTGGTCATGAGATTATCAAAAAGGATCTTCACCTAGATCCTTTTAAAT<br>TAAAAATGAAGTTTTAAATCAATCTAAAGTATATATGAGTAAACTTGGTCTG<br>ACAGTTACCAATGCTTAATCAGTGAGGCACCTATCTCAGCGATCTGTCTATT<br>TCGTTCATCCATAGTTGCCTGACTCCCCGTCGTGTAGATAACTACGATACGG<br>GAGGGCTTACCATCTGGCCCCAGTGCTGCAATGATACCGCGAGACCCACGC<br>TCACCGGCTCCAGATTTATCAGCAATAAACCAGCCAGCCGGAAGGGCCGAG<br>CGCAGAAGTGGTCCTGCAACTTTATCCGCCTCCATCCAGTCTATTAATTGTT<br>GCCGGGAAGCTAGAGTAAGTAGTTCGCCAGTTAATAGTTTGCGCAACGTTG<br>TTGCCATTGCTACAGGCATCGTGGTGTCACGCTCGTCGTTTGGTATGGCTTC<br>ATTCAGCTCCGGTTCCCAACGATCAAGGCGAGTTACATGATCCCCCATGTTG<br>TGCAAAAAAGCGGTTAGCTCCTTCGGTCCTCCGATCGTTGTCAGAAGTAAGT<br>TGGCCGCAGTGTTATCACTCATGGTTATGGCAGCACTGCATAATTCTCTTAC<br>TGTCATGCCATCCGTAAGATGCTTTTCTGTGACTGGTGAGTACTCAACCAAG<br>TCATTCTGAGAATAGTGTATGCGGCGACCGAGTTGCTCTTGCCCGGCGTCAA<br>TACGGGATAATACCGCGCCACATAGCAGAACTTTAAAAGTGCTCATCATTG<br>GAAAACGTTCTTCGGGGCGAAAACTCTCAAGGATCTTACCGCTGTTGAGAT<br>CCAGTTCGATGTAACCCACTCGTGCACCCAACTGATCTTCAGCATCTTTTAC<br>TTTCACCAGCGTTTCTGGGTGAGCAAAAACAGGAAGGCAAAATGCCGCAAA<br>AAAGGGAATAAGGGCGACACGGAAATGTTGAATACTCATACTCTTCCTTTT<br>TCAATATTATTGAAGCATTTATCAGGGTTATTGTCTCATGAGCGGATACATA<br>TTTGAATGTATTTAGAAAAATAAACAAATAGGGGTTCCGCGCACATTTCCCC<br>GAAAAGTGCCACCTGACGTCTAAGAAACCATTATTATCATGACATTAACCT<br>ATAAAAATAGGCGTATCACGAGGCC |
| 121 | FC550A-<br>empty vector<br>(EVmRuby) | GCCCCTGCAGCCGAATTATATTATTTTTGCCAAATAATTTTTAACAAAAGCT<br>CTGAAGTCTTCTTCATTTAAATTCTTAGATGATACTTCATCTGGAAAATTGTC<br>CCAATTAGTAGCATCACGCTGTGAGTAAGTTCTAAACCATTTTTTTATTGTT<br>GTATTATCTCTAATCTTACTACTCGATGAGTTTTCGGTATTATCTCTATTTTT<br>AACTTGGAGCAGGTTCCATTCATTGTTTTTTTTCATCATAGTGAATAAAATCA<br>ACTGCTTTAACACTTGTGCCTGAACACCATATCCATCCGGCGTAATACGACT<br>CACTATAGGGAGAGCGGCCGCCAGATCTTCCGGATGGCTCGAGTTTTTCAG<br>CAAGATCATGCCTGCTATTGTCTTCCCAATCCTCCCCCTTGCTGTCCTGCCCC<br>ACCCCACCCCCCAGAATAGAATGACACCTACTCAGACAATGCGATGCAATT<br>TCCTCATTTTATTAGGAAAGGACAGTGGGAGTGGCACCTTCCAGGGTCAAG<br>GAAGGCACGGGGGAGGGGCAAACAACAGATGGCTGGCAACTAGAAGGCAC<br>AGTCGCATATGTCAGGCACCGGGCTTGCGGGTCATGCACCAGGTGCGCGGT<br>CCTTCGGGCACCTCGACGTCGGCGGTGACGGTGAAGCCGAGCCGCTCGTAG<br>AAGGGGAGGTTGCGGGGCGCGGATGTCTCCAGGAAGGCGGGCACCCCGGC<br>GCGCTCGGCCGCCTCCACTCCGGGGAGCACGACGGCGCTGCCCAGACCCTT<br>GCCCTGGTGGTCGGGCGAGACGCCGACGGTGGCCAGGAACCACGCGGGCTC<br>CTTGGGCCGGTGCGGCGCCAGGAGGCCTTCCATCTGTTGCTGCGCGGCCAG<br>CCGGGAACCGCTCAACTCGGCCATGCGCGGGCCGATCTCGGCGAACACCGC<br>CCCCGCTTCGACGCTCTCCGGCGTGGTCAGACCGCCACCGCGGCGCCGTC<br>GTCCGCGACCCACACCTTGCCGATGTCGAGCCCGACGCGCGTGAGGAAGAG<br>TTCTTGCAGCTCGGTGACCCGCTCGATGTGGCGGTCCGGATCGACGGTGTGG<br>CGCGTGGCGGGGTAGTCGGCGAACGCGGCGGCGAGGGTGCGTACGGCCCT<br>GGGGACGTCGTCGCGGGTGGCGAGGCGCACCGTGGGCTTGTACTCGGTCAT<br>AGGACCGGGGTTTCTTCCACGTCTCCTGCTTGCTTTAACAGAGAGAAGTTC<br>GTGGCACCGGATCCTCCAGCGCCTGTGCTATGTCTGCCCTCAGCTCTCTCAT<br>ATTGTTCCACGATGGTGTAGTCCCCATTATGGCTGATAATGTCGAGTTTAAT<br>ATCAGTCATGTAGGCGCCAGGCAGCTGCACTTGTTTCTTGGCCTTGTAGGTT<br>GTTTTGACCTCGGCATCGTAGTGTCCTCCGTCTTTGAGTTTCAGTCTCATTTT<br>AATTTCGCCTTTCAGAGCGCCATCCTCAGGATACATTCTCTCGGTGGAGGCT<br>TCCCATCCCATTGTTTTTTTTTGCATGACAGGGCCATCGGAGGGGGAAGTTGG<br>TTCCTCTGAGTTTCACCTTATAAATAAACTCTCCGTCCTGGAGGGTGCTATC<br>TTGTGTGACTGTCACCACGCCTCCGTCCTCGAAGTTCATGAATCTCTCCCAC<br>TTGAAGCCTTCAGGGAAGGAGAGCTTCAGATAGTCAGGGATGTCGGCAGGG<br>TGTTTAACATAGGCTTTGCTTCCGTACTGGAACTGAGGGCTCAGAATATCCC<br>AGGAGAAGGGGAGGGGTCCTCCTTTTGTGACCTTGAGCTTAGCGGTTTGTGT |

9. SEQUENCE APPENDIX

| SEQ ID NO: | Description | Sequence |
|---|---|---|

```
GCCCTCGTAAGGCCGGCCTTCTCCTTCTCCCTCAATCTCGAACTCGTGTCCG
TTGACGCTTCCCTCCATCTTGACCTTAAATCTCATAAACTCTTTGATGACATC
CTCCGGAGCTGGCCATGGTGGCGATCGATAGGTCGAAAGGCCCGGAGATGAG
GAAGAGGAGAACAGCGCGGCAGACGTGCGCTTTTGAAGCGTGCAGAATGC
CGGGCCTCCGGAGGACCTTCGGGCGCCCGCCCCGCCCCTGAGCCCGCCCCT
GAGCCCGCCCCCGGACCCACCCTTCCCAGCTGCTGAGCCCAGAAAGCGAAG
GAGCAAAGCTGCTATTGGCCGCTGCCCAAAGGCCTACCCGCTTCCATTGCT
CAGCGGTGCTGTCCATCTGCACGAGACTAGTGAGACGTGCTACTTCCATTTG
TCACGTCCTGCACGACGCGAGCTGCGGGGGGGGGGGGGAACTTCCTGACTAG
GGGAGGAGTAGAAGGTGGCGCGAAGGGGCCACCAAAGAACGGAGCCGGTT
GGCGCTACCGGTGGATGTGGAATGTGTGCGAGGCCAGAGGCCACTTGTGTA
GCGCCAAGTGCCAGCGGGGCTGCTAAAGCGCATGCTCCAGACTGCCTTGGG
AAAAGCGCCTCCCCTACCCGGTAGAATTATCTTTCTAGAAAGGATCTGCGAT
CGCTCCGGTGCCCGTCAGTGGGCAGAGCGCACATCGCCCACAGTCCCCGAG
AAGTTGGGGGGAGGGGTCGGCAATTGAACGGGTGCCTAGAGAAGGTGGCG
CGGGGTAAACTGGGAAAGTGATGTCGTGTACTGGCTCCGCCTTTTTCCCGAG
GGTGGGGGAGAACCGTATATAAGTGCAGTAGTCGCCGTGAACGTTCTTTTT
CGCAACGGGTTTGCCGCCAGAACACAGCTGAAGCTTCGAGGGGCTCGCATC
TCTCCTTCACGCGCCCGCCGCCCTACCTGAGGCCGCCATCCACGCCGGTTGA
GTCGCGTTCTGCCGCCTCCCGCCTGTGGTGCCTCCTGAACTGCGTCCGCCGT
CTAGGTAAGTTTAAAGCTCAGGTCGAGACCGGGCCTTTGTCCGGCGCTCCCT
TGGAGCCTACCTAGACTCAGCCGGCTCTCCACGCTTTGCCTGACCCTGCTTG
CTCAACTCTACGTCTTTGTTTCGTTTTCTGTTCTGCGCCGTTACAGATCCAAG
CTGTGACCGGCGCCTACGAATTCGATATCGGTACCGCTAGCCCTAGGACGC
GTCAGACATGATAAGATACATTGATGAGTTTGGACAAACCACAACTAGAAT
GCAGTGAAAAAAATGCTTTATTTGTGAAATTTGTGATGCTATTGCTTTATTT
GTAACCATTATAAGCTGCAATAAACAAGTTAACAACAACAATTGCATTCAT
TTTATGTTTCAGGTTCAGGGGGAGGTGTGGGAGGTTTTTTATCGTTCTTCTTT
TATTCTCTCAAGATTTTCAGGCTGTATATTAAAACTTATATTAAGAACTATG
CTAACCACCTCATCAGGAACCGTTGTAGGTGGCGTGGGTTTTCTTGGCAATC
GACTCTCATGAAAACTACGAGCTAAATATTCAATATGTTCCTCTTGACCAAC
TTTATTCTGCATTTTTTTTGAACGAGGTTTAGAGCAAGCTTGTCGACGATGT
AGGTCACGGTCTCGAAGCCGCGGTGCGGGTGCCAGGGCGTGCCCTTGGGCT
CCCCGGGCGCGTACTCCACCTCACCCATCTGGTCCATCATGATGAACGGGTC
GAGGTGGCGGTAGTTGATCCCGGCGAACGCGCGGCGCACCGGGAAGCCCTC
GCCCTCGAAACCGCTGGGCGCGGTGGTCACGGTGAGCACGGGACGTGCGAC
GGCGTCGGCGGGTGCGGATACGCGGGGCAGCGTCAGCGGGTTCTCGACGGT
CACGGCGGGCATGTCGACAAGCTTCAGGAAACTGAGACAGGAATTTTATTA
AAAATTTAAATTTTGAAGAAAGTTCAGGGTTAATAGCATCCATTTTTTGCTT
TGCAAGTTCCTCAGCATTCTTAACAAAAGACGTCTCTTTTGACATGTTTAAA
GTTTAAACCTCCTGTGTGAAATTATTATCCGCTCATAATTCCACACATTATA
CGAGCCGGAAGCATAAAGTGTAAAGCCTGGGGTGCCTAATGAGTGAGCTAA
CTCACATTAATTGCGTTGCGCTCACTGCCCAATTGCTTTCCAGTCGGGAAACC
TGTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATA
GGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAA
GGATCTTCACCTAGATCCTTTTAAATTAAAAATGAAGTTTTAAATCAATCTA
AAGTATATATGAGTAAACTTGGTCTGACAGTTACCAATGCTTAATCAGTGA
GGCACCTATCTCAGCGATCTGTCTATTTCGTTCATCCATAGTTGCCTGACTCC
CCGTCGTGTAGATAACTACGATACGGGAGGGCTTACCATCTGGCCCCAGTG
CTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAA
GGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTT
```

-continued

---

9. SEQUENCE APPENDIX

---

| SEQ ID NO: | Description | Sequence |
|---|---|---|
| | | TCTGTGACTGGTGAGTACTCAACCAAGTCATTCTGAGAATAGTGTATGCGGC |
| | | GACCGAGTTGCTCTTGCCCGGCGTCAATACGGGATAATACCGCGCCACATA |
| | | GCAGAACTTTAAAAGTGCTCATCATTGGAAAACGTTCTTCGGGGCGAAAAC |
| | | TCTCAAGGATCTTACCGCTGTTGAGATCCAGTTCGATGTAACCCACTCGTGC |
| | | ACCCAACTGATCTTCAGCATCTTTTACTTTCACCAGCGTTTCTGGGTGAGCA |
| | | AAAACAGGAAGGCAAAATGCCGCAAAAAAGGGAATAAGGGCGACACGGA |
| | | AATGTTGAATACTCATACTCTTCCTTTTTCAATATTATTGAAGCATTTATCAG |
| | | GGTTATTGTCTCATGAGCGGATACATATTTGAATGTATTTAGAAAAATAAAC |
| | | AAATAGGGGTTCCGCGCACATTTCCCCGAAAAGTGCCACCTGACGTCTAAG |
| | | AAACCATTATTATCATGACATTAACCTATAAAAATAGGCGTATCACGAGGC |
| | | C |
| 122 | FC550A-eBFP2 empty vector (EVeBFP2) | GCCCCTGCAGCCGAATTATATTATTTTTGCCAAATAATTTTTAACAAAAGCT |
| | | CTGAAGTCTTCTTCATTTAAATTCTTAGATGATACTTCATCTGGAAAATTGTC |
| | | CCAATTAGTAGCATCACGCTGTGAGTAAGTTCTAAACCATTTTTTTATTGTT |
| | | GTATTATCTCTAATCTTACTACTCGATGAGTTTTCGGTATTATCTCTATTTTT |
| | | AACTTGGAGCAGGTTCCATTCATTGTTTTTTTTCATCATAGTGAATAAAATCA |
| | | ACTGCTTTAACACTTGTGCCTGAACACCATATCCATCCGGCGTAATACGACT |
| | | CACTATAGGGAGAGCGGCCGCCAGATCTTCCGGATGGCTCGAGTTTTTCAG |
| | | CAAGATCATGCCTGCTATTGTCTTCCCAATCCTCCCCCTTGCTGTCCTGCCCC |
| | | ACCCCACCCCCCAGAATAGAATGACACCTACTCAGACAATGCGATGCAATT |
| | | TCCTCATTTTATTAGGAAAGGACAGTGGGAGTGGCACCTTCCAGGGTCAAG |
| | | GAAGGCACGGGGGAGGGGCAAACAACAGATGGCTGGCAACTAGAAGGCAC |
| | | AGTCGCATATGTCAGGCACCGGGCTTGCGGGTCATGCACCAGGTGCGCGGT |
| | | CCTTCGGGCACCTCGACGTCGGCGGTGACGGTGAAGCCGAGCCGCTCGTAG |
| | | AAGGGGGAGGTTGCGGGGCGCGGATGTCTCCAGGAAGGCGGGCACCCCGGC |
| | | GCGCTCGGCCGCCTCCACTCCGGGGAGCACGACGGCGCTGCCCAGACCCTT |
| | | GCCCTGGTGGTCGGGCGAGACGCCGACGGTGGCCAGGAACCACGCGGGCTC |
| | | CTTGGGCCGGTGCGGCGCCAGGAGGCCTTCCATCTGTTGCTGCGCGGCCAG |
| | | CCGGGAACCGCTCAACTCGGCCATGCGCGGGCCGATCTCGGCGAACACCGC |
| | | CCCCGCTTCGACGCTCTCCGGCGTGGTCCAGACCGCCACCGCGGCGCCGTC |
| | | GTCCGCGACCCACACCTTGCCGATGTCGAGCCCGACGCGCGTGAGGAAGAG |
| | | TTCTTGCAGCTCGGTGACCCGCTCGATGTGGCGGTCCGGATCGACGGTGTGG |
| | | CGCGTGGCGGGGTAGTCGGCGAACGCGGCGGCGAGGGTGCGTACGGCCCT |
| | | GGGGACGTCGTCGCGGGTGGCGAGGCGCACCGTGGGCTTGTACTCGGTCAT |
| | | AGGACCGGGGTTTTCTTCCACGTCTCCTGCTTGCTTTAACAGAGAGAAGTTC |
| | | GTGGCACCGGATCCCTTGTACAGCTCGTCCATGCCGAGAGTGATCCCGGCG |
| | | GCGGTGCGGAACTCCAGCAGGACCATGTGATCGCGCTTCTCGTTGGGGTCTT |
| | | TGCTCAGCACGGACTGGGTGCTCAGGTAGTGGCTGTCGGGCAGCAGCACGG |
| | | GGCCGTCGCCGATGGGGGTGTTCTGCTGGTAGTGGTCGGCGAGCTGCACGC |
| | | TGCCGTCCTCCACGTTGTGGCGGATCTTGAAGTTCACCTTGATGCCGTTCTT |
| | | CTGCTTGACGGCCATGATATAGATGTTGTGGCTGTTGAAGTTGTACTCCAGC |
| | | TTGTGCCCCAGGATGTTGCCGTCCTCCTTGAAGTCGACGCCCTTCAGCTCGA |
| | | TGCGGTTCACTAGGGTGTCGCCCTCGAACTTCACCTCGGCGCGGGTCTTGTA |
| | | GGTGCCGTCGTCCTTGAAGAAGATGGTGCGCTCCTGGACGTAGCCTTCGGG |
| | | CATGGCGGACTTGAAGAAGTCGTGCTGCTTCATGTGGTCGGGGTAGCGGGC |
| | | GAAGCACTGCACGCCGTGGCTCAGGGTGGTCACGAGGGTGGGCCAGGGCA |
| | | CGGGCAGCTTGCCGGTGGTGCAGATGAACTTCAGGGTCAGCTTGCCGTTGG |
| | | TGGCATCGCCCTCGCCCTCGCCCCTCACGCTGAACTTGTGGCCGTTTACGTC |
| | | GCCGTCCAGCTCGACCAGGATGGGCACCACCCCGGTGAACAGCTCCTCGCC |
| | | CTTGCTCACCATGGTGGCGATCGATAGGTCGAAAGGCCCGGAGATGAGGAA |
| | | GAGGAGAACAGCGCGGCAGACGTGCGCTTTTGAAGCGTGCAGAATGCCGG |
| | | GCCTCCGGAGGACCTTCGGGCGCCCGCCCCGCCCCTGAGCCCGCCCCTGAG |
| | | CCCGCCCCCGGACCCACCCTTCCCAGCTGCTGAGCCCAGAAAGCGAAGGAG |
| | | CAAAGCTGCTATTGGCCGCTGCCCCAAAGGCCTACCCGCTTCCATTGCTCAG |
| | | CGGTGCTGTCCATCTGCACGAGACTAGTGAGACGTGCTACTTCCATTTGTCA |
| | | CGTCCTGCACGACGCGAGCTGCGGGGGGGGGGGGGAACTTCCTGACTAGGGG |
| | | AGGAGTAGAAGGTGGCGCGAAGGGGCCACCAAAGAACGGAGCCGGTTGGC |
| | | GCTACCGGTGGATGTGGAATGTGTGCGAGGCCAGAGGCCACTTGTGTAGCG |
| | | CCAAGTGCCAGCGGGGCTGCTAAAGCGCATGCTCCAGACTGCCTTGGGAAA |
| | | AGCGCCTCCCCTACCCGGTAGAATTATCTTTCTAGAAAGGATCTGCGATCGC |
| | | TCCGGTGCCCGTCAGTGGGCAGAGCGCACATCGCCCACAGTCCCCGAGAAG |
| | | TTGGGGGGAGGGGTCGGCAATTGAACGGGTGCCTAGAGAAGGTGGCGCGG |
| | | GGTAAACTGGGAAAGTGATGTCGTGTACTGGCTCCGCCTTTTTCCCGAGGGT |
| | | GGGGGAGAACCGTATATAAGTGCAGTAGTCGCCGTGAACGTTCTTTTTTCGC |
| | | AACGGGTTTGCCGCCAGAACACAGCTGAAGCTTCGAGGGGCTCGCATCTCT |
| | | CCTTCACGCGCCCGCCGCCCTACCTGAGGCCGCCATCCACGCCGGTTGAGTC |
| | | GCGTTCTGCCGCCTCCCGCCTGTGGTGCCTCCTGAACTGCGTCCGCCGTCTA |
| | | GGTAAGTTTAAAGCTCAGGTCGAGACCGGGCCTTTGTCCGGCGCTCCCTTGG |
| | | AGCCTACCTAGACTCAGCCGGCTCTCCACGCTTTGCCTGACCCTGCTTGCTC |
| | | AACTCTACGTCTTTGTTTCGTTTTCTGTTCTGCGCCGTTACAGATCCAAGCTG |
| | | TGACCGGCGCCTACGAATTCGATATCGGTACCGCTAGCCCTAGGACGCGTC |
| | | AGACATGATAAGATACATTGATGAGTTTGGACAAACCACAACTAGAATGCA |

9. SEQUENCE APPENDIX

SEQ
ID
NO:  Description    Sequence

GTGAAAAAAATGCTTTATTTGTGAAATTTGTGATGCTATTGCTTTATTTGTA
ACCATTATAAGCTGCAATAAACAAGTTAACAACAACAATTGCATTCATTTTA
TGTTTCAGGTTCAGGGGGAGGTGTGGGAGGTTTTTTATCGTTCTTCTTTTATT
CTCTCAAGATTTTCAGGCTGTATATTAAAACTTATATTAAGAACTATGCTAA
CCACCTCATCAGGAACCGTTGTAGGTGGCGTGGGTTTTCTTGGCAATCGACT
CTCATGAAAACTACGAGCTAAATATTCAATATGTTCCTCTTGACCAACTTTA
TTCTGCATTTTTTTTGAACGAGGTTTAGAGCAAGCTTGTCGACGATGTAGGT
CACGGTCTCGAAGCCGCGGTGCGGGTGCCAGGGCGTGCCCTTGGGCTCCCC
GGGCGCGTACTCCACCTCACCCATCTGGTCCATCATGATGAACGGGTCGAG
GTGGCGGTAGTTGATCCCGGCGAACGCGCGGCGCACCGGGAAGCCCTCGCC
CTCGAAACCGCTGGGCGCGGTGGTCACGGTGAGCACGGGACGTGCGACGGC
GTCGGCGGGTGCGGATACGCGGGGCAGCGTCAGCGGGTTCTCGACGGTCAC
GGCGGGCATGTCGACAAGCTTCAGGAAACTGAGACAGGAATTTTATTAAAA
ATTTAAATTTTGAAGAAAGTTCAGGGTTAATAGCATCCATTTTTTGCTTTGC
AAGTTCCTCAGCATTCTTAACAAAAGACGTCTCTTTTGACATGTTTAAAGTT
TAAACCTCCTGTGTGAAATTATTATCCGCTCATAATTCCACACATTATACGA
GCCGGAAGCATAAAGTGTAAAGCCTGGGGTGCCTAATGAGTGAGCTAACTC
ACATTAATTGCGTTGCGCTCACTGCCAATTGCTTTCCAGTCGGGAAACCTGT
CGTGCCAGCTGCATTAATGAATCGGCCAACGCGCGGGGAGAGGCGGTTTGC
GTATTGGGCGCTCTTCCGCTTCCTCGCTCACTGACTCGCTGCGCTCGGTCGTT
CGGCTGCGGCGAGCGGTATCAGCTCACTCAAAGGCGGTAATACGGTTATCC
ACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCT
CCGCCCCCCTGACGAGCATCACAAAAATCGACGCTCAAGTCAGAGGTGGCG
AAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAG
TTCGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCGG
TAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTG
GAACGAAAACTCACGTTAAGGGATTTTGGTCATGAGATTATCAAAAAGGAT
CTTCACCTAGATCCTTTTAAATTAAAAATGAAGTTTTAAATCAATCTAAAGT
ATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGC
AATGATACCGCGAGACCCACGCTCACCGGCTCCAGATTTATCAGCAATAAA
CCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCA
GTTAATAGTTTGCGCAACGTTGTTGCCATTGCTACAGGCATCGTGGTGTCAC
GCTCGTCGTTTGGTATGGCTTCATTCAGCTCCGGTTCCCAACGATCAAGGCG
AGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGT
GACTGGTGAGTACTCAACCAAGTCATTCTGAGAATAGTGTATGCGGCGACC
GAGTTGCTCTTGCCCGGCGTCAATACGGGATAATACCGCGCCACATAGCAG
AACTTTAAAAGTGCTCATCATTGGAAAACGTTCTTCGGGGCGAAAACTCTC
AAGGATCTTACCGCTGTTGAGATCCAGTTCGATGTAACCCACTCGTGCACCC
AACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGT
TGAATACTCATACTCTTCCTTTTTCAATATTATTGAAGCATTTATCAGGGTTA
TTGTCTCATGAGCGGATACATATTTGAATGTATTTAGAAAAATAAACAAAT
AGGGGTTCCGCGCACATTTCCCCGAAAAGTGCCACCTGACGTCTAAGAAAC
CATTATTATCATGACATTAACCTATAAAAATAGGCGTATCACGAGGCC

123  Consensus     MAAMAAGSITTLPALPEDGGSGAFPPGHFKDPKRLYCKNGGFFLRIHPDGRVD
     FGF2          GVREKSDPHIKLQLQAEERGVVSIKGVCANRYLAMKEDGRLLASKCATDECFF
                   FERLESNNYNTYRSRKYSSWYVALKRTGQYKLGPKTGPGQKAILFLPMSAKS*

124  human FGF2    MAAGSITTLPALPEDGGSGAFPPGHFKDPKRLYCKNGGFFLRIHPDGRVDGVRE
                   KSDPHIKLQLQAEERGVVSIKGVCANRYLAMKEDGRLLASKCVTDECFFFERL
                   ESNNYNTYRSRKYTSWYVALKRTGQYKLGSKTGPGQKAILFLPMSAKS*

125  Consensus     GPETLCGAELVDALQFVCGDRGFYFSKPTGYGSSSRRLHHKGIVDECCFQSCDL
     IGF1          RRLEMYCAPIKPPKSA 126  Bovine IGF1   GPETLCGAELVDALQFVCGDRGFYFSKPTGYGSSSRRLHHKGIVDECCFQSCDL
                   RRLEMYCAPIKPPKSA -continued

9. SEQUENCE APPENDIX

| SEQ ID NO: | Description | Sequence |
|---|---|---|
| 127 | Porcine IGF1 | GPETLCGAELVDALQFVCGDRGFYFSKPTGYGSSSRRLHHKGIVDECCFQSCDL RRLEMYCAPIKPPKSA |
| 128 | Human IGF | GPETLCGAELVDALQFVCGPRGFYFSKPTGYGSSIRRLHHKGIVDECCFQSCDL RRLEMYCAPIKPTKAA |
| 129 | Consensus PDGFb | MCPQPARLEMNRCWALFLSLCCYLRLVSAEGDPIPEELYEMLSDHSIRSFDDLQ RLLHGDSVEEDGAELDLNXTRSHSGGELESLSRGRRSLGSXTIAEPAVIAECKTR TEVFEISRRLIDRTNANFLVWPPCVEVQRCSGCCNNRNVQCRPTQVQXRXVQV XKIEIVRKKPIFKKATVTLEDHLACRCETVXAXRPVTRXPGSSQEQRXAXTPQT RVTIRTVRVRRPPKGKHRKFKHTHDKTALKETLGA |
| 130 | Bovine PDGFb | MNRCWALFLSLCCYLRLVSAEGDPIPEELYKMLSDHSIRSFDDLQRLLHGDSVD EDGAELDLNLTRSHSGGELESLSRGRRSLGSPTVAAEPAVIAECKTRTEVFEISR RLIDRTNANFLVWPPCVEVQRCSGCCNNRNVQCRPTQVQDRKVQVKKIEIVRK KKIFKKATVTLVDHLACRCETVVARAVTRTPGSSQEQRARTPQTRVTIRTVRVR RPPKGKHRKFKHTHDKTALKETLGA |
| 131 | Human PDGFb | MNRCWALFLSLCCYLRLVSAEGDPIPEELYEMLSDHSIRSFDDLQRLLHGDPGE EDGAELDLNMTRSHSGGELESLARGRRSLGSLTIAEPAMIAECKTRTEVFEISRR LIDRTNANFLVWPPCVEVQRCSGCCNNRNVQCRPTQVQLRPVQVRKIEIVRKK PIFKKATVTLEDHLACKCETVAAARPVTRSPGGSQEQRAKTPQTRVTIRTVRVR RPPKGKHRKFKHTHDKTALKETLGA |

*Indicates a stop codon

10. EQUIVALENTS AND INCORPORATION BY REFERENCE

All references cited herein are incorporated by reference to the same extent as if each individual publication, database entry (e.g., Genbank sequences or GeneID entries), patent application, or patent, was specifically and individually indicated incorporated by reference in its entirety, for all purposes. This statement of incorporation by reference is intended by Applicants, pursuant to 37 C.F.R. § 1.57(b)(1), to relate to each and every individual publication, database entry (e.g., Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

While the invention has been particularly shown and described with reference to a preferred embodiment and various alternate embodiments, it is understood by persons skilled in the relevant art that various changes in form and details can be made therein without departing from the spirit and scope of the invention

What is claimed is:

1. A method for culturing an avian cell line in a cell culture media, said method comprising:

(a) seeding an edible cell culture media with an edible, avian cell line arising from cells transduced with a polynucleotide comprising a single coding sequence encoding a single growth factor receptor or growth factor, which is an FGFR, a PDGFR, an activated FGFR, or an activated PDGFR, or a combination of solely a coding sequence encoding an FGFR or an activated FGFR and a coding sequence encoding an IGF;

wherein the polynucleotide is engineered to express the coding sequence or the combination of coding sequences in the cell line; and (b) culturing the cell line in the cell culture media substantially free of exogenous growth factors, wherein the cell line proliferates in the absence of exogenous growth factors over 72 hours of culture to a cell density equivalent to a cell density over 72 hours of culture time of a comparable cell line not comprising the polynucleotide and cultured in the presence of the exogenous growth factors.

2. The method of claim 1, wherein the cells are transduced with only the polynucleotide encoding the single growth factor or growth factor receptor.

3. The method of claim 1, wherein the coding sequence encodes an FGFR or activated FGFR.

4. The method of claim 1, wherein the coding sequence encodes a PDGFR or activated PDGFR.

5. The method of claim 1, wherein the polynucleotide comprises the combination of a coding sequence encoding an FGFR or an activated FGFR and a coding sequence encoding IGF.

6. The method of claim 1, wherein the activated FGFR is FGFR3 having an N540K modification, a K650E modification, a myrist modification, or some combination thereof.

7. The method of claim 1, wherein the cell line is cultured in an absence of serum.

8. The method of claim 1, wherein the cell line is capable of proliferating to a cell density double the seeded cell density over 72 hours of culture time without exogenous growth factors.

9. The method of claim 1, wherein the cell line is cultured to a cell density of 1 million cells per milliliter or more.

10. The method of claim 1, wherein the coding sequence for the IGF encodes a fusion protein comprising the IGF and a signal peptide, wherein the signal peptide is IL2 signal peptide.

11. The method of claim 1, wherein the coding sequence encodes an FGFR and is one of FGFR1, FGFR2, FGFR3, or FGFR4.

12. The method of claim 1, wherein the cell line is derived from chicken.

13. The method of claim 1, wherein the cells of the cell line are myoblasts, myocytes, satellite cells, side population cells, muscle derived stem cells, mesenchymal stem cells, myogenic pericytes, mesoangioblasts, or fibroblasts.

14. The method of claim 1, further comprising the step of forming cell line into a cell-based food product suitable for consumption.

15. A method for culturing an edible, avian cell line in a cell culture media, said method comprising:

(a) seeding an edible cell culture media with an edible, avian cell line arising from cells transduced with a polynucleotide comprising a combination of solely a coding sequence encoding IGF1 and a coding sequence encoding FGF;

wherein the polynucleotide is engineered to express the coding sequences in the cell line; and (b) culturing the cell line in the cell culture media substantially free of exogenous growth factors, wherein the cell line proliferates in the absence of the exogenous growth factors over 72 hours of culture to a cell density equivalent to a cell density over 72 hours of culture time of a comparable cell line not comprising the polynucleotide and cultured in the presence of exogenous IGF1 and FGF.

16. The method of claim 15, wherein the cell line is derived from chicken.

17. The method of claim 15, wherein the cells of the cell line are myoblasts, myocytes, satellite cells, side population cells, muscle derived stem cells, mesenchymal stem cells, myogenic pericytes, mesoangioblasts, or fibroblasts.

18. The method of claim 15, further comprising the step of forming the cell line into a cell-based food product suitable for consumption.

19. A method for culturing an edible, avian cell line in a cell culture media, said method comprising:

(a) seeding an edible cell culture media with an edible, avian cell line arising from cells transduced with
   a polynucleotide comprising a single coding sequence of a single growth factor, which encodes FGF2 or FGF3;
   wherein the polynucleotide is engineered to express the coding sequence in the cell line; and (b) culturing the cell line in the cell culture media substantially free of exogenous growth factors, wherein the cell line is capable of proliferating to a cell density higher than the seeded cell density over 72 hours of culture time of a comparable cell line not comprising the polynucleotide.

20. The method of claim 19, wherein the cell line is derived from chicken.

21. The method of claim 19, wherein the cells of the cell line are myoblasts, myocytes, satellite cells, side population cells, muscle derived stem cells, mesenchymal stem cells, myogenic pericytes, mesoangioblasts, or fibroblasts.

22. The method of claim 19, further comprising the step of forming the cell line into a cell-based food product suitable for consumption.

* * * * *